(12) United States Patent
Braun et al.

(10) Patent No.: US 12,071,425 B2
(45) Date of Patent: Aug. 27, 2024

(54) PHENOXY-PYRIDYL-PYRIMIDINE COMPOUNDS AND METHODS OF USE

(71) Applicant: Genentech, Inc., South San Francisco, CA (US)

(72) Inventors: Marie-Gabrielle Braun, San Francisco, CA (US); Cuong Q. Ly, Burlingame, CA (US); Georgette Castanedo, Redwood City, CA (US); Paul Gibbons, San Francisco, CA (US); Wendy Lee, San Ramon, CA (US); Joachim Rudolph, Burlingame, CA (US); Nicole Alice Blaquiere, Oakland, CA (US); Jacob Bradley Schwarz, San Ramon, CA (US); Ramsay Beveridge, Pointe-Claire (CA); Jean-Philippe Leclerc, Laval (CA); Alexandre Lemire, Blainville (CA); Leo Fu, Shanghai (CN)

(73) Assignee: Genentech, Inc., South San Francisco, CA (US)

( * ) Notice: Subject to any disclaimer, the term of this patent is extended or adjusted under 35 U.S.C. 154(b) by 776 days.

(21) Appl. No.: 17/275,606

(22) PCT Filed: Sep. 12, 2019

(86) PCT No.: PCT/US2019/050749
§ 371 (c)(1),
(2) Date: Mar. 11, 2021

(87) PCT Pub. No.: WO2020/056089
PCT Pub. Date: Mar. 19, 2020

(65) Prior Publication Data
US 2023/0057166 A1 Feb. 23, 2023

(30) Foreign Application Priority Data

Sep. 12, 2018 (WO) ............... PCT/CN2018/105183

(51) Int. Cl.
| | | |
|---|---|---|
| *C07D 401/14* | (2006.01) | |
| *A61K 45/06* | (2006.01) | |
| *C07D 401/04* | (2006.01) | |
| *C07D 413/14* | (2006.01) | |
| *C07D 471/04* | (2006.01) | |
| *C07D 471/08* | (2006.01) | |

(52) U.S. Cl.
CPC ............ *C07D 401/14* (2013.01); *A61K 45/06* (2013.01); *C07D 401/04* (2013.01); *C07D 413/14* (2013.01); *C07D 471/04* (2013.01); *C07D 471/08* (2013.01)

(58) Field of Classification Search
CPC .. C07D 401/14; C07D 401/04; C07D 413/14; C07D 471/04; C07D 471/08; A61K 45/06
See application file for complete search history.

(56) References Cited

U.S. PATENT DOCUMENTS

| | | |
|---|---|---|
| 3,773,919 A | 11/1973 | Boswell et al. |
| 7,868,177 B2 | 1/2011 | Cee et al. |
| 7,880,000 B2 | 2/2011 | Geuns-Meyer et al. |
| 8,476,434 B2 | 7/2013 | Geuns-Meyer et al. |
| 8,815,885 B2 | 8/2014 | Walter et al. |
| 9,382,230 B2 | 7/2016 | Walter et al. |

(Continued)

FOREIGN PATENT DOCUMENTS

| | | |
|---|---|---|
| JP | A 2007/536280 | 12/2007 |
| JP | A 2010/514689 | 5/2010 |

(Continued)

OTHER PUBLICATIONS

Cross et al., "The molecular basis for selective inhibition of unconventional mRNA splicing by an IRE1-binding small molecule," PNAS, 109(15):E869-E878, (Apr. 10, 2012).

(Continued)

*Primary Examiner* — Timothy R Rozof
(74) *Attorney, Agent, or Firm* — Alston & Bird LLP

(57) ABSTRACT

Described herein are phenoxy-pyridyl-pyrimidine compounds with inositol requiring enzyme 1 (IRE1) modulation activity or function having the Formula I structure or stereoisomers, tautomers, or pharmaceutically acceptable salts thereof, and with the substituents and structural features described herein. Also described are pharmaceutical compositions and medicaments that include the Formula I compounds, as well as methods of using such IRE1 modulators, alone and in combination with other therapeutic agents, for treating diseases or conditions that are mediated or dependent upon estrogen receptors.

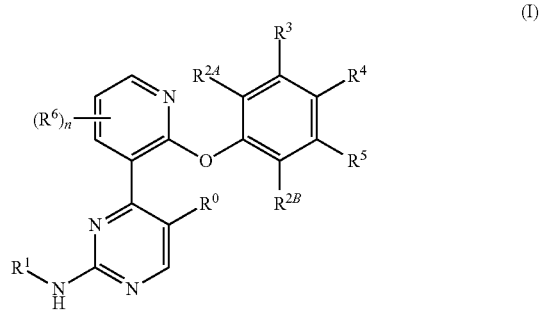

26 Claims, No Drawings

(56) References Cited

U.S. PATENT DOCUMENTS

| | | | |
|---|---|---|---|
| 2006/0009453 A1* | 1/2006 | Geuns-Meyer | C07D 401/04 544/333 |
| 2010/0048597 A1 | 2/2010 | Beckwith et al. | |
| 2016/0024094 A1 | 1/2016 | Backes et al. | |
| 2018/0346447 A1 | 12/2018 | Vacca et al. | |

FOREIGN PATENT DOCUMENTS

| | | |
|---|---|---|
| JP | 6925435 B2 | 8/2021 |
| JP | A 2021/536496 | 12/2021 |
| WO | WO 96/15111 | 5/1996 |
| WO | WO 01/19825 A1 | 3/2001 |
| WO | WO 02/18380 A1 | 3/2002 |
| WO | WO 2004/063195 A1 | 7/2004 |
| WO | WO 2005/034869 A2 | 4/2005 |
| WO | WO 2005/113494 | 12/2005 |
| WO | WO 2006/002367 A1 | 1/2006 |
| WO | WO 2006/039718 A2 | 4/2006 |
| WO | WO 2006/056863 A1 | 6/2006 |
| WO | WO 2006/082492 A1 | 8/2006 |
| WO | WO 2007/100646 A1 | 9/2007 |
| WO | WO 2007/136465 A2 | 11/2007 |
| WO | WO 2008/033999 A1 | 3/2008 |
| WO | WO 2008/055842 A1 | 5/2008 |
| WO | WO 2010/031056 | 3/2010 |
| WO | WO 2011/097526 A1 | 8/2011 |
| WO | WO 2013/067423 A1 | 5/2013 |
| WO | WO 2013/090840 A1 | 6/2013 |
| WO | WO 2014/052669 A1 | 4/2014 |
| WO | WO 2014/179496 A1 | 11/2014 |
| WO | WO 2014/179498 A1 | 11/2014 |
| WO | WO 2014/182829 A1 | 11/2014 |
| WO | WO 2018/102751 A1 | 6/2018 |
| WO | WO 2018/222918 A1 | 12/2018 |
| WO | WO 2020/117635 A1 | 6/2020 |
| WO | WO 2020/142612 A1 | 7/2020 |
| WO | WO 2020/227020 A1 | 11/2020 |
| WO | WO 2021/145521 A1 | 7/2021 |

OTHER PUBLICATIONS

Ghosh, et al., "Allosteric inhibition of the IRE1α Rnase preserves cell viability and function during endoplasmic reticulum stress," Cell, 158(3):534-548 (2014).
Ranatunga et al., "Synthesis of Novel Tricyclic Chromenone-Based Inhibitors of IRE-1 RNase Activity" Journal of Medicinal Chemistry, 57:4289-4301, (2014).
Volkmann et al., "Potent and Selective Inhibitors of the Inositol-requiring Enzyme 1 Endoribonuclease," Journal of Biological Chemistry, 286(14):12743-12755, (Apr. 8, 2011).
Wang et al., "Divergent allosteric control of the IRE1α endoribonuclease using kinase inhibitors," Nature Chemical Biology, 8:982-989, (Dec. 2012).
Wang et al., "Protein misfolding in the endoplasmic reticulum as a conduit to human disease," Nature, 529:326-335 (Jan. 21, 2016).
GC Application No. 2019-38265, Examination Report dated Jul. 28, 2021.
WIPO Application No. PCT/US2019/050698, PCT International Preliminary Report on Patentability mailed Mar. 25, 2021.
WIPO Application No. PCT/US2019/050698, PCT International Search Report and Written Opinion of the International Searching Authority mailed Nov. 18, 2019.
Adachi et al., "ATF6 Is a Transcription Factor Specilaizing in the Regulation of Quality Control Proteins in the Endoplasmic Reticulum," Cell Struct. Func., 33:75-89, (2008).
Arai et al., "Transformation-associated gene regulation by ATF6α during hepatocarcinogenesis," FEBS Letts., 580:184-190, (2006).
Baek et al., "Involvement of Endoplasmic Reticulum Stress in Myofibroblastic Differentiation of Lung Fibroblasts," Am J. Resp. Cell Mol. Bio., 46:731-739, (2012).

Bogaert, S. et al., "Involvement of Endoplasmic Reticulum Stress in Inflammatory Bowel Disease: A Different Implication for Colonic and Ileal Disease?" PLOS One, 6(10):e25589, (2011).
Cao, S.S. et al., "The Unfolded Protein Response and Chemical Chaperones Reduce Protein Misfolding and Colitis in Mice," Gastroent, 144:989-1000, (2013).
Chiang, C-K. et al., "Endoplasmic Reticulum Stress Implicated in the Development of Renal Fibrosis," Mol. Med., 17:1295-1305, (2011).
Galligan et al., "Oxidative Stress and the ER Stress Response in a Murine Model for Early-Stage Alcoholic Liver Disease," J. Toxicol., 2012(207594), 12 pgs., (2012).
Ji, C., "New Insights into the Pathogenesis of Alcholol-Induced Er Stress and Liver Diseases," Int. J. Hepatol., 2014(513787):1-11, (2014).
Schröder et al., "ER stress and the unfolded protein response," Mutation Research, 569:29-63, (2005).
Shin et al., "SIRT7 Represses Myc Activity to Suppress ER Stress and Prevent Fatty Liver Disease," Cell Reports, 5:654-665, (2013).
Sovolyova et al., "Stressed to death—mechanisms of ER stress-induced celll death," Biol Chem, 395:1-13, (2014).
Spitler et al., "Endoplasmic Reticulum Stress Contributes to Aortic Stiffening via Proapoptotic and Fibrotic Signaling Mechanismis," Hypertension, 63:e40-45, (2014).
Tanjore, H. et al., "Endoplasmic Reticulum Stress as A Pro-Fibrotic Stimulus," Biochim Biophys Acta, 1832:940-947, (2013).
Walter, P. et al., "The Unfolded Protein Response: From Stress Pathway to Homeostatic Regulation," Science, 334:1081-1086, (2011).
Yamamoto et al., "Differential Contributions of ATF6 and XBP1 to the Activation of Endoplasmic Reticulum Stress-Responsive cis-Acting Elements ERSE, UPRE and ERSE-II," J. Biochem., 136:343-50, (2004).
WIPO Application No. PCT/US2020/018499, PCT International Search Report and Written Opinion of the International Searching Authority mailed Jun. 17, 2020.
EP Application No. 20711446.3, Office Action mailed May 19, 2023.
WIPO Application No. PCT/US2020/037233, PCT International Preliminary Report on Patentability mailed Dec. 23, 2021.
Beveridge et al., "Identification of BRaf-Sparing Amino-Thienopyrimidines with Potent IRE1α Inhibitory Activity," ACS Medicinal Chemistry Letters, 11(12):2389-2396, (Oct. 16, 2020).
Registry(STN) [online], Dec. 7, 2011, [search date: Jan. 5, 2024] CAS No. 1348150-26-4.
Registry(STN) [online], Dec. 7, 2011, [search date: Jan. 5, 2024] CAS No. 1350015-88-1.
EP Application No. 20702937.2, Office Action mailed Oct. 30, 2023.
JP Application No. 2021-539020, Reason for Refusal mailed Feb. 6, 2024.
JP Application No. 2021-548153, Reason for Refusal mailed Jan. 16, 2024.
Harrington et al., "Unfolded Protein Response in Cancer: IRE1α Inhibition by Selective Kinase Ligands Does Not Impair Tumor Cell Viability," ACS Medicinal Chemistry Letters, 6(1):68-72, (Sep. 29, 2014).
Taiwanese Application No. 108132813, Office Action dated Oct. 29, 2020.
WIPO Application No. PCT/US2019/050749, PCT International Preliminary Report on Patentability mailed Mar. 25, 2021.
WIPO Application No. PCT/US2019/050749, PCT International Search Report and Written Opinion of the International Searching Authority mailed Nov. 21, 2019.
Binet, F. et al., "Neuronal ER Stress Impedes Myeloid-Cell-Induced Vascular Regeneration through IRE1α Degradation of Netrin-1," Cell Metabol., 17:353-371, (2013).
Bowen, T. et al., "MicroRNAs, transforming growth factor beta-1, and tissue fibrosis," J. Pathol., 229:274-285, (2013).
Cee, Victor J. et al., "Pyridyl-pyrimidine benzimidazole derivatives as potent, selective, and orally bioavailable inhibitors of Tie-2 kinase," Bioorganic & Medicinal Chemistry Letters, 19:424-427, (2009).

(56) References Cited

OTHER PUBLICATIONS

Chen, Y. et al., "IRE1: ER stress sensor and cell fate executor," Trends Cell Biol., 23:547-555, (2013).

Cheng, A. C. et al., "Analysis of Kinase Inhibitor Selectivity using a Thermodynamics-Based Partition Index," J. Med. Chem. 53(11):4502-4510, (2010).

Davis, M., "Comprehensive analysis of kinase inhibitor selectivity," Nature Biotechnology, 29(11):1046-1051, (Nov. 1, 2011).

Heindryckx, F. et al., "Endoplasmic reticulum stress enhances fibrosis through IRE1α-mediated degradation of miR-150 and XBP-1 splicing," EMBO Molecular Medicine, 8(7):729-744, 2016.

Hollien, J. et al., "Decay of Endoplasmic Reticulum-Localized mRNAs During the Unfolded Protein Response," Science, 313:104-107, (2006).

Lu, M. et al., "Opposing unfolded-protein-response signals converge on death receptor 5 to control apoptosis," Science, 345:98-101, (2014).

Ren, L. et al., "The discovery of potent and selective pyridopyrimidin-7-one based inhibitors of B-RafV600E kinase," Bioorganic & Medicinal Chemistry Letters, 22:3387-3391, (2012).

Sriburi, R. et al., "XBP1: a link between the unfolded protein response, lipid biosynthesis, and biogenesis of the endoplasmic reticulum," J. Cell. Bio., 167:35-41, (2004).

Tirasophon, W. et al., "The endoribonuclease activity of mammalian IRE1 autoregulates its mRNA and is required for the unfolded protein response," Genes & Develop., 14:2725-2736, (2000).

Upton, J-P. et al., "IRE1α cleaves select microRNAs during ER stress to derepress translation of proapoptotic Caspase-2," Science, 338:818-822, (2012).

EP Application No. 20 702 937.2, Communication pursuant to Article 94(3) EPC mailed Nov. 18, 2022.

JP Application No. 2021-513790, Office Action and Search Report issued Mar. 15, 2022.

\* cited by examiner

PHENOXY-PYRIDYL-PYRIMIDINE COMPOUNDS AND METHODS OF USE

CROSS-REFERENCE TO RELATED APPLICATIONS

This application is a 35 U.S.C. § 371 national stage of International Application No. PCT/US2019/050749, filed Sep. 12, 2019, which claims the benefit of and priority to Chinese International Application Serial No. PCT/CN2018/105183, filed Sep. 12, 2018, hereby incorporated by reference in their entirety.

BACKGROUND OF THE INVENTION

The kinase/endoribonuclease inositol requiring enzyme 1 (IRE1α), one of the key sensors of misfolded protein accumulation in the endoplasmic reticulum that triggers the unfolded protein response (UPR), is a potential therapeutic target for diverse diseases including cancer for inhibitors that bind to the ATP-binding site on the kinase moiety of IRE1α and block its endoribonuclease activity. IRE1α is a transmembrane, bifunctional protein with a luminal domain that binds to misfolded proteins, a transmembrane segment, and a cytoplasmic portion consisting of a kinase moiety and a tandem endoribonuclease domain. Structure-activity relationship (SAR) studies led to compounds selective in recombinant IRE1α kinase screens and potent against endoribonuclease activity of recombinant IRE1α as well as cellular IRE1α. IRE1α activity mediates certain cytoprotective and pro-survival functions of the UPR, increases viability and growth in certain tumor cell lines, and can be an effective therapeutic target for specific small molecule inhibitors that block malignant tumor growth, contrary to an earlier report (Harrington, P. E. et al (2015) ACS Med. Chem. Lett. 6:68-72). In addition, inhibitors of IRE1α can be therapeutically useful for other types of diseases besides cancer including certain autoimmune, neurodegenerative, fibrotic and metabolic disorders (Wang M. and Kaufman, R. J. (2016) Nature 529:326-335).

Homeostatic regulation of protein folding in the endoplasmic reticulum (ER) is under the control of three key intracellular signaling pathways: IRE1α, PERK, and ATF6, which together orchestrate the unfolded protein response (UPR) (Schroder, et al (2005) Mutat Res-Fund Mol Mech Metagenesis 569:29-63). An increase in demand for protein folding in the ER or certain types of cellular injury or stress lead to the accumulation of unfolded proteins in the ER—a condition called ER stress. Cells respond to ER stress by activating the UPR to help adjust or maintain their high-fidelity protein synthetic capacity (Walter, P. and Ron, D. (2011) Science, 334:1081-1086). IRE1α is the most evolutionarily conserved of the three branches of the UPR. Importantly, the UPR makes life/death decisions for the cell, depending on the severity and duration of ER stress, and the final outcome is either cell survival and recovery or programmed cell death (apoptosis) (Sovolyova et al, (2014) Biol Chem 395: 1-13). All three pathways of the UPR form a coordinated reaction to the accumulation of unfolded proteins; and several studies have demonstrated that there is cross talk between the different pathways (Yamamoto et al, J. Biochem (2004) 136:343-350); Arai et al, FEBS Letts. (2006) 580:184-190; Adachi et al, Cell Struct. Func. (2008) 33:75-89). ER stress and activation of the UPR can be caused by mechanical injury, inflammation, genetic mutations, infections, oxidative stress, metabolic stress, and other types of cellular stress associated with malignancy. ER stress has also been implicated in diseases that result in fibrotic remodeling of internal organs, such as chronic liver diseases (Galligan et al, J. Toxicol. (2012) Vol. 2012, Article ID 207594, 12 pgs.; Shin et al, Cell Reports (2013) 5:654-665; Ji, Int J. Hepatol. (2014) Vol. 2014, Article ID 513787, 11 pages), pulmonary fibrosis (Baek et al, Am. J. Resp. Cell Mol. Bio. (2012) 46:731-739); Tanjore et al, Biochim Biophys Acta (2012, online), (2013) 1832:940-947), kidney fibrosis (Chiang et al, Mol. Med. (2011) 17:1295-1305), cardiovascular disease (Spitler & Webb, Hypertension (2014) 63:e40-e45), and inflammatory bowel disease (Bogaert et al, PLoS One (2011) 6(10) e25589; Cao et al, Gastroent (2013) 144:989-1000).

IRE1α is a transmembrane, bifunctional protein with cytoplasmic kinase and endoribonuclease activity. The N-terminal domain of IRE1α is proposed to sense the presence of unfolded proteins in the ER lumen, triggering activation of the cytoplasmic kinase domain, which, in turn, activates the C-terminal endoribonuclease. IRE1α transmits information across the ER lipid bilayer (Tirasophon et al, Genes & Develop. (2000) 14:2725-2736). Increased ER protein load and presence of unfolded proteins leads to the dissociation of the ER chaperone GRP78/BiP from IRE1α molecules, which bind to misfolded proteins and then undergo dimerization and trans-autophosphorylation in the cytoplasmic kinase domain. This leads to activation of the IRE1α endoribonuclease moiety in the cytosol. The IRE1α endoribonuclease has the ability to cleave the mRNA that encodes unspliced X box protein 1 (XBP1u); this excises a 26-nucleotide intron and leads to formation of spliced XBP1 (XBP1s) mRNA, which encodes a potent transcription factor. After transport into the nucleus, the XBP1s protein binds to UPR promoter elements to initiate transcription of genes that enhance the ability of the ER to cope with unfolded proteins, for example, through enhanced ER-associated degradation of misfolded proteins, and through elevated levels of chaperones and disulfide isomerases that support protein folding in the ER. IRE1α activation is also associated with enlargement of the ER volume, which has been interpreted as an adaptive mechanism to increase protein folding capacity (Sriburi et al, J. Cell. Bio. (2004) 167:35-41); (Chen, Y. (2013) Trends Cell Biol., 23,547-555). In addition, the IRE1α endoribonuclease cleaves various mRNAs in a process called regulated IRE1α-dependent decay of mRNA (RIDD), which reduces both protein translation and import of proteins into the ER to help reestablish homeostasis (Hollien & Weissman, Science (2006) 313:104-107). In cancer cells, IRE1α suppresses ER-stress-induced apoptosis by reducing the mRNA levels of death receptor 5 (DR5) through RIDD (Lu et al., Science (2014) 345:98-101).

Besides degrading mRNA (Binet et al, Cell Metabol. (2013) 17:353-371), it was recently shown that IRE1α also has the ability to degrade microRNAs (miRs) (Upton et al, Science (2012) 338:818-822). miRs are short noncoding RNA oligonucleotides consisting of 17-25 nucleotides that generally act to inhibit gene expression by binding to complementary sequences in the 30-untranslated region of target mRNAs, either to repress mRNA translation or to induce mRNA cleavage. A number of cellular functions such as proliferation, differentiation, and apoptosis are regulated by miRs, and aberrant miR expression is observed in a variety of human diseases including fibrosis (Bowen et al, J. Pathol (2013) 229:274-285). Inhibitors that specifically target individual components of the UPR have recently been described. The inhibitor 4μ8C that stably binds to lysine 907 in the IRE1α endoribonuclease domain has been shown to inhibit both RIDD activity and XBP-1 splicing (Cross et al, Proc Natl. Acad. Sci. (2012) 109:E869-E878). High levels of 4 µ8C cause no measurable toxicity in cells and concentrations ranging from 80 to 1281M of 4µ8C completely block XBP1 splicing without affecting IRE1α (alpha) kinase activity (Cross et al, 2012). The inhibitor 4µ8C thus represents an important tool to delineate the functions of IRE1α in vivo as IRE1α-knockout mice die during embryonic development. Inhibition of IRE1α prevents activation of myofibroblasts and reduces fibrosis in animal models of liver and skin fibrosis. Pharmacological inhibition of IRE1α could revert the profibrotic phenotype of activated myofibroblasts isolated from patients with scleroderma and indicates that ER stress inhibitors should be taken into consideration when developing new strategies for the treatment of fibrotic diseases (Heindryckx, F. et al (2016) EMBO Molecular Medicine Vol 8(7): 729-744).

Activation of the UPR has been shown to be an important survival pathway for tumors of secretory cell origin like multiple myeloma that have a very high protein synthesis burden. Therefore, efforts to disrupt the UPR by blocking the IRE1α endoribonuclease cleavage and activation of XBP1 have been an active area of cancer research. As a specific IRE1α RNase product, XBP1s is a direct indicator of functional IRE1 inhibition. A potent and selective IRE1α inhibitor would serve as an important tool to test the hypothesis that, without full UPR activation, tumor cells would be driven to apoptosis. IRE1α inhibitors and activating compounds have been reported (Harrington, P. E. et al (2015) ACS Med. Chem. Lett. 6:68-72; Volkmann, K., et al (2011) J. Biol. Chem, 286:12743-12755; Cross, B. C. S., et al (2012) Proc. Natl. Acad. Sci. U.S.A., 109E869-E878; Wang, L., et al (2012) Nat. Chem Biol., 8:982-989; Ghosh, R., et al (2014) Cell, 158:534-548; Ranatunga, S., et al (2014) J. Med. Chem, 57, 4289-4301; U.S. Pat. Nos. 9,382, 230; 8,815,885).

There remains a need for potent and selective inhibitors having suitable pharmacological properties for the treatment of IRE1-related diseases or disorders in patients.

BRIEF SUMMARY OF THE INVENTION

Disclosed are phenoxy-pyridyl-pyrimidine compounds that target IRE1α, compositions containing these compounds, and methods for the treatment of IRE1-related diseases or disorders.

In one aspect, provided is a compound of Formula (I), or a pharmaceutically acceptable salt thereof as detailed herein. Also provided is a pharmaceutical composition comprising a compound of Formula (I), or a pharmaceutically acceptable salt thereof, and one or more pharmaceutically acceptable excipients.

In another aspect, provided is a method for treating an IRE1-related disease or disorder in a subject in need thereof comprising administering to the subject an effective amount of a compound of Formula (I) or a pharmaceutically acceptable salt thereof. In some embodiments, the subject is a human. In some embodiments, the IRE1-related disease or disorder is a cancer. In some embodiments, the method further comprises administering an anti-cancer agent to the subject.

Also provided is a compound of Formula (I), or a pharmaceutically acceptable salt thereof for use in a method of treating an IRE1-related disease or disorder.

Still further provided herein is a compound of Formula (I), or a pharmaceutically acceptable salt thereof for use in a method of treating cancer.

Also provided is use of a compound of Formula (I) or a pharmaceutically acceptable salt thereof, in a method detailed herein (e.g., treatment of an IRE1-related disease or disorder).

Also provided is use of a compound of Formula (I) or a pharmaceutically acceptable salt thereof, for the manufacture of a medicament for use in a method detailed herein (e.g., treatment of an IRE1-related disease or disorder).

Also provided is a kit for treating an IRE1-related disease or disorder, the kit comprising a pharmaceutical composition comprising a compound of Formula (I) or a pharmaceutically acceptable salt thereof; and instructions for use.

In still another aspect provided herein is a method of inhibiting or killing a cancer cell expressing Ire1, where the method comprises contacting the cancer cell expressing Ire1 with a compound or pharmaceutically acceptable salt thereof described herein.

In yet another aspect provided herein is a method of modulating Ire1 activity, where the method comprises contacting Ire1 with a compound or pharmaceutically acceptable salt thereof described herein.

Also provided is a kit for treating cancer, where the kit comprises a pharmaceutical composition comprising a the compound described herein, or a pharmaceutically acceptable salt thereof; and instructions for use.

In another aspect provided herein is a method of making a compound of Formula (I). Also provided are compound intermediates useful in synthesis of a compound of Formula (I) or a pharmaceutically acceptable salt thereof described herein.

DETAILED DESCRIPTION OF THE INVENTION

Disclosed herein, are phenoxy-pyridyl-pyrimidine compounds of Formula (I), including pharmaceutically acceptable salts thereof and pharmaceutical compositions thereof that are inhibitors or modulators of IRE1α. As such, the compounds and compositions are useful in treating diseases and disorders mediated by IRE1α.

While the disclosure herein provides enumerated embodiments, it will be understood that they are not intended to limit the invention to those embodiments. On the contrary, the disclosure is intended to cover all alternatives, modifications, and equivalents which can be included within the scope of the present invention as defined by the claims. One skilled in the art will recognize many methods and materials similar or equivalent to those described herein. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the methods and materials are described below. All publications, patent applications, patents, and other references mentioned herein are incorporated by reference in their entirety. The nomenclature used in this Application is based on IUPAC systematic nomenclature, unless indicated otherwise.

Definitions

"Alkyl" as used herein refers to a saturated linear (i.e. unbranched) or branched univalent hydrocarbon chain or combination thereof, having the number of carbon atoms designated (i.e., $C_{1-10}$ means one to ten carbon atoms). Particular alkyl groups are those having 1 to 20 carbon atoms (a "$C_{1-20}$ alkyl"), having a 1 to 8 carbon atoms (a "$C_{1-8}$ alkyl"), having 1 to 6 carbon atoms (a "$C_{1-6}$ alkyl"), having 2 to 6 carbon atoms (a "$C_{2-6}$ alkyl"), or having 1 to 4 carbon atoms (a "$C_{1-4}$ alkyl"). Examples of alkyl group include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear (i.e., unbranched) or branched univalent hydrocarbon chain or combination thereof, having at least one site of olefinic unsaturation (i.e., having at least one moiety of the formula C=C) and having the number of carbon atoms designated (i.e., $C_{2-10}$ means two to ten carbon atoms). The alkenyl group can be in "cis" or "trans" configurations, or alternatively in "E" or "Z" configurations. Particular alkenyl groups are those having 2 to 20 carbon atoms (a "$C_{2-20}$ alkenyl"), having a 2 to 8 carbon atoms (a "$C_{2-8}$ alkenyl"), having 2 to 6 carbon atoms (a "$C_{2-6}$ alkenyl"), or having 2 to 4 carbon atoms (a "$C_{2-4}$ alkenyl"). Example of alkenyl group include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkynyl" as used herein refers to an unsaturated linear (i.e. unbranched) or branched univalent hydrocarbon chain or combination thereof, having at least one site of acetylenic unsaturation (i.e., having at least one moiety of the formula C≡C) having the number of carbon atoms designated (i.e., $C_{2-10}$ means two to ten carbon atoms). Particular alkynyl groups are those having 2 to 20 carbon atoms (a "$C_{2-20}$ alkynyl"), having a 2 to 8 carbon atoms (a "$C_{2-8}$ alkynyl"), having 2 to 6 carbon atoms (a "$C_{2-6}$ alkynyl"), having 2 to 4 carbon atoms (a "$C_{2-4}$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Alkylene" as used herein refers to the same residues as alkyl, but having bivalency. Particular alkylene groups are those having 1 to 6 carbon atoms (a "$C_{1-6}$ alkylene"), 1 to 5 carbon atoms (a "$C_{1-5}$ alkylene"), having 1 to 4 carbon atoms (a "$C_{1-4}$ alkylene"), or 1 to 3 carbon atoms (a "$C_{1-3}$ alkylene"). Examples of alkylene include, but are not limited to, groups such as methylene (—$CH_2$—), ethylene (—$CH_2$—$CH_2$—), propylene (—$CH_2$—$CH_2$—$CH_2$—), butylene (—$CH_2$—$CH_2$—$CH_2$—$CH_2$—), and the like.

"Cycloalkyl" as used herein refers to non-aromatic, saturated or unsaturated cyclic univalent hydrocarbon structures having the number of carbon atoms designated (i.e., ($C_{3-10}$ means three to ten carbon atoms). Cycloalkyl can consist of one ring, such as cyclohexyl, or multiple rings, such as adamantly, but excludes aryl groups. A cycloalkyl comprising more than one ring can be fused, spiro, or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_{3-8}$ cycloalkyl"), or having 3 to 6 carbon atoms (a "$C_{3-6}$ cycloalkyl"). Examples of cycloalkyl include, but are not limited to, cyclopropyl, cyclobutyl, cyclopentyl, cyclohyxyl, 1-cyclohexenyl, 3-cyclohexenyl, cycloheptyl, norbornyl, and the like.

"Aryl" as used herein refers to an unsaturated aromatic carbocyclic group having a single ring (e.g., phenyl) or multiple condensed rings (e.g., naphthyl or anthryl) which condensed rings can or can not be aromatic. Particular aryl groups are those having from 6 to 14 annular (i.e., ring) carbon atoms (a "$C_{6-14}$ aryl"). An aryl group having more than one ring where at least one ring is non-aromatic can be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" as used herein refers to an unsaturated aromatic cyclic group having from 1 to 14 annular (i.e., ring) carbon atoms and at least one annular heteroatom, including but not limited to heteroatoms such as nitrogen, phosphorus, oxygen and sulfur. A heteroaryl group can have a single ring (e.g., pyridyl, furyl) or multiple condensed rings (e.g., indolizinyl, benzothienyl) which condensed rings can or can not be aromatic. Particular heteroaryl groups are 5- to 14-membered rings having 1 to 12 annular (i.e., ring) carbon atoms and 1 to 6 annular (i.e., ring) heteroatoms independently selected from nitrogen, phosphorus, oxygen and sulfur; 5- to 10-membered rings having 1 to 8 annular carbon atoms and 1 to 4 annular heteroatoms independently selected from nitrogen, phosphorus, oxygen and sulfur; and 5-, 6- or 7-membered rings having 1 to 5 annular carbon atoms and 1 to 4 annular heteroatoms independently selected from nitrogen, oxygen and sulfur In one variation, heteroaryl include monocyclic aromatic 5-, 6- or 7-membered rings having from 1 to 6 annular carbon atoms and 1 to 4 annular heteroatoms independently selected from nitrogen, oxygen and sulfur. In another variation, heteroaryl includes polycyclic aromatic rings having from 1 to 12 annular carbon atoms and 1 to 6 annular heteroatoms independently selected from nitrogen, phosphorus, oxygen and sulfur. A heteroaryl group having more than one ring where at least one ring is non-aromatic can be connected to the parent structure at either an aromatic ring position or at a non-aromatic ring position. In one variation, a heteroaryl group having more than one ring where at least one ring is non-aromatic is connected to the parent structure at an aromatic ring position.

"Heterocycle", "heterocyclic", or "heterocyclyl" as used herein refers to a saturated or an unsaturated non-aromatic cyclic group having a single ring or multiple condensed rings, and having from 1 to 14 annular (i.e., ring) carbon atoms and from 1 to 6 annular (i.e., ring) heteroatoms, such as nitrogen, phosphorus, sulfur or oxygen, and the like. A heterocycle comprising more than one ring can be fused, spiro or bridged, or any combination thereof. In fused ring systems, one or more can be fused rings can be cycloalkyl. Particular heterocyclyl groups are 3- to 14-membered rings having 1 to 13 annular carbon atoms and 1 to 6 annular heteroatoms independently selected from nitrogen, phosphorus, oxygen and sulfur; 3- to 12-membered rings having 1 to 11 annular carbon atoms and 1 to 6 annular heteroatoms independently selected from nitrogen, phosphorus, oxygen and sulfur; 3- to 10-membered rings having 1 to 9 annular carbon atoms and 1 to 4 annular heteroatoms independently selected from nitrogen, phosphorus, oxygen and sulfur; 3- to 8-membered rings having 1 to 7 annular carbon atoms and 1 to 4 annular heteroatoms independently selected from nitrogen, phosphorus, oxygen and sulfur; and 3- to 6-membered rings having 1 to 5 annular carbon atoms and 1 to 4 annular heteroatoms independently selected from nitrogen, phosphorus, oxygen and sulfur. In one variation, heterocyclyl include monocyclic 3-, 4-, 5-, 6- or 7-membered rings having from 1 to 2, 1 to 3, 1 to 4, 1 to 5 or 1 to 6 annular carbon atoms and 1 to 2, 1 to 3 or 1 to 4 annular heteroatoms independently selected from nitrogen, phosphorus, oxygen and sulfur. In another variation, heterocyclyl includes polycyclic non-aromatic rings having from 1 to 12 annular carbon atoms and 1 to 6 annular heteroatoms independently selected from nitrogen, phosphorus, oxygen and sulfur.

"Halo" or Halogen" refers to fluoro, chloro, bromo and/or iodo. Where a residue is substituted with more than one halogen, it can be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which can be but are not necessarily the same halo; thus 4-chloro-3-fluorophenyl is within the scope of dihaloaryl. An alkyl group in which one or more hydrogen is replaced with a halo group is referred to as a "haloalkyl", for example, "$C_{1-6}$ haloalkyl." An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Carbonyl" refers to the group C=O.

"Thiocarbonyl" refers to the group C=S.

"Oxo" refers to the moiety =O.

The terms "treat" and "treatment" refer to therapeutic treatment, wherein the object is to slow down (lessen) an undesired physiological change or disorder, such as the development or spread of arthritis or cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those with the condition or disorder.

The phrase "effective amount" means an amount of a compound or pharmaceutically acceptable salt thereof that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein or (iv) favorably alters the clinical response of a patient to the treatment, where the inhibition and favorability is relative to a control (e.g. non-treatment or prior treatment with an anti-cancer agent such as that described herein). In the case of cancer, the effective amount of the drug can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug can prevent growth and/or kill existing cancer cells, it can be cytostatic and/or cytotoxic. For cancer therapy, efficacy can be measured, for example, by assessing the time to disease progression (TTP) and/or determining the response rate (RR).

The term "clinical response" refers to inhibition of disease progression, inhibition of tumor growth, reduction of primary tumor, relief of tumor-related symptoms, inhibition of tumor secreted factors (including tumor secreted hormones, such as those that contribute to carcinoid syndrome), delayed appearance of primary or secondary tumors, slowed development of primary or secondary tumors, decreased occurrence of primary or secondary-tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. In general, clinical response refers to primary or secondary measures of efficacy known and understood in the art. Treatment and clinical response as described herein can be assessed using international standards for a given condition.

The term "Time To Progression" or "TTP" as used herein refers to the time from treatment onset until tumor progression.

The term "Progression Free Survival" or "PFS" refers to the time from treatment onset until tumor progression or death. In one embodiment, PFS rates can be computed using the Kaplan-Meier estimates.

The clinical response of a patient described herein can be characterized as a complete or partial response. "Complete response" (CR) refers to an absence of clinically detectable cancer with normalization of any previously abnormal radiographic studies, bone marrow, and cerebrospinal fluid (CSF) or abnormal monoclonal protein measurements. "Partial response" (PR) refers to at least about a 10%, 20%, 30%, 40%, 50%, 60%, 70%, 80%, or 90% decrease in all measurable cancer burden (i.e., the number of malignant cells present in the subject, or the measured bulk of tumor masses or the quantity of abnormal monoclonal protein). The term "treatment" includes both a complete and a partial response.

The terms "patient" and "subject" are used interchangeably herein and refer to an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having cancer, in particular, a cancer described herein. In one embodiment, a patient is a human having histologically or cytologically-confirmed cancer, including subjects who have progressed CHI (or not been able to tolerate) standard anticancer therapy or for whom no standard anti cancer therapy exists.

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), small-cell lung cancer, non-small cell lung cancer (NSCLC), lung adenocarcinoma, squamous cell lung cancer, peritoneum cancer, hepatocellular cancer, stomach cancer, gastrointestinal cancer, esophageal cancer, pancreatic cancer, glioblastoma, cervical cancer, ovarian cancer, liver cancer, bladder cancer, breast cancer, colon cancer, rectal cancer, colorectal cancer, endometrial cancer, uterine cancer, salivary gland carcinoma, renal cancer, prostate cancer, vulval cancer, thyroid cancer, hepatocellular carcinoma (HCC), anal carcinoma, penile carcinoma, or head and neck cancer.

"Hematological malignancies" (British spelling "Haematological" malignancies) are the types of cancer that affect blood, bone marrow, and lymph nodes. As the three are intimately connected through the immune system, a disease affecting one of the three will often affect the others as well: although lymphoma is a disease of the lymph nodes, it often spreads to the bone marrow, affecting the blood. Hematological malignancies are malignant neoplasms (i.e. cancer), and they are generally treated by specialists in hematology and/or oncology. Hematological malignancies can derive from either of the two major blood cell lineages: myeloid and lymphoid cell lines. Lymphomas, lymphocytic leukemias, and myeloma are from the lymphoid line, while acute and chronic myelogenous leukemia, myelodysplastic syndromes and myeloproliferative diseases are myeloid in origin. Exemplary leukemias include acute lymphoblastic leukemia (ALL), acute myelogenous leukemia (AML), chronic lymphocytic leukemia (CLL), chronic myelogenous leukemia (CML), acute monocytic leukemia (AMOL) and small lymphocytic lymphoma (SLL). Exemplary lymphomas include Hodgkin's lymphomas (all four subtypes) and Non-Hodgkin's lymphomas (NHL, all subtypes).

A "anti-cancer agent" is a chemical compound useful in the treatment of cancer, regardless of mechanism of action. Classes of anti-cancer agents include, but are not limited to: alkylating agents, antimetabolites, anti-hormone therapies, endocrine therapies, immunomodulatory agents, spindle poison plant alkaloids, cytotoxic/antitumor antibiotics, topoisomerase inhibitors, antibodies, photosensitizers, and kinase inhibitors. Anti-cancer agents include compounds used in targeted therapy and conventional chemotherapy.

Exemplary anti-cancer agents include proteasome inhibitors such as bortezomib (VELCADE), carfilzomib (KYPROLIS) and ixazomib (NINLARO). Other examples include immunomodulatory agents such as lenalidomide (REVLIMID) and pomalidomide (POMALYST).

Other exemplary anti-cancer agents include inhibitors of B-cell receptor targets such as BTK, Bcl-2 and JAK inhibitors and include, for example, venetoclax (VENCLEXTA) and ibrutinib (IMBRUVICA).

Additional anti-cancer agents include, for example, Abemaciclib (VERZENIO); abiraterone (ZYTIGA, YONSA); aclarubicin; acivicin; acodazole; acronine; actinomycin; acylfulvene; adecypenol; adozelesin; adriamycin; aldesleukin; altretamine; ambamustine; ambomycin; ametantrone; amidox; amifostine; aminoglutethimide; aminolevulinic acid; amrubicin; amsacrine; anagrelide; anastrozole; andrographolide; antarelix; anthramycin; aphidicolin glycinate; apurinic acid; ARRY-300; arabinoside; asperlin; asulacrine; atamestane; atrimustine; azasetron; azatoxin; azatyrosine; azacitidine; AZD6244; AZD8330; azetepa; azotomycin; balanol; batimastat; bendamustine; benzochlorins; benzodopa; benzoylstaurosporine; beta-alethine; betaclamycin B; betulinic acid; bicalutamide; binimetinib; bisantrene; bisaziridinylspermine; bisnafide; bistratene; bleomycin; busulfan; bizelesin; breflate; bortezomib; brequinar; bropirimine; budotitane; buthionine; bryostatin; cactinomycin; calusterone; calcipotriol; calphostin C; camptothecin; capecitabine (XELODA); caracemide; carbetimer; carboplatin; carboquone; carmustine; carubicin; carzelesin; castanospermine; celecoxib; cetrorelix; cetuximab (ERBITUX); chloroquinoxaline; cicaprost; chlorambucil; chlorofusin; cisplatin; cladribine; clomifene; clotrimazole; crisnatol; crisnatol; cypemycin; cyclophosphamide; cytarabine; cytostatin; dacarbazine; dactinomycin; daratumamab; daunorubicin; decarbazine; dacliximab; dasatinib; decitabine; deslorelin; dexamethasone; dexifosfamide; dexrazoxane; dexverapamil; dexormaplatin; dezaguanine; diaziquone; dihydrotaxol; docosanol; dolasetron; docetaxel; doxorubicin; doxifluridine; droloxifene; dromostanolone; dronabinol; duazomycin; ebselen; ecomustine; edelfosine; edrecolomab; edatrexate; eflomithine; elemene; emitefur; elsamitrucin; enloplatin; enpromate; epipropidine; epirubicin; episteride; erbulozole; erlotinib (TARCEVA); esorubicin; estramustine; etanidazole; etoposide; etoprine; exemestane; fadrozole; fazarabine; fenretinide; filgrastim; finasteride; flavopiridol; flezelastine; fluasterone; floxuridine; fludarabine; fludarabine; fluorodaunorubicin; forfenimex; formestane; fluorouracil; floxouridine; flurocitabine; fosquidone; fostriecin; fotemustine; fulvestrant (FASLODEX); gadolinium; gallium; galocitabine; ganirelix; gemcitabine; geldanamycin; gefitinib; gossyphol; hydroxyurea; hepsulfam; heregulin; ibandronate; ibrutinib; idarubicin; idelalisib (ZYDELIG), ifosfamide; canfosfamide; ilmofosine; iproplatin; idoxifene; idramantone; ilmofosine; ilomastat; imatinib mesylate (GLEEVEC); imiquimod; iobenguane; iododoxorubicin; ipomeanol; irinotecan; itasetron; iimofosine; lanreotide; lapatinib (TYKERB); leinamycin; lenograstim; lentinan; leptolstatin; letrozole; leuprorelin; levamisole; liarozole; lobaplatin; lombricine; lometrexol; lonidamine; lonafamib (SARASAR); losoxantrone; lovastatin; loxoribine; lurtotecan; lapatinib; leucovorin; lometrexol; lomustine; maitansine; marimastat; masoprocol; maspin; menogaril; merbarone; meterelin; methioninase; metoclopramide; mifepristone; miltefosine; mirimostim; mitoguazone; mitolactol; mitonafide; mitoxantrone; mofarotene; molgramostim; mopidamol; maytansine; megestrol acetate; melengestrol acetate; melphalan; mercaptopurine; methotrexate; methotrexate sodium; metoprine; meturedepa; mitinmitomycin; mitosper; mitotane; mitoxantrone; mycophenolic acid; nafarelin; nagrestip; napavin; nedaplatin; nemorubicin; neridronic acid; nilutamide; nisamycin; oblimersen (GENASENSE); octreotide; okicenone; onapristone; ondansetron; ormaplatin; oxisuran; oxaloplatin; osaterone; oxaliplatin; oxaunomycin; palauamine; palbociclib (IBRANCE); panitumumab (VECTIBIX); panomifene; pegaspargase; picibanil; pirarubicin; piritrexim; prednisone; prednisolone, paclitaxel; nab-paclitaxel (ABRAXANE); prednimustine; procarbazine; puromycin; raltitrexed; ramosetron; rapamycin (RAPAMUNE); rhizoxin; ribociclib (KISQALI), rituximab; rogletimide; rohitukine; romurtide; roquinimex; romidepsin; safingol; saintopin; sargramostim; semustine; sizofiran; sobuzoxane; sorafenib (NEXAVAR); sunitinib; spiromustine; squalamine; suradista; suramin; s wains onine; spiroplatin; streptonigrin; streptozocin; sulofenur; tallimustine; tamoxifen; tauromustine; tazarotene; tellurapyrylium; temoporfin; temozolomide; teniposide; tetrachlorodecaoxide; tetrazomine; thrombopoietin; thymalfasin; thymotrinan; tirapazamine; toremifene; tretinoin; trimetrexate; triptorelin; tropisetron; talisomycin; taxotere; teroxirone; testolactone; thiamiprine; thiotepa; tirapazamine; toremifene; trastuzumab; trastuzumab emtansine; trestolone acetate; triciribine phosphate; trimetrexate; uracil mustard; vandetanib (CAPRELSA); variolin B; velaresol; veramine; verteporfin; vemurafenib; vinorelbine; vinxaltine; vitaxin; vinblastine; vincristine; vindesine; vinepidine; vinglycinate; vinleurosine; vinorelbine; vinrosidine; vinzolidine; vorozole; wortmannin; zanoterone; zeniplatin; zilascorb; zinostatin stimalamer; zinostatin; and zorubicin.

In some embodiments, an anti-cancer agent includes, for example, idelalisib (ZYDELIG), docetaxel, fluorouracil, gemcitabine (GEMZAR), cisplatin, cis-diamine, carboplatin, paclitaxel, nab-paclitaxel, trastuzumab (HERCEPTIN), temozolomide, tamoxifen, 4-hydroxytamoxifen, and doxorubicin.

Also included in the definition of anti-cancer agent are: (i) anti-estrogens and selective estrogen receptor modulators (SERMs), including, for example, tamoxifen, raloxifene, droloxifene, 4-hydroxytamoxifen, trioxifene, ketoxifene, LY117018, onapristone, and toremifine citrate; (ii) selective estrogen receptor modulators (SERDs) such as brilanestrant, GDC-0927, GDC-9545, AZ94%, AZ9833, GNE-274, and fulvestrant (FASLODEX); (iii) aromatase inhibitors such as, for example, 4(5)-imidazoles, aminoglutethimide, megestrol acetate, exemestane, formestanie, fadrozole, vorozole, letrozole, and anastrozole; (iv) anti-androgens such as apalutamide, abiraterone, enzalutamide, flutamide, nilutamide, bicalutamide, leuprolide, and goserelin.

Further included in the definition of anti-cancer agents are: (iv) MEK inhibitors such as cobimetinib; (v) lipid kinase inhibitors, such as taselisib; (vi) antisense oligonucleotides such as oblimersen; (vii) ribozymes such as VEGF expression inhibitors such as angiozyme; (viii) vaccines such as gene therapy vaccines, for example, ALLOVECTIN, LEUVECTIN, and VAXID; (ix) topoisomerase 1 inhibitors such as LURTOTECAN®; ABARELIX® rmRH; and (x) anti-angiogenic agents such as bevacizumab.

In some embodiments herein, the anti-cancer agents is a therapeutic antibody such as atezolizumab, nivolumab, daratumumab, pembrolizumab, alemtuzumab, bevacizumab; cetuximab; panitumumab, rituximab, pertuzumab, trastuzumab, trastuzumab emtansine, or tositumomab.

A "metabolite" is a product produced through metabolism in the body of a specified compound or salt thereof. Metabolites of a compound can be identified using routine techniques and their activities determined using tests such as those described herein. Such products can result for example from the oxidation, reduction, hydrolysis, amidation, deamidation, esterification, deesterification, enzymatic cleavage, and the like, of the administered compound. Accordingly, provided herein are metabolites of compounds or pharmaceutically acceptable salts thereof described herein, including compounds produced by a process comprising contacting a Formula I compound or a pharmaceutically acceptable salt thereof with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds or pharmaceutically acceptable salts thereof described herein can contain asymmetric or chiral centers, and therefore exist in different stereoisomeric forms. It is intended that all stereoisomeric forms of the compounds or pharmaceutically acceptable salts thereof described herein, including but not limited to, diastereomers, enantiomers and atropisomers, as well as mixtures thereof such as racemic mixtures, form part of this disclosure. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity. Enantiomers can be separated from a racemic mixture by a chiral separation method, such as supercritical fluid chromatography (SFC). Assignment of configuration at chiral centers in separated stereoisomers can be tentative, and depicted in Table 1 structures for illustrative purposes, before stereochemistry is definitively established, such as from x-ray crystallographic data.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, aryl-aliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins.

A "solvate" refers to an association or complex of one or more solvent molecules and a compound described herein. Examples of solvents that form solvates include, but are not limited to, water (i.e., "hydrate"), isopropanol, ethanol, methanol, DMSO, ethylacetate (EtOAc), acetic acid (AcOH), and ethanolamine.

The term "$EC_{50}$" is the half maximal effective concentration" and denotes the plasma concentration of a particular compound required for obtaining 50% of the maximum of a particular effect in vivo.

The term "Ki" is the inhibition constant and denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (-log Ki), in which higher values indicate exponentially greater potency.

The term "$IC_{50}$" is the half maximal inhibitory concentration and denotes the concentration of a particular compound required for obtaining 50% inhibition of a biological process in vitro. $IC_{50}$ values can be converted logarithmically to $pIC_{50}$ values (-log $IC_{50}$), in which higher values indicate exponentially greater potency. The $IC_{50}$ value is not an absolute value but depends on experimental conditions e.g. concentrations employed, and can be converted to an absolute inhibition constant (Ki) using the Cheng-Prusoff equation (Biochem Pharmacol. (1973) 22:3099). Other percent inhibition parameters, such as $IC_{70}$, $IC_{90}$, etc., can be calculated.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds or pharmaceutically acceptable salts thereof described herein described herein include isotopes of hydrogen, carbon, nitrogen, oxygen, phosphorous, fluorine, and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Various isotopically labeled compounds or pharmaceutically acceptable salts thereof described herein, for example those into which radioactive isotopes such as $^3H$ and $^{14}C$ are incorporated. Such isotopically labeled compounds can be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labeled or substituted therapeutic compounds or pharmaceutically acceptable salts thereof described herein can have improved DMPK (drug metabolism and pharmacokinetics) properties, relating to distribution, metabolism, and excretion (ADME). Substitution with heavier isotopes such as deuterium can afford certain therapeutic advantages resulting from greater metabolic stability, for example increased in vivo half-life or reduced dosage requirements. An 18F labeled compound can be useful for PET or SPECT studies. Isotopically labeled compounds or pharmaceutically acceptable salts thereof described herein thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2H$ or D) can afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, can be defined by an isotopic enrichment factor. In the compounds or pharmaceutically acceptable salts thereof described herein described herein, any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds or pharmaceutically acceptable salts thereof described herein any atom specifically designated as a deuterium (D) is meant to represent deuterium.

Phenoxy-Pyridyl-Pyrimidine Compounds

The compounds disclosed herein are compounds of Formula (I) or pharmaceutically acceptable salts, solvates (e.g., hydrates), prodrugs, metabolites, or derivatives thereof, and pharmaceutical compositions thereof, which are potentially useful in the treatment of diseases, conditions and/or disorders modulated by inositol requiring enzyme 1 (IRE1). In one aspect provided herein are compounds of Formula (I) or pharmaceutically acceptable salts thereof, and pharmaceutical compositions comprising such compounds.

In one aspect, provided is a compound of Formula (I):

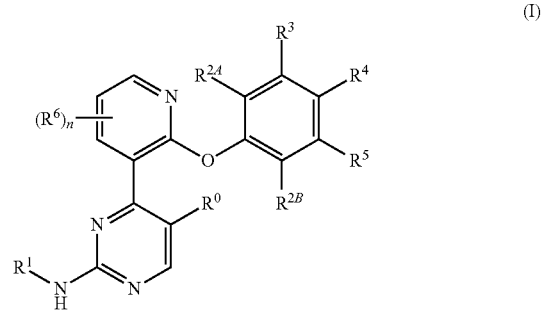

or a pharmaceutically acceptable salt thereof, wherein:

$R^0$ is hydrogen or fluoro;

$R^1$ is $C_{3-12}$ cycloalkyl, 3- to 14-membered heterocyclyl, 5- to 14-membered heteroaryl, —($C_{1-6}$ alkylene)-($C_3$-$C_{12}$ cycloalkyl), or —($C_{1-6}$ alkylene)-(3- to 14-membered heterocyclyl), —($C_{1-6}$ alkylene)-$OR^{1c}$, or —($C_{1-6}$ alkylene)-$NR^{1a}R^{1b}$; wherein the $C_{3-12}$ cycloalkyl, 3- to 14-membered heterocyclyl, 5- to 14-membered heteroaryl, and $C_{1-6}$ alkylene of $R^1$ are independently optionally substituted with 1, 2, 3, 4 or 5 substituents independently selected from $R^{10}$;

each $R^{1a}$, $R^{1b}$ and $R^{1c}$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{1a}$ and $R^{1b}$ are optionally substituted with 1, 2, 3, 4 or 5 substituents independently selected from $R^{10}$;

$R^{2A}$ and $R^{2B}$ are independently hydrogen, halogen, cyano, $C_{1-6}$ alkyl, $C_{1-6}$ haloalkyl, $C_{3-6}$ cycloalkyl, —O($C_{1-6}$ alkyl), or —O($C_{1-6}$ haloalkyl);

$R^3$ is hydrogen, halogen, cyano, $C_{1-6}$ alkyl, $C_{1-6}$ haloalkyl, $C_{3-6}$ cycloalkyl, —O($C_{1-6}$ alkyl), or —O($C_{1-6}$ haloalkyl);

$R^4$ and $R^5$ are independently hydrogen, halogen, cyano, nitro, $C_{1-6}$ alkyl, $C_{2-6}$ alkenyl, $C_{2-6}$ alkynyl, $C_{3-12}$ cycloalkyl, $C_{6-20}$ aryl, 3- to 14-membered heterocyclyl, 5- to 14-membered heteroaryl, —$OR^{7A}$, —$NR^{8A}R^{8B}$, —$NR^8C(O)R^7$, —$NR^8C(O)OR^{7A}$, —$NR^8C(O)NR^{8A}R^{8B}$, —$NR^8SO_2R^9$, —$NR^8SO_2NR^{8A}R^{8B}$, —$NR^8S(O)(=NR^{8C})R^9$, —$C(O)N(R^8)SO_2R^9$, —$C(O)NR^{8A}R^{8B}$, —$C(O)R^7$, —$C(O)OR^{7A}$, —$SO_2R^9$, —$NR^8S(O)(=NR^{8C})R^9$, or —$SO_2NR^{8A}R^{8B}$; wherein the $C_{1-6}$ alkyl, $C_{3-12}$ cycloalkyl, $C_{6-20}$ aryl, 3- to 14-membered heterocyclyl, and 5- to 14-membered heteroaryl of $R^4$ and $R^5$ are optionally substituted with 1, 2, 3, 4 or 5 substituents independently selected from $R^{10}$;

n is 0, 1, 2, or 3;

each $R^6$ is independently halogen, cyano, nitro, $C_{1-6}$ alkyl, $C_{1-6}$ haloalkyl, $C_{3-6}$ cycloalkyl, —O($C_{1-6}$ alkyl), —O($C_{1-6}$ haloalkyl), —$SO_2C_{1-6}$ alkyl) or —$SO_2(C_{1-6}$ haloalkyl);

each $R^7$ is independently hydrogen, $NHR^9$, $C_{1-6}$ alkyl, $C_{2-6}$ alkenyl, $C_{3-8}$ cycloalkyl, 5- to 14-membered heteroaryl, or 3- to 12-membered heterocyclyl; wherein the $C_{1-6}$ alkyl, $C_{2-6}$ alkenyl, $C_{3-8}$ cycloalkyl, 5- to 14-membered heteroaryl and 3- to 12-membered heterocyclyl of $R^7$ and $R^{7A}$ are optionally substituted with 1, 2, 3, 4 or 5 substituents independently selected from $R^{10}$;

each $R^{7A}$ is independently hydrogen, $C_{1-6}$ alkyl, $C_{2-6}$ alkenyl, $C_{3-8}$ cycloalkyl, $C_{6-10}$ aryl, 5- to 14-membered heteroaryl, or 3- to 12-membered heterocyclyl; wherein the $C_{1-6}$ alkyl, $C_{2-6}$ alkenyl, $C_{3-8}$ cycloalkyl, $C_{6-10}$ aryl, 5- to 14-membered heteroaryl and 3- to 12-membered heterocyclyl of $R^7$ and $R^{7A}$ are optionally substituted with 1, 2, 3, 4 or 5 substituents independently selected from $R^{10}$;

each $R^8$ is independently hydrogen or $C_1$-$C_6$ alkyl;

each $R^{8A}$ is independently hydrogen or $C_1$-$C_6$ alkyl;

each $R^{8B}$ is independently hydrogen, $C_{1-6}$ alkyl, $C_{2-6}$ alkenyl, $C_{3-8}$ cycloalkyl, $C_{6-10}$ aryl, or 3- to 12-membered heterocyclyl; wherein the $C_{1-6}$ alkyl, $C_{2-6}$ alkenyl, $C_{3-5}$ cycloalkyl, $C_{6-10}$ aryl, and 3- to 12-membered heterocyclyl of $R^{8B}$ are optionally substituted with 1, 2, 3, 4 or 5 substituents independently selected from $R^{10}$;

each $R^{8C}$ is independently hydrogen or $C_1$-$C_6$ alkyl;

each $R^9$ is independently $C_{1-6}$ alkyl, $C_{2-6}$ alkenyl, $C_{3-8}$ cycloalkyl, $C_{6-10}$ aryl, 5- to 14-membered heteroaryl and 3- to 12-membered heterocyclyl; wherein the $C_{1-6}$ alkyl, $C_{2-6}$ alkenyl, $C_{3-8}$ cycloalkyl, $C_{6-10}$ aryl, 5- to 14-membered heteroaryl and 3- to 12-membered heterocyclyl are optionally substituted with 1, 2, 3, 4 or 5 substituents independently selected from $R^{10}$;

each $R^{10}$ is independently oxo, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, —$C(O)R^a$, —$C(O)OR^b$, —$C(O)NR^cR^d$, —$OR^b$, —$OC(O)R^a$, —$OC(O)NR^cR^d$, —$SR^b$, —$S(O)R^e$, —$S(O)_2R^e$, —$S(O)(=NH)R^e$, —$S(O)_2NR^cR^d$, —$NR^cR^d$, —$N(R^f)C(O)R^a$, —$N(R^f)C(O)OR^b$, —$N(R^f)C(O)NR^cR^d$, —$N(R^f)S(O)_2R^e$, —$N(R^fS(O)_2NR^cR^d$, —$P(O)R^gR^h$, or —$SiR^iR^jR^k$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^{10}$ are each optimally substituted with 1, 2, 3 or 4 substituents selected from $R^{11}$;

each $R^a$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl and 3- to 12-membered heterocyclyl of $R^a$ are each optimally substituted with 1, 2, 3 or 4 substituents independently selected from $R^{11}$;

each $R^b$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^b$ are each optimally substituted with 1, 2, 3 or 4 substituents independently selected from $R^{11}$;

each $R^c$ and $R^d$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^c$ and $R^d$ are each optimally substituted with 1, 2, 3 or 4 substituents independently selected from $R^{11}$;

or $R^c$ and $R^d$ are taken together with the nitrogen atom to which they are attached to form a 4- to 12-membered heterocyclyl optimally substituted with 1, 2, 3 or 4 substituents independently selected from $R^{11}$;

each $R^e$ is independently $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^e$ are each optionally substituted with 1, 2, 3 or 4 substituents independently selected from $R^{11}$;

each $R^f$ is independently hydrogen or $C_{1-6}$ alkyl;

each $R^g$ and $R^h$ is independently $C_{1-6}$ alkyl, $C_{3-8}$ cycloalkyl, $C_{6-10}$ aryl, 5- to 10-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^g$ and $R^h$ are each optionally substituted with 1, 2, 3 or 4 substituents independently selected from $R^{11}$;

or $R^g$ and $R^h$ are taken together with the phosphorus atom to which they are attached to form a 4- to 12-membered heterocyclyl optimally substituted with 1, 2, 3 or 4 substituents independently selected from $R^{11}$;

each $R^i$, $R^j$ and $R^k$ is independently $C_{1-6}$ alkyl;

each $R^{11}$ is independently oxo, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl, 3- to 8-membered heterocyclyl, halogen, cyano, —C(O)$R^{a1}$, —C(O)O$R^{b1}$, —C(O)N$R^{c1}R^{d1}$, —O$R^{b1}$, —OC(O)$R^{a1}$, —OC(O)N$R^{c1}R^{d1}$, —S$R^{b1}$, —S(O)$R^{e1}$, —S(O)$_2R^{e1}$, —S(O)$_2$N$R^{c1}R^{d1}$, —N$R^{c1}R^{d1}$, —N($R^{f1}$)C(O)$R^{a1}$, —N($R^{f1}$)C(O)O$R^{b1}$, —N($R^{f1}$)C(O)N$R^{c1}R^{d1}$, —N($R^{f1}$)S(O)$_2R^{e1}$, —N($R^{f1}$)S(O)$_2$N$R^{c1}R^{d1}$, —P(O)$R^{g1}R^{h1}$, or —Si$R^{i1}R^{j1}R^{k1}$; wherein the $C_{1-6}$ alkyl, $C_{2-6}$ alkenyl, $C_{2-6}$ alkynyl, $C_{3-6}$ cycloalkyl, $C_{6-14}$ aryl, 5- to 14-membered heteroaryl and 3- to 14-membered heterocyclyl of $R^{11}$ are each optionally substituted with 1, 2, 3 or 4 substituents independently selected from $R^{12}$;

each $R^{a1}$ is independently hydrogen, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl and 3- to 8-membered heterocyclyl of $R^{a1}$ are each optionally substituted with 1, 2, 3 or 4 substituents independently selected from $R^{12}$;

each $R^{b1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{b1}$ are each optionally substituted with 1, 2, 3 or 4 substituents independently selected from $R^{12}$;

each $R^{c1}$ and $R^{d1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{c1}$ and $R^{d1}$ are each optionally substituted with 1, 2, 3 or 4 substituents independently selected from $R^{12}$;

or $R^{c1}$ and $R^{d1}$ are taken together with the nitrogen atom to which they are attached to form a 4- to 8-membered heterocyclyl optionally substituted with 1, 2, 3 or 4 substituents independently selected from $R^{12}$;

each $R^{e1}$ is independently $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{e1}$ are each optionally substituted with 1, 2, 3 or 4 substituents independently selected from $R^{12}$;

each $R^{f1}$ is independently hydrogen or $C_{1-6}$ alkyl;

each $R^{g1}$ and $R^{h1}$ is independently $C_{1-6}$ alkyl, $C_{3-6}$ cycloalkyl, $C_{6-10}$ aryl, 5- to 10-membered heteroaryl, 3- to 8-membered heterocyclyl, or —O—$C_{1-6}$ alkyl; herein the $C_{1-6}$ alkyl, $C_{3-6}$ cycloalkyl, $C_{6-10}$ aryl, 5- to 10-membered heteroaryl and 3- to 8-membered heterocyclyl of $R^{g1}$ and $R^{h1}$ are each optionally substituted with 1, 2, 3 or 4 substituents independently selected from $R^{12}$;

or $R^{g1}$ and $R^{h1}$ are taken together with the phosphorus atom to which they are attached to form a 4- to 8-membered heterocyclyl optionally substituted with 1, 2, 3 or 4 substituents independently selected from $R^{12}$;

each $R^{i1}$, $R^{j1}$ and $R^{k1}$ is independently $C_{1-6}$ alkyl;

each $R^{12}$ is independently oxo, $C_{1-6}$ alkyl, $C_{3-6}$ cycloalkyl, $C_6$ aryl, 5- to 6-membered heteroaryl, 3- to 6-membered heterocyclyl, halogen, cyano, —C(O)$R^{a2}$, —C(O)O$R^{b2}$, —C(O)N$R^{c2}R^{d2}$, —O$R^{b2}$, —OC(O)$R^{a2}$, —OC(O)N$R^{c2}R^{d2}$, —S(O)$_2R^{e2}$, —S(O)$_2$N$R^{c2}R^{d2}$, —N$R^{c2}R^{d2}$, —N($R''$)C(O)$R^{a2}$, —N($R''$)C(O)O$R^{b2}$, —N($R^{f2}$)C(O)N$R^{c2}R^{d2}$, —N($R^{f2}$)S(O)$_2R^{e2}$, —N($R^{f2}$)S(O)$_2$N$R^{c2}R^{d2}$, or —P(O)$R^{g2}R^{h2}$; wherein the $C_{1-6}$ alkyl, $C_{3-6}$ cycloalkyl, $C_6$ aryl, 5- to 6-membered heteroaryl and 3- to 6-membered heterocyclyl of $R^{12}$ are each optionally substituted with 1, 2, 3 or 4 substituents independently selected from $R^{13}$;

each $R^{a2}$ is independently hydrogen, $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{a2}$ are each optionally substituted with 1, 2, 3 or 4 substituents independently selected from $R^{13}$;

each $R^{b2}$ is independently hydrogen, $C_{1-6}$ alkyl, $C_{3-6}$ cycloalkyl or 3- to 6-membered heterocyclyl; wherein the $C_{1-6}$ alkyl, $C_{3-6}$ cycloalkyl and 3- to 6-membered heterocyclyl of $R^{b2}$ are each optionally substituted with 1, 2, 3 or 4 substituents independently selected from $R^{13}$;

each $R^{c2}$ and $R^{d2}$ is independently hydrogen, $C_{1-6}$ alkyl, $C_{3-6}$ cycloalkyl or 3- to 8-membered heterocyclyl; wherein the $C_{1-6}$ alkyl, $C_{3-6}$ cycloalkyl and 3- to 8-membered heterocyclyl of $R^{c2}$ and $R^{d2}$ are each optionally substituted with 1, 2, 3 or 4 substituents independently selected from $R^{13}$;

or $R^{c2}$ and $R^{d2}$ are taken together with the nitrogen atom to which they are attached to form a 4- to 6-membered heterocyclyl optionally substituted with 1, 2, 3 or 4 substituents independently selected from $R^{13}$;

each $R^{e2}$ is independently $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of are each optimally substituted with 1, 2, 3 or 4 substituents independently selected from $R^{13}$;

each $R^{f2}$ is independently hydrogen or $C_{1-6}$ alkyl;

each $R^{g2}$ and $R^{h2}$ is independently $C_{1-6}$ alkyl, $C_{3-6}$ cycloalkyl, 3- to 8-membered heterocyclyl, or —O—$C_{1-6}$ alkyl; herein the $C_{1-6}$ alkyl, $C_{3-6}$ cycloalkyl, and 3- to 8-membered heterocyclyl of $R^{g2}$ and $R^{h2}$ are each optionally substituted with 1, 2, 3 or 4 substituents independently selected from $R^{13}$;

or $R^{g2}$ and $R^{h2}$ are taken together with the phosphorus atom to which they are attached to form a 4- to 6-membered heterocyclyl optimally substituted with 1, 2, 3 or 4 substituents independently selected from $R^{13}$; and each $R^{13}$ is independently oxo, halogen, hydroxyl, —O($C_{1-6}$ alkyl), cyano, $C_{1-6}$ alkyl or $C_{1-6}$ haloalkyl.

In some embodiments of the compound of the Formula I, or stereoisomers, tautomers, or pharmaceutically acceptable salts thereof, the compound is other than Compound Nos. 1x-12x of Table 1X. In some embodiments of the Formula I, or stereoisomers, tautomers, or pharmaceutically acceptable salts thereof, wherein $R^{8B}$ is other than hydrogen or optimally substituted phenyl. In some embodiments of the Formula I, or stereoisomers, tautomers, or pharmaceutically acceptable salts thereof, wherein $R^4$ is other than —NHC(O)NH—$R^{8B}$ wherein $R^{8B}$ is optimally substituted phenyl or optionally substituted alkyl.

It is intended and understood that each and every variation of $R^0$, $R^{2A}$, $R^{2B}$, $R^3$, $R^6$ and n described for the Formula (I) can be combined, the same as if each and every combination is specifically and individually described. For example, in some embodiments, $R^0$ is H; $R^{2A}$ and $R^{2B}$ are independently

TABLE 1X

| No. | Name |
|---|---|
| 1x | Benzamide, 3-[[3-[2-[[2-(diethylamino)ethyl]amino]-4-pyrimidinyl]-2-pyridinyl]oxy]-4-methyl-N-[2-methyl-3-(1-methylethyl)phenyl]- |
| 2x | 2-Pyrrolidinone, 1-[3-[[4-[2-(4-amino-2-methylphenoxy)-3-pyridinyl]-2-pyrimidinyl]amino]propyl]- |
| 3x | 4-Morpholinepropanamine, N-[4-[2-(4-amino-2-methylphenoxy)-3-pyridinyl]-2-pyrimidinyl]- |
| 4x | Urea, N-(3-fluoro-4-methylphenyl)-N'-[4-[[3-[2-[[3-(4-morpholinyl)propyl]amino]-4-pyrimidinyl]-2-pyridinyl]oxy]phenyl]- |
| 5x | Urea, N-(2,3-dihydro-1H-inden-5-yl)-N'-[4-[[3-[2-[[3-(4-morpholinyl)propyl]amino]-4-pyrimidinyl]-2-pyridinyl]oxy]phenyl]- |
| 6x | Urea, N-(4-chlorophenyl)-N'-[4-[[3-[2-[[3-(4-morpholinyl)propyl]amino]-4-pyrimidinyl]-2-pyridinyl]oxy]phenyl]- |
| 7x | Urea, N-[3-methyl-4-[[3-[2-[[3-(2-oxo-1-pyrrolidinyl)propyl]amino]-4-pyrimidinyl]-2-pyridinyl]oxy]phenyl]-N'-[3-(trifluoromethyl)phenyl]- |
| 8x | Urea, N-(5-chloro-2-methoxyphenyl)-N'-[3-methyl-4-[[3-[2-[[3-(2-oxo-1-pyrrolidinyl)propyl]amino]-4-pyrimidinyl]-2-pyridinyl]oxy]phenyl]- |
| 9x | Urea, N-(5-chloro-2-methoxyphenyl)-N'-[3-methyl-4-[[3-[2-[[3-(4-morpholinyl)propyl]amino]-4-pyrimidinyl]-2-pyridinyl]oxy]phenyl]- |
| 10x | Benzamide, 3-[[3-[2-[[2-(diethylamino)ethyl]amino]-4-pyrimidinyl]-2-pyridinyl]oxy]-4-methyl-N-[2-(4-morpholinyl)-5-(trifluoromethyl)phenyl]- |
| 11x | Benzamide, N-(5-cyclohexyl-2-methoxyphenyl)-3-[[3-[2-[[2-(diethylamino)ethyl]amino]-4-pyrimidinyl]-2-pyridinyl]oxy]-4-methyl- |
| 12x | Benzamide, 3-[[3-[2-[[2-(diethylamino)ethyl]amino]-4-pyrimidinyl]-2-pyridinyl]oxy]-4-methyl-N-[3-(1-methylethyl)phenyl]- |

In some embodiments, the compound is of the Formula (I) or a pharmaceutically acceptable salt thereof, wherein $R^0$ is hydrogen or fluoro. In some embodiments, $R^0$ is H.

In some embodiments, the compound is of the Formula (I), or a pharmaceutically acceptable salt thereof, wherein $R^{2A}$ and $R^{2B}$ are independently hydrogen, halogen, cyano, $C_{1-6}$ alkyl, $C_{1-6}$ haloalkyl, $C_{3-6}$ cycloalkyl, —O($C_{1-6}$ alkyl), or —O($C_{1-6}$ haloalkyl). In some embodiments, $R^{2A}$ and $R^{2B}$ are independently hydrogen, halogen, cyano, $C_{1-6}$ alkyl, or —O($C_{1-6}$alkyl). In some embodiments, $R^{2A}$ and $R^{2B}$ are independently H, F, Cl or $C_1$-$C_6$ alkyl (e.g., methyl). In some embodiments, one of $R^{2A}$ and $R^{2B}$ is hydrogen and the other one of $R^{2A}$ and $R^{2B}$ is hydrogen, fluoro or methyl. In some embodiments, $R^{2A}$ and $R^{2B}$ are each hydrogen. In some embodiments, $R^{2A}$ and $R^{2B}$ are each fluoro. In some embodiments, $R^{2A}$ and $R^{2B}$ are each methyl. In some embodiments, $R^{2A}$ is H, F or methyl, and $R^{2B}$ is H, F, Cl or —CH$_3$.

In some embodiments, the compound is of the Formula (I) or a pharmaceutically acceptable salt thereof, wherein $R^3$ is hydrogen, halogen, cyano, $C_{1-6}$ alkyl, $C_{1-6}$ haloalkyl, $C_{3-6}$ cycloalkyl, —O($C_{1-6}$ alkyl), or —O($C_{1-6}$ haloalkyl). In some embodiments, $R^3$ is hydrogen, halogen, cyano, $C_{1-6}$ alkyl, $C_{1-6}$ haloalkyl, or —O($C_{1-6}$ alkyl). In some embodiments, $R^3$ is H, F, Cl, —CN, $C_{1-6}$ alkyl (e.g., methyl), or $C_{1-6}$ haloalkyl (e.g., trifluoromethyl). In one variation, $R^3$ is H, F, Cl, —CN, —CH$_3$, or —CF$_3$.

In some embodiments, the compound is of the Formula (I) or a pharmaceutically acceptable salt thereof, wherein 0, 1, 2, or 3; and each $R^6$ is independently halogen, cyano, nitro, $C_{1-6}$ alkyl, $C_{1-6}$ haloalkyl, $C_{3-6}$ cycloalkyl, —O($C_{1-6}$ alkyl), —O($C_{1-6}$ haloalkyl), —SO$_2$($C_{1-6}$ alkyl) or —SO$_2$($C_{1-6}$ haloalkyl). In some embodiments, n is 0. (i.e., $R^6$ is absent). In some embodiments, n is 1 and $R^6$ is F, Cl, —CN, —NO$_2$, —O—($C_{1-6}$ alkyl) or $C_{1-6}$ alkyl. In some embodiments, n is 1 and $R^6$ is F, Cl, —CN, —O—($C_{1-6}$ alkyl) (e.g., —OCH$_3$), or $C_{1-6}$ alkyl (e.g., methyl and ethyl).

H, F, Cl or $C_1$-$C_6$ alkyl (e.g., methyl); $R^3$ is H, F, Cl, —CN, $C_{1-6}$ alkyl (e.g., methyl), or $C_{1-6}$ haloalkyl (e.g., trifluoromethyl); n is 0 and $R^6$ is absent. In one variation, $R^0$ is H; $R^{2A}$ and $R^{2B}$ are independently H, F, Cl or methyl; $R^3$ is H, F, Cl, —CN, methyl, or trifluoromethyl; and n is 0.

In some embodiments, the compound is of the Formula (I) or a pharmaceutically acceptable salt thereof, wherein $R^5$ is hydrogen, halogen, cyano, nitro, $C_{1-6}$ alkyl, $C_{2-6}$ alkenyl, $C_{2-6}$ alkynyl, $C_{3-12}$ cycloalkyl, $C_{6-20}$ aryl, 3- to 14-membered heterocyclyl, 5- to 14-membered heteroaryl, —OR$^{7A}$, —NR$^{8A}$R$^{8B}$, —NR$^8$C(O)R$^7$, —NR$^8$C(O)OR$^{7A}$, —NR$^8$C(O)NR$^{8A}$R$^{8B}$, —NR$^8$SO$_2$R$^9$, —NR$^8$SO$_2$NR$^{8A}$R$^{8B}$, —NR$^8$S(O)(=NR$^{8C}$)R$^9$, —C(O)N(R$^8$)SO$_2$R$^9$, —C(O)NR$^{8A}$R$^{8B}$, —C(O)R$^7$, —C(O)OR$^{7A}$, —SO$_2$R$^9$, —NR$^8$S(O)(=NR$^{8C}$)R$^9$, or —SO$_2$NR$^{8A}$R$^{8B}$; wherein the $C_{1-6}$ alkyl, $C_{3-12}$ cycloalkyl, $C_{6-20}$ aryl, 3- to 14-membered heterocyclyl, and 5- to 14-membered heteroaryl of $R^5$ are optionally substituted with 1, 2, 3, 4 or 5 substituents independently selected from $R^{10}$. In some embodiments, $R^5$ is H, F, Cl, —CN, or $C_{1-6}$ alkyl optionally substituted with 1, 2, 3, 4 or 5 substituents independently selected from $R^{10}$. In some embodiments, $R^5$ is H, F, Cl, —CN, $C_{1-6}$ alkyl optionally substituted with 1, 2, 3, 4 or 5 substituents independently selected from $R^{10}$, —NR$^8$SO$_2$R$^9$, —NR$^{8A}$R$^{8B}$, or —C(O)N(R$^8$)SO$_2$R$^9$. In some embodiments, $R^5$ is H, F, Cl, —CN, $C_{1-6}$ alkyl (e.g., —CH$_3$) or $C_{1-6}$ haloalkyl (e.g., —CF$_3$). In some embodiments, $R^5$ is H, F, Cl, —CN, —CH$_3$, or —CF$_3$. In one embodiment, $R^5$ is NHC(O)NHR$^9$, where R$^9$ is as described herein.

In some embodiments, $R^5$ is $C_{1-6}$ alkyl substituted with 1, 2, 3, 4 or 5 substituents independently selected from $R^{10}$, —NR$^8$SO$_2$R$^9$, —NR$^{8A}$R$^{8B}$, or —C(O)N(R$^8$)SO$_2$R$^9$. In some of these embodiments, $R^4$ is H, F, Cl, —CN, $C_{1-6}$ alkyl (e.g., —CH$_3$) or $C_{1-6}$ haloalkyl (e.g., —CF$_3$). In some of these embodiments, $R^4$ is H, F, Cl, —CN, —CH$_3$, or —CF$_3$. In one variation, $R^4$ is H, and $R^5$ is —($C_{1-6}$ alkylene)-N(R$^f$)

C(O)R$^a$; C$_{1-6}$ alkyl substituted with 1, 2, 3, 4 or 5 substituents independently selected from R$^{10}$, —NH—SO$_2$R$^9$, —NH—R$^{8B}$, or —C(O)NH—SO$_2$R$^9$. In a specific variation, R$^5$ is —CH$_2$NHC(O)-(cyclopropyl), —NHCH$_2$CH(OH)CF$_3$ or —C(O)NHSO$_2$-(2-chlorophenyl). In another variation, R$^5$ is —NHSO$_2$R$^9$, and R$^9$ is C$_{1-6}$ alkyl optionally substituted with 1, 2, 3, 4 or 5 substituents independently selected from R$^{10}$, or C$_{6-10}$ aryl optionally substituted with 1, 2, 3, 4 or 5 substituents independently selected from R$^{10}$. In another specific variation, R$^5$ is —NHSO$_2$-(2-chlorophenyl), —NHSO$_2$—CH$_2$CH$_2$CH$_3$ or —NHSO$_2$—CH$_2$-(phenyl).

In some embodiments, the compound is of the Formula (I) or a pharmaceutically acceptable salt thereof, wherein R$^4$ is hydrogen, halogen, cyano, nitro, C$_{1-6}$ alkyl, C$_{2-6}$ alkenyl, C$_{2-6}$ alkynyl, C$_{3-12}$ cycloalkyl, C$_{6-20}$ aryl, 3- to 14-membered heterocyclyl, 5- to 14-membered heteroaryl, —OR$^{7A}$, —NR$^{8A}$R$^{8B}$, —NR$^8$C(O)R$^7$, —NR$^8$C(O)OR$^{7A}$, —NR$^8$C(O)NR$^{8A}$R$^{8B}$, —NR$^8$SO$_2$R$^9$, —NR$^8$SO$_2$NR$^{8A}$R$^{8B}$, —NR$^8$S(O)(=NR$^{8C}$)R$^9$, —C(O)N(R$^8$)SO$_2$R$^9$, —C(O)NR$^{8A}$R$^{8B}$, —C(O)R$^7$, —C(O)OR$^{7A}$, —SO$_2$R$^9$, —NR$^8$S(O)(=NR$^{8C}$)R$^9$, or —SO$_2$NR$^{8A}$R$^{8B}$; wherein the C$_{1-6}$ alkyl, C$_{3-12}$ cycloalkyl, C$_{6-20}$ aryl, 3- to 14-membered heterocyclyl, and 5- to 14-membered heteroaryl of R$^4$ and R$^5$ are optionally substituted with 1, 2, 3, 4 or 5 substituents independently selected from R$^{10}$. In some embodiments, R$^4$ is hydrogen, halogen, cyano, nitro, C$_{1-6}$ alkyl, C$_{2-6}$ alkenyl, C$_{2-6}$ alkynyl, C$_{3-12}$ cycloalkyl, C$_{6-20}$ aryl, 3- to 14-membered heterocyclyl, 5- to 14-membered heteroaryl, —OR$^{7A}$, —NR$^{8A}$R$^{8B}$, —NR$^8$C(O)R$^7$, —NR$^8$C(O)OR$^{7A}$, —NR$^8$SO$_2$R$^9$, —NR$^8$SO$_2$NR$^{8A}$R$^{8B}$, —NR$^8$S(O)(=NR$^{8C}$)R$^9$, —C(O)N(R$^8$)SO$_2$R$^9$, —C(O)NR$^{8A}$R$^{8B}$, —C(O)R$^7$, —C(O)OR$^{7A}$, —SO$_2$R$^9$, —NR$^8$S(O)(=NR$^{8C}$)R$^9$, or —SO$_2$NR$^{8A}$R$^{8B}$; wherein the C$_{1-6}$ alkyl, C$_{3-12}$ cycloalkyl, C$_{6-20}$ aryl, 3- to 14-membered heterocyclyl, and 5- to 14-membered heteroaryl of R$^4$ and R$^5$ are optionally substituted with 1, 2, 3, 4 or 5 substituents independently selected from R$^{10}$; wherein R$^8$ and R$^{8A}$ are independently hydrogen or C$_1$-C$_6$ alkyl, and R$^{8B}$ is independently C$_{1-6}$ alkyl, C$_{1-6}$ alkenyl, C$_{3-8}$ cycloalkyl, or 3- to 12-membered heterocyclyl; wherein the C$_{1-6}$ alkyl, C$_{2-6}$ alkenyl, C$_{3-8}$ cycloalkyl, and 3- to 12-membered heterocyclyl of R$^{8B}$ are optionally substituted with 1, 2, 3, 4 or 5 substituents independently selected from R$^{10}$. In some embodiments, R$^4$ is —NR$^8$C(O)R$^7$ or —NR$^8$SO$_2$R$^9$. In some of these embodiments, R$^5$ is H, F, Cl, —CN, —CH$_3$, or —CF$_3$.

In some embodiments, R$^4$ is —NHC(O)R$^7$, wherein R$^7$ is C$_{1-6}$ alkyl optionally substituted with 1, 2, 3, 4 or 5 substituents independently selected from R$^{10}$, or C$_{3-8}$ cycloalkyl optionally substituted with 1, 2, 3, 4 or 5 substituents independently selected from R$^{10}$. In some particular embodiments, R$^7$ is cyclopropyl, spiro[2.2]pentyl, cyclohexylmethyl or 4-chlorobenzyl. In some embodiments, R$^7$ is cyclopentyl, cyclohexyl, phenyl, 2-chlorophenyl, 3-cyanophenyl, 4-cyanophenyl, 2-methoxyphenyl, 3-methoxyphenyl, 4-methoxyphenyl, 3-(difluoromethoxy)phenyl, 3-(trifluoromethoxy)phenyl, 4-(trifluoromethoxy)phenyl, 3,5-difluorophenyl, 3-pyridyl, 1-methyl-1H-imidazol-4-yl, 1-methyl-1H-pyrazol-4-yl, benzyl, 2-fluorobenzyl, 3-fluorobenzyl, 4-fluorobenzyl, 2-cyanobenzyl, 4-cyanobenzyl, 3-chlorobenzyl, 4-chlorobenzyl, (1-methyl-1H-pyrazol-3-yl)methyl, (5-methylisoxazol-3-yl)methyl, (pyridin-2-yl)methyl, (pyridin-3-yl)methyl, (pyridin-4-yl)methyl, (6-(trifluoromethyl)pyridin-3-yl)methyl, (1-fluorocyclopropyl)methyl, cyclobutylmethyl, (2,2-difluorocyclobutyl)methyl, (3,3-difluorocyclobutyl)methyl, cyclopentylmethyl, cyclohexylmethyl, (spiro[3.3]heptan-2-yl)methyl, 2-(cyclohexyl)ethyl, 2-(2,2-difluorocyclopropyl)ethyl, n-propyl, 3-cyano-2,2-dimethylpropyl, 3,3,3-trifluoropropyl, n-butyl, 2,2-difluorobutyl, 3,3-difluorobutyl, 3,3-dimethylbutyl, 3-cyano-3-methylbutyl, or 4,4-dimethylpentyl.

In some embodiments, R$^4$ is —NH—SO$_2$R$^9$, wherein R$^9$ is C$_{1-6}$ alkyl, C$_{3-8}$ cycloalkyl, C$_{6-10}$ aryl, or 5- to 14-membered heteroaryl, wherein the C$_{1-6}$ alkyl, Cis cycloalkyl, C$_{6-10}$ aryl and 5- to 14-membered heteroaryl of R$^9$ are independently optionally substituted with 1, 2, 3, 4 or 5 substituents independently selected from R$^{10}$. In some of these embodiments, R$^9$ is C$_{1-6}$ alkyl optionally substituted with 1, 2, 3 or 4 substituents independently selected from R$^{10}$. In some of these embodiments, R$^9$ is C$_{1-6}$ haloalkyl (e.g., C$_{1-6}$ fluoroalkyl). In some of these embodiments, R$^9$ is C$_{3-8}$ cycloalkyl optionally substituted with 1, 2, 3, 4 or 5 substituents independently selected from R$^{10}$. In some of these embodiments, R$^9$ is C$_{6-10}$ aryl optionally substituted with 1, 2, 3, 4 or 5 substituents independently selected from R$^{10}$. In some of these embodiments, R$^9$ is phenyl substituted with 1, 2, 3, 4 or 5 substituents independently selected from R$^{10}$. In some of these embodiments, R$^9$ is 5- to 14-membered heteroaryl optionally substituted with 1, 2, 3, 4 or 5 substituents independently selected from R$^{10}$.

In some embodiments, R$^9$ is C$_{1-6}$ haloalkyl (e.g., C$_{1-6}$ fluoroalkyl). In some embodiments, R$^9$ is benzyl optionally substituted with 1, 2, 3, 4 or 5 substituents independently selected from R$^{10}$. In some embodiments, R$^9$ is benzyl where the phenyl ring is optionally substituted with 1, 2 or 3 substituents independently selected from R$^{10}$. In some embodiments, R$^9$ is benzyl optionally substituted with 1, 2, 3, 4 or 5 substituents independently selected from the group consisting of fluoro, chloro, bromo, —CH$_3$, —CH$_2$CH$_3$, —CH$_2$OH, and —CN.

In some particular embodiments, R$^9$ is cyclopentyl, cyclohexyl, phenyl, 2-chlorophenyl, 3-cyanophenyl, 4-cyanophenyl, 2-methoxyphenyl, 3-methoxyphenyl, 4-methoxyphenyl, 3-(difluoromethoxy)phenyl, 3-(trifluoromethoxy)phenyl, 4-(trifluoromethoxy)phenyl, 3,5-difluorophenyl, 3-pyridyl, 1-methyl-1H-imidazol-4-yl, 1-methyl-1H-pyrazol-4-yl, benzyl, 2-fluorobenzyl, 3-fluorobenzyl, 4-fluorobenzyl, 2-cyanobenzyl, 4-cyanobenzyl, 3-chlorobenzyl, 4-chlorobenzyl, (1-methyl-1H-pyrazol-3-yl)methyl, (5-methylisoxazol-3-yl)methyl, (pyridin-2-yl)methyl, (pyridin-3-yl)methyl, (pyridin-4-yl)methyl, (6-(trifluoromethyl)pyridin-3-yl)methyl, (1-fluorocyclopropyl)methyl, cyclobutylmethyl, (2,2-difluorocyclobutyl)methyl, (3,3-difluorocyclobutyl)methyl, cyclopentylmethyl, cyclohexylmethyl, (spiro[3.3]heptan-2-yl)methyl, 2-(cyclohexyl)ethyl, 2-(2,2-difluorocyclopropyl)ethyl, n-propyl, 3-cyano-2,2-dimethylpropyl, 3,3,3-trifluoropropyl, n-butyl, 2,2-difluorobutyl, 3,3-difluorobutyl, 3,3-dimethylbutyl, 3-cyano-3-methylbutyl, or 4,4-dimethylpentyl. In some particular embodiments, R$^9$ is cyclopropyl, spiro[2.2]pentyl, cyclohexylmethyl or 4-chlorobenzyl. In some embodiments, R$^9$ is selected from the group consisting of benzyl, cyclopropyl, cyclopropylmethyl, cyclobutyl, cyclobutylmethyl, cyclopentanyl, cyclopentanylmethyl, cyclohexyl, cyclohexylmethyl, pyrrolidin-1-yl, piperidin-1-yl, pyridyl, pyridylmethyl, tetrahydrofuranyl, tetrahydrofuranylmethyl, and tetrahydropyranyl, tetrahydropyranylmethyl, thiazolyl, and thiazolylmethyl; each of which is optionally and independently substituted with one or more substituents selected from fluoro, chloro, bromo, —CH$_3$, —CH$_2$CH$_3$, —CH$_2$OH, and —CN.

In some embodiments, R$^4$ is —NHC(O)R$^7$, wherein R$^7$ is cyclopropyl, spiro[2.2]pentyl, cyclohexylmethyl or 4-chlorobenzyl. In one embodiment, R$^4$ is NHC(O)NHR$^9$, where R$^9$ is as described herein.

In some embodiments, $R^4$ is —NH—SO$_2$R$^9$, wherein $R^9$ is cyclopentyl, cyclohexyl, phenyl, 2-chlorophenyl, 3-cyanophenyl, 4-cyanophenyl, 2-methoxyphenyl, 3-methoxyphenyl, 4-methoxyphenyl, 3-(difluoromethoxy)phenyl, 3-(trifluoromethoxy)phenyl, 4-(trifluoromethoxy)phenyl, 3,5-difluorophenyl, 3-pyridyl, 1-methyl-1H-imidazol-4-yl, 1-methyl-1H-pyrazol-4-yl, benzyl, 2-fluorobenzyl, 3-fluorobenzyl, 4-fluorobenzyl, 2-cyanobenzyl, 4-cyanobenzyl, 3-chlorobenzyl, 4-chlorobenzyl, (1-methyl-1H-pyrazol-3-yl)methyl, (5-methylisoxazol-3-yl)methyl, (pyridin-2-yl)methyl, (pyridin-3-yl)methyl, (pyridin-4-yl)methyl, (6-(trifluoromethyl)pyridin-3-yl)methyl, (1-fluorocyclopropyl)methyl, cyclobutylmethyl, (2,2-difluorocyclobutyl)methyl, (3,3-difluorocyclobutyl)methyl, cyclopentylmethyl, cyclohexylmethyl, (spiro[3.3]heptan-2-yl)methyl, 2-(cyclohexyl)ethyl, 2-(2,2-difluorocyclopropyl)ethyl, n-propyl, 3-cyano-2,2-dimethylpropyl, 3,3,3-trifluoropropyl, n-butyl, 2,2-difluorobutyl, 3,3-difluorobutyl, 3,3-dimethylbutyl, 3-cyano-3-methylbutyl, or 4,4-dimethylpentyl.

In some embodiments, $R^5$ is cyclopropanecarboxamidomethyl, (3,3,3-trifluoro-2-hydoxy-1-propyl)amino, or 2-chlorobenzenesulfonamidocarbonyl. In some embodiments, $R^5$ is —NH—SO$_2$R$^9$, wherein $R^9$ is 2-chloropheyl, benzyl or n-propyl. In some of these embodiments, $R^4$ is H.

It is intended and understood that each and every variation of $R^0$, $R^{2A}$, $R^{2B}$, $R^3$, $R^6$ and n, or a combination thereof, described for the Formula (I) can be combined with each and every variation of $R^4$ and $R^5$, or combinations thereof, described for the Formula (I), the same as if each and every combination is specifically and individually described. For example, in some embodiments, $R^0$ is H; $R^{2A}$ and $R^{2B}$ are independently H, F, Cl or C$_1$-C$_6$ alkyl (e.g., methyl); $R^3$ is H, F, Cl, —CN, C$_{1-6}$ alkyl (e.g., methyl), or C$_{1-6}$ haloalkyl (e.g., trifluoromethyl); n is 0; $R^4$ is —NR$^8$C(O)R$^7$ or —NR$^8$SO$_2$R$^9$; and $R^5$ is H, F, Cl, —CN, C$_{1-6}$ alkyl (e.g., —CH$_3$) or C$_{1-6}$ haloalkyl (e.g., —CF$_3$). In one variation, $R^0$ is H; $R^{2A}$ and $R^{2B}$ are independently H, F, Cl or methyl; $R^3$ is H, F, Cl, —CN, methyl, or trifluoromethyl; n is 0; $R^4$ is —NR$^8$C(O)R$^7$ or —NR$^8$SO$_2$R$^9$; $R^5$ is H, F, Cl, —CN, —CH$_3$, or —CF$_3$; $R^7$ is C$_{1-6}$ alkyl optionally substituted with 1, 2, 3, 4 or 5 substituents independently selected from $R^{10}$, or C$_{3-8}$ cycloalkyl optionally substituted with 1, 2, 3, 4 or 5 substituents independently selected from $R^{10}$; and $R^9$ is C$_{1-6}$ alkyl, C$_{3-8}$ cycloalkyl, C$_{6-10}$ aryl, or 5- to 14-membered heteroaryl, herein the C$_{1-6}$ alkyl, C$_{3-8}$ cycloalkyl, C$_{6-10}$ aryl and 5- to 14-membered heteroaryl of $R^9$ are independently optionally substituted with 1, 2, 3, 4 or 5 substituents independently selected from $R^{10}$. In some embodiments, $R^0$ is H; $R^{2A}$ and $R^{2B}$ are independently H, F, Cl or C$_1$-C$_6$ alkyl (e.g., methyl); $R^3$ is H, F, Cl, —CN, C$_{1-6}$ alkyl (e.g., methyl), or C$_{1-6}$ haloalkyl (e.g., trifluoromethyl); n is 0; $R^4$ is H, F, Cl, —CN, C$_{1-6}$ alkyl (e.g., —CH$_3$) or C$_{1-6}$ haloalkyl (e.g., —CF$_3$); and $R^5$ is C$_{1-6}$ alkyl substituted with 1, 2, 3, 4 or 5 substituents independently selected from $R^{10}$, —NR$^8$SO$_2$R$^9$, —NR$^{8A}$R$^{8B}$, or —C(O)N(R$^8$)SO$_2$R$^9$. In one variation, $R^0$ is H; $R^{2A}$ and $R^{2B}$ are independently H, F, Cl or methyl; $R^3$ is H, F, Cl, —CN, methyl, or trifluoromethyl; n is 0; $R^4$ is H, and $R^5$ is —(C$_{1-6}$ alkylene)-N(R$^f$)C(O)R$^a$; C$_{1-6}$ alkyl substituted with 1, 2, 3, 4 or 5 substituents independently selected from $R^{10}$, —NH—SO$_2$R$^9$, —NH—R$^{8B}$, or —C(O)NH—SO$_2$R$^9$.

In some embodiments, the compound is of the Formula (I) or a pharmaceutically acceptable salt thereof, wherein $R^1$ is C$_{3-12}$ cycloalkyl, 3- to 14-membered heterocyclyl, 5- to 14-membered heteroaryl, —(C$_{1-6}$ alkylene)-(C$_3$-C$_{12}$ cycloalkyl), or —(C$_{1-6}$ alkylene)-(3- to 14-membered heterocyclyl), —(C$_{1-6}$ alkylene)-OR$^{1c}$, or —(C$_{1-6}$ alkylene)-NR$^{1a}$R$^{1b}$; wherein the C$_{3-12}$ cycloalkyl, 3- to 14-membered heterocyclyl, 5- to 14-membered heteroaryl, and C$_{1-6}$ alkylene of R$^1$ are independently optimally substituted with 1, 2, 3, 4 or 5 substituents independently selected from $R^{10}$. In some embodiments, $R^1$ is C$_{3-12}$ cycloalkyl, 3- to 14-membered heterocyclyl, 5- to 14-membered heteroaryl, —(C$_{1-6}$ alkylene)-(C$_3$-C$_{12}$ cycloalkyl), or —(C$_{1-6}$ alkylene)-(3- to 14-membered heterocyclyl), or —(C$_{1-6}$ alkylene)-NR$^{1a}$R$^{1b}$; wherein the C$_{3-12}$ cycloalkyl, 3- to 14-membered heterocyclyl, 5- to 14-membered heteroaryl, and C$_{1-6}$ alkylene of R$^1$ are independently optimally substituted with 1, 2, 3, 4 or 5 substituents independently selected from $R^{10}$. In some embodiments, $R^1$ is C$_{3-12}$ cycloalkyl; 3- to 14-membered heterocyclyl; —(C$_{1-6}$ alkylene)-(3- to 14-membered heterocyclyl), or —(C$_{1-6}$ alkylene)-NR$^{1a}$R$^{1b}$; wherein the C$_{3-12}$ cycloalkyl, 3- to 14-membered heterocyclyl, and C$_{1-6}$ alkylene of R$^1$ are independently optimally substituted with 1, 2, 3, 4 or 5 substituents independently selected from $R^{10}$. In some embodiments, $R^1$ is C$_{3-12}$ cycloalkyl optionally substituted with 1, 2, 3, 4 or 5 substituents independently selected from $R^{10}$. In some embodiments, $R^1$ is 3- to 14-membered heterocyclyl optionally substituted with 1, 2, 3, 4 or 5 substituents independently selected from $R^{10}$. In some embodiments, $R^1$ is cyclohexyl or piperidinyl, each is independently optionally substituted with 1, 2, 3, 4 or 5 substituents independently selected from the group consisting of F, —CH$_3$, —OH, oxo, and —NH$_2$. In some of these embodiments, $R^1$ is selected from the group consisting of piperidin-3-yl, 5-fluoropiperidin-3-yl, 5-methylpiperidin-3-yl and 5-fluoro-5-methylpiperidin-3-yl. In some of these embodiments, $R^1$ is —(C$_{1-6}$ alkylene)-(3- to 14-membered heterocyclyl) optionally substituted with 1, 2, 3, 4 or 5 substituents independently selected from $R^{10}$. In some embodiments, $R^1$ is —(C$_{1-6}$ alkylene)-NR$^{1a}$R$^{1b}$. In some of these embodiments, R$^{1a}$ and R$^{1b}$ are independently hydrogen or C$_{1-6}$ alkyl.

It is intended and understood that each and every variation of $R^0$, $R^{2A}$, $R^{2B}$, $R^3$, $R^4$, $R^5$, $R^6$ and n, or a combination thereof, described for the Formula (I) can be combined with each and every variation of R$^1$ described for the Formula (I), the same as if each and every combination is specifically and individually described. For example, in some embodiments, $R^0$ is H; R$^1$ is C$_{3-12}$ cycloalkyl; 3- to 14-membered heterocyclyl; —(C$_{1-6}$ alkylene)-(3- to 14-membered heterocyclyl), or —(C$_{1-6}$ alkylene)-NR$^{1a}$R$^{1b}$; wherein the C$_{3-12}$ cycloalkyl, 3- to 14-membered heterocyclyl, and C$_{1-6}$ alkylene of R$^1$ are independently optionally substituted with 1, 2, 3, 4 or 5 substituents independently selected from $R^{10}$; $R^{2A}$ and $R^{2B}$ are independently H, F, Cl or C$_1$-C$_6$ alkyl (e.g., methyl); $R^3$ is H, F, Cl, —CN, C$_{1-6}$ alkyl (e.g., methyl), or C$_{1-6}$ haloalkyl (e.g., trifluoromethyl); n is 0; $R^4$ is —NR$^8$C(O)R$^7$ or —NR$^8$SO$_2$R$^9$; and $R^5$ is H, F, Cl, —CN, C$_{1-6}$ alkyl (e.g., —CH$_3$) or C$_{1-6}$ haloalkyl (e.g., —CF$_3$). In one variation, $R^0$ is H; R$^1$ is piperidin-3-yl, 5-fluoropiperidin-3-yl, 5-methylpiperidin-3-yl or 5-fluoro-5-methylpiperidin-3-yl; $R^{2A}$ and $R^{2B}$ are independently H, F, Cl or methyl; $R^3$ is H, F, Cl, —CN, methyl, or trifluoromethyl; n is 0; $R^4$ is —NR$^8$C(O)R$^7$ or —NR$^8$SO$_2$R$^9$; $R^5$ is H, F, Cl, —CN, —CH$_3$, or —CF$_3$; $R^7$ is C$_{1-6}$ alkyl optionally substituted with 1, 2, 3, 4 or 5 substituents independently selected from $R^{10}$, or C$_{3-8}$ cycloalkyl optionally substituted with 1, 2, 3, 4 or 5 substituents independently selected from $R^{10}$; and $R^9$ is C$_{1-6}$ alkyl, C$_{3-8}$ cycloalkyl, C$_{6-10}$ aryl, or 5- to 14-membered heteroaryl, wherein the C$_{1-6}$ alkyl, C$_{3-8}$ cycloalkyl, C$_{6-10}$ aryl and 5- to 14-membered heteroaryl of $R^9$ are independently optionally substituted with 1, 2, 3, 4 or 5 substituents independently selected from $R^{10}$.

In some embodiments, $R^0$ is H; $R^1$ is $C_{3-12}$ cycloalkyl; 3- to 14-membered heterocyclyl; —($C_{1-6}$ alkylene)-(3- to 14-membered heterocyclyl), or —($C_{1-6}$ alkylene)-$NR^{1a}R^{1b}$; wherein the $C_{3-12}$ cycloalkyl, 3- to 14-membered heterocyclyl, and $C_{1-6}$ alkylene of $R^1$ are independently optimally substituted with 1, 2, 3, 4 or 5 substituents independently selected from $R^{10}$; $R^{2A}$ and $R^{2B}$ are independently H, F, Cl or $C_1$-$C_6$ alkyl (e.g., methyl); $R^3$ is H, F, Cl, —CN, $C_{1-6}$ alkyl (e.g., methyl), or $C_{1-6}$ haloalkyl (e.g., trifluoromethyl); n is 0; $R^4$ is H, F, Cl, —CN, $C_{1-6}$ alkyl (e.g., —$CH_3$) or $C_{1-6}$ haloalkyl (e.g., —$CF_3$); and $R^5$ is $C_{1-6}$ alkyl substituted with 1, 2, 3, 4 or 5 substituents independently selected from $R^{10}$, —$NR^8SO_2R^9$, —$NR^{8A}R^{8B}$, or —$C(O)N(R^8)SO_2R^9$. In one variation, $R^0$ is H; $R^1$ is piperidin-3-yl, 5-fluoropiperidin-3-yl, 5-methylpiperidin-3-yl or 5-fluoro-5-methylpiperidin-3-yl; $R^{2A}$ and $R^{2B}$ are independently H, F, Cl or methyl; $R^3$ is H, F, Cl, —CN, methyl, or trifluoromethyl; n is 0; $R^4$ is H, and $R^5$ is —($C_{1-6}$ alkylene)-$N(R^f)C(O)R^a$; $C_{1-6}$ alkyl substituted with 1, 2, 3, 4 or 5 substituents independently selected from $R^{10}$, —NH—$SO_2R^9$, —NH—$R^{8B}$, or —C(O)NH—$SO_2R^9$.

In some embodiments, the compound is of the Formula (I) or a pharmaceutically acceptable salt thereof, wherein the compound is of the Formula (Ia):

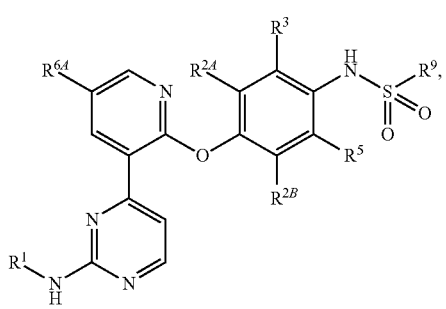

(Ia)

wherein $R^{6A}$ is hydrogen or $R^6$; and $R^1$, $R^{2A}$, $R^{2B}$, $R^3$, $R^5$, $R^6$ and $R^9$ are as detailed herein for Formula (I) or variations thereof. In some embodiments, each $R^{6A}$ and $R^{2A}$ is H, each $R^{2B}$, $R^3$ and $R^5$ is F, and $R^1$ and $R^9$ are as detailed herein for Formula (I).

In some embodiments, the compound is of the Formula (I) or a pharmaceutically acceptable salt thereof, wherein the compound is of the Formula (Ib):

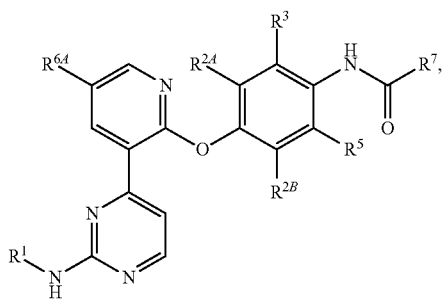

(Ib)

wherein $R^{6A}$ is hydrogen or $R^6$; and $R^1$, $R^{2A}$, $R^{2B}$, $R^3$, $R^5$, $R^6$ and $R^7$ are as detailed herein for Formula (I) or variations thereof. In some embodiments, each $R^{6A}$ and $R^{2A}$ is H, each $R^{2B}$, $R^3$ and $R^5$ is F, and $R^1$ and $R^7$ are as detailed herein for Formula (I). In one embodiment, $R^7$ is $NHR^9$, where $R^9$ is as described herein.

In some embodiments, the compound is of the Formula (I) or a pharmaceutically acceptable salt thereof, wherein the compound is of the Formula (Ic):

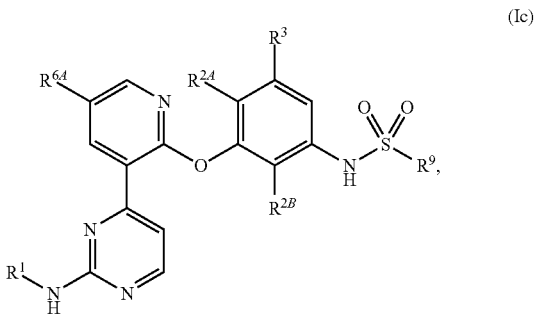

(Ic)

wherein $R^{6A}$ is hydrogen or $R^6$; and $R^1$, $R^{2A}$, $R^{2B}$, $R^3$, $R^6$ and $R^9$ are as detailed herein for Formula (I).

In some embodiments, the compound is of the Formula (I) or a pharmaceutically acceptable salt thereof, wherein the compound is of the Formula (Id):

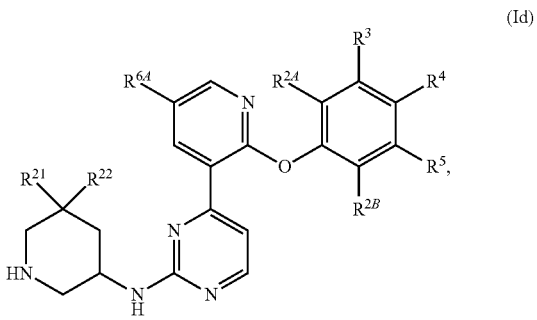

(Id)

herein $R^{6A}$ is hydrogen or $R^6$; $R^{21}$ and $R^{22}$ are independently H, F, —$CH_3$ or —$NH_2$; and $R^{2A}$, $R^{2B}$, $R^3$, $R^4$, $R^5$ and $R^6$ are as detailed herein for Formula (I) or variations thereof. In some embodiments, each $R^{6A}$ and $R^{2A}$ is H, each $R^{2B}$, $R^3$ and $R^5$ is F, and $R^4$ is as detailed herein for Formula (I).

In some embodiments, the compound is of the Formula (Id-1), (Id-2), (Id-3), (Id-4), (Id-5), (Id-6) or (Id-7):

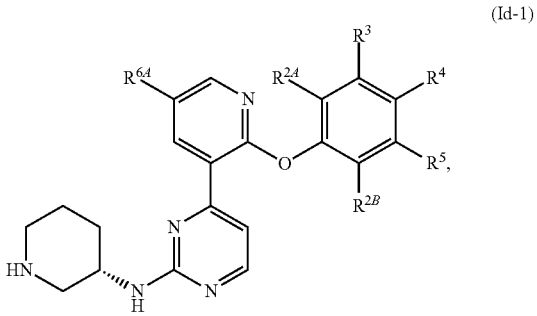

(Id-1)

(Id-2)
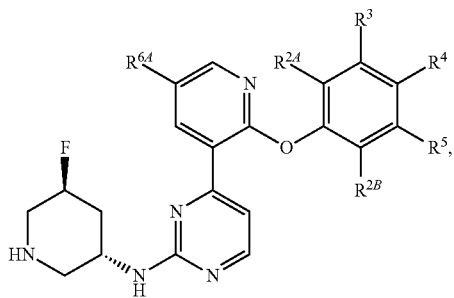

(Id-3)
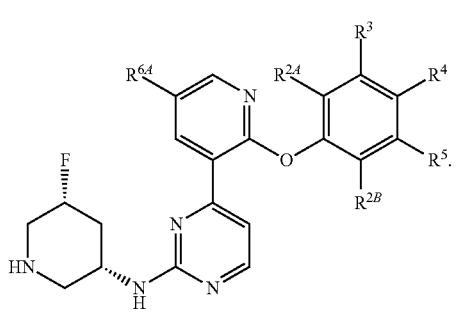

(Id-4)
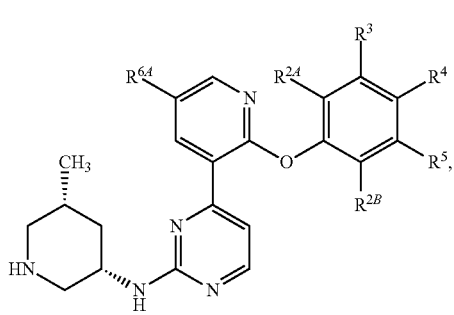

(Id-5)
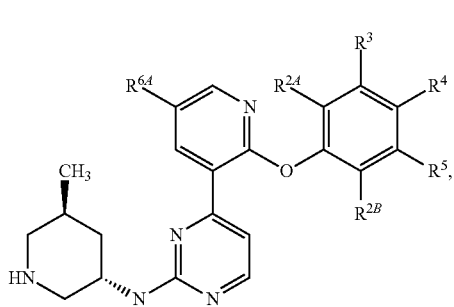

(Id-6)
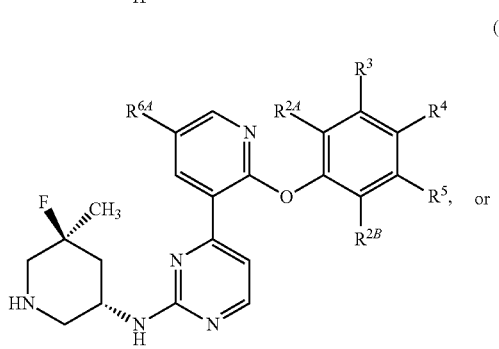

or (Id-7)
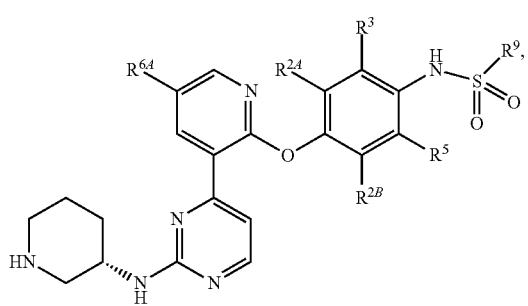

or a pharmaceutically acceptable salt thereof, wherein $R^{6A}$ is hydrogen or $R^6$; and $R^{2A}$, $R^{2B}$, $R^3$, $R^4$, $R^5$ and $R^6$ are as detailed herein for Formula (I) or variations thereof. In some embodiments, each $R^{6A}$ and $R^{2A}$ is H, each $R^{2B}$, $R^3$ and $R^5$ is F, and $R^4$ is as detailed herein for Formula (I).

In some embodiments, the compound is of the Formula (I) or a pharmaceutically acceptable salt thereof, wherein the compound is of the Formula (Ie):

(Ie)

wherein $R^{6A}$ is hydrogen or $R^6$; $R^{21}$ and $R^{22}$ are independently H, F, —CH₃ or —NH₂; and $R^{2A}$, $R^{2B}$, $R^3$, $R^5$, $R^6$ and $R^9$ are as detailed herein for Formula (I) or variations thereof. In some embodiments, each $R^{6A}$ and $R^{2A}$ is H, each $R^{2B}$, $R^3$ and $R^5$ is F, and $R^9$ is as detailed herein for Formula (I).

In some embodiments, the compound is of the Formula (Ie-1), (Ie-2), (Ie-3), (Ie-4), (Ie-5), (Ie-6) or (Ie-7):

(Ie-1)

-continued (Ie-2)

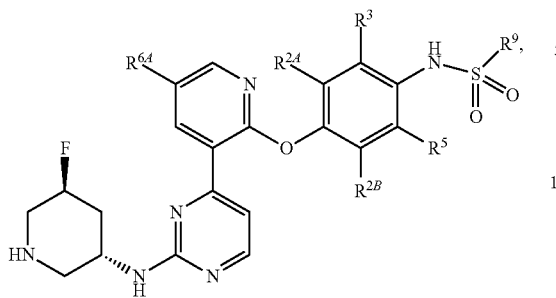

(Ie-3)

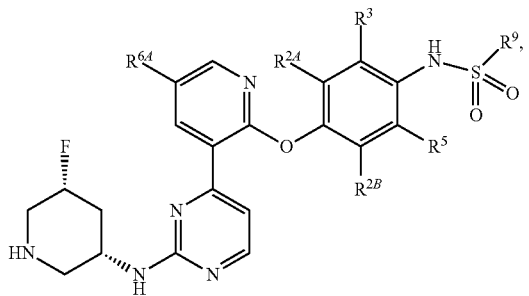

(Ie-4)

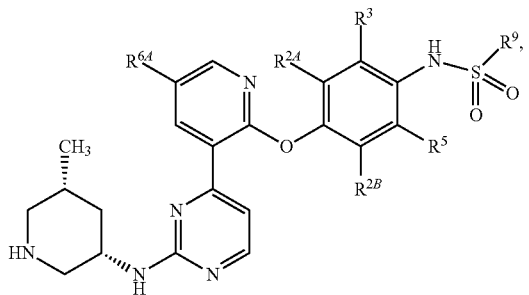

(Ie-5)

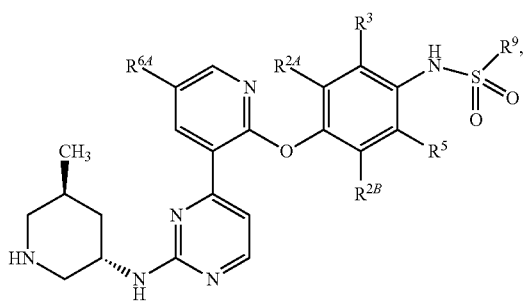

(Ie-6)

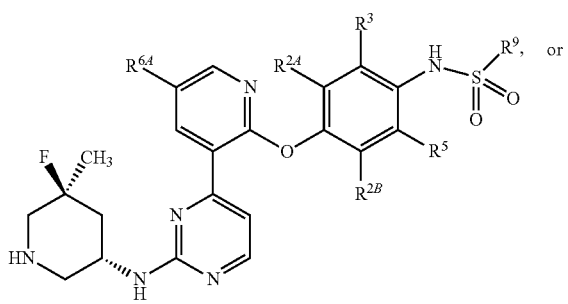

-continued (Ie-7)

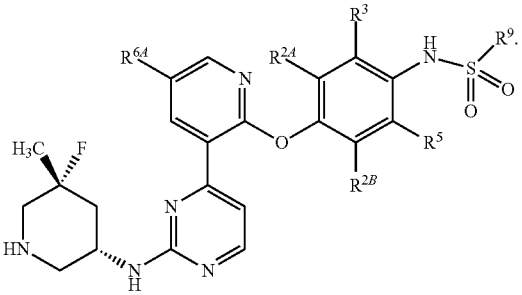

or a pharmaceutically acceptable salt thereof, wherein $R^{6A}$ is hydrogen or $R^6$; and $R^{2A}$, $R^{2B}$, $R^3$, $R^5$, $R^6$ and $R^9$ are as detailed herein for Formula (I). In some embodiments, each $R^{6A}$ and $R^{2A}$ is H, each $R^{2B}$, $R^3$ and $R^5$ is F, and $R^9$ is as detailed herein for Formula (I).

In some embodiments of the compound or pharmaceutically acceptable salt thereof of the Formula (Ia), (Ib), (Ic), (Id), (Id-1), (Id-2), (Id-3), (Id-4), (Id-5), (Id-6), (Id-7), (Ie), (Ie-1), (Ie-2), (Ie-3), (Ie-4), (Ie-5), (Ie-6) or (Ie-7), or variations thereof, $R^{6A}$ is H.

In some embodiments of the compound or pharmaceutically acceptable salt thereof of the Formula (I), or variations thereof where applicable, or a salt (e.g., a pharmaceutically acceptable salt) thereof, each $R^{10}$ is independently oxo, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, —C(O)R$^a$, —C(O)OR$^b$, —C(O)NR$^c$R$^d$, —OR$^b$, —OC(O)R$^a$, —OC(O)NR$^c$R$^d$, —SR$^b$, —S(O)R$^e$, —S(O)$_2$R$^e$, —S(O)(=NH)R$^e$, —S(O)$_2$NR$^c$R$^d$, —NR$^c$R$^d$, —N(R$^f$)C(O)R$^a$, —N(R$^f$)C(O)OR$^b$, —N(R$^f$)C(O)NR$^c$R$^d$, —N(R$^f$)S(O)$_2$R$^e$, or —N(R$^f$)S(O)$_2$NR$^c$R$^d$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^{10}$ are each optionally substituted with 1, 2, 3 or 4 substituents independently selected from $R^{11}$.

In one variation, $R^{10}$ is independently oxo; $C_{1-6}$ alkyl optionally substituted with 1, 2, 3 or 4 substituents independently selected from $R^{11}$; 5- to 10-membered heteroaryl optionally substituted with 1, 2, 3 or 4 substituents independently selected from $R^{11}$; halogen, cyano, —OR$^b$, —NR$^c$R$^d$, —N(R$^f$)C(O)R$^a$, or —N(R$^f$)S(O)$_2$R$^e$.

In one variation, $R^{10}$ is independently oxo, halogen, cyano, $C_{1-6}$ alkyl optionally substituted with 1, 2, 3 or 4 substituents independently selected from $R^{11}$, or —OR$^b$.

In one variation, $R^{10}$ is independently —NR$^c$R$^d$, —N(R$^f$)C(O)R$^a$, —N(R$^f$)C(O)OR$^b$, —N(R$^f$)C(O)NR$^c$R$^d$, —N(R$^f$)S(O)$_2$R$^e$, or —N(R$^f$)S(O)$_2$NR$^c$R$^d$.

In one variation, $R^{10}$ is independently oxo, —OR$^b$, —OC(O)R$^a$, —OC(O)NR$^c$R$^d$, —SR$^b$, —S(O)R$^e$, —S(O)$_2$R$^e$, or —S(O)$_2$NR$^c$R$^d$.

In one variation, each $R^{10}$ is independently $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, —C(O)R$^a$, —C(O)OR$^b$, —C(O)NR$^c$R$^d$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^{10}$ are each optionally substituted with 1, 2, 3 or 4 substituents independently selected from $R^{11}$.

In one variation, each $R^{10}$ is independently $C_{1-6}$ alkyl, $C_{2-6}$ alkenyl, $C_{2-6}$ alkynyl, each optionally substituted with 1, 2, 3 or 4 substituents independently selected from $R^{11}$.

In one variation, $R^{10}$ is $C_{1-6}$ alkyl optionally substituted with 1, 2, 3 or 4 substituents independently selected from $R^{11}$. In one variation, $R^{10}$ is 3- to 12-membered heterocyclyl optionally substituted with 1, 2, 3 or 4 substituents independently selected from $R^{11}$.

In one variation, $R^{10}$ is halogen, cyano, $-NR^cR^d$, $-C(O)NR^cR^d$, $-OR^b$, $-S(O)_2R^e$, $C_{1-6}$ haloalkyl, $-(C_{1-6}$ alkylene)-OH, or $-(C_{1-6}$ alkylene)-OH.

In one variation, $R^{10}$ is hydroxyl, cyano, halogen, $-CHF_2$, $-CF_3$, $-NH_2$, $-NH(C_{1-6}$ alkyl), $-N(C_{1-6}$ alkyl)$_2$, $-O(C_{1-6}$ alkyl), $-SO_2(C_{1-6}$ alkyl), $-S(O)_2NR^cR^d$, $-C(O)NR^cR^d$, or $-N(R^f)C(O)R^a$.

In some embodiments, each $R^a$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl and 3- to 12-membered heterocyclyl of $R^a$ are each optionally substituted with 1, 2, 3 or 4 substituents independently selected from $R^{11}$. In one variation, $R^a$ is independently hydrogen or $C_{1-6}$ alkyl. In one variation, $R^a$ is independently $C_{1-6}$ alkyl (e.g., methyl).

In some embodiments, each $R^b$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^b$ are each optionally substituted with 1, 2, 3 or 4 substituents independently selected from $R^{11}$. In one variation, $R^b$ is independently hydrogen or $C_{1-6}$ alkyl. In one variation, $R^b$ is independently $C_{1-6}$ haloalkyl (e.g., $-CF_3$).

In some embodiments, each $R^c$ and $R^d$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^c$ and $R^d$ are each optionally substituted with 1, 2, 3 or 4 substituents independently selected from $R^{11}$; or $R^c$ and $R^d$ are taken together with the nitrogen atom to which they are attached to form a 4- to 12-membered heterocyclyl optionally substituted with 1, 2, 3 or 4 substituents independently selected from $R^{11}$. In one variation, each $R^c$ and $R^d$ is independently hydrogen or $C_{1-6}$ alkyl.

In some embodiments, each $R^e$ is independently $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^e$ are each optionally substituted with 1, 2, 3 or 4 substituents independently selected from $R^{11}$. In one variation, $R^e$ is independently $C_{1-6}$ alkyl. In one variation, $R^e$ is phenyl optionally substituted with 1, 2, 3 or 4 substituents independently selected from $R^{11}$.

In some embodiments, each $R^f$ is independently hydrogen or $C_{1-6}$ alkyl. In one variation, $R^f$ is hydrogen.

In some embodiments, each $R^{11}$ is independently oxo, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl, 3- to 8-membered heterocyclyl, halogen, cyano, $-C(O)R^{a1}$, $-C(O)OR^{b1}$, $-C(O)NR^{c1}R^{d1}$, $-OR^{b1}$, $-OC(O)R^{a1}$, $-OC(O)NR^{c1}R^{d1}$, $-SR^{b1}$, $-S(O)R^{e1}$, $-S(O)_2R^{e1}$, $-S(O)_2NR^{c1}R^{d1}$, $-NR^{c1}R^{d1}$, $-N(R^{f1})C(O)R^{a1}$, $-N(R^{f1})C(O)OR^{b1}$, $-N(R^{f1})C(O)NR^{c1}R^{d1}$, $-N(R^{f1})S(O)_2R^{e1}$, or $-N(R^{f1})S(O)_2NR^{c1}R^{d1}$; wherein the $C_{1-6}$ alkyl, $C_{2-6}$ alkenyl, $C_{2-6}$ alkynyl, $C_{3-6}$ cycloalkyl, $C_{6-14}$ aryl, 5- to 14-membered heteroaryl and 3- to 14-membered heterocyclyl of $R^{11}$ are each optionally substituted with 1, 2, 3 or 4 substituents independently selected from $R^{12}$.

In one variation, each $R^{11}$ is independently oxo, $C_{1-6}$ alkyl, $C_{3-6}$ cycloalkyl, 3- to 8-membered heterocyclyl, halogen, cyano, or $-OR^{b1}$; wherein the $C_{1-6}$ alkyl, $C_{3-6}$ cycloalkyl, and 3- to 14-membered heterocyclyl of $R^{11}$ are each optionally substituted with 1, 2, 3 or 4 substituents independently selected from $R^{12}$.

In one variation, $R^{11}$ is $C_{1-6}$ alkyl optionally substituted with 1, 2, 3 or 4 substituents independently selected from $R^{12}$. In one variation, $R^{11}$ is 3- to 8-membered heterocyclyl optionally substituted with 1, 2, 3 or 4 substituents independently selected from $R^{12}$.

In one variation, $R^{11}$ is halogen, cyano, $-NR^{c1}R^{d1}$, $-C(O)NR^{c1}R^{d1}$, $-OR^{b1}$, $-S(O)_2R^{e1}$, $C_{1-6}$ haloalkyl, $-(C_{1-6}$ alkylene)-OH, or $-(C_{1-6}$ alkylene)-OH.

In one variation, $R^{11}$ is hydroxl, cyano, halogen, $-CHF_2$, $-CF_3$, $-NH_2$, $-NH(C_{1-6}$ alkyl), $-N(C_{1-6}$ alkyl)$_2$, $-O(C_{1-6}$ alkyl), $-SO_2(C_{1-6}$ alkyl), $-S(O)_2NR^{c1}R^{d1}$, $-C(O)NR^{c1}R^{d1}$, or $-N(R^{f1})C(O)R^{a1}$.

In one variation, $R^{11}$ is halogen, cyano, $-O(C_{1-6}$ alkyl), $-O(C_{1-6}$ alkylene)-$NH_2$, or $-(C_{1-6}$alkylene)-OH.

In some embodiments, each $R^{a1}$ is independently hydrogen, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl and 3- to 8-membered heterocyclyl of $R^{a1}$ are each optionally substituted with 1, 2, 3 or 4 substituents independently selected from $R^{12}$.

In some embodiments, each $R^{b1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{b1}$ are each optionally substituted with 1, 2, 3 or 4 substituents independently selected from $R^{12}$. In one variation, $R^{b1}$ is independently hydrogen or $C_{1-6}$ alkyl.

In some embodiments, each $R^{c1}$ and $R^{d1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{c1}$ and $R^{d1}$ are each optionally substituted with 1, 2, 3 or 4 substituents independently selected from $R^{12}$; or $R^{c1}$ and $R^{d1}$ are taken together with the nitrogen atom to which they are attached to form a 4- to 8-membered heterocyclyl optionally substituted with 1, 2, 3 or 4 substituents independently selected from $R^{12}$. In one variation, each $R^{c1}$ and $R^{d1}$ is independently hydrogen or $C_{1-6}$ alkyl.

In some embodiments, each $R^{e1}$ is independently $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{e1}$ are each optionally substituted with 1, 2, 3 or 4 substituents independently selected from $R^{12}$. In one variation, $R^{e1}$ is independently $C_{1-6}$ alkyl.

In some embodiments, each $R^{f1}$ is independently hydrogen or $C_{1-6}$ alkyl. In one variation, $R^{f1}$ is hydrogen.

In some embodiments, each $R^{12}$ is independently oxo, $C_{1-6}$ alkyl, $C_{3-6}$ cycloalkyl, $C_6$ aryl, 5- to 6-membered heteroaryl, 3- to 6-membered heterocyclyl, halogen, cyano, $-C(O)R^{a2}$, $-C(O)OR^{b2}$, $-C(O)NR^{c2}R^{d2}$, $-OR^{b2}$, $-OC(O)R^{a2}$, $-OC(O)NR^{c2}R^{d2}$, $-S(O)_2R^{e2}$, $-S(O)_2NR^{c2}R^{d2}$, —NR$^{c2}$R$^{d2}$, —N(R$^{f2}$)C(O)R$^{a2}$, —N(R$^{f2}$)C(O)OR$^{b2}$, —N(R$^{f2}$)C(O)NR$^{c2}$R$^{d2}$, —N(R$^{f2}$)S(O)$_2$R$^{e2}$, or —N(R$^{f2}$)S(O)$_2$NR$^{c2}$R$^{d2}$; wherein the C$_{1-6}$ alkyl, C$_{3-6}$ cycloalkyl, C$_6$ aryl, 5- to 6-membered heteroaryl and 3- to 6-membered heterocyclyl of R$^{12}$ are each optionally substituted with 1, 2, 3 or 4 substituents independently selected from R$^{13}$.

In one variation, each R$^{12}$ is independently oxo, halogen, cyano, —OR$^{b2}$, or C$_{1-6}$ alkyl optionally substituted with 1, 2, 3 or 4 substituents independently selected from R$^{13}$. In one variation, each R$^{12}$ is independently oxo, halogen, cyano, or hydroxyl.

In one variation, R$^{12}$ is C$_{1-6}$ alkyl optionally substituted with 1, 2, 3 or 4 substituents independently selected from R$^{13}$.

In one variation, R$^{12}$ is oxo, hydroxyl, C$_{1-6}$ alkyl, or —O(C$_{1-6}$ alkyl).

In some embodiments, each R$^{a2}$ is independently hydrogen, C$_{1-6}$ alkyl, C$_{3-6}$ cycloalkyl, C$_6$ aryl, 5- to 6-membered heteroaryl or 3- to 6-membered heterocyclyl; wherein the C$_{1-6}$ alkyl, C$_{3-6}$ cycloalkyl, C$_6$ aryl, 5- to 6-membered heteroaryl and 3- to 6-membered heterocyclyl of R$^{a2}$ are each optionally substituted with 1, 2, 3 or 4 substituents independently selected from R$^{13}$. In one variation, R$^{a2}$ is independently hydrogen or C$_{1-6}$ alkyl.

In some embodiments, each R$^{b2}$ is independently hydrogen, C$_{1-6}$ alkyl, C$_{3-6}$ cycloalkyl or 3- to 6-membered heterocyclyl; wherein the C$_{1-6}$ alkyl, C$_{3-6}$ cycloalkyl and 3- to 6-membered heterocyclyl of R$^{b2}$ are each optionally substituted with 1, 2, 3 or 4 substituents independently selected from R$^{13}$. In one variation, R$^{b2}$ is hydrogen.

In some embodiments, each R$^{c2}$ and R$^{*2}$ is independently hydrogen, C$_{1-6}$ alkyl, C$_{3-6}$ cycloalkyl or 3- to 8-membered heterocyclyl; wherein the C$_{1-6}$ alkyl, C$_{3-6}$ cycloalkyl and 3- to 8-membered heterocyclyl of R$^{c2}$ and R$^{d2}$ are each optionally substituted with 1, 2, 3 or 4 substituents independently selected from R$^{13}$; or R$^{c2}$ and R$^{d2}$ are taken together with the nitrogen atom to which they are attached to form a 4- to 6-membered heterocyclyl optionally substituted with 1, 2, 3 or 4 substituents independently selected from R$^{13}$. In one variation, each R$^{c2}$ and R$^{d2}$ is independently hydrogen or C$_{1-6}$ alkyl.

In some embodiments, each R$^{e2}$ is independently C$_{1-6}$ alkyl, C$_{3-6}$ cycloalkyl, C$_6$ aryl, 5- to 6-membered heteroaryl or 3- to 6-membered heterocyclyl; wherein the C$_{1-6}$ alkyl, C$_{3-6}$ cycloalkyl, C$_6$ aryl, 5- to 6-membered heteroaryl and 3- to 6-membered heterocyclyl of R$^{e2}$ are each optionally substituted with 1, 2, 3 or 4 substituents independently selected from R$^{13}$. In one variation, R$^{e2}$ is independently C$_{1-6}$ alkyl.

In some embodiments, each R$^{f2}$ is independently hydrogen or C$_{1-6}$ alkyl. In one variation, R$^{f2}$ is hydrogen.

In some embodiments, each R$^{13}$ is independently oxo, halogen, hydroxyl, —O(C$_{1-6}$ alkyl), cyano, C$_{1-6}$ alkyl or C$_{1-6}$ haloalkyl.

In one variation, each R$^{13}$ is independently halogen, hydroxyl, —O(C$_{1-6}$ alkyl), cyano, or C$_{1-6}$ alkyl.

In one variation, R$^{13}$ is oxo, hydroxyl, C$_{1-6}$ alkyl, or —O(C$_{1-6}$ alkyl).

Representative compounds are listed in Table 1. It is understood that individual enantiomers and diastereomers are included in the table below by Compound No. and Compound Name, and their corresponding structures can be readily determined therefrom. In some instances, the enantiomers or diastereomers are identified by their respective properties, for example, retention times on a chiral HPLC or its biological activities, and the absolute stereo configurations of the chiral centers are arbitrarily assigned.

TABLE 1

| No. | Structure | Name |
| --- | --- | --- |
| 101 | 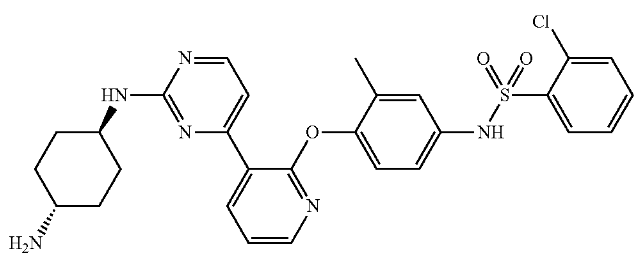 [SMILES: Cc1cc(NS(=O)(=O)c2ccccc2Cl)ccc1Oc1ncccc1-c1ccnc(N[C@H]2CC[C@H](N)CC2)n1] | N-[4-[[3-[2-[(4-aminocyclohexyl)amino]pyrimidin-4-yl]-2-pyridyl]oxy]-3-methyl-phenyl]-2-chloro-benzenesulfonamide |
| 102 | 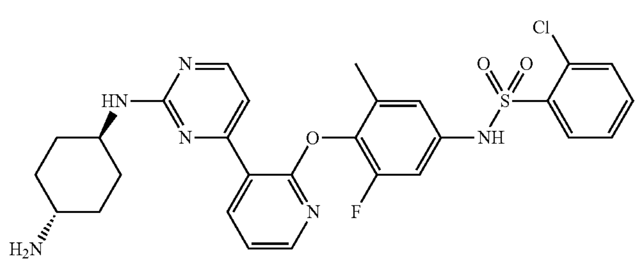 [SMILES: Cc1cc(NS(=O)(=O)c2ccccc2Cl)cc(F)c1Oc1ncccc1-c1ccnc(N[C@H]2CC[C@H](N)CC2)n1] | N-[4-[[3-[2-[(4-aminocylcohexyl)amino]pyrimidin-4-yl]-2-pyridyl]oxy]-3-fluoro-5-methyl-phenyl]-2-chloro-benzenesulfonamide |

TABLE 1-continued

| No. | Structure | Name |
|---|---|---|
| 103 | 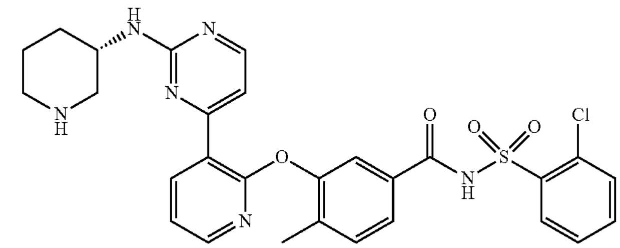 [SMILES: Cc1ccc(C(=O)NS(=O)(=O)c2ccccc2Cl)cc1Oc1ncccc1-c1ccnc(N[C@H]2CCCNC2)n1] | (S)-N-((2-chlorophenyl)sulfonyl)-4-methyl-3-((3-(2-(piperidin-3-ylamino)pyrimidin-4-yl)pyridin-2-yl)oxy)benzamide |
| 104 | 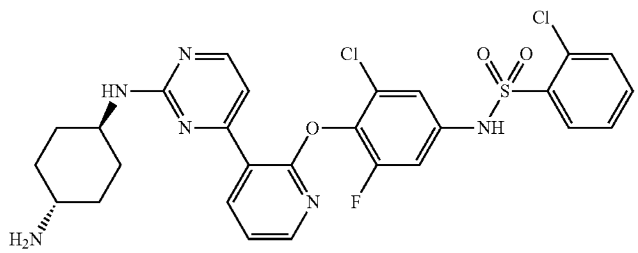 | N-[4-[[3-[2-[(4-aminocyclohexyl)amino]pyrimidin-4-yl]-2-pyridyl]oxy]-3-chloro-5-fluoro-phenyl]-2-chloro-benzenesulfonamide |
| 105 | 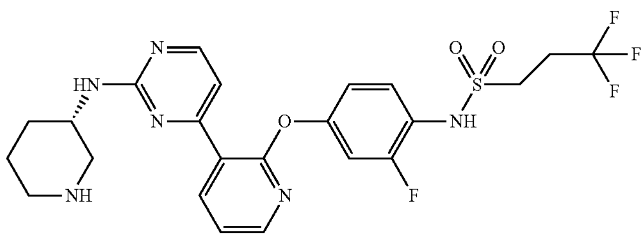 [SMILES: O=S(=O)(CCC(F)(F)F)Nc1ccc(Oc2ncccc2-c2ccnc(N[C@H]3CCCNC3)n2)cc1F] | (S)-3,3,3-trifluoro-N-(2-fluoro-4-((3-(2-(piperidin-3-ylamino)pyrimidin-4-yl)pyridin-2-yl)oxy)phenyl)propane-1-sulfonamide |
| 106 | 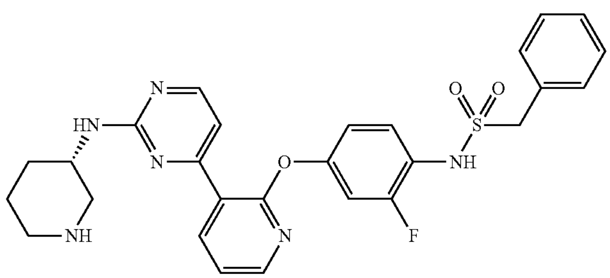 | (S)-N-(2-fluoro-4-((3-(2-(piperidin-3-ylamino)pyrimidin-4-yl)pyridin-2-yl)oxy)phenyl)-1-phenylmethanesulfonamide |
| 107 | 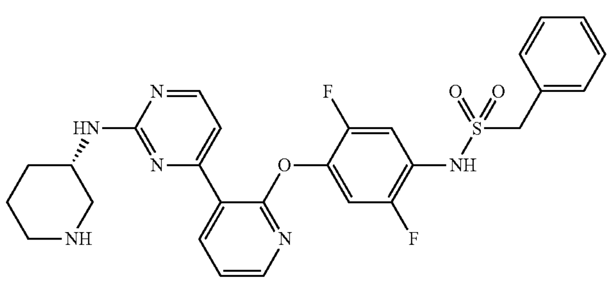 [SMILES: O=S(=O)(Cc1ccccc1)Nc1cc(F)c(Oc2ncccc2-c2ccnc(N[C@H]3CCCNC3)n2)cc1F] | (S)-N-(2,5-difluoro-4-((3-(2-(piperidin-3-ylamino)pyrimidin-4-yl)pyridin-2-yl)oxy)phenyl)-1-phenylmethanesulfonamide |
| 108 | 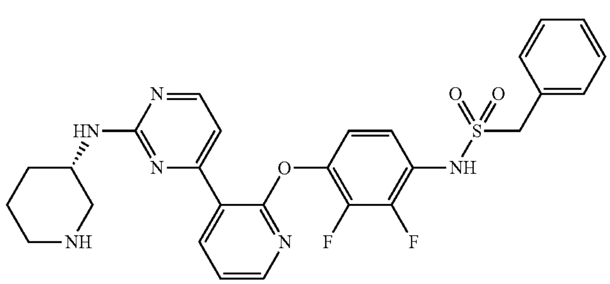 [SMILES: O=S(=O)(Cc1ccccc1)Nc1ccc(Oc2ncccc2-c2ccnc(N[C@H]3CCCNC3)n2)c(F)c1F] | (S)-N-(2,3-difluoro-4-((3-(2-(piperidin-3-ylamino)pyrimidin-4-yl)pyridin-2-yl)oxy)phenyl)-1-phenylmethanesulfonamide |

TABLE 1-continued

| No. | Structure | Name |
|---|---|---|
| 109 | 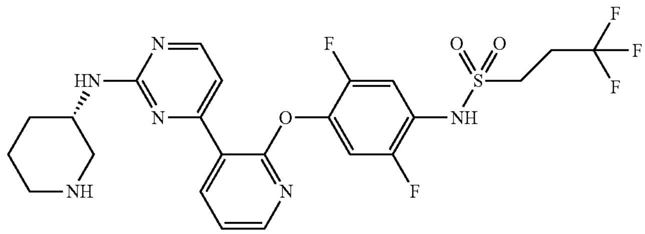 [SMILES: O=S(=O)(CCC(F)(F)F)Nc1cc(F)c(Oc2ncccc2-c2ccnc(N[C@H]3CCCNC3)n2)cc1F] | (S)-N-(2,5-difluoro-4-((3-(2-(piperidin-3-ylamino)pyrimidin-4-yl)pyridin-2-yl)oxy)phenyl)-3,3,3-trifluoropropane-1-sulfonamide |
| 110 | 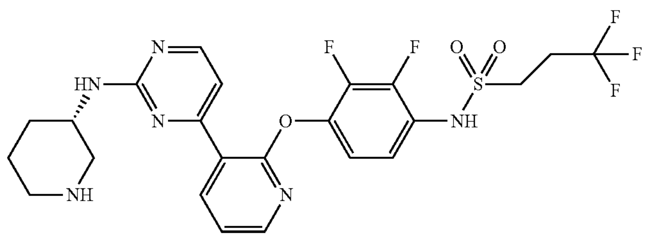 [SMILES: O=S(=O)(CCC(F)(F)F)Nc1ccc(Oc2ncccc2-c2ccnc(N[C@H]3CCCNC3)n2)c(F)c1F] | (S)-N-(2,5-difluoro-4-((3-(2-(piperidin-3-ylamino)pyrimidin-4-yl)pyridin-2-yl)oxy)phenyl)-3,3,3-trifluoropropane-1-sulfonamide |
| 111 | 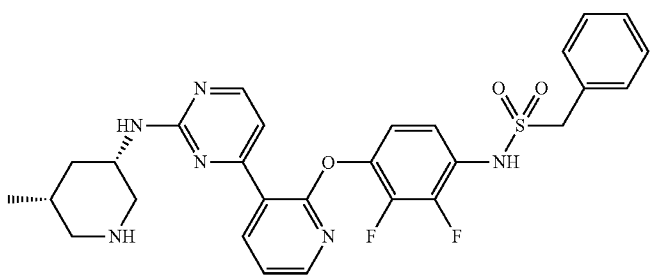 [SMILES: C[C@H]1CNC[C@@H](Nc2nccc(-c3cccnc3Oc3ccc(NS(=O)(=O)Cc4ccccc4)c(F)c3F)n2)C1] | N-(2,3-difluoro-4-((3-(2-(((3S,5R)-5-methylpiperidin-3-yl)amino)pyrimidin-4-yl)pyridin-2-yl)oxy)phenyl)-1-phenylmethanesulfonamide |
| 112 | 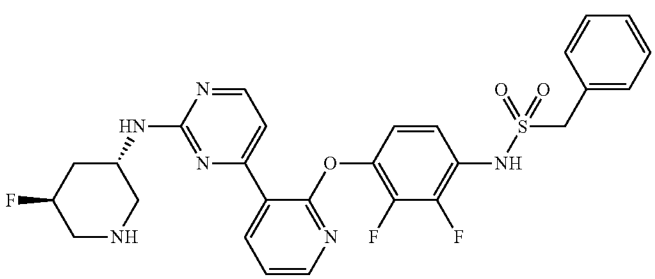 [SMILES: O=S(=O)(Cc1ccccc1)Nc1ccc(Oc2ncccc2-c2ccnc(N[C@@H]3CNC[C@@H](F)C3)n2)c(F)c1F] | N-(2,3-difluoro-4-((3-(2-(((3S,5S)-5-fluoropipeiridn-3-yl)amino)pyrimidin-4-yl)pyridin-2-yl)oxy)phenyl)-1-phenylmethanesulfonamide |
| 113 | 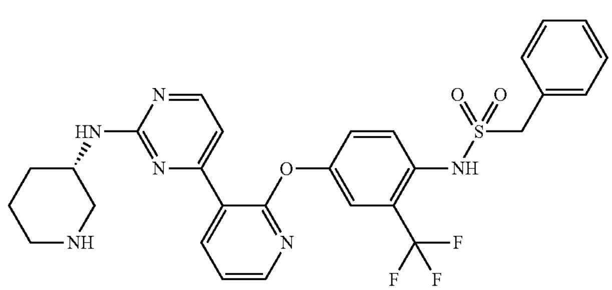 [SMILES: O=S(=O)(Cc1ccccc1)Nc1ccc(Oc2ncccc2-c2ccnc(N[C@H]3CCCNC3)n2)cc1C(F)(F)F] | (S)-1-phenyl-N-(4-((3-(2-(piperidin-3-ylamino)pyrimidin-4-yl)pyridin-2-yl)oxy)-2-(trifluoromethyl)phenyl)methanesulfonamide |

TABLE 1-continued

| No. | Structure | Name |
|---|---|---|
| 114 | 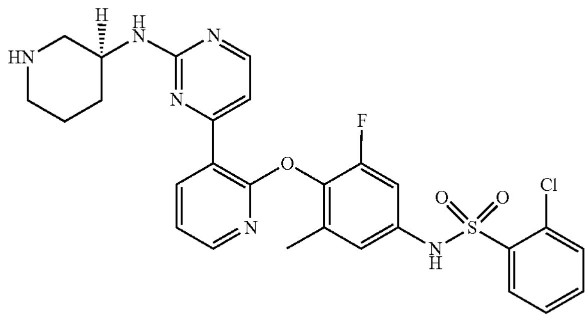 [SMILES: Cc1cc(NS(=O)(=O)c2ccccc2Cl)cc(F)c1Oc1ncccc1-c1ccnc(N[C@H]2CCCNC2)n1] | (S)-2-chloro-N-(3-fluoro-5-methyl-4-((3-(2-(piperidin-3-ylamino)pyrimidin-4-yl)pyridin-2-yl)oxy)phenyl)benzenesulfonamide |
| 115 | 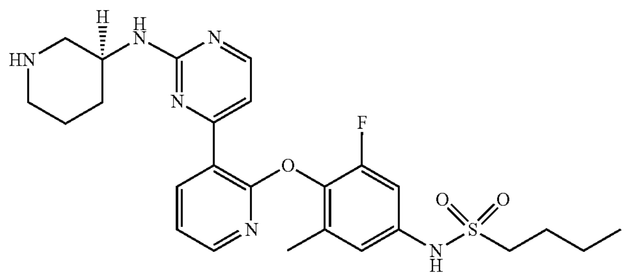 [SMILES: CCCCS(=O)(=O)Nc1cc(C)c(Oc2ncccc2-c2ccnc(N[C@H]3CCCNC3)n2)c(F)c1] | (S)-N-(3-fluoro-5-methyl-4-((3-(2-(piperidin-3-ylamino)pyrimidin-4-yl)pyridin-2-yl)oxy)phenyl)butane-1-sulfonamide |
| 116 | 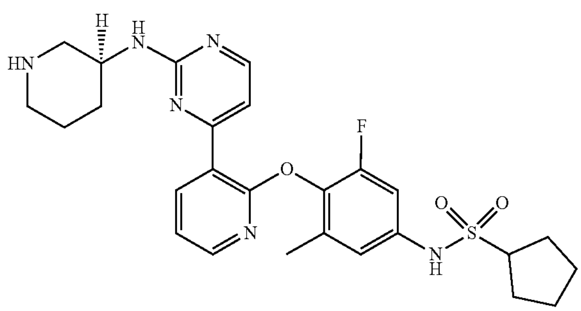 [SMILES: Cc1cc(NS(=O)(=O)C2CCCC2)cc(F)c1Oc1ncccc1-c1ccnc(N[C@H]2CCCNC2)n1] | (S)-N-(3-fluoro-5-methyl-4-((3-(2-(piperidin-3-ylamino)pyrimidin-4-yl)pyridin-2-yl)oxy)phenyl)cyclopentanesulfonamide |
| 117 | 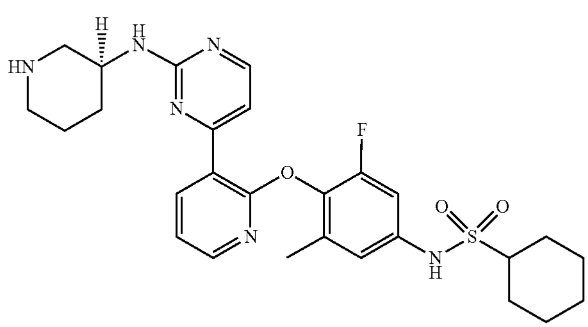 [SMILES: Cc1cc(NS(=O)(=O)C2CCCCC2)cc(F)c1Oc1ncccc1-c1ccnc(N[C@H]2CCCNC2)n1] | (S)-N-(3-fluoro-5-methyl-4-((3-(2-(piperidin-3-ylamino)pyrimidi-4-yl)pyridin-2-yl)oxy)phenyl)cyclohexanesulfonamide |
| 118 | 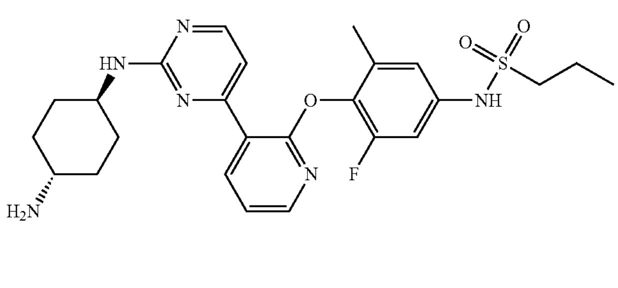 [SMILES: CCCS(=O)(=O)Nc1cc(C)c(Oc2ncccc2-c2ccnc(N[C@H]3CC[C@H](N)CC3)n2)c(F)c1] | N-(4-((3-(2-(((1r,4r)-4-aminocyclohexyl)amino)pyrimidin-4-yl)pyridin-2-yl)oxy)-3-fluoro-5-methylphenyl)propane-1-sulfonamide |

TABLE 1-continued

| No. | Structure | Name |
|---|---|---|
| 119 | 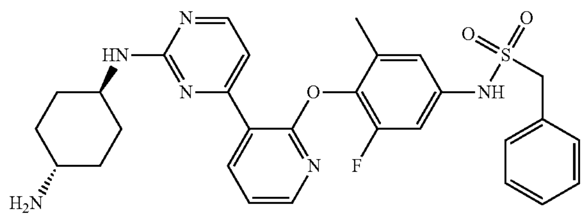 [SMILES: Cc1cc(NS(=O)(=O)Cc2ccccc2)cc(F)c1Oc1ncccc1-c1ccnc(N[C@H]2CC[C@H](N)CC2)n1] | N-(4-((3-(2-(((1r,4r)-4-aminocyclohexyl)amino)pyrimidin-4-yl)pyridin-2-yl)oxy)-3-fluoro-5-methylphenyl)-1-phenylmethanesulfonamide |
| 120 | 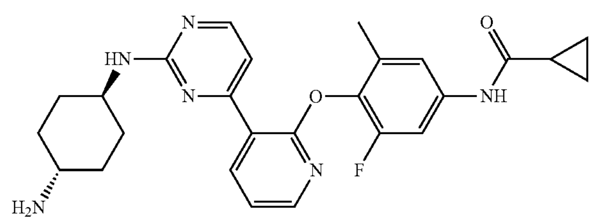 [SMILES: Cc1cc(NC(=O)C2CC2)cc(F)c1Oc1ncccc1-c1ccnc(N[C@H]2CC[C@H](N)CC2)n1] | N-(4-((3-(2-(((1r,4r)-4-aminocyclohexyl)amino)pyrimidin-4-yl)pyridin-2-yl)oxy)-3-fluoro-5-methylphenyl)cyclopropanecarboxamide |
| 121 | 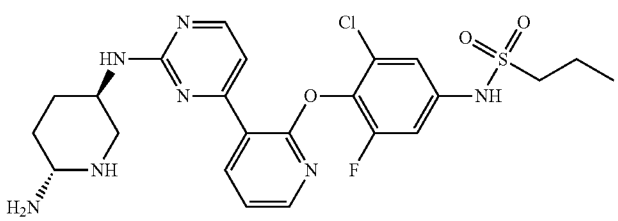 [SMILES: CCCS(=O)(=O)Nc1cc(F)c(Oc2ncccc2-c2ccnc(N[C@@H]3CC[C@@H](N)NC3)n2)c(Cl)c1] | N-(4-((3-(2-(((1r,4r)-4-aminocyclohexyl)amino)pyrimidin-4-yl)pyridin-2-yl)oxy)-3-chloro-5-fluorophenyl)propane-1-sulfonamide |
| 122 | 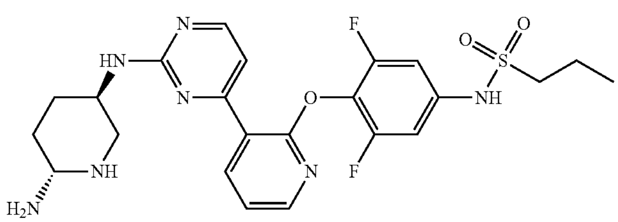 [SMILES: CCCS(=O)(=O)Nc1cc(F)c(Oc2ncccc2-c2ccnc(N[C@@H]3CC[C@@H](N)NC3)n2)c(F)c1] | N-(4-((3-(2-(((1r,4r)-4-aminocyclohexyl)amino)pyrimidin-4-yl)pyridin-2-yl)oxy)-3,5-difluorophenyl)propane-1-sulfonamide |
| 123 | 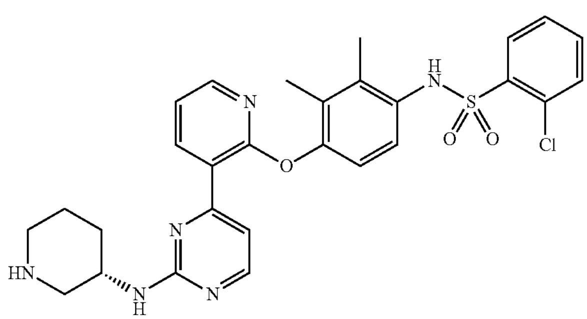 [SMILES: Cc1c(NS(=O)(=O)c2ccccc2Cl)ccc(Oc2ncccc2-c2ccnc(N[C@H]3CCCNC3)n2)c1C] | (S)-2-Chloro-N-(2,3-dimethyl-4-((3-(2-(piperidin-3-ylamino)pyrimidin-4-yl)pyridin-2-yl)oxy)phenyl)benzenesulfonamide |
| 124 | 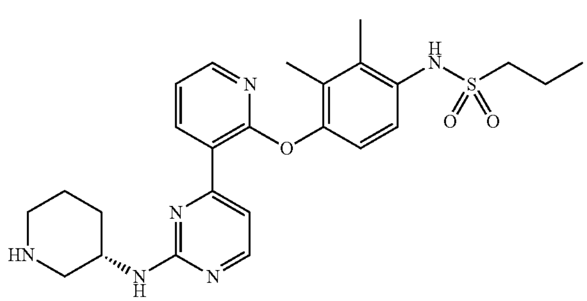 [SMILES: CCCS(=O)(=O)Nc1ccc(Oc2ncccc2-c2ccnc(N[C@H]3CCCNC3)n2)c(C)c1C] | (S)-N-(2,5-Dimethyl-4-((3-(2-(piperidin-3-ylamino)pyrimidin-4-yl)pyridin-2-yl)oxy)phenyl)propane-1-sulfonamide |

TABLE 1-continued

| No. | Structure | Name |
|---|---|---|
| 125 | 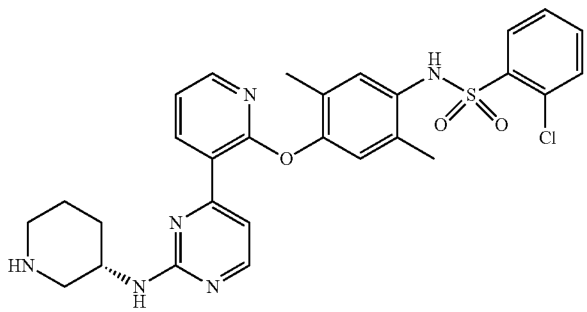 [SMILES: Cc1cc(Oc2ncccc2-c2ccnc(N[C@H]3CCCNC3)n2)c(C)cc1NS(=O)(=O)c1ccccc1Cl] | (S)-2-chloro-N-(2,5-dimethyl-4-((3-(2-(piperidin-3-ylamino)pyrimidin-4-yl)pyridin-2-yl)oxy)phenyl)benzenesulfonamide |
| 126 | 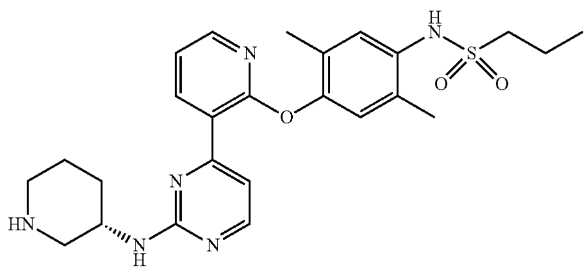 [SMILES: CCCS(=O)(=O)Nc1cc(C)c(Oc2ncccc2-c2ccnc(N[C@H]3CCCNC3)n2)cc1C] | (S)-N-(2,5-Dimethyl-4-((3-(2-(piperidin-3-ylamino)pyrimidin-4-yl)pyridin-2-yl)oxy)phenyl)propane-1-sulfonamide |
| 127 | 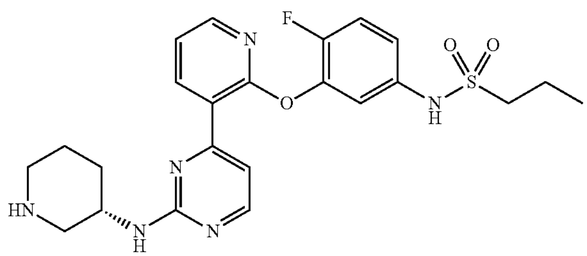 [SMILES: CCCS(=O)(=O)Nc1ccc(F)c(Oc2ncccc2-c2ccnc(N[C@H]3CCCNC3)n2)c1] | (S)-N-(4-fluoro-3-((3-(2-(piperidin-3-ylamino)pyrimidin-4-yl)pyridin-2-yl)oxy)phenyl)propane-1-sulfonamide |
| 128 | 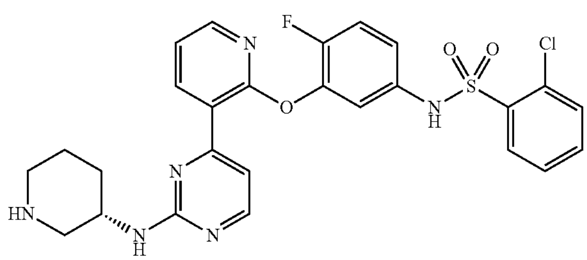 [SMILES: O=S(=O)(Nc1ccc(F)c(Oc2ncccc2-c2ccnc(N[C@H]3CCCNC3)n2)c1)c1ccccc1Cl] | (S)-2-Chloro-N-(4-fluoro-3-((3-(2-(piperidin-3-ylamino)pyrimidin-4-yl)pyridin-2-yl)oxy)phenyl)benzenesulfonamdie |
| 129 | 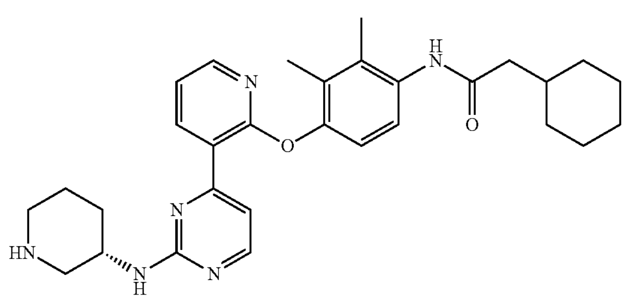 [SMILES: Cc1c(NC(=O)CC2CCCCC2)ccc(Oc2ncccc2-c2ccnc(N[C@H]3CCCNC3)n2)c1C] | (S)-2-Cyclohexyl-N-(2,3-dimethyl-4-((3-(2-(piperiidn-3-ylamino)pyrimidin-4-yl)pyridin-2-yl)oxy)phenyl)acetamide |

TABLE 1-continued

| No. | Structure | Name |
|---|---|---|
| 130 | 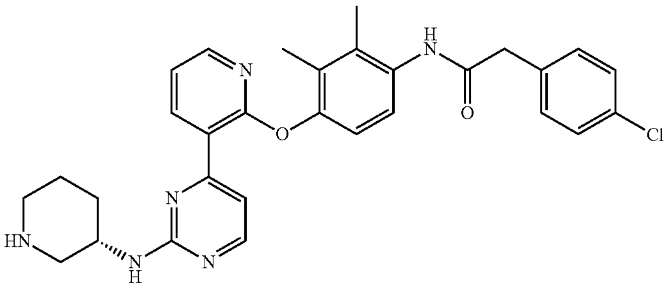 [SMILES: Cc1c(NC(=O)Cc2ccc(Cl)cc2)ccc(Oc2ncccc2-c2ccnc(N[C@H]3CCCNC3)n2)c1C] | (S)-2-(4-Chlorophenyl)-N-(2,3-dimethyl-4-((3-(2-(piperidin-3-ylamino)pyrimidin-4-yl)pyridin-2-yl)oxy)phenyl)acetamide |
| 131 | 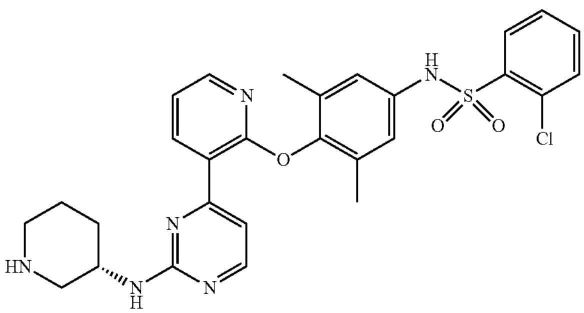 [SMILES: Cc1cc(NS(=O)(=O)c2ccccc2Cl)cc(C)c1Oc1ncccc1-c1ccnc(N[C@H]2CCCNC2)n1] | (S)-2-chloro-N-(3,5-dimethyl-4-((3-(2-(piperidin-3-ylamino)pyrimiin-4-yl)pyridin-2-yl)oxy)phenyl)benzenesulfonamide |
| 132 | 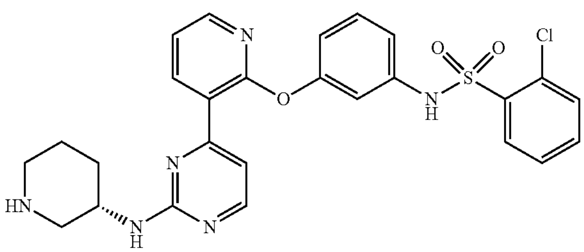 [SMILES: O=S(=O)(Nc1cccc(Oc2ncccc2-c2ccnc(N[C@H]3CCCNC3)n2)c1)c1ccccc1Cl] | (S)-2-chloro-N-(3-((3-(2-(piperidin-3-ylamino)pyrimidin-4-yl)pyridin-2-yl)oxy)phenyl)benzenesulfonamide |
| 133 | 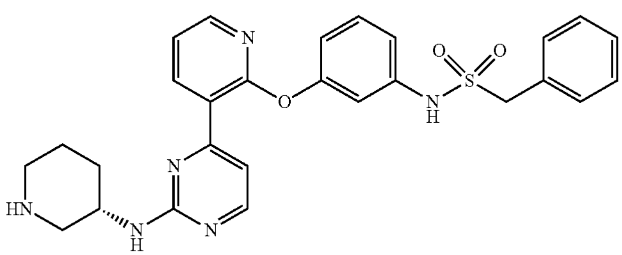 [SMILES: O=S(=O)(Cc1ccccc1)Nc1cccc(Oc2ncccc2-c2ccnc(N[C@H]3CCCNC3)n2)c1] | (S)-1-phenyl-N-(3-((3-(2-(piperidin-3-ylamino)pyrimidi-4-yl)pyridin-2-yl)oxy)phenyl)methanesulfonamide |
| 134 | 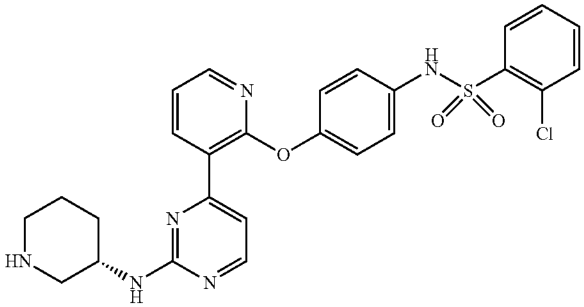 [SMILES: O=S(=O)(Nc1ccc(Oc2ncccc2-c2ccnc(N[C@H]3CCCNC3)n2)cc1)c1ccccc1Cl] | (S)-2-chloro-N-(4-((3-(2-(piperidin-3-ylamino)pyrimidin-4-yl)pyridin-2-yl)oxy)phenyl)benzenesulfoanmdie |

TABLE 1-continued

| No. | Structure | Name |
|---|---|---|
| 135 | 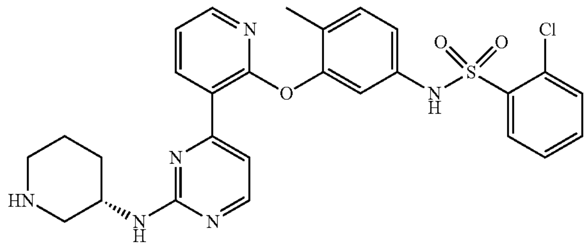 [SMILES: Cc1ccc(NS(=O)(=O)c2ccccc2Cl)cc1Oc1ncccc1-c1ccnc(N[C@H]2CCCNC2)n1] | (S)-2-chloro-N-(4-methyl-3-((3-(2-(piperidin-3-ylamino)pyrimidin-4-yl)pyridin-2-yl)oxy)phenyl)benzenesulfonamide |
| 136 | 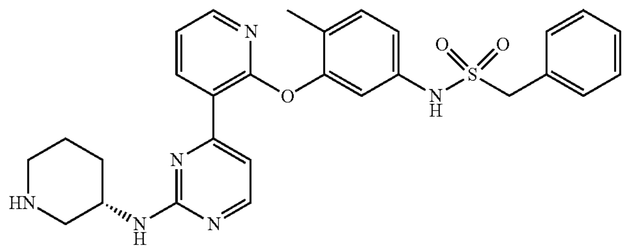 [SMILES: Cc1ccc(NS(=O)(=O)Cc2ccccc2)cc1Oc1ncccc1-c1ccnc(N[C@H]2CCCNC2)n1] | (S)-N-(4-methyl-3-((3-(2-(piperidin-3-ylamino)pyrimidin-4-yl)pyridin-2-yl)oxy)phenyl)-1-phenylmethaensulfonamide |
| 137 | 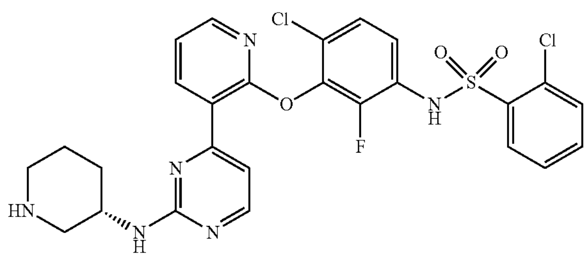 [SMILES: O=S(=O)(Nc1ccc(Cl)c(Oc2ncccc2-c2ccnc(N[C@H]3CCCNC3)n2)c1F)c1ccccc1Cl] | (S)-2-chloro-N-(4-chloro-2-fluoro-3-((3-(2-(piperidin-3-ylamino)pyrimidin-4-yl)pyridin-2-yl)oxy)phenyl)benzenesulfonamide |
| 138 | 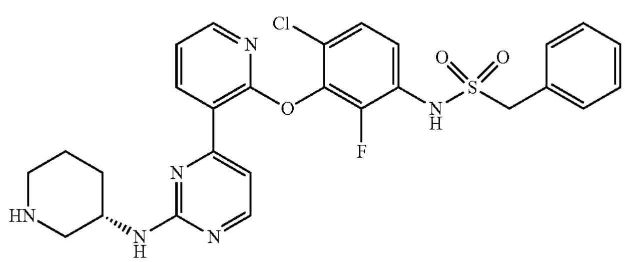 [SMILES: O=S(=O)(Cc1ccccc1)Nc1ccc(Cl)c(Oc2ncccc2-c2ccnc(N[C@H]3CCCNC3)n2)c1F] | (S)-N-(4-chloro-2-fluoro-3-((3-(2-(piperidin-3-ylamino)pyrimidin-4-yl)pyridin-2-yl)oxy)phenyl)-1-phenylmethanesulfonamide |
| 139 | 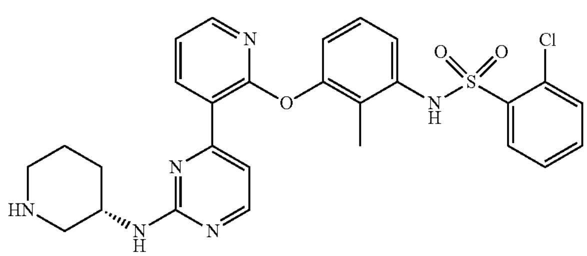 | (S)-2-chloro-N-(2-methyl-3-((3-(2-(piperidin-3-ylamino)pyrimidin-4-yl)pyridin-2-yl)oxy)phenyl)benzenesulfonamide |
| 140 | 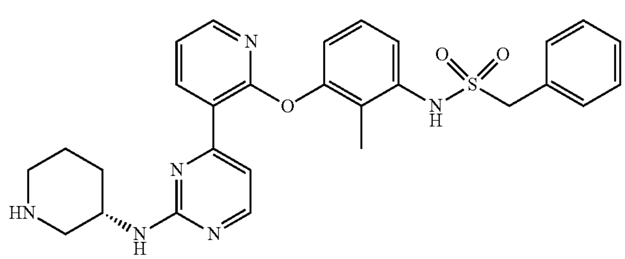 | (S)-N-(2-methyl-3-((3-(2-(piperidin-3-ylamino)pyrimidin-4-yl)pyridin-2-yl)oxy)phenyl)-1-phenylmethanesulfonamide |

TABLE 1-continued

| No. | Structure | Name |
|---|---|---|
| 141 | 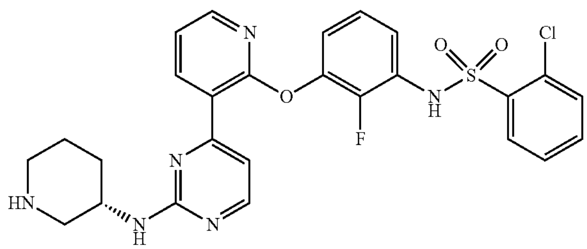 [SMILES: Cc1c(NS(=O)(=O)c2ccccc2Cl)cccc1Oc1ncccc1-c1ccnc(N[C@H]2CCCNC2)n1] | (S)-2-chloro-N-(2-fluoro-3-((3-(2-(piperidin-3-ylamino)pyrimidin-4-yl)pyridin-2-yl)oxy)phenyl)benzenesulfonamide |
| 142 | 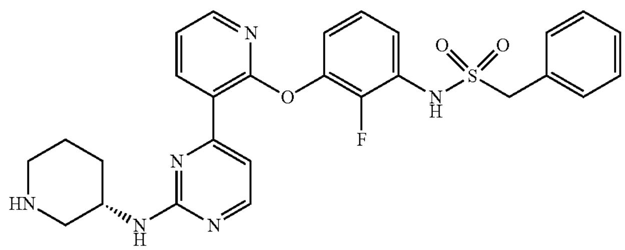 [SMILES: Cc1c(NS(=O)(=O)Cc2ccccc2)cccc1Oc1ncccc1-c1ccnc(N[C@H]2CCCNC2)n1] | (S)-N-(2-fluoro-3-((3-(2-(piperidin-3-ylamino)pyrimidin-4-yl)pyridin-2-yl)oxy)phenyl)-1-phenylmethanesulfonamide |
| 143 | 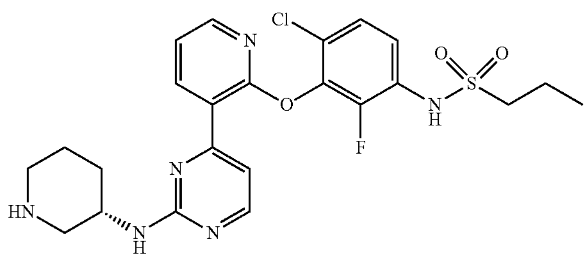 [SMILES: CCCS(=O)(=O)Nc1ccc(Cl)c(Oc2ncccc2-c2ccnc(N[C@H]3CCCNC3)n2)c1F] | (S)-N-(4-chloro-2-fluoro-3-((3-(2-(piperidin-3-ylamino)pyrimidin-4-yl)pyridin-2-yl)oxy)phenyl)propane-1-sulfonamide |
| 144 | 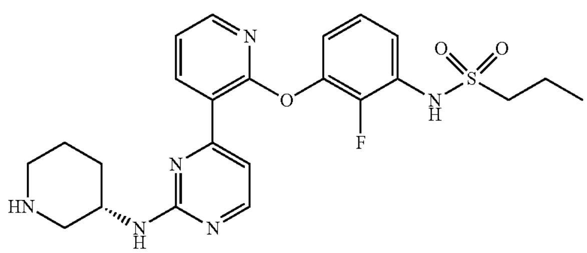 [SMILES: CCCS(=O)(=O)Nc1cccc(Oc2ncccc2-c2ccnc(N[C@H]3CCCNC3)n2)c1F] | (S)-N-(2-fluoro-3-((3-(2-(piperidin-3-ylamino)pyrimidin-4-yl)pyridin-2-yl)oxy)phenyl)propane-1-sulfonamide |
| 145 | 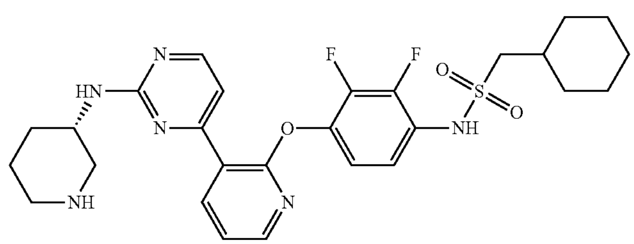 [SMILES: O=S(=O)(CC1CCCCC1)Nc1ccc(Oc2ncccc2-c2ccnc(N[C@H]3CCCNC3)n2)c(F)c1F] | (S)-1-cyclohexyl-N-(2,3-difluoro-4-((3-(2-(piperidin-3-ylamino)pyrimidin-4-yl)pyridin-2-yl)oxy)phenyl)methanesulfonamide |
| 146 | 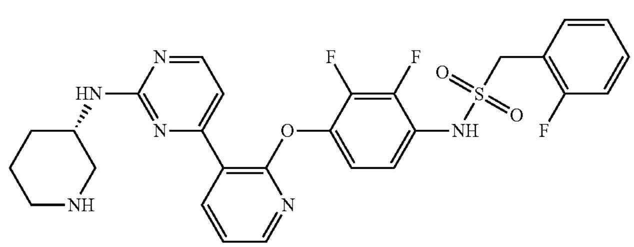 [SMILES: O=S(=O)(Cc1ccccc1F)Nc1ccc(Oc2ncccc2-c2ccnc(N[C@H]3CCCNC3)n2)c(F)c1F] | (S)-N-(2,3-difluoro-4-((3-(2-(piperidin-3-ylamino)pyrimidin-4-yl)pyridin-2-yl)oxy)phenyl)-1-(2-fluorophenyl)methanesulfonamide |

TABLE 1-continued

| No. | Structure | Name |
|---|---|---|
| 147 | 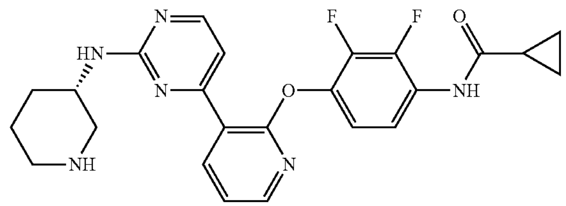 [SMILES: O=C(Nc1ccc(Oc2ncccc2-c2ccnc(N[C@H]3CCCNC3)n2)c(F)c1F)C1CC1] | (S)-N-(2,3-difluoro-4-(3-(2-(piperidin-3-ylamino)pyrimidin-4-yl)pyridin-2-yloxy)phenyl)cyclopropanecarboxamide |
| 148 | 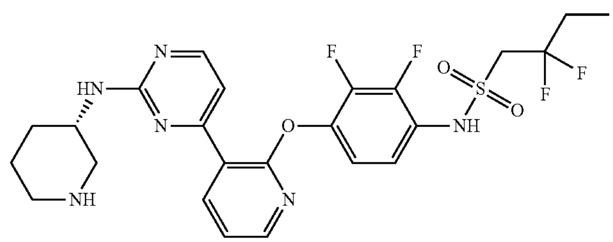 [SMILES: CCC(F)(F)CS(=O)(=O)Nc1ccc(Oc2ncccc2-c2ccnc(N[C@H]3CCCNC3)n2)c(F)c1F] | (S)-N-(2,3-Difluoro-4-((3-(2-(piperidin-3-ylamino)pyrimidin-4-yl)pyridin-2-yl)oxy)phenyl)-2,2-difluorobutane-1-sulfonamide |
| 149 | 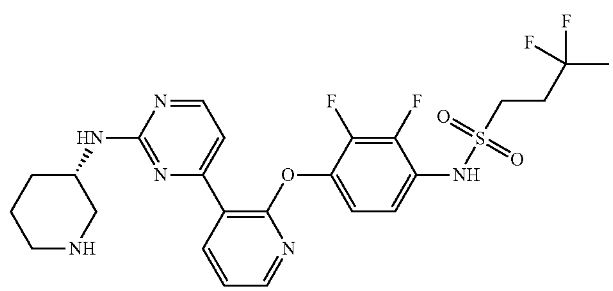 [SMILES: CC(F)(F)CCS(=O)(=O)Nc1ccc(Oc2ncccc2-c2ccnc(N[C@H]3CCCNC3)n2)c(F)c1F] | (S)-N-(2,3-difluoro-4-((3-(2-(piperidin-3-ylamino)pyrimidin-4-yl)pyridin-2-yl)oxy)phenyl)-3,3-difluorobutane-1-sulfonamide |
| 150 | 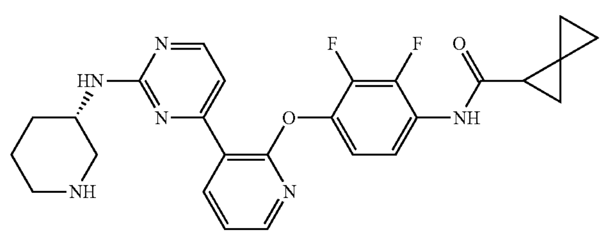 [SMILES: O=C(Nc1ccc(Oc2ncccc2-c2ccnc(N[C@H]3CCCNC3)n2)c(F)c1F)C1CC12CC2] | N-(2,3-difluoro-4-((3-(2-(((S)-piperidin-3-yl)amino)pyrimidin-4-yl)pyridin-2-yl)oxy)phenyl)spiro[2.2]pentane-1-carboxamide |
| 151 | 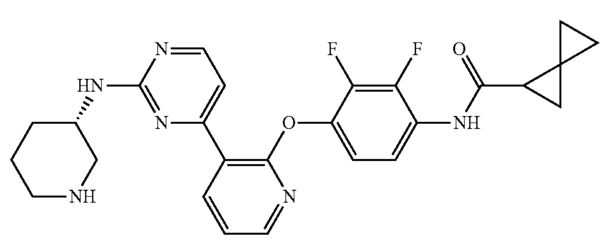 [SMILES: O=C(Nc1ccc(Oc2ncccc2-c2ccnc(N[C@H]3CCCNC3)n2)c(F)c1F)C1CC12CC2] | N-(2,3-difluoro-4-((3-(2-(((S)-piperidin-3-yl)amino)pyrimidin-4-yl)pyridin-2-yl)oxy)phenyl)spiro[2.2]pentane-1-carboxamide |
| 152 | 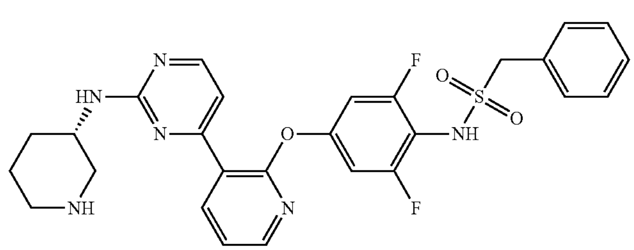 [SMILES: O=S(=O)(Cc1ccccc1)Nc1c(F)cc(Oc2ncccc2-c2ccnc(N[C@H]3CCCNC3)n2)cc1F] | (S)-N-(2,6-difluoro-4-((3-(2-(piperidin-3-ylamino)pyrimidin-4-yl)pyridin-2-yl)oxy)phenyl)-1-phenylmethanesulfonamide |

TABLE 1-continued

| No. | Structure | Name |
|---|---|---|
| 153 | 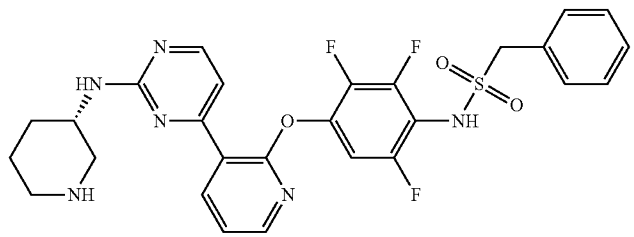 [SMILES: O=S(=O)(Cc1ccccc1)Nc1c(F)cc(Oc2ncccc2-c2ccnc(N[C@H]3CCCNC3)n2)c(F)c1F] | (S)-1-phenyl-N-(2,3,6-trifluoro-4-((3-(2-(piperidin-3-ylamino)pyrimidin-4-yl)pyridin-2-yl)oxy)phenyl)methanesulfonamide |
| 154 | 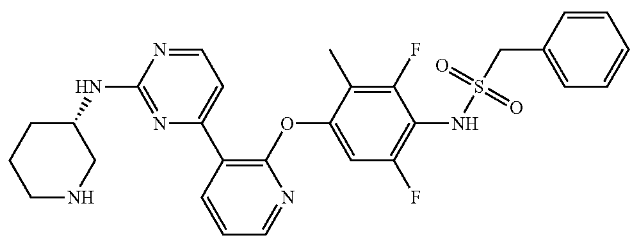 | (S)-N-(2,6-difluoro-3-methyl-4-(3-(2-(piperidin-3-ylamino)pyrimidin-4-yl)pyridin-2-yloxy)phenyl)(phenyl)methanesulfonamide |
| 155 | 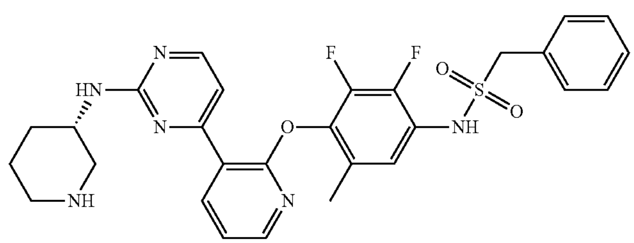 | (S)-N-(2,3-difluoro-5-methyl-4-((3-(2-(piperidin-3-ylamino)pyrimidin-4-yl)pyridin-2-yl)oxy)phenyl)-1-phenylmethanesulfonamide |
| 156 | 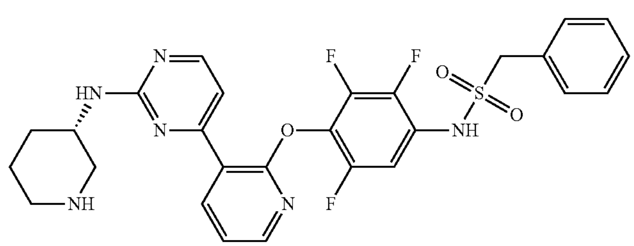 [SMILES: O=S(=O)(Cc1ccccc1)Nc1cc(F)c(Oc2ncccc2-c2ccnc(N[C@H]3CCCNC3)n2)c(F)c1F] | (S)-1-phenyl-N-(2,3,5-trifluoro-4-((3-(2-(piperidin-3-ylamino)pyrimidin-4-yl)pyridin-2-yl)oxy)phenyl)methanesulfonamide |
| 157 | 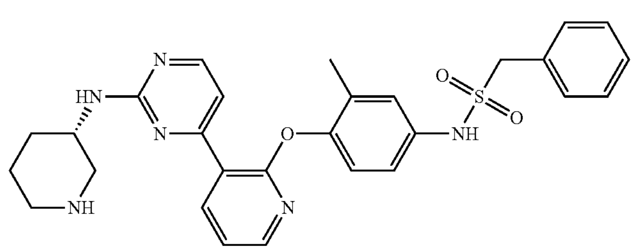 | (S)-N-(3-methyl-4-((3-(2-(piperidin-3-ylamino)pyrimidin-4-yl)pyridin-2-yl)oxy)phenyl)-1-phenylmethanesulfonamide |
| 158 | 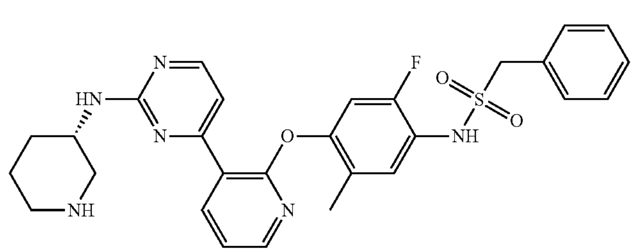 | (S)-N-(2-fluoro-5-methyl-4-(3-(2-(piperidin-3-ylamino)pyrimidin-4-yl)pyridin-2-yloxy)phenyl)(phenyl)methanesulfonamide |

TABLE 1-continued

| No. | Structure | Name |
|---|---|---|
| 159 | 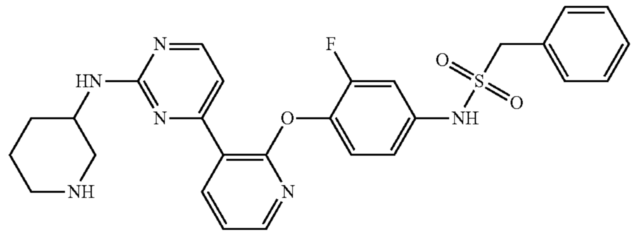 [SMILES: Cc1cc(NS(=O)(=O)Cc2ccccc2)ccc1Oc1ncccc1-c1ccnc(N[C@H]2CCCNC2)n1] | (S)-N-(3-fluoro-4-((3-(2-(piperidin-3-ylamino)pyrimidin-4-yl)pyridin-2-yl)oxy)phenyl)-1-phenylmethanesulfonamide |
| 160 | 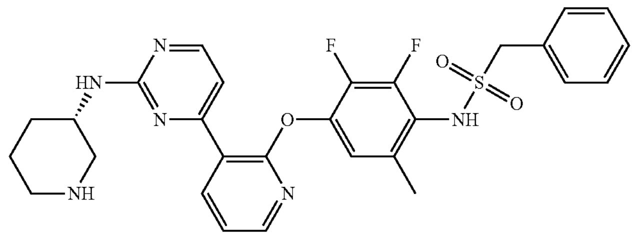 | (S)-N-(2,3-difluoro-6-methyl-4-((3-(2-(piperiidn-3-ylamino)pyrimidin-4-yl)pyridin-2-yl)oxy)phenyl)-1-phenylmethanesulfonamide |
| 161 | 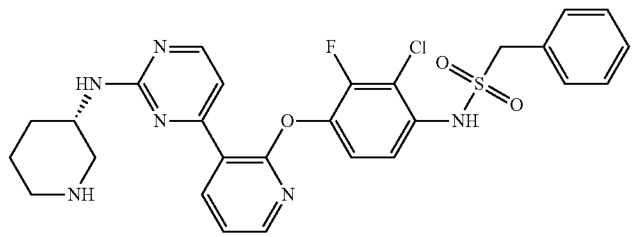 [SMILES: O=S(=O)(Cc1ccccc1)Nc1ccc(Oc2ncccc2-c2ccnc(N[C@H]3CCCNC3)n2)c(F)c1Cl] | (S)-N-(2-chloro-3-fluoro-4-((3-(2-(piperidin-3-ylamino)pyrimidin-4-yl)pyridin-2-yl)oxy)phenyl)-1-phenylmethanesulfonamide |
| 162 | 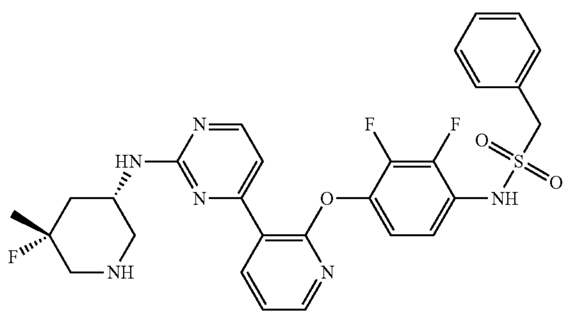 [SMILES: C[C@]1(F)CNC[C@@H](Nc2nccc(-c3cccnc3Oc3ccc(NS(=O)(=O)Cc4ccccc4)c(F)c3F)n2)C1] | N-(2,3-difluoro-4-((3-(2-(((3S,5R)-5-fluoro-5-methylpiperidin-3-yl)amino)pyrimidin-4-yl)pyridin-2-yl)oxy)phenyl)-1-phenylmethanesulfonamide |
| 163 | 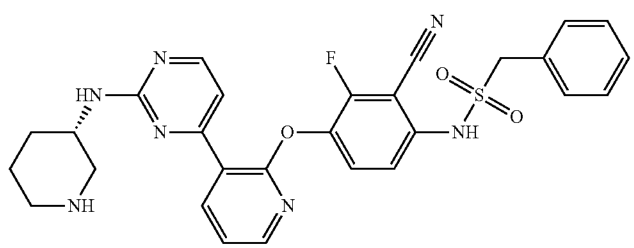 [SMILES: N#Cc1c(NS(=O)(=O)Cc2ccccc2)ccc(Oc2ncccc2-c2ccnc(N[C@H]3CCCNC3)n2)c1F] | (S)-N-(2-cyano-3-fluoro-4-((3-(2-(piperidin-3-ylamino)pyrimidin-4-yl)pyridin-2-yl)oxy)phenyl)-1-phenylmethanesulfonamide |
| 164 | 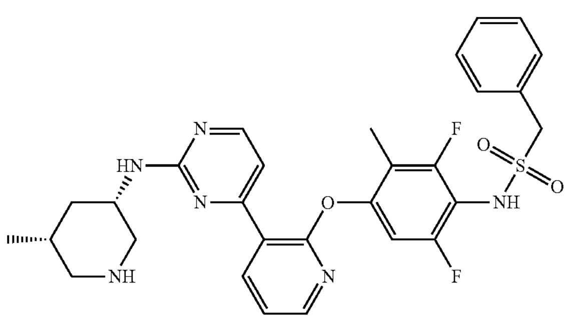 [SMILES: Cc1c(Oc2ncccc2-c2ccnc(N[C@@H]3CNC[C@H](C)C3)n2)cc(F)c(NS(=O)(=O)Cc2ccccc2)c1F] | N-(2,6-difluoro-3-methyl-4-((3-(2-(((3S,5R)-5-methyl-3-piperidyl)amino)pyrimidin-4-yl)-2-pyridyl)oxy)phenyl)-1-phenyl-methanesulfonamide |

TABLE 1-continued

| No. | Structure | Name |
|---|---|---|
| 165 | 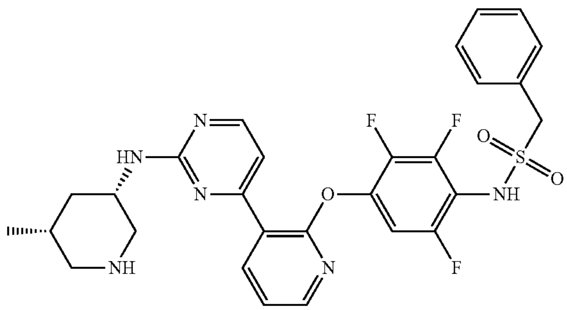 [SMILES: C[C@H]1CNC[C@@H](Nc2nccc(-c3cccnc3Oc3cc(F)c(NS(=O)(=O)Cc4ccccc4)c(F)c3F)n2)C1] | 1-phenyl-N-(2,3,6-trifluoro-4-((3-(2-(((3S,5R)-5-methyl-3-piperidyl)amino)pyrimidin-4-yl)-2-pyridyl)oxy)phenyl)methanesulfonamide |
| 166 | 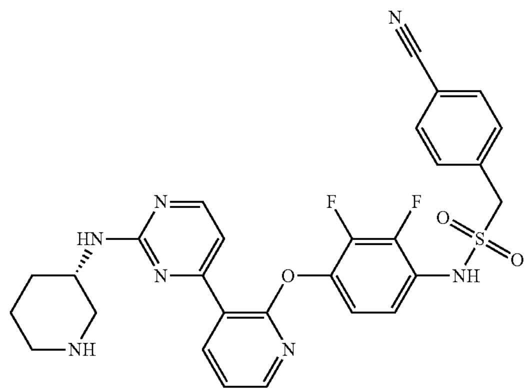 [SMILES: N#Cc1ccc(CS(=O)(=O)Nc2ccc(Oc3ncccc3-c3ccnc(N[C@H]4CCCNC4)n3)c(F)c2F)cc1] | (S)-1-(4-cyanophenyl)-N-(2,3-difluoro-4-((3-(2-(piperidin-3-ylamino)pyrimidin-4-yl)pyridin-2-yl)oxy)phenyl)methanesulfonamide |
| 167 | 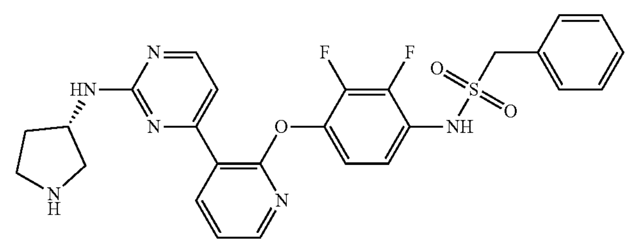 [SMILES: O=S(=O)(Cc1ccccc1)Nc1ccc(Oc2ncccc2-c2ccnc(N[C@H]3CCNC3)n2)c(F)c1F] | (S)-N-(2,3-difluoro-4-((3-(2-(pyrrolidin-3-ylamino)pyrimidin-4-yl)pyridin-2-yl)oxy)phenyl)-1-phenylmethanesulfonamide |
| 168 | 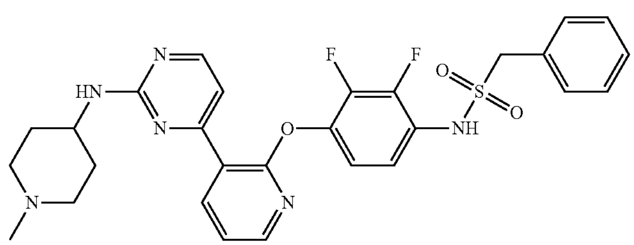 [SMILES: CN1CCC(Nc2nccc(-c3cccnc3Oc3ccc(NS(=O)(=O)Cc4ccccc4)c(F)c3F)n2)CC1] | N-(2,3-difluoro-4-((3-(2-((1-methylpiperidin-4-yl)amino)pyrimidin-4-yl)pyridin-2-yl)oxy)phenyl)-1-phenylmethanesulfonamide |
| 169 | 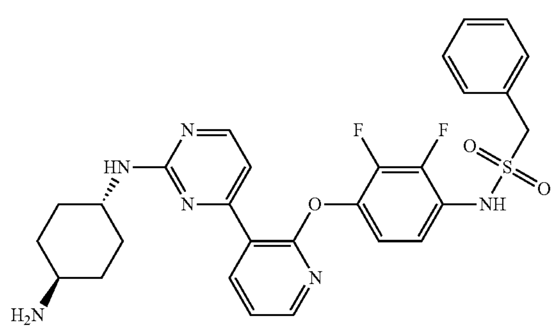 [SMILES: N[C@H]1CC[C@H](Nc2nccc(-c3cccnc3Oc3ccc(NS(=O)(=O)Cc4ccccc4)c(F)c3F)n2)CC1] | N-(4-((3-(2-(((1r,4r)-4-aminocyclohexyl)amino)pyrimidin-4-yl)pyridin-2-yl)oxy)-2,3-difluorophenyl)-1-phenylmethanesulfonamide |

TABLE 1-continued

| No. | Structure | Name |
|---|---|---|
| 170 | 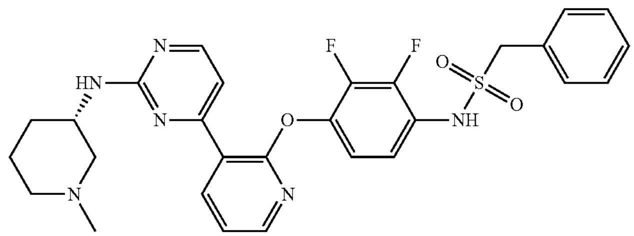 [SMILES: CN1CCC[C@H](Nc2nccc(-c3cccnc3Oc3ccc(NS(=O)(=O)Cc4ccccc4)c(F)c3F)n2)C1] | (S)-N-(2,3-difluoro-4-((3-(2-((1-methylpiperidin-3-yl)amino)pyrimidin-4-yl)pyridin-2-yl)oxy)phenyl)-1-phenylmethanesulfonamide |
| 171 | 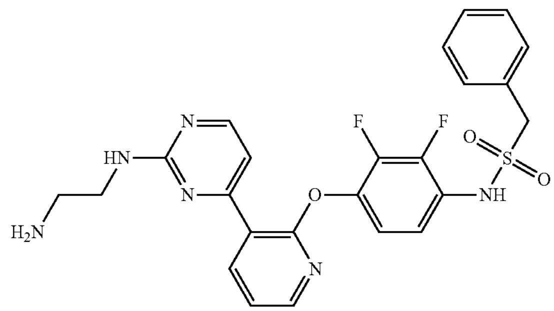 [SMILES: NCCNc1nccc(-c2cccnc2Oc2ccc(NS(=O)(=O)Cc3ccccc3)c(F)c2F)n1] | N-(4-((3-(2-((2-aminoethyl)amino)pyrimidin-4-yl)pyridin-2-yl)oxy)-2,3-difluorophenyl)-1-phenylmethanesulfonamide |
| 172 | 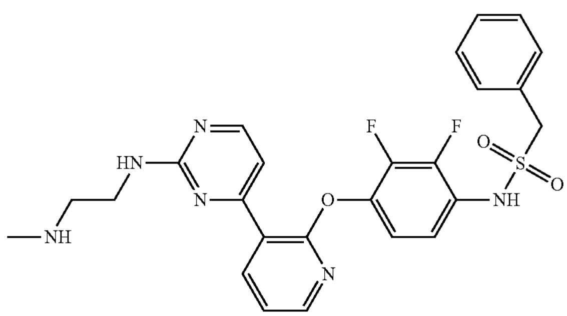 [SMILES: CNCCNc1nccc(-c2cccnc2Oc2ccc(NS(=O)(=O)Cc3ccccc3)c(F)c2F)n1] | N-(2,3-difluoro-4-((3-(2-(2-(methylamino)ethylamino)pyrimidin-4-yl)-2-pyridyl)oxy)phenyl)-1-phenyl-methanesulfonamide |
| 173 | 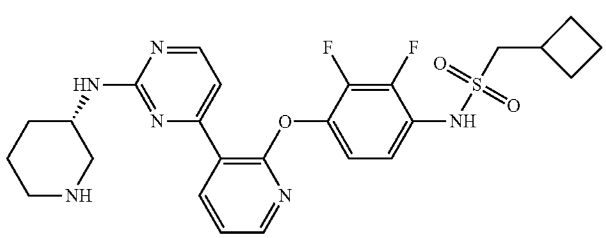 [SMILES: O=S(=O)(CC1CCC1)Nc1ccc(Oc2ncccc2-c2ccnc(N[C@H]3CCCNC3)n2)c(F)c1F] | (S)-1-cyclobutyl-N-(2,3-difluoro-4-((3-(2-(piperidin-3-ylamino)pyrimidin-4-yl)pyridin-2-yl)oxy)phenyl)methanesulfonamide |
| 174 | 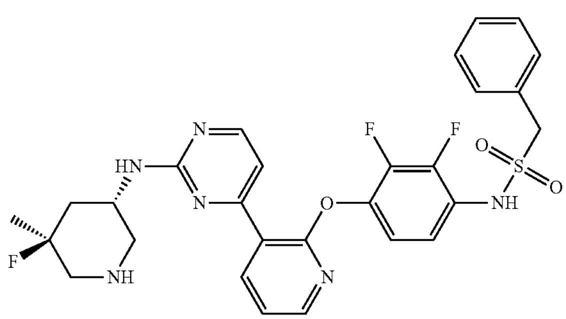 [SMILES: C[C@@]1(F)CNC[C@@H](Nc2nccc(-c3cccnc3Oc3ccc(NS(=O)(=O)Cc4ccccc4)c(F)c3F)n2)C1] | N-(2,3-difluoro-4-((3-(2-(((3S,5S)-5-fluoro-5-methylpiperidin-3-yl)amino)pyrimidin-4-yl)pyridin-2-yl)oxy)phenyl)-1-phenylmethanesulfonamide |

TABLE 1-continued

| No. | Structure | Name |
|---|---|---|
| 175 | 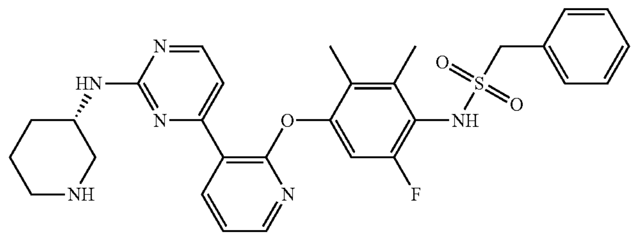 [SMILES: Cc1c(Oc2ncccc2-c2ccnc(N[C@H]3CCCNC3)n2)cc(F)c(NS(=O)(=O)Cc2ccccc2)c1C] | (S)-N-(6-fluoro-2,3-dimethyl-4-((3-(2-(piperidin-3-ylamino)pyrimidin-4-yl)pyridin-2-yl)oxy)phenyl)-1-phenylmethanesulfonamide |
| 176 | 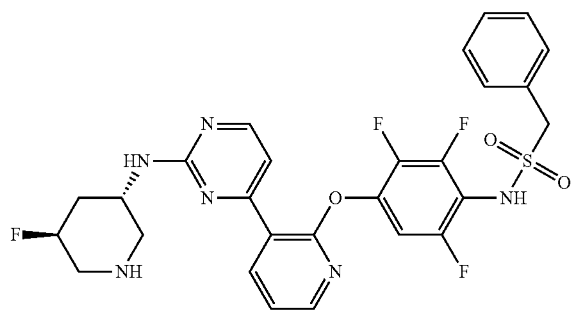 | 1-phenyl-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 177 | 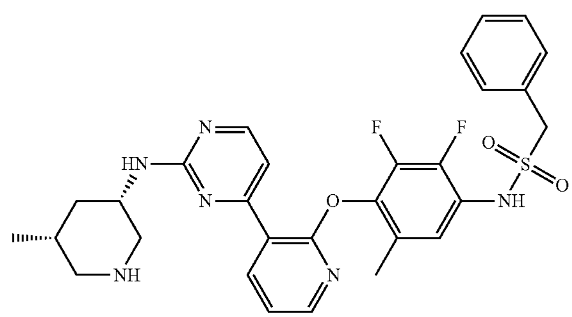 [SMILES: Cc1cc(NS(=O)(=O)Cc2ccccc2)c(F)c(F)c1Oc1ncccc1-c1ccnc(N[C@@H]2CNC[C@H](C)C2)n1] | N-(2,3-difluoro-5-methyl-4-((3-(2-(((3S,5R)-5-methyl-3-piperidyl)amino)pyrimidin-4-yl)-2-pyridyl)oxy)phenyl)-1-phenyl-methanesulfonamide |
| 178 | 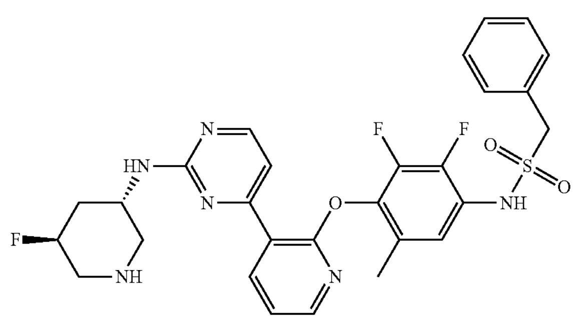 [SMILES: Cc1cc(NS(=O)(=O)Cc2ccccc2)c(F)c(F)c1Oc1ncccc1-c1ccnc(N[C@@H]2CNC[C@@H](F)C2)n1] | N-(2,3-difluoro-4-((3-(2-(((3S,5S)-5-fluoro-3-piperidyl)amino)pyrimidin-4-yl)-2-pyridyl)oxy)-5-methyl-phenyl)-1-phenyl-methanesulfonamide |
| 179 | 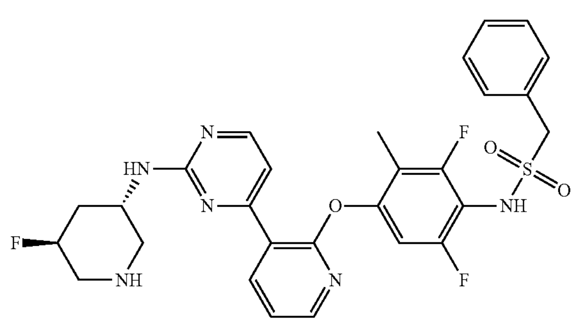 [SMILES: Cc1c(Oc2ncccc2-c2ccnc(N[C@@H]3CNC[C@@H](F)C3)n2)cc(F)c(NS(=O)(=O)Cc2ccccc2)c1F] | N-(2,6-difluoro-4-((3-(2-(((3S,5S)-5-fluoro-3-piperidyl)amino)pyrimidin-4-yl)-2-pyridyl)oxy)-3-methyl-phenyl)-1-phenyl-methanesulfonamide |

TABLE 1-continued

| No. | Structure | Name |
|---|---|---|
| 180 | 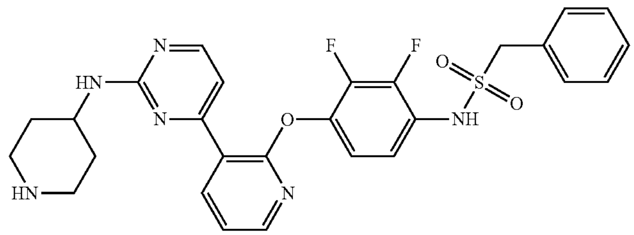 | N-(2,3-difluoro-4-((3-(2-(4-piperidylamino)pyrimidin-4-yl)-2-pyridyl)oxy)phenyl)-1-phenyl-methanesulfonamide |
| 181 | 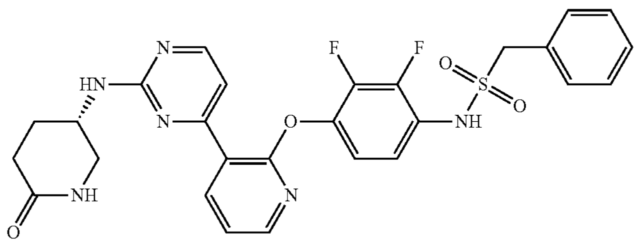 [SMILES: O=C1CC[C@H](Nc2nccc(-c3cccnc3Oc3ccc(NS(=O)(=O)Cc4ccccc4)c(F)c3F)n2)CN1] | (S)-N-(2,3-difluoro-4-((3-(2-((6-oxopiperidin-3-yl)amino)pyrimidin-4-yl)pyridin-2-yl)oxy)phenyl)-1-phenylmethanesulfonamide |
| 182 | 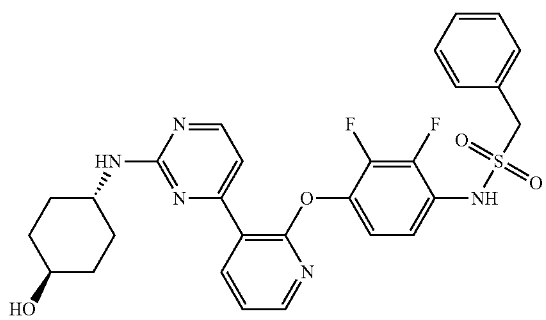 [SMILES: O=S(=O)(Cc1ccccc1)Nc1ccc(Oc2ncccc2-c2ccnc(N[C@H]3CC[C@H](O)CC3)n2)c(F)c1F] | N-(2,3-difluoro-4-((3-(2-(((1r,4r)-4-hydroxycyclohexyl)amino)pyrimidin-4-yl)pyridin-2-yl)oxy)phenyl)-1-phenylmethanesulfonamide |
| 183 | 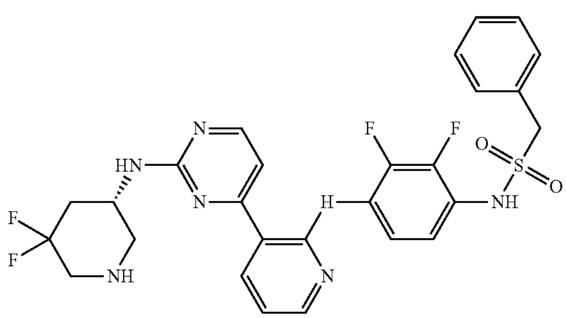 | (S)-N-(4-((3-(2-((5,5-difluoropiperidin-3-yl)amino)pyrimidin-4-yl)pyridin-2-yl)oxy)-2,3-difluorophenyl)-1-phenylmethanesulfonamide |
| 184 | 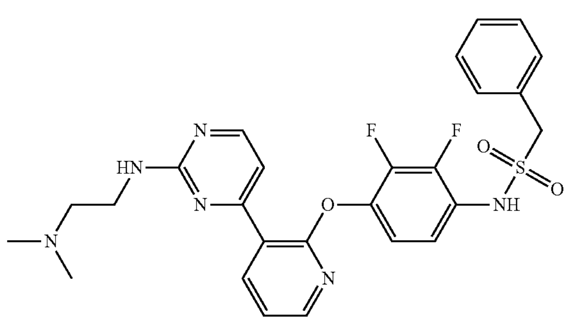 [SMILES: CN(C)CCNc1nccc(-c2cccnc2Oc2ccc(NS(=O)(=O)Cc3ccccc3)c(F)c2F)n1] | N-(4-((3-(2-((2-(dimethylamino)ethyl)amino)pyrimidin-4-yl)pyridin-2-yl)oxy)-2,3-difluorophenyl)-1-phenylmethanesulfonamide |

TABLE 1-continued

| No. | Structure | Name |
|---|---|---|
| 185 186 | | N-(4-((3-(2-(3-azabicyclo[3.1.0]hexan-5-ylamino)pyrimidin-4-yl)-2-pyridyl)oxy)-2,3-difluoro-phenyl)-1-phenyl-methanesulfonamide |
| 187 | 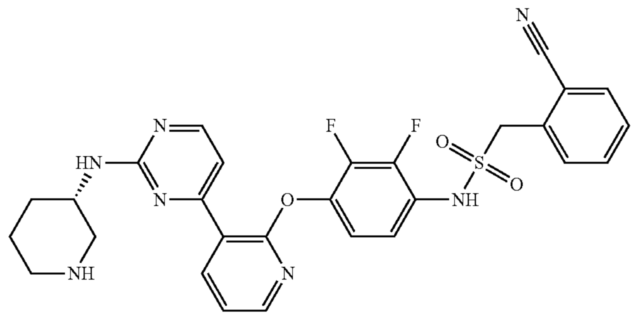 [SMILES: N#Cc1ccccc1CS(=O)(=O)Nc1ccc(Oc2ncccc2-c2ccnc(N[C@H]3CCCNC3)n2)c(F)c1F] | (S)-1-(2-cyanophenyl)-N-(2,3-difluoro-4-((3-(2-(piperidin-3-ylamino)pyrimidin-4-yl)pyridin-2-yl)oxy)phenyl)methanesulfonamide |
| 188 | 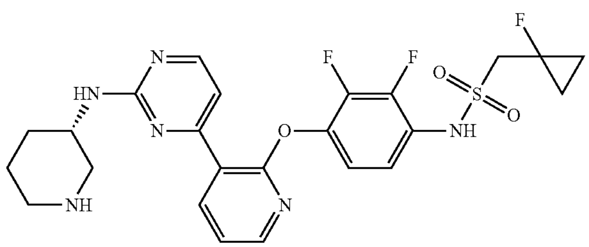 [SMILES: O=S(=O)(CC1(F)CC1)Nc1ccc(Oc2ncccc2-c2ccnc(N[C@H]3CCCNC3)n2)c(F)c1F] | (S)-N-(2,3-difluoro-4-((3-(2-(piperidin-3-ylamino)pyrimidin-4-yl)pyridin-2-yl)oxy)phenyl)-1-(1-fluorocyclopropyl)methanesulfonamide |
| 189 | 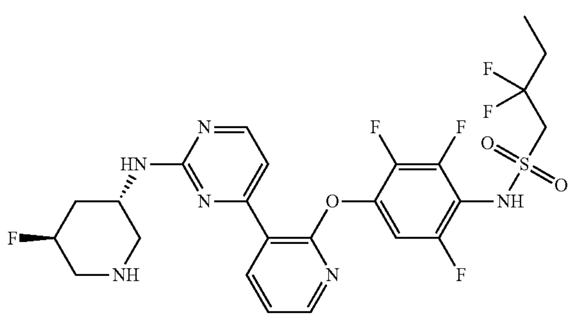 [SMILES: CCC(F)(F)CS(=O)(=O)Nc1c(F)cc(Oc2ncccc2-c2ccnc(N[C@@H]3CNC[C@@H](F)C3)n2)c(F)c1F] | 2,2-difluoro-N-(2,3,6-trifluoro-4-((3-(2-(((3S,5S)-5-fluoro-3-piperidyl)amino)pyrimidin-4-yl)-2-pyridyl)oxy)phenyl)butane-1-sulfonamide |
| 190 | 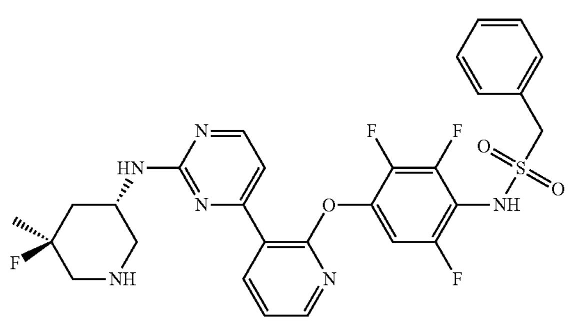 | 1-phenyl-N-(2,3,6-trifluoro-4-((3-(2-(((3S,5S)-5-fluoro-5-methyl-3-piperidyl)amino)pyrimidin-4-yl)-2-pyridyl)oxy)phenyl)methanesulfonamide |

TABLE 1-continued

| No. | Structure | Name |
|---|---|---|
| 191 | 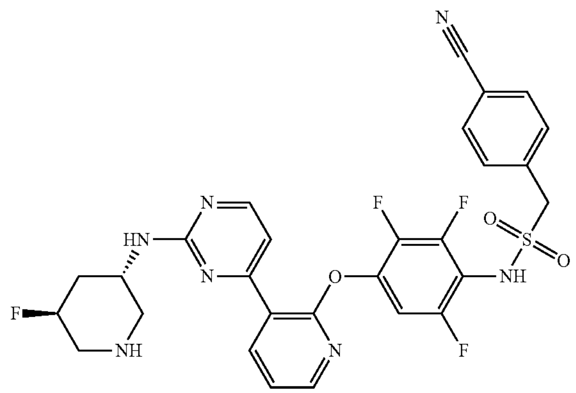 [SMILES: N#Cc1ccc(CS(=O)(=O)Nc2c(F)cc(Oc3ncccc3-c3ccnc(N[C@@H]4CNC[C@@H](F)C4)n3)c(F)c2F)cc1] | 1-(4-cyanophenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 192 | 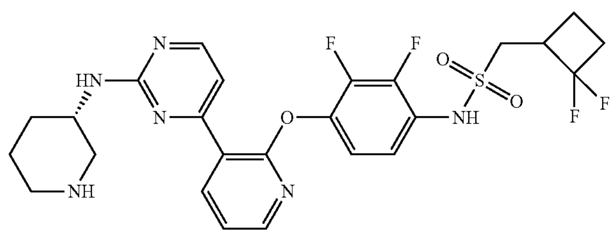 [SMILES: O=S(=O)(CC1CCC1(F)F)Nc1ccc(Oc2ncccc2-c2ccnc(N[C@H]3CCCNC3)n2)c(F)c1F] | N-(2,3-difluoro-4-((3-(2-(((S)-piperidin-3-yl)amino)pyrimidin-4-yl)pyridin-2-yl)oxy)phenyl)-1-(2,2-difluorocyclobutyl)methanesulfonamide |
| 193 | 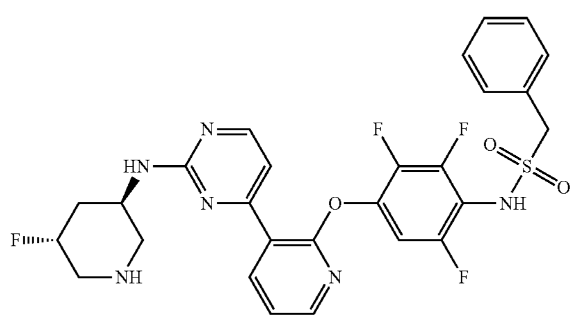 [SMILES: O=S(=O)(Cc1ccccc1)Nc1c(F)cc(Oc2ncccc2-c2ccnc(N[C@H]3CNC[C@H](F)C3)n2)c(F)c1F] | 1-phenyl-N-(2,3,6-trifluoro-4-((3-(2-(((3R,5R)-5-fluoro-3-piperidyl)amino)pyrimidin-4-yl)-2-pyridyl)oxy)phenyl)methanesulfonamide |
| 194 | 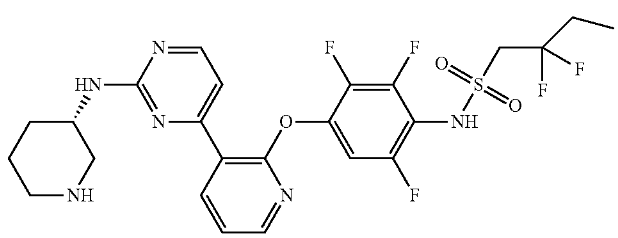 [SMILES: CCC(F)(F)CS(=O)(=O)Nc1c(F)cc(Oc2ncccc2-c2ccnc(N[C@H]3CCCNC3)n2)c(F)c1F] | (S)-2,2-difluoro-N-(2,3,6-trifluoro-4-((3-(2-(piperidin-3-ylamino)pyrimidin-4-yl)pyridin-2-yl)oxy)phenyl)butane-1-sulfonamide |
| 195 | 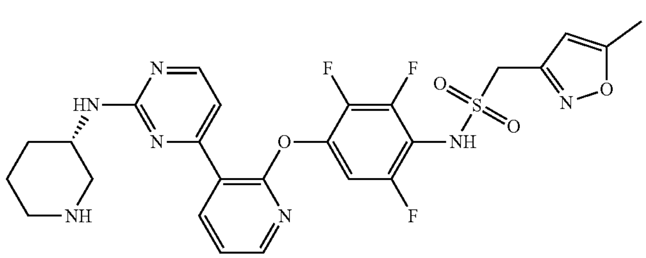 [SMILES: Cc1cc(CS(=O)(=O)Nc2c(F)cc(Oc3ncccc3-c3ccnc(N[C@H]4CCCNC4)n3)c(F)c2F)no1] | (S)-1-(5-methylisoxazol-3-yl)-N-(2,3,6-trifluoro-4-((3-(2-(piperidin-3-ylamino)pyrimidin-4-yl)pyridin-2-yl)oxy)phenyl)methanesulfonamide |

TABLE 1-continued

| No. | Structure | Name |
|---|---|---|
| 196 | 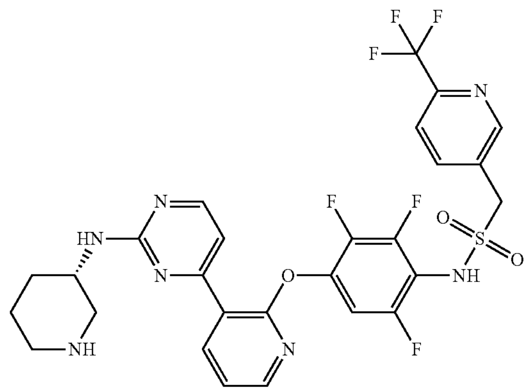 [SMILES: O=S(=O)(Cc1ccc(C(F)(F)F)nc1)Nc1c(F)cc(Oc2ncccc2-c2ccnc(N[C@H]3CCCNC3)n2)c(F)c1F] | (S)-N-(2,3,6-trifluoro-4-((3-(2-(piperidin-3-ylamino)pyrimidin-4-yl)pyridin-2-yl)oxy)phenyl)-1-(6-(trifluoromethyl)pyridin-3-yl)methanesulfonamide |
| 197 | 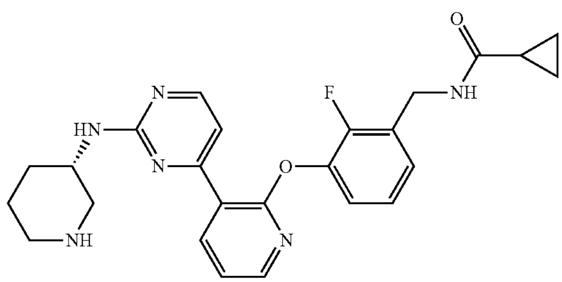 [SMILES: O=C(NCc1cccc(Oc2ncccc2-c2ccnc(N[C@H]3CCCNC3)n2)c1F)C1CC1] | (S)-N-(2-fluoro-3-((3-(2-(piperidin-3-ylamino)pyrimidin-4-yl)pyridin-2-yl)oxy)benzyl)cyclopropanecarboxamide |
| 198 199 | | 1-phenyl-N-(2,3,6-trifluoro-4-((3-(2-(piperidin-3-ylmethyl)pyrimidin-4-yl)pyridin-2-yl)oxy)phenyl)methanesulfonamide |
| 200 201 | | 1,1,1-trifluoro-3-((2-fluoro-3-((3-(2-(((S)-piperidin-3-yl)amino)pyrimidin-4-yl)pyridin-2-yl)oxy)phenyl)amino)propan-2-ol |
| 202 | 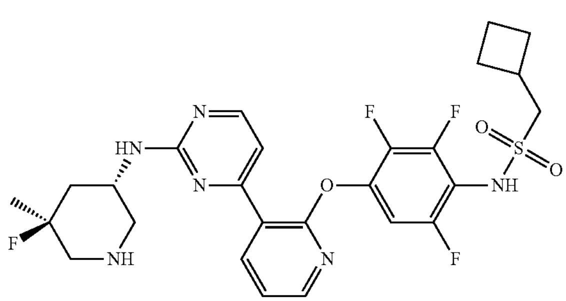 [SMILES: C[C@@]1(F)CNC[C@@H](Nc2nccc(-c3cccnc3Oc3cc(F)c(NS(=O)(=O)CC4CCC4)c(F)c3F)n2)C1] | 1-cyclobutyl-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide |

TABLE 1-continued

| No. | Structure | Name |
|---|---|---|
| 203 | 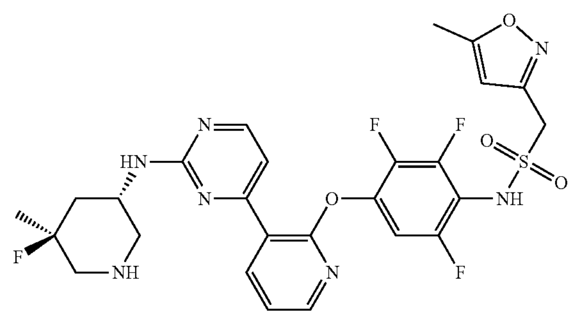 [SMILES: Cc1cc(CS(=O)(=O)Nc2c(F)cc(Oc3ncccc3-c3ccnc(N[C@@H]4CNC[C@@](C)(F)C4)n3)c(F)c2F)no1] | 1-(5-methylisoxazol-3-yl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide |
| 204 | 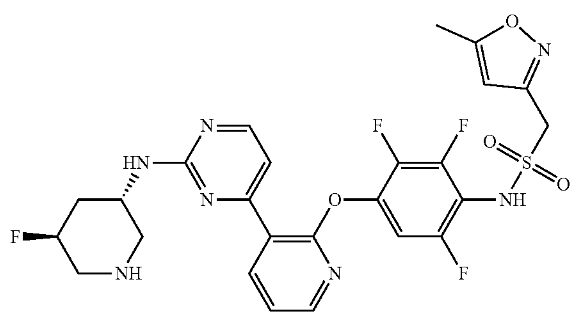 [SMILES: Cc1cc(CS(=O)(=O)Nc2c(F)cc(Oc3ncccc3-c3ccnc(N[C@@H]4CNC[C@@H](F)C4)n3)c(F)c2F)no1] | 1-(5-methylisoxazol-3-yl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 205 | 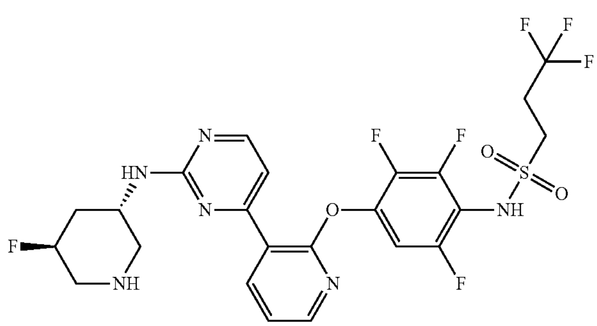 [SMILES: O=S(=O)(CCC(F)(F)F)Nc1c(F)cc(Oc2ncccc2-c2ccnc(N[C@@H]3CNC[C@@H](F)C3)n2)c(F)c1F] | 3,3,3-trifluoro-N-(2,3,6-trifluoro-4-((3-(2-(((3S,5S)-5-fluoro-3-piperidyl)amino)pyrimidin-4-yl)-2-pyridyl)oxy)phenyl)propane-1-sulfonamide |
| 206 | 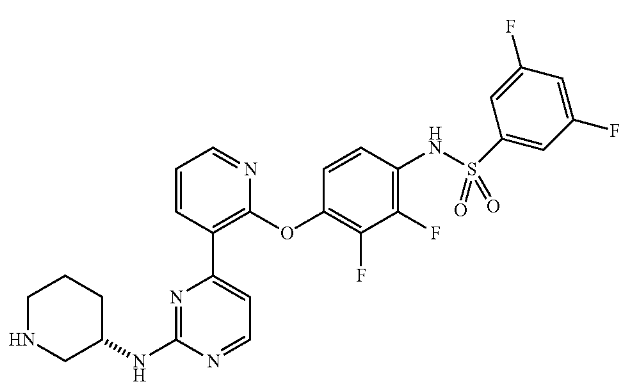 [SMILES: O=S(=O)(Nc1ccc(Oc2ncccc2-c2ccnc(N[C@H]3CCCNC3)n2)c(F)c1F)c1cc(F)cc(F)c1] | (S)-N-(2,3-difluoro-4-((3-(2-(piperidin-3-ylamino)pyrimidin-4-yl)pyridin-2-yl)oxy)phenyl)-3,5-difluorobenzenesulfonamide |

TABLE 1-continued

| No. | Structure | Name |
|---|---|---|
| 207 | 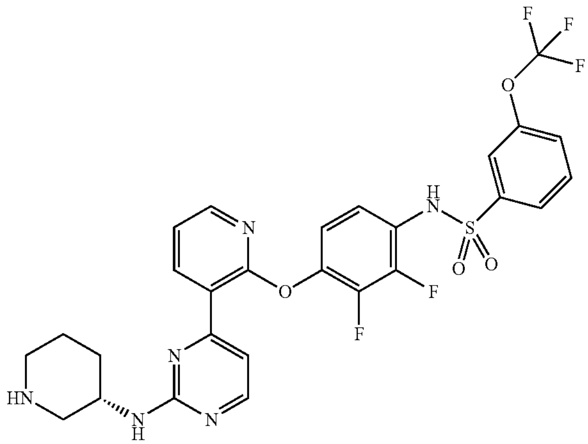 [SMILES: O=S(=O)(Nc1ccc(Oc2ncccc2-c2ccnc(N[C@H]3CCCNC3)n2)c(F)c1F)c1cccc(OC(F)(F)F)c1] | (S)-N-(2,3-difluoro-4-((3-(2-(piperidin-3-ylamino)pyrimidin-4-yl)pyridin-2-yl)oxy)phenyl)-3-(trifluoromethoxy)benzenesulfonamide |
| 208 | 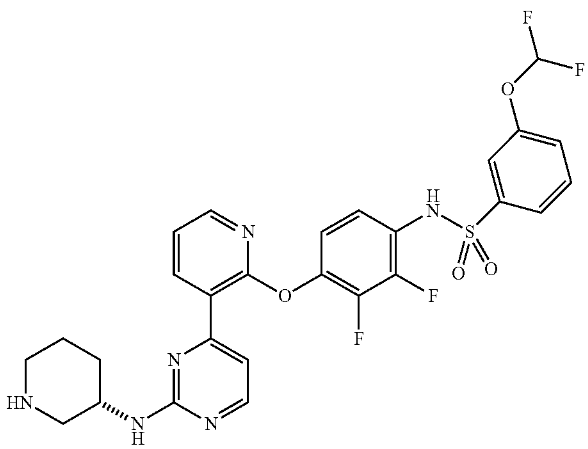 [SMILES: O=S(=O)(Nc1ccc(Oc2ncccc2-c2ccnc(N[C@H]3CCCNC3)n2)c(F)c1F)c1cccc(OC(F)F)c1] | (S)-N-(2,3-difluoro-4-((3-(2-(piperidin-3-ylamino)pyrimidin-4-yl)pyridin-2-yl)oxy)phenyl)-3-(difluoromethoxy)benzenesulfonamide |
| 209 | 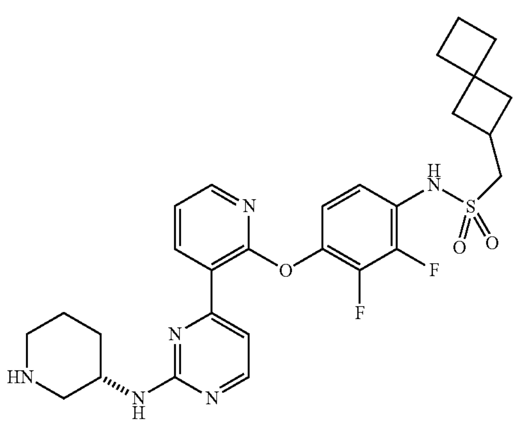 [SMILES: O=S(=O)(CC1CC2(CCC2)C1)Nc1ccc(Oc2ncccc2-c2ccnc(N[C@H]3CCCNC3)n2)c(F)c1F] | (S)-N-(2,3-difluoro-4-((3-(2-(piperidin-3-ylamino)pyrimidin-4-yl)pyridin-2-yl)oxy)phenyl)-1-(spiro[3.3]heptan-2-yl)methanesulfonamide |

TABLE 1-continued

| No. | Structure | Name |
|---|---|---|
| 210 | 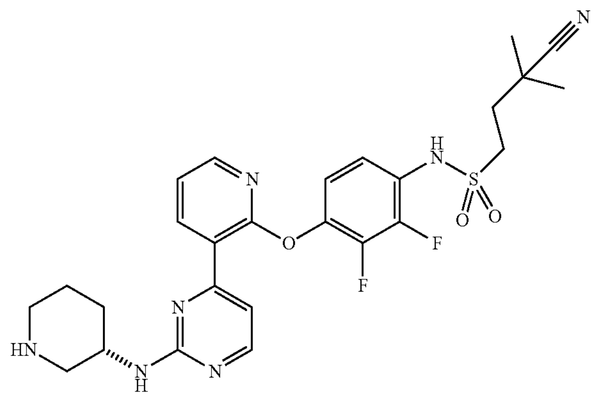 [SMILES: CC(C)(C#N)CCS(=O)(=O)Nc1ccc(Oc2ncccc2-c2ccnc(N[C@H]3CCCNC3)n2)c(F)c1F] | (S)-3-cyano-N-(2,3-difluoro-4-((3-(2-(piperidin-3-ylamino)pyrimidin-4-yl)pyridin-2-yl)oxy)phenyl)-3-methylbutane-1-sulfonamide |
| 211 | 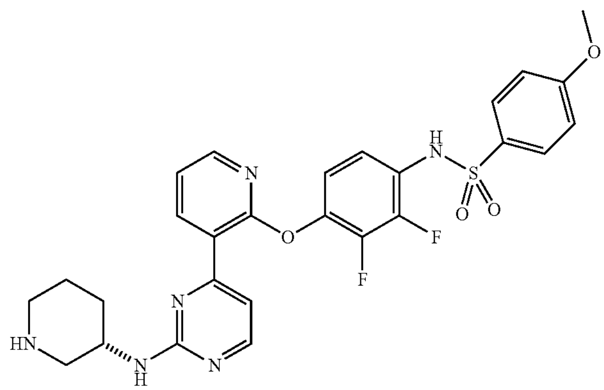 [SMILES: COc1ccc(S(=O)(=O)Nc2ccc(Oc3ncccc3-c3ccnc(N[C@H]4CCCNC4)n3)c(F)c2F)cc1] | (S)-N-(2,3-difluoro-4-((3-(2-(piperidin-3-ylamino)pyrimidin-4-yl)pyridin-2-yl)oxy)phenyl)-4-methoxybenzenesulfonamide |
| 212 | 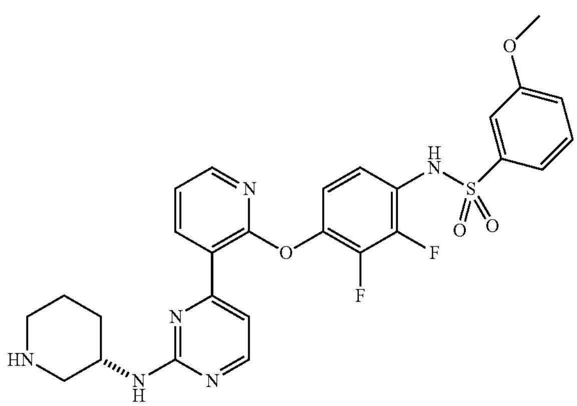 [SMILES: COc1cccc(S(=O)(=O)Nc2ccc(Oc3ncccc3-c3ccnc(N[C@H]4CCCNC4)n3)c(F)c2F)c1] | (S)-N-(2,3-difluoro-4-((3-(2-(piperidin-3-ylamino)pyrimidin-4-yl)pyridin-2-yl)oxy)phenyl)-3-methoxybenzenesulfonamide |
| 213 | 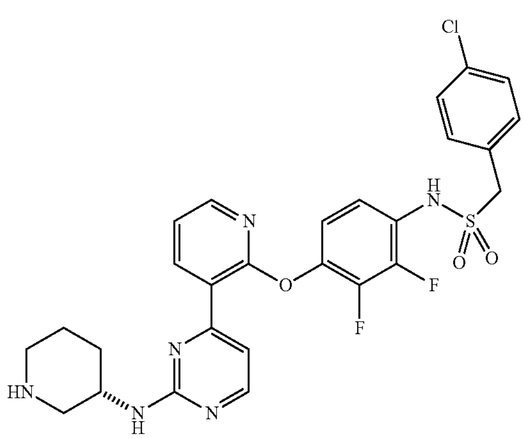 [SMILES: O=S(=O)(Cc1ccc(Cl)cc1)Nc1ccc(Oc2ncccc2-c2ccnc(N[C@H]3CCCNC3)n2)c(F)c1F] | (S)-1-(4-chlorophenyl)-N-(2,3-difluoro-4-((3-(2-(piperidin-3-ylamino)pyrimidin-4-yl)pyridin-2-yl)oxy)phenyl)methanesulfonamide |

TABLE 1-continued

| No. | Structure | Name |
|---|---|---|
| 214 | 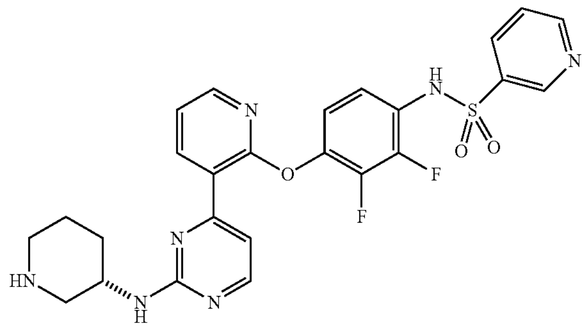 [SMILES: O=S(=O)(Nc1ccc(Oc2ncccc2-c2ccnc(N[C@H]3CCCNC3)n2)c(F)c1F)c1cccnc1] | (S)-N-(2,3-difluoro-4-((3-(2-(piperidin-3-ylamino)pyrimidin-4-yl)pyridin-2-yl)oxy)phenyl)pyridine-3-sulfonamide |
| 215 | 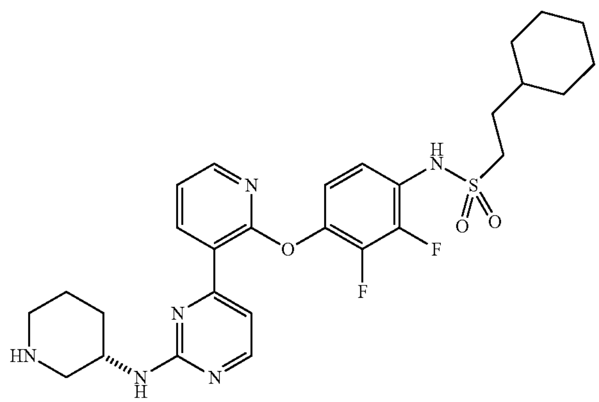 [SMILES: O=S(=O)(CCC1CCCCC1)Nc1ccc(Oc2ncccc2-c2ccnc(N[C@H]3CCCNC3)n2)c(F)c1F] | (S)-2-cyclohexyl-N-(2,3-difluoro-4-((3-(2-(piperidin-3-ylamino)pyrimidin-4-yl)pyridin-2-yl)oxy)phenyl)ethane-1-sulfonamide |
| 216 | 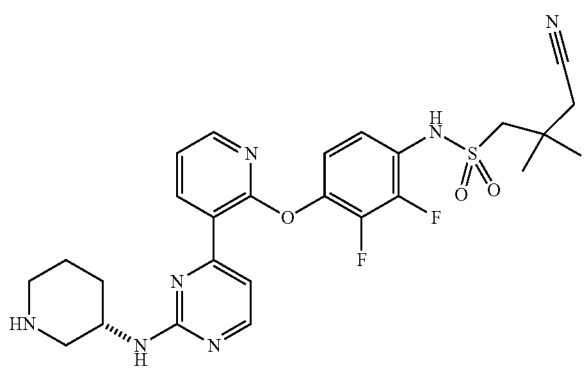 [SMILES: CC(C)(CC#N)CS(=O)(=O)Nc1ccc(Oc2ncccc2-c2ccnc(N[C@H]3CCCNC3)n2)c(F)c1F] | (S)-3-cyano-N-(2,3-difluoro-4-((3-(2-(piperidine-3-ylamino)pyrimidin-4-yl)pyridin-2-yl)oxy)phenyl)-2,2-dimethylpropane-1-sulfonamide |
| 217 | 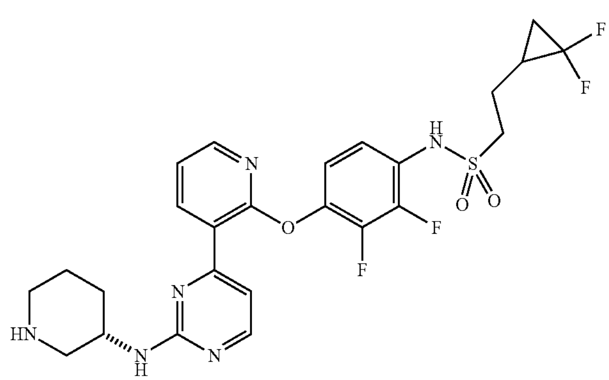 [SMILES: O=S(=O)(CCC1CC1(F)F)Nc1ccc(Oc2ncccc2-c2ccnc(N[C@H]3CCCNC3)n2)c(F)c1F] | N-(2,3-difluoro-4-((3-(2-(((S)-piperidin-3-yl)amino)pyrimidin-4-yl)pyridin-2-yl)oxy)phenyl)-2-(2,2-difluorocyclopropyl)ethane-1-sulfonamide |

TABLE 1-continued

| No. | Structure | Name |
|---|---|---|
| 218 | 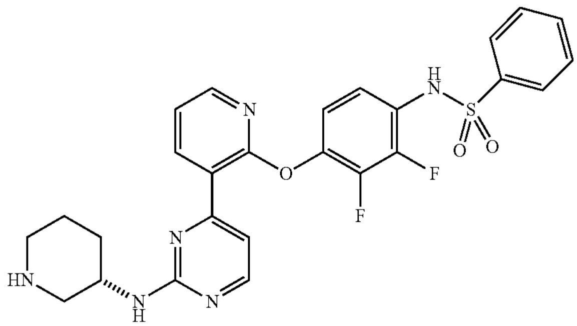 [SMILES: O=S(=O)(Nc1ccc(Oc2ncccc2-c2ccnc(N[C@H]3CCCNC3)n2)c(F)c1F)c1ccccc1] | (S)-N-(2,3-difluoro-4-((3-(2-(piperidin-3-ylamino)pyrimidin-4-yl)pyridin-2-yl)oxy)phenyl)benzenesulfonamide |
| 219 | 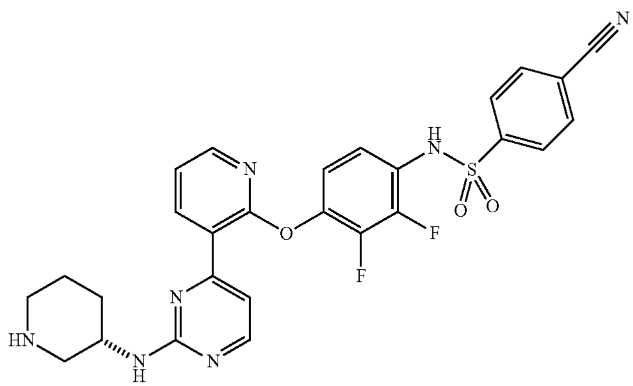 [SMILES: N#Cc1ccc(S(=O)(=O)Nc2ccc(Oc3ncccc3-c3ccnc(N[C@H]4CCCNC4)n3)c(F)c2F)cc1] | (S)-4-cyano-N-(2,3-difluoro-4-((3-(2-(piperidin-3-ylamino)pyrimidin-4-yl)pyridin-2-yl)oxy)phenyl)benzenesulfonamide |
| 220 | 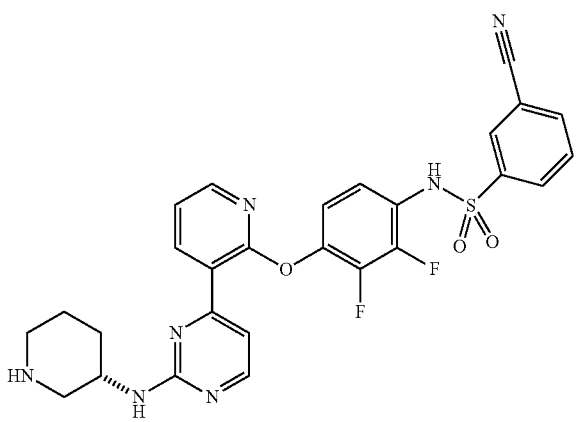 [SMILES: N#Cc1cccc(S(=O)(=O)Nc2ccc(Oc3ncccc3-c3ccnc(N[C@H]4CCCNC4)n3)c(F)c2F)c1] | (S)-3-cyano-N-(2,3-difluoro-4-((3-(2-(piperidin-3-ylamino)pyrimidin-4-yl)pyridin-2-yl)oxy)phenyl)benzenesulfonamide |
| 221 | 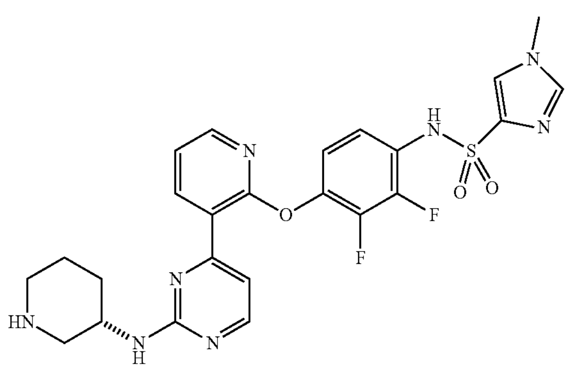 [SMILES: Cn1cnc(S(=O)(=O)Nc2ccc(Oc3ncccc3-c3ccnc(N[C@H]4CCCNC4)n3)c(F)c2F)c1] | (S)-N-(2,3-difluoro-4-((3-(2-(piperidin-3-ylamino)pyrimidin-4-yl)pyridin-2-yl)oxy)phenyl)-1-methyl-1H-imidazole-4-sulfonamide |

TABLE 1-continued

| No. | Structure | Name |
| --- | --- | --- |
| 222 | 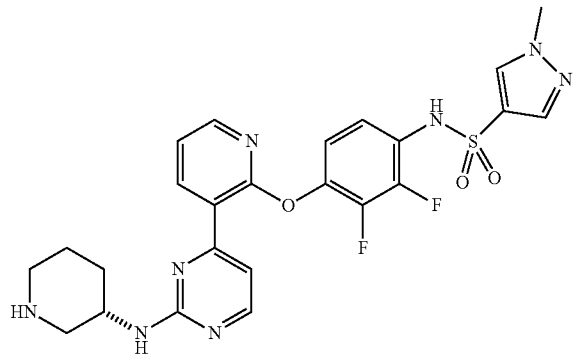 [SMILES: Cn1cc(S(=O)(=O)Nc2ccc(Oc3ncccc3-c3ccnc(N[C@H]4CCCNC4)n3)c(F)c2F)cn1] | (S)-N-(2,3-difluoro-4-((3-(2-(piperidin-3-ylamino)pyrimidin-4-yl)pyridin-2-yl)oxy)phenyl)-1-methyl-1H-pyrazole-4-sulfonamide |
| 223 | 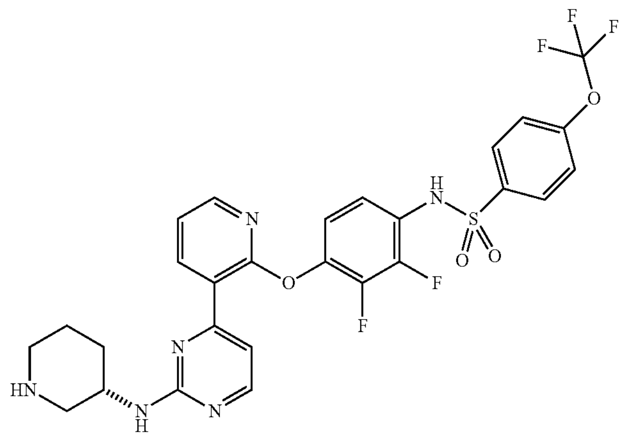 [SMILES: O=S(=O)(Nc1ccc(Oc2ncccc2-c2ccnc(N[C@H]3CCCNC3)n2)c(F)c1F)c1ccc(OC(F)(F)F)cc1] | (S)-N-(2,3-difluoro-4-((3-(2-(piperidin-3-ylamino)pyrimidin-4-yl)pyridin-2-yl)oxy)phenyl)-4-(trifluoromethoxy)benzenesulfonamide |
| 224 | 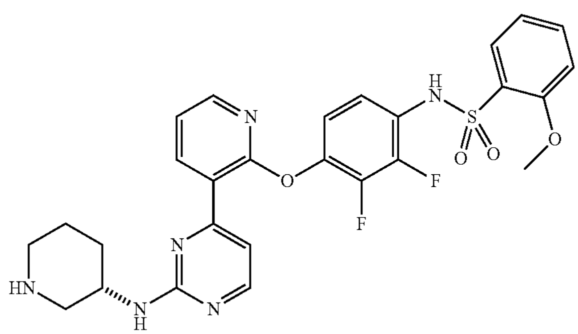 [SMILES: COc1ccccc1S(=O)(=O)Nc1ccc(Oc2ncccc2-c2ccnc(N[C@H]3CCCNC3)n2)c(F)c1F] | (S)-N-(2,3-difluoro-4-((3-(2-(piperidin-3-ylamino)pyrimidin-4-yl)pyridin-2-yl)oxy)phenyl)-2-methoxybenzenesulfonamide |
| 225 | 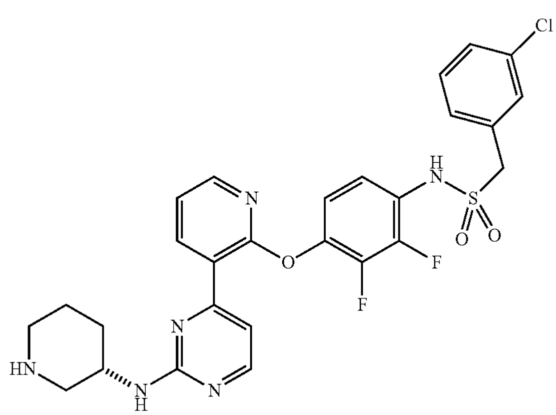 [SMILES: O=S(=O)(Cc1cccc(Cl)c1)Nc1ccc(Oc2ncccc2-c2ccnc(N[C@H]3CCCNC3)n2)c(F)c1F] | (S)-1-(3-chlorophenyl)-N-(2,3-difluoro-4-((3-(2-(piperidin-3-ylamino)pyrimidin-4-yl)pyridin-2-yl)oxy)phenyl)methanesulfonamide |

TABLE 1-continued

| No. | Structure | Name |
|---|---|---|
| 226 | 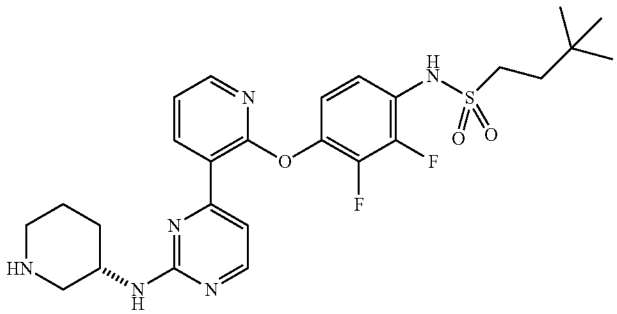 [SMILES: CC(C)(C)CCS(=O)(=O)Nc1ccc(Oc2ncccc2-c2ccnc(N[C@H]3CCCNC3)n2)c(F)c1F] | (S)-N-(2,3-difluoro-4-((3-(2-(piperidin-3-ylamino)pyrimidin-4-yl)pyridin-2-yl)oxy)phenyl)-3,3-dimethylbutane-1-sulfonamide |
| 227 | 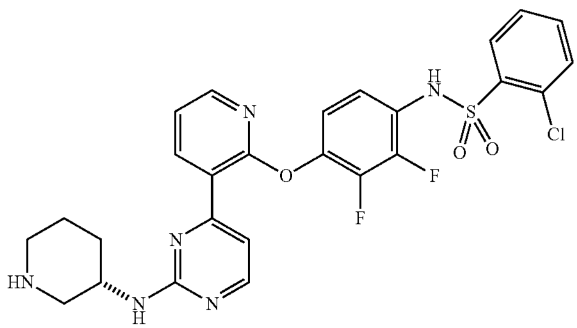 [SMILES: O=S(=O)(Nc1ccc(Oc2ncccc2-c2ccnc(N[C@H]3CCCNC3)n2)c(F)c1F)c1ccccc1Cl] | (S)-2-chloro-N-(2,3-difluoro-4-((3-(2-(piperidin-3-ylamino)pyrimidin-4-yl)pyridin-2-yl)oxy)phenyl)benzenesulfonamide |
| 228 | 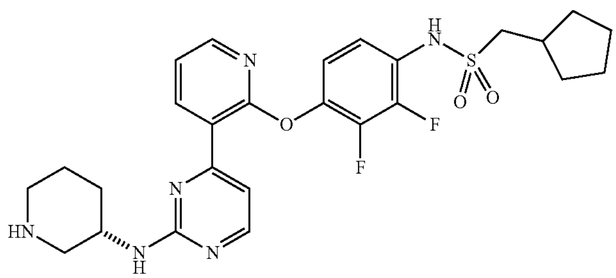 [SMILES: O=S(=O)(CC1CCCC1)Nc1ccc(Oc2ncccc2-c2ccnc(N[C@H]3CCCNC3)n2)c(F)c1F] | (S)-1-cyclopentyl-N-(2,3-difluoro-4-((3-(2-(piperidin-3-ylamino)pyrimidin-4-yl)pyridin-2-yl)oxy)phenyl)methanesulfonamide |
| 229 | 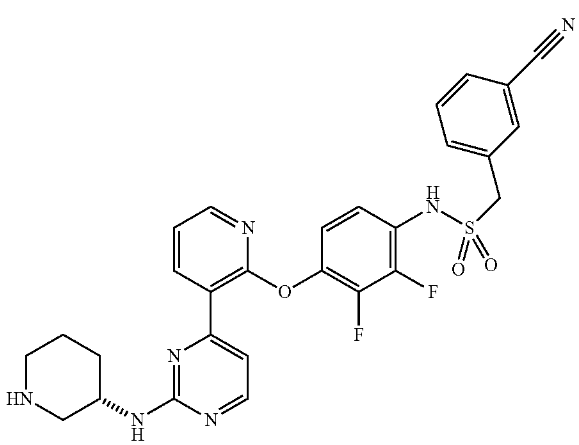 [SMILES: N#Cc1cccc(CS(=O)(=O)Nc2ccc(Oc3ncccc3-c3ccnc(N[C@H]4CCCNC4)n3)c(F)c2F)c1] | (S)-1-(3-cyanophenyl)-N-(2,3-difluoro-4-((3-(2-(piperidin-3-ylamino)pyrimidin-4-yl)pyridin-2-yl)oxy)phenyl)methanesulfonamide |

TABLE 1-continued

| No. | Structure | Name |
|-----|-----------|------|
| 230 | 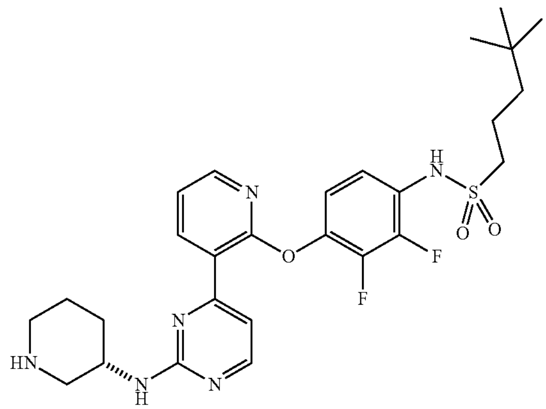 [SMILES: CC(C)(C)CCCS(=O)(=O)Nc1ccc(Oc2ncccc2-c2ccnc(N[C@H]3CCCNC3)n2)c(F)c1F] | (S)-N-(2,3-difluoro-4-((3-(2-(piperidin-3-ylamino)pyrimidin-4-yl)pyridin-2-yl)oxy)phenyl)-4,4-dimethylpentane-1-sulfonamide |
| 231 | 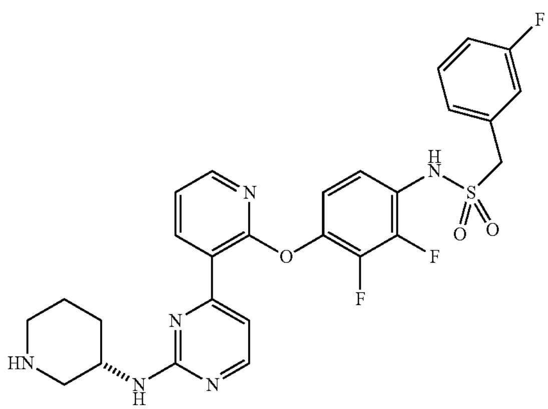 [SMILES: O=S(=O)(Cc1cccc(F)c1)Nc1ccc(Oc2ncccc2-c2ccnc(N[C@H]3CCCNC3)n2)c(F)c1F] | (S)-N-(2,3-difluoro-4-((3-(2-(piperidin-3-ylamino)pyrimidin-4-yl)pyridin-2-yl)oxy)phenyl)-1-(3-fluorophenyl)methanesulfonamide |
| 232 | 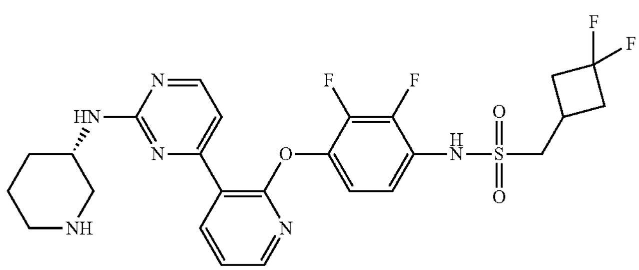 [SMILES: O=S(=O)(CC1CC(F)(F)C1)Nc1ccc(Oc2ncccc2-c2ccnc(N[C@H]3CCCNC3)n2)c(F)c1F] | (S)-N-(2,3-difluoro-4-(3-(2-(piperidin-3-ylamino)pyrimidin-4-yl)pyridin-2-yloxy)phenyl)-1-(3,3-difluorocyclobutyl)methanesulfonamide |
| 233 | 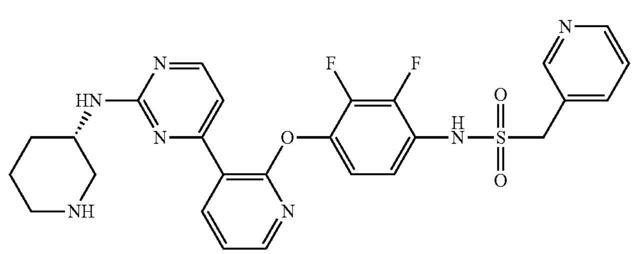 [SMILES: O=S(=O)(Cc1cccnc1)Nc1ccc(Oc2ncccc2-c2ccnc(N[C@H]3CCCNC3)n2)c(F)c1F] | (S)-N-(2,3-difluoro-4-(3-(2-(piperidin-3-ylamino)pyrimidin-4-yl)pyridin-2-yloxy)phenyl)-1-(pyridin-3-yl)methanesulfonamide |
| 234 | 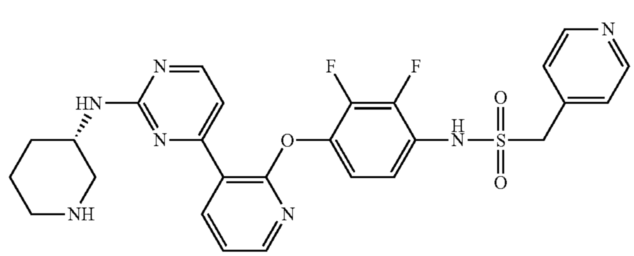 [SMILES: O=S(=O)(Cc1ccncc1)Nc1ccc(Oc2ncccc2-c2ccnc(N[C@H]3CCCNC3)n2)c(F)c1F] | (S)-N-(2,3-difluoro-4-(3-(2-(piperidin-3-ylamino)pyrimidin-4-yl)pyridin-2-yloxy)phenyl)-1-(pyridin-4-yl)methanesulfonamide |

TABLE 1-continued

| No. | Structure | Name |
|---|---|---|
| 235 | 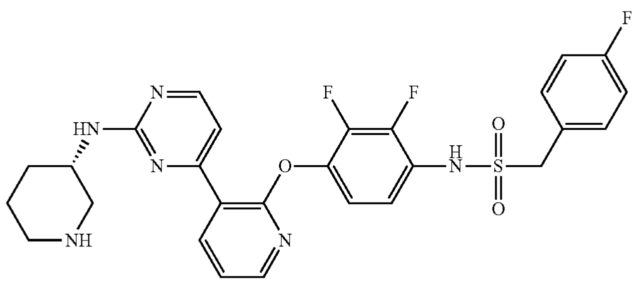 [SMILES: O=S(=O)(Cc1ccc(F)cc1)Nc1ccc(Oc2ncccc2-c2ccnc(N[C@H]3CCCNC3)n2)c(F)c1F] | (S)-N-(2,3-difluoro-4-(3-(2-(piperidin-3-ylamino)pyrimidin-4-yl)pyridin-2-yloxy)phenyl)-1-(4-fluorophenyl)methanesulfonamide |
| 236 | 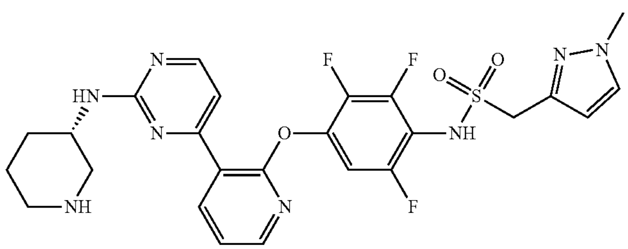 [SMILES: Cn1ccc(CS(=O)(=O)Nc2c(F)cc(Oc3ncccc3-c3ccnc(N[C@H]4CCCNC4)n3)c(F)c2F)n1] | (S)-1-(1-methyl-1H-pyrazol-3-yl)-N-(2,3,6-trifluoro-4-(3-(2-(piperidin-3-ylamino)pyrimidin-4-yl)pyridin-2-yloxy)phenyl)methanesulfonamide |
| 237 | 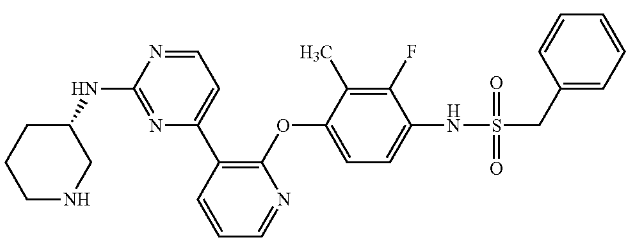 [SMILES: Cc1c(Oc2ncccc2-c2ccnc(N[C@H]3CCCNC3)n2)ccc(NS(=O)(=O)Cc2ccccc2)c1F] | N-[2-fluoro-3-methyl-4-[[3-[2-[[(3S)-3-piperidyl]amino]pyrimidin-4-yl]-2-pyridyl]oxy]phenyl]-1 phenylmethanesulfonamide |
| 238 | 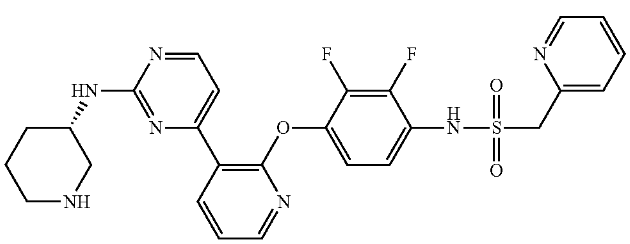 | (S)-N-(2,3-difluoro-4-(3-(2-(piperidin-3-ylamino)pyrimidin-4-yl)pyridin-2-yloxy)phenyl)-1-(pyridin-2-yl)methanesulfonamide |
| 239 | 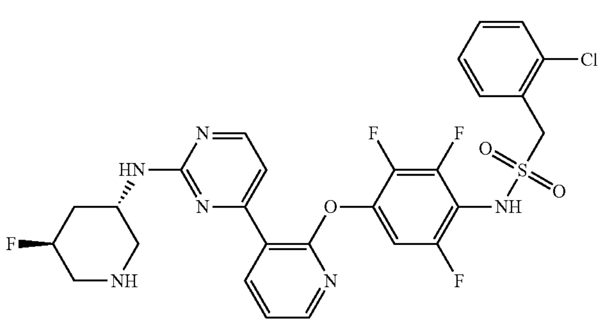 [SMILES: O=S(=O)(Cc1ccccc1Cl)Nc1c(F)cc(Oc2ncccc2-c2ccnc(N[C@@H]3CNC[C@@H](F)C3)n2)c(F)c1F] | 1-(2-chlorophenyl)-N-(2,3,6-trifluoro-4-((3-(2-(((3S,5S)-5-fluoropiperiidn-3-yl)amino)pyrimidin-4-yl)pyridin-2-yl)oxy)phenyl)methanesulfonamide |

TABLE 1-continued

| No. | Structure | Name |
|---|---|---|
| 240 | 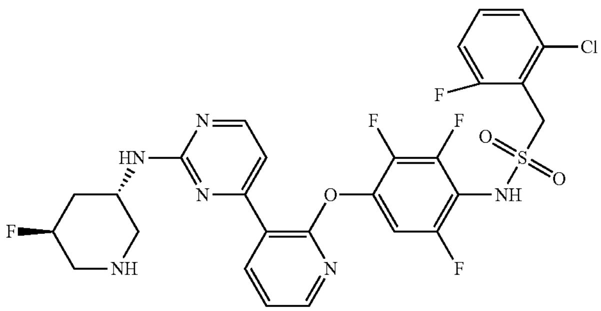 | 1-(2-chloro-6-fluorophenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 241 | 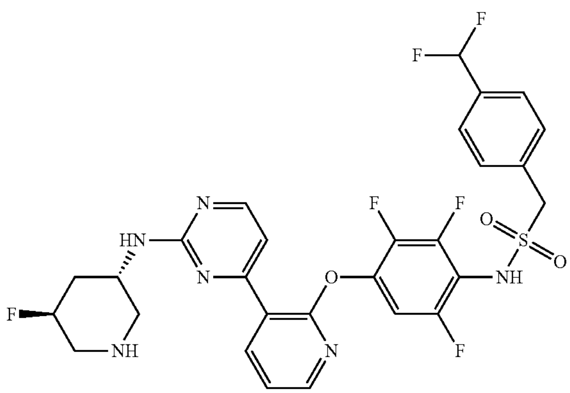 [SMILES: O=S(=O)(Cc1ccc(C(F)F)cc1)Nc1c(F)cc(Oc2ncccc2-c2ccnc(N[C@@H]3CNC[C@@H](F)C3)n2)c(F)c1F] | 1-(4-(difluoromethyl)phenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 242 | 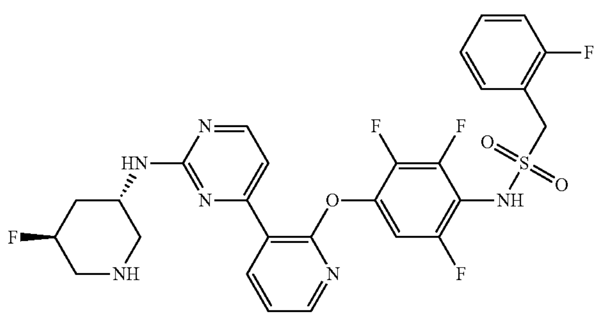 [SMILES: O=S(=O)(Cc1ccccc1F)Nc1c(F)cc(Oc2ncccc2-c2ccnc(N[C@@H]3CNC[C@@H](F)C3)n2)c(F)c1F] | 1-(2-fluorophenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 243 | 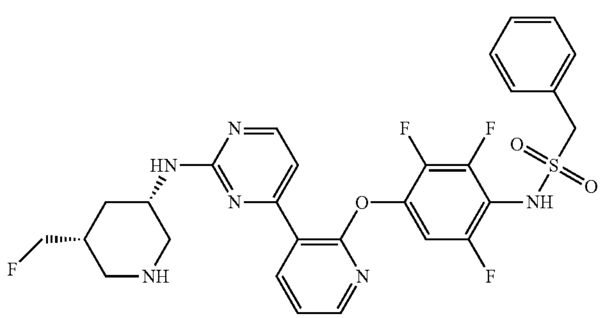 [SMILES: O=S(=O)(Cc1ccccc1)Nc1c(F)cc(Oc2ncccc2-c2ccnc(N[C@@H]3CNC[C@H](CF)C3)n2)c(F)c1F] | 1-phenyl-N-(2,3,6-trifluoro-4-((3-(2-(((3S,5R)-5-(fluoromethyl)piperidin-3-yl)amino)pyrimidin-4-yl)pyridin-2-yl)oxy)phenyl)methanesulfonamide |

TABLE 1-continued

| No. | Structure | Name |
|---|---|---|
| 244 | 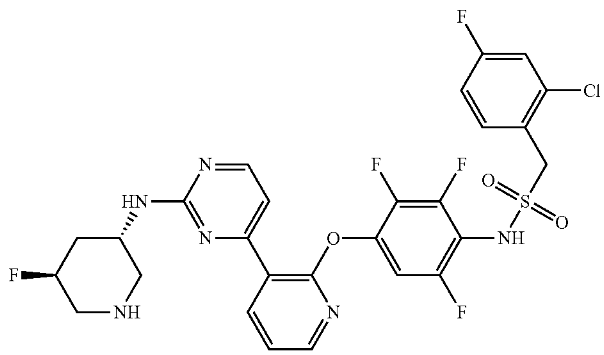 [SMILES: O=S(=O)(Cc1ccc(F)cc1Cl)Nc1c(F)cc(Oc2ncccc2-c2ccnc(N[C@@H]3CNC[C@@H](F)C3)n2)c(F)c1F] | 1-(2-chloro-4-fluorophenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 245 | 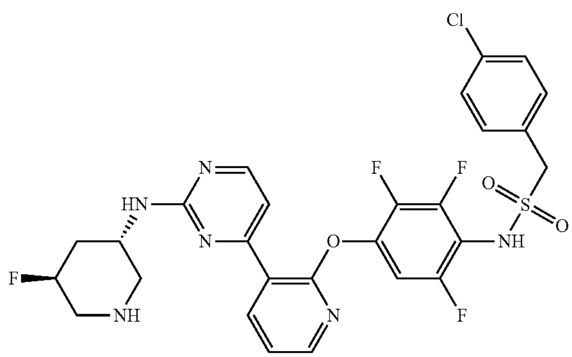 | 1-(4-chlorophenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 246 | 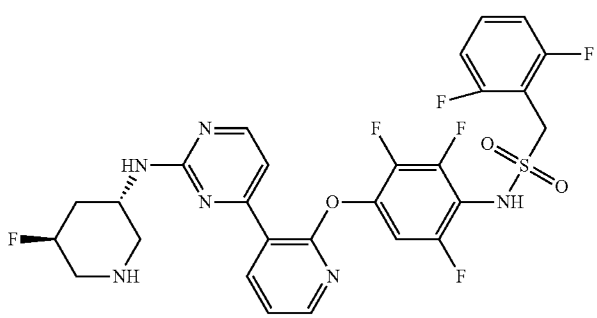 [SMILES: O=S(=O)(Cc1c(F)cccc1F)Nc1c(F)cc(Oc2ncccc2-c2ccnc(N[C@@H]3CNC[C@@H](F)C3)n2)c(F)c1F] | 1-(2,6-difluorophenyl)-N-(2,3,6-trifluoro-4-((3-(2-(((3S,5S)-5-fluoropiperidn-3-yl)amino)pyrimidin-4-yl)pyridin-2-yl)oxy)phenyl)methanesulfonamide |
| 247 | 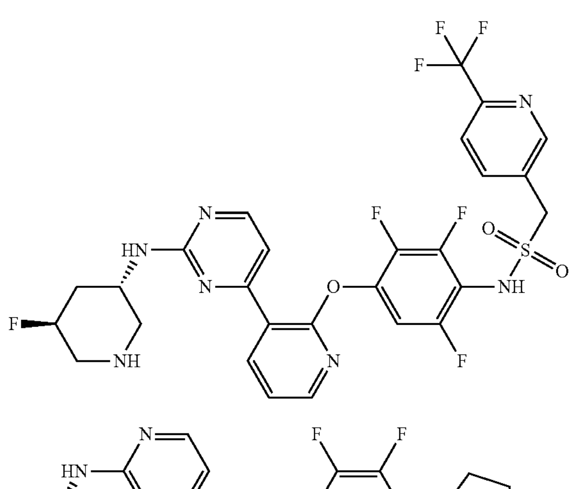 | N-(2,3,6-trifluoro-4-((3-(2-(((3S,5S)-5-fluoropiperidin-3-yl)amino)pyrimidin-4-yl)pyridin-2-yl)oxy)phenyl)-1-(6-(trifluoromethyl)pyridin-3-yl)methanesulfonamide |
| 248 249 | | 1-(2,3-difluoro-4-((3-(2-(((S)-piperidin-3-yl)amino)pyrimidin-4-yl)pyridin-2-yl)oxy)phenyl)-3-ethylpyrrolidin-2-one |

TABLE 1-continued

| No. | Structure | Name |
|---|---|---|
| 250 | 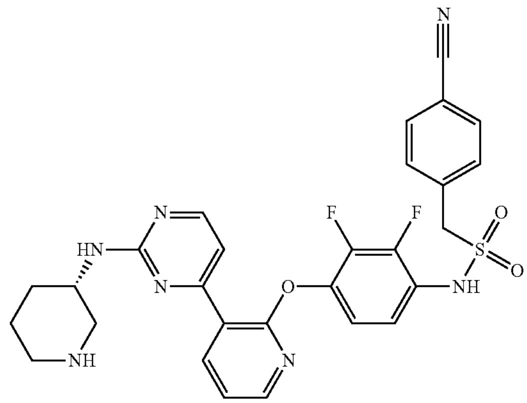 [SMILES: N#Cc1ccc(CS(=O)(=O)Nc2ccc(Oc3ncccc3-c3ccnc(N[C@H]4CCCNC4)n3)c(F)c2F)cc1] | (S)-1-(4-cyanophenyl)-N-(2,3-difluoro-4-((3-(2-(piperidin-3-ylamino)pyrimidin-4-yl)pyridin-2-yl)oxy)phenyl)methanesulfonamide |
| 251 | 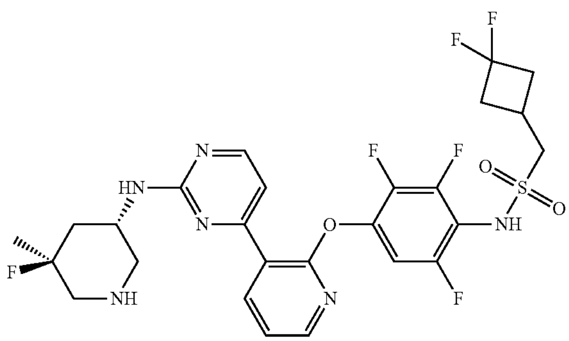 [SMILES: C[C@@]1(F)CNC[C@@H](Nc2nccc(-c3cccnc3Oc3cc(F)c(NS(=O)(=O)CC4CC(F)(F)C4)c(F)c3F)n2)C1] | 1-(3,3-difluorocyclobutyl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide |
| 252 | 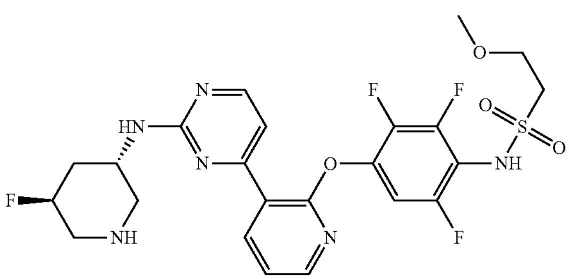 [SMILES: COCCS(=O)(=O)Nc1c(F)cc(Oc2ncccc2-c2ccnc(N[C@@H]3CNC[C@@H](F)C3)n2)c(F)c1F] | 2-methoxy-N-(2,3,6-trifluoro-4-((3-(2-(((3S,5S)-5-fluoropiperidin-3-yl)amino)pyrimidin-4-yl)pyridin-2-yl)oxy)phenyl)ethane-1-sulfonamide |
| 253 | 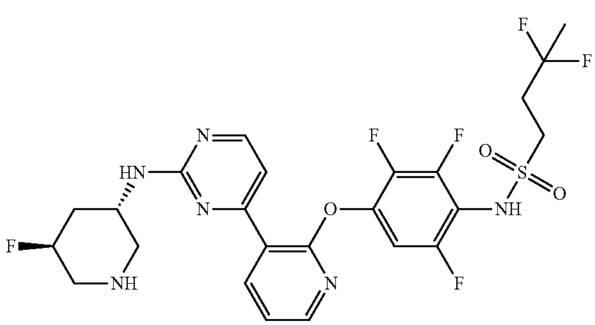 [SMILES: CC(F)(F)CCS(=O)(=O)Nc1c(F)cc(Oc2ncccc2-c2ccnc(N[C@@H]3CNC[C@@H](F)C3)n2)c(F)c1F] | 3,3-difluoro-N-(2,3,6-trifluoro-4-((3-(2-(((3S,5S)-5-fluoropiperidin-3-yl)amino)pyrimidin-4-yl)pyridin-2-yl)oxy)phenyl)butane-1-sulfonamide |

TABLE 1-continued

| No. | Structure | Name |
|---|---|---|
| 254 | 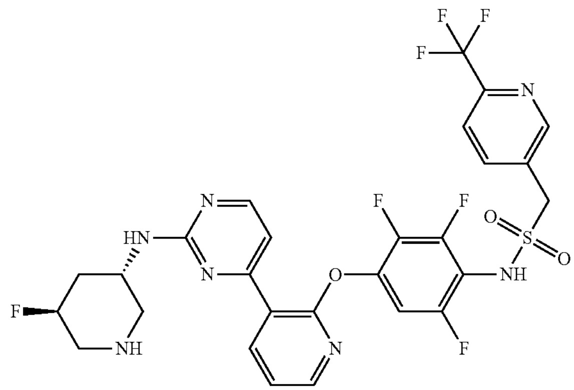 [SMILES: O=S(=O)(Cc1ccc(C(F)(F)F)nc1)Nc1c(F)cc(Oc2ncccc2-c2ccnc(N[C@@H]3CNC[C@@H](F)C3)n2)c(F)c1F] | N-(2,3,6-trifluoro-4-((3-(2-(((3S,5S)-5-fluoropiperidin-3-yl)amino)pyrimidin-4-yl)pyridin-2-yl)oxy)phenyl)-1-(6-(trifluoromethyl)pyridin-3-yl)methanesulfonamide |
| 255 | 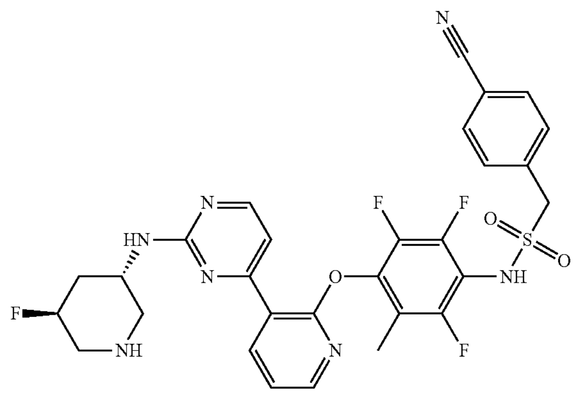 [SMILES: Cc1c(F)c(NS(=O)(=O)Cc2ccc(C#N)cc2)c(F)c(F)c1Oc1ncccc1-c1ccnc(N[C@@H]2CNC[C@@H](F)C2)n1] | 1-(4-cyanophenyl)-N-(2,3,6-trifluoro-4-((3-(2-(((3S,5S)-5-fluoropiperidin-3-yl)amino)pyrimidin-4-yl)pyridin-2-yl)oxy)-5-methylphenyl)methanesulfonamide |
| 256 | 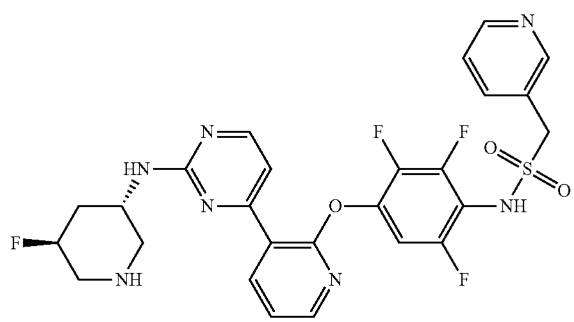 [SMILES: O=S(=O)(Cc1cccnc1)Nc1c(F)cc(Oc2ncccc2-c2ccnc(N[C@@H]3CNC[C@@H](F)C3)n2)c(F)c1F] | 1-(pyridin-3-yl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 257 | 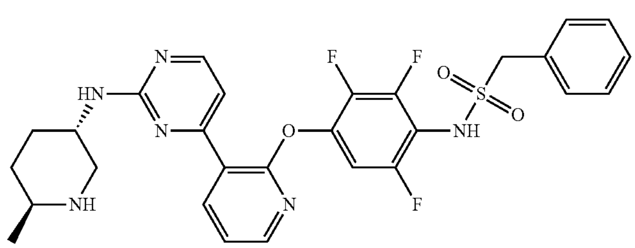 [SMILES: C[C@H]1CC[C@H](Nc2nccc(-c3cccnc3Oc3cc(F)c(NS(=O)(=O)Cc4ccccc4)c(F)c3F)n2)CN1] | 1-phenyl-N-(2,3,6-trifluoro-4-((3-(2-(((3S,6S)-6-methylpiperidin-3-yl)amino)pyrimidin-4-yl)pyridin-2-yl)oxy)phenyl)methanesulfonamide |
| 258 | 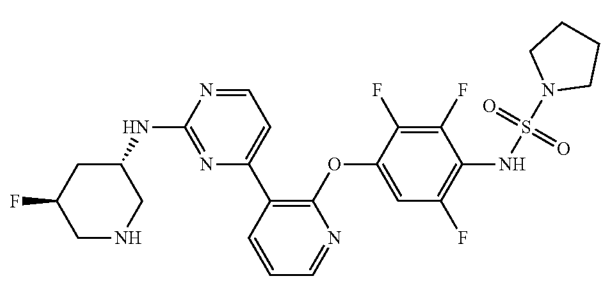 [SMILES: O=S(=O)(Nc1c(F)cc(Oc2ncccc2-c2ccnc(N[C@@H]3CNC[C@@H](F)C3)n2)c(F)c1F)N1CCCC1] | N-(2,3,6-trifluoro-4-((3-(2-(((3S,5S)-5-fluoropiperidin-3-yl)amino)pyrimidin-4-yl)pyridin-2-yl)oxy)phenyl)pyrrolidine-1-sulfonamide |

TABLE 1-continued

| No. | Structure | Name |
|---|---|---|
| 259 | 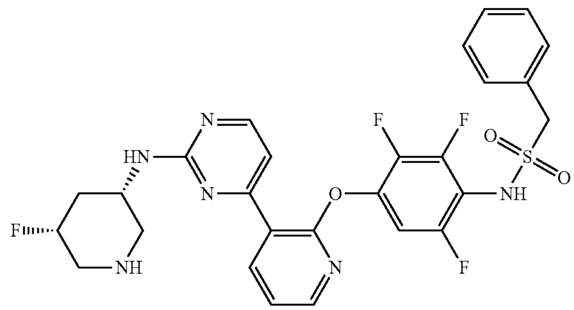 [SMILES: O=S(=O)(Cc1ccccc1)Nc1c(F)cc(Oc2ncccc2-c2ccnc(N[C@@H]3CNC[C@H](F)C3)n2)c(F)c1F] | 1-phenyl-N-(2,3,6-trifluoro-4-((3-(2-(((3S,5R)-5-fluoropiperidin-3-yl)amino)pyrimidin-4-yl)pyridin-2-yl)oxy)phenyl)methanesulfonamide |
| 260 | 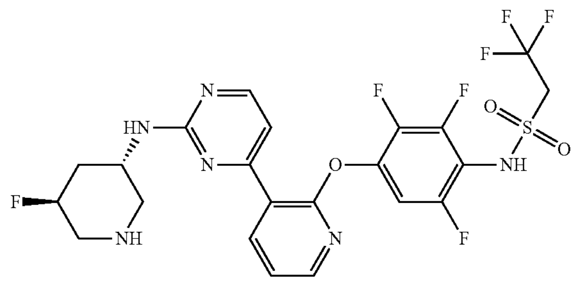 [SMILES: O=S(=O)(CC(F)(F)F)Nc1c(F)cc(Oc2ncccc2-c2ccnc(N[C@@H]3CNC[C@@H](F)C3)n2)c(F)c1F] | 2,2,2-trifluoro-N-(2,3,6-trifluoro-4-((3-(2-(((3S,5S)-5-fluoropiperidin-3-yl)amino)pyrimidin-4-yl)pyridin-2-yl)oxy)phenyl)ethane-1-sulfonamide hydrochloride |
| 261 | 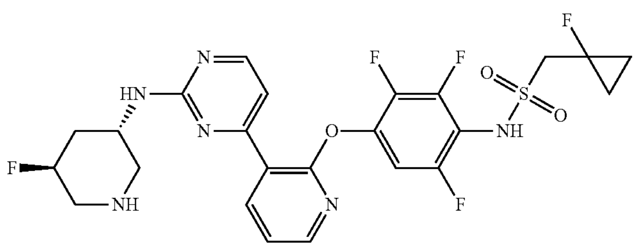 [SMILES: O=S(=O)(CC1(F)CC1)Nc1c(F)cc(Oc2ncccc2-c2ccnc(N[C@@H]3CNC[C@@H](F)C3)n2)c(F)c1F] | 1-(1-fluorocyclopropyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 262 | 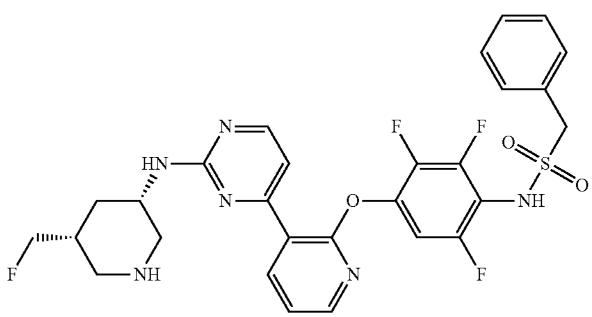 [SMILES: O=S(=O)(Cc1ccccc1)Nc1c(F)cc(Oc2ncccc2-c2ccnc(N[C@@H]3CNC[C@H](CF)C3)n2)c(F)c1F] | 1-phenyl-N-(2,3,6-trifluoro-4-((3-(2-(((3S,5R)-5-(fluoromethyl)piperidin-3-yl)amino)pyrimidin-4-yl)pyridin-2-yl)oxy)phenyl)methanesulfonamide |
| 263 | 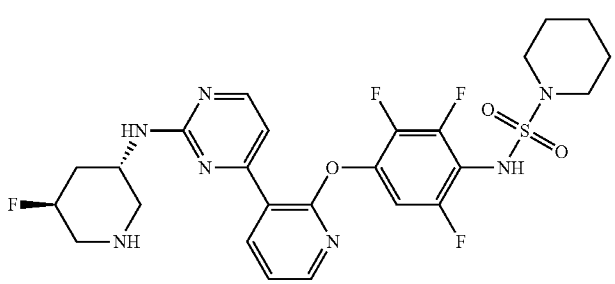 [SMILES: O=S(=O)(Nc1c(F)cc(Oc2ncccc2-c2ccnc(N[C@@H]3CNC[C@@H](F)C3)n2)c(F)c1F)N1CCCCC1] | N-(2,3,6-trifluoro-4-((3-(2-(((3S,5S)-5-fluoropiperidin-3-yl)amino)pyrimidin-4-yl)pyridin-2-yl)oxy)phenyl)piperidine-1-sulfonamide |

TABLE 1-continued

| No. | Structure | Name |
|---|---|---|
| 264, 265 | | 1-(2,2-difluorocyclobutyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 266 | 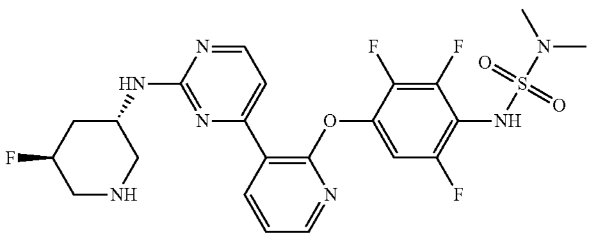 [SMILES: CN(C)S(=O)(=O)Nc1c(F)cc(Oc2ncccc2-c2ccnc(N[C@@H]3CNC[C@@H](F)C3)n2)c(F)c1F] | 4-(2-(4-(dimethylsulfamoylamino)-2,3,5-trifluoro-phenoxy)-3-pyridyl)-2-(((3S,5S)-5-fluoro-3-piperidyl)amino)pyrimidine |
| 267 | 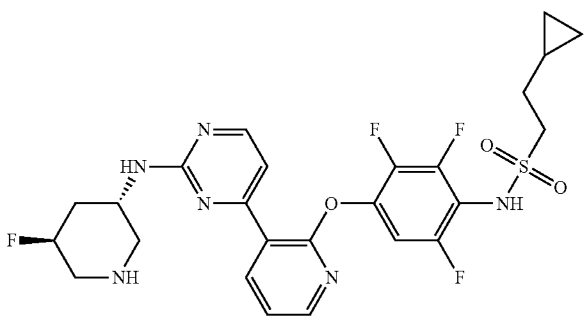 [SMILES: O=S(=O)(CCC1CC1)Nc1c(F)cc(Oc2ncccc2-c2ccnc(N[C@@H]3CNC[C@@H](F)C3)n2)c(F)c1F] | 2-cyclopropyl-N-(2,3,6-trifluoro-4-((3-(2-(((3S,5S)-5-fluoropiperidin-3-yl)amino)pyrimidin-4-yl)pyridin-2-yl)oxy)phenyl)ethane-1-sulfonamide |
| 268 | 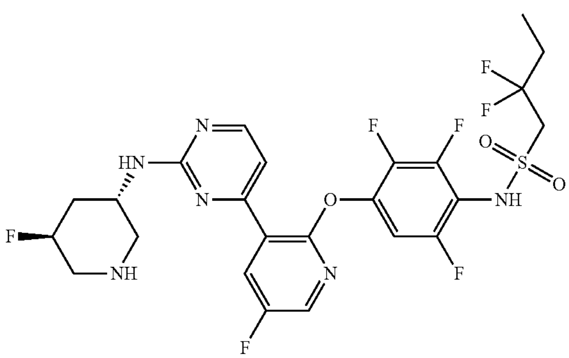 [SMILES: CCC(F)(F)CS(=O)(=O)Nc1c(F)cc(Oc2ncc(F)cc2-c2ccnc(N[C@@H]3CNC[C@@H](F)C3)n2)c(F)c1F] | 2,2-difluoro-N-(2,3,6-trifluoro-4-((5-fluoro-3-(2-(((3S,5S)-5-fluoropiperidin-3-yl)amino)pyrimidin-4-yl)pyridin-2-yl)oxy)phenyl)butane-1-sulfonamide |
| 269 | 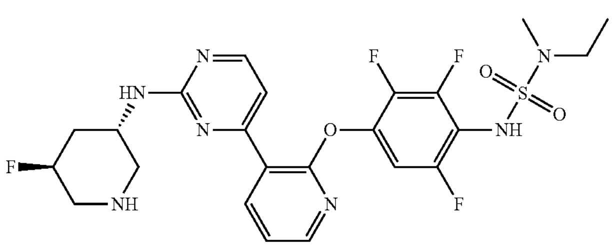 [SMILES: CCN(C)S(=O)(=O)Nc1c(F)cc(Oc2ncccc2-c2ccnc(N[C@@H]3CNC[C@@H](F)C3)n2)c(F)c1F] | 4-(2-(4-((ethyl(methyl)sulfamoyl)amino)-2,3,5-trifluoro-phenoxy)-3-pyridyl)-2-(((3S,5S)-5-fluoro-3-piperidyl)amino)pyrimidine |

TABLE 1-continued

| No. | Structure | Name |
|---|---|---|
| 270 | 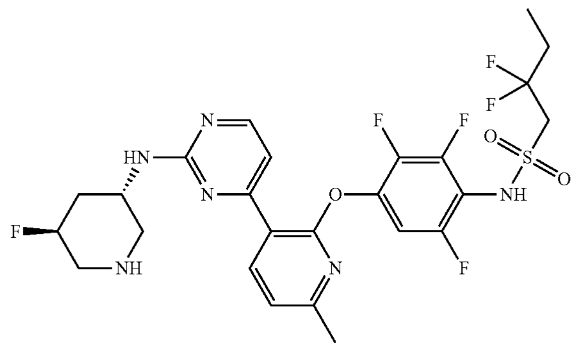 [SMILES: CCC(F)(F)CS(=O)(=O)Nc1c(F)cc(Oc2nc(C)ccc2-c2ccnc(N[C@@H]3CNC[C@@H](F)C3)n2)c(F)c1F] | 2,2-difluoro-N-(2,3,6-trifluoro-4-((3-(2-(((3S,5S)-5-fluoropiperidin-3-yl)amino)pyrimidin-4-yl)-6-methylpyridin-2-yl)oxy)phenyl)butane-1-sulfonamide |
| 271 | 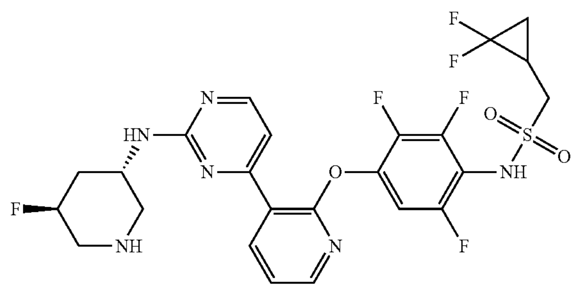 [SMILES: O=S(=O)(CC1CC1(F)F)Nc1c(F)cc(Oc2ncccc2-c2ccnc(N[C@@H]3CNC[C@@H](F)C3)n2)c(F)c1F] | 1-(2,2-difluorocyclopropyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 272 | 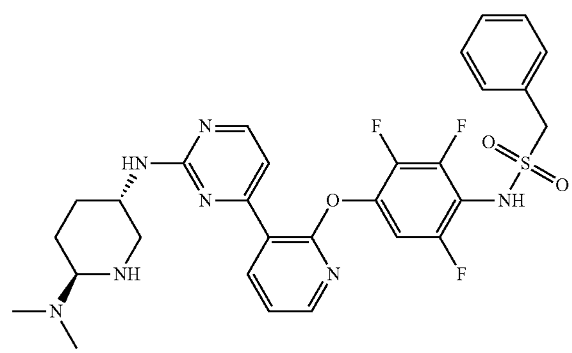 [SMILES: CN(C)[C@H]1CC[C@H](Nc2nccc(-c3cccnc3Oc3cc(F)c(NS(=O)(=O)Cc4ccccc4)c(F)c3F)n2)CN1] | N-(4-((3-(2-(((1r,4r)-4-(dimethylamino)cyclohexyl)amino)pyrimidin-4-yl)pyridin-2-yl)oxy)-2,3,6-trifluorophenyl)-1-phenylmethanesulfonamide hydrochloride |
| 273 274 | | N-(2,3-difluoro-4-((3-(2-(((S)-piperidin-3-yl)amino)pyrimidin-4-yl)pyridin-2-yl)oxy)phenyl)-N'-methyl-1-phenylmethanesulfonimidamide |
| 275 | 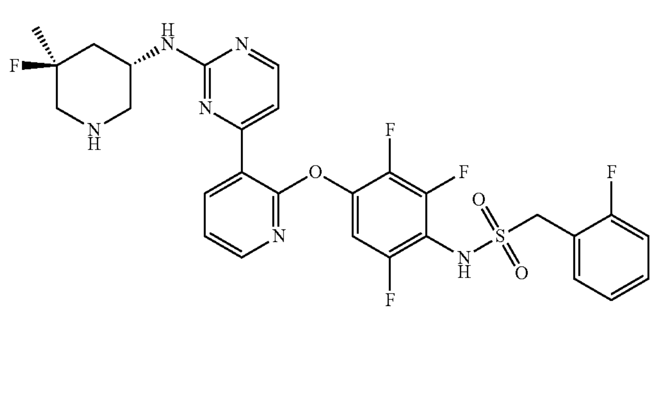 [SMILES: C[C@@]1(F)CNC[C@@H](Nc2nccc(-c3cccnc3Oc3cc(F)c(NS(=O)(=O)Cc4ccccc4F)c(F)c3F)n2)C1] | 1-(2-fluorophenyl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide |

TABLE 1-continued

| No. | Structure | Name |
|---|---|---|
| 276 | 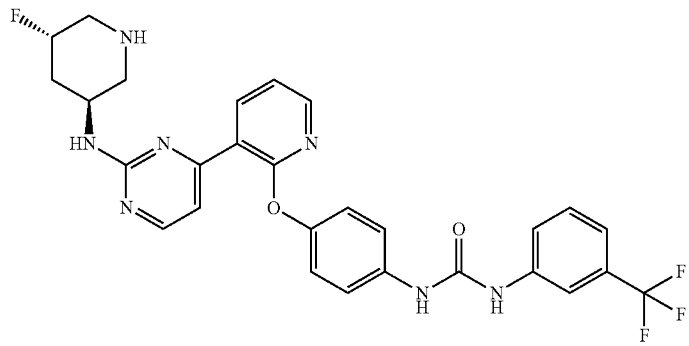 [SMILES: O=C(Nc1ccc(Oc2ncccc2-c2ccnc(N[C@@H]3CNC[C@@H](F)C3)n2)cc1)Nc1cccc(C(F)(F)F)c1] | 1-(4-((3-(2-(((3S,5S)-5-Fluoropiperidin-3-yl)amino)pyrimidin-4-yl)pyridin-2-yl)oxy)phenyl)-3-(3-(trifluoromethyl)phenyl)urea |
| 277 278 | 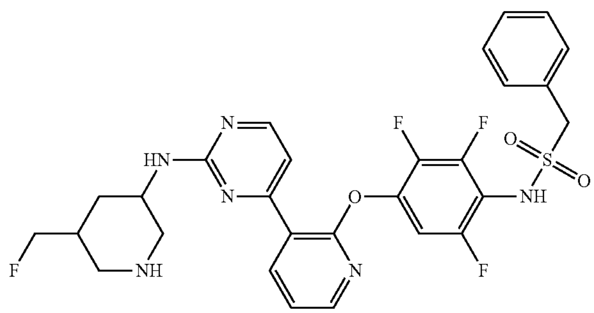 [SMILES: O=S(=O)(Cc1ccccc1)Nc1c(F)cc(Oc2ncccc2-c2ccnc(NC3CNCC(CF)C3)n2)c(F)c1F] | 1-phenyl-N-(2,3,6-trifluoro-4-((3-(2-((5-(fluoromethyl)piperidin-3-yl)amino)pyrimidin-4-yl)pyridin-2-yl)oxy)phenyl)methanesulfonamide |
| 279 | 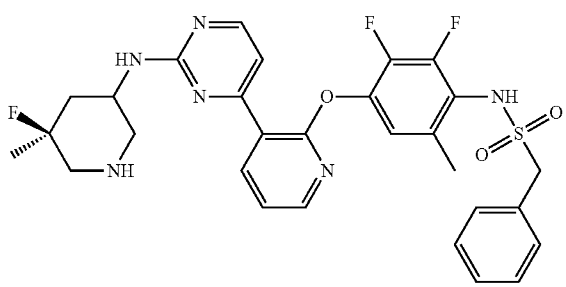 [SMILES: Cc1cc(Oc2ncccc2-c2ccnc(NC3CNC[C@@](C)(F)C3)n2)c(F)c(F)c1NS(=O)(=O)Cc1ccccc1] | N-(2,3-difluoro-4-((3-(2-(((3S,5S)-5-fluoro-5-methylpiperidin-3-yl)amino)pyrimidin-4-yl)pyridin-2-yl)oxy)-6-methylphenyl)-1-phenylmethanesulfonamide |
| 280 | 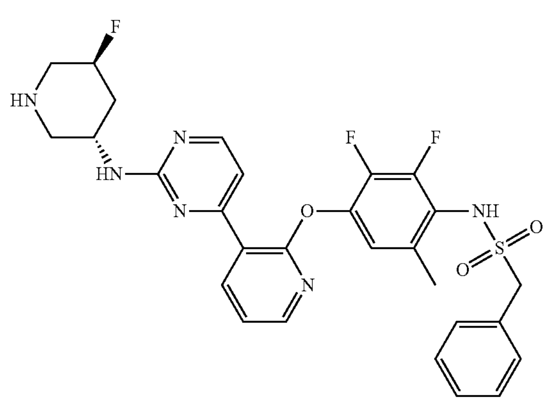 [SMILES: Cc1cc(Oc2ncccc2-c2ccnc(N[C@@H]3CNC[C@@H](F)C3)n2)c(F)c(F)c1NS(=O)(=O)Cc1ccccc1] | N-(2,3-difluoro-4-((3-(2-(((3S,5S)-5-fluoropiperidn-3-yl)amino)pyrimidin-4-yl)pyridin-2-yl)oxy)-6-methylphenyl)-1-phenylmethanesulfonamide |

TABLE 1-continued

| No. | Structure | Name |
|---|---|---|
| 281 | 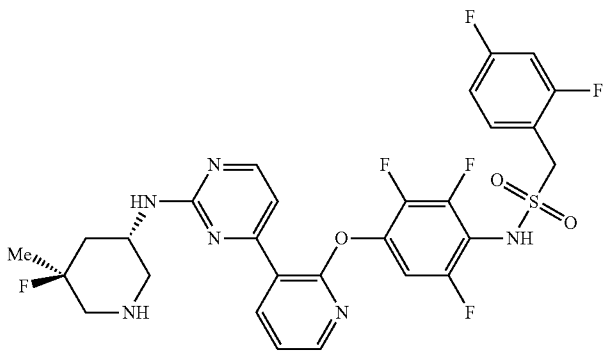 [SMILES: C[C@@]1(F)CNC[C@@H](Nc2nccc(-c3cccnc3Oc3cc(F)c(NS(=O)(=O)Cc4ccc(F)cc4F)c(F)c3F)n2)C1] | 1-(2,4-difluorophenyl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide |
| 282 | 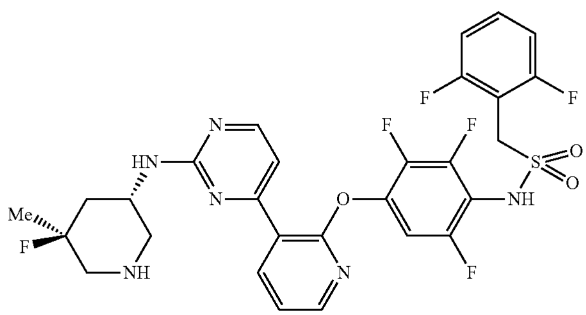 [SMILES: C[C@@]1(F)CNC[C@@H](Nc2nccc(-c3cccnc3Oc3cc(F)c(NS(=O)(=O)Cc4c(F)cccc4F)c(F)c3F)n2)C1] | 1-(2,6-difluorophenyl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide |
| 283 | 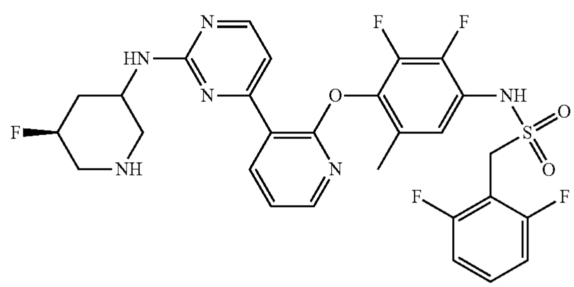 [SMILES: Cc1cc(NS(=O)(=O)Cc2c(F)cccc2F)c(F)c(F)c1Oc1ncccc1-c1ccnc(NC2CNC[C@@H](F)C2)n1] | N-(2,3-difluoro-4-((3-(2-(((3S,5S)-5-fluoropiperidin-3-yl)amino)pyrimidin-4-yl)pyridin-2-yl)oxy)-5-methylphenyl)-1-(2,6-difluorophenyl)methanesulfonamide |
| 284 | 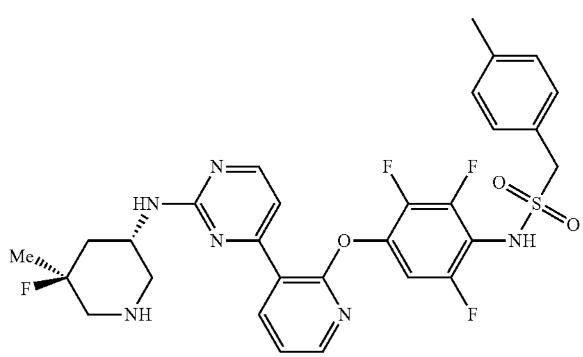 [SMILES: Cc1ccc(CS(=O)(=O)Nc2c(F)cc(Oc3ncccc3-c3ccnc(N[C@@H]4CNC[C@@](C)(F)C4)n3)c(F)c2F)cc1] | 1-p-tolyl-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide |

TABLE 1-continued

| No. | Structure | Name |
|---|---|---|
| 285 | 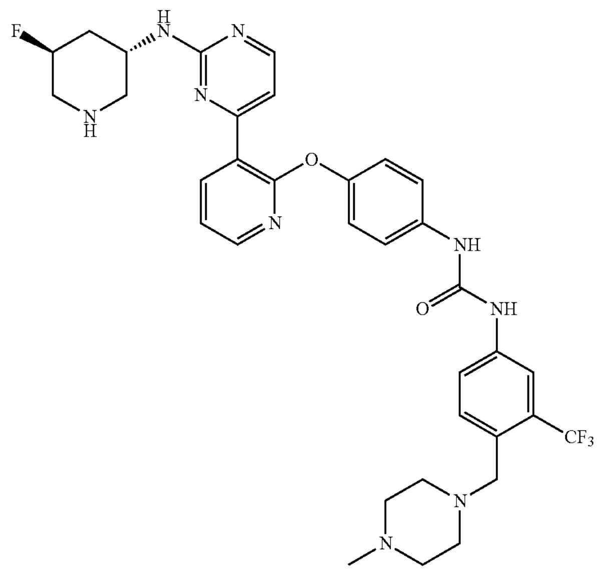 [SMILES: CN1CCN(Cc2ccc(NC(=O)Nc3ccc(Oc4ncccc4-c4ccnc(N[C@@H]5CNC[C@@H](F)C5)n4)cc3)cc2C(F)(F)F)CC1] | 1-(4-((3-(2-(((3S,5S)-5-fluoropiperidin-3-yl)amino)pyrimidin-4-yl)pyridin-2-yl)oxy)phenyl)-3-(4-((4-methylpiperazin-1-yl)methyl)-3-(trifluoromethyl)phenyl)urea hydrochloride |
| 286 | 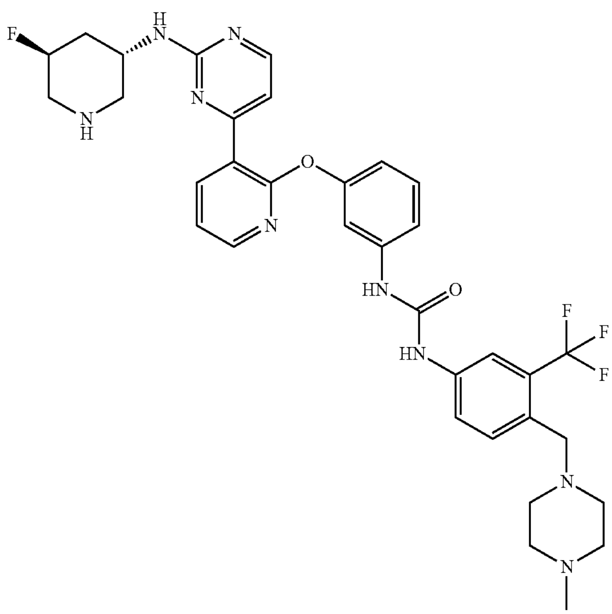 [SMILES: CN1CCN(Cc2ccc(NC(=O)Nc3cccc(Oc4ncccc4-c4ccnc(N[C@@H]5CNC[C@@H](F)C5)n4)c3)cc2C(F)(F)F)CC1] | 1-(3-((3-(2-(((3S,5S)-5-fluoropiperidin-3-yl)amino)pyrimidin-4-yl)pyridin-2-yl)oxy)phenyl)-3-(4-((4-methylpiperazin-1-yl)methyl)-3-(trifluoromethyl)phenyl)urea hydrochloride |
| 287 288 | | N-(4-((3-(2-((1-azabicyclo[3.3.1]nonan-3-yl)amino)pyrimidin-4-yl)pyridin-2-yl)oxy)-2,3,6-trifluorophenyl)-1-phenylmethanesulfonamide hydrochloride |

TABLE 1-continued

| No. | Structure | Name |
|---|---|---|
| 290 | 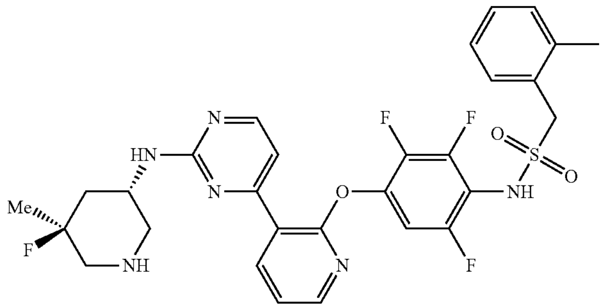 [SMILES: Cc1ccccc1CS(=O)(=O)Nc1c(F)cc(Oc2ncccc2-c2ccnc(N[C@@H]3CNC[C@@](C)(F)C3)n2)c(F)c1F] | 1-o-tolyl-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide |
| 291 | 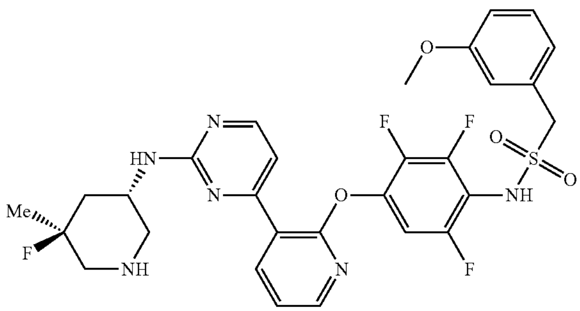 [SMILES: COc1cccc(CS(=O)(=O)Nc2c(F)cc(Oc3ncccc3-c3ccnc(N[C@@H]4CNC[C@@](C)(F)C4)n3)c(F)c2F)c1] | 1-(3-methoxyphenyl)-N-(2,3,6-trifluoro-4-((3-(2-(((3S,5S)-5-fluoro-5-methylpiperidin-3-l)amino)pyrimidin-4-yl)pyridin-2-yl)oxy)phenyl)methanesulfonamide |
| 292 | 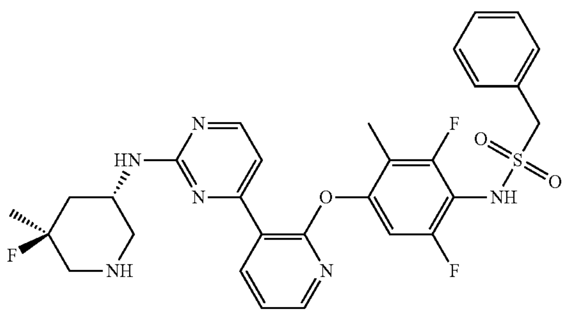 [SMILES: Cc1c(Oc2ncccc2-c2ccnc(N[C@@H]3CNC[C@@](C)(F)C3)n2)cc(F)c(NS(=O)(=O)Cc2ccccc2)c1F] | N-(2,6-difluoro-4-((3-(2-(((3S,5S)-5-fluoro-5-methylpiperidin-3-yl)amino)pyrimidin-4-yl)pyridin-2-yl)oxy)-3-methylphenyl)-1-phenylmethanesulfonamide |
| 293 | 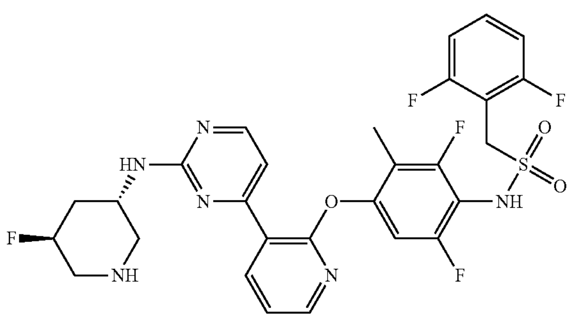 [SMILES: Cc1c(Oc2ncccc2-c2ccnc(N[C@@H]3CNC[C@@H](F)C3)n2)cc(F)c(NS(=O)(=O)Cc2c(F)cccc2F)c1F] | N-(2,6-difluoro-4-((3-(2-(((3S,5S)-5-fluoropiperidin-3-yl)amino)pyrimidin-4-yl)pyridin-2-yl)oxy)-3-methylphenyl)-1-(2,6-difluorophenyl)methanesulfonamide |
| 294 295 | | 1-phenyl-N-(2,3,6-trifluoro-4-((3-(2-((5-(fluoromethyl)-5-methylpiperidin-3-yl)amino)pyrimidin-4-yl)pyridin-2-yl)oxy)phenyl)methanesulfonamide |

TABLE 1-continued

| No. | Structure | Name |
|---|---|---|
| 296 | 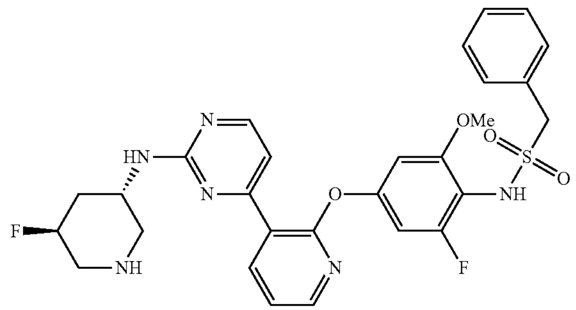 [SMILES: COc1cc(Oc2ncccc2-c2ccnc(N[C@@H]3CNC[C@@H](F)C3)n2)cc(F)c1NS(=O)(=O)Cc1ccccc1] | N-(2-fluoro-4-((3-(2-(((3S,5S)-5-fluoropiperidin-3-yl)amino)pyrimidin-4-yl)pyridin-2-yl)oxy)-6-methoxyphenyl)-1-phenylmethanesulfonamide |
| 297 | 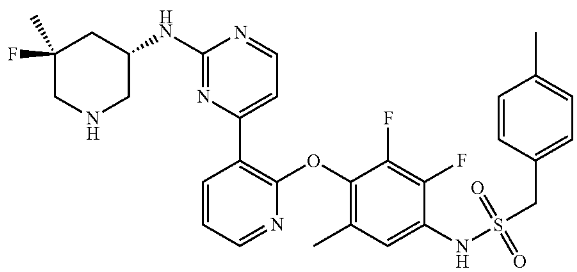 [SMILES: Cc1ccc(CS(=O)(=O)Nc2cc(C)c(Oc3ncccc3-c3ccnc(N[C@@H]4CNC[C@@](C)(F)C4)n3)c(F)c2F)cc1] | N-(2,3-difluoro-4-((3-(2-(((3S,5S)-5-fluoro-5-methylpiperidin-3-yl)amino)pyrimidin-4-yl)pyridin-2-yl)oxy)-5-methylphenyl)-1-(p-tolyl)methanesulfonamide |
| 298 299 300 301 | | N-(4-((3-(2-((1,1-difluoro-5-azaspiro[2.5]octan-7-yl)amino)pyrimidin-4-yl)pyridin-2-yl)oxy)-2,3,6-trifluorophenyl)-1-phenylmethanesulfonamide |
| 302 303 | | N-(4-((3-(2-((5-(difluoromethyl)piperidin-3-yl)amino)pyrimidin-4-yl)pyridin-2-yl)oxy)-2,3,6-trifluorophenyl)-1-phenylmethanesulfonamide |
| 304 | 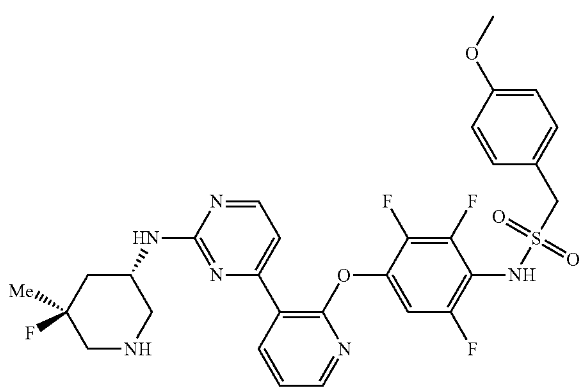 [SMILES: COc1ccc(CS(=O)(=O)Nc2c(F)cc(Oc3ncccc3-c3ccnc(N[C@@H]4CNC[C@@](C)(F)C4)n3)c(F)c2F)cc1] | 1-(4-methoxyphenyl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide |

TABLE 1-continued

| No. | Structure | Name |
|---|---|---|
| 305 | 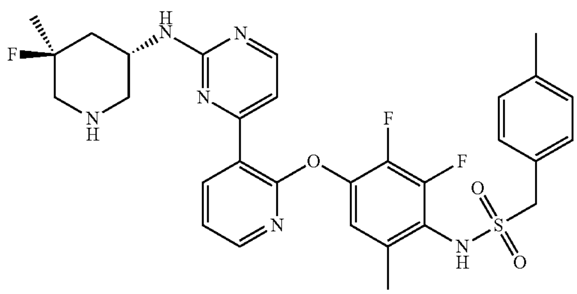 [SMILES: Cc1ccc(CS(=O)(=O)Nc2c(C)cc(Oc3ncccc3-c3ccnc(N[C@@H]4CNC[C@@](C)(F)C4)n3)c(F)c2F)cc1] | N-(2,3-difluoro-4-((3-(2-(((3S,5S)-5-fluoro-5-methylpiperidin-3-yl)amino)pyrimidin-4-yl)pyridin-2-yl)oxy)-6-methylphenyl)-1-(p-tolyl)methanesulfonamide |
| 306 307 308 | | N-(4-((3-(2-((4-(dimethylamino)-3-fluorocyclohexyl)amino)pyrimidin-4-yl)pyridin-2-yl)oxy)-2,3,6-trifluorophenyl)-1-phenylmethanesulfonamide |
| 309 | 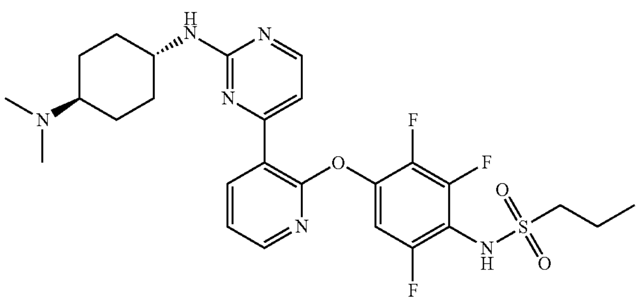 [SMILES: CCCS(=O)(=O)Nc1c(F)cc(Oc2ncccc2-c2ccnc(N[C@H]3CC[C@H](N(C)C)CC3)n2)c(F)c1F] | N-(4-((3-(2-(((1r,4r)-4-(dimethylamino)cyclohexyl)amino)pyrimidin-4-yl)pyridin-2-yl)oxy)-2,3,6-trifluorophenyl)propane-1-sulfonamide |
| 310 | 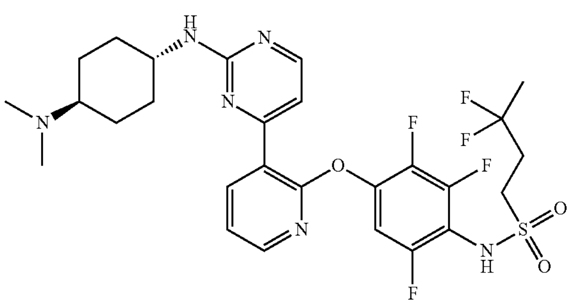 [SMILES: CN(C)[C@H]1CC[C@H](Nc2nccc(-c3cccnc3Oc3cc(F)c(NS(=O)(=O)CCC(C)(F)F)c(F)c3F)n2)CC1] | N-(4-((3-(2-(((1r,4r)-4-(dimethylamino)cyclohexyl)amino)pyrimidin-4-yl)pyridin-2-yl)oxy)-2,3,6-trifluorophenyl)-3,3-difluorobutane-1-sulfonamide |
| 311 | 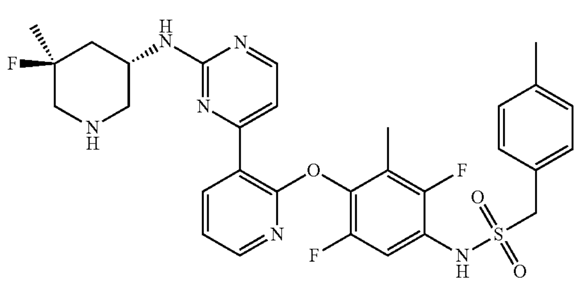 | N-(2,5-difluoro-4-((3-(2-(((3S,5S)-5-fluoro-5-methylpiperidin-3-yl)amino)pyrimidin-4-yl)pyridin-2-yl)oxy)-3-methylphenyl)-1-(p-tolyl)methanesulfonamide |

TABLE 1-continued

| No. | Structure | Name |
|---|---|---|
| 312 | 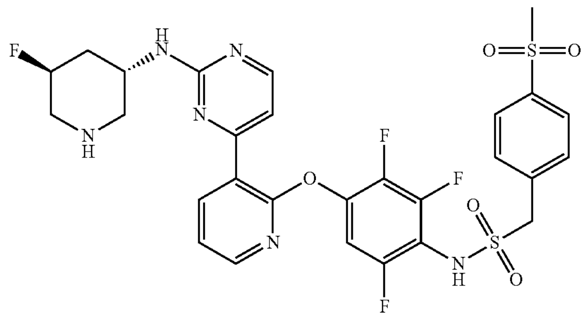 [SMILES: CS(=O)(=O)c1ccc(CS(=O)(=O)Nc2c(F)cc(Oc3ncccc3-c3ccnc(N[C@@H]4CNC[C@@H](F)C4)n3)c(F)c2F)cc1] | 1-(4-(methylsulfonyl)phenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 313 | 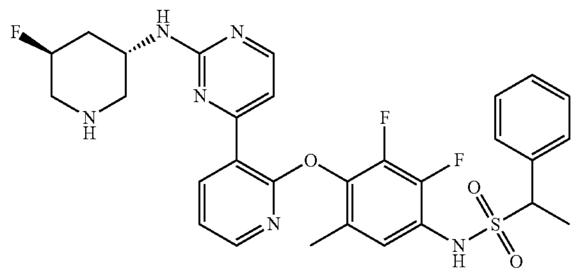 [SMILES: Cc1cc(NS(=O)(=O)C(C)c2ccccc2)c(F)c(F)c1Oc1ncccc1-c1ccnc(N[C@@H]2CNC[C@@H](F)C2)n1] | N-(2,3-difluoro-4-((3-(2-(((3S,5S)-5-fluoropiperidin-3-yl)amino)pyrimidin-4-yl)pyridin-2-yl)oxy)-5-methylphenyl)-1-phenylethane-1-sulfonamide hydrochloride |
| 314 | 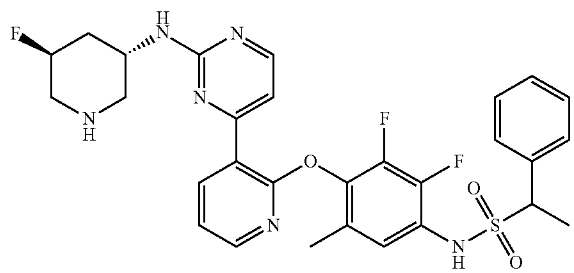 [SMILES: Cc1cc(NS(=O)(=O)C(C)c2ccccc2)c(F)c(F)c1Oc1ncccc1-c1ccnc(N[C@@H]2CNC[C@@H](F)C2)n1] | N-(2,3-difluoro-4-((3-(2-(((3S,5S)-5-fluoropiperidin-3-yl)amino)pyrimidin-4-yl)pyridin-2-yl)oxy)-5-methylphenyl)-1-phenylethane-1-sulfonamide |
| 315 | 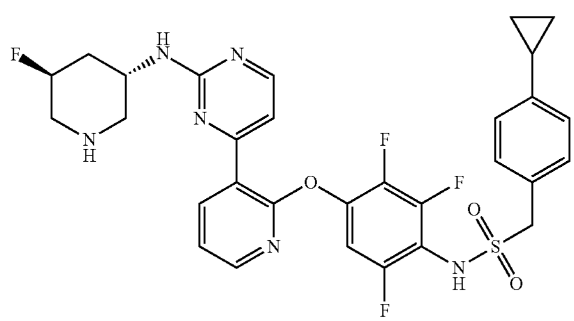 [SMILES: O=S(=O)(Cc1ccc(C2CC2)cc1)Nc1c(F)cc(Oc2ncccc2-c2ccnc(N[C@@H]3CNC[C@@H](F)C3)n2)c(F)c1F] | 1-(4-cyclopropylphenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 316 | 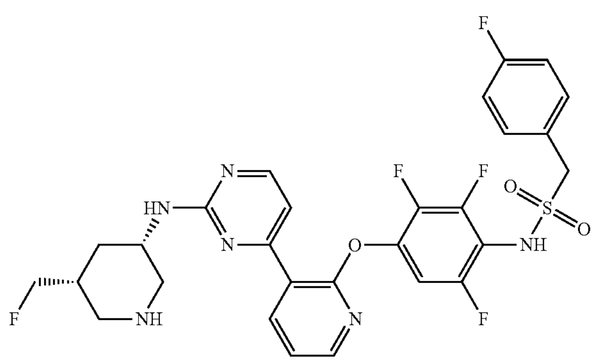 [SMILES: O=S(=O)(Cc1ccc(F)cc1)Nc1c(F)cc(Oc2ncccc2-c2ccnc(N[C@@H]3CNC[C@H](CF)C3)n2)c(F)c1F] | 1-(4-fluorophenyl)-N-(2,3,6-trifluoro-4-((3-(2-(((3S,5R)-5-(fluoromethyl)piperidin-3-yl)amino)pyrimidin-4-yl)pyridin-2-yl)oxy)phenyl)methanesulfonamide |

TABLE 1-continued

| No. | Structure | Name |
|---|---|---|
| 317 318 319 | | 1-phenyl-N-(2,3,6-trifluoro-4-((3-(2-((5-methoxypiperidin-3-yl)amino)pyrimidin-4-yl)pyridin-2-yl)oxy)phenyl)methanesulfonamide |
| 320 | 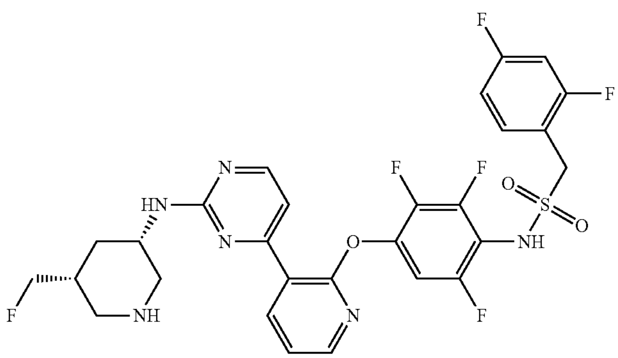 [SMILES: O=S(=O)(Cc1ccc(F)cc1F)Nc1c(F)cc(Oc2ncccc2-c2ccnc(N[C@@H]3CNC[C@H](CF)C3)n2)c(F)c1F] | 1-(2,4-difluorophenyl)-N-(2,3,6-trifluoro-4-((3-(2-(((3S,5R)-5-(fluoromethyl)piperidin-3-yl)amino)pyrimidin-4-yl)pyridin-2-yl)oxy)phenyl)methanesulfonamide |
| 321 | 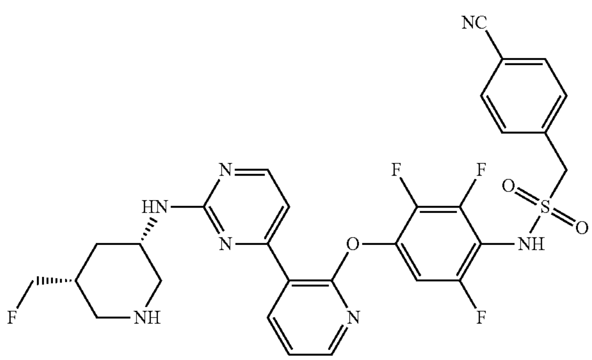 [SMILES: N#Cc1ccc(CS(=O)(=O)Nc2c(F)cc(Oc3ncccc3-c3ccnc(N[C@@H]4CNC[C@H](CF)C4)n3)c(F)c2F)cc1] | 1-(4-cyanophenyl)-N-(2,3,6-trifluoro-4-((3-(2-(((3S,5R)-5-(fluoromethyl)piperidin-3-yl)amino)pyrimidin-4-yl)pyridin-2-yl)oxy)phenyl)methanesulfonamide |
| 322 | 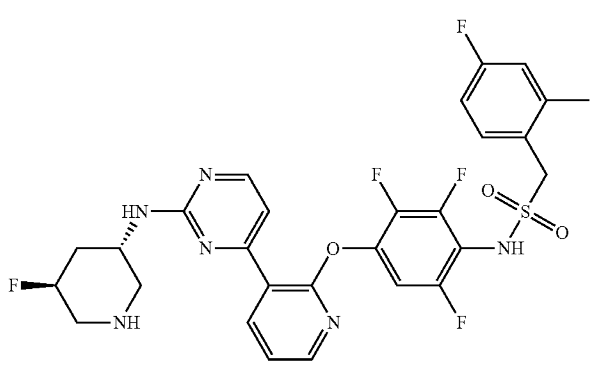 [SMILES: Cc1cc(F)ccc1CS(=O)(=O)Nc1c(F)cc(Oc2ncccc2-c2ccnc(N[C@@H]3CNC[C@@H](F)C3)n2)c(F)c1F] | 1-(4-fluoro-2-methylphenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |

TABLE 1-continued

| No. | Structure | Name |
|---|---|---|
| 323 | 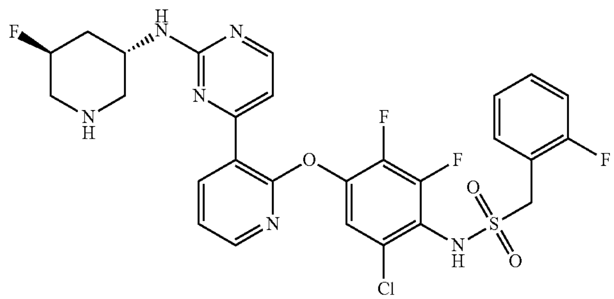 [SMILES: O=S(=O)(Cc1ccccc1F)Nc1c(Cl)cc(Oc2ncccc2-c2ccnc(N[C@@H]3CNC[C@@H](F)C3)n2)c(F)c1F] | N-(6-chloro-2,3-difluoro-4-((3-(2-(((3S,5S)-5-fluoropiperidin-3-yl)amino)pyrimidin-4-yl)pyridin-2-yl)oxy)phenyl)-1-(2-fluorophenyl)methanesulfonamide |
| 324 325 326 327 | | N-(4-((3-(2-((5-cyclopropylpiperidin-3-yl)amino)pyrimidin-4-yl)pyridin-2-yl)oxy)-2,3,6-trifluorophenyl)-1-(2-fluorophenyl)methanesulfonamide |
| 328 329 330 331 | | 1-phenyl-N-(2,3,6-trifluoro-4-((3-(2-((5-(methoxymethyl)piperidin-3-yl)amino)pyrimidin-4-yl)pyridin-2-yl)oxy)phenyl)methanesulfonamide |
| 332 | 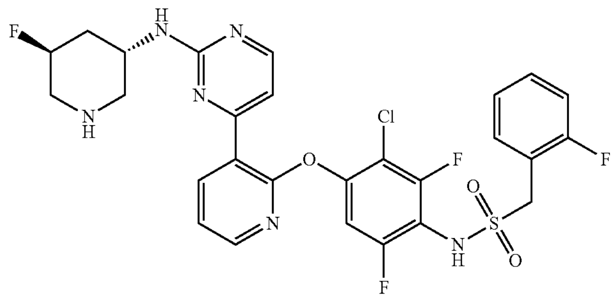 [SMILES: O=S(=O)(Cc1ccccc1F)Nc1c(F)cc(Oc2ncccc2-c2ccnc(N[C@@H]3CNC[C@@H](F)C3)n2)c(Cl)c1F] | N-(3-chloro-2,6-difluoro-4-((3-(2-(((3S,5S)-5-fluoropiperidin-3-yl)amino)pyrimidin-4-yl)pyridin-2-yl)oxy)phenyl)-1-(2-fluorophenyl)methanesulfonamide |

TABLE 1-continued

| No. | Structure | Name |
|---|---|---|
| 333 | 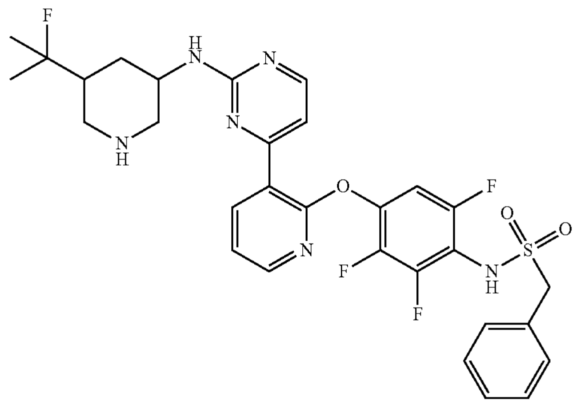 [SMILES: CC(C)(F)C1CNCC(Nc2nccc(-c3cccnc3Oc3cc(F)c(NS(=O)(=O)Cc4ccccc4)c(F)c3F)n2)C1] | 1-phenyl-N-(2,3,6-trifluoro-4-((3-(2-((5-(2-fluoropropan-2-yl)piperidin-3-yl)amino)pyrimidin-4-yl)pyridin-2-yl)oxy)phenyl)methanesulfonamide hydrochloride |
| 334 335 336 | | 1-phenyl-N-(2,3,6-trifluoro-4-((3-(2-((5-(2-fluoropropan-2-yl)piperidin-3-yl)amino)pyrimidin-4-yl)pyridin-2-yl)oxy)phenyl)methanesulfonamide |
| 337 | 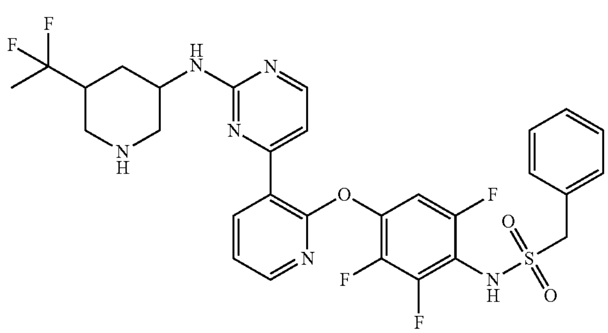 [SMILES: CC(F)(F)C1CNCC(Nc2nccc(-c3cccnc3Oc3cc(F)c(NS(=O)(=O)Cc4ccccc4)c(F)c3F)n2)C1] | N-(4-((3-(2-((5-(1,1-difluoroethyl)piperidin-3-yl)amino)pyrimidin-4-yl)pyridin-2-yl)oxy)-2,3,6-trifluorophenyl)-1-phenylmethanesulfonamdie hydrochloride |
| 338 339 | | N-(4-((3-(2-((5-(1,1-difluoroethyl)piperidin-3-yl)amino)pyrimidin-4-yl)pyridin-2-yl)oxy)-2,3,6-trifluorophenyl)-1-phenylmethanesulfonamide |

TABLE 1-continued

| No. | Structure | Name |
|---|---|---|
| 340 | 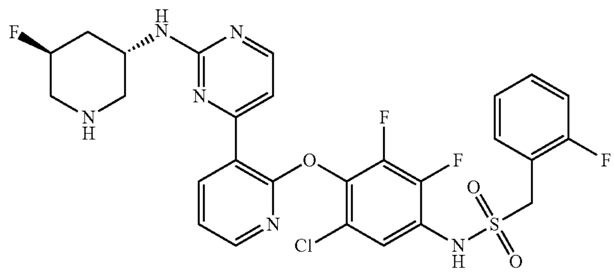 [SMILES: O=S(=O)(Cc1ccccc1F)Nc1cc(Cl)c(Oc2ncccc2-c2ccnc(N[C@@H]3CNC[C@@H](F)C3)n2)c(F)c1F] | N-(5-chloro-2,3-difluoro-4-((3-(2-(((3S,5S)-5-fluoropiperidin-3-yl)amino)pyrimidin-4-yl)pyridin-2-yl)oxy)phenyl)-1-(2-fluorophenyl)methanesulfonamide |
| 341 | 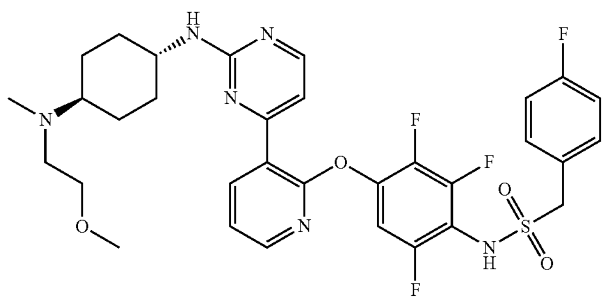 [SMILES: COCCN(C)[C@H]1CC[C@H](Nc2nccc(-c3cccnc3Oc3cc(F)c(NS(=O)(=O)Cc4ccc(F)cc4)c(F)c3F)n2)CC1] | 1-(4-fluorophenyl)-N-(2,3,6-trifluoro-4-((3-(2-(((1r,4r)-4-((2-methoxyethyl)(methyl)amino)cyclohexyl)amino)pyrimidin-4-yl)pyridin-2-yl)oxy)phenyl)methanesulfonamide hydrochloride |
| 342 343 344 345 | | 1-phenyl-N-(2,3,6-trifluoro-4-((3-(2-((5-(1-fluoroethyl)piperidin-3-yl)amino)pyrimidin-4-yl)pyridin-2-yl)oxy)phenyl)methanesulfonamide hydrochloride |
| 346 347 348 349 | | 1-phenyl-N-(2,3,6-trifluoro-4-((3-(2-((5-(1-fluoroethyl)piperidin-3-yl)amino)pyrimidin-4-yl)pyridin-2-yl)oxy)phenyl)methanesulfonamide |

TABLE 1-continued

| No. | Structure | Name |
|---|---|---|
| 350 | 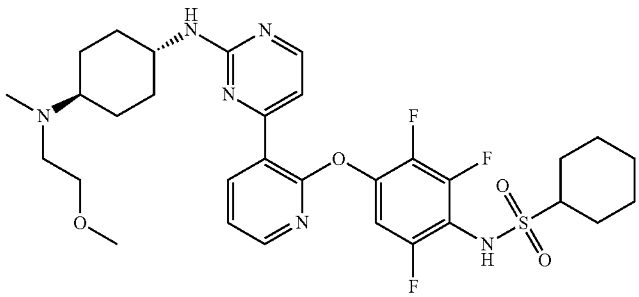 [SMILES: COCCN(C)[C@H]1CC[C@H](Nc2nccc(-c3cccnc3Oc3cc(F)c(NS(=O)(=O)C4CCCCC4)c(F)c3F)n2)CC1] | N-(2,3,6-trifluoro-4-((3-(2-(((1r,4r)-4-((2-methoxyethyl)(methyl)amino)cyclohexyl)amino)pyrimidin-4-yl)pyridin-2-yl)oxy)phenyl)cyclohexanesulfonamide |
| 351 | 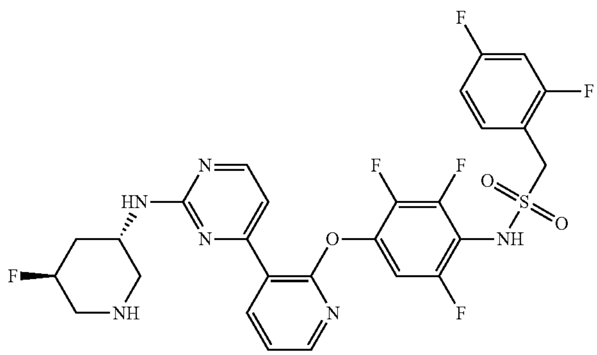 [SMILES: O=S(=O)(Cc1ccc(F)cc1F)Nc1c(F)cc(Oc2ncccc2-c2ccnc(N[C@@H]3CNC[C@@H](F)C3)n2)c(F)c1F] | 1-(2,4-difluorophenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide |
| 352 | 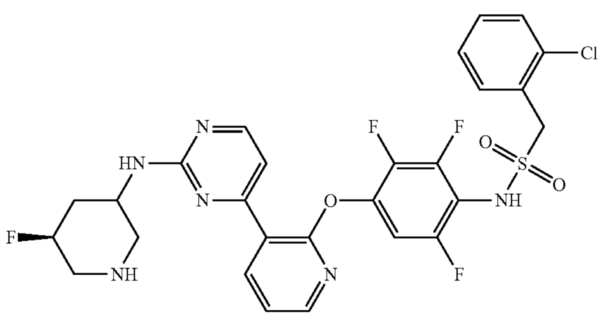 | 1-(2-chlorophenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide |
| 353 | 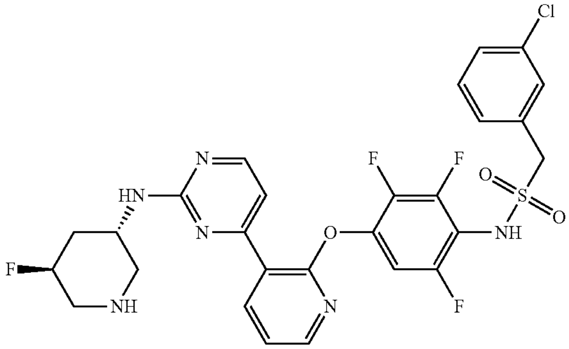 | 1-(3-chlorophenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide |

TABLE 1-continued

| No. | Structure | Name |
|---|---|---|
| 354 | 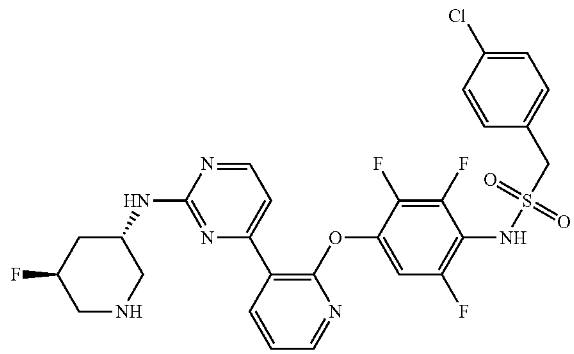 [SMILES: O=S(=O)(Cc1ccc(Cl)cc1)Nc1c(F)cc(Oc2ncccc2-c2ccnc(N[C@@H]3CNC[C@@H](F)C3)n2)c(F)c1F] | 1-(4-chlorophenyl)-N-[2,3,6-trifluroo-4-[[3-[2-[[(3S,5S)-5-fluoro-3-piperidyl]amino]pyrimidin-4-yl]-2-pyridyl]oxy]phenyl]methanesulfonamide |
| 355 | 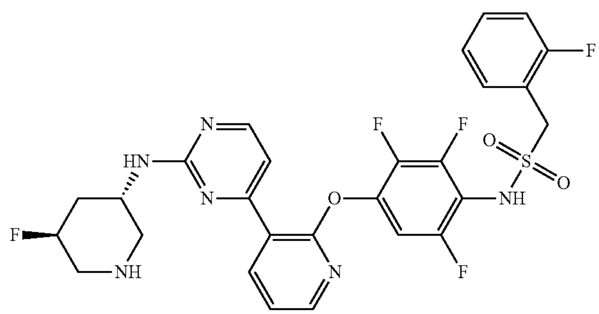 [SMILES: O=S(=O)(Cc1ccccc1F)Nc1c(F)cc(Oc2ncccc2-c2ccnc(N[C@@H]3CNC[C@@H](F)C3)n2)c(F)c1F] | 1-(2-fluorophenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide |
| 356 | 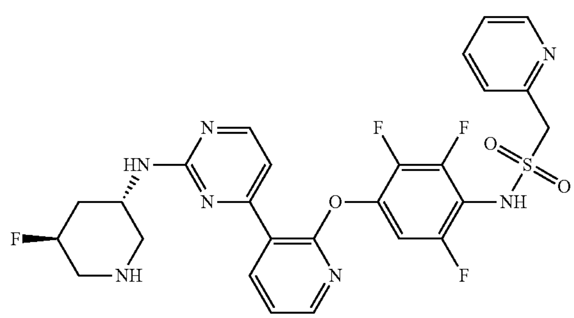 | 1-(2-pyridyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide |
| 357 | 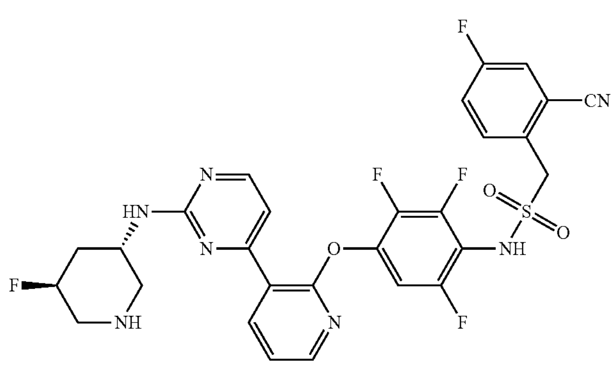 | 1-(2-cyano-4-fluoro-phenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide |

TABLE 1-continued

| No. | Structure | Name |
| --- | --- | --- |
| 358 | 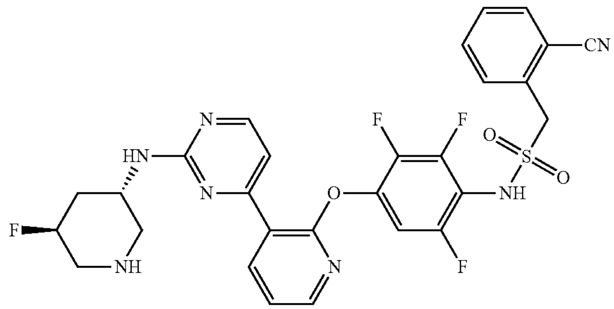 | 1-(2-cyanophenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide |
| 359 | 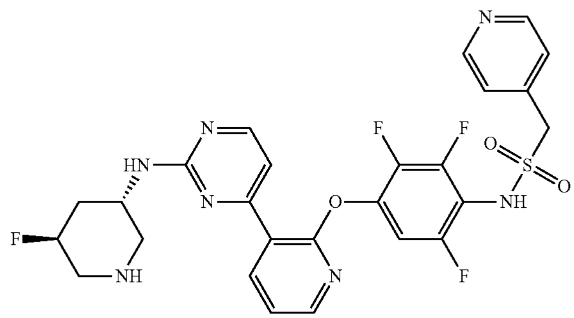 [SMILES: O=S(=O)(Cc1ccncc1)Nc1c(F)cc(Oc2ncccc2-c2ccnc(N[C@@H]3CNC[C@@H](F)C3)n2)c(F)c1F] | 1-(4-pyridyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide |
| 360 | 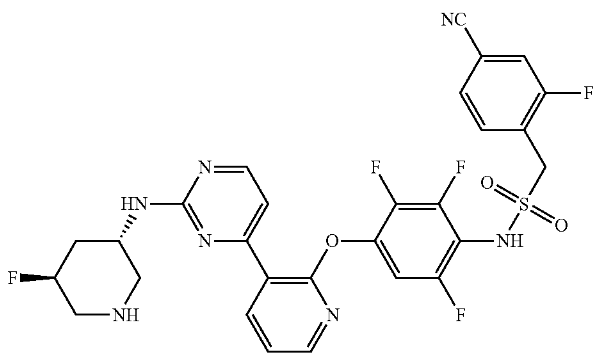 | 1-(4-cyano-2-fluoro-phenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide |
| 361 | 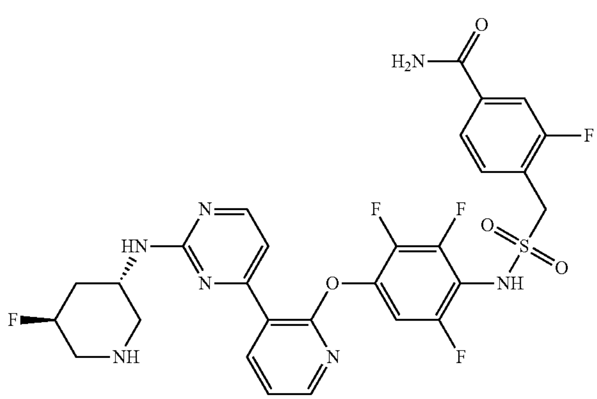 [SMILES: NC(=O)c1ccc(CS(=O)(=O)Nc2c(F)cc(Oc3ncccc3-c3ccnc(N[C@@H]4CNC[C@@H](F)C4)n3)c(F)c2F)c(F)c1] | 3-fluoro-4-[[2,3,6-trifluoro-4-[[3-[2-[[(3S,5S)-5-fluoro-3-piperidyl]amino]pyrimidin-4-yl]-2-pyridyl]oxy]phenyl]sulfamoyl-methyl]benzamide |

TABLE 1-continued

| No. | Structure | Name |
|---|---|---|
| 362 | 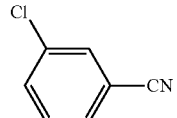 | 1-(4-chloro-2-cyano-phenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide |
| 363 | 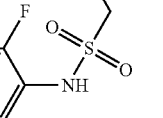 | 1-(2,6-difluorophenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide |
| 364 | 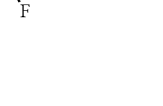 | 1-(4-chloro-2-fluoro-phenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide |
| 365 | 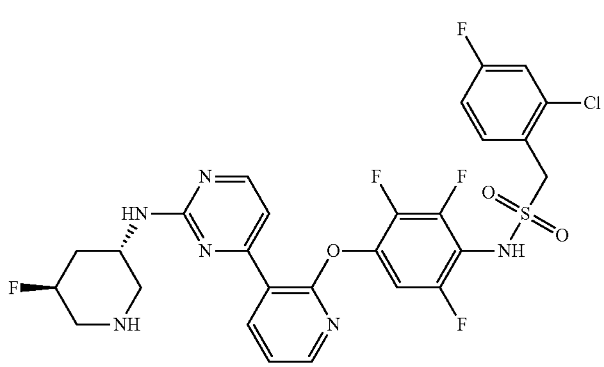 [SMILES: O=S(=O)(Cc1ccc(F)cc1Cl)Nc1c(F)cc(Oc2ncccc2-c2ccnc(N[C@@H]3CNC[C@@H](F)C3)n2)c(F)c1F] | 1-(2-chloro-4-fluoro-phenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide |

TABLE 1-continued

| No. | Structure | Name |
|---|---|---|
| 366 | 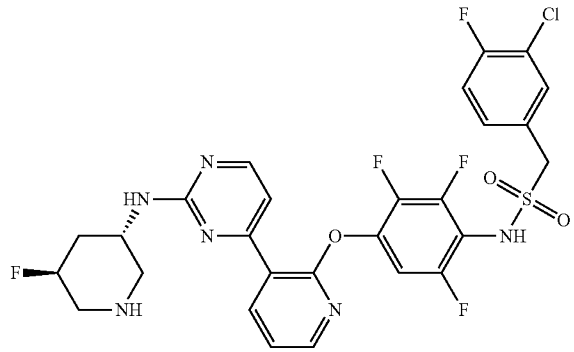 [SMILES: O=S(=O)(Cc1ccc(F)c(Cl)c1)Nc1c(F)cc(Oc2ncccc2-c2ccnc(N[C@@H]3CNC[C@@H](F)C3)n2)c(F)c1F] | 1-(3-chloro-4-fluoro-phenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide |
| 367 | 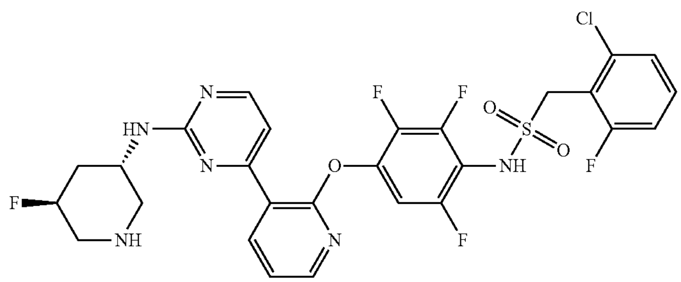 [SMILES: O=S(=O)(Cc1c(F)cccc1Cl)Nc1c(F)cc(Oc2ncccc2-c2ccnc(N[C@@H]3CNC[C@@H](F)C3)n2)c(F)c1F] | 1-(2-chloro-6-fluorophenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 368 | 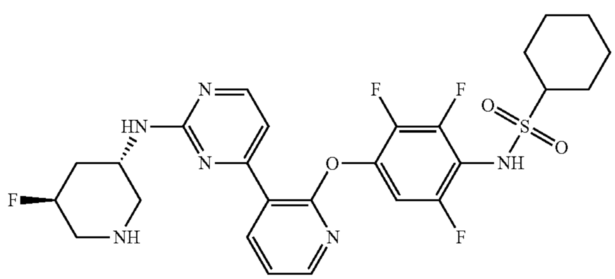 [SMILES: O=S(=O)(Nc1c(F)cc(Oc2ncccc2-c2ccnc(N[C@@H]3CNC[C@@H](F)C3)n2)c(F)c1F)C1CCCCC1] | N-(2,3,6-trifluoro-4-((3-(2-(((3S,5S)-5-fluoropiperidin-3-yl)amino)pyrimidin-4-yl)pyridin-2-yl)oxy)phenyl)cyclohexanesulfonamide |
| 369 | 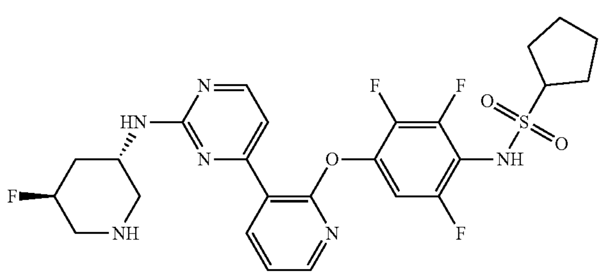 [SMILES: O=S(=O)(Nc1c(F)cc(Oc2ncccc2-c2ccnc(N[C@@H]3CNC[C@@H](F)C3)n2)c(F)c1F)C1CCCC1] | N-(2,3,6-trifluoro-4-((3-(2-(((3S,5S)-5-fluoropiperidin-3-yl)amino)pyrimidin-4-yl)pyridin-2-yl)oxy)phenyl)cyclopentanesulfonamide |
| 370 | 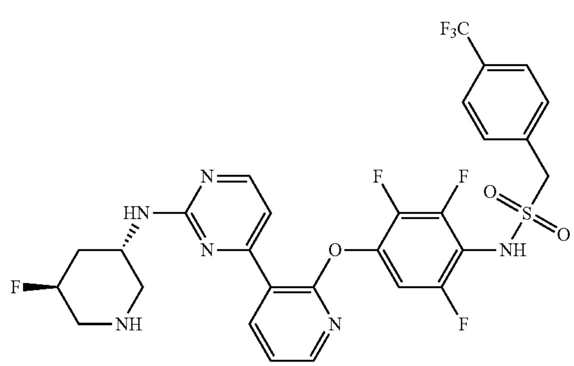 | N-(2,3,6-trifluoro-4-((3-(2-(((3S,5S)-5-fluoropiperidin-3-yl)amino)pyrimidin-4-yl)pyridin-2-yl)oxy)phenyl)-1-(4-(trifluoromethyl)phenyl)methanesulfonamide |

TABLE 1-continued

| No. | Structure | Name |
|---|---|---|
| 371 | 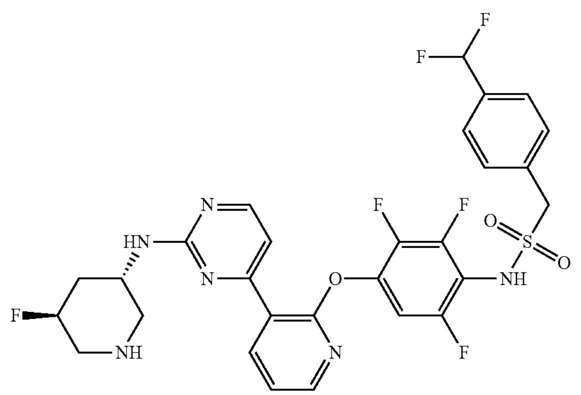 [SMILES: O=S(=O)(Cc1ccc(C(F)F)cc1)Nc1c(F)cc(Oc2ncccc2-c2ccnc(N[C@@H]3CNC[C@@H](F)C3)n2)c(F)c1F] | 1-(4-(difluoromethyl)phenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 372 | 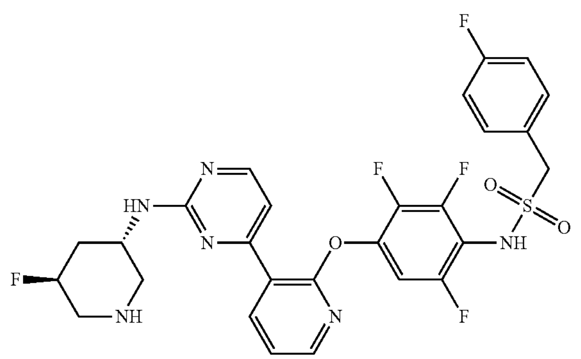 [SMILES: O=S(=O)(Cc1ccc(F)cc1)Nc1c(F)cc(Oc2ncccc2-c2ccnc(N[C@@H]3CNC[C@@H](F)C3)n2)c(F)c1F] | 1-(4-fluorophenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 373 | 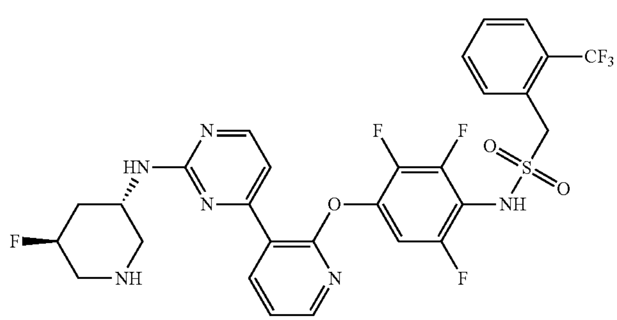 [SMILES: O=S(=O)(Cc1ccccc1C(F)(F)F)Nc1c(F)cc(Oc2ncccc2-c2ccnc(N[C@@H]3CNC[C@@H](F)C3)n2)c(F)c1F] | N-(2,3,6-trifluoro-4-((3-(2-(((3S,5S)-5-fluoropiperidin-3-yl)amino)pyrimidin-4-yl)pyridin-2-yl)oxy)phenyl)-1-(2-(trifluoromethyl)phenyl)methanesulfonamide |
| 374 | 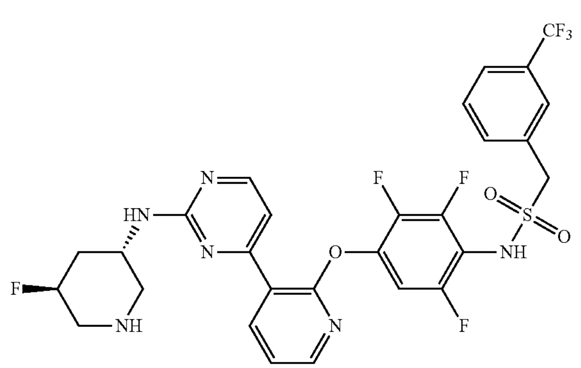 [SMILES: O=S(=O)(Cc1cccc(C(F)(F)F)c1)Nc1c(F)cc(Oc2ncccc2-c2ccnc(N[C@@H]3CNC[C@@H](F)C3)n2)c(F)c1F] | N-(2,3,6-trifluoro-4-((3-(2-(((3S,5S)-5-fluoropiperidin-3-yl)amino)pyrimidin-4-yl)pyridin-2-yl)oxy)phenyl)-1-(3-(trifluoromethyl)phenyl)methanesulfonamide |

TABLE 1-continued

| No. | Structure | Name |
|---|---|---|
| 375 | 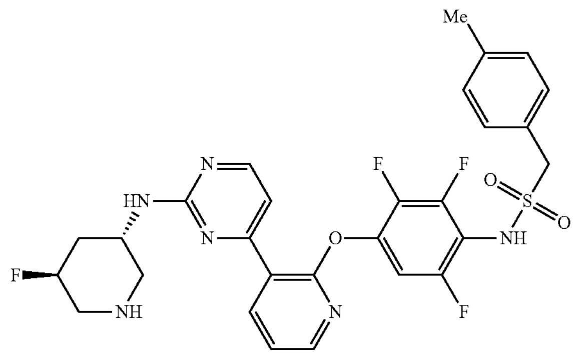 | 1-p-tolyl-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 376 | 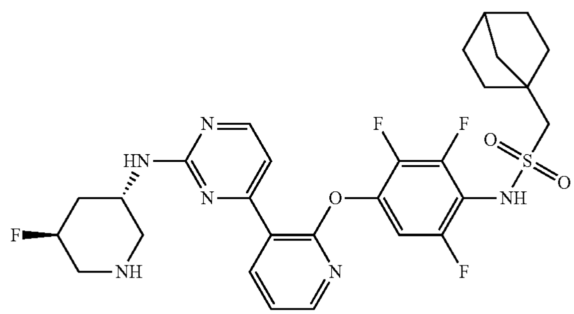 [SMILES: O=S(=O)(CC12CCC(CC1)C2)Nc1c(F)cc(Oc2ncccc2-c2ccnc(N[C@@H]3CNC[C@@H](F)C3)n2)c(F)c1F] | 1-(bicyclo[2.2.1]heptan-1-yl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 377 | 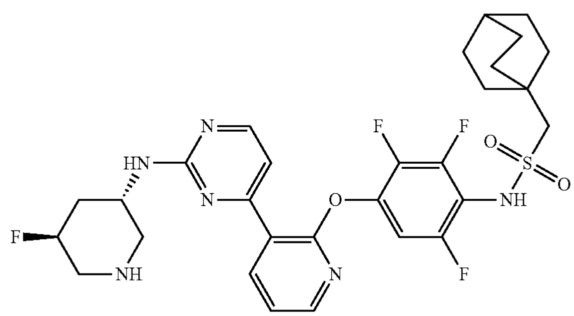 [SMILES: O=S(=O)(CC12CCC(CC1)CC2)Nc1c(F)cc(Oc2ncccc2-c2ccnc(N[C@@H]3CNC[C@@H](F)C3)n2)c(F)c1F] | 1-(bicyclo[2.2.2]octan-1-yl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 378 | 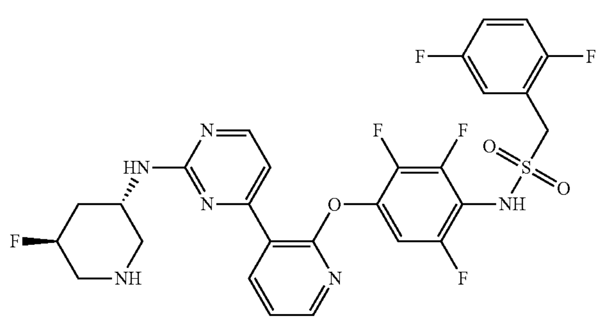 [SMILES: O=S(=O)(Cc1cc(F)ccc1F)Nc1c(F)cc(Oc2ncccc2-c2ccnc(N[C@@H]3CNC[C@@H](F)C3)n2)c(F)c1F] | 1-(2,5-difluorophenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 379 | 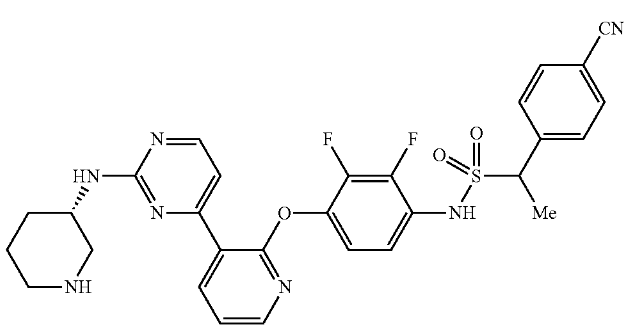 [SMILES: CC(c1ccc(C#N)cc1)S(=O)(=O)Nc1ccc(Oc2ncccc2-c2ccnc(N[C@H]3CCCNC3)n2)c(F)c1F] | 1-(4-cyanophenyl)-N-(2,3-difluoro-4-((3-(2-(((S)-piperidin-3-yl)amino)pyrimidin-4-yl)pyridin-2-yl)oxy)phenyl)ethane-1-sulfonamide |

TABLE 1-continued

| No. | Structure | Name |
|---|---|---|
| 380 | 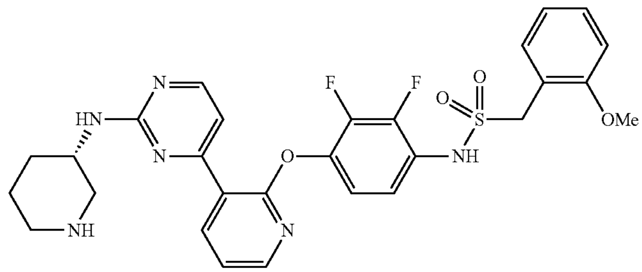 [SMILES: COc1ccccc1CS(=O)(=O)Nc1ccc(Oc2ncccc2-c2ccnc(N[C@H]3CCCNC3)n2)c(F)c1F] | (S)-N-(2,3-difluoro-4-((3-(2-(piperidin-3-ylamino)pyrimidin-4-yl)pyridin-2-yl)oxy)phenyl)-1-(2-methoxyphenyl)methanesulfonamide |
| 381 | 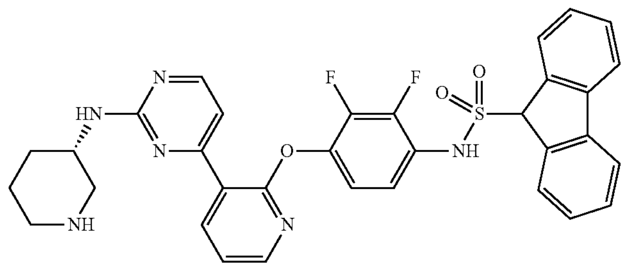 [SMILES: O=S(=O)(Nc1ccc(Oc2ncccc2-c2ccnc(N[C@H]3CCCNC3)n2)c(F)c1F)C1c2ccccc2-c2ccccc21] | (S)-N-(2,3-difluoro-4-((3-(2-(piperidin-3-ylamino)pyrimidin-4-yl)pyridin-2-yl)oxy)phenyl)-9H-fluorene-9-sulfonamide |
| 382 | 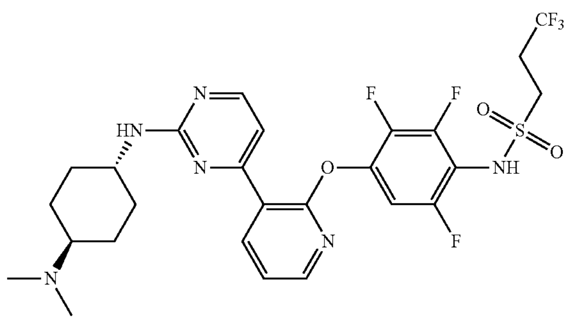 [SMILES: CN(C)[C@H]1CC[C@H](Nc2nccc(-c3cccnc3Oc3cc(F)c(NS(=O)(=O)CCC(F)(F)F)c(F)c3F)n2)CC1] | N-(4-((3-(2-(((1r,4r)-4-(dimethylamino)cyclohexyl)amino)pyrimidin-4-yl)pyridin-2-yl)oxy)-2,3,6-trifluorophenyl)-3,3,3-trifluoropropane-1-sulfonamide |
| 383 | 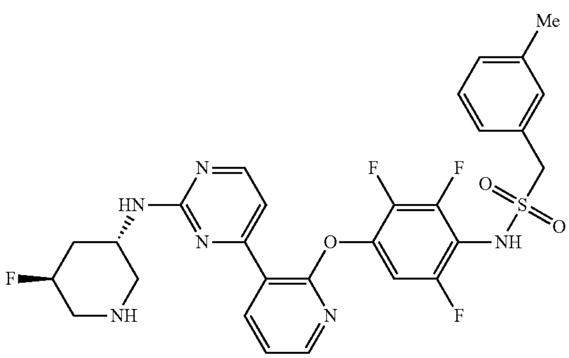 | 1-m-tolyl-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 384 | 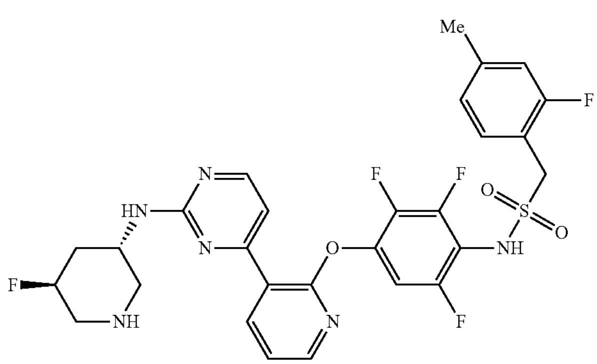 | 1-(2-fluoro-4-methylphenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |

TABLE 1-continued

| No. | Structure | Name |
|---|---|---|
| 385 | 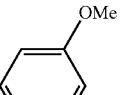 | 1-(3-methoxyphenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 386 | 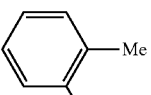 | 1-o-tolyl-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide |
| 387 | 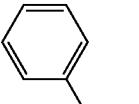 | (*S)-1-phenyl-N-(2,3,6-trifluoro-4-((3-(2-(((3S,5S)-5-fluoropiperidin-3-yl)amino)ppyrimidin-4-yl)pyridin-2-yl)oxy)phenyl)ethane-1-sulfonamide |
| 388 | 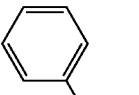 | (*R)-1-phenyl-N-(2,3,6-trifluoro-4-((3-(2-(((3S,5S)-5-fluoropiperidin-3-yl)amino)pyrimidin-4-yl)pyridin-2-yl)oxy)phenyl)ethane-1-sulfonamide |

TABLE 1-continued

| No. | Structure | Name |
|---|---|---|
| 389 | 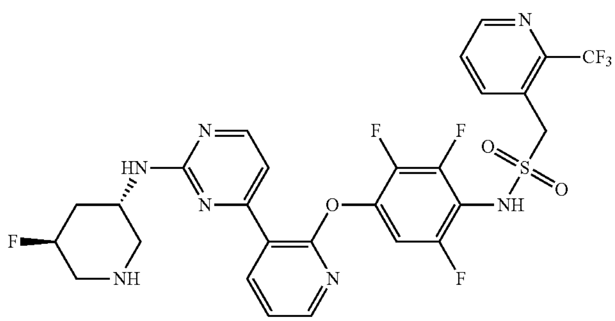 [SMILES: O=S(=O)(Cc1cccnc1C(F)(F)F)Nc1c(F)cc(Oc2ncccc2-c2ccnc(N[C@@H]3CNC[C@@H](F)C3)n2)c(F)c1F] | N-(2,3,6-trifluoro-4-((3-(2-(((3S,5S)-5-fluoropiperidin-3-yl)amino)pyrimidin-4-yl)pyridin-2-yl)oxy)phenyl)-1-(2-(trifluoromethyl)pyridin-3-yl)methanesulfonamide |

*arbitrarily assigned

In some embodiments, provided is a compound selected from Compound Nos. 101-389 in Table 1, or a pharmaceutically acceptable salt thereof. In some embodiments, provided is a compound selected from Compound Nos. 101-238 or 248-389 in Table 1, or a pharmaceutically acceptable salt thereof.

Preparation of Formula I Compounds

Formula I compounds can be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9): 1910-16, (1985); Helvetica Chimica Acta, 41:1052-60, (1958); Arzneimittel-Forschung, 40(12): 1328-31, (1990), each of which are expressly incorporated by reference. Starting materials are generally available from commercial sources such as Aldrich Chemicals (Milwaukee, WI) or are readily prepared using methods (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database). Formula I compounds can also be made following the procedures found in U.S. Pat. Nos. 8,476,434, 7,880,000, WO 2005/113494, U.S. Pat. No. 7,868,177, and WO 2007/100646.

Synthetic chemistry transformations and protecting group methodologies (protection and deprotection) useful in synthesizing Formula I compounds and necessary reagents and intermediates include, for example, those described in R. Larock, Comprehensive Organic Transformations, VCH Publishers (1989); T. W. Greene and P. G. M. Wuts, Protective Groups in Organic Synthesis, 3$^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I can be prepared singly or as compound libraries comprising at least 2, for example 5 to 1,000 compounds, or 10 to 100 compounds. Libraries of compounds of Formula I can be prepared by a combinatorial split and mix approach or by multiple parallel syntheses using, for example, either solution phase or solid phase chemistry. Thus according to a further aspect provided herein is a compound library comprising at least 2 compounds, or pharmaceutically acceptable salts thereof as described herein.

The Examples provide exemplary methods for preparing Formula I compounds. Those skilled in the art will appreciate that other synthetic routes can be used to synthesize the Formula I compounds. Although specific starting materials and reagents are depicted and discussed in the Examples, other starting materials and reagents can be easily substituted to provide a variety of derivatives and/or reaction conditions. In addition, many of the exemplary compounds prepared by the described methods can be further modified in light of this disclosure using conventional chemistry.

In preparing compounds of Formula I, protection of remote functionality (e.g., primary or secondary amine) of intermediates can be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection can be readily determined. For a general description of protecting groups and their use, see T. W. Greene, Protective Groups in Organic Synthesis, John Wiley & Sons, New York, 1991.

In the methods of preparing Formula I compounds, it can be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds or pharmaceutically acceptable salts thereof described herein can be atropisomers (e.g., substituted biaryls). Enantiomers can also be separated by use of a chiral HPLC column.

A single stereoisomer, e.g., an enantiomer, substantially free of its stereoisomer can be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds or pharmaceutically acceptable salts thereof described herein can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts can be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Compounds of Formula (I) can be prepared by procedures in the Examples, the General Procedures, and generally by Schemes 1-4, where R groups are as described herein,

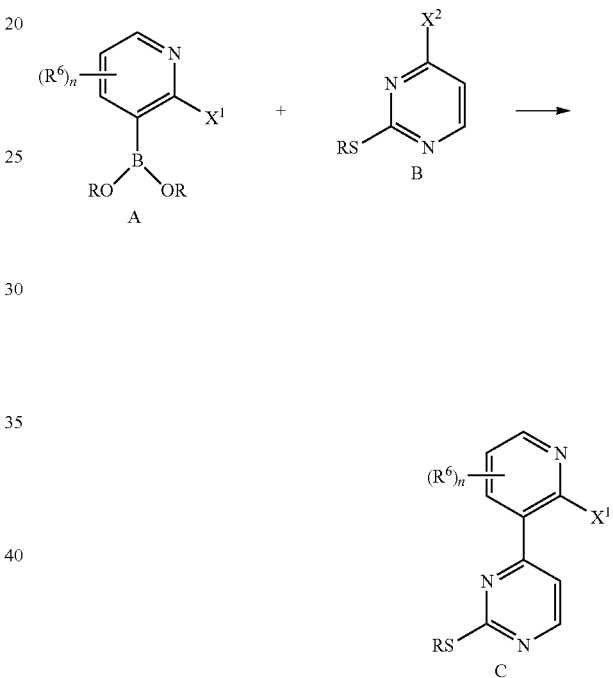

Scheme 1

Scheme 1 shows coupling of a (2-halopyridin-3-yl)boronic acid or ester compound A (R=H, $C_1$-$C_6$ alkyl, pinacol; $X^1$=halogen) with a 4-chloro-2-(methylthio)pyrimidine compound B (R=$C_1$-$C_6$ alkyl, $X^2$=halogen) under palladium catalysis to form 4-(2-halopyridin-3-yl)-2-(alkylthio)pyrimidine compound C.

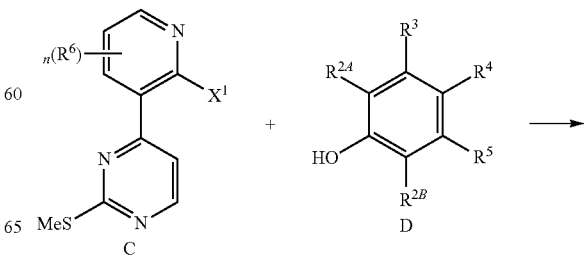

Scheme 2

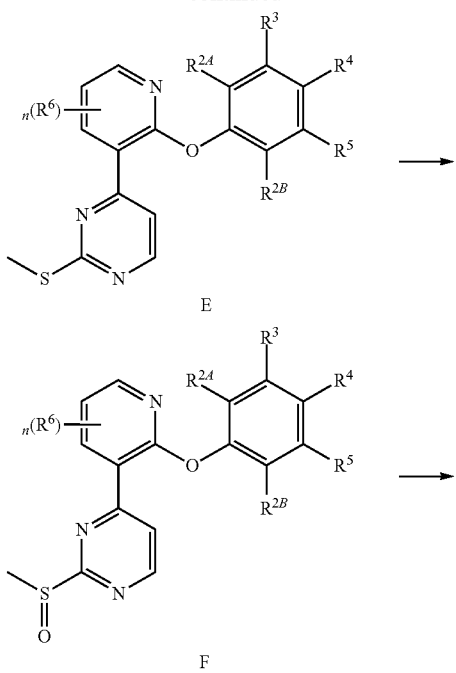

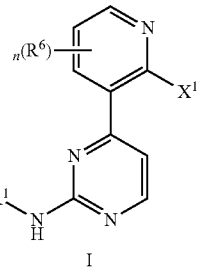

Scheme 3 shows an alternative route to Formula I compounds where a 4-(2-halopyridin-3-yl)-2-(alkylthio)pyrimidine compound C is oxidized to a 4-(2-halopyridin-3-yl)-2-(alkylsulfinyl)pyrimidine compound H. The sulfoxide is displaced with a primary amine (R¹—NH₂) to form a 4-(2-halopyridin-3-yl)-I-alkylpyrimidin-2-amine compound I. Coupling of compound I with a phenol compound D forms a Formula I compound, or an intermediate to be converted to a Formula I compound.

Scheme 2 shows coupling of a phenol compound D with a 4-(2-halopyridin-3-yl)-2-(alkylthio)pyrimidine compound C to form a 4-(2-(phenyloxy)pyridin-3-yl)pyrimidine-2-alkylthiol E compound. Oxidation of the sulfur atom forms 2-(alkylsulfinyl)-4-(2-(phenyloxy)pyridin-3-yl)pyrimidine compound F. The sulfoxide is displaced with a primary amine (R¹—NH₂) to form a Formula I or I' compound, or an intermediate to be converted to a Formula I or I' compound.

Scheme 4

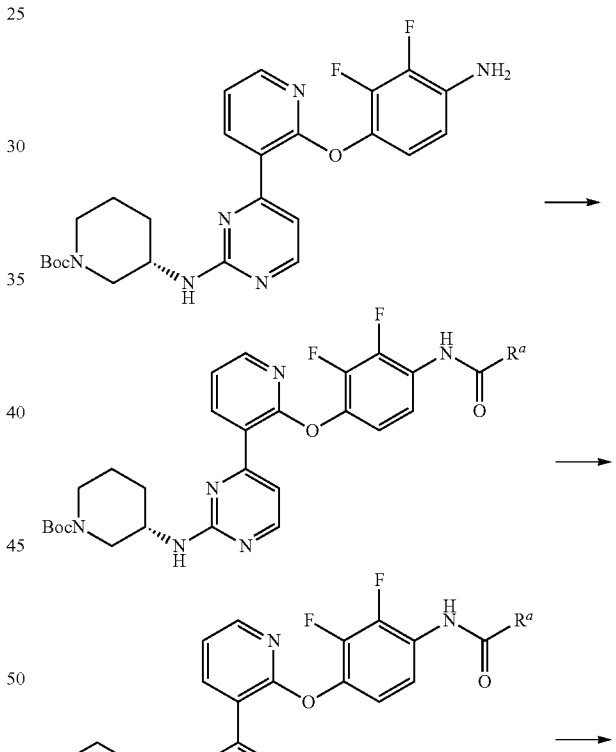

Scheme 3

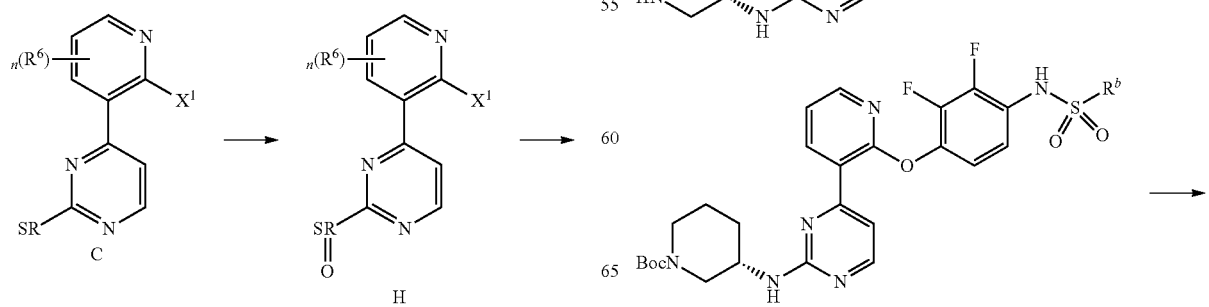

-continued

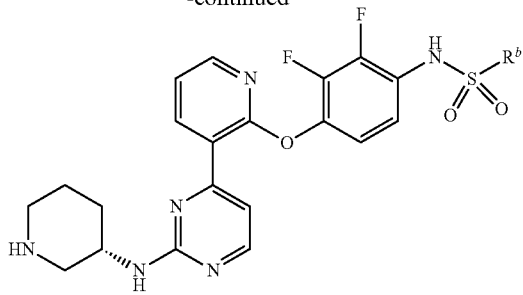

Scheme 4 shows the general preparation of exemplary compounds from aniline intermediate, tert-butyl (S)-3-((4-(2-(4-amino-2,3-difluorophenoxy)pyridin-3-yl)pyrimidin-2-yl)amino)piperidine-1-carboxylate. The aniline intermediate is treated with a carboxlic acid ($R^aCOOH$) and a coupling reagent, such as 1-[Bis(dimethylamino)methylene]-1H-1,2,3-triazolo[4,5-b]pyridinium 3-oxid hexafluorophosphate (HATU) as in General Procedure C, or alternatively with an acid chloride ($R^aCOCl$) and an amine base such as diisopropylethylamine (DIPEA) or pyridine, to form Boc-protected, amide intermediates (top). The aniline intermediate is treated with a sulfonyl chloride ($R^bSO_2Cl$) and an amine base to form Boc-protected, sulfonamide intermediates (middle) as in General Procedure A. The Boc-protected intermediates are deprotected with acid, such as hydrochloric acid as in General Procedure B, to form exemplary compounds, such as those in Table 1 and the Examples.

The following General Procedures illustrate synthetic reactions and operations useful to prepare certain Example compounds (Table A1). The reagents, solvents, amounts, equivalents, and conditions are illustrative and exemplary, and not meant to be limiting.

General Procedure A—Sulfonamide Synthesis

To a solution of the aniline (1.0 equiv) in pyridine (5 mL/mmol) and a solvent such as dichloromethane (DCM) at 0° C. or room temperature (rt) was added the corresponding sulfonyl chloride (1.2 equiv typically otherwise noted). After the addition was completed, the reaction solution was stirred at rt for about 16 h. Water (10 mL) was added. The mixture was extracted with DCM. The organic layer was dried over anhydrous sodium sulfate, filtered and concentrated in vacuo.

General Procedure B—Boc Deprotection

To a mixture of the tert-butyl-carbamate (Boc) intermediate (100 mg, 0.16 mmol) in DCM (25 mL/mmol) or EtOAc was added hydrochloric acid (4 M in dioxane, 10 mL/mmol). The mixture was then stirred at rt for 1 h and concentrated in vacuo or the resulting HCl salt was isolated by filtration.

General Procedure C—Amide Coupling Using Carboxylic Acids

To a solution of the aniline intermediate (1.05 equiv otherwise indicated) and DIPEA (3.0 equiv otherwise indicated) in DCM (16 mL/mmol otherwise indicated) was added HATU (2.0 equiv otherwise indicated). The mixture was stirred at rt for 0.5 h. The acid (1.0 equiv otherwise indicated) was added and the resulting mixture was refluxed overnight. The mixture was diluted in DCM, washed with water and brine, dried on anhydrous sodium sulfate, and concentrated in vacuo. Alternatively, to a solution of the aniline in $CH_2Cl_2$ was added the acid chloride followed by addition of $(iPr)_2NEt$ or $Et_3N$ or pyridine and stirring at rt. Alternatively, to a solution of the aniline in DMF was added the carboxylic acid and HATU followed by addition of $(iPr)_2NEt$ or $Et_3N$ and stirring at rt. Other coupling reagents can be used in General Procedure C. The crude product was isolated and purified using known methods or as described in the Examples.

General Procedure D—Cbz Deprotection

A mixture of benzyl-carbamate, palladium on carbon (Pd/C) and ammonium formate in iPrOH was heated at 60° C. When complete, the mixture was filtered through celite using MeOH/$CH_2Cl_2$ and concentrated in vacuo.

Analytical Methods:

LCMS (Liquid Chromatography Mass Spectrometry) methods to separate and characterize the exemplary compounds are performed on one or more of the following:

SHIMADZU LC-MS 2010EV coupled with SHIMADZU LC20AB using ESI as ionization source. The LC separation was using Column: MERCK, RP-18e 25-2 mm; Detector: PDA, ELSD; Wavelength: UV 220 nm; Column temperature: 50° C.; mobile Phase: 1.5 mL/4 L TFA in water (solvent A) and 0.75 mL/4 L TFA in acetonitrile (solvent B), using the elution gradient 5%-95% (solvent B) over 0.7 minutes and holding at 95% for 0.4 minutes at a flow rate of 1.5 mL/min;

SHIMADZU LC-MS 2010EV coupled with SHIMADZU LC20AB using ESI as ionization source. The LC separation was using Column: MERCK, RP-18e 25-2 mm; Detector: PDA, ELSD; Wavelength: UV 220 nm; Column temperature: 50° C.; mobile Phase: 1.5 mL/4 L TFA in water (solvent A) and 0.75 mL/4 L TFA in acetonitrile (solvent B), using the elution gradient 5%-95% (solvent B) over 0.7 minutes and holding at 95% for 0.4 minutes at a flow rate of 1.5 mL/min;

Agilent 1200 Series coupled with 6110 Quadrupole mass spectrometer, using ESI as ionization source. The LC separation was using Column: Xtimate C18 2.1×30 mm, 3 μm; Wavelength: UV 220 nm; Column temperature: 50° C.; Detector: PDA&ELSD. mobile Phase: 1.5 mL/4 L TFA in water (solvent A) and 0.75 mL/4 LTFA in acetonitrile (solvent B), using the elution gradient 10%-80% (solvent B) over 0.9 minutes and holding at 80% for 0.6 minutes at a flow rate of 1.2 mL/min.

SHIMADZU 2020 HPLC coupled with SHIMADZU MSD mass spectrometer using ESI as ionization source. The LC separation was using an Shim-Pack XR-ODS-C18, 50×3.0 mm column with a 1 ml/minute flow rate. Solvent A is water with 0.05% TFA and solvent B is acetonitrile with 0.05% TFA. The gradient consisted with 5-100% solvent B over 2.2 minutes and hold 100% B for 1 minute. LC column temperature is 40° C. UV absorbance was collected from 190 nm to 400 nm and mass spec full scan was applied to all experiments.

SHIMADZU 2020 HPLC coupled with SHIMADZU MSD mass spectrometer using ESI as ionization source. The LC separation was using an Gemini-NX 3μ C18 110A, 50×3.0 mm column with a 1.2 ml/minute flow rate. Solvent A is water with 0.4% $NH_4HCO3$ and solvent B is acetonitrile. The gradient consisted with 10-50% solvent B over 4 minutes and hold 50% B for 1.2 minutes. LC column temperature is 40° C. UV absorbance was collected from 190 nm to 400 nm and mass spec full scan was applied to all experiments.

SHIMADZU UFLC-MS 2010EV coupled with SHIMADZU MSD mass spectrometer using ESI as ionization source. The LC separation was using a Shim-pack XR-ODS-C18, 50×3.0 mm column with a 1 ml/minute flow rate. Solvent A is water with 0.05% TFA and solvent B is acetonitrile with 0.05% TFA. The gradient consisted with 5-100% solvent B over 2.2 minutes and hold 100% B for 1 minute. LC column temperature is 40° C. UV absorbance was collected from 190 nm to 400 nm and mass spec full scan was applied to all experiments.

Waters Alliance 2695 HPLC with column heater coupled with Waters ZQ 2000 mass spectrometer using ESI as ionization source (ES+, 100-1200 amu). The LC separation was using an XBridge C18, 3.5 µm, 4.6×30 mm column at 25° C. with a 3.0 mL/minute flow rate. Solvent A is Milli-Q H2O+10 mM Ammonium Formate pH: 3.8, and solvent B is acetonitrile. The gradient consisted of isocratic 5% solvent B for 0.2 min, 5% to 100% B in 1.8 minutes; hold 100% B for 1 minute. LC column temperature is 25° C. UV absorbance was collected from 195-320 nm using a Waters PDA 996 UV detector and mass spec full scan was applied to all experiments.

Waters Alliance 2695 HPLC with column heater coupled with Waters ZQ 2000 mass spectrometer using ESI as ionization source (ES+, 100-1200 amu). The LC separation was using an XBridge C18, 3.5 µm, 4.6×30 mm column at 25° C. with a 3.0 mL/minute flow rate. Solvent A is Milli-Q H2O+10 mM Ammonium Bicarbonate pH: 10, and solvent B is acetonitrile. The gradient consisted of isocratic 5% solvent B for 0.2 min, 5% to 100% B in 1.8 minutes; hold 100% B for 1 minute. LC column temperature is 25° C. UV absorbance was collected from 195-320 nm using a Waters PDA 996 UV detector and mass spec full scan was applied to all experiments.

Biological Evaluation

The relative efficacies of Formula I compounds or pharmaceutically acceptable salts thereof as described herein as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Inhibition of IRE1α RNase activity was determined in an enzyme assay that measured cleavage of the XBP1 stem loop by autophosphorylated IRE1α This assay format was chosen to ensure that inhibitors of either the IRE1α kinase or the RNase domains would be identified. Binding to the ATP pocket and inhibition of IRE1α kinase activity are not necessarily required to inhibit the RNase activity. Compounds were also profiled in cellular assays by direct measurement of XBP1s (B-DNA assay) or by quantification of the luciferase signal in HT1080 XBP1-Luc, which carries a luciferase fusion that is only in frame and expressed from the spliced XBP1 transcript In the IRE1α enzyme and XPB1-Luc assays, phenoxy-pyridyl-pyrimidine compounds described herein (e.g., compounds in Table A1) demonstrated activity.

Cell proliferation, cytotoxicity, and cell viability of the Formula I compounds including pharmaceutically acceptable salts thereof can be measured by the CellTiter-Glo® Luminescent Cell Viability Assay (Promega Corp.). The CellTiter-Glo® Luminescent Cell Viability Assay is a homogeneous method of determining the number of viable cells in culture based on quantitation of the ATP present, an indicator of metabolically active cells. The CellTiter-Glo® Assay is designed for use with multiwell formats, making it ideal for automated high-throughput screening (HTS), cell proliferation and cytotoxicity assays. The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

Biological activity of Formula I compounds and pharmaceutically acceptable salts thereof was measured by an IRE1 biochemical binding assay (Example B1), a biochemical RNase assay (Example B2), a cellular PD assay, XBP1s-LUC reporter (Example B3), and an IRE1α-based inhibition of multiple myeloma (MM) cell proliferation assay.

Administration of Compounds

Compounds described herein can be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds can be administered by intralesional administration, including perfusing or otherwise contacting the graft with the inhibitor before transplantation. It will be appreciated that the preferred route can vary with for example the condition of the recipient. Where the compound is administered orally, it can be formulated as a pill, capsule, tablet, etc. with a pharmaceutically acceptable carrier or excipient. Where the compound is administered parenterally, it can be formulated with a pharmaceutically acceptable parenteral vehicle and in a unit dosage injectable form, as detailed below.

Thus, in one aspect provided herein is a pharmaceutical composition comprising a compound or pharmaceutically acceptable salt thereof as described herein and one or more pharmaceutically acceptable excipients. In one embodiment, compounds described herein are administered as pharmaceutical compositions capable of being administered to a subject orally or parenterally. The compounds described herein can be formulated for topical or parenteral use where the compound is dissolved or otherwise suspended in a solution suitable for injections, suspensions, syrups, creams, ointments, gels, sprays, solutions and emulsions.

Oral administration can promote patient compliance in taking the compound (e.g. formulated as a pharmaceutical composition), thereby increasing compliance and efficacy. Oral pharmaceutical compositions comprising a compound described herein include, but are not limited to, tablets (e.g. coated, non-coated and chewable) and capsules (e.g. hard gelatin capsules, soft gelatin capsules, enteric coated capsules, and sustained release capsules). Tablets can be prepared by direct compression, by wet granulation, or by diy granulation. Oral pharmaceutical compositions comprising a compound described herein can be formulated for delayed or prolonged release.

A dose to treat human patients can range from about 10 mg to about 1000 mg of Formula I compound. A typical dose can be about 100 mg to about 300 mg of the compound. A dose can be administered once a day (QID), twice per day (BID), or more frequently, depending on the pharmacokinetic and pharmacodynamic properties, including absorption, distribution, metabolism, and excretion of the particular compound. In addition, toxicity factors can influence the dosage and administration regimen. When administered orally, the pill, capsule, or tablet can be ingested daily or less frequently for a specified period of time. The regimen can be repeated for a number of cycles of therapy.

Methods of Treatment

In one aspect provided herein, Formula I compounds or pharmaceutically acceptable salts thereof are useful for treating a patient suffering from a disease or disorder arising from abnormal cell growth, function or behavior associated with the UPR pathway such as cancer, an immune disorder, cardiovascular disease, viral infection, inflammation, a metabolism/endocrine disorder or a neurological disorder, can thus be treated by a method comprising the administration thereto of a compound or pharmaceutically acceptable salts thereof described herein as defined above. Thus, provided herein are methods of treating cancer by administering to a patient having cancer an effective amount of a compound or pharmaceutically acceptable salt thereof described herein. The condition of the patient can thereby be improved or ameliorated.

The methods provided herein include treatment of solid tumors/cancers. For example, administration of a compound or pharmaceutically acceptable salt thereof described herein can be performed for patients having breast cancer, ovary cancer, cervix cancer, prostate cancer, testis cancer, genitourinary tract cancer, esophagus cancer, larynx cancer, glioblastoma, neuroblastoma, stomach cancer, skin cancer, keratoacanthoma, lung cancer, epidermoid carcinoma, large cell cancer, non-small cell lung cancer (NSCLC), small cell carcinoma, lung adenocarcinoma, bone cancer, colon cancer, adenoma, pancreatic cancer, adenocarcinoma, thyroid cancer, follicular carcinoma, undifferentiated carcinoma, papillary carcinoma, seminoma, melanoma, sarcoma, bladder carcinoma, liver carcinoma and biliary passages, kidney carcinoma, buccal cavity cancer, naso-pharyngeal cancer, pharynx cancer, lip cancer, tongue cancer, mouth cancer, small intestine cancer, colon-rectum cancer, large intestine cancer, rectum cancer, bronchial cancer, hepatocellular cancer, gastric cancer, endometrial cancer, melanoma, renal cancer, urinary bladder cancer, uterine corpus cancer, and uterine cervix cancer.

In another embodiment, the methods provided herein include treatment of cancer by administering to a patient having cancer an effective amount of a compound or pharmaceutically acceptable salt thereof where the cancer comprises squamous cell carcinoma, small-cell lung cancer, non-small cell lung cancer (NSCLC), lung adenocarcinoma, squamous cell lung cancer, peritoneum cancer, hepatocellular cancer, stomach cancer, gastrointestinal cancer, esophageal cancer, pancreatic cancer, glioblastoma, cervical cancer, ovarian cancer, liver cancer, bladder cancer, breast cancer, colon cancer, rectal cancer, colorectal cancer, endometrial cancer, uterine cancer, salivary gland carcinoma, renal cancer, prostate cancer, vulval cancer, thyroid cancer, hepatocellular carcinoma (HCC), anal carcinoma, penile carcinoma, or head and neck cancer.

In certain embodiments, the cancer is breast cancer. The breast cancer can be Stage I, II, III, or IV as understood in the art. In one embodiment, the breast cancer is triple negative breast cancer (TNBC). In another embodiment, the breast cancer is Her2 negative breast cancer.

In another aspect provided herein are methods of treating hematological cancers such as, for example, lymphoma, lymphocytic leukemia (acute (ALL) and chronic (CLL), multiple myeloma (MM), acute myelogenous leukemia (AML), chronic myelogenous leukemia (CML), myelodysplastic syndrome (MDS), myeloproliferative disease (MPD), or non-Hodgkin lymphoma In one embodiment, the methods herein include treatment of lymphoma lymphocytic leukemia multiple myeloma (MM), acute myelogenous leukemia (AML), chronic myelogenous leukemia (CML), myelodysplastic syndrome (MDS), or myeloproliferative disease (MPD) by administering an effective amount of a compound described herein.

In one embodiment, is a method of treating MM by administering to a patient having MM an effective amount of compound described herein.

In one aspect, provided is a method of treating an IRE1-related disease or disorder in a patient comprising administering an effective amount of a compound of Formula (I) or pharmaceutically acceptable salt thereof, to a patient with an IRE1-related disease or condition. In another aspect, the method comprises administering to a patient with an IRE1-related disease or condition an effective amount of a pharmaceutical composition comprising a compound of Formula (I) or a pharmaceutically acceptable salt thereof and one or more pharmaceutically acceptable carrier excipients. In some embodiments, the compound is of the Formula I excluding compounds of Table 1X. In other embodiments, the compound is of the Formula I including compounds of Table 1X. In some embodiments, the compound is selected from Table 1, or a pharmaceutically acceptable salt thereof. In some embodiments, the patient is a human patient.

In one embodiment, the cancer is an Ire1-mediated cancer (i.e. a cancer having abnormal expression or activity of Ire1 relative to a control). In me embodiment, the Ire1-mediated cancer has increased expression of Ire1. In another embodiment, the Ire1-mediated cancer has increased activity of Ire1. Such increases can be measured against a control (e.g. against a patient having predetermined Ire1 function, expression, activity; or for example measure in a single patient before, during, or after treatment with a compound or pharmaceutically acceptable salt thereof described herein).

In another aspect provided herein is a compound of Formula I or a pharmaceutically acceptable salt thereof for use in a method for treating an IRE1-related disease or disorder. In one aspect, provided is a use of a compound of Formula I or pharmaceutically acceptable salt thereof, in the manufacture of a medicament for the treatment of an IRE1-related disease or disorder.

In some embodiments of the method of treating an IRE1-related disease or disorder in a patient comprising administering an effective amount of a compound of Formula I or pharmaceutically acceptable salt thereof to a patient with an IRE1-related disease or condition, the method further comprising administering one or more additional therapeutic agent(s) selected from the group consisting of an anti-inflammatory agent, a corticosteroid, an immunomodulatory agent, anti-cancer agent as described herein, an apoptosis-enhancer, a neurotropic factor, an agent for treating cardiovascular disease, an agent for treating liver disease, an anti-viral agent, an agent for treating blood disorders, an agent for treating diabetes, an agent for treating metabolic disorders, an agent for treating autoimmune disorders, an agent for treating immunodeficiency disorders, and combinations thereof. In some embodiments, the additional therapeutic agent is a corticosteroid, a proteasome inhibitor, an IMiD, an antibody, or a combination thereof. In some embodiments, the additional therapeutic agent is a proteasome inhibitor (e.g. carfilzomib, bortezomib, or ixazomib). In some embodiments, the additional therapeutic agent is an IMiD (e.g. lenalidomide or pomalidomide). In some embodiments, the additional therapeutic agent is an antibody (e.g., an anti-CD38 antibody, an anti-VEGF-A antibody, an anti-PD-1 antibody, an anti-PD-L1 antibody or an anti-interleukin-6 antibody). In some embodiments, the additional therapeutic agent is a corticosteroid (e.g., dexamethasone). In some embodiments, the method further comprises radiotherapy.

Also provided herein is a method of treating a disease caused by abnormal levels of Ire1 activity in a human or animal patient in need of such treatment with a Formula I compound or a pharmaceutically acceptable salt thereof described herein. The disease can be caused by an amount of Ire1 activity that is too low or too high. For example, the disease can be caused by a deficiency in Ire1 activity or by abnormally high Ire1 activity (e.g., hyperactivity of Ire1). The method includes administering to the patient a effective amount of an Ire1 modulator Formula I compound or a pharmaceutically acceptable salt thereof described herein.

Ire1 deficiency is a decreased amount of Ire1 activity compared to normal levels of Ire1 activity in a particular subject or a population of healthy subjects. The decreased amount of Ire1 activity results in excessive amounts of misfolded protein accumulation thereby causing the disease state.

Ire1 hyperactivity is an increased amount of Ire1 activity compared to normal levels of Ire1 activity in a particular subject or a population of healthy subjects. The increased amount of Ire1 activity can result in, for example, excessive amounts of cell proliferation thereby causing the disease state.

In some embodiments, the disease is associated with Ire1 deficiency. Such diseases include, but are not limited to, cystic fibrosis, retinitis pigmentosa, diabetes, or a neurodegenerative disease. The neurodegenerative disease can include Alexander's disease, Alper's disease, Alzheimer's disease, Amyotrophic lateral sclerosis, Ataxia telangiectasia, Batten disease (also known as Spielmeyer-Vogt-Sjogren-Batten disease). Bovine spongiform encephalopathy (BSF), Canavan disease, Cockayne syndrome, Corticobasal degeneration, Creutzfeldt-Jakob disease, Huntington's disease, HIV-associated dementia, Kennedy's disease, Krabbe's disease, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoff s disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, or Tabes dorsalis.

In other embodiments, the disease is associated with abnormally high Ire1. Such diseases include, but are not limited, to cancers, inflammatory diseases, and autoimmune diseases. Exemplary cancers include, but am not limited to, breast cancer and multiple myeloma. In me embodiment, the disease is multiple myeloma. In (me embodiment, the disease is a triple-negative breast cancer. Exemplary inflammatory diseases include, but are not limited to, asthma, chronic inflammation, chronic prostatitis, glomerulonephritis, hypersensitivities, inflammatory bowel diseases, pelvic inflammatory disease; reperfusion injury, rheumatoid arthritis, transplant rejection, and vasculitis. Exemplary autoimmune diseases include, but are not limited to, XBP1-linked Crohn's disease, Coeliac disease, diabetes mellitus type 1 (IDDM), systemic lupus erythematosus (SLE), Sjogren's syndrome, Churg-Strauss Syndrome, Hashimoto's thyroiditis, Graves' disease, idiopathic thrombocytopenic purpura, and rheumatoid arthritis. In one embodiment, the disease is XBP1-linked. Crohn's disease.

In one aspect provided herein is a method of treating atherosclerosis or the progression of atherosclerosis by administering an effective amount of a compound or pharmaceutically acceptable salt thereof described herein. In one embodiment, administration of a compound or pharmaceutically acceptable salt thereof described herein reduces the number of macrophages in an atherosclerotic lesion. Such reduction can be imparted, in some embodiments, without altering apoptosis state. In another embodiment, administration of a compound or pharmaceutically acceptable salt thereof as described herein inhibits or reduces the production of IL-1β, CCL2, and chemokine receptor 2.

Pharmaceutical Formulations

Compounds or pharmaceutically acceptable salts thereof as described herein can be formulated in accordance with standard pharmaceutical practice as a pharmaceutical composition. Thus, further provided herein is a pharmaceutical composition comprising a compound or pharmaceutically acceptable salt thereof and one or more pharmaceutically acceptable excipients.

A typical formulation is prepared by mixing a compound or pharmaceutically acceptable salt thereof as described herein and an excipient. Suitable carriers, diluents and excipients include, but are not limited to, materials such as carbohydrates, waxes, water soluble and/or swellable polymers, hydrophilic or hydrophobic materials, gelatin, oils, solvents, water and the like. The particular excipient used will depend upon the means and purpose for which the compound or pharmaceutically acceptable salt thereof as described herein is being applied. Solvents are generally selected based CHI solvents recognized as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound described herein or pharmaceutical composition thereof) or aid in the manufacturing of the pharmaceutical product (i.e., medicament).

The formulations can be prepared using conventional dissolution and mixing procedures. For example, the bulk drug substance (i.e., compound or pharmaceutically acceptable salt thereof as described herein or stabilized form thereof (e.g., complex with a cyclodextrin derivative or other known complexation agent) is dissolved in a suitable solvent in the presence of one or more of the excipients described above. The compound or pharmaceutically acceptable salt thereof as described herein is typically formulated into pharmaceutical dosage forms to provide an easily controllable dosage of the drug and to enable patient compliance with the prescribed regimen.

The pharmaceutical composition (or formulation) for application can be packaged in a variety of wav s depending upon the method used for administering the drug. Generally, an article for distribution includes a container having deposited therein the pharmaceutical formulation in an appropriate form. Suitable containers include materials such as bottles (plastic and glass), sachets, ampoules, plastic bags, metal cylinders, and the like. The container can also include a tamper-proof assemblage to prevent indiscreet access to the contents of the package. In addition, the container has deposited thereon a label that describes the contents of the container. The label can also include appropriate warnings.

Pharmaceutical formulations of the compounds or pharmaceutically acceptable salts thereof as described herein can be prepared for various routes and types of administration. For example, a compound or pharmaceutically acceptable salt thereof as described herein having the desired degree of purity can optionally be mixed with one or more pharmaceutically acceptable excipients (Remington's Pharmaceutical Sciences (1980) 16th edition, Osol, A Ed.), in the form of a lyophilized formulation, milled powder, or an aqueous solution. Formulation can be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but can range from about 3 to about 8. For example, formulation in an acetate buffer at pH 5 can be a suitable embodiment.

The pharmaceutical composition ordinarily can be stored as a solid composition, a lyophilized formulation or as an aqueous solution.

The pharmaceutical compositions described herein can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable pharmaceutically acceptable excipients are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds or pharmaceutically acceptable salts thereof as described herein may be prepared. Suitable examples of sustained-release preparations include semi permeable matrices of solid hydrophobic polymers containing a compound or pharmaceutically acceptable salt thereof as described herein, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations can conveniently be presented in unit dosage form and can be prepared by any methods. Techniques and formulations generally are found in Remington's Pharmaceutical Sciences (Mack Publishing Co., Easton, PA). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound or pharmaceutically acceptable salt thereof as described herein suitable for oral administration can be prepared as discrete units such as pills, capsules, cachets or tablets each containing a predetermined amount of such compound or pharmaceutically acceptable salt thereof. Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent The tablets can optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs can be prepared for oral use. Formulations of compounds or pharmaceutically acceptable salts thereof as described herein intended for oral use can be prepared according to any method for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients can be employed with either a paraffinic or a water-miscible ointment base. Alternatively, the active ingredients can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs. The oily phase of the emulsions of compositions provided herein can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat Together, the emulsifiers) with or without stabilizers) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of described herein include Tween® 60, Span® 80, cetostearyl alcohol, benzyl alcohol, myristyl alcohol, glyceryl mono-stearate and sodium lauryl sulfate.

Aqueous suspensions comprising compounds or pharmaceutically acceptable salts thereof as described herein can contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds or pharmaceutically acceptable salts thereof as described herein can be in the form of a sterile injectable preparation, such as a sterile injectable aqueous or oleaginous suspension. This suspension can be formulated using suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment or prophylaxis disorders as described below.

Formulations suitable for vaginal administration can be presented as pessaries, tampons, creams, gels, pastes, foams or spray formulations containing in addition to the active ingredient such carriers considered to be appropriate.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The compounds or pharmaceutically acceptable salts thereof as described herein can be used in veterinary compositions comprising at least one active ingredient as above defined together with a veterinary carrier. Veterinary carriers are materials useful for the purpose of administering the composition and can be solid, liquid or gaseous materials which are otherwise inert or acceptable in the veterinary field and are compatible with the active ingredient. These veterinary compositions can be administered parenterally, orally or by any other desired route.

Combination Therapy

The compounds of Formula I can be employed alone or in combination with additional therapeutic agents for the treatment of a disease or disorder described herein, such as inflammation or a hyperproliferative disorder (e.g., cancer). In certain embodiments, a compound of Formula I or a pharmaceutically acceptable salt thereof as described herein is combined in a pharmaceutical combination formulation, or dosing regimen as combination therapy, with an additional, second therapeutic compound that has anti-inflammatory or anti-hyperproliferative properties or that is useful for treating an inflammation, immune-response disorder, or hyperproliferative disorder (e.g., cancer). The additional therapeutic can be a Bcl-2 inhibitor, a JAK inhibitor, a PI3K inhibitor, an mTOR inhibitor, an anti-inflammatory agent, an immunomodulatory agent, anti-cancer agent as described herein, an apoptosis-enhancer, a neurotropic factor, an agent for treating cardiovascular disease, an agent for treating liver disease, an anti-viral agent, an agent for treating blood disorders, an agent for treating diabetes, and an agent for treating immunodeficiency disorders. The second therapeutic agent can be an NSAID anti-inflammatory agent. The second therapeutic agent can be an anti-cancer agent as described herein. The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition provided herein comprises a compound of Formula I, or a stereoisomer, tautomer, solvate, metabolite, or pharmaceutically acceptable salt thereof, in combination with a therapeutic agent such as an NSAID.

The combination therapy can be administered as a simultaneous or sequential regimen. When administered sequentially, the combination can be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and can be lowered due to the combined action (synergy) of the newly identified agent and other therapeutic agents or treatments.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I or a or pharmaceutically acceptable salt thereof, can be combined with other therapeutic, hormonal or antibody agents such as those described herein, as well as combined with surgical therapy and radiotherapy. Combination therapies provided herein thus comprise the administration of at least one compound of Formula I or pharmaceutically acceptable salt thereof, and the use of at least one other cancer treatment method. The amounts of the compound(s) of Formula I or pharmaceutically acceptable salts thereof described herein, and the other pharmaceutically active therapeutic agent(s) and the relative timings of administration will be selected in order to achieve the desired combined therapeutic effect.

In some embodiments, a compound of Formula I, or a pharmaceutically acceptable salt thereof, is used in combination with an aromatase inhibitor, a phosphoinositide 3-kinase (PI3K)/mTOR pathway inhibitor, a CDK 4/6 inhibitor, a HER-2 inhibitor, a SERM, a SERD, an EGFR inhibitor, a PD-1 inhibitor, poly ADP-ribose polymerase (PARP) inhibitor, a histone deacetylase (HDAC) inhibitor, an HSP90 inhibitor, a VEGFR inhibitor, an AKT inhibitor, chemotherapy, or any combination thereof.

In some embodiments, a pharmaceutical composition comprising a compound of Formula I, or a pharmaceutically acceptable salt thereof, is administered in combination with a therapeutic agent selected from paclitaxel, anastrozole, exemestane, cyclophosphamide, epirubicin, fulvestrant, letrozole, palbociclib, gemcitabine, trastuzumab (HERCEPTTN®, Genentech), trastuzumab emtansine (KADCYLA®, Genentech), pegfilgrastim, filgrastim, tamoxifen, docetaxel, toremifene, vinorelbine, capecitabine, and ixabepilone.

In some embodiments, a compound of Formula I, or a pharmaceutically acceptable salt thereof, is used in combination with hormone blocking therapy, chemotherapy, radiation therapy, monoclonal antibodies, or combinations thereof.

Metabolites of Compounds of Formula I

Also provided herein are in vivo metabolic products of compounds or pharmaceutically acceptable salts thereof as described herein. Such products can result for example from the oxidation, reduction, hydrolysis, amidation, deamidation, esterification, deesterification, enzymatic cleavage, and the like, of the administered compound. Accordingly, provided herein are compounds produced by a process comprising contacting a compound or pharmaceutically acceptable salt thereof described herein with a mammal for a period of time sufficient to yield a metabolic product thereof.

Metabolite products typically are identified by preparing a radiolabelled (e.g., 14C or 3H) isotope of a compound or pharmaceutically acceptable salt thereof as described herein, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies. The metabolite products, so long as they are not otherwise found in vivo, are useful in diagnostic assays for therapeutic dosing of the compounds or pharmaceutically acceptable salts thereof described herein.

Articles of Manufacture

In another aspect provided herein is an article of manufacture, or kit, containing materials useful for the treatment of the diseases and disorders described above is provided. In one embodiment, the kit comprises a container comprising a compound of Formula I or pharmaceutically acceptable salt thereof. The kit can further comprise a label or package insert on or associated with the container. Suitable containers include, for example, bottles, vials, syringes, blister pack, etc. The container can be formed from a variety of materials such as glass or plastic. The container can hold a compound of Formula I or a formulation thereof which is effective for treating the condition and can have a sterile access port (for example, the container can be an intravenous solution bag or a vial having a stopper pierceable by a hypodermic injection needle). At least one active agent in the composition is a compound of Formula I or a pharmaceutically acceptable salt thereof. The label or package insert indicates that the composition is used for treating the condition of choice, such as cancer. In addition, the label or package insert can indicate that the patient to be treated is one having a disorder such as a hyperproliferative disorder, atherosclerosis, neurodegeneration, cardiac hypertrophy, pain, migraine or a neurotraumatic disease or event. In one embodiment, the label or package inserts indicates that the composition comprising a compound of Formula I or a pharmaceutically acceptable salt thereof can be used to treat a disorder resulting from abnormal cell growth. In one embodiment, the label or package inserts indicates that the composition comprising a compound of Formula I or a pharmaceutically acceptable salt thereof can be used to treat a disorder resulting from atherosclerosis. The label or package insert can also indicate that the composition can be used to treat other disorders. Alternatively, or additionally, the article of manufacture can further comprise a second container comprising a pharmaceutically acceptable buffer, such as bacteriostatic water for injection (BWFI), phosphate-buffered saline, Ringer's solution and dextrose solution. It can further include other materials desirable from a commercial and user standpoint, including other buffers, diluents, filters, needles, and syringes.

The kit can further comprise directions for the administration of the compound of Formula I or a pharmaceutically acceptable salt thereof and, if present, the second pharmaceutical formulation. For example, if the kit comprises a first composition comprising a compound of Formula I or a pharmaceutically acceptable salt thereof and a second pharmaceutical formulation, the kit can further comprise directions for the simultaneous, sequential or separate administration of the first and second pharmaceutical compositions to a patient in need thereof.

In another embodiment, the kits are suitable for the delivery of solid oral forms of a compound of Formula I or a pharmaceutically acceptable salt thereof, such as tablets or capsules. Such a kit preferably includes a number of unit dosages. Such kits can include a card having the dosages oriented in the order of their intended use. An example of such a kit is a blister pack. Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit can comprise (a) a first container with a compound of Formula I or a pharmaceutically acceptable salt thereof contained therein; and optionally (b) a second container with a second pharmaceutical formulation contained therein, wherein the second pharmaceutical formulation comprises a second compound with anti-hyperproliferative activity. Alternatively, or additionally, the kit can further comprise a third container comprising a pharmaceutically-acceptable buffer, such as bacteriostatic water for injection (BWFI), phosphate-buffered saline, Ringer's solution and dextrose solution. It can further include other materials desirable from a commercial and user standpoint, including other buffers, diluents, filters, needles, and syringes.

In certain other embodiments wherein the kit comprises a composition of Formula I or a pharmaceutically acceptable salt thereof and a second therapeutic agent, the kit can comprise a container for containing the separate compositions such as a divided bottle or a divided foil packet, however, the separate compositions can also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

EMBODIMENTS

Embodiment 1: A Compound of Formula (I)

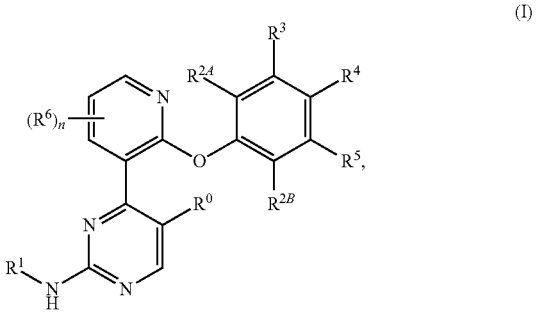

or a pharmaceutically acceptable salt thereof, wherein:
$R^0$ is hydrogen or fluoro;
$R^1$ is $C_{3-12}$ cycloalkyl, 3- to 14-membered heterocyclyl, 5- to 14-membered heteroaryl, —($C_{1-6}$ alkylene)-($C_3$-$C_{12}$ cycloalkyl), or —($C_{1-6}$ alkylene)-(3- to 14-membered heterocyclyl), —($C_{1-6}$ alkylene)-$OR^{1c}$, or —($C_{1-6}$ alkylene)-$NR^{1a}R^{1b}$; wherein the $C_{3-12}$ cycloalkyl, 3- to 14-membered heterocyclyl, 5- to 14-membered heteroaryl, and $C_{1-6}$ alkylene of $R^1$ are independently optionally substituted with 1, 2, 3, 4 or 5 substituents independently selected from $R^{10}$;
each $R^{1a}$, $R^{1b}$ and $R^{1c}$ is independently hydrogen, $C_{1-6}$ alkyl, $C_{3-8}$ cycloalkyl, $C_{6-10}$ aryl, 5- to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{1a}$ and $R^{1b}$ are optionally substituted with 1, 2, 3, 4 or 5 substituents independently selected from $R^{10}$;
$R^{2A}$ and $R^{2B}$ are independently hydrogen, halogen, cyano, $C_{1-6}$ alkyl, $C_{1-6}$ haloalkyl, $C_{3-6}$ cycloalkyl, —O($C_{1-6}$ alkyl), or —O($C_{1-6}$ haloalkyl);
$R^3$ is hydrogen, halogen, cyano, $C_{1-6}$ alkyl, $C_{1-6}$ haloalkyl, $C_{3-6}$ cycloalkyl, —O($C_{1-6}$ alkyl), or —O($C_{1-6}$ haloalkyl);
$R^4$ and $R^5$ are independently hydrogen, halogen, cyano, nitro, $C_{1-6}$ alkyl, $C_{2-6}$ alkenyl, $C_{2-6}$ alkynyl, $C_{3-12}$ cycloalkyl, $C_{6-20}$ aryl, 3- to 14-membered heterocyclyl, 5- to 14-membered heteroaryl, —$OR^{7A}$, —$NR^{8A}R^{8B}$, —$NR^8C(O)R^7$, —$NR^8C(O)OR^{7A}$, —$NR^8C(O)NR^{8A}R^{8B}$, —$NR^8SO_2R^9$, —$NR^8SO_2NR^{8A}R^{8B}$, —$NR^8S(O)(=NR^{8C})R^9$, —$C(O)N(R^8)SO_2R^9$, —$C(O)NR^{8A}R^{8B}$, —$C(O)R^7$, —$C(O)OR^{7A}$, —$SO_2R^9$, —$NR^8S(O)(=NR^{8C})R^9$, or —$SO_2NR^{8A}R^{8B}$; wherein the $C_{1-6}$ alkyl, $C_{3-12}$ cycloalkyl, $C_{6-20}$ aryl, 3- to 14-membered heterocyclyl, and 5- to 14-membered heteroaryl of $R^4$ and $R^5$ are optionally substituted with 1, 2, 3, 4 or 5 substituents independently selected from $R^{10}$;
n is 0, 1, 2, or 3;
each $R^6$ is independently halogen, cyano, nitro, $C_{1-6}$ alkyl, $C_{1-6}$ haloalkyl, $C_{3-6}$ cycloalkyl, —O($C_{1-6}$ alkyl), —O($C_{1-6}$ haloalkyl), —$SO_2$($C_{1-6}$ alkyl) or —$SO_2$($C_{1-6}$ haloalkyl);
each $R^7$ is independently hydrogen, $C_{1-6}$ alkyl, $C_{2-6}$ alkenyl, $C_{3-8}$ cycloalkyl, 5- to 14-membered heteroaryl, or 3- to 12-membered heterocyclyl; wherein the $C_{1-6}$ alkyl, $C_{2-6}$ alkenyl, $C_{3-8}$ cycloalkyl, 5- to 14-membered heteroaryl and 3- to 12-membered heterocyclyl of $R^7$ and $R^{7A}$ are optionally substituted with 1, 2, 3, 4 or 5 substituents independently selected from $R^{10}$;
each $R^{7A}$ is independently hydrogen, $C_{1-6}$ alkyl, $C_{2-6}$ alkenyl, $C_{3-8}$ cycloalkyl, $C_{6-10}$ aryl, 5- to 14-membered heteroaryl, or 3- to 12-membered heterocyclyl; wherein the $C_{1-6}$ alkyl, $C_{2-6}$ alkenyl, $C_{3-8}$ cycloalkyl, $C_{6-10}$ aryl, 5- to 14-membered heteroaryl and 3- to 12-membered heterocyclyl of $R^7$ and $R^{7A}$ are optionally substituted with 1, 2, 3, 4 or 5 substituents independently selected from $R^{10}$;
each $R^8$ is independently hydrogen or $C_1$-$C_6$ alkyl;
each $R^{8A}$ is independently hydrogen or $C_1$-$C_6$ alkyl;
each $R^{8B}$ is independently hydrogen, $C_{1-6}$ alkyl, $C_{2-6}$ alkenyl, $C_{3-8}$ cycloalkyl, $C_{6-10}$ aryl, or 3- to 12-membered heterocyclyl; wherein the $C_{1-6}$ alkyl, $C_{2-6}$ alkenyl, $C_{3-8}$ cycloalkyl, $C_{6-10}$ aryl, and 3- to 12-membered heterocyclyl of $R^{8B}$ are optionally substituted with 1, 2, 3, 4 or 5 substituents independently selected from $R^{10}$;
each $R^{8C}$ is independently hydrogen or $C_1$-$C_6$ alkyl;
each $R^9$ is independently $C_{1-6}$ alkyl, $C_{2-6}$ alkenyl, $C_{3-8}$ cycloalkyl, $C_{6-10}$ aryl, 5- to 14-membered heteroaryl and 3- to 12-membered heterocyclyl; wherein the $C_{1-6}$ alkyl, $C_{2-6}$ alkenyl, $C_{3-8}$ cycloalkyl, $C_{6-10}$ aryl, 5- to 14-membered heteroaryl and 3- to 12-membered heterocyclyl are optionally substituted with 1, 2, 3, 4 or 5 substituents independently selected from $R^{10}$; or,
each $R^9$ is independently $C_{1-6}$ alkyl, $C_{2-6}$ alkenyl, $C_{3-8}$ cycloalkyl, $C_{6-10}$ aryl, 5- to 14-membered heteroaryl and 3- to 12-membered heterocyclyl; wherein the $C_{1-6}$ alkyl, $C_{2-6}$ alkenyl, $C_{3-8}$ cycloalkyl, $C_{6-10}$ aryl, 5- to 14-membered heteroaryl and 3- to 12-membered heterocyclyl are optionally substituted with 1, 2, 3, 4 or 5 substituents independently selected from $R^{10}$;
each $R^{10}$ is independently oxo, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, —$C(O)R^a$, —$C(O)OR^b$, —$C(O)NR^cR^d$, —$OR^b$, —$OC(O)R^a$, —$OC(O)NR^cR^d$, —$SR^b$, —$S(O)R^e$, —$S(O)_2R^e$, —$S(O)(=NH)R^e$, —$S(O)_2NR^cR^d$, —$NR^cR^d$, —$N(R^f)C(O)R^a$, —$N(R^f)C(O)OR^b$, —$N(R^f)C(O)NR^cR^d$, —$N(R^f)S(O)_2R^e$, —$N(R^f)S(O)_2NR^cR^d$, —$P(O)R^gR^h$, or —$SiR^iR^jR^k$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^{10}$ are each optionally substituted with 1, 2, 3 or 4 substituents independently selected from $R^{11}$;
each $R^a$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl and 3- to 12-membered heterocyclyl of $R^a$ are each optionally substituted with 1, 2, 3 or 4 substituents independently selected from $R^{11}$;
each $R^b$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^b$ are each optimally substituted with 1, 2, 3 or 4 substituents independently selected from $R^{11}$;
each $R^c$ and $R^d$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^c$ and $R^d$ are each optimally substituted with 1, 2, 3 or 4 substituents independently selected from $R^{11}$;

or $R^c$ and $R^d$ are taken together with the nitrogen atom to which they are attached to form a 4- to 12-membered heterocyclyl optimally substituted with 1, 2, 3 or 4 substituents independently selected from $R^{11}$;

each $R^e$ is independently $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^e$ are each optionally substituted with 1, 2, 3 or 4 substituents independently selected from $R^{11}$;

each $R^f$ is independently hydrogen or $C_{1-6}$ alkyl;

each $R^g$ and $R^h$ is independently $C_{1-6}$ alkyl, $C_{3-8}$ cycloalkyl, $C_{6-10}$ aryl, 5- to 10-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^g$ and $R^h$ are each optionally substituted with 1, 2, 3 or 4 substituents independently selected from $R^{11}$;

or $R^g$ and $R^h$ are taken together with the phosphorus atom to which they are attached to form a 4- to 12-membered heterocyclyl optimally substituted with 1, 2, 3 or 4 substituents independently selected from $R^{11}$;

each $R^i$, $R^j$ and $R^k$ is independently $C_{1-6}$ alkyl;

each $R^{11}$ is independently oxo, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl, 3- to 8-membered heterocyclyl, halogen, cyano, —C(O)$R^{a1}$, —C(O)O$R^{b1}$, —C(O)N$R^{c1}R^{d1}$, —O$R^{b1}$, —OC(O)$R^{a1}$, —OC(O)N$R^{c1}R^{d1}$, —S$R^{b1}$, —S(O)$R^{e1}$, —S(O)$_2R^{e1}$, —S(O)$_2$N$R^{c1}R^{d1}$, —N$R^{c1}R^{d1}$, —N($R^{f1}$)C(O)$R^{a1}$, —N($R^{f1}$)C(O)O$R^{b1}$, —N($R^{f1}$)C(O)N$R^{c1}R^{d1}$, —N($R^{f1}$)S(O)$_2R^{e1}$, —N($R^{f1}$)S(O)$_2$N$R^{c1}R^{d1}$, —P(O)$R^{g1}R^{h1}$, or —Si$R^{i1}R^{j1}R^{k1}$; wherein the $C_{1-6}$ alkyl, $C_{2-6}$ alkenyl, $C_{2-6}$ alkynyl, $C_{3-6}$ cycloalkyl, $C_{6-14}$ aryl, 5- to 14-membered heteroaryl and 3- to 14-membered heterocyclyl of $R^{11}$ are each optionally substituted with 1, 2, 3 or 4 substituents independently selected from $R^{12}$;

each $R^{a1}$ is independently hydrogen, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl and 3- to 8-membered heterocyclyl of $R^{a1}$ are each optionally substituted with 1, 2, 3 or 4 substituents independently selected from $R^{12}$;

each $R^{b1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{b1}$ are each optionally substituted with 1, 2, 3 or 4 substituents independently selected from $R^{12}$;

each $R^{c1}$ and $R^{d1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{c1}$ and $R^{d1}$ are each optionally substituted with 1, 2, 3 or 4 substituents independently selected from $R^{12}$;

or $R^{c1}$ and $R^{d1}$ are taken together with the nitrogen atom to which they are attached to form a 4- to 8-membered heterocyclyl optionally substituted with 1, 2, 3 or 4 substituents independently selected from $R^{12}$;

each $R^{e1}$ is independently $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{e1}$ are each optionally substituted with 1, 2, 3 or 4 substituents independently selected from $R^{12}$;

each $R^{f1}$ is independently hydrogen or $C_{1-6}$ alkyl;

each $R^{g1}$ and $R^{h1}$ is independently $C_{1-6}$ alkyl, $C_{3-6}$ cycloalkyl, $C_{6-10}$ aryl, 5- to 10-membered heteroaryl, 3- to 8-membered heterocyclyl, or —O—$C_{1-6}$ alkyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{g1}$ and $R^{h1}$ are each optionally substituted with 1, 2, 3 or 4 substituents independently selected from $R^{12}$;

or $R^{g1}$ and $R^{h1}$ are taken together with the phosphorus atom to which they are attached to form a 4- to 8-membered heterocyclyl optionally substituted with 1, 2, 3 or 4 substituents independently selected from $R^{12}$;

each $R^{i1}$, $R^{j1}$ and $R^{k1}$ is independently $C_{1-6}$ alkyl;

each $R^{12}$ is independently oxo, $C_{1-6}$ alkyl, $C_{3-6}$ cycloalkyl, $C_6$ aryl, 5- to 6-membered heteroaryl, 3- to 6-membered heterocyclyl, halogen, cyano, —C(O)$R^{a2}$, —C(O)O$R^{b2}$, —C(O)N$R^{c2}R^{d2}$, —O$R^{a2}$, —OC(O)$R^{a2}$, —OC(O)N$R^{c2}R^{d2}$, —S(O)$_2R^{e2}$, —S(O)$_2$N$R^{c2}R^{d2}$, —N$R^{c2}R^{d2}$, —N($R^{f2}$)C(O)$R^{a2}$, —N($R^{f2}$)C(O)O$R^{b2}$, —N($R^{f2}$)C(O)N$R^{c2}R^{d2}$, —N($R^{f2}$)S(O)$_2R^{e2}$, —N($R^{f2}$)S(O)$_2$N$R^{c2}R^{d2}$, or —P(O)$R^{g2}R^{h2}$; wherein the $C_{1-6}$ alkyl, $C_{3-6}$ cycloalkyl, $C_6$ aryl, 5- to 6-membered heteroaryl and 3- to 6-membered heterocyclyl of $R^{12}$ are each optionally substituted with 1, 2, 3 or 4 substituents independently selected from $R^{13}$;

each $R^{a2}$ is independently hydrogen, $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{a2}$ are each optionally substituted with 1, 2, 3 or 4 substituents independently selected from $R^{13}$;

each $R^{b2}$ is independently hydrogen, $C_{1-6}$ alkyl, $C_{3-6}$ cycloalkyl or 3- to 6-membered heterocyclyl; wherein the $C_{1-6}$ alkyl, $C_{3-6}$ cycloalkyl and 3- to 6-membered heterocyclyl of $R^{b2}$ are each optionally substituted with 1, 2, 3 or 4 substituents independently selected from $R^{13}$;

each $R^{c2}$ and $R^{d2}$ is independently hydrogen, $C_{1-6}$ alkyl, $C_{3-6}$ cycloalkyl or 3- to 8-membered heterocyclyl; wherein the $C_{1-6}$ alkyl, $C_{3-6}$ cycloalkyl and 3- to 8-membered heterocyclyl of $R^{c2}$ and $R^{d2}$ are each optionally substituted with 1, 2, 3 or 4 substituent independently selected from $R^{13}$;

or $R^{c2}$ and $R^{d2}$ are taken together with the nitrogen atom to which they are attached to form a 4- to 6-membered heterocyclyl optionally substituted with 1, 2, 3 or 4 substituents independently selected from $R^{13}$;

each $R^{e2}$ is independently $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{e2}$ are each optionally substituted with 1, 2, 3 or 4 substituents independently selected from $R^{13}$;

each $R^{f2}$ is independently hydrogen or $C_{1-6}$ alkyl;

each $R^{g2}$ and $R^{h2}$ is independently $C_{1-6}$ alkyl, $C_{3-6}$ cycloalkyl, 3- to 8-membered heterocyclyl, or —O—$C_{1-6}$ alkyl; wherein the $C_{1-6}$ alkyl, $C_{3-6}$ cycloalkyl, and 3- to 8-membered heterocyclyl of $R^{g2}$ and $R^{h2}$ are each optionally substituted with 1, 2, 3 or 4 substituents independently selected from $R^{13}$;

or $R^{g2}$ and $R^{h2}$ are taken together with the phosphorus atom to which they are attached to form a 4- to 6-membered heterocyclyl optionally substituted with 1, 2, 3 or 4 substituents independently selected from $R^{13}$; and each $R^{13}$ is independently oxo, halogen, hydroxyl, —O($C_{1-6}$ alkyl), cyano, $C_{1-6}$ alkyl or $C_{1-6}$ haloalkyl;

provided that the compound is other than Compound Nos. 1x-12x in Table 1X and salts thereof.

Embodiment 2: The compound of embodiment 1, wherein $R^{2A}$ and $R^{2B}$ are independently H, F, Cl or $C_1$-$C_6$ alkyl.

Embodiment 3: The compound of embodiment 2, wherein $R^{2A}$ is H, F or methyl, and $R^{2B}$ is H, F, Cl or —$CH_3$.

Embodiment 4: The compound of any one of embodiments 1 to 3, wherein $R^3$ is H, F, Cl, —CN, $C_{1-6}$ alkyl, or $C_{1-6}$ haloalkyl.

Embodiment 5: The compound of embodiment 4, wherein $R^3$ is H, F, Cl, —CN, —$CH_3$, or —$CF_3$.

Embodiment 6: The compound of any one of embodiments 1 to 5, wherein n is 0.

Embodiment 7: The compound of any one of embodiments 1 to 6, wherein $R^5$ is H, F, Cl, —CN, or $C_{1-6}$ alkyl optionally substituted with 1, 2, 3, 4 or 5 substituents independently selected from $R^{10}$.

Embodiment 8: The compound of embodiment 7, wherein $R^5$ is H, F, Cl, —CN, —$CH_3$, or —$CF_3$.

Embodiment 9: The compound of any one of embodiments 1 to 6, wherein $R^5$ is H, F, Cl, —CN, $C_{1-6}$ alkyl optionally substituted with 1, 2, 3, 4 or 5 substituents independently selected from $R^{10}$, —$NR^8SO_2R^9$, —$NR^{8A}R^{8B}$, or —C(O)N($R^8$)$SO_2R^9$.

Embodiment 10: The compound of embodiment 9, wherein $R^5$ is $C_{1-6}$ alkyl substituted with 1, 2, 3, 4 or 5 substituents independently selected from $R^{10}$, —$NR^8SO_2R^9$, —$NR^{8A}R^{8B}$, or —C(O)N($R^8$)$SO_2R^9$.

Embodiment 11: The compound of embodiment 10, wherein $R^4$ is H, F, Cl, —CN, —$CH_3$, or —$CF_3$.

Embodiment 12: The compound of embodiment 10 or 11, wherein $R^4$ is H, and $R^5$ is —($C_{1-6}$ alkylene)-N($R^f$)C(O)$R^a$; $C_{1-6}$ alkyl substituted with 1, 2, 3, 4 or 5 substituents independently selected from $R^{10}$, —NH—$SO_2R^9$, —NH—$R^{8B}$, or —C(O)NH—$SO_2R^9$.

Embodiment 13: The compound of embodiment 12, wherein $R^5$ is —$CH_2NHC(O)$-(cyclopropyl), —$NHCH_2CH(OH)CF_3$, or —C(O)$NHSO_2$-(2-chlorophenyl).

Embodiment 14: The compound of embodiment 12, wherein $R^5$ is —$NHSO_2R^9$, and $R^9$ is $C_{1-6}$ alkyl optionally substituted with 1, 2, 3, 4 or 5 substituents independently selected from $R^{10}$, or $C_{6-10}$ aryl optionally substituted with 1, 2, 3, 4 or 5 substituents independently selected from $R^{10}$.

Embodiment 15: The compound of embodiment 14, wherein $R^5$ is —$NHSO_2$-(2-chlorophenyl), —$NHSO_2$—$CH_2CH_2CH_3$, or —$NHSO_2$—$CH_2$-(phenyl).

Embodiment 16: The compound of any one of embodiments 1 to 9, wherein $R^4$ is —$NR^8C(O)R^7$ or —$NR^8SO_2R^9$.

Embodiment 17: The compound of embodiment 16, wherein $R^4$ is —NHC(O)$R^7$, and $R^7$ is $C_{1-6}$ alkyl optionally substituted with 1, 2, 3, 4 or 5 substituents independently selected from $R^{10}$, or $C_{3-8}$ cycloalkyl optionally substituted with 1, 2, 3, 4 or 5 substituents independently selected from $R^{10}$.

Embodiment 18: The compound of embodiment 16, wherein $R^4$ is —NH—$SO_2R^9$, and $R^9$ is $C_{1-6}$ alkyl, $C_{3-8}$ cycloalkyl, $C_{6-10}$ aryl, or 5- to 14-membered heteroaryl, wherein the $C_{1-6}$ alkyl, $C_{3-8}$ cycloalkyl, $C_{6-10}$ aryl and 5- to 14-membered heteroaryl of $R^9$ are independently optionally substituted with 1, 2, 3, 4 or 5 substituents independently selected from $R^{10}$.

Embodiment 19: The compound of embodiment 18, wherein $R^9$ is $C_{1-6}$ alkyl optionally substituted with 1, 2, 3, 4 or 5 substituents independently selected from $R^{10}$.

Embodiment 20: The compound of embodiment 18, wherein $R^9$ is $C_{3-8}$ cycloalkyl optionally substituted with 1, 2, 3, 4 or 5 substituents independently selected from $R^{10}$.

Embodiment 21: The compound of embodiment 18, wherein $R^9$ is $C_{6-10}$ aryl optionally substituted with 1, 2, 3, 4 or 5 substituents independently selected from $R^{10}$.

Embodiment 22: The compound of embodiment 18, wherein $R^9$ is 5- to 14-membered heteroaryl optionally substituted with 1, 2, 3, 4 or 5 substituents independently selected from $R^{10}$.

Embodiment 23: The compound of embodiment 18, wherein $R^9$ is selected from the group consisting of cyclopentyl, cyclohexyl, phenyl, 2-chlorophenyl, 3-cyanophenyl, 4-cyanophenyl, 2-methoxyphenyl, 3-methoxyphenyl, 4-methoxyphenyl, 3-(difluoromethoxy)phenyl, 3-(trifluoromethoxy)phenyl, 4-(trifluoromethoxy)phenyl, 3,5-difluorophenyl, 3-pyridyl, 1-methyl-1H-imidazol-4-yl, 1-methyl-1H-pyrazol-4-yl, benzyl, 2-fluorobenzyl, 3-fluorobenzyl, 4-fluorobenzyl, 2-cyanobenzyl, 4-cyanobenzyl, 3-chlorobenzyl, 4-chlorobenzyl, (1-methyl-1H-pyrazol-3-yl)methyl, (5-methylisoxazol-3-yl)methyl, (pyridin-2-yl)methyl, (pyridin-3-yl)methyl, (pyridin-4-yl)methyl, (6-(trifluoromethyl)pyridin-3-yl)methyl, (1-fluorocyclopropyl)methyl, cyclobutylmethyl, (2,2-difluorocyclobutyl)methyl, (3,3-difluorocyclobutyl)methyl, cyclopentylmethyl, cyclohexylmethyl, (spiro[3.3]heptan-2-yl)methyl, 2-(cyclohexyl)ethyl, 2-(2,2-difluorocyclopropyl)ethyl, n-propyl, 3-cyano-2,2-dimethylpropyl, 3,3,3-trifluoropropyl, n-butyl, 2,2-difluorobutyl, 3,3-difluorobutyl, 3,3-dimethylbutyl, 3-cyano-3-methylbutyl and 4,4-dimethylpentyl.

Embodiment 24: The compound of embodiment 16, wherein $R^7$ is selected from the group consisting of cyclopropyl, spiro[2.2]pentyl, cyclohexylmethyl and 4-chlorobenzyl.

Embodiment 25: The compound of any one of embodiments 1 to 24, wherein $R^1$ is $C_{3-12}$ cycloalkyl; 3- to 14-membered heterocyclyl; —($C_{1-6}$ alkylene)-(3- to 14-membered heterocyclyl), or —($C_{1-6}$ alkylene)-$NR^{1a}R^{1b}$; wherein the $C_{3-12}$ cycloalkyl, 3- to 14-membered heterocyclyl, and $C_{1-6}$ alkylene of $R^1$ are independently optimally substituted with 1, 2, 3, 4 or 5 substituents independently selected from $R^{10}$.

Embodiment 26: The compound of embodiment 25, wherein $R^1$ is $C_{3-12}$ cycloalkyl optionally substituted with 1, 2, 3, 4 or 5 substituents independently selected from $R^{10}$.

Embodiment 27: The compound of embodiment 25, wherein $R^1$ is 3- to 14-membered heterocyclyl optionally substituted with 1, 2, 3, 4 or 5 substituents independently selected from $R^{10}$.

Embodiment 28: The compound of embodiment 25, wherein $R^1$ is cyclohexyl or piperidinyl, each is independently optionally substituted with 1, 2, 3, 4 or 5 substituents independently selected from the group consisting of F, —$CH_3$, —OH, oxo, and —$NH_2$.

Embodiment 29: The compound of embodiment 28, wherein $R^1$ is selected from the group consisting of piperidin-3-yl, 5-fluoropiperidin-3-yl, 5-methylpiperidin-3-yl and 5-fluoro-5-methylpiperidin-3-yl.

Embodiment 30: The compound of embodiment 25, wherein $R^1$ is —($C_{1-6}$ alkylene)-(3- to 14-membered heterocyclyl) optimally substituted with 1, 2, 3, 4 or 5 substituents independently selected from $R^{10}$.

Embodiment 31: The compound of embodiment 25, wherein $R^1$ is —($C_{1-6}$ alkylene)-$NR^{1a}R^{1b}$.

Embodiment 32: The compound of embodiment 31, wherein $R^{1a}$ and $R^{1b}$ are independently hydrogen or $C_{1-6}$ alkyl.

Embodiment 33: The compound of any me of embodiments 1 to 32, wherein $R^0$ is H.

Embodiment 34: The compound of embodiment 1, wherein the compound is of the Formula (Ia):

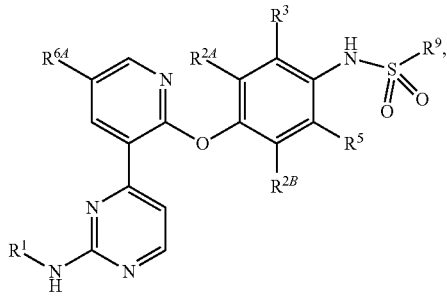

wherein $R^{6A}$ is hydrogen or $R^6$; and $R^1$, $R^{2A}$, $R^{2B}$, $R^3$, $R^5$, $R^6$ and $R^9$ are as defined in embodiment 1.

Embodiment 35: The compound of embodiment 1, wherein the compound is of the Formula (Ib):

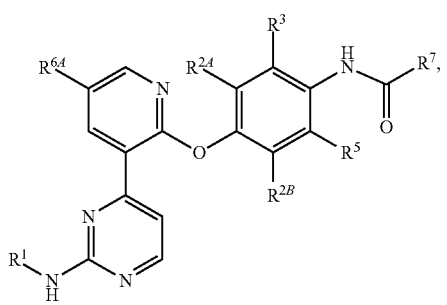

wherein $R^{6A}$ is hydrogen or $R^6$; and $R^1$, $R^{2A}$, $R^{2B}$, $R^3$, $R^5$, $R^6$ and $R^7$ are as defined in embodiment 1.

Embodiment 36: The compound of embodiment 1, wherein the compound is of the Formula (Ic):

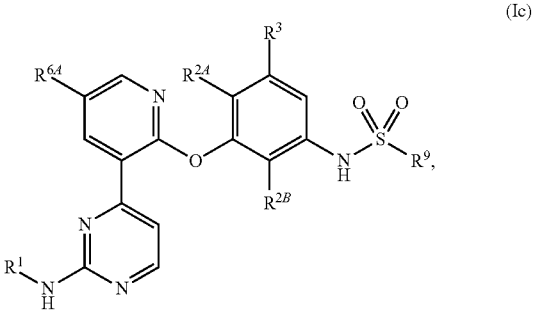

wherein $R^{6A}$ is hydrogen or $R^6$; and $R^1$, $R^{2A}$, $R^{2B}$, $R^3$, $R^6$ and $R^9$ are as defined in embodiment 1.

Embodiment 37: The compound of embodiment 1, wherein the compound is of the Formula (Id):

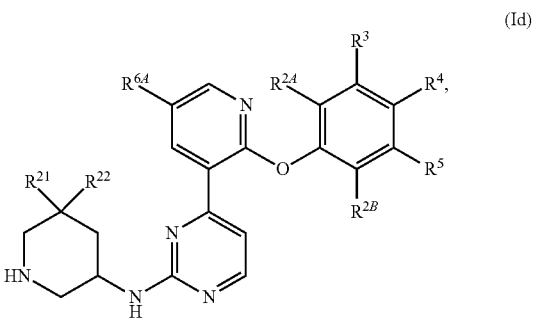

wherein $R^{6A}$ is hydrogen or $R^6$; $R^{21}$ and $R^{22}$ are independently H, F, —$CH_3$ or —$NH_2$, and $R^{2A}$, $R^{2B}$, $R^3$, $R^4$, $R^5$ and $R^6$ are as defined in embodiment 1.

Embodiment 38: The compound of embodiment 37, wherein the compound is of the Formula (Id-1), (Id-2), (Id-3), (Id-4), (Id-5), (Id-6) or (Id-7):

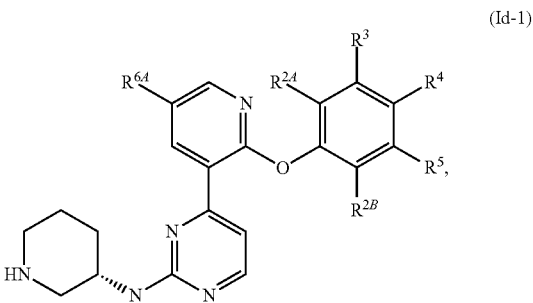

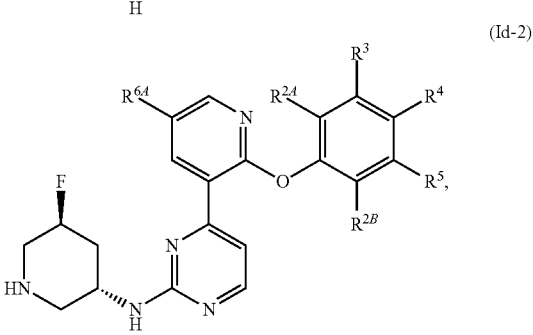

(Id-3)
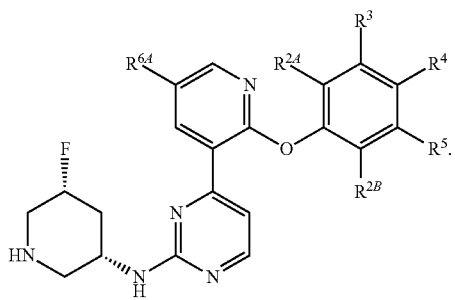
(Id-4)
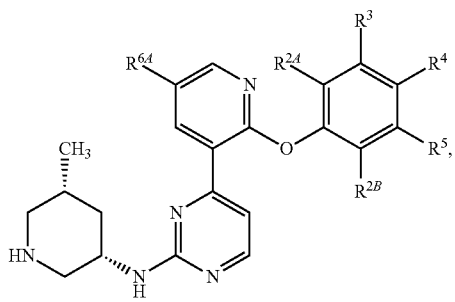
(Id-5)
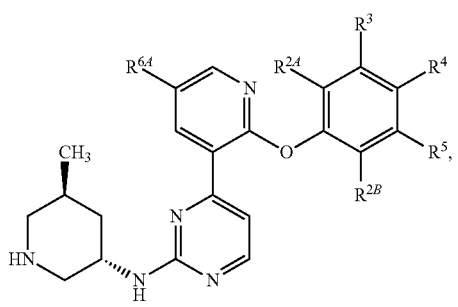
(Id-6)
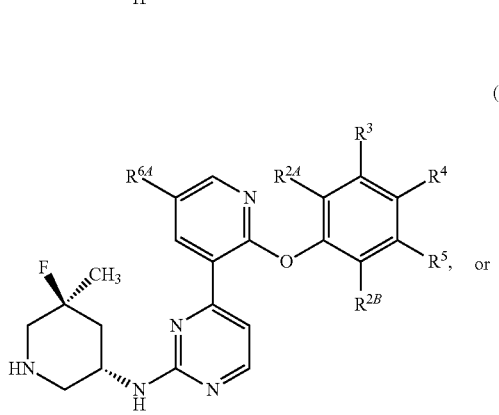
or
(Id-7)
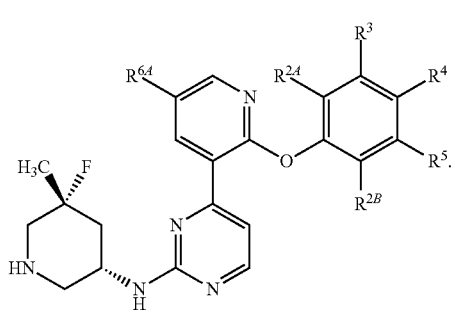
Embodiment 39: The compound of embodiment 1, wherein the compound is of the Formula (Ie):
(Ie)
wherein $R^{6A}$ is hydrogen or $R^6$; $R^{21}$ and $R^{22}$ are independently H, F, —CH$_3$ or —NH$_2$. and $R^{2A}$, $R^{2B}$, $R^3$, $R^5$, $R^6$ and $R^9$ are as defined in embodiment 1.
Embodiment 40: The compound of embodiment 39, wherein the compound is of the Formula (Ie-1), (Ie-2), (Ie-3), (Ie-4), (Ie-5), (Ie-6) or (Ie-7):
(Ie-1)
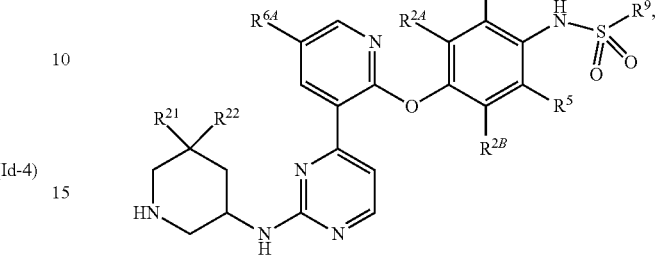
(Ie-2)
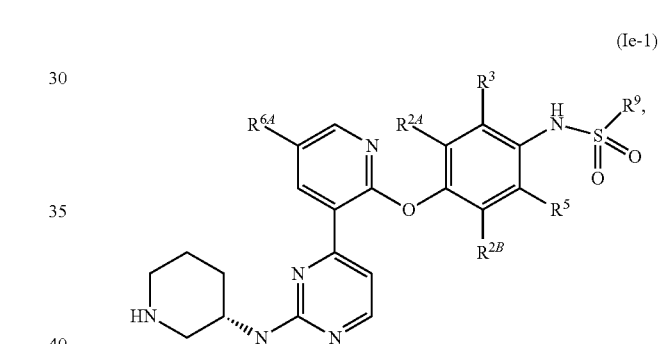
(Ie-3)
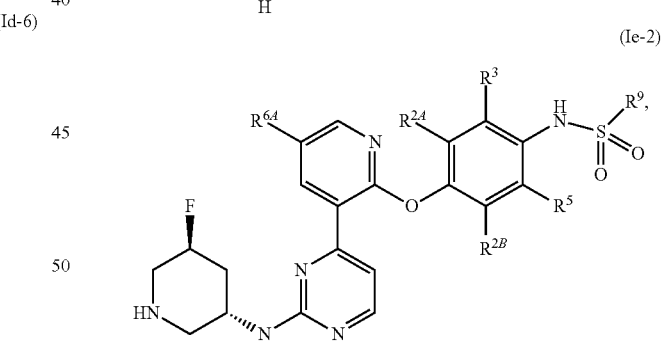
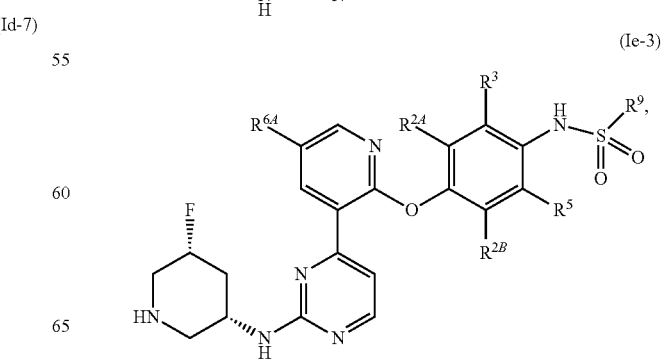

-continued (Ie-4)
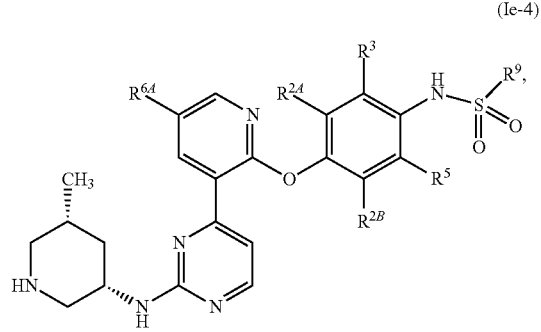

(Ie-5)
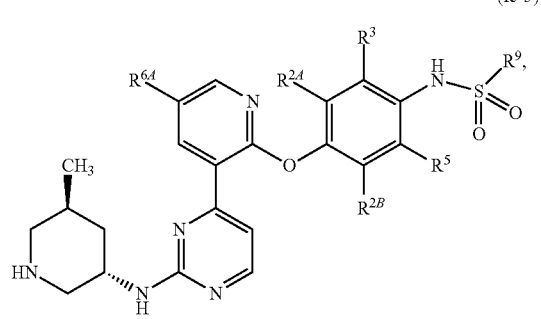

(Ie-6)
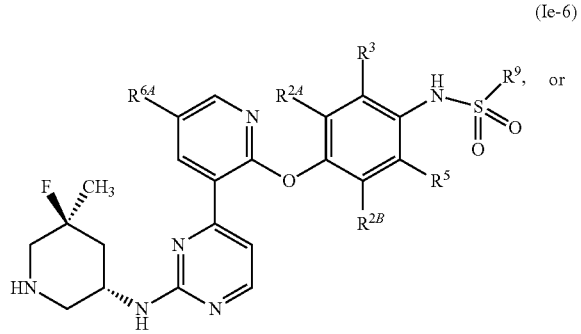

(Ie-7)
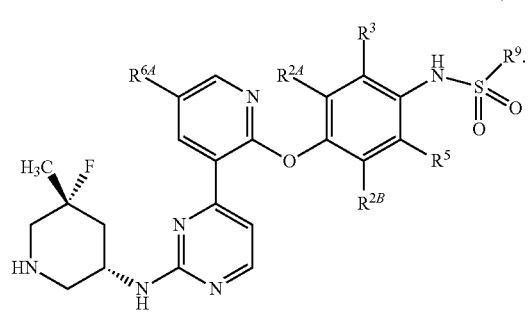

Embodiment 41: The compound of any one of embodiments 34 to 40, wherein $R^{6A}$ is H.

Embodiment 42: The compound of embodiment 1, wherein the compound is selected from Compound Nos. 101-247 in Table 1, or a pharmaceutically acceptable salt thereof; or the compound is selected from Compound Nos. 101-238 in Table 1, or a pharmaceutically acceptable salt thereof; or the compound is selected from Compound Nos. 101-389 in Table 1, or a pharmaceutically acceptable salt thereof; or the compound is selected from Compound Nos. 101-238 and 248-389 in Table 1, or a pharmaceutically acceptable salt thereof; or the compound is selected from Compound Nos. 248-389 in Table 1, or a pharmaceutically acceptable salt thereof; or the compound is selected from Compound Nos. 101-238, 248-380 and 382-389 in Table 1, or a pharmaceutically acceptable salt thereof; or the compound is selected from Compound Nos. 248-380 and 382-389 in Table 1, or a pharmaceutically acceptable salt thereof.

Embodiment 43: A pharmaceutical composition comprising a compound of any of embodiments 1 to 42, or a pharmaceutically acceptable salt thereof, and one or more pharmaceutically acceptable excipients.

Embodiment 44: A method of treating an IRE1-related disease or disorder, the method comprising administering to the subject having an IRE1-related disease or disorder an effective amount of the compound of any of embodiments 1 to 42 or a pharmaceutically acceptable salt thereof, or the pharmaceutical composition of embodiment 43.

Embodiment 45: The method of embodiment 44, wherein the IRE1-related disease or disorder is cancer.

Embodiment 46: The method of embodiment 45, wherein the cancer is squamous cell carcinoma, small-cell lung cancer, non-small cell lung cancer (NSCLC), lung adenocarcinoma, squamous cell lung cancer, peritoneum cancer, hepatocellular cancer, stomach cancer, gastrointestinal cancer, esophageal cancer, pancreatic cancer, glioblastoma, cervical cancer, ovarian cancer, liver cancer, bladder cancer, breast cancer, colon cancer, rectal cancer, colorectal cancer, endometrial cancer, uterine cancer, salivary gland carcinoma, renal cancer, prostate cancer, vulval cancer, thyroid cancer, hepatocellular carcinoma (HCC), anal carcinoma, penile carcinoma, or head and neck cancer.

Embodiment 47: The method of embodiment 45, wherein the cancer is lymphoma, lymphocytic leukemia, multiple myeloma (MM), acute myelogenous leukemia (AML), chronic myelogenous leukemia (CML), myelodysplastic syndrome (MDS), or myeloproliferative disease (MPD).

Embodiment 48: The method of embodiment 44, wherein the IRE1-related disease or disorder is multiple myeloma.

Embodiment 49: The method of embodiment 44, wherein the IRE1-related disease or disorder is a triple-negative breast cancer (TNBC).

Embodiment 50: The method of any one of embodiments 44 to 49, further comprising administering one or more additional therapeutic agent(s) selected from the group consisting of an anti-inflammatory agent, a corticosteroid, an immunomodulatory agent, anti-cancer agent, an apoptosis-enhancer, a neurotropic factor, an agent for treating cardiovascular disease, an agent for treating liver disease, an anti-viral agent, an agent for treating blood disorders, an agent for treating diabetes, an agent for treating metabolic disorders, an agent for treating autoimmune disorders, and an agent for treating immunodeficiency disorders.

Embodiment 51: The method of embodiment 50, wherein the additional therapeutic agent is a corticosteroid, a proteasome inhibitor, an immunomodulatory agent, an anti-CD38 antibody, an anti-VEGF-A antibody, an anti-PD-1 antibody, an anti-PD-L1 antibody, or an anti-interleukin-6 antibody, or a combination thereof.

Embodiment 52: The method of embodiment 51, wherein the corticosteroid comprises dexamethasone Embodiment 53: The method of embodiment 51, wherein proteasome inhibitor comprises carfilzomib, ixazomib or bortezomib.

Embodiment 54: The method of embodiment 51, wherein immunomodulatory agent comprises lenalidomide or pomalidomide.

Embodiment 55: The method of embodiment 51, wherein the anti-PD-L1 antibody comprises, avelumab, durvalumab, or atezolizumab.

Embodiment 56: The method of embodiment 51, wherein the anti-PD-1 antibody comprises pembrolizumab or nivolumab.

Embodiment 57: The method of any one of embodiments 44 to 56, further comprising administering radiotherapy.

Embodiment 58: Use of a compound according to any of embodiments 1 to 42, or a pharmaceutically acceptable salt thereof, or a pharmaceutical composition according to embodiment 43, in the manufacture of a medicament for the treatment of an IRE1-related disease or disorder.

Embodiment 59: The use of embodiment 58, wherein the IRE1-related disease or disorder is cancer.

Embodiment 60: The method of embodiment 59, wherein the cancer is squamous cell carcinoma, small-cell lung cancer, non-small cell lung cancer (NSCLC), lung adenocarcinoma, squamous cell lung cancer, peritoneum cancer, hepatocellular cancer, stomach cancer, gastrointestinal cancer, esophageal cancer, pancreatic cancer, glioblastoma, cervical cancer, ovarian cancer, liver cancer, bladder cancer, breast cancer, colon cancer, rectal cancer, colorectal cancer, endometrial cancer, uterine cancer, salivary gland carcinoma, renal cancer, prostate cancer, vulval cancer, thyroid cancer, hepatocellular carcinoma (HCC), anal carcinoma, penile carcinoma, or head and neck cancer.

Embodiment 61: The method of embodiment 59, wherein the cancer is lymphoma, lymphocytic leukemia, multiple myeloma (MM), acute myelogenous leukemia (AML), chronic myelogenous leukemia (CML), myelodysplastic syndrome (MDS), or myeloproliferative disease (MPD).

Embodiment 62: The method of embodiment 58, wherein the IRE1-related disease or disorder is multiple myeloma.

Embodiment 63: The method of embodiment 58, wherein the IRE1-related disease or disorder is a triple-negative breast cancer (TNBC).

Embodiment 64: A compound according to any of embodiments 1 to 42, or a pharmaceutically acceptable salt thereof, or a pharmaceutical composition according to embodiment 43, for use in a method for treating an IRE1-related disease or disorder.

Embodiment 65: A method of inhibiting or killing a cancer cell expressing Ire1, the method comprising contacting the cancer cell expressing Ire1 with a compound or pharmaceutically acceptable salt thereof, of any one of embodiments 1 to 42 or a pharmaceutical composition of embodiment 43.

Embodiment 66: The method of embodiment 65, wherein the inhibiting or killing is performed in vivo Embodiment 67: The method of embodiment 65, wherein the cancer cell expressing Ire1 is in a human Embodiment 68: A method of modulating Ire1 activity, the method comprising contacting Ire1 with a compound or pharmaceutically acceptable salt thereof of any me of embodiments 1 to 42 or a pharmaceutical composition of embodiment 43.

Embodiment 69: A kit for treating a condition mediated by IRE1, comprising:

a) a pharmaceutical composition of claim 45; and b) instructions for use.

The following examples are offered by way of illustration and not by way of limitation.

EXAMPLES

Synthetic Examples

Exemplary Formula I compounds in Table 1 were made, characterized, and tested for binding to IRE1α (alpha). Where more than (me name is associated with a Formula I compound or intermediate, the chemical structure shall define the compound. Listed in Table A1 are the compound names (including the salt form where applicable), MS m/z for $[M+H]^{30}$, $^1$H NMR data, and the Example # where the synthetic protocols or analoguous synthetic protocols are described.

TABLE A1

| Cpd No. | Name | MS m/z | $^1$H NMR (ppm) | Synth. Method |
|---|---|---|---|---|
| 101 | N-[4-[[3-[2-[(4-aminocyclohexyl)amino]pyrimidin-4-yl]-2-pyridyl]oxy]-3-methyl-phenyl]-2-chloro-benzenesulfonamide hydrochloride | 565.1 | (400 MHz, CD$_3$OD) δ 8.50 (dd, J = 7.6, 2.0 Hz, 1H), 8.32 (d, J = 5.6 Hz, 1H), 8.12 (dd, J = 4.8, 2.0 Hz, 1H), 8.08-8.06 (m, 1H), 7.60-7.57 (m, 2H), 7.48-7.43 (m, 2H), 7.24-7.21 (m, 1H), 7.10-7.09 (m, 1H), 7.06-7.04 (m, 1H), 6.91-6.89 (m, 1H), 3.98-3.90 (m, 1H), 3.17-3.14 (m, 1H), 2.25-2.22 (m, 2H), 2.11-2.03 (m, 2H), 2.03 (s, 3H), 1.61-1.49 (m, 4H). | Example 1 |
| 102 | N-[4-[[3-[2-[(4-aminocyclohexyl)amino]pyrimidin-4-yl]-2-pyridyl]oxy]-3-fluoro-5-methyl-phenyl]-2-chloro-benzenesulfonamide hydrochloride | 583.2 | (400 MHz, CD$_3$OD) δ 8.52 (d, J = 7.6 Hz, 1H), 8.32 (d, J = 6.0 Hz, 1H), 8.13 (d, J = 7.6 Hz, 2H), 7.61-7.57 (m, 2H), 7.51-7.47 (m, 2H), 7.28-7.25 (m, 1H), 6.94-6.89 (m, 2H), 4.13-3.84 (m, 1H), 3.20-3.14 (m, 1H), 2.24 (d, J = 11.2 Hz, 2H), 2.14 (d, J = 12.0 Hz, 2H), 2.08 (s, 3H), 1.65-1.48 (m, 4H). | Example 2 |
| 103 | (S)-N-((2-chlorophenyl)sulfonyl)-4-methyl-3-((3-(2-(piperidin-3-ylamino)pyrimidin-4-yl)pyridin-2-yl)oxy)benzamide | 579.2 | (400 MHz, CD$_3$OD) δ 8.33 (d, J = 4.8 Hz, 1H), 8.28 (d, J = 6.4 Hz, 1H), 8.17-8.13 (m, 2H), 7.80 (d, J = 7.6 Hz, 1H), 7.67 (s, 1H), 7.46-7.41 (m, 3H), 7.28 (d, J = 7.6 Hz, 1H), 7.21-7.19 (m, 2H), 4.27-4.23 (m, 1H), 3.63-3.61 (m, 1H), 3.36-3.35 (m, 1H), 2.96-2.82 (m, 2H), 2.19 (s, 3H), 2.07-1.98 (m, 2H), 1.79-1.67 (m, 2H). | Example 3 |

TABLE A1-continued

| Cpd No. | Name | MS m/z | ¹H NMR (ppm) | Synth. Method |
|---|---|---|---|---|
| 104 | N-[4-[[3-[2-[(4-aminocyclohexyl)amino]pyrimidin-4-yl]-2-pyridyl]oxy]-3-chloro-5-fluoro-phenyl]-2-chloro-benzenesulfonamide hydrochloride | 603 | (400 MHz, CD₃OD) δ 8.51-8.50 (m, 1H), 8.34 (d, J = 6.0 Hz, 1H), 8.18-8.13 (m, 2H), 7.63 (d, J = 3.6 Hz, 2H), 7.55-7.48 (m, 2H), 7.30 (dd, J = 7.6, 4.8 Hz, 1H), 7.13 (s, 1H), 7.06 (dd, J = 11.2, 2.4 Hz, 1H), 4.05-3.87 (m, 1H), 3.19-3.14 (m, 1H), 2.24 (d, J = 12.4 Hz, 2H), 2.13 (d, J = 12.4 Hz, 2H), 1.64-1.47 (m, 4H). | Example 4 |
| 105 | (S)-3,3,3-trifluoro-N-(2-fluoro-4-((3-(2-(piperidin-3-ylamino)pyrimidin-4-yl)pyridin-2-yl)oxy)phenyl)propane-1-sulfonamide hydrochloride | 541.1 | (400 MHz, CD₃OD) δ .78 (br s, 1H), 8.47 (d, J = 6.6 Hz, 1H), 8.35 (dd, J = 4.7, 1.9 Hz, 1H), 7.90 (br s, 1H), 7.57 (t, J = 8.9 Hz, 1H), 7.35-7.44 (m, 1H), 7.21 (br d, J = 11 Hz, 1H), 7.07 (br d, J = 8.8 Hz, 1H), 4.64 (br s, 1H), 3.64 (br dd, J = 11.9, 3.5 Hz, 1H), 3.32-3.39 (m, 3H), 3.00-3.16 (m, 2H), 2.69-2.85 (m, 2H), 2.19-2.29 (m, 1H), 2.07-2.18 (m, 1H), 1.78-2.03 (m, 2H). | Example 5 |
| 106 | (S)-N-(2-fluoro-4-((3-(2-(piperidin-3-ylamino)pyrimidin-4-yl)pyridin-2-yl)oxy)phenyl)-1-phenylmethanesulfonamide hydrochloride | 535.2 | (400 MHz, CD₃OD) δ 8.75 (br s, 1H), 8.47 (d, J = 6.8 Hz, 1H), 8.36 (dd, J = 4.9, 2.0 Hz, 1H), 7.89 (br d, J = 6.2 Hz, 1H), 7.33-7.47 (m, 7H), 7.14 (dd, J = 11.1, 2.5 Hz, 1H), 6.93-7.01 (m, 1H), 4.63 (br s, 1H), 4.46 (s, 2H), 3.64 (dd, J = 12.3, 3.8 Hz, 1H), 3.35-3.43 (m, 1H), 3.03-3.16 (m, 2H), 2.19-2.30 (m, 1H), 2.09-2.18 (m, 1H), 1.80-2.02 (m, 2H). | Example 5 |
| 107 | (S)-N-(2,5-difluoro-4-((3-(2-(piperidin-3-ylamino)pyrimidin-4-yl)pyridin-2-yl)oxy)phenyl)-1-phenylmethanesulfonamide hydrochloride | 553.2 | (400 MHz, CD₃OD) δ 8.73 (br s, 1H), 8.48 (d, J = 6.4 Hz, 1H), 8.33 (dd, J = 1.76, 4.85 Hz, 1H), 7.85 (d, J = 4.41 Hz, 1H), 7.37-7.43 (m, 3H), 7.31-7.36 (m, 3H), 7.24 (ddd, J = 7.17, 11.08, 16.37 Hz, 2H), 4.61 (br s, 1H), 4.51 (s, 2H), 3.65 (dd, J = 3.64, 12.24 Hz, 1H), 3.35-3.42 (m, 1H), 3.02-3.15 (m, 2H), 2.20-2.28 (m, 1H), 2.09-2.18 (m, 1H), 1.80-2.02 (m, 2H). | Example 5 |
| 108 | (S)-N-(2,3-difluoro-4-((3-(2-(piperidin-3-ylamino)pyrimidin-4-yl)pyridin-2-yl)oxy)phenyl)-1-phenylmethanesulfonamide hydrochloride | 553.2 | (400 MHz, CD₃OD) δ 8.72 (br s, 1H), 8.48 (dd, J = 6.5, 2.1 Hz, 1H), 8.33 (br d, J = 4.6 Hz, 1H), 7.85 (br s, 1H), 7.31-7.43 (m, 6H), 7.24 (dt, J = 2.4, 8.6 Hz, 1H), 7.00-7.11 (m, 1H), 4.57 (br s, 1H), 4.51 (s, 2H), 3.65 (dd, J = 3.1, 12.1 Hz, 1H), 3.39 (br d, J = 12.8 Hz, 1H), 3.02-3.15 (m, 2H), 2.24 (br d, J = 12.57 Hz, 1H), 2.08-2.19 (m, 1H), 1.79-2.01 (m, 2H). | Example 5 |
| 109 | (S)-N-(2,5-difluoro-4-((3-(2-(piperidin-3-ylamino)pyrimidin-4-yl)pyridin-2-yl)oxy)phenyl)-3,3,3-trifluoropropane-1-sulfonamide hydrochloride | 559.1 | (400 MHz, CD₃OD) δ 8.75 (br s, 1H), 8.48 (d, J = 6.6 Hz, 1H), 8.33 (d, J = 5.1 Hz, 1H), 7.90 (br d, J = 5.7 Hz, 1H), 7.48 (dd, J = 7.39, 11.14 Hz, 1H), 7.35-7.44 (m, 2H), 4.63 (br s, 1H), 3.65 (br d, J = 3.64, 12.46 Hz, 1H), 3.36-3.43 (m, 3H), 3.01-3.16 (m, 2H), 2.67-2.85 (m, 2H), 2.25 (br d, J = 9.70 Hz, 1H), 2.07-2.18 (m, 1H), 1.80-2.02 (m, 2H). | Example 5 |
| 110 | (S)-N-(2,5-difluoro-4-((3-(2-(piperidin-3-ylamino)pyrimidin-4-yl)pyridin-2-yl)oxy)phenyl)-3,3,3-trifluoropropane-1-sulfonamide hydrochloride | | (400 MHz, DMSO-d₆) δ 8.80 (br s, 1H), 8.49 (d, J = 6.8 Hz, 1H), 8.33 (dd, J = 2.0, 4.9 Hz, 1H), 7.93 (br d, J = 6.4 Hz, 1H), 7.45-7.37 (m, 2H), 7.24-7.17 (m, 1H), 4.67 (br s, 1H), 3.66 (br dd, J = 3.6, 12.2 Hz, 1H), 3.45-3.36 (m, 3H), 3.15-3.03 (m, 2H), 2.83-2.71 (m, 2H), 2.29-2.09 (m, 2H), 2.02-1.84 (m, 2H). | Example 5 |
| 111 | N-(2,3-difluoro-4-((3-(2-(((3S,5R)-5-methylpiperidin-3-yl)amino)pyrimidin-4-yl)pyridin-2-yl)oxy)phenyl)-1-phenylmethanesulfonamide hydrochloride | 567.5 | (400 MHz, DMSO-d₆) δ 9.98 (s, 1 H), 9.40-9.28 (m, 2H), 8.69-8.45 (m, 2H), 8.25 (d, J = 2.8 Hz, 1 H), 7.67 (s, 1 H), 7.40-7.35 (m, 7H), 7.25-7.21 (m, 2H), 4.56 (s, 2 H), 4.34 (s, 1 H), 3.44 (s), 3.19-3.17 (m), 2.61-2.58 (m, 1H), 2.44-2.41 (m, 1H), 2.06-2.02 (m, 2H), 1.31-1.25 (m, 1H), 0.94 (d, J = 6.8 Hz, 1 H). | Example 6 |
| 112 | N-(2,3-difluoro-4-((3-(2-(((3S,5S)-5-fluoropiperidin-3-yl)amino)pyrimidin-4-yl)pyridin-2-yl)oxy)phenyl)-1-phenylmethanesulfonamide | 571.1 | (400 MHz, DMSO-d₆) δ 9.78 (s, 1H), 9.24 (s, 1H), 8.46-8.48 (m, 1H), 8.25-8.27 (m, 1H), 7.68 (s, 1H), 7.37-7.40 (m, 7H), 7.18-7.23 (m, 2H), 5.23 (d, J = 48.8 Hz, 1H), 4.56 (s, 2H), 4.49 (s, 1H), 3.45-3.62 (m, 3H), 3.13-3.30 (m, | Example 6 |

TABLE A1-continued

| Cpd No. | Name | MS m/z | ¹H NMR (ppm) | Synth. Method |
|---|---|---|---|---|
| | | | 1H), 2.50-2.85 (m, 1H), 2.33 (s, 1H), 1.86-2.01 (m, 1H). | |
| 113 | (S)-1-phenyl-N-(4-((3-(2-(piperidin-3-ylamino)pyrimidin-4-yl)pyridin-2-yl)oxy)-2-(trifluoromethyl)phenyl)methanesulfonamide | 585.3 | (400 MHz, DMSO-d₆) δ 8.41-8.32 (M, 2H), 8.22 (dd, J = 4.8, 2.2 Hz), 7.46-7.12 (m, 10H), 7.06 (dd, J = 9.0, 2.8 Hz), 4.16-4.08 (br s, 2H), 3.97 (s, 2H), 3.20-3.07 (m, 1H), 2.83-2.70 (m, 2H), 1.98-1.91 (m, 1H), 1.80-1.70 (m, 1H), 1.70-1.54 (m, 2H). | Example 5 |
| 114 | (S)-2-chloro-N-(3-fluoro-5-methyl-4-((3-(2-(piperidin-3-ylamino)pyrimidin-4-yl)pyridin-2-yl)oxy)phenyl)benzenesulfonamide hydrochloride | 569.1 | (400 MHz, DMSO-d₆) δ 10.91 (s, 1H), 9.01 (s, 1H), 8.63 (s, 1H), 8.41 (d, J = 4.8 Hz, 1H), 8.15-8.10 (m, 2H), 7.69-7.57 (m, 3H), 7.38-7.25 (m, 2H), 6.90-6.85 (m, 2H), 4.35-4.20 (m, 1H), 3.41-3.37 (m, 1H), 3.19-3.15 (m, 1H), 2.87-2.73 (m, 2H), 2.03 (s, 3H), 2.00-1.85 (m, 2H), 1.80-1.58 (m, 2H). | Example 7 |
| 115 | (S)-N-(3-fluoro-5-methyl-4-((3-(2-(piperidin-3-ylamino)pyrimidin-4-yl)pyridin-2-yl)oxy)phenyl)butane-1-sulfonamide hydrochloride | 515.1 | (400 MHz, DMSO-d₆) δ 8.42 (s, 1H), 8.37 (d, J = 5.2 Hz, 1H), 8.16-8.15 (m, 1H), 7.31-7.28 (m, 1H), 7.24 (d, J = 4.8 Hz, 1H), 7.12 (d, J = 7.6 Hz, 1H), 6.99-6.89 (m, 2H), 3.94-3.80 (m, 1H), 3.20-3.04 (m, 4H), 2.83-2.76 (m, 1H), 2.47-2.37 (m, 2H), 2.10 (s, 3H), 1.95-1.86 (m, 1H), 1.73-1.60 (m, 3H), 1.53-1.32 (m, 4H), 0.86 (t, J = 7.2 Hz, 3H). | Example 7 |
| 116 | (S)-N-(3-fluoro-5-methyl-4-((3-(2-(piperidin-3-ylamino)pyrimidin-4-yl)pyridin-2-yl)oxy)phenyl)cyclopentanesulfonamide hydrochloride | 527.1 | (400 MHz, DMSO-d₆) δ 10.00 (s, 1H), 9.63-9.14 (m, 2H), 8.89-8.65 (m, 1H), 8.47 (d, J = 5.2 Hz, 1H), 8.21 (d, J = 3.6 Hz, 1H), 8.11-7.70 (m, 1H), 7.56-7.29 (m, 2H), 7.09-6.92 (m, 2H), 4.50-4.20 (m, 1H), 3.71-3.58 (m, 1H), 3.49-3.33 (m, 1H), 3.24-3.08 (m, 1H), 2.89-2.73 (m, 2H), 2.11 (s, 3H), 2.03-1.98 (m, 1H), 1.96-1.85 (m, 5H), 1.83-1.73 (m, 1H), 1.69-1.42 (m, 5H). | Example 7 |
| 117 | (S)-N-(3-fluoro-5-methyl-4-((3-(2-(piperidin-3-ylamino)pyrimidin-4-yl)pyridin-2-yl)oxy)phenyl)cyclohexanesulfonamide hydrochloride | 541.1 | (400 MHz, DMSO-d₆) δ 10.01 (s, 1H), 9.66-9.23 (m, 2H), 8.86-8.67 (m, 1H), 8.47 (d, J = 5.2 Hz, 1H), 8.26-8.19 (m, 1H), 7.60-7.38 (m, 1H), 7.37-7.28 (m, 1H), 7.07-7.01 (m, 1H), 6.98 (s, 1H), 4.55-4.18 (m, 1H), 3.44-3.35 (m, 1H), 3.22-3.14 (m, 1H), 3.13-3.04 (m, 1H), 2.91-2.75 (m, 2H), 2.11 (s, 3H), 2.08-1.96 (m, 3H), 1.95-1.86 (m, 1H), 1.84-1.72 (m, 3H), 1.70-1.54 (m, 2H), 1.51-1.34 (m, 2H), 1.33-1.19 (m, 2H), 1.18-1.05 (m, 1H). | Example 7 |
| 118 | N-(4-((3-(2-(((1r,4r)-4-aminocyclohexyl)amino)pyrimidin-4-yl)pyridin-2-yl)oxy)-3-fluoro-5-methylphenyl)propane-1-sulfonamide hydrochloride | 515.1 | (400 MHz, DMSO-d₆) δ 10.07 (s, 1H), 8.46 (s, 2H), 8.31-8.14 (m, 4H), 7.53-7.33 (m, 2H), 7.07-6.95 (m, 2H), 4.00-3.78 (m, 1H), 3.15 (t, J = 7.6 Hz, 2H), 3.06-2.95 (m, 1H), 2.13 (s, 3H), 2.10-1.99 (m, 4H), 1.75-1.67 (m, 2H), 1.58-1.37 (m, 4H), 8.47 (t, J = 7.2 Hz, 3H). | Example 2 |
| 119 | N-(4-((3-(2-(((1r,4r)-4-aminocyclohexyl)amino)pyrimidin-4-yl)pyridin-2-yl)oxy)-3-fluoro-5-methylphenyl)-1-phenylmethanesulfonamide hydrochloride | 563.1 | (400 MHz, DMSO-d₆) δ 10.08 (s, 1H), 8.46 (m, 2H), 8.29-8.10 (m, 5H), 7.46-7.42 (m, 1H), 7.39-7.31 (m, 6H), 6.97-6.89 (m, 2H), 4.57 (s, 2H), 3.92-3.79 (m, 1H), 3.07-2.94 (m, 1H), 2.12 (s, 3H), 2.09-1.99 (m, 4H), 1.55-1.36 (m, 4H). | Example 2 |
| 120 | N-(4-((3-(2-(((1r,4r)-4-aminocyclohexyl)amino)pyrimidin-4-yl)pyridin-2-yl)oxy)-3-fluoro-5-methylphenyl)cyclopropanecarboxamide hydrochloride | 477.2 | (400 MHz, DMSO-d₆) δ 10.56 (s, 1H), 8.44 (s, 2H), 8.25-8.21 (m, 1H), 8.16-8.09 (m., 3H), 7.61-7.55 (m, 1H), 7.44-7.39 (m, 1H), 7.37-7.32 (m, 1H), 7.29 (s, 1H), 3.06-2.95 (m, 1H), 2.11 (s, 3H), 2.08-1.98 (m, 4H), 1.87-1.79 (m, 1H), 1.58-1.32 (m, 5H), 0.84-0.78 (m, 4H). | Example 2 |
| 121 | N-(4-((3-(2-(((1r,4r)-4-aminocyclohexyl)amino)pyrimidin-4-yl)pyridin-2-yl)oxy)-3-chloro-5-fluorophenyl)propane-1-sulfonamide hydrochloride | 535.0 | (400 MHz, DMSO-d₆) δ 10.40 (s, 1H), 8.45 (s, 2H), 8.27-8.22 (m, 1H), 8.15-8.05 (m, 2H), 7.45-7.35 (m, 2H), 7.26-7.15 (m, 2H), 3.90-3.80 (m, 1H), 3.23 (t, J = 7.6 Hz, 2H), 3.05-2.95 (m, 1H), 2.15-1.95 (m, 4H), 1.77-1.67 (m, 2H), 1.55-1.33 (m, 4H), 0.97 (t, J = 7.2 Hz, 3H). | Example 9 |

TABLE A1-continued

| Cpd No. | Name | MS m/z | ¹H NMR (ppm) | Synth. Method |
|---|---|---|---|---|
| 122 | N-(4-((3-(2-(((1r,4r)-4-aminocyclohexyl)amino)pyrimidin-4-yl)pyridin-2-yl)oxy)-3,5-difluorophenyl)propane-1-sulfonamide hydrochloride | 519.1 | (400 MHz, DMSO-$d_6$) δ 10.36 (s, 1H), 8.45-8.38 (m, 2H), 8.25-8.23 (m, 1H), 8.00-7.90 (m, 2H), 7.60-7.50 (m, 1H), 7.40-7.35 (m, 1H), 7.22-7.18 (m, 1H), 7.04 (d, J = 9.2 Hz, 2H), 3.80-3.70 (m, 1H), 3.23 (t, J = 7.6 Hz, 2H), 3.05-2.95 (m, 1H), 2.07-2.95 (m, 4H), 1.73-1.64 (m, 2H), 1.50-1.30 (m, 4H), 0.98 (t, J = 7.2 Hz, 3H). | Example 8 |
| 123 | (S)-2-Chloro-N-(2,3-dimethyl-4-((3-(2-(piperidin-3-ylamino)pyrimidin-4-yl)pyridin-2-yl)oxy)phenyl)benzenesulfonamide | 565.1 | (400 MHz, DMSO-$d_6$) δ 8.38 (s, 2H), 8.37-8.32 (m, 1H), 8.12 (dd, J = 4.8, 2.0 Hz, 1H), 7.84 (dd, J = 7.8, 1.7 Hz, 1H), 7.65-7.59 (m, 1H), 7.59-7.52 (m, 1H), 7.45-7.39 (m, 1H), 7.27-7.18 (m, 2H), 7.10 (d, J = 7.9 Hz, 1H), 6.79-6.67 (m, 2H), 3.88 (s, 1H), 3.10 (d, J = 12.0 Hz, 1H), 2.83 (d, J = 13.0 Hz, 1H), 2.48-2.42 (m, 2H), 2.13 (s, 3H), 1.92 (s, 3H), 1.90 (d, J = 4.1 Hz, 2H), 1.70-1.63 (m, 1H), 1.52-1.42 (m, 2H). | Example 10 |
| 124 | (S)-N-(2,5-Dimethyl-4-((3-(2-(piperidin-3-ylamino)pyrimidin-4-yl)pyridin-2-yl)oxy)phenyl)propane-1-sulfonamide | 497.2 | (400 MHz, DMSO-$d_6$) δ 8.41 (s, 2H), 8.35 (d, J = 5.1 Hz, 1H), 8.17 (dd, J = 4.8, 2.0 Hz, 1H), 7.30-7.24 (m, 2H), 7.16 (s, 1H), 7.07 (d, J = 8.0 Hz, 1H), 6.98 (s, 1H), 3.84 (s, 1H), 3.12-3.02 (m, 2H), 2.79 (d, J = 12.3 Hz, 1H), 2.47-2.37 (m, 4H), 2.25 (s, 3H), 2.02 (s, 3H), 1.90 (t, J = 5.6 Hz, 1H), 1.82-1.72 (m, 2H), 1.67-1.60 (m, 1H), 1.44 (q, J = 13.4, 12.5 Hz, 2H), 1.01 (t, J = 7.5 Hz, 3H). | Example 10 |
| 125 | (S)-2-chloro-N-(2,5-dimethyl-4-((3-(2-(piperidin-3-ylamino)pyrimidin-4-yl)pyridin-2-yl)oxy)phenyl)benzenesulfonamide | 565.2 | (400 MHz, DMSO-$d_6$) δ 8.38 (s, 1H), 8.34 (d, J = 5.1 Hz, 1H), 8.14 (dd, J = 4.8, 2.0 Hz, 1H), 7.87 (dd, J = 7.9, 1.7 Hz, 1H), 7.64 (dd, J = 8.0, 1.3 Hz, 1H), 7.58 (td, J = 7.6, 1.7 Hz, 1H), 7.44 (td, J = 7.6, 1.4 Hz, 1H), 7.28-7.19 (m, 2H), 7.11 (d, J = 7.9 Hz, 1H), 6.84 (d, J = 11.5 Hz, 2H), 3.89 (s, 1H), 3.12 (d, J = 12.2 Hz, 1H), 2.85 (d, J = 12.1 Hz, 1H), 2.48-2.41 (m, 2H), 2.05 (s, 3H), 1.94-1.88 (m, 2H), 1.87 (s, 3H), 1.67 (d, J = 6.7 Hz, 1H), 1.48 (t, J = 8.9 Hz, 2H). | Example 10 |
| 126 | (S)-N-(2,5-Dimethyl-4-((3-(2-(piperidin-3-ylamino)pyrimidin-4-yl)pyridin-2-yl)oxy)phenyl)propane-1-sulfonamide | 497.2 | (400 MHz, DMSO-$d_6$) δ 8.41 (s, 2H), 8.35 (d, J = 5.1 Hz, 1H), 8.17 (dd, J = 4.8, 2.0 Hz, 1H), 7.30-7.24 (m, 2H), 7.16 (s, 1H), 7.07 (d, J = 8.0 Hz, 1H), 6.98 (s, 1H), 3.84 (s, 1H), 3.12-3.02 (m, 2H), 2.79 (d, J = 12.3 Hz, 1H), 2.47-2.37 (m, 4H), 2.25 (s, 3H), 2.02 (s, 3H), 1.90 (t, J = 5.6 Hz, 1H), 1.82-1.72 (m, 2H), 1.67-1.60 (m, 1H), 1.44 (q, J = 13.4, 12.5 Hz, 2H), 1.01 (t, J = 7.5 Hz, 3H). | Example 10 |
| 127 | (S)-N-(4-fluoro-3-((3-(2-(piperidin-3-ylamino)pyrimidin-4-yl)pyridin-2-yl)oxy)phenyl)propane-1-sulfonamide | 487.2 | (400 MHz, DMSO-$d_6$) δ 8.41 (s, 1H), 8.38 (d, J = 5.1 Hz, 1H), 8.20 (dd, J = 4.8, 1.9 Hz, 1H), 7.37-7.29 (m, 2H), 7.19 (d, J = 5.1 Hz, 1H), 7.15-7.06 (m, 3H), 3.86 (d, J = 10.5 Hz, 1H), 3.13-3.03 (m, 3H), 2.80 (d, J = 12.4 Hz, 1H), 2.42 (dd, J = 11.7, 8.8 Hz, 1H), 2.07 (s, 2H), 1.90 (d, J = 3.4 Hz, 1H), 1.73-1.60 (m, 2H), 1.45 (q, J = 13.0, 12.4 Hz, 2H), 0.94 (t, J = 7.4 Hz, 3H). | Example 10 |
| 128 | (S)-2-Chloro-N-(4-fluoro-3-((3-(2-(piperidin-3-ylamino)pyrimidin-4-yl)pyridin-2-yl)oxy)phenyl)benzenesulfonamide | 555.1 | (400 MHz, DMSO-$d_6$) δ 8.38 (d, J = 5.1 Hz, 1H), 8.36 (s, 1H), 8.16 (dd, J = 4.8, 1.9 Hz, 1H), 7.97-7.92 (m, 1H), 7.55-7.46 (m, 2H), 7.40 (ddd, J = 7.8, 6.8, 1.9 Hz, 1H), 7.30 (dd, J = 7.5, 4.8 Hz, 1H), 7.26 (d, J = 7.7 Hz, 1H), 7.15 (d, J = 5.1 Hz, 1H), 7.06 (dd, J = 10.4, 8.9 Hz, 1H), 6.85 (dd, J = 7.1, 2.7 Hz, 1H), 6.80 (ddd, J = 8.8, 4.0, 2.7 Hz, 1H), 3.97 (s, 1H), 3.24 (s, 1H), 3.00 (d, J = 12.3 Hz, 1H), 2.68-2.52 (m, 2H), 1.98-1.87 (m, 1H), 1.75 (d, J = 5.9 Hz, 1H), 1.53 (t, J = 9.2 Hz, 2H). | Example 10 |

TABLE A1-continued

| Cpd No. | Name | MS m/z | ¹H NMR (ppm) | Synth. Method |
|---|---|---|---|---|
| 129 | (S)-2-Cyclohexyl-N-(2,3-dimethyl-4-((3-(2-(piperidin-3-ylamino)pyrimidin-4-yl)pyridin-2-yl)oxy)phenyl)acetamide | 515.1 | (400 MHz, DMSO-$d_6$) δ 9.34 (s, 1H), 8.41 (s, 2H), 8.37 (d, J = 5.1 Hz, 1H), 8.16 (dd, J = 4.8, 2.0 Hz, 1H), 7.31-7.22 (m, 2H), 7.09 (t, J = 8.8 Hz, 2H), 6.89 (d, J = 8.5 Hz, 1H), 3.87 (s, 1H), 3.08 (d, J = 11.8 Hz, 1H), 2.80 (d, J = 12.4 Hz, 1H), 2.47-2.37 (m, 3H), 2.21 (d, J = 6.8 Hz, 2H), 2.11 (s, 3H), 2.01 (s, 3H), 1.91 (s, 1H), 1.71 (dd, J = 32.3, 14.1 Hz, 5H), 1.46 (q, J = 13.5, 12.7 Hz, 2H), 1.22 (dq, J = 24.6, 11.8, 11.3 Hz, 3H), 1.02 (q, J = 11.4, 11.0 Hz, 2H). | Example 11 |
| 130 | (S)-2-(4-Chlorophenyl)-N-(2,3-dimethyl-4-((3-(2-(piperidin-3-ylamino)pyrimidin-4-yl)pyridin-2-yl)oxy)phenyl)acetamide | 543.2 | (400 MHz, DMSO-$d_6$) δ 9.65 (s, 1H), 8.41 (s, 1H), 8.36 (d, J = 5.1 Hz, 1H), 8.15 (dd, J = 4.8, 2.0 Hz, 1H), 7.41 (s, 4H), 7.30-7.22 (m, 2H), 7.12 (d, J = 8.6 Hz, 1H), 7.06 (d, J = 8.0 Hz, 1H), 6.90 (d, J = 8.5 Hz, 1H), 3.84 (s, 1H), 3.68 (s, 2H), 3.07 (d, J = 11.7 Hz, 1H), 2.78 (d, J = 12.4 Hz, 1H), 2.46-2.37 (m, 3H), 2.07 (s, 3H), 2.00 (s, 3H), 1.91 (d, J = 11.1 Hz, 1H), 1.67-1.58 (m, 1H), 1.46 (dt, J = 26.4, 14.0 Hz, 2H). | Example 11 |
| 131 | (S)-2-chloro-N-(3,5-dimethyl-4-((3-(2-(piperidin-3-ylamino)pyrimidin-4-yl)pyridin-2-yl)oxy)phenyl)benzenesulfonamide hydrochloride | 565.2 | (500 MHz, $d_6$-DMSO) δ 10.53 (s, 1H), 9.11-8.70 (br s, 1H), 8.87 (s, 1H), 8.68-8.20 (br s, 1H), 8.41 (d, J = 5.2 Hz, 1H), 8.12 (dd, J = 4.8, 1.8 Hz, 1H), 8.08 (d, J = 7.2 Hz, 1H), 7.72-7.61 (m, 2H), 7.61-7.51 (m, 1H), 7.47 (d, J = 7.4 Hz, 1H), 7.41 (s, 1H), 7.24 (dd, J = 7.5, 4.8 Hz, 1H), 6.87 (s, 2H), 4.30-4.15 (m, 1H), 3.77-3.65 (m, 1H), 3.19 (d, J = 12.3 Hz, 1H), 2.92-2.73 (m, 2H), 2.05-1.95 (m, 1H), 1.94-1.90 (m, 7H), 1.73 (q, J = 13.3 Hz, 1H), 1.61 (q, J = 10.4 Hz, 1H). | Example 12 |
| 132 | (S)-2-chloro-N-(3-((3-(2-(piperidin-3-ylamino)pyrimidin-4-yl)pyridin-2-yl)oxy)phenyl)benzenesulfonamide hydrochloride | 537.1 | (400 MHz, $d_6$-DMSO) δ 10.82 (s, 1H), 9.15-8.89 (m, 2H), 8.57 (s, 1H), 8.40 (d, J = 5.2 Hz, 1H), 8.19 (dd, J = 4.8, 2.0 Hz, 1H), 8.03-7.99 (m, 1H), 7.65 (dd, J = 4.9, 1.2 Hz, 2H), 7.60-7.48 (m, 2H), 7.33 (dd, J = 7.6, 4.8 Hz, 1H), 7.28-7.18 (m, 2H), 6.93 (ddd, J = 8.2, 2.1, 0.8 Hz, 1H), 6.84 (t, J = 2.1 Hz, 1H), 6.79 (ddd, J = 8.2, 2.3, 0.8 Hz, 1H), 4.22 (s, 1H), 3.39 (d, J = 10.7 Hz, 1H), 3.18 (d, J = 13.0 Hz, 1H), 2.92-2.72 (m, 2H), 2.02-1.84 (m, 2H), 1.79-1.54 (m, 2H). | Example 13 |
| 133 | (S)-1-phenyl-N-(3-((3-(2-(piperidin-3-ylamino)pyrimidin-4-yl)pyridin-2-yl)oxy)phenyl)methanesulfonamide hydrochloride | 517.2 | (400 MHz, $d_6$-DMSO) δ 10.01 (s, 1H), 9.20-8.85 (m, 2H), 8.58 (s, 1H), 8.45 (d, J = 5.2 Hz, 1H), 8.27 (dd, J = 4.8, 2.0 Hz, 1H), 7.60 (d, J = 6.9 Hz, 1H), 7.40-7.30 (m, 6H), 7.29-7.23 (m, 2H), 7.05 (dd, J = 8.2, 1.3 Hz, 1H), 6.93-6.85 (m, 2H), 4.49 (s, 2H), 4.24 (s, 1H), 3.40 (d, J = 12.4 Hz, 1H), 3.19 (d, J = 11.9 Hz, 1H), 2.92-2.73 (m, 2H), 1.95 (ddd, J = 18.4, 13.7, 4.1 Hz, 2H), 1.82-1.53 (m, 2H). | Example 14 |
| 134 | (S)-2-chloro-N-(4-((3-(2-(piperidin-3-ylamino)pyrimidin-4-yl)pyridin-2-yl)oxy)phenyl)benzenesulfonamide hydrochloride | 537.0 | (400 MHz, $d_6$-DMSO) δ 10.64 (s, 1H), 8.71 (br.s, 2H), 8.57-8.42 (m, 1H), 8.38 (d, J = 5.2 Hz, 1H), 8.17 (dd, J = 4.8, 1.9 Hz, 1H), 8.04 (d, J = 8.5 Hz, 1H), 7.71-7.61 (m, 2H), 7.53 (ddd, J = 8.4, 6.7, 2.1 Hz, 1H), 7.46 (d, J = 6.9 Hz, 1H), 7.27 (dd, J = 7.5, 4.9 Hz, 2H), 7.14 (d, J = 9.0 Hz, 2H), 7.05 (d, J = 8.9 Hz, 2H), 4.26-4.10 (m, 1H), 3.40 (d, J = 12.5 Hz, 1H), 3.18 (d, J = 12.5 Hz, 1H), 2.92-2.70 (m, 2H), 2.01-1.82 (m, 2H), 1.76-1.51 (m, 2H). | Example 15 |
| 135 | (S)-2-chloro-N-(4-methyl-3-((3-(2-(piperidin-3-ylamino)pyrimidin-4-yl)pyridin-2-yl)oxy)phenyl)benzenesulfonamide hydrochloride | 551.0 | (400 MHz, $d_6$-DMSO) δ 10.65 (s, 1H), 9.16-8.82 (m, 2H), 8.61 (s, 1H), 8.41 (d, J = 5.2 Hz, 1H), 8.13 (dd, J = 4.8, 2.0 Hz, 1H), 7.99-7.94 (m, 1H), 7.64 (dd, J = 4.9, 1.2 Hz, 2H), 7.60-7.52 (m, 1H), 7.53-7.44 (m, 1H), 7.29 (dd, J = 7.6, 4.8 Hz, 2H), 7.14 (d, J = 8.3 Hz, 1H), 6.88 (dd, J = 8.2, 2.2 Hz, 1H), 6.78 (d, J = 2.2 | Example 16 |

TABLE A1-continued

| Cpd No. | Name | MS m/z | ¹H NMR (ppm) | Synth. Method |
|---|---|---|---|---|
| | | | Hz, 1H), 4.25 (s, 1H), 3.43-3.35 (m, 1H), 3.24-3.11 (m, 1H), 2.93-2.72 (m, 2H), 2.04-1.85 (m, 5H), 1.84-1.52 (m, 2H). | |
| 136 | (S)-N-(4-methyl-3-((3-(2-(piperidin-3-ylamino)pyrimidin-4-yl)pyridin-2-yl)oxy)phenyl)-1-phenylmethanesulfonamide hydrochloride | 531.1 | (400 MHz, d₆-DMSO) δ 9.87 (s, 1H), 9.23-8.88 (m, 2H), 8.46 (d, J = 5.3 Hz, 1H), 8.23 (dd, J = 4.8, 2.0 Hz, 1H), 7.60 (s, 1H), 7.42 (s, 1H), 7.36-7.29 (m, 4H), 7.28-7.21 (m, 3H), 7.01 (dd, J = 8.2, 2.2 Hz, 1H), 6.84 (d, J = 2.2 Hz, 1H), 4.44 (s, 2H), 4.27 (s, 1H), 3.47-3.32 (m, 2H), 3.25-3.12 (m, 1H), 2.92-2.74 (m, 2H), 2.06-1.95 (m, 4H), 1.95-1.85 (m, 1H), 1.85-1.52 (m, 2H). | Example 17 |
| 137 | (S)-2-chloro-N-(4-chloro-2-fluoro-3-((3-(2-(piperidin-3-ylamino)pyrimidin-4-yl)pyridin-2-yl)oxy)phenyl)benzenesulfonamide hydrochloride | 589.0 | (400 MHz, d₆-DMSO) δ 10.74 (s, 1H), 9.00-8.73 (m, 2H), 8.58 (s, 1H), 8.45 (d, J = 5.1 Hz, 1H), 8.14 (dd, J = 4.8, 1.9 Hz, 1H), 7.96-7.91 (m, 1H), 7.71-7.63 (m, 2H), 7.58-7.49 (m, 2H), 7.40 (dd, J = 9.0, 1.9 Hz, 1H), 7.36 (dd, J = 7.6, 4.8 Hz, 1H), 7.29 (d, J = 3.9 Hz, 1H), 7.19 (dd, J = 8.9, 7.9 Hz, 1H), 4.23 (s, 1H), 3.40 (d, J = 11.1 Hz, 1H), 3.19 (d, J = 12.5 Hz, 1H), 2.82 (td, J = 20.8, 10.6 Hz, 2H), 2.03-1.85 (m, 2H), 1.66 (dq, J = 33.4, 10.8 Hz, 2H). | Example 19 |
| 138 | (S)-N-(4-chloro-2-fluoro-3-((3-(2-(piperidin-3-ylamino)pyrimidin-4-yl)pyridin-2-yl)oxy)phenyl)-1-phenylmethanesulfonamide | 569.0 | (400 MHz, d₆-DMSO) δ δ 8.54-8.39 (m, 2H), 8.27-8.18 (m, 2H), 7.43-7.20 (m, 10H), 7.09 (dd, J = 9.1, 1.6 Hz, 1H), 4.16-4.05 (m, 3H), 3.06 (d, J = 12.3 Hz, 1H), 2.76-2.59 (m, 3H), 2.01-1.90 (m, 1H), 1.88-1.76 (m, 1H), 1.68-1.51 (m, 2H). | Example 20 |
| 139 | (S)-2-chloro-N-(2-methyl-3-((3-(2-(piperidin-3-ylamino)pyrimidin-4-yl)pyridin-2-yl)oxy)phenyl)benzenesulfonamide hydrochloride | 551.2 | (400 MHz, d₆-DMSO) δ 10.00 (s, 1H), 8.84 (br s, 2H), 8.71-8.21 (br s, 1H), 8.40 (d, J = 5.2 Hz, 1H), 8.13 (dd, J = 4.8, 1.9 Hz, 1H), 7.85 (dd, J = 7.9, 1.6 Hz, 1H), 7.70 (dd, J = 8.0, 1.3 Hz, 1H), 7.64 (td, J = 7.7, 1.6 Hz, 1H), 7.49 (td, J = 7.7, 1.4 Hz, 2H), 7.33 (s, 1H), 7.25 (dd, J = 7.6, 4.8 Hz, 1H), 7.10 (t, J = 8.1 Hz, 1H), 6.96 (d, J = 7.8 Hz, 1H), 6.79 (d, J = 7.9 Hz, 1H), 4.21 (s, 1H), 3.17 (d, J = 12.6 Hz, 1H), 2.89-2.70 (m, 2H), 1.95 (m, 4H), 1.88 (dd, J = 10.6, 4.4 Hz, 1H), 1.78-1.65 (m, 1H), 1.58 (q, J = 10.4 Hz, 1H). | Example 21 |
| 140 | (S)-N-(2-methyl-3-((3-(2-(piperidin-3-ylamino)pyrimidin-4-yl)pyridin-2-yl)oxy)phenyl)-1-phenylmethanesulfonamide hydrochloride | 531.2 | (400 MHz, d₆-DMSO) δ 9.28 (s, 1H), 8.88 (s, 1H), 9.22-8.73 (m, 1H), 8.44 (d, J = 5.2 Hz, 1H), 8.72-8.25 (m, 1H), 8.19 (dd, J = 4.8, 1.9 Hz, 1H), 7.52 (d, J = 7.3 Hz, 1H), 7.44-7.33 (m, 6H), 7.29 (dd, J = 7.6, 4.8 Hz, 1H), 7.26-7.21 (m, 1H), 7.19 (dd, J = 8.0, 1.3 Hz, 1H), 7.01 (dd, J = 7.7, 1.2 Hz, 1H), 4.49 (d, J = 8.7 Hz, 2H), 4.24 (s, 1H), 3.19 (d, J = 16.1 Hz, 1H), 2.94-2.74 (m, 2H), 2.00 (s, 4H), 1.91 (d, J = 14.5 Hz, 1H), 1.73 (q, J = 11.6 Hz, 1H), 1.61 (q, J = 9.9 Hz, 1H). | Example 22 |
| 141 | (S)-2-chloro-N-(2-fluoro-3-((3-(2-(piperidin-3-ylamino)pyrimidin-4-yl)pyridin-2-yl)oxy)phenyl)benzenesulfonamide hydrochloride | 555.0 | (400 MHz, d₆-DMSO) δ 10.56 (s, 1H), 8.84-8.63 (m, 2H), 8.59-8.45 (m, 1H), 8.42 (d, J = 5.1 Hz, 1H), 8.14 (dd, J = 4.8, 1.9 Hz, 1H), 7.92 (d, J = 7.4 Hz, 1H), 7.72-7.62 (m, 2H), 7.51 (ddd, J = 8.4, 6.5, 2.2 Hz, 2H), 7.31 (dd, J = 7.5, 4.8 Hz, 1H), 7.25 (d, J = 4.1 Hz, 1H), 7.23-7.08 (m, 3H), 4.29-4.08 (m, 1H), 3.20 (d, J = 11.6 Hz, 2H), 2.95-2.72 (m, 2H), 2.05-1.83 (m, 2H), 1.79-1.49 (m, 2H). | Example 23 |
| 142 | (S)-N-(2-fluoro-3-((3-(2-(piperidin-3-ylamino)pyrimidin-4-yl)pyridin-2-yl)oxy)phenyl)-1-phenylmethanesulfonamide hydrochloride | 535.0 | (400 MHz, d₆-DMSO) δ 9.83 (s, 1H), 8.85-8.61 (m, 2H), 8.61-8.49 (m, 1H), 8.46 (d, J = 5.2 Hz, 1H), 8.23 (dd, J = 4.8, 1.8 Hz, 1H), 7.52 (d, J = 7.2 Hz, 1H), 7.43-7.29 (m, 7H), 7.28-7.12 (m, 3H), 4.51 (s, 2H), 4.41-4.00 (m, 1H), 3.20 (d, J = 12.4 Hz, 2H), 2.83 (td, J = 21.5, 11.3 Hz, 2H), 1.95 (ddd, J = 17.6, 12.5, 4.4 Hz, 2H), 1.81-1.51 (m, 2H). | Example 24 |

TABLE A1-continued

| Cpd No. | Name | MS m/z | ¹H NMR (ppm) | Synth. Method |
|---|---|---|---|---|
| 143 | (S)-N-(4-chloro-2-fluoro-3-((3-(2-(piperidin-3-ylamino)pyrimidin-4-yl)pyridin-2-yl)oxy)phenyl)propane-1-sulfonamide hydrochloride | 521.0 | (400 MHz, d₆-DMSO) δ 9.95 (s, 1H), 9.02-8.74 (m, 2H), 8.73-8.29 (m, 1H), 8.47 (d, J = 5.2 Hz, 1H), 8.21 (dd, J = 4.8, 1.9 Hz, 1H), 7.56 (d, J = 7.4 Hz, 1H), 7.46 (dd, J = 9.0, 1.7 Hz, 1H), 7.43-7.31 (m, 3H), 4.24 (s, 1H), 3.42 (d, J = 12.7 Hz, 1H), 3.19 (d, J = 12.1 Hz, 1H), 3.16-3.09 (m, 2H), 2.93-2.72 (m, 2H), 2.00 (dd, J = 12.4, 4.1 Hz, 1H), 1.95-1.85 (m, 1H), 1.72 (p, J = 7.4 Hz, 2H), 1.61 (q, J = 10.9 Hz, 1H), 0.95 (t, J = 7.4 Hz, 3H). | Example 25 |
| 144 | (S)-N-(2-fluoro-3-((3-(2-(piperidin-3-ylamino)pyrimidin-4-yl)pyridin-2-yl)oxy)phenyl)propane-1-sulfonamidehydrochloride | 487.1 | (400 MHz, d₆-DMSO) δ 9.79 (s, 1H), 9.04-8.77 (m, 2H), 8.73-8.48 (m, 1H), 8.45 (d, J = 5.2 Hz, 1H), 8.21 (dd, J = 4.8, 1.9 Hz, 1H), 7.55 (d, J = 7.3 Hz, 1H), 7.41-7.28 (m, 3H), 7.29-7.18 (m, 2H), 4.33-4.14 (m, 1H), 3.41 (d, J = 11.3 Hz, 1H), 3.19 (d, J = 13.4 Hz, 1H), 3.14-3.04 (m, 2H), 2.93-2.73 (m, 2H), 2.07-1.84 (m, 2H), 1.80-1.67 (m, 3H), 1.67-1.54 (m, 1H), 0.95 (t, J = 7.4 Hz, 3H). | Example 26 |
| 145 | (S)-1-cyclohexyl-N-(2,3-difluoro-4-((3-(2-(piperidin-3-ylamino)pyrimidin-4-yl)pyridin-2-yl)oxy)phenyl)methanesulfonamide hydrochloride | 559.2 | (300 MHz, DMSO-d₆) δ 9.97 (s, 1H), 9.25-9.50 (brs, 2H), 8.80-8.60 (m, 1H), 8.48 (d, J = 5.4 Hz, 1H), 8.26 (dd, J = 4.8, 1.6 Hz, 1H), 8.00-7.85 (brs, 1H), 7.40-7.25 (m, 4H), 4.35 (s, 1H), 3.40 (d, J = 7.0 Hz, 1H), 3.18 (d, J = 12.3 Hz, 1H), 3.09 (d, J = 5.7 Hz, 2H), 2.89-2.76 (m, 2H), 2.05-1.83 (m, 6H), 1.61 (d, J = 13.8 Hz, 4H), 1.34-1.00 (m, 5H). | Example 27 |
| 146 | (S)-N-(2,3-difluoro-4-((3-(2-(piperidin-3-ylamino)pyrimidin-4-yl)pyridin-2-yl)oxy)phenyl)-1-(2-fluorophenyl)methanesulfonamide hydrochloride | 571.1 | (400 MHz, CD₃OD) δ 8.71 (s, 1H), 8.49 (d, J = 6.2 Hz, 1H), 8.33 (s, 1H), 7.80 (s, 1H), 7.57-7.47 (m, 1H), 7.46-7.36 (m, 2H), 7.34-7.26 (m, 1H), 7.26-7.00 (m, 3H), 4.61 (s, 3H), 3.72-3.58 (m, 1H), 3.40 (d, J = 12.9 Hz, 1H), 3.19-3.03 (m, 2H), 2.24 (s, 1H), 2.18-2.10 (m, 1H), 1.95-1.85 (m, 2H). | Example 27 |
| 147 | (S)-N-(2,3-difluoro-4-(3-(2-(piperidin-3-ylamino)pyrimidin-4-yl)pyridin-2-yloxy)phenyl)cyclopropanecarboxamide hydrochloride | 467.2 | (400 MHz, CD₃OD) δ 8.77 (d, J = 8.0 Hz, 1H), 8.50 (d, J = 6.6 Hz, 1H), 8.33 (dd, J = 4.8, 1.9 Hz, 1H), 7.91 (d, J = 5.5 Hz, 1H), 7.80-7.66 (m, 1H), 7.41 (dd, J = 2.2, 4.8 Hz, 1H), 7.43-7.39 (m, 1H), 4.63 (s, 1H), 3.67 (dd, J = 12.2, 3.9 Hz, 1H), 3.43-3.38 (m, 1H), 3.19-3.01 (m, 2H), 2.32-2.21 (m, 1H), 2.18-2.12 (m, 1H), 2.07-1.81 (m, 3H), 1.02-0.90 (m, 4H). | Example 28 |
| 148 | (S)-N-(2,3-Difluoro-4-((3-(2-(piperidin-3-ylamino)pyrimidin-4-yl)pyridin-2-yl)oxy)phenyl)-2,2-difluorobutane-1-sulfonamide hydrochloride | 555.1 | (400 MHz, CD₃OD) δ 8.63 (s, 1H), 8.49-8.43 (m, 1H), 8.26 (s, 1H), 7.67 (s, 1H), 7.46-7.31 (m, 2H), 7.16 (t, J = 8.4 Hz, 1H), 4.45 (s, 1H), 3.87 (t, J = 13.3 Hz, 2H), 3.65 (d, J = 13.8 Hz, 1H), 3.38 (d, J = 12.9 Hz, 1H), 3.07 (t, J = 11.4 Hz, 2H), 2.22-2.12 (m, 4H), 1.95-1.77 (m, 2H), 1.07 (t, J = 7.5 Hz, 3H) | Example 27 |
| 149 | (S)-N-(2,3-difluoro-4-((3-(2-(piperidin-3-ylamino)pyrimidin-4-yl)pyridin-2-yl)oxy)phenyl)-3,3-difluorobutane-1-sulfonamide hydrochloride | 555.1 | (300 MHz, CD₃OD) δ 8.83-8.80 (m, 1H), 8.522 (d, J = 6.6 Hz, 1H), 8.37-3.35 (m, 1H), 7.96 (d, J = 6.6 Hz, 1H), 7.50-7.36 (m, 2H), 7.34-7.16 (m, 1H), 4.69 (s, 1H), 3.69 (d, J = 12.0 Hz, 1H), 3.48-3.35 (m, 3H), 3.24-3.02 (m, 2H), 2.59-2.37 (m, 2H), 2.28 (d, J = 12.4 Hz, 1H), 2.16-2.14 (m, 1H), 2.10-1.86 (m, 2H), 1.70 (t, J = 18.0 Hz, 3H). | Example 27 |
| 150 | N-(2,3-difluoro-4-((3-(2-(((S)-piperidin-3-yl)amino)pyrimidin-4-yl)pyridin-2-yl)oxy)phenyl)spiro[2.2]pentane-1-carboxamide hydrochloride | 493.2 | (400 MHz, CD₃OD) δ 8.78 (d, J = 7.6 Hz, 1H), 8.50 (d, J = 6.8 Hz, 1H), 8.33 (d, J = 4.8 Hz, 1H), 7.92 (d, J = 6.6 Hz, 1H), 7.73 (d, J = 8.5 Hz, 1H), 7.41 (d, J = 4.8 Hz, 1H), 7.18-7.08 (m, 1H), 4.65 (s, 1H), 3.71-3.63 (m, 1H), 3.53-3.38 (m, 1H), 3.08 (dd, J = 13.4, 4.2 Hz, 2H), 2.28 (dd, J = 7.2, 4.8 Hz, 2H), 2.27-2.09 (m, 1H), 2.05-1.83 (m, 2H), 1.65-1.49 (m, 1H), 1.48-1.39 (m, 1H), 1.06-0.87 (m, 4H). | Example 29 |
| 151 | N-(2,3-difluoro-4-((3-(2-(((S)-piperidin-3-yl)amino)pyrimidin-4- | 493.2 | (400 MHz, CD₃OD) δ 8.77 (s, 1H), 8.50 (d, J = 6.8 Hz, 1H), 8.33 (dd, J = 4.8, 2.0 Hz, 1H), 7.92 (s, 1H), 7.79-7.68 (m, | Example 29 |

TABLE A1-continued

| Cpd No. | Name | MS m/z | ¹H NMR (ppm) | Synth. Method |
|---|---|---|---|---|
| | yl)pyridin-2-yl)oxy)phenyl)spiro[2.2]pentane-1-carboxamide hydrochloride | | 1H), 7.41 (dd, J = 7.6, 4.8 Hz, 1H), 7.19-7.10 (m, 1H), 4.64 (s, 1H), 3.71-3.63 (m, 1H), 3.44-3.36 (m, 1H), 3.19-3.05 (m, 2H), 2.29-2.20 (m, 2H), 2.16-2.08 (m, 1H), 2.05-1.85 (m, 2H), 1.59-1.54 (m, 1H), 1.45 (dd, J = 7.2, 3.6 Hz, 1H), 1.06-0.87 (m, 4H). | |
| 152 | (S)-N-(2,6-difluoro-4-((3-(2-(piperidin-3-ylamino)pyrimidin-4-yl)pyridin-2-yl)oxy)phenyl)-1-phenylmethanesulfonamide hydrochloride | 553.2 | (400 MHz, CD₃OD) δ 8.77 (s, 1H), 8.49 (d, J = 6.4 Hz, 1H), 8.42-8.40 (m, 1H), 7.86 (s, 1H), 7.53-7.36 (m, 6H), 7.11-7.04 (m, 2H), 4.63 (s, 1H), 4.52 (s, 2H), 3.68-3.61 (m, 1H), 3.41-3.37 (m, 1H), 3.11 (m, 2H), 2.29-2.09 (m, 2H), 1.93 (m, 2H). | Example 27 |
| 153 | (S)-1-phenyl-N-(2,3,6-trifluoro-4-((3-(2-(piperidin-3-ylamino)pyrimidin-4-yl)pyridin-2-yl)oxy)phenyl)methanesulfonamide hydrochloride | 571.2 | (400 MHz, CD₃OD) δ 8.78 (s, 1H), 8.51 (d, J = 6.5 Hz, 1H), 8.42-8.35 (m, 1H), 7.87 (s, 1H), 7.54-7.37 (m, 6H), 7.31-7.24 (m, 1H), 4.62 (s, 1H), 4.56 (s, 2H), 3.71-3.62 (m, 1H), 3.44-3.37 (m, 1H), 3.18-3.05 (m, 2H), 2.32-2.22 (m, 1H), 2.19-2.11 (m, 1H), 2.06-1.84 (m, 2H). | Example 30 |
| 154 | (S)-N-(2,6-difluoro-3-methyl-4-(3-(2-(piperidin-3-ylamino)pyrimidin-4-yl)pyridin-2-yloxy)phenyl)(phenyl)methanesulfonamide hydrochloride | 567.2 | (300 MHz, CD₃OD) δ 8.81 (d, J = 7.8 Hz, 1H), 8.51 (d, J = 6.6 Hz, 1H), 8.37 (dd, J = 4.8, 1.9 Hz, 1H), 7.92 (d, J = 6.6 Hz, 1H), 7.53-7.50 (m, 2H), 7.47-7.31 (m, 4H), 7.01 (dd, J = 10.2, 2.1 Hz, 1H), 4.64 (s, 1H), 4.54 (s, 2H), 3.78-3.59 (m, 1H), 3.43-3.39 (m, 1H), 3.17-3.06 (m, 2H), 2.39-2.11 (m, 2H), 2.09 (s, 3H), 2.05-1.77 (m, 2H). | Example 27 |
| 155 | (S)-N-(2,3-difluoro-5-methyl-4-((3-(2-(piperidin-3-ylamino)pyrimidin-4-yl)pyridin-2-yl)oxy)phenyl)-1-phenylmethanesulfonamide | 567.2 | (400 MHz, CD₃OD) δ 8.57 (d, J = 7.2 Hz, 1H), 8.39 (d, J = 5.2 Hz, 1H), 8.15 (dd, J = 4.9, 1.9 Hz, 1H), 7.47-7.38 (m, 3H), 7.39-7.32 (m, 3H), 7.28 (dd, J = 7.6, 4.8 Hz, 1H), 7.05 (dd, J = 8.1, 1.8 Hz, 1H), 4.47 (s, 2H), 4.26-4.08 (m, 1H), 3.40 (dd, J = 12.0, 3.9 Hz, 1H), 3.12-3.07 (m, 1H), 2.86-2.66 (m, 2H), 2.25-2.10 (m, 1H), 2.08 (s, 3H), 1.96-1.91 (m, 1H), 1.83-1.57 (m, 2H). | Example 27 |
| 156 | (S)-1-phenyl-N-(2,3,5-trifluoro-4-((3-(2-(piperidin-3-ylamino)pyrimidin-4-yl)pyridin-2-yl)oxy)phenyl)methanesulfonamide hydrochloride | 571.2 | (400 MHz, CD₃OD) 8.66 (d, J = 7.7 Hz, 1H), 8.48 (d, J = 5.9 Hz, 1H), 8.31 (d, J = 3.8 Hz, 1H), 7.65 (s, 1H), 7.45-7.33 (m, 6H), 7.13-7.04 (m, 2H), 4.57 (s, 2H), 4.48 (s, 1H), 3.70-3.62 (m, 1H), 3.38 (d, J = 12.6 Hz, 1H), 3.07 (t, J = 11.2 Hz, 2H), 2.23 (d, J = 12.3 Hz, 1H), 2.13-2.11 (m, 1H), 1.91-1.80 (m, 2H). | Example 30 |
| 157 | (S)-N-(3-methyl-4-((3-(2-(piperidin-3-ylamino)pyrimidin-4-yl)pyridin-2-yl)oxy)phenyl)-1-phenylmethanesulfonamide | 531.1 | (400 MHz, CD₃OD) δ 8.57 (d, J = 7.2 Hz, 1H), 8.36 (d, J = 5.2 Hz, 1H), 8.15 (d, J = 2.0 Hz, 1H), 7.43-7.39 (d, J = 5.2 Hz, 1H), 7.37 (m, 5H), 7.25 (d, J = 7.6, 1H), 7.12 (d, J = 7.2 Hz, 2H), 7.05-6.99 (m, 1H), 4.43 (s, 2H), 4.09 (s, 1H), 3.32 (d, J = 12.4 Hz, 1H), 3.02 (d, J = 12.4 Hz, 1H), 2.74-2.57 (m, 2H), 2.13-2.05 (m, 4H), 1.86 (d, J = 12.0 Hz, 1H), 1.67 (s, 1H), 1.66-1.57 (m, 1H). | Example 27 |
| 158 | (S)-N-(2-fluoro-5-methyl-4-(3-(2-(piperidin-3-ylamino)pyrimidin-4-yl)pyridin-2-yloxy)phenyl)(phenyl)methanesulfonamide | 549.2 | (400 MHz, CD₃OD) δ 8.56 (d, J = 12 Hz, 1H), 8.35 (d, J = 8 Hz, 1H), 8.18-8.16 (m, 1H), 7.44-7.40 (m, 2H), 7.38-7.33 (m, 4H), 7.29-7.24 (m, 2H), 6.95 (d, J = 10.9 Hz, 1H), 4.45 (s, 2H), 4.06 (s, 1H), 3.29 (d, J = 4.0 Hz, 1H), 2.98 (d, J = 12.8 Hz, 1H), 2.69-2.53 (m, 2H), 2.12-2.05 (m, 5H), 1.87-1.80 (m, 1H), 1.71-1.52 (m, 1H). | Example 27 |
| 159 | (S)-N-(3-fluoro-4-((3-(2-(piperidin-3-ylamino)pyrimidin-4-yl)pyridin-2-yl)oxy)phenyl)-1-phenylmethanesulfonamide | 535.2 | (400 MHz, CD₃OD) δ 8.55 (d, J = 7.5 Hz, 1H), 8.35 (d, J = 5.2 Hz, 1H), 8.16 (dd, J = 4.9, 2.0 Hz, 1H), 7.38-7.34 (m, 6H), 7.32-6.98(m, 4H), 4.44 (s, 2H), 4.05 (s, 1H), 3.35-3.28 (m, 1H), 2.99-2.95 (m, 1H), 2.67-2.52 (m, 2H), 2.12 (d, J = 11.4 Hz, 1H), 1.82-1.59 (m, 3H). | Example 27 |
| 160 | (S)-N-(2,3-difluoro-6-methyl-4-((3-(2-(piperidin-3-ylamino)pyrimidin-4- | 567.2 | (300 MHz, CD₃OD) δ 8.58 (dd, J = 7.6, 1.9 Hz, 1H), 8.38 (d, J = 5.2 Hz, 1H), 8.15 (dd, J = 4.9, 1.9 Hz, 1H), 7.51-7.20 | Example 27 |

TABLE A1-continued

| Cpd No. | Name | MS m/z | $^1$H NMR (ppm) | Synth. Method |
|---|---|---|---|---|
| | yl)pyridin-2-yl)oxy)phenyl)-1-phenylmethanesulfonamide | | (m, 7H), 7.06 (dd, J = 8.1, 2.2 Hz, 1H), 4.45 (s, 2H), 4.21-4.06 (m, 1H), 3.39-3.35 (m, 1H), 3.15-2.98 (m, 1H), 2.86-2.55 (m, 2H), 2.24-1.99 (m, 4H), 1.99-1.83 (m, 1H), 1.81-1.54 (m, 2H). | |
| 161 | (S)-N-(2-chloro-3-fluoro-4-((3-(2-(piperidin-3-ylamino)pyrimidin-4-yl)pyridin-2-yl)oxy)phenyl)-1-phenylmethanesulfonamide | 569.1 | (400 MHz, DMSO-d$_6$) 8.60-8.42 (brs, 2H), 8.22 (dd, J = 4.8, 2.0 Hz, 1H), 8.07 (br, 1H), 7.41-7.16 (m, 9H), 7.02 (t, J = 9.1 Hz, 1H), 4.11 (s, 3H), 3.34 (d, J = 12.0 Hz, 2H), 3.10 (d, J = 12.7 Hz, 1H), 2.84-2.62 (m, 2H), 1.97 (d, J = 11.6 Hz, 1H), 1.85 (d, J = 12.8 Hz, 1H), 1.71-1.52 (m, 2H). | Example 34 |
| 162 | N-(2,3-difluoro-4-((3-(2-(((3S,5R)-5-fluoro-5-methylpiperidin-3-yl)amino)pyrimidin-4-yl)pyridin-2-yl)oxy)phenyl)-1-phenylmethanesulfonamide | 585.2 | (300 MHz, CD$_3$OD) δ 8.51 (d, J = 7.5 Hz, 1H), 8.38 (d, J = 5.2 Hz, 1H), 8.19 (dd, J = 4.9, 1.9 Hz, 1H), 7.52-7.21 (m, 8H), 7.14-6.94 (m, 1H), 4.50 (s, 2H), 4.27 (s, 1H), 3.10-2.71 (m, 4H), 2.18-2.00 (m, 2H), 1.40 (d, J = 21.9 Hz, 3H). | Example 42 |
| 163 | (S)-N-(2-cyano-3-fluoro-4-((3-(2-(piperidin-3-ylamino)pyrimidin-4-yl)pyridin-2-yl)oxy)phenyl)-1-phenylmethanesulfonamide hydrochloride | 560.2 | (300 MHz, CD$_3$OD) 8.73 (d, J = 7.7 Hz, 1H), 8.48 (d, J = 6.5 Hz, 1H), 8.33 (dd, J = 4.8, 1.8 Hz, 1H), 7.83 (d, J = 6.5 Hz, 1H), 7.55 (t, J = 8.8 Hz, 1H), 7.51-7.32 (m, 6H), 7.25 (dd, J = 9.1, 1.6 Hz, 1H), 4.61 (s, 3H), 3.66 (d, J = 12.3 Hz, 1H), 3.44-3.31 (m, 1H), 3.16-3.00 (m, 2H), 2.26-2.11 (m, 2H), 1.97-1.87 (m, 2H). | Example 27 |
| 164 | N-(2,6-difluoro-3-methyl-4-((3-(2-(((3S,5R)-5-methyl-3-piperidyl)amino)pyrimidin-4-yl)-2-pyridyl)oxy)phenyl)-1-phenyl-methanesulfonamide | 581.2 | (400 MHz, CD$_3$OD) δ 8.54 (d, J = 7.6 Hz, 1H), 8.35 (d, J = 5.2 Hz, 1H), 8.20 (dd, J = 4.9, 1.9 Hz, 1H), 7.50 (dd, J = 7.4, 2.1 Hz, 2H), 7.45-7.24 (m, 5H), 6.87 (d, J = 10.3, 1.9 Hz, 1H), 4.48 (s, 2H), 4.11-4.01 (m, 1H), 3.40-3.36 (m, 1H), 3.01 (d, J = 13.6 Hz, 1H), 2.36 (t, J = 11.5 Hz, 1H), 2.28-2.11 (m, 2H), 2.07 (s, 3H), 1.84-1.73 (m, 1H), 1.20-1.11 (m, 1H), 0.95 (d, J = 6.6 Hz, 3H). | Example 36 |
| 165 | 1-phenyl-N-(2,3,6-trifluoro-4-((3-(2-(((3S,5R)-5-methyl-3-piperidyl)amino)pyrimidin-4-yl)-2-pyridyl)oxy)phenyl)methane sulfonamide | 585.2 | (300 MHz, CD$_3$OD) δ 8.52 (d, J = 8.2 Hz, 1H), 8.37 (d, J = 5.2 Hz, 1H), 8.20 (dd, J = 4.8, 1.9 Hz, 1H), 7.50 (dd, J = 7.5, 2.1 Hz, 2H), 7.41-7.26 (m, 5H), 7.07-6.97 (m, 1H), 4.41 (s, 2H), 4.15 (s, 1H), 3.50 (d, J = 9.1 Hz, 1H), 3.10 (d, J = 10.4 Hz, 1H), 2.45 (t, J = 11.6 Hz, 1H), 2.31 (t, J = 12.1 Hz, 1H), 2.17 (d, J = 12.9 Hz, 1H), 1.85 (s, 1H), 1.23 (q, J = 12.1 Hz, 1H), 1.00 (d, J = 6.6 Hz, 3H). | Example 36 |
| 166 | (S)-1-(4-cyanophenyl)-N-(2,3-difluoro-4-((3-(2-(piperidin-3-ylamino)pyrimidin-4-yl)pyridin-2-yl)oxy)phenyl)methanesulfonamide | 578.2 | (400 MHz, DMSO-d$_6$) δ 8.71-8.30 (m, 3H), 8.24 (d, J = 6.4 Hz, 1H), 7.83 (d, J = 8.0 Hz, 2H), 7.57 (d, J = 8.0 Hz, 2H), 7.47-7.53(m, 1H), 7.37-7.32 (m, 2H), 7.23-7.18 (m, 1H), 7.11-7.06 (m, 1H), 4.54(s, 2H), 4.22-4.11 (m, 1H), 3.43-3.40 (m, 1H), 3.32-3.31 (m, 1H), 3.21-3.17 (m, 1H), 2.88-2.78 (m, 2H), 2.07-1.88 (m, 2H), 1.72-1.59 (m, 2H). | Example 27 |
| 167 | (S)-N-(2,3-difluoro-4-((3-(2-(pyrrolidin-3-ylamino)pyrimidin-4-yl)pyridin-2-yl)oxy)phenyl)-1-phenylmethanesulfonamide | 539.2 | (400 MHz, DMSO-d$_6$) δ 8.45-8.42 (m, 2H), 8.23 (dd, J = 4.8, 2.0 Hz, 1H), 7.55 (d, J = 6.0 Hz, 1H), 7.35-7.24 (m, 7H), 7.18 (t, J = 8.9 Hz, 1H), 6.90 (t, J = 8.7 Hz, 1H), 4.47 (d, J = 5.6 Hz, 1H), 4.13 (s, 2H), 3.33-3.19 (m, 2H), 3.15-3.02 (m, 2H), 2.19-2.10 (m, 1H), 1.98-1.90 (m, 1H) | Example 37 |
| 168 | N-(2,3-difluoro-4-((3-(2-((1-methylpiperidin-4-yl)amino)pyrimidin-4-yl)pyridin-2-yl)oxy)phenyl)-1-phenylmethanesulfonamide | 567.2 | (400 MHz, DMSO-d$_6$) δ 9.80 (s, 1H), 8.39 (d, J = 5.1 Hz, 2H), 8.23 (dd, J = 4.8, 1.9 Hz, 1H), 7.40-7.31 (m, 6H), 7.27-7.09 (m, 4H), 4.45 (s, 2H), 3.81 (s, 1H), 2.87 (d, J = 11.3 Hz, 2H), 2.27 (s, 3H), 2.18 (t, J = 11.7 Hz, 2H), 1.92 (d, J = 12.4 Hz, 2H), 1.64-1.54 (m, 2H). | Example 37 |
| 169 | N-(4-((3-(2-(((1r,4r)-4-aminocyclohexyl)amino)pyrimidin-4-yl)pyridin-2-yl)oxy)-2,3-difluorophenyl)-1-phenylmethanesulfonamide | 567.2 | (400 MHz, DMSO-d$_6$) δ 8.39-8.26 (m, 2H), 8.21 (d, J = 4.0 Hz, 1H), 7.48 (s, 2H), 7.29-7.08 (m, 10H), 6.84-6.80 (m, 1H), 4.04 (s, 2H), 3.72 (s, 1H), 2.93 (s, 1H), 1.98-1.80 (m, 4H), 1.38-1.19 (m, 4H). | Example 38 |

TABLE A1-continued

| Cpd No. | Name | MS m/z | ¹H NMR (ppm) | Synth. Method |
|---|---|---|---|---|
| 170 | (S)-N-(2,3-difluoro-4-((3-(2-((1-methylpiperidin-3-yl)amino)pyrimidin-4-yl)pyridin-2-yl)oxy)phenyl)-1-phenylmethanesulfonamide | 567.2 | (300 MHz, CD₃OD) δ 8.61-8.55 (m, 1H), 8.37-8.35 (m, 1H), 8.20-8.17 (m, 1H), 7.44-7.23 (m, 8H), 7.06-6.99 (m, 1H), 4.50 (s, 2H), 4.26-4.15 (m, 1H), 3.16-3.10 (m, 1H), 2.82-2.70 (m, 1H), 2.35 (s, 3H), 2.20-1.99 (m, 3H), 1.85-1.76 (m, 2H), 1.53-1.36 (m, 1H). | Example 38 |
| 171 | N-(4-((3-(2-((2-aminoethyl)amino)pyrimidin-4-yl)pyridin-2-yl)oxy)-2,3-difluorophenyl)-1-phenylmethanesulfonamide | 513.2 | (400 MHz, DMSO-d₆) δ 8.56-8.43 (m, 2H), 8.32-8.31 (m, 1H), 7.64-7.55 (m, 1H), 7.45-7.37 (m, 6H), 7.25-7.17 (m, 2H), 4.56 (s, 2H), 3.82-3.61 (m, 2H), 3.15-3.08 (m, 2H). | Example 38 |
| 172 | N-(2,3-difluoro-4-((3-(2-(2-(methylamino)ethylamino)pyrimidin-4-yl)-2-pyridyloxy)phenyl)-1-phenyl-methanesulfonamide | 527.1 | (400 MHz, CD₃OD) δ 8.53-8.51 (m, 1H), 8.36 (d, J = 5.6 Hz, 1H), 8.18-8.16 (m, 1H), 7.41-7.40 (m, 3H), 7.39-7.31(m, 3H), 7.28-7.20 (m, 2H), 6.92-6.88 (m, 1H), 4.40 (s, 2H), 3.72-3.61 (m, 2H), 3.04 (t, J = 6.0 Hz, 2H), 2.49 (s, 3H). | Example 38 |
| 173 | (S)-1-cyclobutyl-N-(2,3-difluoro-4-((3-(2-(piperidin-3-ylamino)pyrimidin-4-yl)pyridin-2-yl)oxy)phenyl)methanesulfonamide | 531.2 | (400 MHz, CD₃OD) δ 8.55 (d, J = 7.8 Hz, 1H), 8.36 (d, J = 7.8 Hz, 1H), 8.18 (d, J = 7.8 Hz, 1H), 7.39-7.28(m, 3H), 7.10-7.06 (m, 1H), 4.12-4.03 (m, 1H), 3.38-3.34 (m, 1H), 3.26 (d, J = 6.6 Hz, 2H), 3.05-3.02 (m, 1H), 2.95-2.85 (m, 1H), 2.72-2.60 (m, 2H), 2.24-1.64 (m, 10H). | Example 27 |
| 174 | N-(2,3-difluoro-4-((3-(2-(((3S,5S)-5-fluoro-5-methylpiperidin-3-yl)amino)pyrimidin-4-yl)pyridin-2-yl)oxy)phenyl)-1-phenylmethanesulfonamide | 585.2 | (400 MHz, CD₃OD) δ 8.55 (d, J = 7.6 Hz, 1H), 8.36 (d, J = 5.2 Hz, 1H), 8.19 (dd, J = 4.9, 1.9 Hz, 1H), 7.44-7.34 (m, 6H), 7.32-7.23 (m, 2H), 7.06-7.00 (m, 1H), 4.50 (s, 2H), 4.35 (s, 1H), 3.36 (s, 1H), 3.01 (m, 1H), 2.62 (dd, J = 34.8, 14.1 Hz, 1H), 2.41-2.34 (m, 2H), 1.74-1.56 (m, 1H), 1.36 (d, J = 20.9 Hz, 3H). | Example 42 |
| 175 | (S)-N-(6-fluoro-2,3-dimethyl-4-((3-(2-(piperidin-3-ylamino)pyrimidin-4-yl)pyridin-2-yl)oxy)phenyl)-1-phenylmethanesulfonamide | 563.3 | (400 MHz, CD₃OD) δ 8.56 (d, J = 7.4 Hz, 1H), 8.35 (d, J = 5.2 Hz, 1H), 8.16 (dd, J = 4.9, 2.0 Hz, 1H), 7.47 (dd, J = 7.1, 2.6 Hz, 2H), 7.40-7.36 (m, 4H), 7.28 (dd, J = 7.6, 4.9 Hz, 1H), 6.89 (d, J = 10.4 Hz, 1H), 4.46 (s, 2H), 4.05 (s, 1H), 3.32-3.27 (m, 1H), 2.97 (d, J = 12.6 Hz, 1H), 2.65-2.52 (m, 2H), 2.39 (s, 3H), 2.11 (s, 1H), 2.09 (s, 3H), 1.81-1.80 (m, 1H), 1.66-1.55 (m, 2H). | Example 27 |
| 176 | 1-phenyl-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 589.2 | (400 MHz, CD₃OD) 8.58 (d, J = 7.0 Hz, 1H), 8.22 (dd, J = 4.9, 1.9 Hz, 1H), 7.52 (d, J = 2.4 Hz, 1H), 7.53-7.50 (m, 2H), 7.43-7.33 (m, 5H), 7.21-7.16 (m, 1H), 4.98-4.87 (m, 1H), 4.52 (s, 2H), 4.47-4.35 (m, 1H), 3.37 (s, 1H), 3.19 (t, J = 13.3 Hz, 1H), 2.85 (dd, J = 37.2, 14.1 Hz, 1H), 2.62-2.51 (m, 1H), 2.49-2.36 (m, 1H), 1.94-1.74 (m, 1H). | Example 40 |
| 177 | N-(2,3-difluoro-5-methyl-4-((3-(2-(((3S,5R)-5-methyl-3-piperidyl)amino)pyrimidin-4-yl)-2-pyridyl)oxy)phenyl)-1-phenyl-methanesulfonamide | 581.2 | (400 MHz, CD₃OD) δ 8.56 (d, J = 8.0 Hz, 1H), 8.38 (d, J = 5.2 Hz, 1H), 8.16-8.14 (m, 1H), 7.46-7.35 (m, 6H), 7.29-7.28 (m, 1H), 7.04 (d, J = 8.1 Hz, 1H), 4.46 (s, 2H), 4.11-4.05 (m, 1H), 3.41-3.35 (m, 1H), 3.04-3.01 (m, 1H), 2.38-2.35 (m, 1H), 2.28-2.16 (m, 2H), 2.09 (s, 3H), 1.85-1.70 (m, 1H), 1.23-1.14 (m, 1H), 0.97 (d, J = 6.4 Hz, 3H). | Example 36 |
| 178 | N-(2,3-difluoro-4-((3-(2-(((3S,5S)-5-fluoro-3-piperidyl)amino)pyrimidin-4-yl)-2-pyridyl)oxy)-5-methyl-phenyl)-1-phenyl-methanesulfonamide | 585.2 | (400 MHz, CD₃OD) δ 8.60 (d, J = 8.0 Hz, 1H), 8.38 (d, J = 5.2 Hz, 1H), 8.16-8.14 (m, 1H), 7.46-7.35 (m, 6H), 7.31-7.28 (m, 1H), 7.04 (d, J = 8.1 Hz, 1H), 4.95-4.80 (m, 1H), 4.51 (s, 2H), 4.40-4.37 (m, 1H), 3.36-3.35 (m, 1H), 3.17-3.10 (m, 1H), 2.87-2.74 (m, 1H), 2.56-2.35 (m, 2H), 2.09 (s, 3H), 1.89-1.79 (m, 1H). | Example 40 |
| 179 | N-(2,6-difluoro-4-((3-(2-(((3S,5S)-5-fluoro-3-piperidyl)amino)pyrimidin- | 585.2 | (400 MHz, CD₃OD) δ 8.57 (d, J = 7.5 Hz, 1H), 8.37 (d, J = 5.2 Hz, 1H), 8.20 (dd, J = 4.9, 2.0 Hz, 1H), 7.50 (dd, J = 7.3, 2.4 | Example 40 |

TABLE A1-continued

| Cpd No. | Name | MS m/z | ¹H NMR (ppm) | Synth. Method |
|---|---|---|---|---|
| | 4-yl)-2-pyridyl)oxy)-3-methyl-phenyl)-1-phenyl-methanesulfonamide | | Hz, 2H), 7.43-7.30 (m, 5H), 6.91 (dd, J = 10.4, 2.0 Hz, 1H), 4.95-4.80 (m, 1H), 4.51 (s, 2H), 4.37 (s, 1H), 3.28 (s, 1H), 3.13 (t, J = 12.6 Hz, 1H), 2.79 (dd, J = 36.4, 14.0 Hz, 1H), 2.52 (t, J = 11.5 Hz, 1H), 2.45-2.32 (m, 1H), 2.08 (d, J = 1.8 Hz, 3H), 1.90-1.75 (m, 1H). | |
| 180 | N-(2,3-difluoro-4-((3-(2-(4-piperidylamino)pyrimidin-4-yl)-2-pyridyl)oxy)phenyl)-1-phenyl-methanesulfonamide | 553.2 | (400 MHz, DMSO-d₆) δ 8.41-8.38 (m, 2H), 8.22 (dd, J = 4.8, 1.9 Hz, 1H), 7.43 (d, J = 7.4 Hz, 1H), 7.32-7.23 (m, 7H), 7.17 (td, J = 9.0, 2.2 Hz, 1H), 6.88 (td, J = 9.0, 2.1 Hz, 1H), 4.12 (s, 2H), 4.02-4.00 (m, 1H), 3.21-3.17 (m, 2H), 2.88 (td, J = 12.3, 3.0 Hz, 2H), 2.02 (d, J = 13.1 Hz, 2H), 1.68-1.58 (m, 2H). | Example 38 |
| 181 | (S)-N-(2,3-difluoro-4-((3-(2-((6-oxopiperidin-3-yl)amino)pyrimidin-4-yl)pyridin-2-yl)oxy)phenyl)-1-phenylmethanesulfonamide | 567.2 | (400 MHz, CD₃OD) δ 8.56 (d, J = 7.6 Hz, 1H), 8.39 (d, J = 7.6 Hz, 1H), 8.18 (d, J = 7.6 Hz, 1H), 7.43-7.23(m, 8H), 7.05-7.02 (m, 1H), 4.51 (s, 2H), 4.42-4.39 (m, 1H), 3.68-3.64 (m, 1H), 3.30-3.27 (m, 1H), 2.58-2.43 (m, 2H), 2.22-2.12 (m, 1H), 2.11-1.97 (m, 1H). | Example 38 |
| 182 | N-(2,3-difluoro-4-((3-(2-(((1r,4r)-4-hydroxycyclohexyl)amino)pyrimidin-4-yl)pyridin-2-yl)oxy)phenyl)-1-phenylmethanesulfonamide | 568.1 | (300 MHz, DMSO-d₆) 9.94 (s, 1H), 8.38 (d, J = 5.2 Hz, 2H), 8.28-8.18 (m, 1H), 7.45-7.33 (m, 6H), 7.24-7.12 (m, 4H), 4.54 (d, J = 5.4 Hz, 3H), 3.74 (s, 1H), 3.42 (s, 1H), 1.96-1.80 (m, 4H), 1.34-1.24 (m, 4H). | Example 38 |
| 183 | (S)-N-(4-((3-(2-((5,5-difluoropiperidin-3-yl)amino)pyrimidin-4-yl)pyridin-2-yl)oxy)-2,3-difluorophenyl)-1-phenylmethanesulfonamide | 589.1 | (400 MHz, DMSO-d₆) δ 8.41 (s, 2H), 8.24 (s, 1H), 7.41-7.16 (m, 10H), 4.55 (s, 2H), 4.13-4.00 (m, 1H), 3.10-3.00 (m, 2H), 2.81-2.68 (m, 1H), 2.45-2.32 (m, 2H), 2.07-1.96 (m, 1H). | Example 38 |
| 184 | N-(4-((3-(2-((2-(dimethylamino)ethyl)amino)pyrimidin-4-yl)pyridin-2-yl)oxy)-2,3-difluorophenyl)-1-phenylmethanesulfonamide | 541.3 | (400 MHz, DMSO-d₆) δ 9.84 (s, 1H), 8.45 (s, 1H), 8.40 (d, J = 5.2 Hz, 1H), 8.23 (d, J = 6.8, 1H), 7.42-7.35 (m, 6H), 7.26 (d, J = 4.8 Hz, 1H), 7.23-7.12 (m, 3H), 4.48 (s, 2H), 3.48 (d, J = 6.4 Hz, 2H), 2.57 (d, J = 6.8 Hz, 2H), 2.28 (s, 6H). | Example 38 |
| 185 | N-(4-((3-(2-(3-azabicyclo[3.1.0]hexan-5-ylamino)pyrimidin-4-yl)-2-pyridyl)oxy)-2,3-difluoro-phenyl)-1-phenyl-methanesulfonamide; Isomer 1 | 551.2 | (300 MHz, CD₃OD) δ 8.56 (d, J = 7.0 Hz, 1H), 8.39 (d, J = 5.2 Hz, 1H), 8.18 (dd, J = 4.9, 1.9 Hz, 1H), 7.44-7.24 (m, 8H), 7.02-7.00 (m, 1H), 4.48 (s, 2H), 3.38 (dd, J = 11.4, 3.7 Hz, 1H), 3.31-3.23 (m, 2H), 3.02 (d, J = 11.4 Hz, 1H), 1.76-1.74 (m, 1H), 1.12-1.10 (m, 1H), 1.04 (t, J = 5.5 Hz, 1H). | Example 41 |
| 186 | N-(4-((3-(2-(3-azabicyclo[3.1.0]hexan-5-ylamino)pyrimidin-4-yl)-2-pyridyl)oxy)-2,3-difluoro-phenyl)-1-phenyl-methanesulfonamide; Isomer 2 | 551.2 | (300 MHz, CD₃OD) δ 8.56 (d, J = 7.0 Hz, 1H), 8.39 (d, J = 5.2 Hz, 1H), 8.18 (dd, J = 4.9, 1.9 Hz, 1H), 7.44-7.24 (m, 8H), 7.02-7.00 (m, 1H), 4.48 (s, 2H), 3.38 (dd, J = 11.4, 3.7 Hz, 1H), 3.31-3.23 (m, 2H), 3.02 (d, J = 11.4 Hz, 1H), 1.76-1.74 (m, 1H), 1.12-1.10 (m, 1H), 1.04 (t, J = 5.5 Hz, 1H). | Example 41 |
| 187 | (S)-1-(2-cyanophenyl)-N-(2,3-difluoro-4-((3-(2-(piperidin-3-ylamino)pyrimidin-4-yl)pyridin-2-yl)oxy)phenyl)methanesulfonamide | 578.2 | (300 MHz, CF₃COOD) δ 9.27 (d, J = 7.2 Hz, 1H), 8.72 (d, J = 6.6 Hz, 1H), 8.57 (d, J = 5.1 Hz, 1H), 7.97-7.90 (m, 2H), 7.87-7.82 (m, 3H), 7.78-7.67 (m, 2H), 7.49 (t, J = 8.1 Hz, 1H), 4.94 (d, J = 8.7 Hz, 3H), 3.92 (d, J = 12.0 Hz, 1H), 3.66 (d, J = 11.7 Hz, 1H), 3.57-3.53 (m, 1H), 3.41-3.38 (m, 1H), 2.44-2.40 (m, 1H), 2.29 (s, 1H), 2.20-2.07 (m, 2H). | Example 27 |
| 188 | (S)-N-(2,3-difluoro-4-((3-(2-(piperidin-3-ylamino)pyrimidin-4-yl)pyridin-2-yl)oxy)phenyl)-1-(1-fluorocyclopropyl)methanesulfonamide | 535.2 | (400 MHz, DMSO-d₆) δ 8.41 (d, J = 5.1 Hz, 2H), 8.22 (dd, J = 4.8, 1.9 Hz, 1H), 7.85 (brs, 1H), 7.33-7.28 (m, 3H), 7.18 (t, J = 8.8 Hz, 1H), 6.94 (t, J = 8.9 Hz, 1H), 4.05 (s, 1H), 3.47 (d, J = 20.9 Hz, 2H), 3.33-3.26 (m, 1H), 3.02 (s, 1H), 2.66 (d, J = 10.6 Hz, 1H), 1.96 (s, 1H), 1.79 (s, 1H), 1.57 (d, J = 9.2 Hz, 2H), 1.12-0.79 (m, 4H). | Example 27 |
| 189 | 2,2-difluoro-N-(2,3,6-trifluoro-4-((3-(2-(((3S,5S)-5-fluoro-3- | 591.1 | (300 MHz, CD₃OD) δ 8.77 (s, 1H), 8.53 (d, J = 6.3 Hz, 1H), 8.37 (d, J = 4.8 Hz, 1H), 7.90 (s, 1H), 7.49-7.42 (m, 1H), | Example 40 |

TABLE A1-continued

| Cpd No. | Name | MS m/z | ¹H NMR (ppm) | Synth. Method |
|---|---|---|---|---|
| | piperidyl)amino)pyrimidin-4-yl)-2-pyridyl)oxy)phenyl)butane-1-sulfonamide | | 7.35-7.24 (m, 1H), 5.43-5.18 (m, 1H), 3.99-3.86 (m, 2H), 3.81-3.63 (m, 2H), 3.52-3.41 (m, 1H), 3.31-3.28 (m, 1H), 3.15 (s, 1H), 2.64 (s, 1H), 2.29-1.96 (m, 3H), 1.12-1.03 (m, 3H). | |
| 190 | 1-phenyl-N-(2,3,6-trifluoro-4-((3-(2-(((3S,5S)-5-fluoro-5-methyl-3-piperidyl)amino)pyrimidin-4-yl)-2-pyridyl)oxy)phenyl)methane sulfonamide | 603.1 | (300 MHz, CD₃OD) δ 8.69 (s, 1H), 8.50-8.48 (m, 1H), 8.33 (s, 1H), 7.71 (s, 1H), 7.56-7.48 (m, 2H), 7.48-7.37 (m, 4H), 7.29-7.18 (m, 1H), 4.88 (s, 2H), 3.79-3.67 (m, 1H), 3.61-3.47 (m, 1H), 3.41-3.37 (m, 1H), 3.29-3.15(m, 1H), 3.03-2.89 (m, 1H), 2.55-2.43 (m, 1H), 2.15-1.88 (m, 1H), 2.51-2.48 (m, 3H). | Example 42 |
| 191 | 1-(4-cyanophenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 614.1 | (300 MHz, CD₃OD) δ 8.72 (s, 1H), 8.51 (d, J = 6.6 Hz, 1H), 8.36 (s, 1H), 7.84-7.67 (m, 5H), 7.45 (d, J = 5.7 Hz, 1H), 7.32-7.23 (m, 1H), 5.45-5.09 (m, 1H), 4.68 (s, 2H), 3.78-3.64 (m, 2H), 3.41-3.36 (m, 1H), 3.31-3.28 (m, 1H), 3.21-3.02 (m, 1H), 2.19 (s, 1H), 2.05 (s, 1H). | Example 40 |
| 192 | N-(2,3-difluoro-4-((3-(2-(((S)-piperidin-3-yl)amino)pyrimidin-4-yl)pyridin-2-yl)oxy)phenyl)-1-(2,2-difluorocyclobutyl)methanesulfonamide hydrochloride | 567.2 | (400 MHz, CD₃OD) δ 8.72 (s, 1H), 8.49 (d, J = 6.2 Hz, 1H), 8.32 (s, 1H), 7.80 (s, 1H), 7.45-7.39 (m, 2H), 7.19 (t, J = 8.8 Hz, 1H), 4.56 (s, 1H), 3.69-3.65 (m, 1H), 3.55-3.52 (m, 1H), 3.38-3.34 (m, 3H), 3.13-3.09 (m, 2H), 2.61-2.47 (m, 2H), 2.27-2.13 (m, 3H), 1.98-1.69 (m, 3H). | Example 27 |
| 193 | 1-phenyl-N-(2,3,6-trifluoro-4-((3-(2-(((3R,5R)-5-fluoro-3-piperidyl)amino)pyrimidin-4-yl)-2-pyridyl)oxy)phenyl)methane sulfonamide | 589.2 | (400 MHz, CD₃OD) δ 8.74 (d, J = 7.6 Hz, 1H), 8.52 (d, J = 6.3 Hz, 1H), 8.37 (d, J = 4.2 Hz, 1H), 7.85 (s, 1H), 7.54-7.40 (m, 6H), 7.31-7.24 (m, 1H), 5.31 (d, J = 44.8 Hz, 1H), 4.56 (s, 2H), 3.77-3.66 (m, 2H), 3.47-3.42 (m, 1H), 3.35-3.31 (m, 1H), 3.13 (t, J = 11.8 Hz, 1H), 2.63 (s, 1H), 2.15 (dt, J = 42.7, 13.3 Hz, 1H). | Example 30 |
| 194 | (S)-2,2-difluoro-N-(2,3,6-trifluoro-4-((3-(2-(piperidin-3-ylamino)pyrimidin-4-yl)pyridin-2-yl)oxy)phenyl)butane-1-sulfonamide | 573.2 | (400 MHz, CD₃OD) δ 8.47 (dd, J = 7.6, 2.0 Hz, 1H), 8.39 (d, J = 5.3 Hz, 1H), 8.19 (dd, J = 4.9, 2.0 Hz, 1H), 7.36 (d, J = 5.3 Hz, 1H), 7.28 (dd, J = 7.6, 4.8 Hz, 1H), 6.94-6.88 (m, 1H), 4.21 (s, 1H), 3.66 (t, J = 13.5 Hz, 2H), 3.53 (s, 1H), 3.27-3.21 (s, 1H), 2.99-2.88 (m, 2H), 2.28-2.13 (m, 3H), 2.02 (s, 1H), 1.86-1.70 (m, 2H), 1.07 (t, J = 7.5 Hz, 3H). | Example 30 |
| 195 | (S)-1-(5-methylisoxazol-3-yl)-N-(2,3,6-trifluoro-4-((3-(2-(piperidin-3-ylamino)pyrimidin-4-yl)pyridin-2-yl)oxy)phenyl)methanesulfonamide | 576.2 | (300 MHz, DMSO-d₆) δ 8.43 (d, J = 5.1 Hz, 3H), 8.33-8.23 (m, 1H), 7.45 (d, J = 7.2 Hz, 1H), 7.39-7.28 (m, 2H), 7.05 (t, J = 8.8 Hz, 1H), 6.32 (d, J = 1.1 Hz, 1H), 4.15 (brs, 1H), 4.04 (s, 2H), 3.42 (s, 2H), 3.17 (d, J = 12.3 Hz, 1H), 2.92-2.68 (m, 2H), 2.38 (d, J = 0.9 Hz, 3H), 2.07-1.82 (m, 2H), 1.74-1.59 (m, 2H). | Example 30 |
| 196 | (S)-N-(2,3,6-trifluoro-4-((3-(2-(piperidin-3-ylamino)pyrimidin-4-yl)pyridin-2-yl)oxy)phenyl)-1-(6-(trifluoromethyl)pyridin-3-yl)methanesulfonamide | 640.2 | (300 MHz, CD₃OD) δ 8.81 (s, 1H), 8.49 (dd, J = 7.6, 1.9 Hz, 1H), 8.40 (d, J = 5.3 Hz, 1H), 8.23-8.14 (m, 2H), 7.82 (d, J = 8.0 Hz, 1H), 7.38 (d, J = 5.2 Hz, 1H), 7.29 (dd, J = 7.6, 4.9 Hz, 1H), 6.97-6.85 (m, 1H), 4.45 (s, 2H), 4.22 (s, 1H), 3.53 (d, J = 13.0 Hz, 1H), 3.25-3.21 (m, 1H), 2.94 (t, J = 11.0 Hz, 2H), 2.17-2.14 (m, 1H), 2.05-2.03 (m, 1H), 1.95-1.63 (m, 2H). | Example 30 |
| 197 | (S)-N-(2-fluoro-3-((3-(2-(piperidin-3-ylamino)pyrimidin-4-yl)pyridin-2-yl)oxy)benzyl)cyclopropane carboxamide | 463.2 | (400 MHz, CD₃OD) δ 8.54 (d, J = 7.6 Hz, 1H), 8.33 (d, J = 5.2 Hz, 1H), 8.19-8.08 (m, 1H), 7.38 (d, J = 5.6 Hz, 1H), 7.30-7.16 (m, 4H), 4.47 (s, 2H), 4.05 (s, 1H), 3.29 (s, 1H), 2.96 (d, J = 12.4 Hz, 1H), 2.67-2.58 (m, 1H), 2.59-2.48 (m, 1H), 2.11 (d, J = 12.4 Hz, 1H), 1.86-1.78 (m, 1H), 1.69-1.51 (m, 3H), 0.98-0.88 (m, 2H), 0.85-0.74 (m, 2H). | Example 43 |
| 198 | 1-phenyl-N-(2,3,6-trifluoro-4-((3-(2-(piperidin-3-ylmethyl)pyrimidin-4-yl)pyridin-2-yl)oxy)phenyl)methanesulfonamide | 570.2 | (400 MHz, CDCl₃) δ 8.70 (d, J = 2.3 Hz, 1H), 8.48 (d, J = 5.4 Hz, 1H), 8.03 (d, J = 4.1 Hz, 1H), 7.92 (d, J = 5.4 Hz, 1H), 7.54-7.47 (m, 2H), 7.38-7.33 (m, 3H), 7.02-6.99 (m, 1H), 6.53-6.51 (m, 1H), | Example 44 |

TABLE A1-continued

| Cpd No. | Name | MS m/z | ¹H NMR (ppm) | Synth. Method |
|---|---|---|---|---|
| | | | 4.35 (s, 2H), 3.16 (d, J = 12.2 Hz, 1H), 3.05 (d, J = 13.3 Hz, 2H), 2.68 (t, J = 12.0 Hz, 1H), 2.41-2.30 (m, 3H), 2.27-2.24 (m, 2H), 1.85 (d, J = 12.7 Hz, 1H), 1.57-1.43 (m, 2H), 1.17 (m, 1H), 1.17 (d, J = 13.2 Hz, 1H). | |
| 199 | 1-phenyl-N-(2,3,6-trifluoro-4-((3-(2-(piperidin-3-ylmethyl)pyrimidin-4-yl)pyridin-2-yl)oxy)phenyl)methanesulfonamide | 570.2 | (300 MHz, CD₃OD) 8.80 (d, J = 5.4 Hz, 1H), 8.61 (dd, J = 2.6, 1.9 Hz, 1H), 8.24 (dd, J = 4.9, 1.9 Hz, 1H), 8.07 (d, J = 5.4 Hz, 1H), 7.54-7.45 (m, 2H), 7.47-7.27 (m, 4H), 6.94-6.87 (m, 1H), 4.34 (s, 2H), 3.32 (s, 1H), 3.21 (d, J = 12.5 Hz, 1H), 3.02-3.00 (m, 2H), 2.87-2.63 (m, 2H), 2.45 (d, J = 11.3 Hz, 1H), 1.90-1.84 (m, 2H), 1.83-1.67 (m, 1H), 1.45-1.31 (m, 1H). | Example 44 |
| 200 | 1,1,1-trifluoro-3-((2-fluoro-3-((3-(2-(((S)-piperidin-3-yl)amino)pyrimidin-4-yl)pyridin-2-yl)oxy)phenyl)amino)propan-2-ol | 493.2 | (300 MHz, CD₃OD) δ 8.54 (d, J = 2.5 Hz, 1H), 8.34 (d, J = 5.3 Hz, 1H), 8.13 (dd, J = 4.9, 2.0 Hz, 1H), 7.38 (d, J = 5.3 Hz, 1H), 7.26 (dd, J = 2.6, 4.9 Hz, 1H), 7.06 (td, J = 8.2, 1.8 Hz, 1H), 6.73 (t, J = 7.4 Hz, 1H), 6.61-6.49 (m, 1H), 4.24-4.16 (m, 1H), 4.11-4.01 (m, 1H), 3.66-3.55 (m, 1H), 3.39-3.36 (m, 1H), 3.31-3.28 (m, 1H), 3.05-2.91 (m, 1H), 2.73-2.49 (m, 2H), 2.13 (s, 1H), 1.82 (s, 1H), 1.73-1.50 (m, 2H). | Example 45 |
| 201 | 1,1,1-trifluoro-3-((2-fluoro-3-((3-(2-(((S)-piperidin-3-yl)amino)pyrimidin-4-yl)pyridin-2-yl)oxy)phenyl)amino)propan-2-ol | 493.2 | (300 MHz, CD₃OD) δ 8.54 (d, J = 7.7 Hz, 1H), 8.34 (d, J = 5.3 Hz, 1H), 8.13 (dd, J = 4.9, 2.0 Hz, 1H), 7.38 (d, J = 5.3 Hz, 1H), 7.26 (dd, J = 7.6, 4.9 Hz, 1H), 7.06 (td, J = 8.2, 1.9 Hz, 1H), 6.73 (t, J = 7.6 Hz, 1H), 6.56 (t, J = 6.9 Hz, 1H), 4.24-4.14 (m, 1H), 4.10-4.00 (m, 1H), 3.64-3.52 (m, 1H), 3.37-3.35 (m, 1H), 3.31-3.27 (m, 1H), 3.00-2.96 (d, J = 12.5 Hz, 1H), 2.75-2.50 (m, 2H), 2.17-2.08 (m, 1H), 1.82 (s, 1H), 1.73-1.54 (m, 2H). | Example 45 |
| 202 | 1-cyclobutyl-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide | 581.2 | (300 MHz, CD₃OD) δ 8.56 (d, J = 7.5 Hz, 1H), 8.37 (d, J = 5.1 Hz, 1H), 8.27-8.16 (m, 1H), 7.40-7.31 (m, 2H), 7.21-7.10 (m, 1H), 4.36 (s, 1H), 3.39-3.34 (m, 3H), 3.12-2.90 (m, 2H), 2.75-2.55 (m, 1H), 2.49-2.19 (m, 4H), 2.09-1.82 (m, 4H), 1.79-1.52(m, 1H), 1.42-1.30 (m, 3H). | Example 42 |
| 203 | 1-(5-methylisoxazol-3-yl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide | 608.2 | (400 MHz, CD₃OD) δ 8.55 (d, J = 7.6 Hz, 1H), 8.38 (d, J = 5.2 Hz, 1H), 8.20 (dd, J = 4.8, 2.0 Hz, 1H), 7.37 (d, J = 5.2 Hz, 1H), 7.32 (dd, J = 7.6, 4.8 Hz, 1H), 7.12-7.08 (m, 1H), 6.38 (d, J = 1.2 Hz, 1H), 4.51 (s, 2H), 4.44 (s, 1H), 3.51-3.42 (m, 1H), 3.23-3.13 (m, 1H), 2.90-2.82 (m, 1H), 2.77 (d, J = 14.0 Hz, 1H), 2.52-2.45 (m, 3H), 2.43-2.34 (m, 1H), 1.84-1.63 (m, 1H), 1.47-1.36(s, 3H). | Example 42 |
| 204 | 1-(5-methylisoxazol-3-yl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 594.1 | (400 MHz, CD₃OD) δ 8.56 (d, J = 7.6 Hz, 1H), 8.39 (d, J = 5.2 Hz, 1H), 8.20 (dd, J = 4.2, 2.0 Hz, 1H), 7.40-7.29 (m, 2H), 7.09 (dd, J = 9.6, 7.2 Hz, 1H), 6.38 (d, J = 1.0 Hz, 1H), 5.09-5.01 (m, 1H), 4.59-4.49 (m, 3H), 3.44 (d, J = 12.8 Hz, 1H), 3.27 (d, J = 12.4 Hz, 1H), 2.99-2.90 (m, 1H), 2.69-2.60 (m, 1H), 2.49-2.41 (m, 4H), 1.94-1.88 (m, 1H). | Example 40 |
| 205 | 3,3,3-trifluoro-N-(2,3,6-trifluoro-4-((3-(2-(((3S,5S)-5-fluoro-3-piperidyl)amino)pyrimidin-4-yl)-2-pyridyl)oxy)phenyl)propane-1-sulfonamide | 595.1 | (300 MHz, CD₃OD) δ 8.55 (d, J = 5.1 Hz, 1H), 8.38 (d, J = 5.4 Hz, 1H), 8.20 (dd, J = 1.8 Hz, 3.0 Hz, 1H), 7.37 (d, J = 5.1 Hz, 1H), 7.34 (d, J = 5.1 Hz, 1H), 7.15-7.08(m, 1H), 5.07-4.91(m, 1H), 4.51-4.36 (m, 1H), 3.46-3.34 (m, 3H), 3.29-3.25 (m, 1H), 3.03-2.78 (m, 3H), 2.68-2.60 (m, 1H), 2.49-2.38 (m, 1H), 1.95-1.80 (m, 1H). | Example 40 |
| 206 | (S)-N-(2,3-difluoro-4-((3-(2-(piperidin-3-ylamino)pyrimidin-4-yl)pyridin-2-yloxy)phenyl)-3,5-difluorobenzenesulfonamide | 575.1 | (400 MHz, DMSO-d₆) δ 8.52 (s, 2H), 8.41 (d, J = 5.1 Hz, 2H), 8.19 (dd, J = 4.8, 2.0 Hz, 1H), 7.43 (d, J = 7.3 Hz, 1H), 7.39-7.24 (m, 5H), 7.06-6.86 (m, 1H), 6.82-6.66 (m, 1H), 4.17 (d, J = 8.4 Hz, 1H), | Example 46 |

TABLE A1-continued

| Cpd No. | Name | MS m/z | ¹H NMR (ppm) | Synth. Method |
|---|---|---|---|---|
| | | | 3.50-3.36 (m, 1H), 3.23-3.11 (m, 1H), 2.97-2.75 (m, 2H), 2.06-1.87 (m, 2H), 1.77-1.56 (m, 2H). | |
| 207 | (S)-N-(2,3-difluoro-4-((3-(2-(piperidin-3-ylamino)pyrimidin-4-yl)pyridin-2-yl)oxy)phenyl)-3-(trifluoromethoxy)benzenesulfonamide | 623.1 | (400 MHz, DMSO-$d_6$) δ 8.62-8.25 (m, 1H), 8.18 (dd, J = 4.8, 2.0 Hz, 1H), 7.73 (dt, J = 7.7, 1.3 Hz, 1H), 7.61-7.58 (m, 1H), 7.55 (t, J = 8.0 Hz, 1H), 7.45-7.36 (m, 2H), 7.32-7.22 (m, 2H), 6.94 (td, J = 9.0, 2.2 Hz, 1H), 6.74 (t, J = 8.4 Hz, 1H), 4.20-4.12 (m, 1H), 3.45-3.37 (m, 1H), 3.53-3.35 (m, 0H), 3.37 (s, 0H), 3.21-3.13 (m, 1H), 2.92-2.71 (m, 2H), 2.01-1.93 (m, 1H), 1.93-1.82 (m, 1H), 1.73-1.54 (m, 2H). | Example 46 |
| 208 | (S)-N-(2,3-difluoro-4-((3-(2-(piperidin-3-ylamino)pyrimidin-4-yl)pyridin-2-yl)oxy)phenyl)-3-(difluoromethoxy)benzenesulfonamide | 605.1 | (400 MHz, DMSO-$d_6$) δ 8.40 (t, J = 6.3 Hz, 3H), 8.18 (dd, J = 4.8, 2.0 Hz, 1H), 7.68-7.57 (m, 1H), 7.49-7.34 (m, 4H), 7.32-7.18 (m, 4H), 6.94 (td, J = 9.0, 2.1 Hz, 1H), 6.79-6.70 (m, 1H), 3.20-3.08 (m, 1H), 2.97-2.63 (m, 3H), 2.06-1.81 (m, 2H), 1.64 (dp, J = 30.8, 10.4, 9.5 Hz, 2H). | Example 46 |
| 209 | (S)-N-(2,3-difluoro-4-((3-(2-(piperidin-3-ylamino)pyrimidin-4-yl)pyridin-2-yl)oxy)phenyl)-1-(spiro[3.3]heptan-2-yl)methanesulfonamide | 571.2 | (400 MHz, DMSO-$d_6$) δ 8.43 (d, J = 5.1 Hz, 1H), 8.23 (dd, J = 4.8, 1.9 Hz, 1H), 7.60-7.12 (m, 5H), 4.15 (s, 1H), 3.23 (d, J = 7.2 Hz, 2H), 3.19-3.09 (m, 1H), 2.89 (s, 2H), 2.84-2.70 (m, 3H), 2.64-2.53 (m, 1H), 2.21-2.12 (m, 2H), 2.08-1.94 (m, 3H), 1.90-1.71 (m, 7H), 1.69-1.54 (m, 1H). | Example 46 |
| 210 | (S)-3-cyano-N-(2,3-difluoro-4-((3-(2-(piperidin-3-ylamino)pyrimidin-4-yl)pyridin-2-yl)oxy)phenyl)-3-methylbutane-1-sulfonamide | 558.1 | (400 MHz, DMSO-$d_6$) δ 8.42 (d, J = 5.1 Hz, 2H), 8.22 (dd, J = 4.8, 1.9 Hz, 1H), 7.43-7.35 (m, 1H), 7.35-7.26 (m, 2H), 7.18-7.07 (m, 1H), 6.97-6.86 (m, 1H), 4.08 (s, 1H), 3.07 (d, J = 12.4 Hz, 1H), 3.01-2.86 (m, 3H), 2.81-2.62 (m, 3H), 2.02-1.88 (m, 3H), 1.88-1.77 (m, 1H), 1.66-1.40 (m, 2H), 1.31 (s, 6H). | Example 46 |
| 211 | (S)-N-(2,3-difluoro-4-((3-(2-(piperidin-3-ylamino)pyrimidin-4-yl)pyridin-2-yl)oxy)phenyl)-4-methoxybenzenesulfonamide | 569.1 | (400 MHz, DMSO-$d_6$) δ 8.39 (d, J = 5.1 Hz, 2H), 8.18 (dd, J = 4.9, 2.0 Hz, 1H), 7.70-7.62 (m, 2H), 7.36-7.22 (m, 3H), 7.03-6.89 (m, 3H), 6.90-6.76 (m, 1H), 5.75 (s, 0H), 4.07 (s, 1H), 3.78 (s, 3H), 3.17 (s, 0H), 3.11-3.01 (m, 1H), 2.81-2.63 (m, 2H), 2.54 (s, 0H), 2.07 (s, 0H), 1.99-1.91 (m, 1H), 1.87-1.77 (m, 1H), 1.68-1.49 (m, 2H). | Example 46 |
| 212 | (S)-N-(2,3-difluoro-4-((3-(2-(piperidin-3-ylamino)pyrimidin-4-yl)pyridin-2-yl)oxy)phenyl)-3-methoxybenzenesulfonamide | 569.1 | (400 MHz, DMSO-$d_6$) δ 8.39 (d, J = 5.1 Hz, 2H), 8.18 (dd, J = 4.8, 2.0 Hz, 1H), 7.44-7.17 (m, 7H), 7.07-6.88 (m, 2H), 6.84-6.68 (m, 1H), 4.11 (s, 1H), 3.76 (s, 3H), 3.19-3.06 (m, 1H), 2.90-2.65 (m, 2H), 2.11-1.75 (m, 2H), 1.73-1.51 (m, 2H). | Example 46 |
| 213 | (S)-1-(4-chlorophenyl)-N-(2,3-difluoro-4-((3-(2-(piperidin-3-ylamino)pyrimidin-4-yl)pyridin-2-yl)oxy)phenyl)methanesulfonamide | 587.1 | (400 MHz, DMSO-$d_6$) δ 8.42 (d, J = 5.1 Hz, 2H), 8.22 (dd, J = 4.8, 1.9 Hz, 1H), 7.45-7.26 (m, 8H), 7.24-7.09 (m, 1H), 7.05-6.83 (m, 1H), 4.17 (s, 2H), 4.08 (s, 1H), 3.11-3.00 (m, 1H), 2.80-2.61 (m, 2H), 2.06-1.93 (m, 1H), 1.91-1.77 (m, 1H), 1.72-1.49 (m, 2H). | Example 46 |
| 214 | (S)-N-(2,3-difluoro-4-((3-(2-(piperidin-3-ylamino)pyrimidin-4-yl)pyridin-2-yl)oxy)phenyl)pyridine-3-sulfonamide | 540.1 | (400 MHz, DMSO-$d_6$) δ 8.84 (d, J = 2.2 Hz, 1H), 8.56 (dd, J = 4.8, 1.7 Hz, 1H), 8.40 (d, J = 5.1 Hz, 2H), 8.27-8.13 (m, 1H), 8.11-7.97 (m, 1H), 7.50-7.34 (m, 2H), 7.32-7.22 (m, 2H), 7.02-6.91 (m, 1H), 6.81-6.61 (m, 1H), 4.37-4.00 (m, 1H), 3.25-3.11 (m, 4H), 2.93-2.71 (m, 2H), 2.05-1.83 (m, 2H), 1.75-1.45 (m, 2H). | Example 46 |
| 215 | (S)-2-cyclohexyl-N-(2,3-difluoro-4-((3-(2-(piperidin-3-ylamino)pyrimidin-4-yl)pyridin-2-yl)oxy)phenyl)ethane-1-sulfonamide | 573.2 | (400 MHz, DMSO-$d_6$) δ 8.39 (d, J = 5.1 Hz, 2H), 8.21 (dd, J = 4.8, 2.0 Hz, 1H), 7.40-7.13 (m, 4H), 7.13-7.00 (m, 1H), 4.03 (d, J = 43.3 Hz, 3H), 3.17 (s, 5H), 3.08-2.87 (m, 3H), 2.73-2.54 (m, 2H), 1.62 (ddt, J = 18.3, 6.7, 2.8 Hz, 8H), 1.16 (tdd, J = 10.5, 7.2, 2.9 Hz, 3H), 0.86 (p, J = 10.3, 9.6 Hz, 3H). | Example 46 |

TABLE A1-continued

| Cpd No. | Name | MS m/z | ¹H NMR (ppm) | Synth. Method |
|---|---|---|---|---|
| 216 | (S)-3-cyano-N-(2,3-difluoro-4-((3-(2-(piperidin-3-ylamino)pyrimidin-4-yl)pyridin-2-yl)oxy)phenyl)-2,2-dimethylpropane-1-sulfonamide | 558.1 | (400 MHz, DMSO-d₆) δ 8.42 (d, J = 5.1 Hz, 1H), 8.33-8.12 (m, 1H), 7.47-7.25 (m, 3H), 7.25-7.11 (m, 1H), 7.04-6.90 (m, 1H), 4.10 (s, 2H), 3.17 (s, 2H), 3.10 (d, J = 13.1 Hz, 1H), 3.02 (s, 2H), 2.78 (s, 2H), 2.75-2.64 (m, 1H), 2.05-1.93 (m, 1H), 1.90-1.81 (m, 1H), 1.72-1.54 (m, 2H), 1.18 (s, 6H). | Example 46 |
| 217 | N-(2,3-difluoro-4-((3-(2-(((S)-piperidin-3-yl)amino)pyrimidin-4-yl)pyridin-2-yl)oxy)phenyl)-2-(2,2-difluorocyclopropyl)ethane-1-sulfonamide | 567.1 | (400 MHz, DMSO-d₆) δ 8.41 (d, J = 5.1 Hz, 2H), 8.21 (dd, J = 4.8, 1.9 Hz, 1H), 7.40-7.22 (m, 3H), 7.24-7.12 (m, 1H), 7.07-6.92 (m, 1H), 4.05 (s, 1H), 3.13-2.98 (m, 3H), 2.78-2.62 (m, 2H), 2.03-1.76 (m, 5H), 1.65-1.41 (m, 2H), 1.25-1.11 (m, 1H). (MD) | Example 46 |
| 218 | (S)-N-(2,3-difluoro-4-((3-(2-(piperidin-3-ylamino)pyrimidin-4-yl)pyridin-2-yl)oxy)phenyl)benzenesulfonamide | 539.1 | (400 MHz, DMSO-d₆) δ 8.39 (d, J = 5.1 Hz, 2H), 8.18 (dd, J = 4.8, 2.0 Hz, 1H), 7.81-7.62 (m, 1H), 7.52-7.32 (m, 4H), 7.33-7.22 (m, 2H), 6.99-6.87 (m, 1H), 6.83-6.66 (m, 1H), 5.75 (s, 1H), 4.23-3.98 (m, 1H), 3.17 (s, 1H), 3.16-3.04 (m, 1H), 2.87-2.62 (m, 2H), 2.05-1.88 (m, 1H), 1.91-1.73 (m, 1H), 1.72-1.51 (m, 2H). | Example 46 |
| 219 | (S)-4-cyano-N-(2,3-difluoro-4-((3-(2-(piperidin-3-ylamino)pyrimidin-4-yl)pyridin-2-yl)oxy)phenyl)benzenesulfonamide | 564.1 | (400 MHz, DMSO-d₆) δ 8.41 (d, J = 5.1 Hz, 1H), 8.18 (dd, J = 4.8, 1.9 Hz, 1H), 7.85 (s, 4H), 7.42 (d, J = 7.3 Hz, 1H), 7.36-7.14 (m, 2H), 7.01-6.86 (m, 1H), 6.79-6.61 (m, 1H), 4.16 (s, 1H), 3.39 (t, J = 5.9 Hz, 2H), 3.24-3.09 (m, 1H), 2.96-2.70 (m, 2H), 1.97 (d, J = 12.1 Hz, 1H), 1.93-1.85 (m, 1H), 1.77-1.49 (m, 2H). | Example 46 |
| 220 | (S)-3-cyano-N-(2,3-difluoro-4-((3-(2-(piperidin-3-ylamino)pyrimidin-4-yl)pyridin-2-yl)oxy)phenyl)benzenesulfonamide | 564.1 | (400 MHz, DMSO-d₆) δ 8.41 (d, J = 5.1 Hz, 1H), 8.18 (dd, J = 4.8, 2.0 Hz, 1H), 8.11-7.91 (m, 2H), 7.94-7.81 (m, 1H), 7.73-7.54 (m, 1H), 7.42 (d, J = 7.4 Hz, 1H), 7.34-7.16 (m, 2H), 7.01-6.83 (m, 1H), 6.81-6.63 (m, 1H), 4.16 (s, 1H), 3.25-3.09 (m, 1H), 2.97-2.71 (m, 2H), 2.08-1.83 (m, 2H), 1.63 (tt, J = 20.8, 10.2 Hz, 1H). | Example 46 |
| 221 | (S)-N-(2,3-difluoro-4-((3-(2-(piperidin-3-ylamino)pyrimidin-4-yl)pyridin-2-yl)oxy)phenyl)-1-methyl-1H-imidazole-4-sulfonamide | 543.1 | (400 MHz, DMSO-d₆) δ 8.38 (d, J = 5.1 Hz, 2H), 8.19 (dd, J = 4.8, 1.9 Hz, 1H), 7.65 (d, J = 1.4 Hz, 1H), 7.55 (d, J = 1.4 Hz, 1H), 7.38-7.21 (m, 3H), 7.16 (td, J = 8.9, 2.2 Hz, 1H), 6.91 (td, J = 8.7, 2.0 Hz, 1H), 4.00 (s, 1H), 3.65 (s, 3H), 3.09-2.93 (m, 1H), 2.79-2.57 (m, 2H), 1.94 (d, J = 6.7 Hz, 1H), 1.83-1.74 (m, 1H), 1.62-1.45 (m, 2H). | Example 46 |
| 222 | (S)-N-(2,3-difluoro-4-((3-(2-(piperidin-3-ylamino)pyrimidin-4-yl)pyridin-2-yl)oxy)phenyl)-1-methyl-1H-pyrazole-4-sulfonamide | 543.1 | (400 MHz, DMSO-d₆) δ 8.40 (d, J = 5.1 Hz, 1H), 8.19 (dd, J = 4.8, 1.9 Hz, 1H), 7.97 (s, 1H), 7.53 (s, 1H), 7.40-7.17 (m, 3H), 7.15-6.93 (m, 1H), 6.94-6.69 (m, 1H), 4.07 (s, 1H), 3.80 (s, 3H), 3.14-3.03 (m, 1H), 2.79-2.60 (m, 2H), 2.04-1.88 (m, 1H), 1.88-1.76 (m, 1H), 1.71-1.48 (m, 2H). | Example 46 |
| 223 | (S)-N-(2,3-difluoro-4-((3-(2-(piperidin-3-ylamino)pyrimidin-4-yl)pyridin-2-yl)oxy)phenyl)-4-(trifluoromethoxy)benzenesulfonamide | 623.1 | (400 MHz, DMSO-d₆) δ 8.41 (d, J = 5.1 Hz, 1H), 8.19 (dd, J = 4.9, 2.0 Hz, 1H), 7.87-7.78 (m, 2H), 7.45 (d, J = 7.3 Hz, 1H), 7.42-7.35 (m, 2H), 7.32-7.23 (m, 2H), 6.97-6.87 (m, 1H), 6.77-6.67 (m, 1H), 4.17-4.08 (m, 1H), 3.17 (d, J = 4.9 Hz, 2H), 2.88-2.71 (m, 2H), 2.01-1.93 (m, 1H), 1.93-1.83 (m, 1H), 1.76-1.50 (m, 2H). | Example 46 |
| 224 | (S)-N-(2,3-difluoro-4-((3-(2-(piperidin-3-ylamino)pyrimidin-4-yl)pyridin-2-yl)oxy)phenyl)-2-methoxybenzenesulfonamide | 569.1 | (400 MHz, DMSO-d₆) δ 8.49-8.28 (m, 2H), 8.18 (dd, 1H), 7.72 (dd, J = 7.8, 1.8 Hz, 1H), 7.54-7.45 (m, 1H), 7.34-7.21 (m, 3H), 7.14 (d, J = 8.1 Hz, 1H), 7.06-6.88 (m, 3H), 3.99 (s, 1H), 3.81 (s, 3H), 3.02-2.92 (m, 1H), 2.67-2.52 (m, 2H), 1.98-1.88 (m, 1H), 1.81-1.71 (m, 1H), 1.60-1.46 (m, 2H), −4.10 (s, 1H). | Example 46 |
| 225 | (S)-1-(3-chlorophenyl)-N-(2,3-difluoro-4-((3-(2- | 587.1 | (400 MHz, DMSO-d₆) δ 8.42 (d, J = 5.1 Hz, 2H), 8.22 (dd, J = 4.8, 1.9 Hz, 1H), | Example 46 |

TABLE A1-continued

| Cpd No. | Name | MS m/z | ¹H NMR (ppm) | Synth. Method |
|---|---|---|---|---|
| | (piperidin-3-ylamino)pyrimidin-4-yl)pyridin-2-yl)oxy)phenyl)methanesulfonamide | | 7.48-7.24 (m, 8H), 7.21-7.12 (m, 1H), 6.99-6.80 (m, 1H), 4.17 (s, 2H), 4.09 (s, 1H), 3.14-3.02 (m, 1H), 2.84-2.60 (m, 2H), 2.11-1.92 (m, 1H), 1.90-1.78 (m, 1H), 1.73-1.51 (m, 2H). | |
| 226 | (S)-N-(2,3-difluoro-4-((3-(2-(piperidin-3-ylamino)pyrimidin-4-yl)pyridin-2-yl)oxy)phenyl)-3,3-dimethylbutane-1-sulfonamide | 547.2 | (400 MHz, DMSO-d₆) δ 8.39 (d, J = 5.1 Hz, 2H), 8.21 (dd, J = 4.8, 2.0 Hz, 1H), 7.44-7.12 (m, 4H), 7.11-6.97 (m, 1H), 3.98 (s, 1H, 3.17 (s, 1H), 3.06-2.81 (m, 3H), 2.66-2.54 (m, 2H), 2.04-1.86 (m, 1H), 1.77-1.69 (m, 1H), 1.67-1.43 (m, 4H), 0.87 (s, 10H). | Example 46 |
| 227 | (S)-2-chloro-N-(2,3-difluoro-4-((3-(2-(piperidin-3-ylamino)pyrimidin-4-yl)pyridin-2-yl)oxy)phenyl)benzenesulfonamide | 587.1 | (400 MHz, DMSO-d₆) δ 8.47-8.30 (m, 2H), 8.22 (dd, J = 4.8, 2.0 Hz, 1H), 7.56-7.47 (m, 1H), 7.46-7.38 (m, 1H), 7.36 (d, J = 7.5 Hz, 1H), 7.33-7.25 (m, 4H), 7.21 (td, 1H), 6.89 (t, J = 8.9, 2.0 Hz, 1H), 4.31 (s, 2H), 4.10 (s, 1H), 3.09 (d, J = 12.7 Hz, 1H), 2.80-2.65 (m, 2H), 2.01-1.93 (m, 1H), 1.89-1.80 (m, 1H), 1.67-1.51 (m, 2H). | Example 46 |
| 228 | (S)-1-cyclopentyl-N-(2,3-difluoro-4-((3-(2-(piperidin-3-ylamino)pyrimidin-4-yl)pyridin-2-yl)oxy)phenyl)methanesulfonamide | 545.3 | (400 MHz, DMSO-d₆) δ 8.51-8.32 (m, 1H), 8.22 (dd, J = 4.8, 2.0 Hz, 1H), 7.33 (dd, J = 7.6, 4.9 Hz, 1H), 7.29-7.16 (m, 3H), 7.07 (t, J = 8.7, 2.0 Hz, 1H), 3.98 (s, 1H), 3.06 (d, J = 6.8 Hz, 2H), 3.00-2.90 (m, 1H), 2.67-2.52 (m, 2H), 2.31-2.18 (m, 1H), 2.00-1.80 (m, 3H), 1.80-1.66 (m, 1H), 1.65-1.41 (m, 5H), 1.33-1.19 (m, 2H). | Example 46 |
| 229 | (S)-1-(3-cyanophenyl)-N-(2,3-difluoro-4-((3-(2-(piperidin-3-ylamino)pyrimidin-4-yl)pyridin-2-yl)oxy)phenyl)methanesulfonamide | 578.2 | (400 MHz, DMSO-d₆) δ 8.43 (d, J = 5.1 Hz, 2H), 8.23 (dd, J = 4.8, 2.0 Hz, 1H), 7.78-7.69 (m, 2H), 7.65 (d, J = 7.8, 1.5 Hz, 1H), 7.52 (t, J = 7.9 Hz, 1H), 7.38 (d, J = 7.5 Hz, 1H), 7.35-7.22 (m, 2H), 7.17 (t, J = 9.0, 2.2 Hz, 1H), 6.88 (t, J = 8.9, 2.0 Hz, 1H), 4.21 (s, 2H), 4.12 (s, 1H), 3.11 (d, J = 12.7 Hz, 1H), 2.83-2.65 (m, 2H), 2.01-1.93 (m, 1H), 1.91-1.81 (m, 1H), 1.72-1.52 (m, 2H). | Example 46 |
| 230 | (S)-N-(2,3-difluoro-4-((3-(2-(piperidin-3-ylamino)pyrimidin-4-yl)pyridin-2-yl)oxy)phenyl)-4,4-dimethylpentane-1-sulfonamide | 561.3 | (400 MHz, DMSO-d₆) δ 8.50-8.32 (m, 1H), 8.21 (dd, J = 4.9, 1.9 Hz, 1H), 7.33 (dd, J = 7.5, 4.8 Hz, 1H), 7.28-7.13 (m, 3H), 7.04 (t, J = 8.8, 2.0 Hz, 1H), 3.96 (s, 1H), 3.20-3.16 (m, 1H), 2.98-2.90 (m, 3H), 2.64-2.52 (m, 1H), 2.00-1.88 (m, 1H), 1.79-1.61 (m, 3H), 1.59-1.47 (m, 2H), 1.28-1.19 (m, 2H), 0.87 (s, 9H). | Example 46 |
| 231 | (S)-N-(2,3-difluoro-4-((3-(2-(piperidin-3-ylamino)pyrimidin-4-yl)pyridin-2-yl)oxy)phenyl)-1-(3-fluorophenyl)methanesulfonamide | 571.2 | (400 MHz, DMSO-d₆) δ 8.42 (d, J = 5.2 Hz, 2H), 8.23 (dd, J = 4.8, 2.0 Hz, 1H), 8.19 (s, 1H), 7.39-7.27 (m, 4H), 7.21-7.05 (m, 4H), 6.91 (td, J = 8.9, 2.0 Hz, 1H), 4.20 (s, 2H), 4.10 (s, 1H), 3.06 (s, 1H), 2.72 (td, J = 13.3, 11.8, 6.6 Hz, 2H), 2.00-1.93 (m, 1H), 1.87-1.79 (m, 1H), 1.60 (q, J = 12.4, 11.3 Hz, 2H). | Example 46 |
| 232 | (S)-N-(2,3-difluoro-4-(3-(2-(piperidin-3-ylamino)pyrimidin-4-yl)pyridin-2-yloxy)phenyl)-1-(3,3-difluorocyclobutyl)methanesulfonamide | 567.2 | (400 MHz, DMSO-d₆) δ 8.48-8.32 (m, 2H), 8.21 (dd, J = 4.9, 1.9 Hz, 1H), 7.35-7.25 (m, 3H), 7.20-7.11 (m, 1H), 6.98-6.89 (m, 1H), 4.11-3.99 (m, 1H), 3.12 (d, J = 6.8 Hz, 2H), 3.06-2.99 (m, 1H), 2.75-2.60 (m, 4H), 2.48-2.36 (m, 2H), 1.99-1.91 (m, 1H), 1.84-1.73 (m, 1H), 1.66-1.49 (m, 2H). | Example 46 |
| 233 | (S)-N-(2,3-difluoro-4-(3-(2-(piperidin-3-ylamino)pyrimidin-4-yl)pyridin-2-yloxy)phenyl)-1-(pyridin-3-yl)methanesulfonamide | 554.2 | (400 MHz, DMSO-d₆) δ 8.66-8.57 (m, 2H), 8.46 (dd, J = 7.5, 2.0 Hz, 1H), 8.43 (d, J = 5.2 Hz, 1H), 8.23 (dd, J = 4.8, 1.9 Hz, 1H), 7.97-7.91 (m, 1H), 7.50 (dd, J = 7.9, 4.9 Hz, 1H), 7.35 (dd, J = 7.6, 4.9 Hz, 1H), 7.31 (d, J = 5.2 Hz, 1H), 7.25-7.12 (m, 2H), 4.65 (s, 2H), 4.30-4.21 (m, 1H), 3.41 (dd, J = 12.1, 4.1 Hz, 1H), 3.23-3.20 (m, 1H), 2.95-2.84 (m, 2H), 2.05-1.89 (m, 2H), 1.82-1.61 (m, 2H). ¹H NMR taken at 360K | Example 46 |
| 234 | (S)-N-(2,3-difluoro-4-(3-(2-(piperidin-3- | 554.2 | (400 MHz, DMSO-d₆) δ 8.58-8.55 (m, 2H), 8.47 (dd, J = 7.7, 1.9 Hz, 1H), 8.42 | Example 46 |

TABLE A1-continued

| Cpd No. | Name | MS m/z | ¹H NMR (ppm) | Synth. Method |
|---|---|---|---|---|
|  | ylamino)pyrimidin-4-yl)pyridin-2-yloxy)phenyl)-1-(pyridin-4-yl)methanesulfonamide |  | (d, J = 5.1 Hz, 1H), 8.23 (dd, J = 4.9, 1.9 Hz, 1H), 7.44-7.40 (m, 2H), 7.35 (dd, J = 7.5, 4.8 Hz, 1H), 7.30 (d, J = 5.2 Hz, 1H), 7.24-7.12 (m, 2H), 4.60 (s, 2H), 4.32-4.22 (m, 1H), 3.40 (dd, J = 11.9, 4.2 Hz, 1H), 3.20-3.12 (m, 1H), 2.93-2.84 (m, 2H), 2.04-1.88 (m, 2H), 1.84-1.60 (m, 2H). ¹H NMR taken at 360K |  |
| 235 | (S)-N-(2,3-difluoro-4-(3-(2-(piperidin-3-ylamino)pyrimidin-4-yl)pyridin-2-yloxy)phenyl)-1-(4-fluorophenyl)methanesulfonamide | 571.2 | (400 MHz, DMSO-d₆) δ 8.51-8.32 (m, 2H), 8.22 (dd, J = 4.8, 2.0 Hz, 1H), 7.40-7.26 (m, 5H), 7.19-7.08 (m, 3H), 6.94-6.86 (m, 1H), 4.17 (s, 2H), 4.07-4.02 (m, 1H), 3.46-3.38 (m, 1H), 3.24-3.16 (m, 1H), 3.07-2.98 (m, 1H), 2.74-2.60 (m, 1H), 1.99-1.92 (m, 1H), 1.84-1.74 (m, 1H), 1.63-1.52 (m, 2H). | Example 46 |
| 236 | (S)-1-(1-methyl-1H-pyrazol-3-yl)-N-(2,3,6-trifluoro-4-(3-(2-(piperidin-3-ylamino)pyrimidin-4-yl)pyridin-2-yloxy)phenyl)methanesulfonamide | 575.2 | (400 MHz, DMSO-d₆) δ 8.51-8.32 (m, 2H), 8.27 (dd, J = 4.9, 1.9 Hz, 1H), 7.55 (d, J = 2.2 Hz, 1H), 7.37-7.30 (m, 2H), 7.28 (d, J = 5.1 Hz, 1H), 7.15-7.07 (m, 1H), 6.27 (d, J = 2.1 Hz, 1H), 4.12-3.96 (m, 3H), 3.78 (s, 3H), 3.06-2.99 (m, 1H), 2.74-2.59 (m, 2H), 1.99-1.92 (m, 1H), 1.84-1.76 (m, 1H), 1.65-1.50 (m, 2H). | Example 30 |
| 237 | N-[2-fluoro-3-methyl-4-[[3-[2-[[(3S)-3-piperidyl]amino]pyrimidin-4-yl]-2-pyridyl]oxy]phenyl]-1 phenylmethanesulfonamide | 549.1 | (400 MHz, DMSO-d₆) δ 8.49-8.32 (m, 3H), 8.22-8.16 (m, 1H), 7.44-7.10 (m, 8H), 6.88 (dd, J = 8.8, 1.6 Hz, 1H), 4.40 (s, 2H), 3.91-3.87 (m, 2H), 3.15-3.08 (m, 1H), 2.88-2.80 (m, 1H), 2.48-2.41 (m, 1H), 2.00 (s, 3H), 1.94-1.88 (m, 1H), 1.70-1.63 (m, 1H), 1.56-1.36 (m, 2H), 1.26-1.13 (m, 1H). | Example 47 |
| 238 | (S)-N-(2,3-difluoro-4-(3-(2-(piperidin-3-ylamino)pyrimidin-4-yl)pyridin-2-yloxy)phenyl)-1-(pyridin-2-yl)methanesulfonamide | 554.2 | (400 MHz, DMSO-d₆) δ 8.52-8.47 (m, 1H), 8.42-8.34 (m, 2H), 8.21 (dd, J = 4.9, 2.1 Hz, 1H), 7.78-7.70 (m, 1H), 7.52 (d, J = 7.8 Hz, 1H), 7.32-7.18 (m, 4H), 7.01-6.92 (m, 1H), 6.84 (d, J = 7.8 Hz, 1H), 4.47 (s, 2H), 4.04-3.94 (m, 1H), 3.21-3.19 (m, 1H), 2.93-2.88 (m, 1H), 2.89 (d, J = 3.8 Hz, 1H), 2.68-2.57 (m, 2H), 2.00-1.89 (m, 1H), 1.78-1.69 (m, 1H), 1.62-1.47 (m, 2H). ¹H NMR taken at 360K | Example 18 |
| 248 | 1-(2,3-difluoro-4-((3-(2-(((S)-piperidin-3-yl)amino)pyrimidin-4-yl)pyridin-2-yl)oxy)phenyl)-3-ethylpyrrolidin-2-one | 495.2 | (400 MHz, CD₃OD) δ 8.55 (d, J = 7.9 Hz, 1H), 8.38 (d, J = 5.3 Hz, 1H), 8.22-8.12 (m, 1H), 7.38 (d, J = 5.3 Hz, 1H), 7.35-7.25 (m, 2H), 7.23-7.14 (m, 1H), 4.14 (s, 1H), 3.94-3.77 (m, 2H), 3.41 (d, J = 13.6 Hz, 1H), 3.10 (d, J = 12.4 Hz, 1H), 2.83-2.58 (m, 3H), 2.52-2.39 (m, 1H), 2.13 (s, 1H), 2.07-1.88 (m, 3H), 1.81-1.49 (m, 3H), 1.08 (t, J = 7.4 Hz, 3H) | Example 48 |
| 249 | 1-(2,3-difluoro-4-((3-(2-(((S)-piperidin-3-yl)amino)pyrimidin-4-yl)pyridin-2-yl)oxy)phenyl)-3-ethylpyrrolidin-2-one | 495.2 | (400 MHz, CD₃OD) δ 8.55 (d, J = 7.9 Hz, 1H), 8.38 (d, J = 5.3 Hz, 1H), 8.22-8.12 (m, 1H), 7.38 (d, J = 5.3 Hz, 1H), 7.35-7.25 (m, 2H), 7.23-7.14 (m, 1H), 4.14 (s, 1H), 3.94-3.77 (m, 2H), 3.41 (d, J = 13.6 Hz, 1H), 3.10 (d, J = 12.4 Hz, 1H), 2.83-2.58 (m, 3H), 2.52-2.39 (m, 1H), 2.13 (s, 1H), 2.07-1.88 (m, 3H), 1.81-1.49 (m, 3H), 1.08 (t, J = 7.4 Hz, 3H) | Example 48 |
| 250 | (S)-1-(4-cyanophenyl)-N-(2,3-difluoro-4-((3-(2-(piperidin-3-ylamino)pyrimidin-4-yl)pyridin-2-yl)oxy)phenyl)methanesulfonamide | 578.2 | (400 MHz, DMSO-d₆) δ 8.71-8.3 (m, 3H), 8.24 (d, J = 6.4 Hz, 1H), 7.83 (d, J = 8.0 Hz, 2H), 7.57 (d, J = 8.0 Hz, 2H), 7.47-7.53 (m, 1H), 7.37-7.32 (m, 2H), 7.23-7.18 (m, 1H), 7.11-7.06 (m, 1H), 4.54 (s, 2H), 4.22-4.11 (m, 1H), 3.43-3.40 (m, 1H), 3.32-3.31 (m, 1H), 3.21-3.17 (m, 1H), 2.88-2.78 (m, 2H), 2.07-1.88 (m, 2H), 1.72-1.59 (m, 2H). | Example 27 |
| 251 | 1-(3,3-difluorocyclobutyl)-N-(2,3,6-trifluoro-4-((3-(2-(((3S,5S)-5-fluoro-5-methylpiperidin-3-yl)amino)pyrimidin-4- | 617.2 | (300 MHz, CD₃OD) δ 8.54 (d, J = 7.2 Hz, 1H), 8.36 (d, J = 5.1 Hz, 1H), 8.22-8.16 (m, 1H), 7.37-7.27 (m, 2H), 7.19-7.08 (m, 1H), 4.46-4.28 (m, 1H), 3.48-3.34 (m, 3H), 3.12-3.01 (m, 1H), 2.93-2.35 | Example 42 |

TABLE A1-continued

| Cpd No. | Name | MS m/z | ¹H NMR (ppm) | Synth. Method |
|---|---|---|---|---|
| | yl)pyridin-2-yl)oxy)phenyl)methanesulfonamide | | (m, 8H), 1.87-1.53 (m, 1H), 1.40-1.33 (m, 3H) | |
| 252 | 2-methoxy-N-(2,3,6-trifluoro-4-((3-(2-(((3S,5S)-5-fluoropiperidin-3-yl)amino)pyrimidin-4-yl)pyridin-2-yl)oxy)phenyl)ethane-1-sulfonamide | 557.1 | (400 MHz, CD₃OD) δ 8.56 (d, J = 7.6 Hz, 1H), 8.37 (d, J = 5.2 Hz, 1H), 8.19 (d, J = 4.8 Hz, 1H), 7.38-7.29 (m, 2H), 7.15 (d, J = 10.2, 1H), 4.99 (s, 1H), 4.42 (s, 1H), 3.94-3.86 (m, 2H), 3.67-3.48 (m, 2H), 3.39 (s, 3H), 3.31-3.26 (m, 1H), 3.23-3.17 (m, 1H), 2.91-2.78 (m, 1H), 2.61-2.52 (m, 1H), 2.49-2.33 (m, 1H), 1.91-1.78 (m, 1H) | Example 40 |
| 253 | 3,3-difluoro-N-(2,3,6-trifluoro-4-((3-(2-(((3S,5S)-5-fluoropiperidin-3-yl)amino)pyrimidin-4-yl)pyridin-2-yl)oxy)phenyl)butane-1-sulfonamide | 591.2 | (400 MHz, CD₃OD) δ 8.56 (d, J = 7.5 Hz, 1H), 8.37 (d, J = 5.2 Hz, 1H), 8.20 (dd, J = 4.9, 1.9 Hz, 1H), 7.37-7.30 (m, 2H), 7.18-7.10 (m, 1H), 4.99 (s, 1H), 4.42 (s, 1H), 3.40-3.35 (m, 3H), 3.21 (t, J = 12.9 Hz, 1H), 2.87 (dd, J = 37.1, 14.2 Hz, 1H), 2.62-2.39 (m, 4H), 1.89-1.64 (m, 4H) | Example 40 |
| 254 | N-(2,3,6-trifluoro-4-((3-(2-(((3S,5S)-5-fluoropiperidin-3-yl)amino)pyrimidin-4-yl)pyridin-2-yl)oxy)phenyl)-1-(6-(trifluoromethyl)pyridin-3-yl)methanesulfonamide | 658.1 | (400 MHz, CD₃OD) δ 8.83 (d, J = 2.0 Hz, 1H), 8.56 (d, J = 7.5 Hz, 1H), 8.39 (d, J = 5.3 Hz, 1H), 8.23-8.15 (m, 2H), 7.86 (d, J = 8.0 Hz, 1H), 7.38 (d, J = 5.2 Hz, 1H), 7.33 (m, 1H), 7.14-7.04 (m, 1H), 5.08-4.91 (m, 1H), 4.62 (s, 2H), 4.47 (s, 1H), 3.44 (d, J = 11.8 Hz, 1H), 3.27 (d, J = 12.1 Hz, 1H), 2.94 (m, 1H), 2.64 (t, J = 11.5 Hz, 1H), 2.50-2.38 (s, 1H), 1.96-1.80 (m, 1H). | Example 40 |
| 255 | 1-(4-cyanophenyl)-N-(2,3,6-trifluoro-4-((3-(2-(((3S,5S)-5-fluoropiperidin-3-yl)amino)pyrimidin-4-yl)pyridin-2-yl)oxy)-5-methylphenyl)methanesulfonamide | 628.2 | (300 MHz, DMSO-d₆) δ 8.48-8.36 (m, 2H), 8.28 (dd, J = 4.8, 1.9 Hz, 1H), 7.95-7.86 (m, 2H), 7.68 (d, J = 8.2 Hz, 2H), 7.60 (dd, J = 9.5, 6.2 Hz, 1H), 7.43 (dd, J = 7.6, 4.9 Hz, 1H), 7.24 (dd, J = 10.3, 6.6 Hz, 2H), 4.91-4.65 (m, 3H), 4.13 (s, 1H), 3.25 (s, 3H), 3.05 (d, J = 13.0 Hz, 1H), 2.91 (t, J = 13.4 Hz, 1H), 2.68 (dd, J = 34.3, 13.9 Hz, 1H), 2.48-2.35 (m, 1H), 2.15 (s, 1H), 1.81 (dt, J = 38.7, 12.0 Hz, 1H) | Example 54 |
| 256 | 1-(pyridin-3-yl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 590.1 | (400 MHz, CD₃OD) δ 8.67 (s, 1H), 8.55-8.51 (m, 2H), 8.36 (d, J = 2.6 Hz, 1H), 8.20-8.18 (m, 1H), 8.01 (d, J = 4.0 Hz, 1H), 7.48-7.47 (m, 1H), 7.40-7.29 (m, 2H), 7.14 (t, J = 3.6 Hz, 1H), 4.99-4.89 (m, 1H), 4.54 (s, 2H), 4.44 (s, 1H), 3.38-3.35 (m, 1H), 3.22-3.13 (m, 1H), 2.93-2.80 (m, 1H), 2.65-2.60 (m, 1H), 2.55-2.41 (m, 1H), 1.93-1.79 (m, 1H) | Example 40 |
| 257 | 1-phenyl-N-(2,3,6-trifluoro-4-((3-(2-(((3S,6S)-6-methylpiperidin-3-yl)amino)pyrimidin-4-yl)pyridin-2-yl)oxy)phenyl)methanesulfonamide | 585.2 | (400 MHz, CD₃OD) δ 8.53 (d, J = 6.4 Hz, 1H), 8.37 (d, J = 5.2 Hz, 1H), 8.19 (d, J = 6.4 Hz, 1H), 7.50-7.48 (m, 2H), 7.38-7.29 (m, 5H), 7.04-6.99 (m, 1H), 4.40 (s, 2H), 4.13-4.02 (m, 1H), 3.54-3.50 (m, 1H), 3.00-2.85 (m, 1H), 2.66-2.60 (m, 1H), 2.19-2.16 (m, 1H), 1.97-1.93 (m, 1H),1.64-1.45 (m, 2H), 1.24 (d, J = 4.8 Hz, 3H) | Example 56 |
| 258 | N-(2,3,6-trifluoro-4-((3-(2-(((3S,5S)-5-fluoropiperidin-3-yl)amino)pyrimidin-4-yl)pyridin-2-yl)oxy)phenyl)pyrrolidine-1-sulfonamide | 568.1 | (400 MHz, CD₃OD) δ 8.56 (d, J = 7.2 Hz, 1H), 8.36 (d, J = 5.2 Hz, 1H), 8.20 (dd, J = 4.8, 2.0 Hz, 1H), 7.37-7.29 (m, 2H), 7.18-7.09 (m, 1H), 4.82 (s, 1H), 4.38 (s, 1H), 3.42-3.34 (m, 4H), 3.29-3.18 (m, 1H), 3.14 (t, J = 12.8 Hz, 1H), 2.88-2.71(m, 1H), 2.58-2.48 (m, 1H), 2.40 (s, 1H), 2.03-1.92 (m, 4H), 1.95-1.73 (m, 1H). | Example 54 |
| 259 | 1-phenyl-N-(2,3,6-trifluoro-4-((3-(2-(((3S,5R)-5-fluoropiperidin-3-yl)amino)pyrimidin-4-yl)pyridin-2-yl)oxy)phenyl)methanesulfonamide | 589.2 | (400 MHz, CD₃OD) δ 8.54 (d, J = 7.6 Hz, 1H), 8.39 (d, J = 5.2 Hz, 1H), 8.22 (dd, J = 4.9, 1.9 Hz, 1H), 7.50-7.48 (m, 2H), 7.41-7.31 (m, 5H), 7.17 (t, J = 7.4 Hz, 1H), 4.71 (d, J = 48.7 Hz, 1H), 4.53 (s, 2H), 4.18 (s, 1H), 3.17-3.16 (m, 2H), 2.81-2.67 (m, 2H), 2.41-2.34 (m, 1H), 1.89 (s, 1H) | Example 40 |
| 260 | 2,2,2-trifluoro-N-(2,3,6-trifluoro-4-((3-(2-(((3S,5S)-5-fluoropiperidin-3-yl)amino)pyrimidin-4- | 581.8 | (400 MHz, CD₃OD) δ 8.74 (s, 1H), 8.51 (t, J = 8.5 Hz, 1H), 8.36 (s, 1H), 7.86-7.85 (m, 1H), 7.43-7.42 (m, 1H), 7.31-7.29 (m, 1H), 5.31 (d, J = 44.7 Hz, 1H), | Example 40 |

TABLE A1-continued

| Cpd No. | Name | MS m/z | ¹H NMR (ppm) | Synth. Method |
|---|---|---|---|---|
| | yl)pyridin-2-yl)oxy)phenyl)ethane-1-sulfonamide hydrochloride | | 4.90-4.80 (s, 1H), 4.35 (q, J = 9.3 Hz, 2H), 3.78-3.64 (m, 2H), 3.50-3.40 (m, 1H), 3.10 (s, 1H), 2.63 (s, 1H), 2.20-2.10 (m, 1H) | |
| 261 | 1-(1-fluorocyclopropyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 571.1 | (400 MHz, CD₃OD) δ 8.57 (d, J = 7.3 Hz, 1H), 8.37 (d, J = 5.3 Hz, 1H), 8.20 (dd, J = 4.8, 1.9 Hz, 1H), 7.38-7.30 (m, 2H), 7.17-7.11 (m, 1H), 5.00-4.80 (m, 1H), 4.42 (s, 1H), 3.80 (s, 1H), 3.74 (d, J = 20.4 Hz, 1H), 3.36-3.31 (m, 1H), 3.21 (t, J = 12.8 Hz, 1H), 2.87 (dd, J = 37.0, 14.2 Hz, 1H), 2.62-2.53 (m, 1H), 2.43 (s, 1H), 1.95-1.75 (m, 1H), 1.25-1.15 (m, 2H), 1.04-0.96 (m, 2H) | Example 40 |
| 262 | 1-phenyl-N-(2,3,6-trifluoro-4-(3-(2-(((3S,5R)-5-(fluoromethyl)piperidin-3-yl)amino)pyrimidin-4-yl)pyridin-2-yl)oxy)phenyl)methanesulfonamide | 603.2 | (400 MHz, CD₃OD) δ 8.54 (d, J = 7.6 Hz, 1H), 8.36 (d, J = 5.2 Hz, 1H), 8.20 (dd, J = 4.9, 1.9 Hz, 1H), 7.50 (dd, J = 7.7, 1.8 Hz, 2H), 7.42-7.35 (m, 1H), 7.39-7.27 (m, 4H), 7.09 (ddd, J = 9.8, 6.6, 2.2 Hz, 1H), 4.49-4.33 (m, 3H), 4.37-4.21 (m, 1H), 4.16 (s, 1H), 3.44 (dd, J = 12.1, 4.3 Hz, 1H), 3.20 (d, J = 11.9 Hz, 1H), 2.49 (d, J = 11.8 Hz, 1H), 2.43 (d, J = 11.1 Hz, 1H), 2.15 (t, J = 14.8 Hz, 2H), 1.35 (q, J = 12.4 Hz, 1H) | Example 61 |
| 263 | N-(2,3,6-trifluoro-4-((3-(2-(((3S,5S)-5-fluoropiperidin-3-yl)amino)pyrimidin-4-yl)pyridin-2-yl)oxy)phenyl)piperidine-1-sulfonamide | 582.2 | (400 MHz, CD₃OD) δ 8.58 (s, 1H), 8.37 (d, J = 5.2 Hz, 1H), 8.21 (dd, J = 4.8, 2.0 Hz, 1H), 7.34 (dd, J = 7.6, 4.8 Hz, 2H), 7.19-7.09 (m, 1H), 4.83 (s, 1H), 4.39 (s, 1H), 3.27 (t, J = 5.2 Hz, 5H), 3.15 (t, J = 13.2 Hz, 1H), 2.88-2.69 (m, 1H), 2.58-2.48 (m, 1H), 2.41 (s, 1H), 1.83 (dt, J = 40.0, 12.0 Hz, 1H), 1.66 (d, J = 5.6 Hz, 4H), 1.60 (d, J = 4.8 Hz, 2H) | Example 57 |
| 264 | 1-(2,2-difluorocyclobutyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 603.1 | (300 MHz, CD₃OD) δ 8.57 (d, J = 7.5 Hz, 1H), 8.38 (d, J = 5.3 Hz, 1H), 8.31-8.20 (m, 1H), 7.41-7.26 (m, 2H), 7.15 (t, J = 8.9 Hz, 1H), 5.10-4.86 (m, 2H), 4.42 (s, 1H), 3.58-3.48 (m, 1H), 3.40-3.37 (m, 2H), 3.21 (t, J = 12.9 Hz, 1H), 2.95-2.86 (m, 1H), 2.70-2.41 (m, 4H), 2.19 (s, 1H), 1.96-1.64 (m, 2H) | Example 40 |
| 265 | 1-(2,2-difluorocyclobutyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 603.2 | (300 MHz, CD₃OD) δ 8.57 (d, J = 7.7 Hz, 1H), 8.38 (d, J = 5.3 Hz, 1H), 8.25-8.14 (m, 1H), 7.40-7.30 (m, 2H), 7.22-7.08 (m, 1H), 5.05-4.80 (m, 2H) 4.42 (s, 1H), 3.59-3.23 (m, 4H), 2.99-2.74 (m, 1H), 2.70-2.37 (m, 4H), 2.19 (s, 1H), 2.00-1.62 (m, 2H) | Example 40 |
| 266 | 4-(2-(4-(dimethylsulfamoylamino)-2,3,5-trifluoro-phenoxy)-3-pyridyl)-2-(((3S,5S)-5-fluoro-3-piperidyl)amino)pyrimidine | 542.1 | (300 MHz, CD₃OD) δ 8.55 (d, J = 7.2 Hz, 1H), 8.34 (d, J = 5.2 Hz, 1H), 8.18 (m, 1H), 7.38-7.26 (m, 2H), 7.20-7.02 (m, 1H), 4.93-4.79 (m, 1H), 4.36 (s, 1H), 3.34-3.33(m, 1H), 3.13 (t, J = 13.6 Hz, 1H), 2.86 (s, 6H), 2.81-2.71 (m, 1H), 2.60-2.45 (m, 1H), 2.39 (s, 1H), 1.96-1.66 (m, 1H) | Example 64 |
| 267 | 2-cyclopropyl-N-(2,3,6-trifluoro-4-((3-(2-(((3S,5S)-5-fluoropiperidin-3-yl)amino)pyrimidin-4-yl)pyridin-2-yl)oxy)phenyl)ethane-1-sulfonamide | 567.2 | (300 MHz, CD₃OD) δ 8.54-8.51 (m, 1H), 8.35 (d, J = 5.1 Hz, 1H), 8.18 (d, J = 5.1 Hz, 1H), 7.34-7.30 (m, 2H), 7.18-7.12 (m, 1H), 5.00-4.88 (m, 2H), 4.80-4.75 (m, 1H), 4.42-4.31 (m, 1H), 3.20-3.02 (m, 2H), 2.88-2.71 (m, 1H), 2.55-2.31 (m, 1H), 1.88-1.76 (m, 3H), 0.89-0.85 (m, 1H), 0.55-0.49 (m, 2H), 0.18-0.13 (m, 2H) | Example 40 |
| 268 | 2,2-difluoro-N-(2,3,6-trifluoro-3-(2-(((3S,5S)-5-fluoropiperidin-3-yl)amino)pyrimidin-4-yl)pyridin-2-yl)oxy)phenyl)butane-1-sulfonamide | 609.2 | (400 MHz, CD₃OD) δ 8.54 (d, J = 6.1 Hz, 2H), 8.27 (s, 1H), 7.83 (s, 1H), 7.29 (t, J = 7.7 Hz, 1H), 5.34-5.23 (m, 1H), 4.99-4.98 (m, 1H), 3.95 (t, J = 13.2 Hz, 2H), 3.81-3.64 (m, 2H), 3.42-3.33 (m, 1H), 3.08 (t, J = 11.7 Hz, 1H), 2.62 (s, 1H), 2.29-2.00 (m, 3H), 1.09 (t, J = 7.5 Hz, 3H) | Example 40 |
| 269 | 4-(2-(4-((ethyl(methyl)sulfamoyl)amino)-2,3,5-trifluoro-phenoxy)- | 556.2 | (400 MHz, CD₃OD) δ 8.57 (d, J = 7.5 Hz, 1H), 8.37 (d, J = 5.3 Hz, 1H), 8.20 (m, 1H), 7.45-7.22 (m, 2H), 7.21-7.01 (m, | Example 64 |

TABLE A1-continued

| Cpd No. | Name | MS m/z | ¹H NMR (ppm) | Synth. Method |
|---|---|---|---|---|
| | 3-pyridyl)-2-(((3S,5S)-5-fluoro-3-piperidyl)amino)pyrimidine | | 1H), 4.91-4.80 (m, 1H), 4.38 (s, 1H), 3.31-3.22 (m, 3H), 3.14 (t, J = 12.8 Hz, 1H), 2.90 (s, 3H), 2.87-2.68 (m, 1H), 2.59-2.49 (m, 1H), 2.41 (s, 1H), 1.95-1.72 (m, 1H), 1.18 (t, J = 7.1 Hz, 3H) | |
| 270 | 2,2-difluoro-N-(2,3,6-trifluoro-4-((3-(2-(((3S,5S)-5-fluoropiperidin-3-yl)amino)pyrimidin-4-yl)-6-methylpyridin-2-yl)oxy)phenyl)butane-1-sulfonamide | 605.2 | (300 MHz, CD₃OD) δ 8.62 (s, 1H), 8.46 (d, J = 6.1 Hz, 1H), 7.78 (s, 1H), 7.26 (dd, J = 13.9, 7.6 Hz, 2H), 5.30 (d, J = 44.8 Hz, 1H), 3.95 (t, J = 13.2 Hz, 2H), 3.68 (d, J = 16.1 Hz, 2H), 3.43 (d, J = 14.3 Hz, 1H), 3.28 (s, 1H), 3.09 (t, J = 11.6 Hz, 1H), 2.62 (s, 1H), 2.46 (s, 3H), 2.31-1.96 (m, 3H), 1.09 (t, J = 7.5 Hz, 3H) | Example 40 |
| 271 | 1-(2,2-difluorocyclopropyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 589.1 | (300 MHz, DMSO-d₆) δ 8.42 (d, J = 5.1 Hz, 2H), 8.27 (dd, J = 4.8, 1.8 Hz, 1H), 7.44-7.31 (m, 3H), 7.29 (s, 1H), 5.01-4.86 (m, 1H), 4.25 (s, 1H), 3.27 (d, J = 7.2 Hz, 2H), 3.17 (d, J = 10.2 Hz, 1H), 3.07 (d, J = 13.5 Hz, 2H), 2.92 (d, J = 13.6 Hz, 1H), 2.58 (s, 1H), 2.21 (s, 2H), 1.82-1.72 (m, 2H), 1.47 (dd, J = 12.6, 4.5 Hz, 1H) | Example 40 |
| 272 | N-(4-((3-(2-(((1r,4r)-4-(dimethylamino)cyclohexyl)amino)pyrimidin-4-yl)pyridin-2-yl)oxy)-2,3,6-trifluorophenyl)-1-phenylmethanesulfonamide hydrochloride | 613.2 | (400 MHz, CD₃OD) δ 8.60 (d, J = 6.2 Hz, 1H), 8.42 (d, J = 6.3 Hz, 1H), 8.35 (d, J = 5.2 Hz, 1H), 7.65 (d, J = 6.3 Hz, 1H), 7.52 (dd, J = 6.7, 2.8 Hz, 2H), 7.42 (dd, J = 5.1, 2.0 Hz, 2H), 7.27 (t, J = 7.2 Hz, 1H), 4.57 (s, 2H), 3.48-3.41 (s, 2H), 2.90 (s, 6H), 2.34 (d, J = 12.5 Hz, 2H), 2.18 (s, 2H), 1.78-1.68 (m, 2H), 1.63 (d, J = 11.1 Hz, 1H), 1.57 (d, J = 11.5 Hz, 1H) | Example 38 |
| 273 | N-(2,3-difluoro-4-((3-(2-(((S)-piperidin-3-yl)amino)pyrimidin-4-yl)pyridin-2-yl)oxy)phenyl)-N'-methyl-1-phenylmethanesulfonimidamide | 566.2 | (300 MHz, DMSO-d₆) δ 8.38-8.36 (m, 2H), 8.20 (dd, J = 4.8, 1.9 Hz, 1H), 7.54-7.36 (m, 5H), 7.34-7.30 (m, 1H), 7.21 (d, J = 5.1 Hz, 1H), 7.13 (d, J = 8.0 Hz, 1H), 7.09-6.94 (m, 2H), 4.64 (s, 2H), 3.83 (s, 1H), 3.07 (d, J = 11.9 Hz, 1H), 2.78 (d, J = 12.4 Hz, 1H), 2.58 (s, 3H), 2.42-2.36 (m, 2H), 1.89 (s, 1H), 1.64-1.61 (m, 1H), 1.49-1.13 (m, 2H) | Example 71 |
| 274 | N-(2,3-difluoro-4-((3-(2-(((S)-piperidin-3-yl)amino)pyrimidin-4-yl)pyridin-2-yl)oxy)phenyl)-N'-methyl-1-phenylmethanesulfonimidamide | 566.2 | (300 MHz, DMSO-d₆) δ 8.37 (d, J = 5.1 Hz, 2H), 8.20 (dd, J = 4.8, 1.9 Hz, 1H), 7.54-(m, 5H), 7.32 (dd, J = 7.5, 4.8 Hz, 1H), 7.21 (d, J = 5.1 Hz, 1H), 7.13 (d, J = 8.0 Hz, 1H), 7.08-6.95 (m, 2H), 4.64 (s, 2H), 3.83 (s, 1H), 3.07 (d, J = 11.7 Hz, 1H), 2.78 (d, J = 12.5 Hz, 1H), 2.58 (s, 3H), 2.51-2.32 (m, 2H), 1.90 (s, 1H), 1.64-1.61 (m, 1H), 1.49-1.13 (m, 2H) | Example 71 |
| 275 | 1-(2-fluorophenyl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide | 621.1 | (300 MHz, CD₃OD) δ 8.55 (d, J = 7.5 Hz, 1H), 8.37 (d, J = 5.2 Hz, 1H), 8.21-8.19 (m, 1H), 7.62-7.54 (m, 1H), 7.44-7.28 (m, 3H), 7.24-7.07 (m, 3H), 4.58 (s, 2H), 4.38 (s, 1H), 3.39-3.37 (m, 1H), 3.07 (t, J = 12.0 Hz, 1H), 2.80-2.69 (m, 1H), 2.59-2.39 (m, 2H), 1.81-1.52 (m, 1H), 1.37 (s, J = 21.0 Hz, 3H) | Example 42 |
| 276 | 1-(4-((3-(2-(((3S,5S)-5-Fluoropiperidin-3-yl)amino)pyrimidin-4-yl)pyridin-2-yl)oxy)phenyl)-3-(3-(trifluoromethyl)phenyl)urea | 568.2 | (400 MHz, DMSO-d₆) δ 9.09 (s, 1H), 8.86 (s, 1H), 8.38 (d, J = 5.1 Hz, 2H), 8.25-8.20 (m, 1H), 8.03 (d, J = 2.3 Hz, 1H), 7.59 (d, J = 8.6 Hz, 1H), 7.55-7.47 (m, 3H), 7.34-7.25 (m, 3H), 7.19 (d, J = 8.0 Hz, 1H), 7.14-7.09 (m, 2H), 4.87-4.74 (m, 1H), 4.15 (s, 1H), 3.05 (d, J = 12.1 Hz, 1H), 2.95-2.85 (m, 1H), 2.73-2.65 (m, 1H), 2.47-2.29 (m, 1H), 2.15 (s, 1H), 1.90-1.75 (m, 1H) | Example 73 |
| 277 | 1-phenyl-N-(2,3,6-trifluoro-4-((3-(2-((5-(fluoromethyl)piperidin-3-yl)amino)pyrimidin-4-yl)pyridin-2-yl)oxy)phenyl)methanesulfonamide | 603.2 | (400 MHz, CD₃OD) δ 8.52 (dd, J = 7.6, 1.9 Hz, 1H), 8.39 (d, J = 5.3 Hz, 1H), 8.20 (dd, J = 4.8, 1.9 Hz, 1H), 7.55-7.48 (m, 2H), 7.43-7.35 (m, 4H), 7.32 (dd, J = 7.5, 4.8 Hz, 1H), 7.09-7.00 (m, 1H), 4.50-4.40 (m, 3H), 4.32-4.26 (m, 2H), | Example 74 |

TABLE A1-continued

| Cpd No. | Name | MS m/z | ¹H NMR (ppm) | Synth. Method |
|---|---|---|---|---|
| | | | 3.25 (d, J = 13.4 Hz, 1H), 3.21-3.13 (m, 1H), 2.99 (dd, J = 13.0, 3.0 Hz, 1H), 2.68 (dd, J = 12.6, 9.9 Hz, 1H), 2.24 (s, 1H), 2.00 (d, J = 13.9 Hz, 1H), 1.79-1.68 (m, 1H) | |
| 278 | 1-phenyl-N-(2,3,6-trifluoro-4-((3-(2-((5-(fluoromethyl)piperidin-3-yl)amino)pyrimidin-4-yl)pyridin-2-yl)oxy)phenyl)methanesulfonamide | 603.2 | (400 MHz, CD₃OD) δ 8.52 (dd, J = 7.6, 1.9 Hz, 1H), 8.39 (d, J = 5.3 Hz, 1H), 8.20 (dd, J = 4.8, 1.9 Hz, 1H), 7.55-7.48 (m, 2H), 7.43-7.35 (m, 4H), 7.32 (dd, J = 7.5, 4.8 Hz, 1H), 7.09-7.00 (m, 1H), 4.50-4.40 (m, 3H), 4.32-4.26 (m, 2H), 3.25 (d, J = 13.4 Hz, 1H), 3.21-3.13 (m, 1H), 2.99 (dd, J = 13.0, 3.0 Hz, 1H), 2.68 (dd, J = 12.6, 9.9 Hz, 1H), 2.24 (s, 1H), 2.00 (d, J = 13.9 Hz, 1H), 1.79-1.68 (m, 1H) | Example 74 |
| 279 | N-(2,3-difluoro-4-((3-(2-(((3S,5S)-5-fluoro-5-methylpiperidin-3-yl)amino)pyrimidin-4-yl)pyridin-2-yl)oxy)-6-methylphenyl)-1-phenylmethane sulfonamide | 599.2 | (400 MHz, CD₃OD) δ 8.59 (d, J = 7.6 Hz, 1H), 8.37 (d, J = 5.2 Hz, 1H), 8.20-8.10 (m, 1H), 7.45-7.39 (m, 4H), 7.42-7.32 (m, 3H), 7.34-7.24 (m, 1H), 7.08-7.01 (m, 1H), 4.50 (s, 2H), 4.36 (s, 1H), 3.36-3.32 (m, 1H), 3.02 (t, J = 12.5 Hz, 1H), 2.68-2.58 (m, 1H), 2.41-2.35 (m, 2H), 2.09 (s, 3H), 1.71-1.61 (m, 1H), 1.36 (d, J = 20.9 Hz, 3H) | Example 42 |
| 280 | N-(2,3-difluoro-4-((3-(2-(((3S,5S)-5-fluoropiperidin-3-yl)amino)pyrimidin-4-yl)pyridin-2-yl)oxy)-6-methylphenyl)-1-phenylmethanesulfonamide | 585.1 | (400 MHz, CD₃OD) δ 8.60 (d, J = 7.5 Hz, 1H), 8.37 (d, J = 5.3 Hz, 1H), 8.16-8.15 (m, 1H), 7.46-7.33 (m, 7H), 7.34-7.24 (m, 1H), 7.08-7.01 (m, 1H), 4.94-4.82 (m, 1H), 4.50 (s, 2H), 4.39 (s, 1H), 3.15-3.13 (m, 1H), 2.85-2.75 (m, 1H), 2.58-2.47 (m, 1H), 2.41-2.40 (m, 1H), 2.09 (t, J = 1.0 Hz, 3H), 1.94-1.74 (m, 1H) | Example 40 |
| 281 | 1-(2,4-difluorophenyl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide | 639.1 | (400 MHz, CD₃OD) δ 8.56 (s, 1H), 8.38 (d, J = 5.2 Hz, 1H), 8.21 (m, 1H), 7.66-7.52 (m, 1H), 7.41-7.26 (m, 2H), 7.13 (t, J = 8.3 Hz, 1H), 7.07-6.90 (m, 2H), 4.55 (s, 2H), 4.38 (s, 1H), 3.39-3.33 (m, 1H), 3.17-3.01 (m, 1H), 2.80-2.69 (m, 1H), 2.43 (t, J = 12.2 Hz, 2H), 1.80-1.68 (m, 1H), 1.45-1.24 (m, 3H) | Example 42 |
| 282 | 1-(2,6-difluorophenyl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide | 639.2 | (400 MHz, CD₃OD) δ 8.56 (d, J = 7.6 Hz, 1H), 8.37 (d, J = 5.2 Hz, 1H), 8.20 (dd, J = 4.8, 2.0 Hz, 1H), 7.45-7.34 (m, 2H), 7.31 (dd, J = 7.6, 4.8 Hz, 1H), 7.06-6.97 (m, 3H), 4.56 (s, 2H), 4.36 (s, 1H), 3.41-3.33 (m, 1H), 3.03 (t, J = 12.4 Hz, 1H), 2.73-2.64 (m, 1H), 2.42-2.36 (m, 2H), 1.74-1.59 (m, 1H), 1.39-1.31 (m, 3H) | Example 42 |
| 283 | N-(2,3-difluoro-4-((3-(2-(((3S,5S)-5-fluoropiperidin-3-yl)amino)pyrimidin-4-yl)pyridin-2-yl)oxy)-5-methylphenyl)-1-(2,6-difluorophenyl)methanesulfonamide | 621.1 | (400 MHz, CD₃OD) δ 8.60 (d, J = 7.5 Hz, 1H), 8.39 (d, J = 5.2 Hz, 1H), 8.21-8.11 (m, 1H), 7.49-7.37 (m, 2H), 7.34-7.24 (m, 1H), 7.16 (d, J = 7.6 Hz, 1H), 7.08-6.98 (m, 2H), 5.00 (s, 1H), 4.65 (s, 2H), 4.44 (s, 1H), 3.38 (d, J = 13.7 Hz, 1H), 3.22 (t, J = 12.7 Hz, 1H), 2.93-2.83 (m, 1H), 2.65-2.54 (m, 1H), 2.44 (s, 1H), 2.09 (t, J = 1.0 Hz, 3H), 1.97-1.76 (m, 1H) | Example 40 |
| 284 | 1-p-tolyl-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide | 617.1 | (300 MHz, CD₃OD) δ 8.54 (d, J = 7.5 Hz, 1H), 8.36 (d, J = 5.4 Hz, 1H), 8.19 (m, 1H), 7.44-7.26 (m, 4H), 7.17 (m, 3H), 4.46 (s, 2H), 4.37 (s, 1H), 3.39-3.33 (m, 1H), 3.15-3.07 (m, 1H), 2.79-2.59 (m, 1H), 2.50-2.31 (m, 5H), 1.67 (m, 1H), 1.37 (d, J = 21.0 Hz, 3H) | Example 42 |
| 285 | 1-(4-((3-(2-(((3S,5S)-5-fluoropiperidin-3-yl)amino)pyrimidin-4-yl)pyridin-2-yl)oxy)phenyl)-3-(4-((4-methylpiperazin-1-yl)methyl)-3-(trifluoromethyl)phenyl)urea hydrochloride | 680.3 | (400 MHz, CD₃OD) δ 8.74 (s, 1H), 8.50 (d, J = 6.5 Hz, 1H), 8.33 (dd, J = 4.8, 1.9 Hz, 1H), 8.10 (d, J = 2.2 Hz, 1H), 8.01-7.88 (m, 2H), 7.80 (d, J = 8.5 Hz, 1H), 7.60-7.55 (m, 2H), 7.36 (dd, J = 7.7, 4.8 Hz, 1H), 7.21-7.14 (m, 2H), 5.32 (d, J = 44.9 Hz, 1H), 4.93 (s, 1H), 4.37 (s, 2H), 3.87-3.65 (m, 4H), 3.65-3.40 (m, 5H), 3.36 (d, J = 3.3 Hz, 2H), 3.14 (t, J = 11.9 Hz, 1H), 3.01 (s, 3H), 2.64 (s, 1H), 2.16 (dt, J = 43.0, 13.9 Hz, 1H) | Example 81 |

TABLE A1-continued

| Cpd No. | Name | MS m/z | ¹H NMR (ppm) | Synth. Method |
|---|---|---|---|---|
| 286 | 1-(3-((3-(2-(((3S,5S)-5-fluoropiperidin-3-yl)amino)pyrimidin-4-yl)pyridin-2-yl)oxy)phenyl)-3-(4-((4-methylpiperazin-1-yl)methyl)-3-(trifluoromethyl)phenyl)urea hydrochloride | 680.3 | (400 MHz, CD₃OD) δ 8.74 (d, J = 7.1 Hz, 1H), 8.51 (d, J = 6.5 Hz, 1H), 8.36 (dd, J = 4.8, 1.9 Hz, 1H), 8.10 (d, J = 2.2 Hz, 1H), 7.95 (d, J = 8.2 Hz, 2H), 7.79 (d, J = 8.5 Hz, 1H), 7.59 (t, J = 2.2 Hz, 1H), 7.44-7.35 (m, 2H), 7.28-7.22 (m, 1H), 6.92-6.85 (m, 1H), 5.32 (d, J = 44.8 Hz, 1H), 4.95 (s, 1H), 4.46 (s, 2H), 3.94-3.34 (m, 11H), 3.15 (t, J = 12.0 Hz, 1H), 3.02 (s, 3H), 2.65 (s, 1H), 2.17 (dt, J = 42.7, 13.4 Hz, 1H) | Example 81 |
| 287 | N-(4-((3-(2-((1-azabicyclo[3.3.1]nonan-3-yl)amino)pyrimidin-4-yl)pyridin-2-yl)oxy)-2,3,6-trifluorophenyl)-1-83phenylmethanesulfonamide hydrochloride | 611.2 | (400 MHz, CD₃OD) δ 8.62 (s, 1H), 8.46 (dd, J = 5.8, 2.1 Hz, 1H), 8.28 (d, J = 4.4 Hz, 1H), 7.57-7.50(m, 3H), 7.42-7.37 (m, 4H), 7.22 (t, J = 8.5 Hz, 1H), 4.88 (s, 1H), 4.87 (s, 1H), 4.73 (s, 1H), 4.55 (s, 2H), 3.99 (dd, J = 13.0, 6.7 Hz, 1H), 3.63 (d, J = 12.8 Hz, 1H), 3.10-3.06 (m, 2H), 2.59-2.50 (m, 2H), 2.44-2.31 (m, 1H), 1.88-1.77 (m, 3H), 1.63 (t, J = 12.9 Hz, 1H). | Example 38 |
| 288 | N-(4-((3-(2-((1-azabicyclo[3.3.1]nonan-3-yl)amino)pyrimidin-4-yl)pyridin-2-yl)oxy)-2,3,6-trifluorophenyl)-1-phenylmethanesulfonamide | 611.2 | (400 MHz, DMSO-d₆) δ 8.41 (s, 2H), 8.26 (d, J = 4.7 Hz, 1H), 7.43-7.33 (m, 7H), 7.23 (d, J = 5.0 Hz, 1H), 7.13 (d, J = 8.1 Hz, 1H), 4.76 (s, 1H), 4.33 (s, 2H), 3.42 (s, 1H), 3.05 (s, 2H), 2.90-2.78 (m, 3H), 2.11 (s, 1H), 1.84-1.81 (m, 5H), 1.58-1.53 (m, 1H) | Example 38 |
| 290 | 1-o-tolyl-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide | 617.1 | (400 MHz, CD₃OD) δ 8.57 (s, 1H), 8.38 (d, J = 5.3 Hz, 1H), 8.32-8.22 (m, 1H), 7.44 (d, J = 7.3 Hz, 1H), 7.37-7.30 (m, 2H), 7.28-7.14 (m, 4H), 4.61 (s, 2H), 4.40-4.35 (m, 1H), 3.40-3.37 (m, 1H), 3.05 (t, J = 11.7 Hz, 1H), 2.50-2.68 (m, 1H), 2.48 (s, 3H), 2.45-2.30 (m, 2H), 1.80-1.67 (m, 1H), 1.37 (d, J = 20.9 Hz, 3H) | Example 42 |
| 291 | 1-(3-methoxyphenyl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide | 633.2 | (400 MHz, CD₃OD) δ 8.56 (s, 1H), 8.38 (d, J = 5.2 Hz, 1H), 8.25-8.21 (m, 1H), 7.38-7.25 (m, 3H), 7.18-7.11 (m, 1H), 7.10-7.05 (m, 2H), 6.97-6.91 (m, 1H), 4.48 (s, 2H), 4.37-4.33 (m, 1H), 3.83 (s, 3H), 3.37-3.33(m, 1H), 3.05 (t, J = 11.6 Hz, 1H), 2.70-2.66 (m, 1H), 2.44-2.31 (m, 2H), 1.67-1.56 (m, 1H), 1.37 (d, J = 21.0 Hz, 3H) | Example 42 |
| 292 | N-(2,6-difluoro-4-((3-(2-(((3S,5S)-5-fluoro-5-methylpiperidin-3-yl)amino)pyrimidin-4-yl)pyridin-2-yl)oxy)-3-methylphenyl)-1-phenylmethanesulfonamide | 599.2 | (300 MHz, CD₃OD) δ 8.68 (s, 1H), 8.46 (d, J = 5.6 Hz, 1H), 8.27 (d, J = 4.6 Hz, 1H), 7.70 (s, 1H), 7.54-7.46 (m, 2H), 7.45-7.32 (m, 4H), 6.95 (d, J = 10.2 Hz, 1H), 4.50 (s, 2H), 3.78-3.43 (m, 2H), 3.27-2.83 (m, 2H), 2.49 (s, 1H), 2.18-1.80 (m, 4H), 1.54 (d, J = 21.5 Hz, 3H), 1.28 (s, 1H) | Example 42 |
| 293 | N-(2,6-difluoro-4-((3-(2-(((3S,5S)-5-fluoropiperidin-3-yl)amino)pyrimidin-4-yl)pyridin-2-yl)oxy)-3-methylphenyl)-1-(2,6-difluorophenyl)methanesulfonamide | 621.1 | (300 MHz, CD₃OD) δ 8.58 (d, J = 7.5 Hz, 1H), 8.37 (d, J = 5.2 Hz, 1H), 8.20 (dd, J = 4.8, 2.0 Hz, 1H), 7.53-7.25 (m, 3H), 7.05 (t, J = 8.0 Hz, 2H), 6.90 (dd, J = 10.4, 2.2 Hz, 1H), 4.98-4.78 (m, 1H), 4.67 (s, 2H), 4.38 (s, 1H), 3.31-3.22 (m, 1H), 3.11 (d, J = 12.2 Hz, 1H), 2.91-2.68 (m, 1H), 2.61-2.33 (m, 2H), 2.08 (d, J = 1.9 Hz, 3H), 1.97-1.67 (m, 1H) | Example 40 |
| 294 | 1-phenyl-N-(2,3,6-trifluoro-4-((3-(2-((5-(fluoromethyl)-5-methylpiperidin-3-yl)amino)pyrimidin-4-yl)pyridin-2-yl)oxy)phenyl)methanesulfonamide | 617.2 | (300 MHz, DMSO-d₆) δ 8.40 (d, J = 5.1 Hz, 2H), 8.32-8.22 (m, 1H), 7.48-7.30 (m, 7H), 7.29-7.19 (m, 2H), 4.73-4.29 (m, 4H), 4.01 (s, 2H), 3.22 (d, J = 11.6 Hz, 1H), 2.84 (d, J = 12.7 Hz, 1H), 2.38-2.28 (m, 2H), 1.92 (d, J = 12.7 Hz, 1H), 1.37-1.23 (m, 1H), 0.92 (s, 3H) | Example 88 |
| 295 | 1-phenyl-N-(2,3,6-trifluoro-4-((3-(2-((5-(fluoromethyl)-5-methylpiperidin-3- | 617.2 | (300 MHz, DMSO-d₆) δ 8.40 (d, J = 5.1 Hz, 2H), 8.32-8.22 (m, 1H), 7.48-7.30 (m, 7H), 7.29-7.18 (m, 2H), 4.70-4.29 | Example 88 |

TABLE A1-continued

| Cpd No. | Name | MS m/z | ¹H NMR (ppm) | Synth. Method |
|---|---|---|---|---|
| | yl)amino)pyrimidin-4-yl)pyridin-2-yl)oxy)phenyl)methanesulfonamide | | (m, 4H), 4.01 (s, 1H), 3.22 (d, J = 11.4 Hz, 1H), 2.84 (d, J = 12.7 Hz, 1H), 2.31 (t, J = 11.7 Hz, 2H), 1.92 (d, J = 12.9 Hz, 1H), 1.30 (t, J = 12.0 Hz, 1H), 0.92 (s, 3H) | |
| 296 | N-(2-fluoro-4-((3-(2-(((3S,5S)-5-fluoropiperidin-3-yl)amino)pyrimidin-4-yl)pyridin-2-yl)oxy)-6-methoxyphenyl)-1-phenylmethanesulfonamide | 583.2 | (300 MHz, DMSO-$d_6$) δ 8.36 (d, J = 5.1 Hz, 1H), 8.26 (dd, J = 4.8, 2.0 Hz, 1H), 7.48-7.29 (m, 6H), 7.21 (dd, J = 16.5, 6.6 Hz, 2H), 6.89-6.81 (m, 1H), 6.79 (dd, J = 10.2, 2.5 Hz, 1H), 4.86-4.70 (m, 1H), 4.42 (s, 2H), 4.13 (s, 1H), 3.84 (s, 3H), 3.02 (d, J = 12.8 Hz, 2H), 2.88 (t, J = 12.9 Hz, 1H), 2.38 (d, J = 11.0 Hz, 2H), 2.12 (s, 1H), 1.92-1.66 (m, 1H) | Example 40 |
| 297 | N-(2,3-difluoro-4-((3-(2-(((3S,5S)-5-fluoro-5-methylpiperidin-3-yl)amino)pyrimidin-4-yl)pyridin-2-yl)oxy)-5-methylphenyl)-1-(p-tolyl)methanesulfonamide | 613.2 | (400 MHz, CD$_3$OD) δ 8.72 (s, 1H), 8.50 (m, 1H), 8.29 (s, 1H), 7.79 (s, 1H), 7.37 (dd, J = 7.7, 4.7 Hz, 1H), 7.33-7.27 (m, 2H), 7.18 (d, J = 7.8 Hz, 2H), 7.00-6.93 (m, 1H), 4.87 (s, 1H), 4.48 (s, 2H), 3.74 (dd, J = 12.1,4.4 Hz, 1H), 3.62-3.52 (m, 1H), 3.20-3.28 (m, 1H), 2.96 (d, J = 11.9 Hz, 1H), 2.53 (m, 1H), 2.33 (s, 3H), 2.11-2.06 (m, 3H), 1.98 (q, J = 12.8 Hz, 1H), 4.57 (d, J = 21.6 Hz, 3H) | Example 42 |
| 298 | N-(4-((3-(2-((1,1-difluoro-5-azaspiro[2.5]octan-7-yl)amino)pyrimidin-4-yl)pyridin-2-yl)oxy)-2,3,6-trifluorophenyl)-1-phenylmethanesulfonamide | 633.1 | (300 MHz, DMSO-$d_6$) δ 8.52-8.35 (m, 2H), 8.29-8.27 (m, 1H), 7.48-7.26 (m, 9H), 4.46 (s, 2H), 4.09-3.92 (m, 1H), 3.22-3.17 (m, 1H), 2.86-2.82 (m, 1H), 2.74-2.59 (m, 2H), 1.95-1.88 (m, 1H), 1.79-1.74 (m, 1H), 1.43-1.24 (m, 2H) | Example 91 |
| 299 | N-(4-((3-(2-((1,1-difluoro-5-azaspiro[2.5]octan-7-yl)amino)pyrimidin-4-yl)pyridin-2-yl)oxy)-2,3,6-trifluorophenyl)-1-phenylmethanesulfonamide | 633.1 | (300 MHz, DMSO-$d_6$) δ 8.52-8.34 (m, 2H), 8.29-8.27 (m, 1H), 7.48-7.26 (m, 9H), 4.45 (s, 2H), 4.02-3.93 (m, 1H), 3.22-3.15 (m, 1H), 2.90-2.52 (m, 3H), 1.96-1.88 (m, 1H), 1.79-1.75 (m, 1H), 1.41-1.24 (m, 2H) | Example 91 |
| 300 | N-(4-((3-(2-((1,1-difluoro-5-azaspiro[2.5]octan-7-yl)amino)pyrimidin-4-yl)pyridin-2-yl)oxy)-2,3,6-trifluorophenyl)-1-phenylmethanesulfonamide | 633.1 | (300 MHz, DMSO-$d_6$) δ 8.61-8.38 (m, 2H), 8.28-8.26 (m, 1H), 7.48-7.30 (m, 9H), 4.46 (s, 2H), 4.06-3.88 (m, 1H), 3.22-3.17 (m, 1H), 2.84-2.60 (m, 2H), 2.05-1.74 (m, 2H), 1.41-1.19 (m, 3H) | Example 91 |
| 301 | N-(4-((3-(2-((1,1-difluoro-5-azaspiro[2.5]octan-7-yl)amino)pyrimidin-4-yl)pyridin-2-yl)oxy)-2,3,6-trifluorophenyl)-1-phenylmethanesulfonamide | 633.1 | (300 MHz, DMSO-$d_6$) δ 8.50-8.41 (m, 2H), 8.28-8.24 (m, 1H), 7.51-7.28 (m, 9H), 4.45 (s, 2H), 4.06-3.82 (m, 1H), 3.22-3.12 (m, 1H), 2.83-2.52 (m, 2H), 2.00-1.78 (m, 2H), 1.41-1.19 (m, 3H) | Example 91 |
| 302 | N-(4-((3-(2-((5-(difluoromethyl)piperidin-3-yl)amino)pyrimidin-4-yl)pyridin-2-yl)oxy)-2,3,6-trifluorophenyl)-1-phenylmethanesulfonamide | 621.2 | (400 MHz, CD$_3$OD) δ 8.56 (d, J = 7.6 Hz, 1H), 8.38 (d, J = 5.2 Hz, 1H), 8.26-8.16 (m, 1H), 7.56-7.46 (m, 2H), 7.45-7.35 (m, 3H), 7.38-7.30 (m, 2H), 7.22-7.12 (m, 1H), 5.79 (td, J = 55.6, 3.6 Hz, 1H), 4.52 (s, 2H), 4.13 (s, 1H), 3.45-3.35 (m, 1H), 3.18 (d, J = 12.4 Hz, 1H), 2.53 (t, J = 12.0 Hz, 1H), 2.49-2.39 (m, 1H), 2.32-2.18 (m, 2H), 1.51-1.43 (m, 1H) | Example 92 |
| 303 | N-(4-((3-(2-((5-(difluoromethyl)piperidin-3-yl)amino)pyrimidin-4-yl)pyridin-2-yl)oxy)-2,3,6-trifluorophenyl)-1-phenylmethane sulfonamide | 621.2 | (400 MHz, CD$_3$OD) δ 8.59 (d, J = 7.5 Hz, 1H), 8.44 (d, J = 5.3 Hz, 1H), 8.29-8.19 (m, 1H), 7.52 (s, 1H), 7.55-7.48 (m, 1H), 7.47-7.37 (m, 4H), 7.41-7.31 (dd, J = 7.6.05 5.95, 4.9 Hz, 1H), 7.25-7.15 (m, 1H), 6.00 (td, J = 55.6, 3.6 Hz, 1H), 4.55 (s, 2H), 4.45 (s, 1H), 3.82-3.72 (m, 1H), 3.56 (d, J = 9.4 Hz, 1H), 2.98 (t, J = 12.6 Hz, 1H), 2.84 (t, J = 11.9 Hz, 1H), 2.65-2.54 (m, 1H), 2.37 (d, J = 12.8 Hz, 1H), 1.74-1.64 (m, 1H) | Example 92 |
| 304 | 1-(4-methoxyphenyl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide | 633.2 | (300 MHz, CD$_3$OD) δ 8.56 (d, J = 7.5 Hz, 1H), 8.37 (d, J = 5.2 Hz, 1H), 8.22-8.21 (m, 1H), 7.45-7.39 (m, 2H), 7.37-7.31 (m, 2H), 7.18-7.14 (m, 1H), 6.97-6.92 (m, 2H), 4.44 (s, 2H), 4.38-4.36 (s, 1H), 3.82 (s, 3H), 3.39-3.36 (m, 1H), 3.05-2.98 (m, 1H), 2.70-2.64 (m, 1H), 2.50-2.39 (m, 2H), 1.79-1.52 (m, 1H), 1.37 (d, J = 21.0 Hz, 3H) | Example 42 |

TABLE A1-continued

| Cpd No. | Name | MS m/z | ¹H NMR (ppm) | Synth. Method |
|---|---|---|---|---|
| 305 | N-(2,3-difluoro-4-((3-(2-(((3S,5S)-5-fluoro-5-methylpiperidin-3-yl)amino)pyrimidin-4-yl)pyridin-2-yl)oxy)-6-methylphenyl)-1-(p-tolyl)methanesulfonamide | 613.2 | (300 MHz, CD₃OD) δ 8.59 (d, J = 7.3 Hz, 1H), 8.37 (d, J = 5.2 Hz, 1H), 8.17-8.15 (m, 1H), 7.40 (d, J = 5.3 Hz, 1H), 7.32-7.27 (m, 3H), 7.17 (d, J = 7.8 Hz, 2H), 7.01-6.95 (m, 1H), 4.46 (s, 2H), 4.36 (s, 1H), 3.36-3.35 (m, 1H), 3.01-3.95 (m, 1H), 2.70-2.62 (m, 1H), 2.44-2.27 (m, 5H), 2.07 (s, 3H), 1.75-1.55 (m, 1H), 1.36 (d, J = 20.9 Hz, 3H) | Example 42 |
| 306 | N-(4-((3-(2-((4-(dimethylamino)-3-fluorocyclohexyl)amino)pyrimidin-4-yl)pyridin-2-yl)oxy)-2,3,6-trifluorophenyl)-1-phenylmethanesulfonamide | 631.2 | (300 MHz, CD₃OD) δ 8.51 (dd, J = 7.6, 1.9 Hz, 1H), 8.37 (d, J = 5.2 Hz, 1H), 8.19 (dd, J = 4.9, 2.0 Hz, 1H), 7.54-7.44 (m, 2H), 7.42-7.25 (m, 5H), 7.16-7.05 (m, 1H), 5.14-4.90 (m, 1H), 4.48 (s, 2H), 4.34 (s, 1H), 2.78-2.62 (m, 1H), 2.50-2.31 (m, 7H), 2.06-1.59 (m, 5H) | Example 95 |
| 307 | N-(4-((3-(2-((4-(dimethylamino)-3-fluorocyclohexyl)amino)pyrimidin-4-yl)pyridin-2-yl)oxy)-2,3,6-trifluorophenyl)-1-phenylmethanesulfonamide hydrochloride | 631.3 | (300 MHz, CD₃OD) δ 8.59 (dd, J = 7.7, 1.9 Hz, 1H), 8.50 (d, J = 6.5 Hz, 1H), 8.43 (dd, J = 6.5, 2.9 Hz, 1H), 8.34 (dd, J = 4.8, 2.0 Hz, 1H), 7.71 (d, J = 6.5 Hz, 1H), 7.50 (dd, J = 6.6, 3.0 Hz, 2H), 7.45-7.34 (m, 4H), 7.30-7.16 (m, 1H), 5.66-5.27 (m, 1H), 4.54 (s, 2H), 3.54 (dd, J = 31.5, 10.5 Hz, 1H), 3.00 (d, J = 7.3 Hz, 6H), 2.65 (s, 5H), 2.40-1.56 (m, 6H) | Example 95 |
| 308 | N-(4-((3-(2-((4-(dimethylamino)-3-fluorocyclohexyl)amino)pyrimidin-4-yl)pyridin-2-yl)oxy)-2,3,6-trifluorophenyl)-1-phenylmethanesulfonamide | 631.3 | (300 MHz, CD₃OD) δ 8.51 (dd, J = 7.6, 1.9 Hz, 1H), 8.37 (d, J = 5.2 Hz, 1H), 8.19 (dd, J = 4.9, 2.0 Hz, 1H), 7.49 (dd, J = 7.0, 2.6 Hz, 2H), 7.42-7.23 (m, 5H), 7.18-7.03 (m, 1H), 5.14-4.87 (m, 1H), 4.48 (s, 2H), 4.34 (s, 1H), 2.78-2.61 (m, 1H), 2.51-2.30 (m, 7H), 2.06-1.53 (m, 5H) | Example 95 |
| 309 | N-(4-((3-(2-(((1r,4r)-4-(dimethylamino)cyclohexyl)amino)pyrimidin-4-yl)pyridin-2-yl)oxy)-2,3,6-trifluorophenyl)propane-1-sulfonamide | 565.2 | (300 MHz, DMSO-d₆) δ 8.41-8.37 (m, 2H), 8.26 (dd, J = 4.8, 1.9 Hz, 1H), 7.41-7.34 (m, 2H), 7.23-7.17 (m, 2H), 3.71 (s, 1H), 3.05 (dd, J = 9.2, 6.2 Hz, 2H), 2.36 (s, 1H), 2.31 (s, 6H), 2.11-2.03 (m, 2H), 1.86-1.74 (m, 4H), 1.39-1.28 (m, 4H), 1.00 (t, J = 7.4 Hz, 3H) | Example 38 |
| 310 | N-(4-((3-(2-(((1r,4r)-4-(dimethylamino)cyclohexyl)amino)pyrimidin-4-yl)pyridin-2-yl)oxy)-2,3,6-trifluorophenyl)-3,3-difluorobutane-1-sulfonamide | 615.2 | (300 MHz, CD₃OD) δ 8.62 (dd, J = 7.7, 1.9 Hz, 1H), 8.41 (d, J = 6.7 Hz, 1H), 8.36 (dd, J = 4.9, 1.9 Hz, 1H), 7.72 (d, J = 6.6 Hz, 1H), 7.42 (dd, J = 7.7, 4.9 Hz, 1H), 7.35-7.17 (m, 1H), 3.48-3.38 (m, 2H), 3.36-3.33 (m, 1H), 3.30-3.32 (m, 1H), 2.90 (s, 6H), 2.63-2.41 (m, 2H), 2.36-2.32 (m, 2H), 2.21-2.17 (m, 2H), 1.77-1.61 (m, 7H) | Example 38 |
| 311 | N-(2,5-difluoro-4-((3-(2-(((3S,5S)-5-fluoro-5-methylpiperidin-3-yl)amino)pyrimidin-4-yl)pyridin-2-yl)oxy)-3-methylphenyl)-1-(p-tolyl)methanesulfonamide | 613.2 | (300 MHz, CD₃OD) δ 8.56 (s, 1H), 8.36 (d, J = 5.1 Hz, 1H), 8.14 (dd, J = 4.6, 1.9 Hz, 1H), 7.39 (d, J = 5.1 Hz, 1H), 7.33-7.23 (m, 3H), 7.16-7.06 (m, 3H), 4.45-4.36 (m, 3H), 3.36-3.32 (m, 2H), 3.09-3.01 (m, 1H), 2.57 (d, J = 14.1 Hz, 1H), 2.36-2.32 (m, 5H), 2.12 (d, J = 2.4 Hz, 3H), 1.39-1.33 (m, 3H) | Example 42 |
| 312 | 1-(4-(methylsulfonyl)phenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 667.1 | (300 MHz, CD₃OD) δ 8.55 (d, J = 7.5 Hz, 1H), 8.37 (d, J = 5.2 Hz, 1H), 8.19 (dd, J = 4.9, 1.9 Hz, 1H), 8.02-7.92 (m, 2H), 7.81-7.72 (m, 2H), 7.40-7.26 (m, 2H), 7.13-7.07 (m, 1H), 5.03-4.87 (m, 1H), 4.59 (s, 2H), 4.43 (s, 1H), 3.38 (d, J = 15.4 Hz, 1H), 3.22 (t, J = 12.9 Hz, 1H), 3.13 (s, 3H), 2.95-2.82 (m, 1H), 2.67-2.53 (m, 1H), 2.43-2.39 (m, 1H), 1.92-1.79 (m 1H) | Example 98 |
| 313 | N-(2,3-difluoro-4-((3-(2-(((3S,5S)-5-fluoropiperidin-3-yl)amino)pyrimidin-4-yl)pyridin-2-yl)oxy)-5-methylphenyl)-1-phenylethane-1-sulfonamide hydrochloride | 599.2 | (300 MHz, DMSO-d₆) δ 9.73 (s, 1H), 9.72-9.55 (m, 1H), 9.38-9.11 (m, 1H), 8.70-8.21 (m, 3H), 7.65-7.62 (m, 1H), 7.47-7.31 (m, 7H), 6.84-6.81 (m, 1H), 5.17-5.14 (m, 1H), 4.62-4.50 (m, 2H), 3.54-3.17 (m, 3H), 2.85-2.73 (m, 1H), 2.41-2.23 (m, 1H), 2.02 (s, 3H), 2.01-1.82 (m, 1H), 1.72 (d, J = 6.9 Hz, 3H) | Example 99 |
| 314 | N-(2,3-difluoro-4-((3-(2-(((3S,5S)-5-fluoropiperidin-3-yl)amino)pyrimidin-4- | 599.2 | (300 MHz, DMSO-d₆) δ 8.50-8.41 (m, 2H), 8.23-8.20 (m, 1H), 7.46-7.24 (m, 8H), 6.88-6.85 (m, 1H), 4.92-4.73 (m, | Example 99 |

TABLE A1-continued

| Cpd No. | Name | MS m/z | ¹H NMR (ppm) | Synth. Method |
|---|---|---|---|---|
| | yl)pyridin-2-yl)oxy)-5-methylphenyl)-1-phenylethane-1-sulfonamide | | 1H), 4.55-4.53 (m, 1H), 4.20-4.18 (m, 1H), 3.12-2.65 (m, 4H), 2.47-2.42 (m, 1H), 2.28-2.08 (m, 1H), 2.04 (s, 3H), 1.90-1.74 (m, 1H), 1.72 (d, J = 6.9 Hz, 3H) | |
| 315 | 1-(4-cyclopropylphenyl)-N-(2,3,6-trifluoro-4-((3-(2-(((3S,5S)-5-fluoropiperidin-3-yl)amino)pyrimidin-4-yl)oxy)phenyl)methanesulfonamide | 629.1 | (300 MHz, CD$_3$OD) δ 8.54 (d, J = 7.5 Hz, 1H), 8.35 (d, J = 5.2 Hz, 1H), 8.19 (dd, J = 4.8, 1.9 Hz, 1H), 7.40-7.26 (m, 4H), 7.10 (t, J = 8.9 Hz, 3H), 5.00-4.69 (m, 1H), 4.48-4.30 (m, 3H), 3.36-3.30 (m, 1H), 3.15 (t, J = 12.9 Hz, 1H), 2.93-2.65 (m, 1H), 2.53 (t, J = 11.4 Hz, 1H), 2.46-2.30 (m, 1H), 2.03-1.64 (m, 2H), 1.06-0.90 (m, 2H), 0.75-0.54 (m, 2H) | Example 98 |
| 316 | 1-(4-fluorophenyl)-N-(2,3,6-trifluoro-4-((3-(2-(((3S,5R)-5-(fluoromethyl)piperidin-3-yl)amino)pyrimidin-4-yl)oxy)phenyl)methanesulfonamide | 621.1 | (300 MHz, CD$_3$OD) δ 8.52 (d, J = 7.6 Hz, 1H), 8.36 (d, J = 5.2 Hz, 1H), 8.19 (dd, J = 4.8, 1.9 Hz, 1H), 7.55-7.46 (m, 2H), 7.36-7.26 (m, 2H), 7.17-7.02 (m, 3H), 4.45 (s, 3H), 4.41-4.08 (m, 2H), 3.67-3.43 (m, 1H), 3.26-3.16 (m, 1H), 2.61-2.35 (m, 2H), 2.27-2.06 (m, 2H), 1.46-1.20 (m, 1H) | Example 61 |
| 317 | 1-phenyl-N-(2,3,6-trifluoro-4-((3-(2-((5-methoxypiperidin-3-yl)amino)pyrimidin-4-yl)oxy)phenyl)methanesulfonamide | 601.2 | (400 MHz, CD$_3$OD) δ 8.53 (d, J = 7.5 Hz, 1H), 8.37 (d, J = 5.3 Hz, 1H), 8.19 (dd, J = 4.8, 1.9 Hz, 1H), 7.58-7.43 (m, 2H), 7.43-7.22 (m, 5H), 7.05 (ddd, J = 10.3, 6.8, 2.3 Hz, 1H), 4.44 (s, 2H), 4.41-4.35 (m, 1H), 3.66-3.62 (m, 1H), 3.42 (s, 3H), 3.30 (d, J = 4.0 Hz, 1H), 3.11 (d, J = 13.5 Hz, 1H), 2.82 (dd, J = 13.5, 2.1 Hz, 1H), 2.61 (dd, J = 12.4, 10.0 Hz, 1H), 2.30 (d, J = 13.6 Hz, 1H), 1.82-1.69 (m, 1H) | Example 108 |
| 318 | 1-phenyl-N-(2,3,6-trifluoro-4-((3-(2-((5-methoxy piperidin-3-yl)amino)pyrimidin-4-yl)oxy)phenyl)methanesulfonamide | 601.2 | (400 MHz, CD$_3$OD) δ 8.54 (s, 1H), 8.49 (d, J = 5.6 Hz, 1H), 8.28 (dd, J = 4.9, 1.9 Hz, 1H), 7.60-7.46 (m, 3H), 7.45-7.33 (m, 4H), 7.20 (ddd, J = 9.2, 6.6, 2.3 Hz, 1H), 4.55 (s, 3H), 3.86 (s, 1H), 3.54 (s, 3H), 3.49 (d, J = 12.7 Hz, 2H), 3.38 (dd, J = 12.9, 3.1 Hz, 1H), 3.29 (dd, J = 13.2, 2.3 Hz, 1H), 2.32-2.11 (m, 2H) | Example 108 |
| 319 | 1-phenyl-N-(2,3,6-trifluoro-4-((3-(2-((5-methoxypiperidin-3-yl)amino)pyrimidin-4-yl)oxy)phenyl)methanesulfonamide | 601.2 | (300 MHz, CD$_3$OD) δ 8.52 (d, J = 7.7 Hz, 1H), 8.36 (d, J = 5.2 Hz, 1H), 8.18 (dd, J = 4.9, 1.9 Hz, 1H), 7.58-7.42 (m, 2H), 7.42-7.18 (m, 5H), 7.05 (ddd, J = 9.8, 6.7, 2.3 Hz, 1H), 4.43 (s, 2H), 4.41-4.35 (m, 1H), 3.66-3.62 (m, 1H), 3.40 (s, 3H), 3.30 (d, J = 4.0 Hz, 1H), 3.10 (d, J = 13.3 Hz, 1H), 2.81 (dd, J = 13.4, 2.1 Hz, 1H), 2.60 (dd, J = 12.5, 10.0 Hz, 1H), 2.29 (d, J = 13.2 Hz, 1H), 1.84-1.58 (m, 1H) | Example 108 |
| 320 | 1-(2,4-difluorophenyl)-N-(2,3,6-trifluoro-4-((3-(2-(((3S,5R)-5-(fluoromethyl)piperidin-3-yl)amino)pyrimidin-4-yl)oxy)phenyl)methanesulfonamide | 639.2 | (300 MHz, CD$_3$OD) δ 8.53 (d, J = 7.6 Hz, 1H), 8.38 (d, J = 5.2 Hz, 1H), 8.21 (dd, J = 4.9, 1.9 Hz, 1H), 7.68-7.54 (m, 1H), 7.44-7.26 (m, 2H), 7.15-6.94 (m, 3H), 4.61-4.06 (m, 5H), 3.59-3.43 (m, 1H), 3.32-3.18 (m, 1H), 2.64-2.42 (m, 2H), 2.19 (d, J = 12.6 Hz, 2H), 1.52-1.26 (m, 1H). | Example 61 |
| 321 | 1-(4-cyanophenyl)-N-(2,3,6-trifluoro-4-((3-(2-(((3S,5R)-5-(fluoromethyl)piperidin-3-yl)amino)pyrimidin-4-yl)oxy)phenyl)methanesulfonamide | 628.2 | (300 MHz, CD$_3$OD) δ 8.52 (d, J = 7.2 Hz, 1H), 8.38 (d, J = 5.3 Hz, 1H), 8.25-8.20 (m, 1H), 7.81-7.71 (m, 4H), 7.39-7.26 (m, 2H), 7.09-6.99 (m, 1H), 4.52 (s, 2H), 4.46-4.31 (m, 1H), 4.29-4.11 (m, 2H), 3.59-3.50 (m, 1H), 3.29-3.26 (m, 1H), 2.76-2.55 (m, 2H), 2.29-2.19 (m, 2H), 1.53-1.42 (m, 1H) | Example 61 |
| 322 | 1-(4-fluoro-2-methylphenyl)-N-(2,3,6-trifluoro-4-((3-(2-(((3S,5S)-5-fluoropiperidin-3-yl)amino)pyrimidin-4-yl)oxy)phenyl)methanesulfonamide | 621.2 | (300 MHz, DMSO-d$_6$) δ 8.39 (d, J = 5.1 Hz, 2H), 8.28-8.26 (m, 1H), 7.45-7.32 (m, 3H), 7.27 (t, J = 7.0 Hz, 2H), 7.10-6.99 (m, 2H), 4.88 (d, J = 47.4 Hz, 1H), 4.43 (s, 2H), 4.21 (s, 1H), 3.20-2.94 (m, 2H), 2.90-2.73 (m, 1H), 2.55-5.51(m, 1H), 2.39 (s, 3H), 2.27-2.19 (m, 1H), 1.94-1.74 (m, 1H) | Example 40 |

| Cpd No. | Name | MS m/z | ¹H NMR (ppm) | Synth. Method |
|---|---|---|---|---|
| 323 | N-(6-chloro-2,3-difluoro-4-((3-(2-(((3S,5S)-5-fluoropiperidin-3-yl)amino)pyrimidin-4-yl)pyridin-2-yl)oxy)phenyl)-1-(2-fluorophenyl)methanesulfonamide | 623.1 | (300 MHz, CD₃OD) δ 8.57 (d, J = 7.5 Hz, 1H), 8.39 (d, J = 5.2 Hz, 1H), 8.26-8.17 (m, 1H), 7.66-7.54 (m, 1H), 7.47-7.29 (m, 4H), 7.28-7.11 (m, 2H), 5.04-4.78 (m, 1H), 4.64 (s, 2H), 4.51-4.31 (m, 1H), 3.43-3.36 (m, 1H), 3.21 (t, J = 12.8 Hz, 1H), 3.00-2.76 (m, 1H), 2.64-2.54 (m, 1H), 2.50-2.31 (m, 1H), 2.02-1.65 (m, 1H) | Example 40 |
| 324 | N-(4-((3-(2-((5-cyclopropylpiperidin-3-yl)amino)pyrimidin-4-yl)pyridin-2-yl)oxy)-2,3,6-trifluorophenyl)-1-(2-fluorophenyl)methanesulfonamide | 629.2 | (400 MHz, DMSO-d₆) δ 8.44 (d, J = 5.1 Hz, 2H), 8.32-8.22 (m, 1H), 8.05 (s, 1H), 7.58-7.48 (m, 1H), 7.38-7.26 (m, 4H), 7.19-7.10 (m, 2H), 7.13-7.03 (m, 1H), 4.22 (s, 3H), 3.31 (d, J = 12.3 Hz, 2H), 3.17-3.07 (m, 1H), 3.07-2.97 (m, 1H), 2.76-2.66 (m, 1H), 2.00-1.96 (m, 1H), 1.74-1.64 (m, 1H), 1.23 (d, J = 10.5 Hz, 1H), 0.69-0.59 (m, 1H), 0.45-0.33 (m, 2H), 0.29-0.22 (m, 1H), 0.17-0.07 (m, 1H) | Example 107 |
| 325 | N-(4-((3-(2-((5-cyclopropylpiperidin-3-yl)amino)pyrimidin-4-yl)pyridin-2-yl)oxy)-2,3,6-trifluorophenyl)-1-(2-fluorophenyl)methanesulfonamide | 629.2 | (400 MHz, DMSO-d₆) δ 8.43 (t, J = 7.8 Hz, 2H), 8.32-8.22 (m, 1H), 8.18-7.95 (m, 1H), 7.58-7.48 (m, 1H), 7.43-7.25 (m, 4H), 7.21-7.02 (m, 3H), 4.19 (s, 3H), 3.30 (s, 2H), 3.12-3.02 (m, 2H), 2.80-2.64 (m, 1H), 1.98 (d, J = 13.7 Hz, 1H), 1.77-1.64 (m, 1H), 1.23 (d, J = 7.0 Hz, 1H), 0.69-0.59 (m, 1H), 0.51-0.34 (m, 2H), 0.26-0.24 (m, 1H), 0.17-0.07 (m, 1H) | Example 107 |
| 326 | N-(4-((3-(2-((5-cyclopropylpiperidin-3-yl)amino)pyrimidin-4-yl)pyridin-2-yl)oxy)-2,3,6-trifluorophenyl)-1-(2-fluorophenyl)methanesulfonamide | 629.2 | (400 MHz, DMSO-d₆) δ 8.57-8.03 (m, 4H), 7.59-7.48 (m, 1H), 7.47-7.25 (m, 4H), 7.22-7.06 (m, 3H), 4.19 (s, 2H), 4.05 (s, 1H), 3.35-3.32 (m, 2H), 3.18 (d, J = 12.1 Hz, 1H), 2.55-2.45 (m, 2H), 2.09 (d, J = 12.3 Hz, 1H), 1.43-1.33 (m, 1H), 1.03 (d, J = 10.8 Hz, 1H), 0.59-0.55 (m, 1H), 0.41 (d, J = 8.4 Hz, 2H), 0.23-0.08 (m, 2H) | Example 107 |
| 327 | N-(4-((3-(2-((5-cyclopropylpiperidin-3-yl)amino)pyrimidin-4-yl)pyridin-2-yl)oxy)-2,3,6-trifluorophenyl)-1-(2-fluorophenyl)methanesulfonamide | 629.2 | (400 MHz, DMSO-d₆) δ 8.53-8.21 (m, 4H), 7.58-7.47 (m, 1H), 7.44 (d, J = 7.6 Hz, 1H), 7.38-7.28 (m, 3H), 7.21-7.07 (m, 3H), 4.19 (s, 2H),4.05 (s, 1H), 3.36 (s, 2H), 3.24-3.13 (m, 1H), 2.62-2.40 (m, 2H), 2.09 (d, J = 12.4 Hz, 1H), 1.44-1.34 (m, 1H), 1.06 (s, 1H), 0.60-0.55 (d, J = 8.8 Hz, 1H), 0.46-0.37 (m, 2H), 0.15 (s, 2H) | Example 107 |
| 328 | 1-phenyl-N-(2,3,6-trifluoro-4-((3-(2-((5-(methoxymethyl)piperidin-3-yl)amino)pyrimidin-4-yl)pyridin-2-yl)oxy)phenyl)methanesulfonamide | 615.3 | (300 MHz, CD₃OD) δ 8.54-18.45 (m, 1H), 8.40 (d, J = 5.1 Hz, 1H), 8.20 (dd, J = 4.8, 2.1 Hz, 1H), 7.50 (d, J = 6.0 Hz, 2H), 7.40-7.26 (m, 5H), 7.02 (t, J = 8.4 Hz, 1H), 4.43 (s, 2H), 4.28 (s, 1H), 3.34-3.33 (m, 5H), 3.25-3.05 (m, 2H), 3.03 (d, J = 12.9 Hz, 1H), 2.75-2.62 (m, 1H), 2.23 (s, 1H), 1.99 (d, J = 12.7 Hz, 1H), 1.74 (d, J = 10.3 Hz, 1H) | Example 108 |
| 329 | 1-phenyl-N-(2,3,6-trifluoro-4-((3-(2-((5-(methoxymethyl)piperidin-3-yl)amino)pyrimidin-4-yl)pyridin-2-yl)oxy)phenyl)methanesulfonamide | 615.3 | (300 MHz, CD₃OD) δ 8.50 (dd, J = 7.5, 1.8 Hz, 1H), 8.40 (d, J = 5.1 Hz, 1H), 8.21 (dd, J = 4.8, 1.8 Hz, 1H), 7.54-7.45 (m, 2H), 7.40-7.27 (m, 5H), 7.09-6.98 (m, 1H), 4.44 (s, 2H), 4.28 (s, 1H), 3.33-3.30 (m, 5H), 3.25-3.04 (m, 3H), 2.76-2.63 (m, 1H), 2.23-2.16(m, 1H), 1.75 (d, J = 14.1 Hz, 1H), 1.81-1.60 (m, 1H) | Example 108 |
| 330 | 1-phenyl-N-(2,3,6-trifluoro-4-((3-(2-((5-(methoxymethyl)piperidin-3-yl)amino)pyrimidin-4-yl)pyridin-2-yl)oxy)phenyl)methanesulfonamide | 615.3 | (300 MHz, CD₃OD) δ 8.52-8.18 (m, 3H), 7.48-7.05 (m, 8H), 4.43 (s, 2H), 4.15 (s, 1H), 3.54-3.52 (m,4H), 3.12-3.10 (m, 3H), 2.44 (d, J = 12.3 Hz, 2H), 2.07 (s, 2H), 1.30 (d, J = 10.8 Hz, 1H) | Example 108 |
| 331 | 1-phenyl-N-(2,3,6-trifluoro-4-((3-(2-((5-(methoxymethyl)piperidin-3-yl)amino)pyrimidin-4-yl)pyridin-2-yl)oxy)phenyl)methanesulfonamide | 615.3 | (300 MHz, CD₃OD) δ 8.51-8.19 (m, 3H), 7.49-7.27 (m, 8H), 4.81-4.75 (m, 2H), 4.42 (s, 2H), 4.14 (s, 1H), 3.56-3.45 (m, 2H), 3.20-3.07 (m, 3H), 2.50-2.41 (m, 2H), 2.18-2.04 (m, 2H), 1.36 (s, 1H) | Example 108 |

TABLE A1-continued

| Cpd No. | Name | MS m/z | ¹H NMR (ppm) | Synth. Method |
|---|---|---|---|---|
| 332 | N-(3-chloro-2,6-difluoro-4-((3-(2-(((3S,5S)-5-fluoropiperidin-3-yl)amino)pyrimidin-4-yl)pyridin-2-yl)oxy)phenyl)-1-(2-fluorophenyl)methanesulfonamide | 623.1 | (300 MHz, CD₃OD) δ 8.57 (d, J = 7.5 Hz, 1H), 8.37 (d, J = 5.2 Hz, 1H), 8.23-8.13 (m, 1H), 7.64-7.53 (m, 1H), 7.46-7.28 (m, 3H), 7.25-7.09 (m, 3H), 4.99-4.87 (m, 1H), 4.58 (s, 2H), 4.40 (s, 1H), 3.33 (s, 1H), 3.17 (t, J = 12.9 Hz, 1H), 2.89-2.79 (m, 1H), 2.55 (t, J = 11.5 Hz, 1H), 2.41 (s, 1H), 1.89-1.79 (m, 1H) | Example 112 |
| 333 | 1-phenyl-N-(2,3,6-trifluoro-4-((3-(2-((5-(2-fluoropropan-2-yl)piperidin-3-yl)amino)pyrimidin-4-yl)pyridin-2-yl)oxy)phenyl)methanesulfonamide hydrochloride | 613.2 | (300 MHz, CD₃OD) δ 8.58-8.46 (m, 2H), 8.29-8.27 (m, 1H), 7.59-7.31 (m, 7H), 7.23-7.12 (m, 1H), 4.54 (s, 3H), 3.81 (d, J = 13.2Hz, 1H), 3.51-3.49 (m, 1H), 3.20 (d, J = 14.4 Hz, 1H), 3.05-3.01 (m, 1H), 2.60-2.47 (m, 1H), 2.21 (d, J = 14.1 Hz, 1H), 1.98-1.84 (m, 1H), 1.51-1.42 (m, 6H) | Example 108 |
| 334 | 1-phenyl-N-(2,3,6-trifluoro-4-((3-(2-((5-(2-fluoropropan-2-yl)piperidin-3-yl)amino)pyrimidin-4-yl)pyridin-2-yl)oxy)phenyl)methanesulfonamide hydrochloride | 613.2 | (300 MHz, CD₃OD) δ 8.58-8.46 (s, 2H), 8.29-8.27 (m, 1H), 7.59-7.31 (m, 7H), 7.23-7.12 (m, 1H), 4.54 (s, 3H), 3.81 (d, J = 13.2Hz, 1H), 3.51-3.49 (m, 1H), 3.20 (d, J = 14.4 Hz, 1H), 3.05-3.01 (m, 1H), 2.60-2.47 (m, 1H), 2.21 (d, J = 14.1 Hz, 1H), 1.98-1.84 (m, 1H), 1.51-1.42 (m, 6H) | Example 108 |
| 335 | 1-phenyl-N-(2,3,6-trifluoro-4-((3-(2-((5-(2-fluoropropan-2-yl)piperidin-3-yl)amino)pyrimidin-4-yl)pyridin-2-yl)oxy)phenyl)methanesulfonamide hydrochloride | 613.2 | (300 MHz, CD₃OD) δ 8.62 (s, 1H), 8.47 (d, J = 5.7 Hz, 1H), 8.29 (d, J = 3.6 Hz, 1H), 7.58 (s, 1H), 7.55-7.46 (m, 2H), 7.45-7.35 (m, 4H), 7.23 (t, J = 9.6 Hz, 1H), 4.56-4.41 (m, 3H), 3.86-3.76 (m, 1H), 3.63-3.60 (m, 1H), 2.95-2.88 (m, 2H), 2.50-2.31 (m, 2H), 1.75-1.65 (m, 1H), 1.57-1.44 (m, 6H) | Example 108 |
| 336 | 1-phenyl-N-(2,3,6-trifluoro-4-((3-(2-((5-(2-fluoropropan-2-yl)piperidin-3-yl)amino)pyrimidin-4-yl)pyridin-2-yl)oxy)phenyl)methanesulfonamide hydrochloride | 613.2 | (300 MHz, CD₃OD) δ 8.62 (s, 1H), 8.46 (d, J = 5.5 Hz, 1H), 8.33-8.25 (m, 1H), 7.60-7.50 (m, 3H), 7.45-7.35 (m, 4H), 7.30-7.16 (m, 1H), 4.56 (s, 3H), 3.85-3.49 (m, 2H), 3.02-2.76 (m, 2H), 2.43-2.17 (m, 2H), 1.72-1.56 (m, 1H), 1.52-1.34 (m, 6H) | Example 108 |
| 337 | N-(4-((3-(2-((5-(1,1-difluoroethyl)piperidin-3-yl)amino)pyrimidin-4-yl)pyridin-2-yl)oxy)-2,3,6-trifluorophenyl)-1-phenylmethanesulfonamide hydrochloride | 635.2 | (300 MHz, CD₃OD) δ 8.53-8.50 (m, 2H), 8.28-8.26 (m, 1H), 7.55-7.50 (m, 3H), 7.43-7.36 (m, 4H), 7.23-7.16 (m, 1H), 4.57 (s, 2H), 4.56-4.49 (m, 1H), 3.88-3.84 (m, 1H), 3.56-3.52 (m, 1H), 3.27-3.23 (m, 1H), 3.16-3.12 (m, 1H), 2.92-2.73 (m, 1H), 2.33-2.28 (m, 1H), 2.09-2.00 (m, 1H), 1.79-1.66 (m, 3H) | Example 108 |
| 338 | N-(4-((3-(2-((5-(1,1-difluoroethyl)piperidin-3-yl)amino)pyrimidin-4-yl)pyridin-2-yl)oxy)-2,3,6-trifluorophenyl)-1-phenylmethanesulfonamide | 635.2 | (300 MHz, CD₃OD) δ 8.57-8.53 (m, 1H), 8.45-8.43 (m, 1H), 8.25-8.22 (m, 1H),7.54-7.50 (m, 2H), 7.43-7.33 (m, 5H), 7.23-7.16 (m, 1H), 4.55 (s, 2H), 4.41-4.23 (m, 1H), 3.76-3.71 (m, 1H), 3.60-3.57 (m, 1H), 2.98-2.76 (m, 2H), 2.62-2.38 (m, 2H), 1.77-1.62 (m, 4H) | Example 108 |
| 339 | N-(4-((3-(2-((5-(1,1-difluoroethyl)piperidin-3-yl)amino)pyrimidin-4-yl)pyridin-2-yl)oxy)-2,3,6-trifluorophenyl)-1-phenylmethanesulfonamide | 635.2 | (300 MHz, CD₃OD) δ 8.57-8.53 (m, 1H), 8.43-8.38 (m, 1H), 8.23-8.22 (m, 1H), 7.54-7.50 (m, 2H), 7.43-7.33 (m, 5H), 7.23-7.16 (m, 1H), 4.53 (s, 2H), 4.27-4.11 (m, 1H), 3.53-3.49 (m, 1H), 3.30-3.25 (m, 1H), 2.66-2.25 (m, 4H), 1.70-1.50 (m, 4H) | Example 108 |
| 340 | N-(5-chloro-2,3-difluoro-4-((3-(2-(((3S,5S)-5-fluoropiperidin-3-yl)amino)pyrimidin-4-yl)pyridin-2-yl)oxy)phenyl)-1-(2-fluorophenyl)methanesulfonamide | 623.1 | (300 MHz, CD₃OD) δ 8.59 (d, J = 7.5 Hz, 1H), 8.39 (d, J = 5.2 Hz, 1H), 8.17 (dd, J = 4.8, 1.8 Hz, 1H), 7.56-7.42 (m, 1H), 7.42-7.26 (m, 3H), 7.23-7.05 (m, 2H), 5.02-4.86 (m, 1H), 4.56 (s, 2H), 4.44 (s, 1H), 3.43-3.32 (m, 1H), 3.22 (t, J = 12.6 Hz, 1H), 2.95 (d, J = 14.4 Hz, 1H), 2.82 (d, J = 14.7 Hz, 1H), 2.59 (t, J = 11.4 Hz, 1H), 1.93-1.72 (m, 1H) | Example 112 |
| 341 | 1-(4-fluorophenyl)-N-(2,3,6-trifluoro-4-((3-(2-(((1r,4r)-4-((2-methoxyethyl)(methyl)amino)cyclohexyl)amino)pyrimidin-4-yl)pyridin-2-yl)oxy)phenyl)methanesulfonamide hydrochloride | 675.3 | (300 MHz, CD₃OD) δ 8.61 (d, J = 8.2 Hz, 1H), 8.42 (d, J = 6.5 Hz, 1H), 8.38-8.36 (m, 1H), 7.70 (d, J = 6.5 Hz, 1H), 7.60-7.54 (m, 2H), 7.43-7.40 (m, 1H), 7.30-7.21 (m, 1H), 7.15-7.09 (m, 2H), 4.56 (s, 2H), 4.21-4.11 (m, 1H), 3.78-3.69 (m, 2H), 3.53 (d, J = 5.6 Hz, 1H), 3.45 (s, | Example 38 |

TABLE A1-continued

| Cpd No. | Name | MS m/z | ¹H NMR (ppm) | Synth. Method |
|---|---|---|---|---|
| | | | 3H), 3.25-3.20 (m, 2H), 2.90 (s, 3H), 2.33 (d, J = 12.3 Hz, 2H), 2.20-2.17 (m, 2H), 1.85-1.79 (m, 2H), 1.72-1.58 (m, 2H) | |
| 342 | 1-phenyl-N-(2,3,6-trifluoro-4-((3-(2-((5-(1-fluoroethyl)piperidin-3-yl)amino)pyrimidin-4-yl)pyridin-2-yl)oxy)phenyl)methanesulfonamide hydrochloride | 617.3 | (300 MHz, CD₃OD) δ 8.63-8.55 (m, 1H), 8.52 (d, J = 5.7 Hz, 1H), 8.30 (dd, J = 4.8, 1.9 Hz, 1H), 7.62 (d, J = 5.7 Hz, 1H), 7.56-7.49 (m, 2H), 7.45-7.34 (m, 4H), 7.27-7.15 (m, 1H), 4.73 (t, J = 6.3 Hz, 1H), 4.60-4.49 (m, 3H), 3.80 (d, J = 13.0 Hz, 1H), 3.55 (d, J = 9.7 Hz, 1H), 3.30-3.22 (m, 1H), 3.12-2.98 (m, 1H), 2.59-2.37 (m, 1H), 2.19-1.83 (m, 2H), 1.45 (dd, J = 24.7, 6.3 Hz, 3H) | Example 108 |
| 343 | 1-phenyl-N-(2,3,6-trifluoro-4-((3-(2-((5-(1-fluoroethyl)piperidin-3-yl)amino)pyrimidin-4-yl)pyridin-2-yl)oxy)phenyl)methanesulfonamide hydrochloride | 617.3 | (300 MHz, CD₃OD) δ 8.71 (s, 1H), 8.48 (d, J = 6.0 Hz, 1H), 8.32 (d, J = 4.7 Hz, 1H), 7.68 (s, 1H), 7.57-7.49 (m, 2H), 7.46-7.36 (m, 4H), 7.31-7.19 (m, 1H), 4.85-4.62 (m, 2H), 4.56 (s, 2H), 3.77 (d, J = 11.8 Hz, 1H), 3.47 (d, J = 11.5 Hz, 1H), 3.11-2.84 (m, 2H), 2.57-2.09 (m, 2H), 1.82-1.59 (m, 1H), 1.41 (dd, J = 24.5, 6.4 Hz, 3H) | Example 108 |
| 344 | 1-phenyl-N-(2,3,6-trifluoro-4-((3-(2-((5-(1-fluoroethyl)piperidin-3-yl)amino)pyrimidin-4-yl)pyridin-2-yl)oxy)phenyl)methanesulfonamide hydrochloride | 617.3 | (300 MHz, CD₃OD) δ 8.70 (s, 1H), 8.48 (d, J = 5.9 Hz, 1H), 8.31 (s, 1H), 7.68 (s, 1H), 7.60-7.48 (m, 2H), 7.47-7.35 (m, 4H), 7.32-7.17 (m, 1H), 4.77-4.67 (m, 1H), 4.56 (s, 3H), 3.85-3.51 (m, 2H), 2.89 (t, J = 12.2 Hz, 2H), 2.25 (d, J = 12.6 Hz, 2H), 1.65 (d, J = 12.8 Hz, 1H), 1.43 (dd, J = 24.6, 6.3 Hz, 3H) | Example 108 |
| 345 | 1-phenyl-N-(2,3,6-trifluoro-4-((3-(2-((5-(1-fluoroethyl)piperidin-3-yl)amino)pyrimidin-4-yl)pyridin-2-yl)oxy)phenyl)methanesulfonamide hydrochloride | 617.3 | (300 MHz, CD₃OD) δ 8.69 (s, 1H), 8.48 (d, J = 5.9 Hz, 1H), 8.32 (d, J = 4.8 Hz, 1H), 7.67 (s, 1H), 7.58-7.47 (m, 2H), 7.47-7.35 (m, 4H), 7.29-7.18 (m, 1H), 4.78-4.67 (m, 1H), 4.56 (s, 3H), 3.89-3.46 (m, 2H), 2.88 (t, J = 12.1 Hz, 2H), 2.25 (d, J = 12.6 Hz, 2H), 1.67 (t, J = 12.5 Hz, 1H), 1.43 (dd, J = 24.6, 6.3 Hz, 3H) | Example 108 |
| 346 | 1-phenyl-N-(2,3,6-trifluoro-4-((3-(2-((5-(1-fluoroethyl)piperidin-3-yl)amino)pyrimidin-4-yl)pyridin-2-yl)oxy)phenyl)methanesulfonamide | 617.1 | (300 MHz, CD₃OD) δ 8.56 (dd, J = 7.6, 1.9 Hz, 1H), 8.50 (d, J = 5.6 Hz, 1H), 8.28 (dd, J = 4.9, 1.9 Hz, 1H), 7.61-7.49 (m, 3H), 7.46-7.35 (m, 4H), 7.30-7.12 (m, 1H), 4.88-4.65 (m, 1H), 4.58-4.50 (m, 3H), 3.82 (d, J = 12.9 Hz, 1H), 3.46-3.20 (m, 2H), 3.07 (t, J = 12.0 Hz, 1H), 2.50 (s, 1H), 2.25 (d, J = 14.3 Hz, 1H), 2.07-1.91 (m, 1H), 1.51-1.35 (m, 3H) | Example 108 |
| 347 | 1-phenyl-N-(2,3,6-trifluoro-4-((3-(2-((5-(1-fluoroethyl)piperidin-3-yl)amino)pyrimidin-4-yl)pyridin-2-yl)oxy)phenyl)methanesulfonamide | 617.3 | (300 MHz, CD₃OD) δ 8.71 (s, 1H), 8.48 (d, J = 6.0 Hz, 1H), 8.32 (d, J = 4.7 Hz, 1H), 7.68 (s, 1H), 7.56-7.50 (m, 2H), 7.45-7.38 (m, 4H), 7.33-7.20 (m, 1H), 4.86-4.63 (m, 2H), 4.56 (s, 2H), 3.76 (d, J = 12.7 Hz, 1H), 3.47 (d, J = 12.1 Hz, 1H), 3.06-2.79 (m, 2H), 2.52-2.08 (m, 2H), 1.66 (d, J = 12.1 Hz, 1H), 1.41 (dd, J = 24.4, 6.3 Hz, 3H) | Example 108 |
| 348 | 1-phenyl-N-(2,3,6-trifluoro-4-((3-(2-((5-(1-fluoroethyl)piperidin-3-yl)amino)pyrimidin-4-yl)pyridin-2-yl)oxy)phenyl)methanesulfonamide | 617.3 | (300 MHz, CD₃OD) δ 8.51 (dd, J = 7.6, 1.9 Hz, 1H), 8.41 (d, J = 5.2 Hz, 1H), 8.21 (dd, J = 4.8, 2.0 Hz, 1H), 7.51 (dd, J = 7.4, 2.2 Hz, 2H), 7.46-7.28 (m, 5H), 7.07 (t, J = 9.7 Hz, 1H), 4.72-4.59 (m, 1H), 4.54-4.43 (m, 2H), 4.28 (s, 1H), 3.40-3.21 (m, 2H), 2.99 (dd, J = 12.9, 2.9 Hz, 1H), 2.72 (dd, J = 12.7, 10.2 Hz, 1H), 2.29-1.87 (m, 2H), 1.87-1.65 (m, 2H), 1.36 (dd, J = 24.6, 6.3 Hz, 3H) | Example 108 |
| 349 | N-(2,3,6-trifluoro-4-((3-(2-(((1r,4r)-4-((2-methoxyethyl)(methyl)amino)cyclohexyl)amino)pyrimidin-4-yl)pyridin-2-yl)oxy)phenyl)cyclohexanesulfonamide | 649.3 | (300 MHz, CD₃OD) δ 8.44-8.42 (m, 1H), 8.32 (d, J = 5.2 Hz, 1H), 8.18-8.15 (m, 1H), 7.32-7.30 (m, 1H), 7.23 (d, J = 5.2 Hz, 1H), 7.12-7.03 (m, 1H), 3.90-3.81 (m, 1H), 3.56 (t, J = 5.6 Hz, 2H), 3.37 (s, 3H), 3.09-3.03 (m, 1H), 2.86 (t, | Example 115 |

TABLE A1-continued

| Cpd No. | Name | MS m/z | ¹H NMR (ppm) | Synth. Method |
|---|---|---|---|---|
| | | | J = 5.6 Hz, 2H), 2.76-2.71 (m, 1H), 2.46 (s, 3H), 2.32 (d, J = 12.5 Hz, 2H), 2.20 (d, J = 12.3 Hz, 2H), 2.01-1.94 (m, 4H), 1.73 (d, J = 11.6 Hz, 1H), 1.57-1.54 (m, 4H), 1.44-1.27 (m, 5H) | |
| 350 | 1-phenyl-N-(2,3,6-trifluoro-4-((3-(2-((5-(1-fluoroethyl)piperidin-3-yl)amino)pyrimidin-4-yl)pyridin-2-yl)oxy)phenyl)methanesulfonamide | 617.3 | (300 MHz, CD₃OD) δ 8.61 (d, J = 7.6 Hz, 1H), 8.53 (d, J = 5.8 Hz, 1H), 8.31 (d, J = 4.8 Hz, 1H), 7.66 (s, 1H), 7.55-7.47 (m, 2H), 7.45-7.36 (m, 4H), 7.23 (t, J = 7.8 Hz, 1H), 4.74-4.60 (m, 2H), 4.56 (s, 2H), 3.78 (d, J = 13.3 Hz, 1H), 3.48-3.22 (m, 2H), 3.08 (t, J = 11.8 Hz, 1H), 2.58-2.41 (m, 1H), 2.34-2.17 (m, 1H), 2.11-1.91 (m, 1H), 1.62-1.36 (m, 3H) | Example 108 |
| 351 | 1-(2,4-difluorophenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide | 625.2 | (400 MHz, DMSO-d₆, 360K) δ 8.46-8.40 (m, 1H), 8.40-8.36 (m, 1H), 8.27-8.19 (m, 1H), 7.62-7.53 (m, 1H), 7.35 (dd, J = 7.6, 4.9 Hz, 1H), 7.32-7.11 (m, 3H), 7.11-7.03 (m, 1H), 6.90-6.83 (m, 1H), 4.92-4.73 (m, 1H), 4.48 (s, 2H), 4.27-4.16 (m, 1H), 2.88-2.73 (m, 2H), 2.61-2.51 (m, 1H), 2.22-2.11 (m, 1H), 2.00-1.79 (m, 1H). | Example 40 |
| 352 | 1-(2-chlorophenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide | 623.2 | (400 MHz, DMSO-d₆, 360K) δ 8.42 (d, J = 5.1 Hz, 1H), 8.27 (dd, J = 5.0, 2.0 Hz, 1H), 7.63-7.55 (m, 1H), 7.54-7.45 (m, 1H), 7.43-7.33 (m, 5H), 7.32-7.26 (m, 1H), 4.96 (d, J = 47.1 Hz, 1H), 4.60 (s, 2H), 4.35-4.17 (m, 1H), 3.15-2.81 (m, 2H), 2.63-2.54 (m, 1H), 2.46-2.42 (m, 1H), 2.28-2.17 (m, 1H), 1.95-1.73 (m, 1H). | Example 40 |
| 353 | 1-(3-chlorophenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide | 623.2 | (400 MHz, DMSO-d₆) δ 8.58-8.46 (m, 1H), 8.44 (d, J = 5.0 Hz, 1H), 8.28 (dd, J = 4.9, 2.0 Hz, 1H), 7.50-7.38 (m, 6H), 7.34-7.28 (m, 1H), 5.12-4.95 (m, 1H), 4.51 (s, 2H), 4.41-4.26 (m, 1H), 3.08-2.91 (m, 3H), 2.68-2.59 (m, 1H), 2.31-2.20 (m, 1H), 2.00-1.74 (m, 1H). | Example 40 |
| 354 | 1-(4-chlorophenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide | 623.2 | (400 MHz, DMSO-d₆) δ 8.42 (d, J = 5.2 Hz, 1H), 8.27 (dd, J = 4.8, 2.0 Hz, 1H), 7.49-7.34 (m, 7H), 7.31-7.26 (m, 1H), 5.06-4.87 (m, 1H), 4.46 (s, 2H), 4.33-4.20 (m, 1H), 2.89 (s, 3H), 2.61-2.53 (m, 1H), 2.47 (d, J = 4.0 Hz, 0H), 2.45-2.38 (m, 0H), 2.27-2.17 (m, 1H), 1.96-1.75 (m, 1H). | Example 40 |
| 355 | 1-(2-fluorophenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide | 607.2 | (400 MHz, DMSO-d₆) δ 8.44 (d, J = 5.2 Hz, 1H), 8.29 (dd, J = 4.9, 1.9 Hz, 1H), 7.56-7.48 (m, 3H), 7.48-7.37 (m, 2H), 7.35-7.30 (m, 1H), 7.30-7.21 (m, 2H), 5.19-5.01 (m, 1H), 4.56 (s, 2H), 4.41-4.33 (m, 1H), 3.17-2.98 (m, 3H), 2.72-2.65 (m, 1H), 2.35-2.21 (m, 1H), 2.00-1.73 (m, 1H). | Example 40 |
| 356 | 1-(2-pyridyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide | 590.2 | (400 MHz, DMSO-d₆) δ 8.55-8.50 (m, 1H), 8.41 (d, J = 5.1 Hz, 1H), 8.30-8.25 (m, 1H), 7.84-7.75 (m, 1H), 7.60-7.54 (m, 1H), 7.40-7.24 (m, 5H), 5.01-4.79 (m, 1H), 4.51 (s, 2H), 4.23-4.19 (m, 1H), 3.20-2.95 (m, 3H), 2.90-2.71 (m, 1H), 2.21-2.15 (m, 1H), 1.94-1.73 (m, 1H). | Example 121 |
| 357 | 1-(2-cyano-4-fluoro-phenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide | 632.1 | (400 MHz, DMSO-d₆, 360K) δ 8.43 (dd, J = 7.5, 2.0 Hz, 1H), 8.39 (d, J = 5.1 Hz, 1H), 8.24 (dd, J = 4.8, 1.9 Hz, 1H), 7.78-7.72 (m, 2H), 7.60-7.53 (m, 1H), 7.35 (dd, J = 7.6, 4.8 Hz, 1H), 7.26-7.19 (m, 2H), 6.95 (d, J = 7.8 Hz, 1H), 4.98-4.81 (m, 1H), 4.59 (s, 2H), 4.31-4.19 (m, 1H), 3.20-3.13 (m, 1H), 2.92-2.81 (m, 2H), 2.66-2.56 (m, 1H), 2.26-2.13 (m, 1H), 1.98-1.81 (m, 1H). | Example 40 |
| 358 | 1-(2-cyanophenyl)-N-[2,3,6-trifluoro-4-[[3-[2-[[(3S,5S)-5-fluoro-3-piperidyl]amino]pyrimidin- | 614.2 | (400 MHz, DMSO-d₆ 360K) δ 8.45-8.41 (m, 1H), 8.38 (d, J = 5.2 Hz, 1H), 8.26-8.22 (m, 1H), 7.81 (d, J = 7.6 Hz, 1H), 7.75-7.65 (m, 2H), 7.57-7.48 (m, | Example 40 |

TABLE A1-continued

| Cpd No. | Name | MS m/z | ¹H NMR (ppm) | Synth. Method |
|---|---|---|---|---|
| | 4-yl]-2-pyridyl]oxy]phenyl]methane sulfonamide | | 1H), 7.35 (dd, J = 7.5, 4.8 Hz, 1H), 7.27-7.18 (m, 2H), 6.92 (d, J = 8.0 Hz, 1H), 4.97-4.77 (m, 1H), 4.60 (s, 2H), 4.28-4.19 (m, 1H), 2.90-2.76 (m, 3H), 2.62-2.55 (m, 1H), 2.24-2.13 (m, 1H), 1.98-1.79 (m, 1H). | |
| 359 | 1-(4-pyridyl)-N-[2,3,6-trifluoro-4-[[3-[2-[[(3S,5S)-5-fluoro-3-piperidyl]amino]pyrimidin-4-yl]-2-pyridyl]oxy]phenyl]methane sulfonamide | 590.2 | NO NMR | Example 40 |
| 360 | 1-(4-cyano-2-fluoro-phenyl)-N-[2,3,6-trifluoro-4-[[3-[2-[[(3S,5S)-5-fluoro-3-piperidyl]amino]pyrimidin-4-yl]-2-pyridyl]oxy]phenyl]methane sulfonamide | 632.2 | (400 MHz, DMSO-$d_6$ 360K) δ 8.42 (dd, J = 7.5, 2.0 Hz, 1H), 8.38 (d, J = 5.1 Hz, 1H), 8.24 (dd, J = 4.8, 2.0 Hz, 1H), 7.80-7.70 (m, 2H), 7.70-7.63 (m, 1H), 7.35 (dd, J = 7.6, 4.8 Hz, 1H), 7.28-7.20 (m, 2H), 6.94-6.87 (m, 1H), 4.98-4.81 (m, 1H), 4.56 (s, 2H), 4.32-4.21 (m, 1H), 3.22-3.11 (m, 1H), 2.97-2.79 (m, 2H), 2.67-2.57 (m, 1H), 2.22-2.18 (m, 1H), 2.00-1.80 (m, 1H). | Example 125 |
| 361 | 3-fluoro-4-[[2,3,6-trifluoro-4-[[3-[2-[[(3S,5S)-5-fluoro-3-piperidyl]amino]pyrimidin-4-yl]-2-pyridyl]oxy]phenyl]sulfamoylmethyl]benzamide | 650.2 | ¹H NMR (400 MHz, DMSO-$d_6$, 360K) δ 8.43 (dd, J = 7.5, 2.0 Hz, 1H), 8.38 (d, J = 5.1 Hz, 1H), 8.24 (dd, J = 4.8, 1.9 Hz, 1H), 7.74-7.65 (m, 2H), 7.64-7.56 (m, 1H), 7.36 (dd, J = 7.5, 4.8 Hz, 1H), 7.33-7.25 (m, 1H), 7.23 (d, J = 5.1 Hz, 1H), 6.91 (d, J = 8.0 Hz, 1H), 4.95-4.75 (m, 1H), 4.54 (s, 2H), 4.29-4.16 (m, 1H), 2.91-2.74 (m, 3H), 2.62-2.52 (m, 1H), 2.23-2.11 (m, 1H), 1.99-1.78 (m, 1H). | Example 40 |
| 362 | 1-(4-chloro-2-cyano-phenyl)-N-[2,3,6-trifluoro-4-[[3-[2-[[(3S,5S)-5-fluoro-3-piperidyl]amino]pyrimidin-4-yl]-2-pyridyl]oxy]phenyl]methane sulfonamide | 648.1 | (400 MHz, DMSO-$d_6$, 360K) δ 8.42 (dd, J = 2.7, 2.0 Hz, 1H), 8.39 (d, J = 5.2 Hz, 1H), 8.24 (dd, J = 4.8, 2.0 Hz, 1H), 7.94 (d, J = 2.2 Hz, 1H), 7.78-7.69 (m, 2H), 7.34 (dd, J = 2.5, 4.8 Hz, 1H), 7.25 (d, J = 5.1 Hz, 1H), 7.23-7.16 (m, 1H), 6.95 (d, J = 8.0 Hz, 1H), 4.98-4.80 (m, 1H), 4.56 (s, 2H), 4.31-4.21 (m, 1H), 3.20-3.13 (m, 1H), 2.87-2.81 (m, 2H), 2.65-2.57 (m, 1H), 2.25-2.14 (m, 1H), 1.98-1.81 (m, 1H). | Example 40 |
| 363 | 1-(2,6-difluorophenyl)-N-[2,3,6-trifluoro-4-[[3-[2-[[(3S,5S)-5-fluoro-3-piperidyl]amino]pyrimidin-4-yl]-2-pyridyl]oxy]phenyl]methane sulfonamide | 625.2 | (400 MHz, DMSO-$d_6$, 360K) δ 8.43 (dd, J = 7.5, 2.0 Hz, 1H), 8.38 (d, J = 5.0 Hz, 1H), 8.24 (dd, J = 4.9, 1.9 Hz, 1H), 7.49-7.41 (m, 1H), 7.38-7.32 (m, 1H), 7.32-7.25 (m, 1H), 7.25-7.20 (m, 1H), 7.13-7.06 (m, 2H), 6.93-6.86 (m, 1H), 4.93-4.76 (m, 1H), 4.54 (s, 2H), 4.29-4.15 (m, 1H), 2.90-2.74 (m, 3H), 2.57 (ddd, J = 12.5, 9.1, 1.9 Hz, 1H), 2.21-2.12 (m, 1H), 1.98-1.80 (m, 1H). | Example 40 |
| 364 | 1-(4-chloro-2-fluoro-phenyl)-N-[2,3,6-trifluoro-4-[[3-[2-[[(3S,5S)-5-fluoro-3-piperidyl]amino]pyrimidin-4-yl]-2-pyridyl]oxy]phenyl]methane sulfonamide | 641.1 | (400 MHz, DMSO-$d_6$, 360K) δ 8.45-8.40 (m, 1H), 8.38 (d, J = 5.1 Hz, 1H), 8.26-8.21 (m, 1H), 7.60-7.52 (m, 1H), 7.40-7.31 (m, 2H), 7.31-7.20 (m, 3H), 6.90-6.83 (m, 1H), 4.92-4.75 (m, 1H), 4.46 (s, 2H), 4.27-4.17 (m, 1H), 2.81-2.73 (m, 2H), 2.61-2.53 (m, 2H), 2.22-2.11 (m, 1H), 1.98-1.80 (m, 1H). | Example 129 |
| 365 | 1-(2-chloro-4-fluoro-phenyl)-N-[2,3,6-trifluoro-4-[[3-[2-[[(3S,5S)-5-fluoro-3-piperidyl]amino]pyrimidin-4-yl]-2-pyridyl]oxy]phenyl]methane sulfonamide | 641.1 | (400 MHz, DMSO-$d_6$, 360K) δ 8.46-8.40 (m, 1H), 8.40-8.35 (m, 1H), 8.26-8.21 (m, 1H), 7.65 (dd, J = 8.8, 6.3 Hz, 1H), 7.44-7.32 (m, 2H), 7.32-7.17 (m, 3H), 6.87 (d, J = 8.0 Hz, 1H), 4.92-4.73 (m, 1H), 4.62 (s, 2H), 4.27-4.17 (m, 1H), 2.90-2.74 (m, 3H), 2.61-2.51 (m, 1H), 2.22-2.10 (m, 1H), 1.98-1.79 (m, 1H). | Example 129 |
| 366 | 1-(3-chloro-4-fluoro-phenyl)-N-[2,3,6-trifluoro-4-[[3-[2-[[(3S,5S)-5-fluoro-3-piperidyl]amino]pyrimidin- | 641.1 | (400 MHz, DMSO-$d_6$, 360K) δ 8.42 (dd, J = 7.5, 2.0 Hz, 1H), 8.37 (d, J = 5.1 Hz, 1H), 8.23 (dd, J = 4.8, 2.0 Hz, 1H), 7.63 (dd, J = 7.3, 2.2 Hz, 1H), 7.47-7.40 (m, | Example 129 |

TABLE A1-continued

| Cpd No. | Name | MS m/z | ¹H NMR (ppm) | Synth. Method |
|---|---|---|---|---|
| | 4-yl]-2-pyridyl]oxy]phenyl]methanesulfonamide | | 1H), 7.38-7.32 (m, 2H), 7.27-7.19 (m, 2H), 6.87-6.80 (m, 1H), 6.03 (s, 1H), 4.90-4.73 (m, 1H), 4.44 (s, 2H), 4.25-4.16 (m, 1H), 3.13-3.05 (m, 2H), 2.89-2.72 (m, 1H), 2.59-2.51 (m, 1H), 2.20-2.11 (m, 1H), 1.98-1.80 (m, 1H). | |
| 367 | 1-(2-chloro-6-fluorophenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 641.1 | (400 MHz, DMSO-d₆, 360K) δ 8.43 (dd, J = 7.6, 1.9 Hz, 1H), 8.38 (d, J = 5.1 Hz, 1H), 8.24 (dd, J = 4.8, 1.9 Hz, 1H), 7.44-7.17 (m, 6H), 6.84 (d, J = 7.9 Hz, 1H), 4.91-4.74 (m, 1H), 4.71-4.66 (m, 2H), 4.27-4.15 (m, 1H), 3.14-3.06 (m, 1H), 2.86-2.73 (m, 2H), 2.60-2.52 (m, 1H), 2.23-2.10 (m, 1H), 1.99-1.80 (m, 1H). | Example 129 |
| 368 | N-(2,3,6-trifluoro-4-((3-(2-(((3S,5S)-5-fluoropiperidin-3-yl)amino)pyrimidin-4-yl)pyridin-2-yl)oxy)phenyl)cyclohexanesulfonamide | 581.2 | (400 MHz, DMSO-d₆, 360K) δ 8.39 (dd, J = 23.5, 6.4 Hz, 2H), 8.23 (d, J = 4.8 Hz, 1H), 7.39-7.25 (m, 2H), 7.20 (d, J = 5.1 Hz, 1H), 6.84-6.77 (m, 1H), 4.86-4.68 (m, 1H), 4.20-4.12 (m, 1H), 2.88-2.63 (m, 5H), 2.23-2.08 (m, 3H), 1.95-1.79 (m, 3H), 1.69-1.61 (m, 1H), 1.55-1.42 (m, 2H), 1.36-1.15 (m, 3H). | Example 129 |
| 369 | N-(2,3,6-trifluoro-4-((3-(2-(((3S,5S)-5-fluoropiperidin-3-yl)amino)pyrimidin-4-yl)pyridin-2-yl)oxy)phenyl)cyclopentanesulfonamide | 567.2 | (400 MHz, DMSO-d₆, 360K) δ 8.39 (dd,, J = 22.4, 6.4 Hz, 2H), 8.23 (d, J = 4.9 Hz, 1H), 7.38-7.31 (m, 1H), 7.29-7.15 (m, 2H), 6.80 (d, J = 8.1 Hz, 1H), 4.85-4.67 (m, 1H), 4.22-4.12 (m, 1H), 3.63-3.54 (m, 1H), 2.86-2.67 (m, 3H), 2.18-2.07 (m, 1H), 2.05-1.92 (m, 5H), 1.90-1.78 (m, 1H), 1.75-1.56 (m, 4H). | Example 129 |
| 370 | N-(2,3,6-trifluoro-4-((3-(2-(((3S,5S)-5-fluoropiperidin-3-yl)amino)pyrimidin-4-yl)pyridin-2-yl)oxy)phenyl)-1-(4-(trifluoromethyl)phenyl)methanesulfonamide | 657.2 | (400 MHz, DMSO-d₆, 360K) δ 8.43 (d, J = 7.5 Hz, 1H), 8.38 (d, J = 5.1 Hz, 1H), 8.24 (d, J = 4.9 Hz, 1H), 7.74-7.64 (m, 4H), 7.40-7.33 (m, 1H), 7.33-7.25 (m, 1H), 7.22 (d, J = 5.1 Hz, 1H), 6.88 (d, J = 8.0 Hz, 1H), 4.93-4.76 (m, 1H), 4.57 (s, 2H), 4.27-4.17 (m, 1H), 2.85-2.74 (m, 3H), 2.61-2.54 (m, 1H), 2.21-2.13 (m, 1H), 1.97-1.81 (m, 1H). | Example 129 |
| 371 | 1-(4-(difluoromethyl)phenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 639.2 | (400 MHz, DMSO-d₆, 360K) δ 8.43 (d, J = 7.4 Hz, 1H), 8.38 (d, J = 5.1 Hz, 1H), 8.27-8.21 (m, 1H), 7.62-7.52 (m, 4H), 7.36 (dd, J = 7.5, 4.8 Hz, 1H), 7.32-7.25 (m, 1H), 7.22 (d, J = 5.1 Hz, 1H), 6.88-6.82 (m, 1H), 4.90-4.74 (m, 1H), 4.52 (s, 2H), 4.25-4.16 (m, 1H), 2.83-2.72 (m, 3H), 2.60-2.53 (m, 1H), 2.14 (d, J = 11.4 Hz, 1H), 1.96-1.82 (m, 1H). | Example 129 |
| 372 | 1-(4-fluorophenyl)-N-(2,3,6-trifluoro-4-(3-(2-(((3S,5S)-5-fluoropiperidin-3-yl)amino)pyrimidin-4-yl)pyridin-2-yl)oxy)phenyl)methanesulfonamide | 607.2 | (400 MHz, DMSO-d₆, 360K) δ 8.42 (d, J = 7.5, 1.9 Hz, 1H), 8.37 (d, J = 5.3, 1.7 Hz, 1H), 8.23 (dd, J = 4.7, 2.0 Hz, 1H), 7.51-7.43 (m, 2H), 7.39-7.31 (m, 1H), 7.29-7.19 (m, 2H), 7.19-7.10 (m, 2H), 6.83 (d, J = 7.8 Hz, 1H), 4.89-4.71 (m, 1H), 4.42 (s, 2H), 4.24-4.13 (m, 1H), 2.87-2.70 (m, 3H), 2.58-2.51 (m, 1H), 2.20-2.09 (m, 1H), 1.96-1.81 (m, 1H). | Example 129 |
| 373 | N-(2,3,6-trifluoro-4-((3-(2-(((3S,5S)-5-fluoropiperidin-3-yl)amino)pyrimidin-4-yl)pyridin-2-yl)oxy)phenyl)-1-(2-(trifluoromethyl)phenyl)methanesulfonamide | 657.2 | (400 MHz, DMSO-d₆, 360K) δ 8.43 (dd, J = 7.5, 1.9 Hz, 1H), 8.38 (d, J = 5.2 Hz, 1H), 8.24 (dd, J = 4.8, 1.9 Hz, 1H), 7.82 (d, J = 7.8 Hz, 1H), 7.74 (dd, J = 7.8, 1.4 Hz, 1H), 7.71-7.63 (m, 1H), 7.59-7.51 (m, 1H), 7.35 (dd, J = 7.6, 4.9 Hz, 1H), 7.33-7.23 (m, 1H), 7.23 (d, J = 5.1 Hz, 1H), 6.90 (d, J = 8.0 Hz, 1H), 4.94-4.74 (m, 1H), 4.66 (s, 2H), 4.28-4.16 (m, 1H), 3.14-3.07 (m, 1H), 2.97-2.74 (m, 2H), 2.62-2.51 (m, 1H), 2.22-2.12 (m, 1H), 1.99-1.78 (m, 1H). | Example 129 |
| 374 | N-(2,3,6-trifluoro-4-((3-(2-(((3S,5S)-5-fluoropiperidin-3-yl)amino)pyrimidin-4-yl)pyridin-2-yl)oxy)phenyl)-1-(3-(trifluoromethyl)phenyl)methanesulfonamide | 657.2 | (400 MHz, DMSO-d₆, 360K) δ 8.43 (dd, J = 7.6, 1.9 Hz, 1H), 8.38 (d, J = 5.1 Hz, 1H), 8.24 (dd, J = 4.8, 1.9 Hz, 1H), 7.82-7.77 (m, 1H), 7.77-7.71 (m, 1H), 7.71-7.64 (m, 1H), 7.64-7.56 (m, 1H), 7.35 (dd, J = 7.6, 4.9 Hz, 1H), 7.31-7.21 (m, 1H), 7.22 (d, J = 5.1 Hz, 1H), 6.89 (d, J = 8.0 Hz, 1H), 4.93-4.73 (m, 1H), 4.56 (s, | Example 129 |

TABLE A1-continued

| Cpd No. | Name | MS m/z | ¹H NMR (ppm) | Synth. Method |
|---|---|---|---|---|
| | | | 2H), 4.28-4.14 (m, 1H), 3.14-3.05 (m, 1H), 2.96-2.73 (m, 2H), 2.61-2.50 (m, 1H), 2.23-2.10 (m, 1H), 1.99-1.78 (m, 1H). | |
| 375 | 1-p-tolyl-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 603.2 | (400 MHz, DMSO-d₆, 360K) δ 8.43 (dd, J = 7.5, 1.9 Hz, 1H), 8.38 (d, J = 5.1 Hz, 1H), 8.24 (dd, J = 4.9, 2.0 Hz, 1H), 7.36 (dd, J = 7.5, 4.8 Hz, 1H), 7.34-7.29 (m, 3H), 7.22 (d, J = 5.1 Hz, 1H), 7.20-7.15 (m, 2H), 6.86 (d, J = 8.0 Hz, 1H), 4.91-4.70 (m, 1H), 4.42 (s, 2H), 4.27-4.12 (m, 1H), 3.09-3.08 (m, 1H), 2.95-2.86 (m, 1H), 2.86-2.71 (m, 1H), 2.57-2.51 (m, 1H), 2.31 (s, 3H), 2.21-2.08 (m, 1H), 1.97-1.79 (m, 1H). | Example 129 |
| 376 | 1-(bicyclo[2.2.1]heptan-1-yl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 607.2 | (400 MHz, DMSO-d₆, 360K) δ 8.43 (dd, J = 7.5, 2.0 Hz, 1H), 8.37 (d, J = 5.1 Hz, 1H), 8.23 (dd, J = 4.7, 1.9 Hz, 1H), 7.35 (ddd, J = 10.9, 7.1, 3.5 Hz, 2H), 7.21 (d, J = 5.2 Hz, 1H), 6.86 (d, J = 8.0 Hz, 1H), 4.89-4.71 (m, 1H), 4.25-4.12 (m, 1H), 3.51 (s, 2H), 2.93-2.71 (m, 3H), 2.58-2.51 (m, 1H), 2.22-2.09 (m, 2H), 1.96-1.79 (m, 1H), 1.69-1.54 (m, 4H), 1.54-1.45 (m, 2H), 1.40 (s, 2H), 1.32-1.24 (m, 2H). | Example 129 |
| 377 | 1-(bicyclo[2.2.2]octan-1-yl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 621.3 | (400 MHz, DMSO-d₆, 360K) δ 8.43 (dd, J = 7.5, 2.0 Hz, 1H), 8.37 (d, J = 5.1 Hz, 1H), 8.23 (dd, J = 4.8, 2.0 Hz, 1H), 7.40-7.29 (m, 2H), 7.20 (d, J = 5.2 Hz, 1H), 6.86 (d, J = 8.0 Hz, 1H), 4.90-4.71 (m, 1H), 4.25-4.12 (m, 1H), 3.10-3.06 (m, 2H), 2.96-2.86 (m, 3H), 2.84-2.71 (m, 1H), 2.56-2.51 (m, 1H), 2.21-2.08 (m, 1H), 1.97-1.77 (m, 1H), 1.67-1.51 (m, 12H). | Example 129 |
| 378 | 1-(2,5-difluorophenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 625.1 | (400 MHz, DMSO-d₆, 360K) δ 8.42 (dd, J = 7.5, 2.0 Hz, 1H), 8.38 (d, J = 5.1 Hz, 1H), 8.24 (dd, J = 4.8, 2.0 Hz, 1H), 7.39-7.32 (m, 2H), 7.26-7.14 (m, 4H), 6.88 (d, J = 7.9 Hz, 1H), 4.93-4.74 (m, 1H), 4.42 (s, 2H), 4.27-4.15 (m, 1H), 2.87-2.74 (m, 3H), 2.55 (ddd, J = 12.5, 8.9, 1.9 Hz, 1H), 2.22-2.11 (m, 1H), 1.97-1.80 (m, 1H). | Example 129 |
| 379 | 1-(4-cyanophenyl)-N-(2,3-difluoro-4-((3-(2-(((S)-piperidin-3-yl)amino)pyrimidin-4-yl)pyridin-2-yl)oxy)phenyl)ethane-1-sulfonamide | 592.2 | (400 MHz, DMSO-d₆, 360K) δ 8.43-8.34 (m, 2H), 8.21 (dd, J = 4.8, 2.0 Hz, 1H), 7.73-7.67 (m, 2H), 7.62-7.56 (m, 2H), 7.32-7.21 (m, 2H), 7.16-7.06 (m, 1H), 6.87 (td, J = 7.4, 6.5, 2.1 Hz, 2H), 4.42 (q, J = 7.0 Hz, 1H), 4.07-3.95 (m, 1H), 3.25-3.21 (m, 1H), 2.94-2.92 (m, 1H), 2.70-2.63 (m, 2H), 1.99-1.91 (m, 1H), 1.82-1.71 (m, 1H), 1.66 (d, J = 7.0 Hz, 3H), 1.63-1.52 (m, 2H). | Example 144 |
| 380 | (S)-N-(2,3-difluoro-4-((3-(2-(piperidin-3-ylamino)pyrimidin-4-yl)pyridin-2-yl)oxy)phenyl)-1-(2-methoxyphenyl)methanesulfonamide | 583.2 | (400 MHz, DMSO-d₆) δ 8.41 (d, J = 5.1 Hz, 1H), 8.22 (dd, J = 4.8, 2.0 Hz, 1H), 7.38-7.18 (m, 6H), 7.02-6.86 (m, 3H), 4.28 (s, 2H), 4.07-3.95 (m, 1H), 3.68 (s, 3H), 3.21-3.18 (m, 1H), 3.02-2.92 (m, 1H), 2.68-2.53 (m, 2H), 1.98-1.91 (m, 1H), 1.81-1.72 (m, 1H), 1.60-1.49 (m, 2H). | Example 144 |
| 381 | (S)-N-(2,3-difluoro-4-((3-(2-(piperidin-3-ylamino)pyrimidin-4-yl)pyridin-2-yl)oxy)phenyl)-9H-fluorene-9-sulfonamide | 627.2 | (400 MHz, DMSO-d₆, 360K) δ 8.49-8.28 (m, 2H), 8.18 (dd, J = 4.6, 2.2 Hz, 1H), 7.92 (d, J = 7.6 Hz, 2H), 7.76 (d, J = 7.5 Hz, 2H), 7.40-7.20 (m, 7H), 6.76-6.67 (m, 2H), 6.67-6.60 (m, 1H), 5.23 (s, 1H), 3.93-3.79 (m, 1H), 2.67-2.64 (m, 1H), 2.34-2.29 (m, 1H), 2.07-1.87 (m, 3H), 1.70-1.36 (m, 3H). | Example 144 |
| 382 | N-(4-((3-(2-(((1r,4r)-4-(dimethylamino)cyclohexyl)amino)pyrimidin-4- | 619.2 | (400 MHz, DMSO-d₆) δ 8.40-8.32 (m, 2H), 8.26 (dd, J = 4.8, 2.0 Hz, 1H), 7.34 (dd, J = 7.6, 4.9 Hz, 1H), 7.24 (d, J = 7.8 | Example 125 step 1; |

TABLE A1-continued

| Cpd No. | Name | MS m/z | ¹H NMR (ppm) | Synth. Method |
|---|---|---|---|---|
| | yl)pyridin-2-yl)oxy)-2,3,6-trifluorophenyl)-3,3,3-trifluoropropane-1-sulfonamide | | Hz, 1H), 7.18 (d, J = 5.1 Hz, 1H), 7.13-7.03 (m, 1H), 3.78-3.67 (m, 1H), 3.02-2.86 (m, 3H), 2.73-2.58 (m, 7H), 2.13-2.02 (m, 2H), 1.99-1.92 (m, 2H), 1.56-1.19 (m, 4H). | Example 129 step 1 |
| 383 | 1-m-tolyl-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 603.2 | (400 MHz, DMSO-d₆, 360K) δ 8.46 (dd, J = 7.6, 2.0 Hz, 1H), 8.42 (d, J = 5.1 Hz, 1H), 8.26 (dd, J = 4.8, 1.9 Hz, 1H), 7.43-7.33 (m, 2H), 7.32-7.13 (m, 6H), 5.20-5.02 (m, 1H), 4.45-4.37 (m, 1H), 3.41-3.29 (m, 2H), 3.21-3.11 (m, 1H), 2.84-2.75 (m, 1H), 2.36-2.27 (m, 4H), 2.03-1.84 (m, 1H), 1.32-1.26 (m, 1H), 0.93-0.79 (m, 1H). | Example 129 |
| 384 | 1-(2-fluoro-4-methylphenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 621.2 | (400 MHz, DMSO-d₆, 360K) δ 8.43 (dd, J = 7.6, 2.0 Hz, 1H), 8.38 (d, J = 5.0 Hz, 1H), 8.24 (dd, J = 4.9, 2.0 Hz, 1H), 7.42-7.27 (m, 3H), 7.22 (d, J = 5.1 Hz, 1H), 7.05-7.00 (m, 2H), 6.88 (d, J = 8.0 Hz, 1H), 4.91-4.73 (m, 1H), 4.47 (s, 2H), 4.26-4.15 (m, 1H), 2.89-2.74 (m, 3H), 2.59-2.51 (m, 1H), 2.33 (s, 3H), 2.20-2.11 (m, 1H), 1.97-1.79 (m, 1H). | Example 129 |
| 385 | 1-(3-methoxyphenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 619.2 | (400 MHz, DMSO-d₆, 360K) δ 8.43 (dd, J = 7.6, 2.0 Hz, 1H), 8.38 (d, J = 5.1 Hz, 1H), 8.24 (dd, J = 4.9, 2.0 Hz, 1H), 7.38-7.25 (m, 3H), 7.22 (d, J = 5.1 Hz, 1H), 7.04-7.00 (m, 2H), 6.94-6.89 (m, 1H), 6.87 (d, J = 8.0 Hz, 1H), 4.89-4.73 (m, 1H), 4.44 (s, 2H), 4.24-4.14 (m, 1H), 3.77 (s, 3H), 2.90 (d, J = 4.3 Hz, 1H), 2.85-2.79 (m, 1H), 2.79-2.72 (m, 1H), 2.57-2.50 (m, 1H), 2.20-2.10 (m, 1H), 1.96-1.80 (m, 1H). | Example 129 |
| 386 | 1-o-tolyl-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide | 603.2 | (400 MHz, DMSO-d₆, 360K) δ 8.43 (dd, J = 7.5, 1.9 Hz, 1H), 8.38 (d, J = 5.1 Hz, 1H), 8.24 (dd, J = 4.8, 1.9 Hz, 1H), 7.38-7.30 (m, 3H), 7.26-7.15 (m, 4H), 6.87 (d, J = 8.0 Hz, 1H), 4.89-4.72 (m, 1H), 4.53 (s, 2H), 4.24-4.14 (m, 1H), 2.90-2.72 (m, 3H), 2.57-2.50 (m, 1H), 2.39 (s, 3H), 2.20-2.10 (m, 1H), 1.96-1.80 (m, 1H). | Example 129 |
| 387 | (*S)-1-phenyl-N-(2,3,6-trifluoro-4-((3-(2-(((3S,5S)-5-fluoropiperidin-3-yl)amino)pyrimidin-4-yl)pyridin-2-yl)oxy)phenyl)ethane-1-sulfonamide | 603.2 | (400 MHz, DMSO-d₆, 360K) δ 8.43 (dd, J = 7.5, 2.0 Hz, 1H), 8.37 (d, J = 5.1 Hz, 1H), 8.24 (dd, J = 4.8, 1.9 Hz, 1H), 7.48-7.44 (m, 2H), 7.38-7.25 (m, 5H), 7.21 (d, J = 5.0 Hz, 1H), 6.85 (d, J = 8.0 Hz, 1H), 4.88-4.71 (m, 1H), 4.44 (q, J = 7.0 Hz, 1H), 4.23-4.13 (m, 1H), 2.89-2.87 (m, 1H), 2.83-2.78 (m, 1H), 2.75-2.70 (m, 1H), 2.56-2.51 (m, 1H), 2.20-2.09 (m, 1H), 1.96-1.79 (m, 1H), 1.76 (d, J = 7.0 Hz, 3H). | Example 99 |
| 388 | (*R)-1-phenyl-N-(2,3,6-trifluoro-4-((3-(2-(((3S,5S)-5-fluoropiperidin-3-yl)amino)pyrimidin-4-yl)pyridin-2-yl)oxy)phenyl)ethane-1-sulfonamide | 603.2 | (400 MHz, DMSO-d₆, 360K) δ 8.43 (dd, J = 7.5, 2.0 Hz, 1H), 8.37 (d, J = 5.1 Hz, 1H), 8.24 (dd, J = 4.8, 1.9 Hz, 1H), 7.48-7.44 (m, 2H), 7.38-7.25 (m, 5H), 7.21 (d, J = 5.0 Hz, 1H), 6.85 (d, J = 8.0 Hz, 1H), 4.88-4.71 (m, 1H), 4.44 (q, J = 7.0 Hz, 1H), 4.23-4.13 (m, 1H), 2.89-2.87 (m, 1H), 2.83-2.78 (m, 1H), 2.75-2.70 (m, 1H), 2.56-2.51 (m, 1H), 2.20-2.09 (m, 1H), 1.96-1.79 (m, 1H), 1.76 (d, J = 7.0 Hz, 3H). | Example 99 |
| 389 | N-(2,3,6-trifluoro-4-((3-(2-(((3S,5S)-5-fluoropiperidin-3-yl)amino)pyrimidin-4-yl)pyridin-2-yl)oxy)phenyl)-1-(2-(trifluoromethyl)pyridin-3-yl)methanesulfonamide | 658.2 | (400 MHz, DMSO-d₆, 360K) δ 8.68 (d, J = 4.6 Hz, 1H), 8.43 (dd, J = 7.5, 2.1 Hz, 1H), 8.39 (d, J = 5.0 Hz, 1H), 8.26-8.20 (m, 2H), 7.74-7.68 (m, 1H), 7.38-7.33 (m, 1H), 7.27-7.20 (m, 2H), 6.95 (d, J = 7.8 Hz, 1H), 4.99-4.82 (m, 1H), 4.65 (s, 2H), 4.33-4.20 (m, 1H), 3.21-3.14 (m, 2H), 2.89-2.82 (m, 1H), 2.67-2.57 (m, 1H), 2.26-2.15 (m, 1H), 1.99-1.81 (m, 1H). | Example 129 |

*= arbitrarily assigned

Abbreviations

ACN: acetonitrile
DCM: dichloromethane
DMF: N,N-dimethylformamide
DMSO: dimethyl sulfoxide
EtOAc: ethyl acetate
EtOH: ethanol
h: hour
HCl: hydrochloric acid
HPLC: High-performance liquid chromatography
IPA: isopropyl alcohol
LCMS: Liquid chromatography-mass spectrometry
MeCN: acetonitrile
THF: tetrahydrofuran Example 1

N-[4-[[3-[2-[(4-Aminocyclohexyl)amino]pyrimidin-4-yl]-2-pyridyl]oxy]-3-methyl-phenyl]-2-chloro-benzenesulfonamide hydrochloride (Compound 101)

Step 1: tert-Butyl N-[4-[[4-[2-(4-amino-2-methyl-phenoxy)-3-pyridyl]pyrimidin-2-yl]amino]cyclohexyl]carbamate

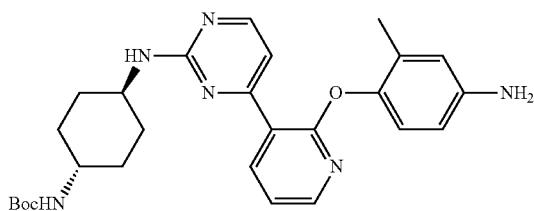

A mixture of tert-butyl (3S)-3-[[4-(2-fluoro-3-pyridyl)pyrimidin-2-yl]amino]piperidine-1-carboxylate (151 mg, 0.41 mmol), 4-amino-2-methylphenol (50 mg, 0.41 mmol) and cesium carbonate (397 mg, 1.22 mmol) in DMSO (1 mL) was degassed 3 times and stirred at 130° C. for 1.5 h under N$_2$. The reaction mixture was cooled to room temperature, diluted with ethyl acetate, washed with water and brine, dried over anhydrous Na$_2$SO$_4$, filtered and concentrated in vacuo. The residue was purified by prep-HPLC (petroleum ether/ethyl acetate=1/1) to give the title compound (110 mg, 55% yield) as a yellow solid. LCMS (ESI) [M+H]$^+$=491.

Step 2: tert-Butyl N-[4-[[4-[2-[4-[(2-chlorophenyl)sulfonylamino]-2-methyl-phenoxy]-3-pyridyl]pyrimidin-2-yl]amino]cyclohexyl]carbamate

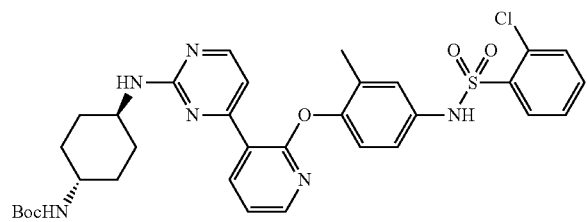 [SMILES: Cc1cc(NS(=O)(=O)c2ccccc2Cl)ccc1Oc1ncccc1-c1ccnc(N[C@H]2CC[C@H](NC(=O)OC(C)(C)C)CC2)n1]

To a solution of tert-butyl N-[4-[[4-[2-(4-amino-2-methyl-phenoxy)-3-pyridyl]pyrimidin-2-yl]amino]cyclohexyl]carbamate (110 mg, 0.22 mmol) in pyridine (2 mL) was added 2-chlorobenzenesulfonylchloride (56 mg, 0.27 mmol) at 0° C. After completion of the addition, the reaction mixture was stirred at room temperature for 4 h. The mixture was concentrated in vacuo, and water was added. The mixture was extracted twice with DCM, dried over anhydrous Na$_2$SO$_4$, filtered and concentrated in vacuo. The residue was purified by prep-TLC (ethyl acetate/:petroleum ether=2:3) to afford the title compound (130 mg, 87% yield) as a yellow solid. LCMS (ESI) [M+H]$^+$=665.

Step 3: N-[4-[[3-[2-[(4-Aminocyclohexyl)amino]pyrimidin-4-yl]-2-pyridyl]oxy]-3-methyl-phenyl]-2-chloro-benzenesulfonamide hydrochloride

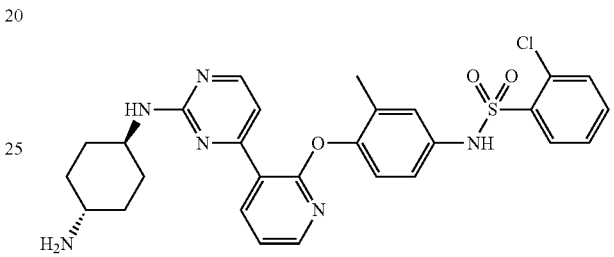

To a mixture of tert-butyl N-[4-[[4-[2-[4-[(2-chlorophenyl)sulfonylamino]-2-methyl-phenoxy]-3-pyridyl]pyrimidin-2-yl]amino]cyclohexyl]carbamate (100 mg, 0.15 mmol) in DCM (8 mL) was added HCl in dioxane (4 mL, 16 mmol). The mixture was then stirred at room temperature for 0.5 h and then concentrated. The residue was purified by prep-HPLC to give the title product (63 mg, 70% yield) as a white solid.

Example 2

N-[4-[[3-[2-[(4-Aminocyclohexyl)amino]pyrimidin-4-yl]-2-pyridyl]oxy]-3-fluoro-5-methyl-phenyl]-2-chloro-benzenesulfonamide hydrochloride Compound 102

Step 1: N-(3-Fluoro-4-hydroxy-phenyl)acetamide

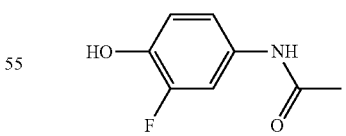

To a solution of 4-amino-2-fluorophenol (3.29 g, 25.9 mmol) and triethylamine (3.61 mL, 25.9 mmol) in methanol (130 mL) was added acetic anhydride (2.64 g, 25.9 mmol) at 0° C. The mixture was allowed to stir at 50° C. for 1.5 h. The solution was then concentrated in vacuo. The residue was purified by silica flash chromatography (petroleum ether/ethyl acetate=1:2) to provide the title compound (1.0 g, 20% yield) as a brown solid. LCMS (ESI) [M+H]$^+$=170.1.

Step 2: N-[3-(Diethylaminomethyl)-5-fluoro-4-hydroxy-phenyl]acetamide

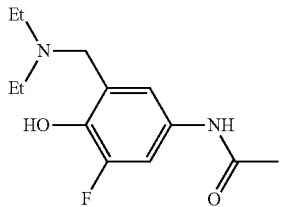 [SMILES: CCN(CC)Cc1cc(NC(C)=O)cc(F)c1O]

To a mixture of N-(3-fluoro-4-hydroxy-phenyl)acetamide (210 mg, 1.24 mmol) and paraformaldehyde (37 mg, 1.24 mmol) in ethanol (6 mL) was added diethylamine (0.26 mL, 2.48 mmol). The mixture was allowed to stir at 70° C. overnight then cooled to room temperature and subsequently concentrated under vacuum. The residue was purified by silica gel column chromatography (petroleum ether/ethyl acetate=1:3) to provide the title compound (110 mg, 34% yield) as a gray solid. LCMS (ESI) [M+H]$^+$=255.1.

Step 3: N-(3-Fluoro-4-hydroxy-5-methyl-phenyl)acetamide

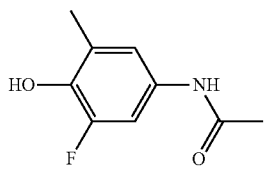

To a solution of N-[3-(diethylaminomethyl)-5-fluoro-4-hydroxy-phenyl]acetamide (230 mg, 0.90 mmol) in methanol (5 mL) was added 10% Pd/C (50 mg). The mixture was purged with H$_2$ 3 times and stirred at 50° C. for 3 days. The mixture was filtered to give the title compound (160 mg, 96% yield) as a white solid. LCMS (ESI) [M+H]$^+$=184.1.

Step 4: 4-Amino-2-fluoro-6-methyl-phenol hydrochloride

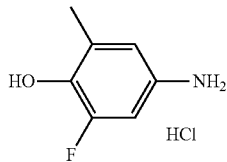

To a solution of N-(3-fluoro-4-hydroxy-5-methyl-phenyl)acetamide (160 mg, 0.87 mmol) in 1,4-dioxane (4 mL) was added HCl (1 mL, 0.87 mmol). The mixture was stirred at 100° C. overnight and subsequently concentrated in vacuo to afford the title compound (150 mg, 96% yield) as a yellow solid. LCMS (ESI) [M+H]$^+$=142.1.

Step 5: tert-butyl ((1r,4r)-4-((4-(2-(4-amino-2-fluoro-6-methylphenoxy)pyridin-3-yl)pyrimidin-2-yl)amino)cyclohexyl)carbamate

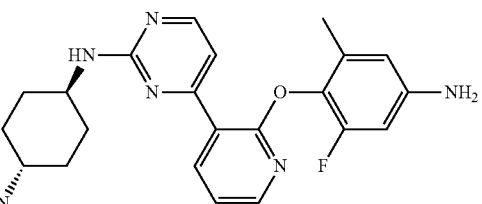

A mixture of tert-butyl N-[4-[[4-(2-fluoro-3-pyridyl)pyrimidin-2-yl]amino]cyclohexyl]carbamate (150 mg, 0.39 mmol), 4-amino-2-fluoro-6-methyl-phenol hydrochloride (150 mg, 0.84 mmol) and cesium carbonate (826 mg, 2.53 mmol) in DMSO (1 mL) was degassed for 3 times and stirred at 130° C. for 1.5 h under N$_2$. The mixture was concentrated in vacuo, and ethyl acetate (30 mL) was added. The mixture was washed with water, brine, dried over anhydrous Na$_2$SO$_4$, filtered and concentrated in vacuo. The crude product was purified by prep-TLC (petroleum ether/ethyl acetate=2:1) to give the title compound (140 mg, 71% yield) as a yellow solid. LCMS (ESI) [M+H]$^+$=509.3.

Step 6: tert-Butyl N-[4-[[4-[2-[4-[(2-chlorophenyl)sulfonylamino]-2-fluoro-6-methyl-phenoxy]-3-pyridyl]pyrimidin-2-yl]amino]cyclohexyl]carbamate

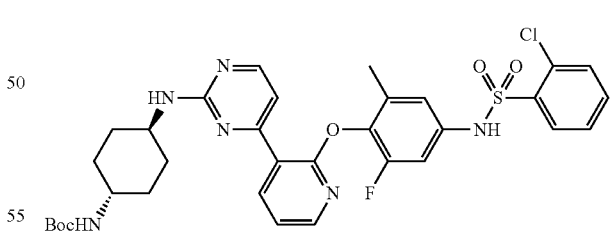

To a solution of tert-butyl N-[4-[[4-[2-(4-amino-2-fluoro-6-methyl-phenoxy)-3-pyridyl]pyrimidin-2-yl]amino]cyclohexyl]carbamate (140 mg, 0.28 mmol) in dry pyridine (2 mL) was added 2-chlorobenzenesulfonylchloride (69 mg, 0.33 mmol) at 0° C. After completion of the addition, the reaction mixture was stirred at room temperature overnight. The mixture was concentrated in vacuo The residue was purified by prep-TLC (ethyl acetate:petroleum ether=1:1) to afford the title compound (140 mg, 74% yield) as a yellow solid. LCMS (ESI) [M+H]$^+$=683.2.

Step 7: N[4-[[3-[2-[(4-Aminocyclohexyl)amino]pyrimidin-4-yl]-2-pyridyl]oxy]-3-fluoro-5-methyl-phenyl]-2-chloro-benzenesulfonamide hydrochloride Step 2: 3-[[3-[2-[[(3S)-1-tert-Butoxycarbonyl-3-piperidyl]amino]pyrimidin-4-yl]-2-pyridyl]oxy]-4-methyl-benzoic acid

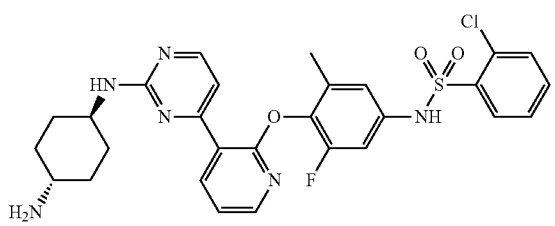

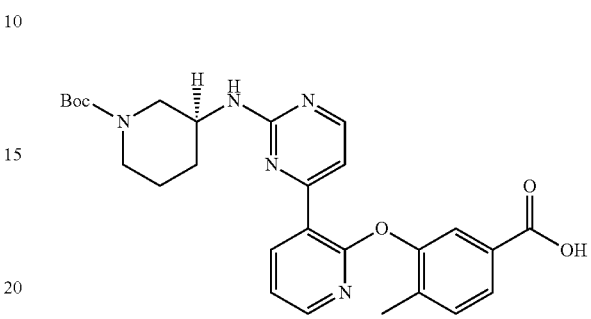

To a solution of tert-butyl N-[4-[[4-[2-[4-[(2-chlorophenyl)sulfonylamino]-2-fluoro-6-methyl-phenoxy]-3-pyridyl]pyrimidin-2-yl]amino]cyclohexyl]carbamate (140 mg, 0.20 mmol) in DCM (4 mL) was added HCl in dioxane (2 mL, 2 mmol). The mixture was then stirred at room temperature for 0.5 h and concentrated in vacuo. The residue was purified by prep-HPLC to give the title compound (53 mg, 41% yield) as a white solid.

Example 3

(S)—N-(2-Chlorophenylsulfonyl)-4-methyl-3-(3-(2-(piperidin-3-ylamino)pyrimidin-4-yl)pyridin-2-yloxy)benzamide hydrochloride (Compound 103)

Step 1: tert-Butyl (3S)-3-[[4-[2-(5-methoxycarbonyl-2-methyl-phenoxy)-3-pyridyl]pyrimidin-2-yl]amino]piperidine-1-carboxylate A mixture of tert-butyl (3S)-3-[[4-[2-(5-methoxycarbonyl-2-methyl-phenoxy)-3-pyridyl]pyrimidin-2-yl]amino]piperidine-1-carboxylate (210 mg, 0.40 mmol) and lithium hydroxide (14 mg, 0.61 mmol) in THF (10 mL) was stirred at room temperature for 2 h. The mixture was concentrated and purified by prep-TLC (petroleum ether/ethyl acetate=1/2) to give 3-[[3-[2-[[(3S)-1-tert-butoxycarbonyl-3-piperidyl]amino]pyrimidin-4-yl]-2-pyridyl]oxy]-4-methyl-benzoic acid (160 mg, 78% yield) as a yellow solid. LCMS (ESI): $[M+H]^+=506.2$.

Step 3: tert-Butyl (3S)-3-[[4-[2-[5-[(2-chlorophenyl)sulfonylcarbamoyl]-2-methyl-phenoxy]-3-pyridyl]pyrimidin-2-yl]amino]piperidine-1-carboxylate

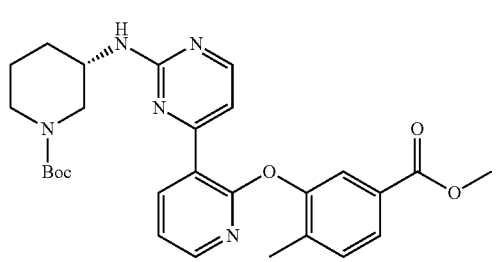 [SMILES: COC(=O)c1ccc(C)c(Oc2ncccc2-c2ccnc(N[C@H]3CCCN(C(=O)OC(C)(C)C)C3)n2)c1]

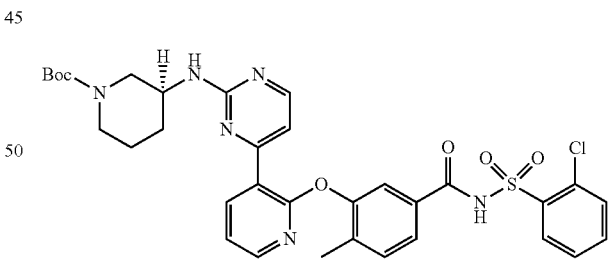

A mixture of tert-butyl (3S)-3-[[4-(2-fluoro-3-pyridyl)pyrimidin-2-yl]amino]piperidine-1-carboxylate (200 mg, 0.54 mmol), methyl 3-hydroxy-4-methyl-benzoate (106 mg, 0.64 mmol) and cesium carbonate (348 mg, 1.07 mmol) in DMSO (3 mL) was stirred at 130° C. for 2 h. The reaction mixture was diluted in ethyl acetate (50 mL), washed with brine and then dried over anhydrous sodium sulfate. Evaporation in vacuo gave the title product as a yellow solid (210 mg), which was used in the next step without further purification. LCMS (ESI): $[M+H]^+=520.3$.

A mixture of 3-[[3-[2-[[(3S)-1-tert-butoxycarbonyl-3-piperidyl]amino]pyrimidin-4-yl]-2-pyridyl]oxy]-4-methyl-benzoic acid (150 mg, 0.30 mmol), 2-chlorobenzenesulfonamide (74 mg, 0.39 mmol), 1-ethyl-3-(3-dimethylaminopropyl)carbodiimide (85 mg, 0.45 mmol), N-hydroxybenzotrizole (60 mg, 0.45 mmol) and N,N-diisopropylethylamine (76 mg, 0.59 mmol) in DCM (15 mL) was stirred at room temperature for 16 h. The mixture was concentrated in vacuo to give the crude product (150 mg) as a yellow oil, which was used in the next step without further purification. LCMS (ESI): $[M+H]^+=679.2$.

Step 4: N-(2-Chlorophenyl)sulfonyl-4-methyl-3-[[3-[2-[[(3S)-3-piperidyl]amino]pyrimidin-4-yl]-2-pyridyl]oxy]benzamide hydrochloride

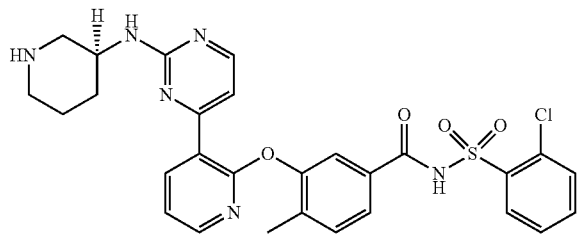 [SMILES: Cc1ccc(C(=O)NS(=O)(=O)c2ccccc2Cl)cc1Oc1ncccc1-c1ccnc(N[C@H]2CCCNC2)n1]

To a solution of tert-butyl (3S)-3-[[4-[2-[5-[(2-chlorophenyl)sulfonylcarbamoyl]-2-methyl-phenoxy]-3-pyridyl]pyrimidin-2-yl]amino]piperidine-1-carboxylate (150 mg, 0.22 mmol) in DCM (10 mL) was added hydrochloric acid (4 M in 1,4-dioxane, 2 mL). The reaction mixture was stirred at room temperature for 1 h, concentrated in vacuo and purified by prep-HPLC to give the title compound (27.5 mg, 20% yield) as a white solid.

Example 4

N-[4-[[3-[2-[(4-Aminocyclohexyl)amino]pyrimidin-4-yl]-2-pyridyl]oxy]-3-chloro-5-fluoro-phenyl]-2-chloro-benzenesulfonamide hydrochloride Compound 104

Step 1: 2-Chloro-N-(3-chloro-5-fluoro-4-methoxyphenyl)benzenesulfonamide

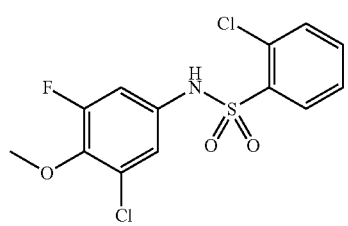 [SMILES: COc1c(F)cc(NS(=O)(=O)c2ccccc2Cl)cc1Cl]

To a solution of 3-chloro-5-fluoro-4-methoxy-aniline (1.0 g, 5.7 mmol) in pyridine (10 mL) was added 2-chlorobenzenesulfonylchloride (1.44 g, 6.83 mmol) at 0° C. After completion of the addition, the reaction mixture was stirred at 20° C. overnight. The reaction mixture was then concentrated in vacuo. The crude product was purified by silica flash chromatography (petroleum ether/ethyl acetate=6/1) to give the title compound (1.9 g, 95% yield) as a yellow solid. LCMS (ESI): [M+H$_2$O]$^+$=367.

Step 2: 2-Chloro-N-(3-chloro-5-fluoro-4-hydroxyphenyl)benzenesulfonamide

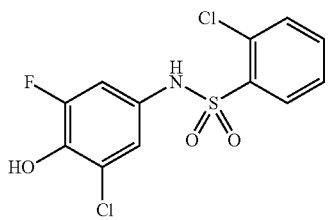 [SMILES: O=S(=O)(Nc1cc(F)c(O)c(Cl)c1)c1ccccc1Cl]

A mixture of 2-chloro-N-(3-chloro-5-fluoro-4-methoxyphenyl)benzenesulfonamide (230 mg, 0.66 mmol) and tribromoborane (2.05 mL, 2.05 mmol) in DCM (5 mL) was stirred at 0° C. for 16 h. Then, methanol was added and the solvent and trimethyl borate were removed in vacuo. The residue was dissolved in methanol and the solution was evaporated again under reduced pressure to remove traces of trimethyl borate. The solid residue was dissolved in ethyl acetate, and the solution was washed with water and dried with anhydrous sodium sulfate. The solvent was removed under reduced pressure, and the crude product was purified by prep-TLC (ethyl acetate/petroleum ether=¼) to provide the title compound (220 mg, 99% yield) as a yellow oil. LCMS (ESI): [M+Na]$^+$=358.

Step 3: tert-Butyl N-[4-[[4-[2-[2-chloro-4-[(2-chlorophenyl)sulfonylamino]-6-fluoro-phenoxy]-3-pyridyl]pyrimidin-2-yl]amino]cyclohexyl]carbamate

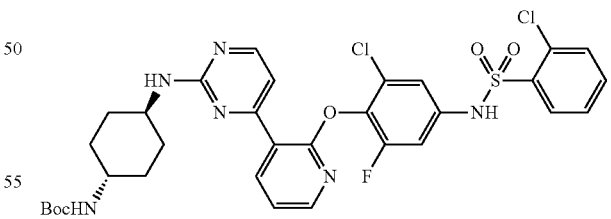

A mixture of 2-chloro-N-(3-chloro-5-fluoro-4-hydroxyphenyl)benzenesulfonamide (220 mg, 0.65 mmol), tert-butyl N-[4-[[4-(2-fluoro-3-pyridyl)pyrimidin-2-yl]amino]cyclohexyl]carbamate (253 mg, 0.65 mmol) and cesium carbonate (213 mg, 0.65 mmol) in DMSO (5 mL) was stirred at 110° C. for 2 h, then concentrated and purified by prep-TLC (petroleum ether/ethyl acetate=1/2) to give the title compound (130 mg, 28% yield) as a yellow solid. LCMS (ESI): [M+H]$^+$=703.

Step 4: N-[4-[[3-[2-[(4-Aminocyclohexyl)amino]pyrimidin-4-yl]-2-pyridyl]oxy]-3-chloro-5-fluorophenyl]-2-chloro-benzenesulfonamide hydrochloride

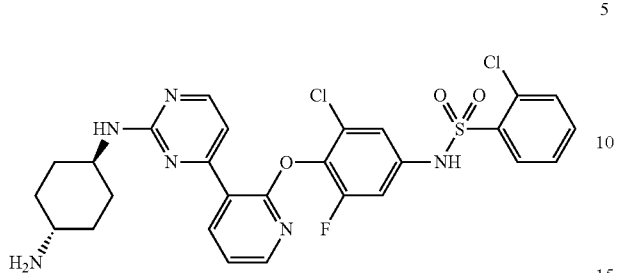

A mixture of tert-butyl N-[4-[[4-[2-[2-chloro-4-[(2-chlorophenyl)sulfonylamino]-6-fluoro-phenoxy]-3-pyridyl]pyrimidin-2-yl]amino]cyclohexyl]carbamate (130 mg, 0.18 mmol) and hydrochloric acid (4 M in 1,4-dioxane, 1.5 mL, 1.5 mmol) in DCM (1.5 mL) was stirred at room temperature for 1 h. The mixture was concentrated and the residue purified by prep-HPLC to give the title compound (87 mg, 73% yield) as a white solid.

Example 5

(S)-3,3,3-Trifluoro-N-(2-fluoro-4-((3-(2-(piperidin-3-ylamino)pyrimidin-4-yl)pyridin-2-yl)oxy)phenyl)propane-1-sulfonamide hydrochloride (Compound 105)

Step 1: 2-Chloro-4-(2-fluoropyridin-3-yl)pyrimidine

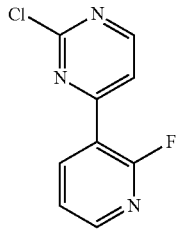 [SMILES: Fc1ncccc1-c1ccnc(Cl)n1]

To a mixture of 2,4-dichloropyrimidine (10.0 g, 67.1 mmol) and (2-fluoropyridin-3-yl)boronic acid (11.4 g, 80.6 mmol) in dioxane (130 mL) and H₂O (50.0 mL) was added tetrakis(triphenylphosphine)palladium(0) (3.88 g, 3.36 mmol) and potassium carbonate (20.0 g, 144 mmol) in one portion at 25° C. under N₂. The mixture was then stirred at 90° C. for 18 h at which LCMS showed that the reaction was complete. The mixture was cooled to 25° C. and poured into water (100 mL). The aqueous phase was extracted with ethyl acetate, and the organic extract was washed twice with brine, dried with anhydrous sodium sulfate, filtered and concentrated in vacuum. The residue was purified by silica gel chromatography (petroleum ether/EtOAc=1/0, 5/1) to afford the title compound (6.00 g, 42.6% yield) as an off-white solid.

Step 2: tert-Butyl (S)-3-((4-(2-fluoropyridin-3-yl)pyrimidin-2-yl)amino)piperidine-1-carboxylate

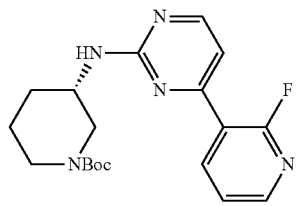 [SMILES: CC(C)(C)OC(=O)N1CCC[C@H](Nc2nccc(-c3cccnc3F)n2)C1]

A mixture of 2-chloro-4-(2-fluoro-3-pyridyl)pyrimidine (75 g, 358 mmol), tert-butyl (3S)-3-aminopiperidine-1-carboxylate (57.3 g, 286.2 mmol), N,N-diisopropylethylamine (187.5 mL 1.07 mol), and cesium fluoride (13.2 mL, 357.81 mmol,) in DMSO (1.40 L) was degassed and purged with N₂ 3 times. The mixture was then stirred at 80° C. for 3 h under N₂ atmosphere. LCMS showed that most of the starting material was consumed, and the desired mass was detected. The reaction mixture was extracted three times with ethyl acetate. The combined organic layers were washed with brine (500 mL), dried over anhydrous Na₂SO₄, filtered and concentrated under reduced pressure. The residue was purified by silica column chromatography (petroleum ether/ethyl acetate=2/1) and recrystallized by petroleum ether/ethyl acetate=1/1 to afford the title compound (54 g, 39.6% yield) as a white solid. LCMS (ESI): [M+H]⁺=374; ¹H NMR (400 MHz, CDCl₃) δ 8.77-8.45 (m, 1H), 8.36 (d, 0.7=4.9 Hz, 1H), 8.26 (d, J=3.1 Hz, 1H), 7.31 (t, J=5.4 Hz, 1H), 7.15 (d, J=2.9 Hz, 1H), 5.49 (br s, 1H), 4.08-3.91 (m, 1H), 3.91-2.99 (m, 3H), 1.98 (br s, 1H), 1.74 (d, J=6.4 Hz, 1H), 1.59 (d, J=6.7 Hz, 2H), 1.37 (s, 9H)

Step 3: tert-Butyl (S)-3-((4-(2-(4-amino-3-fluorophenoxy)pyridin-3-yl)pyrimidin-2-yl)amino)piperidine-1-carboxylate

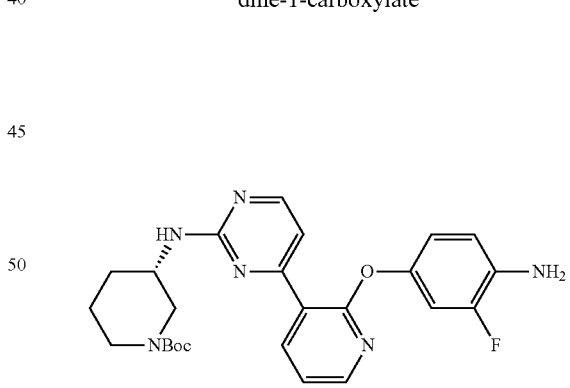

To a mixture of tert-butyl (S)-3-((4-(2-fluoropyridin-3-yl)pyrimidin-2-yl)amino)piperidine-1-carboxylate (1.21 g, 3.23 mmol) and 4-amino-3-fluorophenol (534 mg, 4.2 mmol) in DMSO (8 mL) was added cesium carbonate (1.52 g, 4.65 mmol) in one portion. The mixture was stirred at 130° C. for 1.5 h. Water was added and the mixture was extracted 3 times with ethyl acetate. The combined organic layers were dried over anhydrous Na₂SO₄, filtered and concentrated in vacuo. The residue was purified by prep-TLC (petroleum ether/ethyl acetate=1/1) to afford the title compound (420 mg, 27.2% yield) as a brown solid.

Step 4: tert-Butyl (S)-3-((4-(2-(3-fluoro-4-((3,3,3-trifluoropropyl)sulfonamido)phenoxy)pyridin-3-yl)pyrimidin-2-yl)amino)piperidine-1-carboxylate

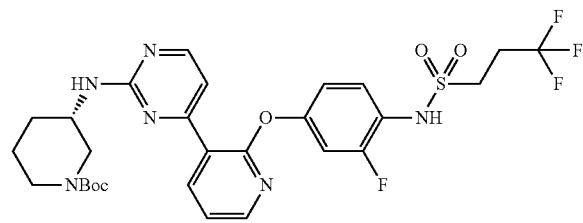 [SMILES: CC(C)(C)OC(=O)N1CCC[C@H](Nc2nccc(-c3cccnc3Oc3ccc(NS(=O)(=O)CCC(F)(F)F)c(F)c3)n2)C1]

To a solution of tert-butyl (3S)-3-[[4-[2-(4-amino-3-fluoro-phenoxy)-3-pyridyl]pyrimidin-2-yl]amino]piperidine-1-carboxylate (150 mg, 0.312 mmol) in chloroform (2.00 mL) and N-methylmorpholine (103 μL, 0.937 mmol) was added 3,3,3-trifluoropropane-1-sulfonyl chloride (61.36 mg, 312.16 umol, 1.00 equiv.) at 0° C., and the mixture was stirred at 25° C. for 1 h. The residue was purified by prep-TLC (petroleum ether/ethyl acetate=1:1.5) to afford the title compound (81.5 mg, 41% yield) as a white solid.

Step 5: (S)-3,3,3-Trifluoro-N-(2-fluoro-4-((3-(2-(piperidin-3-ylamino)pyrimidin-4-yl)pyridin-2-yl)oxy)phenyl)propane-1-sulfonamide hydrochloride

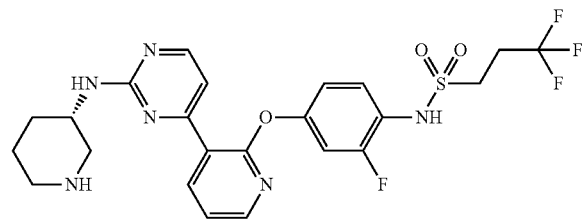 [SMILES: O=S(=O)(CCC(F)(F)F)Nc1ccc(Oc2ncccc2-c2ccnc(N[C@H]3CCCNC3)n2)cc1F]

A mixture of tert-butyl (S)-3-((4-(2-(3-fluoro-4-((3,3,3-trifluoropropyl)sulfonamido) phenoxy)pyridin-3-yl) pyrimidin-2-yl)amino)piperidine-1-carboxylate (171 mg, 0.267 mmol) in hydrochloric acid (4 M in ethyl acetate, 15 mL) was stirred at 15° C. for 1 h. The mixture was concentrated in vacuo. The residue was purified by prep-HPLC to afford the title compound (65.4 mg, 45% yield) as a yellow solid.

Example 6

N-(2,3-Difluoro-4-((3-(2-(((3S,5R)-5-methylpiperidin-3-yl)amino)pyrimidin-4-yl)pyridin-2-yl)oxy)phenyl)-1-phenylmethanesulfonamide hydrochloride Compound 111

Step 1: Benzyl (3S,5R)-3-((4-(2-fluoropyridin-3-yl)pyrimidin-2-yl)amino)-5-methylpiperidine-1-carboxylate

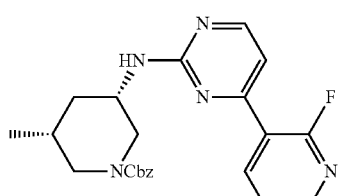

To a mixture of 2-chloro-4-(2-fluoropyridin-3-yl)pyrimidine (6.04 g, 24.3 mmol) in DMSO (110 mL) was added benzyl (3S,5R)-3-amino-5-methylpiperidine-1-carboxylate (6 g, 28.6 mmol), N,N-diisopropylethylamine (15 mL, 85.9 mmol,) and cesium carbonate (4.35 g, 28.6 mmol) at 20° C. The reaction mixture was degassed and purged with N₂ 3 times. The mixture was then stirred at 80° C. for 3 h under N₂ atmosphere. The mixture was cooled to ° C., quenched with water (100 mL) and extracted with ethyl acetate. The combined organic layers were dried over anhydrous Na₂SO₄, filtered and concentrated in vacuo. The residue was purified by silica column chromatography (petroleum ether/ethyl acetate=15/1 to 6/1) to give the title compound (6.5 g, 51% yield) as a light yellow solid. LCMS (ESI): [M+H]⁺=422.

Step 2: Benzyl (3S,5R)-3-((4-(2-(4-amino-2,3-difluorophenoxy)pyridin-3-yl)pyrimidin-2-yl)amino)-5-methylpiperidine-1-carboxylate

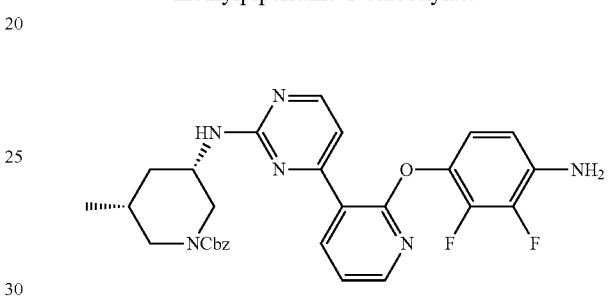

A mixture of benzyl (3S,5R)-3-((4-(2-fluoropyridin-3-yl)pyrimidin-2-yl)amino)-5-methylpiperidine-1-carboxylate (1 g, 2.37 mmol), 4-amino-2,3-difluorophenol (344 mg, 2.37 mmol), cesium carbonate (928 mg, 2.85 mmol) in DMSO (20 mL) was degassed and purged with N₂ 3 times. The mixture was stirred at 130° C. for 1.5 h under N₂ atmosphere and then cooled to room temperature. Water was added, and the mixture was then extracted with ethyl acetate. The combined organic layers were dried over anhydrous Na₂SO₄, filtered and concentrated in vacuo. The residue was purified by silica column chromatography (petroleum ether/ethyl acetate=20/1 to 1:1) to provide the title compound (3.9 g, 43% yield) as a brown solid.

Step 3: Benzyl (3S,5R)-3-((4-(2-(2,3-difluoro-4-((phenylmethyl)sulfonamido)phenoxy)pyridin-3-yl)pyrimidin-2-yl)amino)-5-methylpiperidine-1-carboxylate

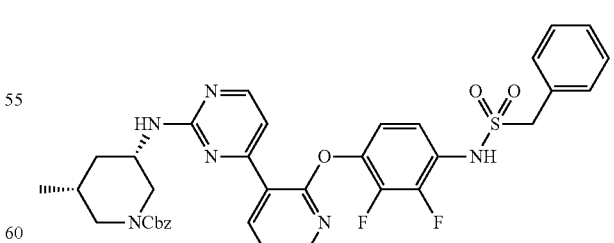

To a solution of benzyl (3S,5R)-3-((4-(2-(4-amino-2,3-difluorophenoxy)pyridin-3-yl)pyrimidin-2-yl)amino)-5-methylpiperidine-1-carboxylate (3.4 g, 6.22 mmol) in CHCl₃ (68 mL) and N-methylmorpholine (1.89 g, 18.7 mmol) was added phenylmethanesulfonyl chloride (1.19 g, 6.22 mmol) at 0° C. The mixture was stirred at 25° C. for 14 h. The reaction mixture was quenched with sat aqueous NaHCO₃ and extracted with DCM. The combined organic layers were dried over anhydrous Na₂SO₄, filtered and concentrated in vacuo. The residue was purified by silica column chromatography (petroleum ether/ethyl acetate=20:1 to 2:1) to give compound the title compound (2 g, 34.6% yield) as a brown solid.

Step 4: N-(2,3-Difluoro-4-((3-(2-(((3S,5R)-5-methylpiperidin-3-yl)amino)pyrimidin-4-yl)pyridin-2-yl)oxy)phenyl)-1-phenylmethanesulfonamide hydrochloride

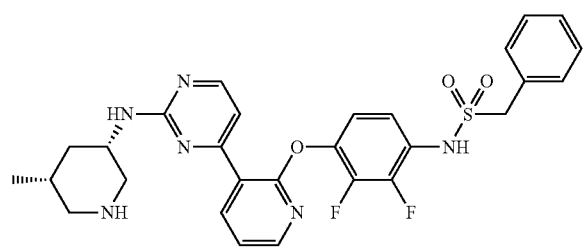

To a solution of benzyl (3S,5R)-3-((4-(2-(2,3-difluoro-4-((phenylmethyl)sulfonamido)phenoxy)pyridin-3-yl)pyrimidin-2-yl)amino)-5-methylpiperidine-1-carboxylate (2 g, 2.15 mmol) in DCM (20 mL) and CH₃CN (20 mL) was added dimethylsulfide (8.02 g, 129 mmol) and boron trifluoride diethyl etherate (9.16 g, 64.5 mmol). The reaction mixture was stirred at 25° C. for 3 h. The mixture was then diluted with ethyl acetate, washed with saturated NaHCO₃ (aq), and then extracted with ethyl acetate. The combined organic layers were washed with brine, dried over anhydrous Na₂SO₄, filtered and concentrated under reduced pressure. The residue was purified by prep-HPLC and lyophilized to provide the title compound (650 mg, 50.1% yield) as a white solid.

Example 7

(S)-2-Chloro-N-(3-fluoro-5-methyl-4-((3-(2-(piperidin-3-ylamino)pyrimidin-4-yl)pyridin-2-yl)oxy)phenyl)benzenesulfonamide hydrochloride (Compound 114)

Step 1: (S)-tert-Butyl 3-((4-(2-(4-amino-2-fluoro-6-methylphenoxy)pyridin-3-yl)pyrimidin-2-yl)amino)piperidine-1-carboxylate

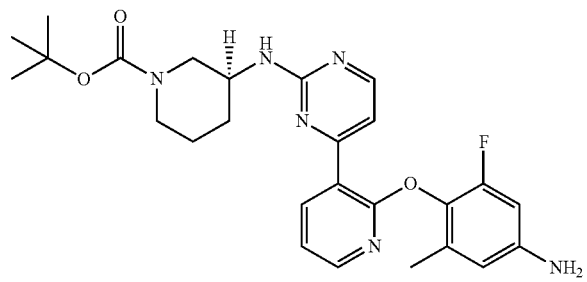 [SMILES: Cc1cc(N)cc(F)c1Oc1ncccc1-c1ccnc(N[C@H]2CCCN(C(=O)OC(C)(C)C)C2)n1]

To a stirred solution of (S)-tert-butyl 3-((4-(2-fluoropyridin-3-yl)pyrimidin-2-yl)amino)piperidine-1-carboxylate (2.02 g, 5.41 mmol) in DMSO (18 mL) was added cesium carbonate (6.60 g, 20.27 mmol) and 4-amino-2-fluoro-6-methylphenol hydrochloride (1.2 g, 6.76 mmol). The mixture was stirred at 130° C. for 13 h. After cooling to room temperature, the mixture was diluted with ethyl acetate (20 mL), washed with water (20 mL) and brine (20 mL×2). The organic phase was dried over anhydrous Na₂SO₄, filtered and concentrated in vacuo. The residue was purified by silica flash chromatography (ethyl acetate/petroleum ether=2:1) to give the title compound (2.2 g, 59% yield) as a yellow solid. LCMS (ESI) [M+Na]$^+$=517.1.

Step 2: (S)-tert-Butyl 3-((4-(2-(4-(2-chlorophenylsulfonamido)-2-fluoro-6-methylphenoxy)pyridin-3-yl)pyrimidin-2-yl)amino)piperidine-1-carboxylate

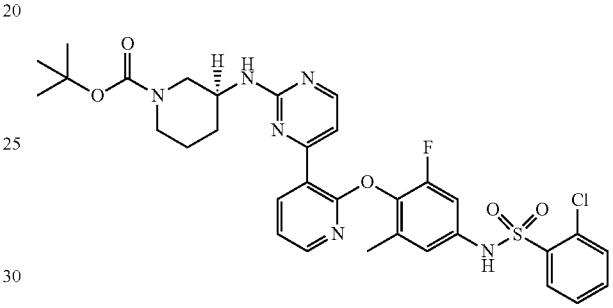

To a solution of (S)-tert-butyl 3-((4-(2-(4-amino-2-fluoro-6-methylphenoxy)pyridin-3-yl)pyrimidin-2-yl)amino)piperidine-1-carboxylate (110 mg, 0.22 mmol) in pyridine (2 mL) was added 2-chlorobenzene-1-sulfonyl chloride (70 mg, 0.33 mmol). The mixture was stirred at room temperature for 2 h. The reaction mixture was concentrated in vacuo and the residue was diluted with ethyl acetate (30 mL), washed with water (30×2 mL) and brine (30 mL). The organic phase was dried over anhydrous Na₂SO₄, filtered and concentrated in vacuo to give the title compound (120 mg crude) as a brown solid, which was used in the next step without further purification. LCMS (ESI) [M+H]$^+$=669.1.

Step 3: (S)-2-Chloro-N-(3-fluoro-5-methyl-4-((3-(2-(piperidin-3-ylamino)pyrimidin-4-yl)pyridin-2-yl)oxy)phenyl)benzenesulfonamide hydrochloride

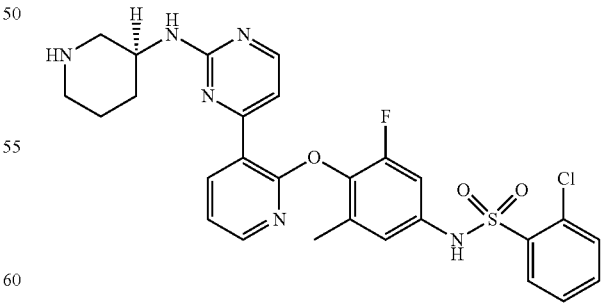

To a solution of (S)-tert-butyl 3-((4-(2-(4-(2-chlorophenylsulfonamido)-2-fluoro-6-methylphenoxy)pyridin-3-yl)pyrimidin-2-yl)amino)piperidine-1-carboxylate (110 mg, 0.16 mmol) in DCM (2 mL) was added 4 M HCl in ethyl acetate (0.12 mL, 0.49 mmol). The mixture was stirred at room temperature for 1 h. The mixture was concentrated in vacuo, and the residue was purified by prep-HPLC (acetonitrile 17-47%/0.05% HCl in water) to give the title compound (36 mg, 35% yield) as a white solid.

Example 8

N-(4-((3-(2-(((1r,4r)-4-Aminocyclohexyl)amino) pyrimidin-4-yl)pyridin-2-yl)oxy)-3,5-difluorophenyl)propane-1-sulfonamide hydrochloride (Compound 122)

Step 1: tert-Butyl ((1r,4r)-4-((4-(2-(4-amino-2,6-difluorophenoxy)pyridin-3-yl)pyrimidin-2-yl)amino) cyclohexyl)carbamate

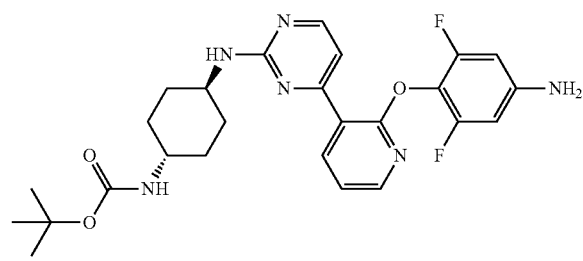

To a stirred solution of tert-butyl ((1r,4r)-4-((4-(2-fluoropyridin-3-yl)pyrimidin-2-yl)amino)cyclohexyl)carbamate (100 mg, 0.26 mmol) in DMSO (3 mL) was added 4-amino-2,6-difluorophenol (45 mg, 0.31 mmol) and cesium carbonate (252 mg, 0.77 mmol). The mixture was stirred at 120° C. for 2 h. After cooling to room temperature, the mixture was diluted with ethyl acetate (20 mL), washed with water (20 mL) and brine (20 mL×2). The organic phase was dried over anhydrous sodium sulfate, filtered and concentrated in vacuo. The residue was purified by silica flash chromatography (petroleum ether/ethyl acetate=1/1) to give the title compound (80 mg, 61% yield) as a yellow solid. LCMS (ESI) [M+Na]$^+$=535.4.

Step 2: tert-Butyl ((1r,4r)-4-((4-(2-(2,6-difluoro-4-(propylsulfonamido)phenoxy)pyridin-3-yl)pyrimidin-2-yl)amino)cyclohexyl)carbamate

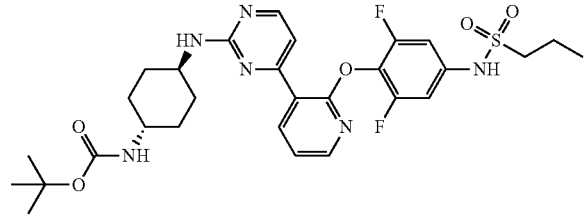 [SMILES: CCCS(=O)(=O)Nc1cc(F)c(Oc2ncccc2-c2ccnc(N[C@H]3CC[C@H](NC(=O)OC(C)(C)C)CC3)n2)c(F)c1]

To a solution of tert-butyl ((1r,4r)-4-((4-(2-(4-amino-2,6-difluorophenoxy)pyridin-3-yl)pyrimidin-2-yl)amino)cyclohexyl)carbamate (80 mg, 0.16 mmol) in pyridine (2 mL) was added propane-1-sulfonyl chloride (27 mg, 0.19 mmol). The mixture was stirred at room temperature for 12 h and concentrated in vacuo. The residue was diluted with ethyl acetate (20 mL), washed with water (20×2 mL) and brine (20 mL). The organic phase was dried over anhydrous Na$_2$SO$_4$, filtered and concentrated in vacuo to give the title compound (100 mg crude) as a brown solid, which was used in the next step without further purification. LCMS (ESI) [M+H]$^+$=619.4.

Step 3: N-(4-((3-(2-(((1r,4r)-4-Aminocyclohexyl) amino)pyrimidin-4-yl)pyridin-2-yl)oxy)-3,5-difluorophenyl)propane-1-sulfonamide hydrochloride

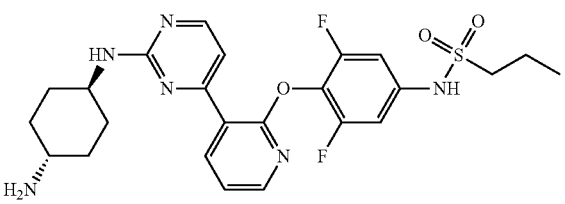 [SMILES: CCCS(=O)(=O)Nc1cc(F)c(Oc2ncccc2-c2ccnc(N[C@H]3CC[C@H](N)CC3)n2)c(F)c1]

To a solution of tert-butyl ((1r,4r)-4-((4-(2-(2,6-difluoro-4-(propylsulfonamido)phenoxy)pyridin-3-yl)pyrimidin-2-yl)amino)cyclohexyl)carbamate (100 mg, 0.16 mmol) in DCM (3 mL) was added 4M hydrochloric acid (0.12 mL, 0.48 mmol) in ethyl acetate. The mixture was stirred at room temperature for 1 h. The mixture was concentrated in vacuo and the residue purified by prep-HPLC (acetonitrile 15-45%/ 0.05% HCl in water) to give the title compound (22 mg, 24% yield) as a yellow solid.

Example 9

N-(4-((3-(2-(((1r,4r)-4-Aminocyclohexyl)amino) pyrimidin-4-yl)pyridin-2-yl)oxy)-3-chloro-5-fluorophenyl)propane-1-sulfonamide hydrochloride Compound 121

Step 1: 4-Amino-2-chloro-6-fluorophenol

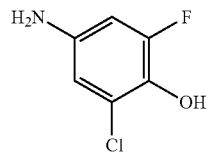

To a solution of 3-chloro-5-fluoro-4-methoxy-aniline (200 mg, 1.14 mmol) in DCM (8 mL) was added tribromoborane (0.33 mL, 3.42 mmol) at −78° C. The reaction was warmed up to room temperature and then stirred at room temperature for 16 h. The reaction was quenched with saturated aqueous NaHCO$_3$ and extracted with ethyl acetate (20 mL). The organic phase was washed with water (20×2 mL), brine (20 mL), dried over anhydrous Na$_2$SO$_4$, filtered and concentrated in vacuo. The residue was purified by silica flash chromatography (petroleum ether/ethyl acetate=3/1) to give the title compound (120 mg, 65% yield) as a white solid. $^1$H NMR (400 MHz, DMSO-d$_6$) δ 8.88 (s, 1H), 6.42-6.37 (m, 1H), 6.37-6.31 (m, 1H), 5.05 (s, 2H).

Step 2: tert-Butyl ((1r,4r)-4-((4-(2-(4-amino-2-chloro-6-fluorophenoxy)pyridin-3-yl)pyrimidin-2-yl)amino)cyclohexyl)carbamate

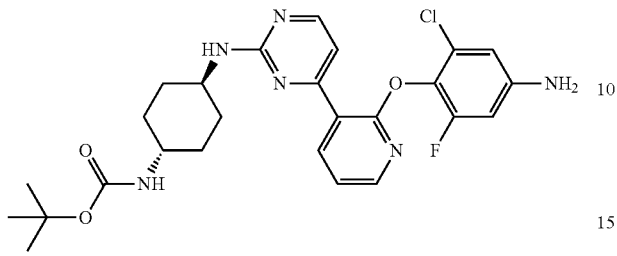

To a stirred solution of tert-butyl ((1r,4r)-4-((4-(2-fluoropyridin-3-yl)pyrimidin-2-yl)amino)cyclohexyl)carbamate (200 mg, 0.52 mmol) in DMSO (3 mL) was added cesium carbonate (505 mg, 1.55 mmol) and 4-amino-2-chloro-6-fluorophenol (125 mg, 0.77 mmol). The mixture was stirred at 120° C. for 2 h. After cooling to room temperature, the mixture was diluted with ethyl acetate (20 mL), washed with water (20×2 mL), and brine (20 mL). The organic phase was dried over anhydrous Na$_2$SO$_4$, filtered and concentrated in vacuo. The crude product was purified by silica flash chromatography (petroleum ether/ethyl acetate=1/1) to give the title compound (80 mg, 29% yield) as a brown solid. LCMS (ESI) [M+H]$^+$=529.1.

Step 3: tert-Butyl ((1r,4r)-4-((4-(2-(2-chloro-6-fluoro-4-(propylsulfonamido)phenoxy)pyridin-3-yl)pyrimidin-2-yl)amino)cyclohexyl)carbamate

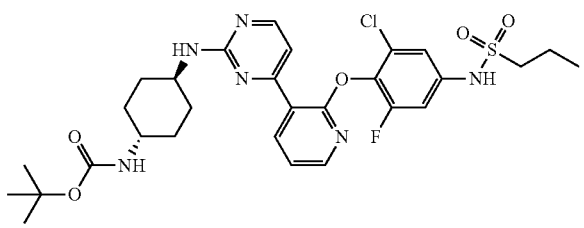

To a solution of tert-butyl ((1r,4r)-4-((4-(2-(4-amino-2-chloro-6-fluorophenoxy)pyridin-3-yl)pyrimidin-2-yl)amino)cyclohexyl)carbamate (80 mg, 0.15 mmol) in pyridine (2 mL) was added propane-1-sulfonyl chloride (26 mg, 0.18 mmol). The mixture was stirred at room temperature for 12 h and concentrated in vacuo. The residue was diluted with ethyl acetate (30 mL), washed with water (30×2 mL) and brine (30 mL). The organic phase was dried over anhydrous Na$_2$SO$_4$, filtered and concentrated in vacuo to give the title compound (100 mg crude) as a brown solid, which was used in the next step without further purification. LCMS (ESI) [M+Na]$^+$=657.2.

Step 4: N-(4-((3-(2-(((1r,4r)-4-Aminocyclohexyl)amino)pyrimidin-4-yl)pyridin-2-yl)oxy)-3-chloro-5-fluorophenyl)propane-1-sulfonamide hydrochloride

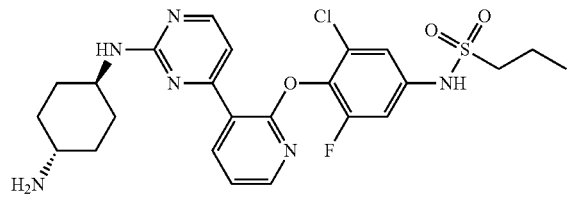

A solution of tert-butyl ((1r,4r)-4-((4-(2-(2-chloro-6-fluoro-4-(propylsulfonamido)phenoxy)pyridin-3-yl)pyrimidin-2-yl)amino)cyclohexyl)carbamate (100 mg, 0.16 mmol) in DCM (2 mL) was added 4M hydrochloric acid (0.12 mL, 0.48 mmol) stirred at room temperature for 2 h. The mixture was concentrated in vacuo and the residue purified by prep-HPLC to give the title compound (20 mg, 21% yield) as a yellow solid.

Example 10

(S)-2-Chloro-N-(2,3-dimethyl-4-((3-(2-(piperidin-3-ylamino)pyrimidin-4-yl)pyridin-2-yl)oxy)phenyl)benzenesulfonamide (Compound 123)

Step 1: tert-Butyl (S)-3-((4-(2-(4-amino-2,3-dimethylphenoxy)pyridin-3-yl)pyrimidin-2-yl)amino)piperidine-1-carboxylate

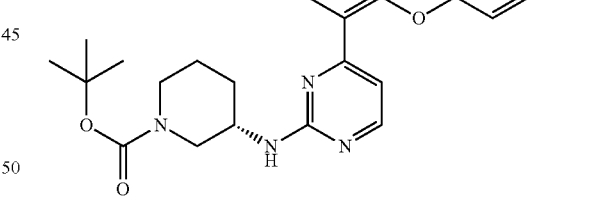

A mixture of tert-butyl (3S)-3-[[4-(2-fluoro-3-pyridyl)pyrimidin-2-yl]amino]piperidine-1-carboxylate 200 mg, 0.53 mmol), 4-amino-2,3-dimethyl-phenol (110.2 mg, 0.80 mmol), and cesium carbonate (349.0 mg, 1.07 mmol) in DMSO (2 mL) was heated at 120° C. for 3 h. The mixture was then cooled and diluted with water. The precipitate was filtered and the aqueous layer extracted with iPrOAc (2×20 mL). The combined organics were washed with brine, dried over MgSO$_4$, filtered, concentrated in vacuo, and dried under high vacuum to afford 246 mg (93.6% yield) of the title compound as a brown solid. The crude material was carried on without further purification. LCMS (ESI) [M+H]$^+$= 491.3

Step 2: tert-Butyl (S)-3-((4-(2-(4-((2-chlorophenyl)sulfonamido)-2,3-dimethylphenoxy)pyridin-3-yl)pyrimidin-2-yl)amino)piperidine-1-carboxylate

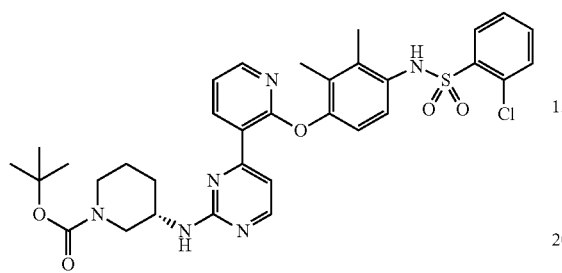

A solution of tert-butyl (3S)-3-[[4-[2-(4-amino-2,3-dimethyl-phenoxy)-3-pyridyl]pyrimidin-2-yl]amino]piperidine-1-carboxylate (123 mg, 0.25 mmol) and 2-chlorobenzenesulfonyl chloride (79.4 mg, 0.38 mmol) in pyridine (1 mL) was stirred at room temperature overnight. It was diluted with water, extracted with iPrOAc (2×10 mL), dried over MgSO$_4$, filtered, concentrated in vacuo, and dried under high vacuum to afford 157 mg (94.1% yield) of the title compound as a brown solid. The crude material was carried on without further purification. LCMS (ESI) [M+H]$^+$=665.2.

Step 3: (S)-2-Chloro-N-(2,3-dimethyl-4-((3-(2-(piperidin-3-ylamino)pyrimidin-4-yl)pyridin-2-yl)oxy)phenyl)benzenesulfonamide

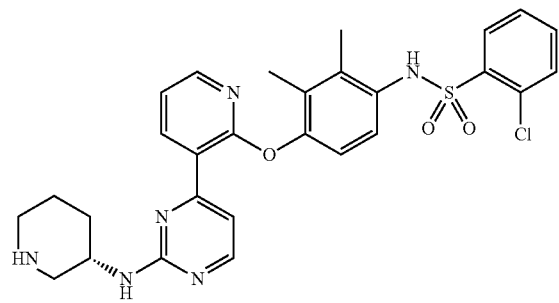 [SMILES: Cc1c(NS(=O)(=O)c2ccccc2Cl)ccc(Oc2ncccc2-c2ccnc(N[C@H]3CCCNC3)n2)c1C]

tert-Butyl (3S)-3-[[4-[2-[4-[(2-chlorophenyl)sulfonylamino]-2,3-dimethyl-phenoxy]-3-pyridyl]pyrimidin-2-yl]amino]piperidine-1-carboxylate (157 mg, 0.24 mmol) was treated with a mixture of 4N HCl/dioxane (2 mL) and 1.25N HCl/EtOH (1 mL) at room temperature for 1 h. It was concentrated in vacuo and dried under high vacuum. The crude material was purified by prep-HPLC to afford 78.6 mg (59% yield) of the title compound as a brown solid.

Example 11

(S)-2-Cyclohexyl-N-(2,3-dimethyl-4-((3-(2-(piperidin-3-ylamino)pyrimidin-4-yl)pyridin-2-yl)oxy)phenyl)acetamide (Compound 129)

Step 1: tert-Butyl (S)-3-((4-(2-(4-(2-cyclohexylacetamido)-2,3-dimethylphenoxy)pyridin-3-yl)pyrimidin-2-yl)amino)piperidine-1-carboxylate

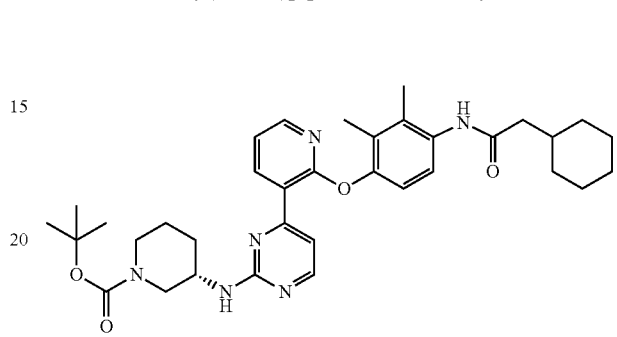

A mixture of tert-butyl (3S)-3-[[4-[2-(4-amino-2,3-dimethyl-phenoxy)-3-pyridyl]pyrimidin-2-yl]amino]piperidine-1-carboxylate (115 mg, 0.23 mmol), 2-cyclohexylacetic acid (50.0 mg, 0.35 mmol), and 1-[bis(dimethylamino)methylene]-1H-1,2,3-triazolo[4,5-b]pyridinium 3-oxid hexafluorophosphate (181.9 mg, 0.47 mmol) in DMF (1.5 mL) was added N,N-diisopropylethylamine (0.12 mL, 0.70 mmol). The reaction mixture was stirred at room temperature overnight. It was diluted with water, extracted with isoprpylacetate (2×10 mL), dried over anhydrous MgSO$_4$, filtered, and concentrated in vacuo. Purification by silica gel chromatography (12 g column; elution with 0-5% MeOH/DCM) afforded 96 mg (66% yield) of the title compound as a yellow solid. LCMS (ESI) [M+H]$^+$=615.1.

Step 2: (S)-2-Cyclohexyl-N-(2,3-dimethyl-4-((3-(2-(piperidin-3-ylamino)pyrimidin-4-yl)pyridin-2-yl)oxy)phenyl)acetamide

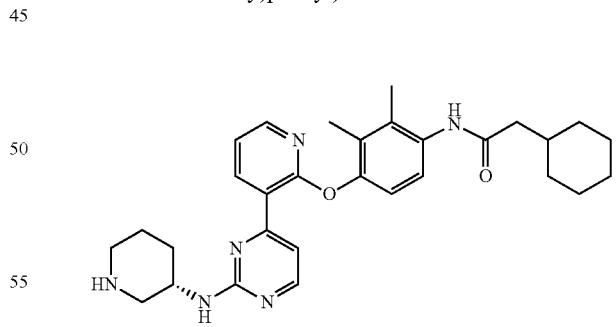

tert-Butyl (3S)-3-[[4-[2-[4-[(2-cyclohexylacetyl)amino]-2,3-dimethyl-phenoxy]-3-pyridyl]pyrimidin-2-yl]amino]piperidine-1-carboxylate (96 mg, 0.15 mmol) was treated with a mixture of 4N HCl/dioxane (2 mL) and 1.25N HCl/EtOH (1 mL) at room temperature for 1 h. The mixture was concentrated in vacuo and dried under high vacuum. The crude material was purified by reverse phase prep-HPLC to afford 53.8 mg (67% yield) of the title compound as an off-white solid.

Example 12

(S)-2-Chloro-N-(3,5-dimethyl-4-((3-(2-(piperidin-3-ylamino)pyrimidin-4-yl)pyridin-2-yl)oxy)phenyl) benzenesulfonamide hydrochloride (Compound 131)

Step 1: (S)-tert-Butyl 3-((4-(2-(2,6-dimethyl-4-nitrophenoxy)pyridin-3-yl)pyrimidin-2-yl)amino)piperidine-1-carboxylate

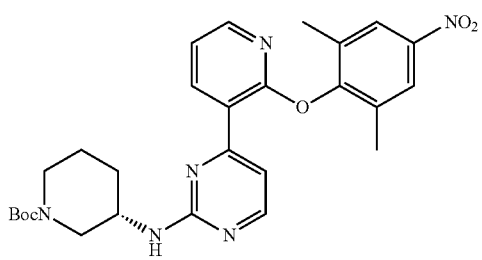 [SMILES: Cc1cc([N+](=O)[O-])cc(C)c1Oc1ncccc1-c1ccnc(N[C@H]2CCCN(C(=O)OC(C)(C)C)C2)n1]

A flask was charged with (S)-tert-butyl 3-((4-(2-fluoropyridin-3-yl)pyrimidin-2-yl)amino)piperidine-1-carboxylate (100 mg, 0.27 mmol), 2,6-dimethyl-4-nitrophenol (45 mg, 0.15 mmol), and cesium carbonate (176 mg, 0.54 mmol) in that order. To the mixture was then added N-methylpyrrolidinone (0.3 mL) and the mixture placed in a 160° C. oil bath overnight. After 16 h, the mixture was purified directly by C18 reverse phase flash chromatography (50-100% ACN/10 mM aqueous ammonium formate, pH=3.8). The product-containing fractions were combined and most of the ACN removed under reduced pressure, followed by dilution with EtOAc and separation of the phases. The organic extract was dried over anhydrous $Na_2SO_4$, filtered and concentrated in vacuo to provide the title compound (40 mg, 28% yield) as a yellow solid. LCMS (ESI) [M+H]$^+$= 521.3. $^1$H NMR (500 MHz, CDCl$_3$) δ 8.93-8.39 (br s, 1H), 8.19 (s, 1H), 8.07 (d, J=3.2 Hz, 1H), 7.97 (s, 2H), 7.45 (s, 1H), 7.13 (dd, J=7.2, 5.1 Hz, 1H), 4.36-3.71 (m, 2H), 3.60 (s, 1H), 3.45-2.75 (m, 3H), 2.10 (s, 6H), 2.03-1.92 (m, 1H), 1.84-1.70 (m, 1H), 1.65 (ddd, J=13.0, 9.0, 4.5 Hz, 1H), 1.61-1.50 (m, 1H), 1.50-1.22 (m, 9H).

Step 2: (S)-tert-Butyl 3-((4-(2-(4-amino-2,6-dimethylphenoxy)pyridin-3-yl)pyrimidin-2-yl)amino)piperidine-1-carboxylate

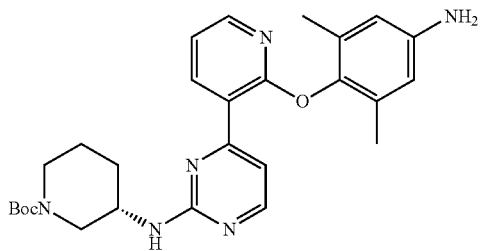 [SMILES: Cc1cc(N)cc(C)c1Oc1ncccc1-c1ccnc(N[C@H]2CCCN(C(=O)OC(C)(C)C)C2)n1]

A solution of (S)-tert-butyl 3-((4-(2-(2,6-dimethyl-4-nitrophenoxy)pyridin-3-yl)pyrimidin-2-yl)amino)piperidine-1-carboxylate (35 mg, 0.067 mmol) and nickel(II) chloride hexahydrate (8.0 mg, 0.03 mmol) in a mixture of MeOH (0.3 mL) and THF (0.3 mL) was cooled to 0° C. and NaBH$_4$ (13 mg, 0.34 mmol) was added. After 5 min, the mixture was diluted with 1M HCl (3 mL) and stirred 5 min at room temperature to give a homogeneous solution. The solution was then treated with concentrated aqueous NH$_4$OH (10 mL) and diluted with EtOAc. The phases were separated and the aqueous phase extracted again with EtOAc. The organic extracts were combined, dried over anhydrous Na$_2$SO$_4$, filtered and concentrated in vacuo. The crude material was dissolved in MeOH (5 mL) and heated at 100° C. in a microwave reactor for 10 min. Subsequent concentration in vacuo provided the title compound (31 mg, 94% yield) as a beige solid. LCMS (ESI) [M+H]$^+$=491.2. $^1$H NMR (500 MHz, CDCl$_3$) δ 8.51 (brs, 1H), 8.27 (d, J=4.8 Hz, 1H), 8.09 (dd, J=4.8, 1.9 Hz, 1H), 7.53 (d, J=3.8 Hz, 1H), 7.00 (dd, J=7.5, 4.8 Hz, 1H), 6.39 (s, 2H), 5.39 (br s, 3H), 4.06-3.95 (m, 1H), 3.56-3.45 (m, 1H), 3.36-2.97 (m, 3H), 1.97-1.91-1.91 (m, 7H), 1.74-1.66 (m, 1H), 1.66-1.52 (m, 2H), 1.40-1.25 (m, 9H).

Step 3: (S)-tert-Butyl 3-((4-(2-(4-(2-chlorophenylsulfonamido)-2,6-dimethylphenoxy)pyridin-3-yl)pyrimidin-2-yl)amino)piperidine-1-carboxylate

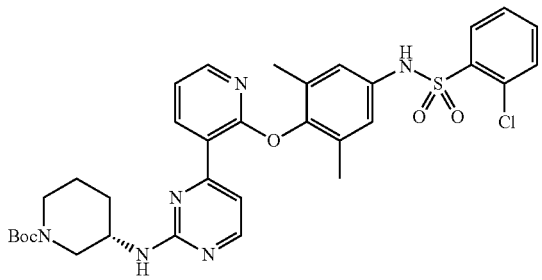 [SMILES: Cc1cc(NS(=O)(=O)c2ccccc2Cl)cc(C)c1Oc1ncccc1-c1ccnc(N[C@H]2CCCN(C(=O)OC(C)(C)C)C2)n1]

To a solution of (S)-tert-butyl 3-((4-(2-(4-amino-2,6-dimethylphenoxy)pyridin-3-yl)pyrimidin-2-yl)amino)piperidine-1-carboxylate (31 mg, 0.063 mmol) in pyridine (0.3 mL) was added 2-chlorobenzenesulfonylchloride (18 mg, 0.08 mmol) and the mixture stirred at room temperature. After 16 h, the mixture was directly purified by C18 reverse phase flash chromatography (40-90% ACN/10 mM aqueous ammonium formate, pH=3.8). The product-containing fractions were combined and lyophilized to provide the title compound (25 mg, 60% yield). LCMS (ESI) [M+H]$^+$= 665.2. $^1$H NMR (500 MHz, CDCl$_3$) δ 8.80-8.30 (br s, 1H), 8.19 (s, 1H), 8.02 (dd, J=4.7, 1.7 Hz, 1H), 7.98 (dd, J=7.9, 1.3 Hz, 1H), 7.53-7.36 (m, 3H), 7.31 (dd, J=11.0, 4.2 Hz, 1H), 7.02 (dd, J=7.5, 4.9 Hz, 1H), 6.94 (s, 1H), 6.81 (s, 2H), 4.01-3.91 (m, 1H), 3.64-3.04 (m, 5H), 1.94 (s, 7H), 1.78-1.68 (m, 1H), 1.62-1.52 (m, 2H), 1.40-1.23 (m, 9H).

Step 4: (S)-2-Chloro-N-(3,5-dimethyl-4-((3-(2-(piperidin-3-ylamino)pyrimidin-4-yl)pyridin-2-yl)oxy)phenyl)benzenesulfonamide hydrochloride

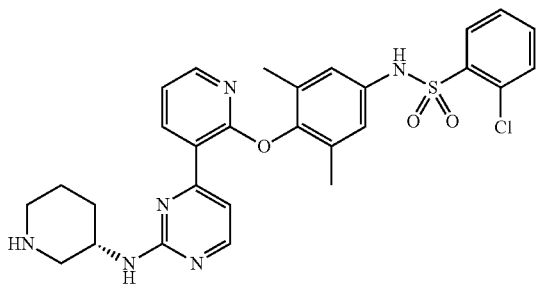 [SMILES: Cc1cc(NS(=O)(=O)c2ccccc2Cl)cc(C)c1Oc1ncccc1-c1ccnc(N[C@H]2CCCNC2)n1]

To a solution of (S)-tert-butyl 3-((4-(2-(4-(2-chlorophenylsulfonamido)-2,6-dimethylphenoxy)pyridin-3-yl)pyrimidin-2-yl)amino)piperidine-1-carboxylate (25 mg, 0.038 mmol) in 1,4-dioxane (0.19 mL) at 0° C. was added 4N HCl in dioxane (0.1 mL, 0.4 mmol) and the mixture stirred at room temperature. After 3 h, the mixture was concentrated in vacuo and the crude residue was purified by C18 reverse phase flash chromatography (20-60% ACN/10 mM aqueous ammonium formate, pH=3.8). The product containing fractions were combined and lyophilized to provide the free base material. This free base material was diluted with 1,4-dioxane (0.19 mL) and then treated with 4N HCl in dioxane (0.05 mL, 0.2 mmol) followed by concentration in vacuo to provide the HCl salt. The salt was dissolved in a mixture of ACN and H$_2$O and lyophilized to provide the title product (23 mg, 75% yield) as a white solid.

Example 13

(S)-2-Chloro-N-(3-((3-(2-(piperidin-3-ylamino)pyrimidin-4-yl)pyridin-2-yl)oxy)phenyl)benzenesulfonamide hydrochloride (Compound 132)

Step 1: (S)-tert-Butyl 3-((4-(2-(3-aminophenoxy)pyridin-3-yl)pyrimidin-2-yl)amino)piperidine-1-carboxylate

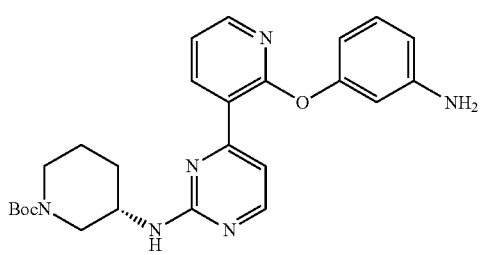 [SMILES: CC(C)(C)OC(=O)N1CCC[C@H](Nc2nccc(-c3cccnc3Oc3cccc(N)c3)n2)C1]

To a solution of 3-aminophenol (141 mg, 1.30 mmol) in DMSO (4.8 mL) was added (S)-tert-butyl 3-((4-(2-fluoropyridin-3-yl)pyrimidin-2-yl)amino)piperidine-1-carboxylate (440 mg, 1.18 mmol) followed by cesium carbonate (811 mg, 2.47 mmol), and the mixture was placed in a 120° C. oil bath overnight. After 16 h, the mixture was diluted with H$_2$O and EtOAc, and the phases were separated. The organic extract was washed with 1N NaOH, then with saturated aqueous NaCl, dried over anhydrous MgSO$_4$, filtered and concentrated in vacuo to provide the crude title compound (680 mg), which was used in the next step without further purification. LCMS (ESI) [M+H]$^+$=463.0.

Step 2: (S)-tert-Butyl 3-((4-(2-(3-(2-chlorophenylsulfonamido)phenoxy)pyridin-3-yl)pyrimidin-2-yl)amino)piperidine-1-carboxylate

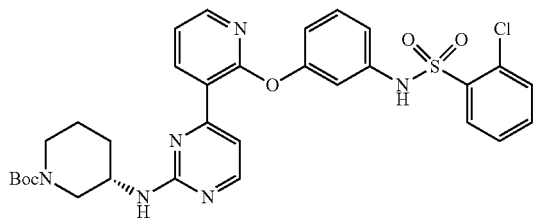 [SMILES: CC(C)(C)OC(=O)N1CCC[C@H](Nc2nccc(-c3cccnc3Oc3cccc(NS(=O)(=O)c4ccccc4Cl)c3)n2)C1]

To a solution of crude (S)-tert-butyl 3-((4-(2-(3-aminophenoxy)pyridin-3-yl)pyrimidin-2-yl)amino)piperidine-1-carboxylate (80 mg, 0.17 mmol) in DCM (0.58 mL) was added 2-chlorobenzenesulfonylchloride (73 mg, 0.35 mmol), followed by addition of pyridine (0.21 mL, 2.59 mmol). The mixture was stirred at room temperature, and after 2 h, volatiles were removed in vacuo. The crude residue was purified by C18 reverse phase flash chromatography (40-80% ACN/10 mM aqueous ammonium formate, pH=3.8). The product-containing fractions were combined and diluted with EtOAc and saturated aqueous NaHCO$_3$, and the phases were separated. The organic extract was washed with saturated aqueous NaCl, dried over anhydrous Na$_2$SO$_4$, filtered and concentrated in vacuo to provide the tide compound (43 mg, 39% yield). LCMS (ESI) [M+H]$^+$=637.2.

Step 3: (S)-2-Chloro-N-(3-((3-(2-(piperidin-3-ylamino)pyrimidin-4-yl)pyridin-2-yl)oxy)phenyl)benzenesulfonamide hydrochloride

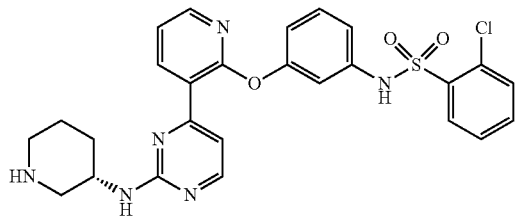 [SMILES: O=S(=O)(Nc1cccc(Oc2ncccc2-c2ccnc(N[C@H]3CCCNC3)n2)c1)c1ccccc1Cl]

To a solution of (S)-tert-butyl 3-((4-(2-(3-(2-chlorophenylsulfonamido)phenoxy)pyridin-3-yl)pyrimidin-2-yl)amino)piperidine-1-carboxylate (43 mg, 0.07 mmol) in 1,4-dioxane (0.31 mL) was added 4N HCl in dioxane (1.0 mL, 4.0 mmol) and the mixture was stirred at room temperature. After 90 min, the mixture was diluted with diethyl ether and the resulting solids filtered off, washed with diethyl ether, dissolved in a mixture of ACN and H$_2$O and lyophilized to provide the title product (40 mg, 100% yield) as a white solid.

Example 14

(S)-1-Phenyl-N-(3-((3-(2-(piperidin-3-ylamino)pyrimidin-4-yl)pyridin-2-yl)oxy)phenyl)methanesulfonamide hydrochloride (Compound 133)

Step 1: (S)-tert-Butyl 3-((4-(2-(3-(phenylmethylsulfonamido)phenoxy)pyridin-3-yl)pyrimidin-2-yl)amino)piperidine-1-carboxylate

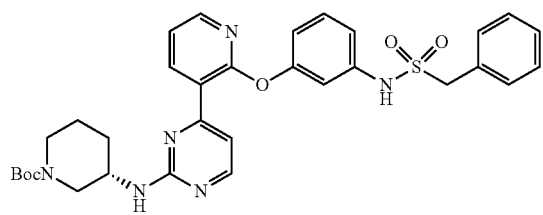 [SMILES: CC(C)(C)OC(=O)N1CCC[C@H](Nc2nccc(-c3cccnc3Oc3cccc(NS(=O)(=O)Cc4ccccc4)c3)n2)C1]

To a solution of crude (S)-tert-butyl 3-((4-(2-(3-aminophenoxy)pyridin-3-yl)pyrimidin-2-yl)amino)piperidine-1-carboxylate (80 mg, 0.17 mmol) in DCM (0.58 mL) was added phenylmethanesulfonylchloride (66 mg, 0.35 mmol) followed by addition of pyridine (0.21 mL, 2.59 mmol). The mixture was stirred at room temperature and after 2.5 h, volatiles were removed in vacuo. The crude residue was purified by C18 reverse phase flash chromatography (40-80% ACN/10 mM aqueous ammonium formate, pH=3.8). The product-containing fractions were combined and diluted with EtOAc and saturated aqueous NaHCO$_3$, and the phases were separated. The organic extract was washed with saturated aqueous NaCl, dried over anhydrous Na$_2$SO$_4$, filtered and concentrated in vacuo to provide the tide compound (49 mg, 46% yield). LCMS (ESI) [M+H]$^+$=617.1.

Step 2: (S)-1-Phenyl-N-(3-((3-(2-(piperidin-3-ylamino)pyrimidin-4-yl)pyridin-2-yl)oxy)phenyl)methanesulfonamide hydrochloride

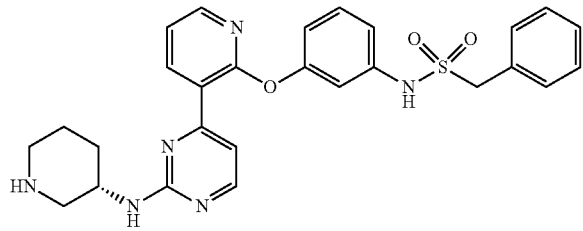

To a solution of (S)-tert-butyl 3-((4-(2-(3-(phenylmethylsulfonamido)phenoxy)pyridin-3-yl)pyrimidin-2-yl)amino)piperidine-1-carboxylate (45 mg, 0.07 mmol) in 1,4-dioxane (0.36 mL) was added 4N HCl in dioxane (1.0 mL, 4.0 mmol) and the mixture was stirred at room temperature. After 90 min, the mixture was diluted with Diethyl ether and the resulting solids were filtered off, washed with Diethyl ether, dissolved in a mixture of ACN and H$_2$O and lyophilized to provide the title product (42 mg, 100% yield) as a white solid.

Example 15

(S)-2-Chloro-N-(4-((3-(2-(piperidin-3-ylamino)pyrimidin-4-yl)pyridin-2-yl)oxy)phenyl)benzenesulfonamide hydrochloride (Compound 134)

Step 1: (S)-tert-Butyl 3-((4-(2-(4-aminophenoxy)pyridin-3-yl)pyrimidin-2-yl)amino)piperidine-1-carboxylate

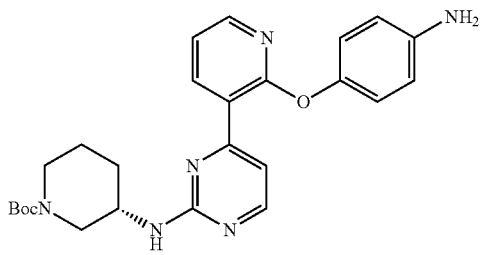 [SMILES: CC(C)(C)OC(=O)N1CCC[C@H](Nc2nccc(-c3cccnc3Oc3ccc(N)cc3)n2)C1]

A solution of (S)-tert-butyl 3-((4-(2-fluoropyridin-3-yl)pyrimidin-2-yl)amino)piperidine-1-carboxylate (200 mg, 0.54 mmol), 4-aminophenol (64 mg, 0.59 mmol), and cesium carbonate (369 mg, 1.12 mmol) in DMSO (2 mL) was placed in a 120° C. oil bath sealed. After 2 h, the mixture was diluted with EtOAc (75 mL), washed with H$_2$O (10 mL) and then with 50% saturated aqueous NaCl (4×10 mL). Drying (Na$_2$SO$_4$), filtration through a short pad of silica gel topped with celite and concentration in vacuo provided the title compound (186 mg, 75% yield) as a brown wax which was used in the next step without further purification. LCMS (ESI) [M+H]$^+$=463.2.

Step 2: (S)-tert-Butyl 3-((4-(2-(4-(2-chlorophenylsulfonamido)phenoxy)pyridin-3-yl)pyrimidin-2-yl)amino)piperidine-1-carboxylate

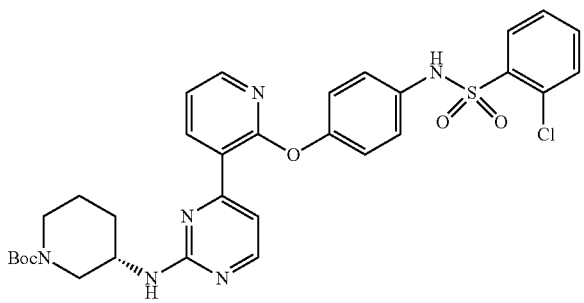 [SMILES: CC(C)(C)OC(=O)N1CCC[C@H](Nc2nccc(-c3cccnc3Oc3ccc(NS(=O)(=O)c4ccccc4Cl)cc3)n2)C1]

To a solution of crude (S)-tert-butyl 3-((4-(2-(4-aminophenoxy)pyridin-3-yl)pyrimidin-2-yl)amino)piperidine-1-carboxylate (60 mg, 0.13 mmol) in a mixture of DCM (2 mL) and pyridine (1 mL) was added 2-chlorobenzenesulfonylchloride (68 mg, 0.32 mmol) and the mixture stirred at room temperature. After 4 h, the mixture was diluted with DCM (50 mL), washed with saturated aqueous NaHCO$_3$ solution (10 mL), dried over anhydrous Na$_2$SO$_4$, filtered and concentrated in vacuo. The crude material was then purified by silica flash chromatography (0-100% EtOAc/hexanes) to provide the title compound (67 mg, 81% yield) as a yellow wax. LCMS (ESI) [M+H]$^+$=637.0.

Step 3: (S)-2-Chloro-N-(4-((3-(2-(piperidin-3-ylamino)pyrimidin-4-yl)pyridin-2-yl)oxy)phenyl)benzenesulfonamide hydrochloride

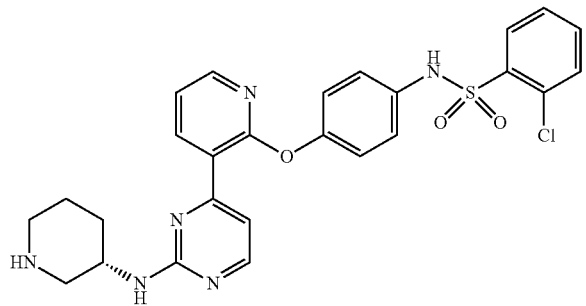 [SMILES: O=S(=O)(Nc1ccc(Oc2ncccc2-c2ccnc(N[C@H]3CCCNC3)n2)cc1)c1ccccc1Cl]

To a solution of (S)-tert-butyl 3-((4-(2-(4-(2-chlorophenylsulfonamido)phenoxy)pyridin-3-yl)pyrimidin-2-yl)amino)piperidine-1-carboxylate (67 mg, 0.11 mmol) in EtOAc (2 mL) was added 4N HCl in dioxane (2.0 mL, 8.0 mmol) and the mixture stirred at room temperature. After 3 h, volatiles were removed under reduced pressure and the crude HCl salt residue was washed with EtOAc (3×3 mL), then ACN (3×3 mL). The crude residue was then sonicated with ACN (3 mL) to produce a suspension and volatiles were removed under reduced pressure (process was repeated 3 times). The resulting solids were dissolved in a mixture of H$_2$O and ACN and lyophilized to provide the title product (35 mg, 58% yield) as a white solid. LCMS (ESI) [M+H]$^+$= 537.0.

Example 16

(S)-2-Chloro-N-(4-methyl-3-((3-(2-(piperidin-3-ylamino)pyrimidin-4-yl)pyridin-2-yl)oxy)phenyl)benzenesulfonamide hydrochloride (Compound 135)

Step 1: (S)-tert-Butyl 3-((4-(2-(5-amino-2-methylphenoxy)pyridin-3-yl)pyrimidin-2-yl)amino)piperidine-1-carboxylate

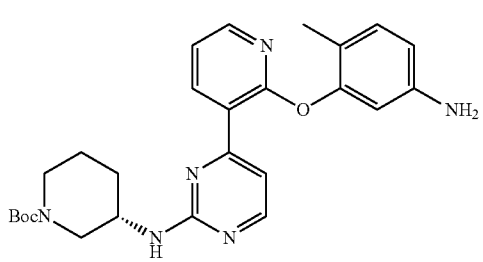 [SMILES: Cc1ccc(N)cc1Oc1ncccc1-c1ccnc(N[C@H]2CCCN(C(=O)OC(C)(C)C)C2)n1]

A solution of (S)-tert-butyl 3-((4-(2-fluoropyridin-3-yl)pyrimidin-2-yl)amino)piperidine-1-carboxylate (200 mg, 0.54 mmol), 5-amino-2-methylphenol (72 mg, 0.59 mmol), and cesium carbonate (369 mg, 1.12 mmol) in DMSO (1.8 mL) was placed in an oil bath that was heated to 120° C. After 3 h, the mixture was diluted with EtOAc (75 mL), washed with H$_2$O (10 mL), then with saturated aqueous NaCl solution (10 mL), dried over MgSO$_4$, filtered and concentrated in vacuo to provide the title compound (278 mg, quant. yield) as a brown foam which was used in the next step without further purification. LCMS (ESI) [M+H]$^+$= 477.3.

Step 2: (S)-tert-Butyl 3-((4-(2-(5-(2-chlorophenylsulfonamido)-2-methylphenoxy)pyridin-3-yl)pyrimidin-2-yl)amino)piperidine-1-carboxylate

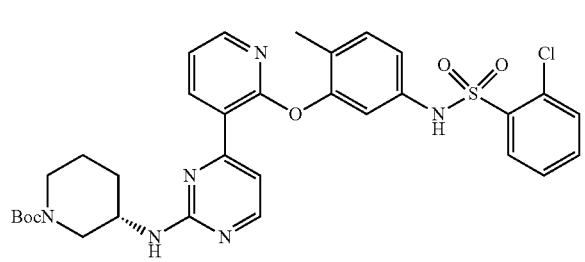 [SMILES: Cc1ccc(NS(=O)(=O)c2ccccc2Cl)cc1Oc1ncccc1-c1ccnc(N[C@H]2CCCN(C(=O)OC(C)(C)C)C2)n1]

To a solution of crude (S)-tert-butyl 3-((4-(2-(5-amino-2-methylphenoxy)pyridin-3-yl)pyrimidin-2-yl)amino)piperidine-1-carboxylate (63 mg, 0.13 mmol) in DCM (0.5 mL) was added 2-chlorobenzenesulfonylchloride (33 mg, 0.16 mmol) and pyridine (0.16 mL), and the mixture was stirred at room temperature. After 16 h, a further portion of 2-chlorobenzenesulfonylchloride (15 mg, 0.07 mmol) was added. After 2 h at room temperature, the volatiles were removed under reduced pressure and the crude residue purified by C18 reverse phase flash chromatography (40-80% ACN/10 mM aqueous ammonium formate, pH=3.8). The product-containing fractions were combined and most of the ACN was removed on a rotovap. The residue was then diluted with EtOAc and saturated aqueous NaHCO$_3$, and the phases were separated. The organic extract was dried over anhydrous Na$_2$SO$_4$, filtered and concentrated in vacuo to provide the title compound (90 mg, 100% yield). LCMS (ESI) [M+H]$^+$=651.1.

Step 3: (S)-2-Chloro-N-(4-methyl-3-((3-(2-(piperidin-3-ylamino)pyrimidin-4-yl)pyridin-2-yl)oxy)phenyl)benzenesulfonamide hydrochloride

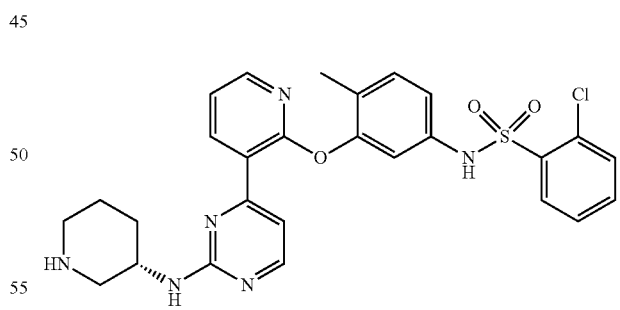

To a solution of (S)-tert-butyl 3-((4-(2-(5-(2-chlorophenylsulfonamido)-2-methylphenoxy)pyridin-3-yl)pyrimidin-2-yl)amino)piperidine-1-carboxylate (86 mg, 0.13 mmol) in 1,4-dioxane (0.5 mL) was added 4N HCl in dioxane (1.0 mL, 4.0 mmol), and the mixture was stirred at room temperature. After 90 min, the mixture was diluted with diethyl ether and the resulting solids were filtered off, washed with diethyl ether, dissolved in a mixture of ACN and H$_2$O and lyophilized to provide the title product (73 mg, 94% yield) as a white solid.

Example 17

(S)—N-(4-Methyl-3-((3-(2-(piperidin-3-ylamino)pyrimidin-4-yl)pyridin-2-yl)oxy)phenyl)-1-phenyl-methanesulfonamide hydrochloride (Compound 136)

Step 1: (S)-tert-Butyl 3-((4-(2-(2-methyl-5-(phenyl-methylsulfonamido)phenoxy)pyridin-3-yl)pyrimidin-2-yl)amino)piperidine-1-carboxylate

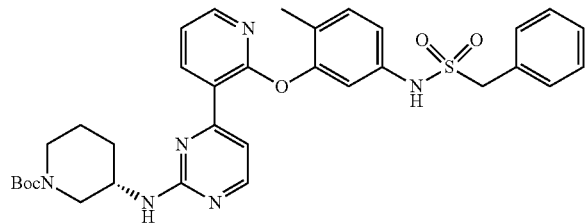 [SMILES: Cc1ccc(NS(=O)(=O)Cc2ccccc2)cc1Oc1ncccc1-c1ccnc(N[C@H]2CCCN(C(=O)OC(C)(C)C)C2)n1]

To a solution of crude (S)-tert-butyl 3-((4-(2-(5-amino-2-methylphenoxy)pyridin-3-yl)pyrimidin-2-yl)amino)piperidine-1-carboxylate (63 mg, 0.13 mmol) in DCM (0.58 mL) was added phenylmethanesulfonyl chloride (38 mg, 0.20 mmol) and pyridine (0.16 mL) and the mixture stirred at room temperature overnight. After 16 h, the volatiles were removed in vacuo and the crude residue purified by C18 reverse phase flash chromatography (40-80% ACN/10 mM aqueous ammonium formate, pH=3.8). The product-containing fractions were combined and most of the ACN was removed under reduced pressure. The residue was diluted with EtOAc and saturated aqueous NaHCO$_3$, and the phases were separated. The organic extract was dried over anhydrous Na$_2$SO$_4$, filtered and concentrated in vacuo to provide the title compound (63 mg, 76% yield). LCMS (ESI) [M+H]$^+$=631.1.

Step 2: (S)—N-(4-Methyl-3-((3-(2-(piperidin-3-ylamino)pyrimidin-4-yl)pyridin-2-yl)oxy)phenyl)-1-phenylmethanesulfonamide hydrochloride

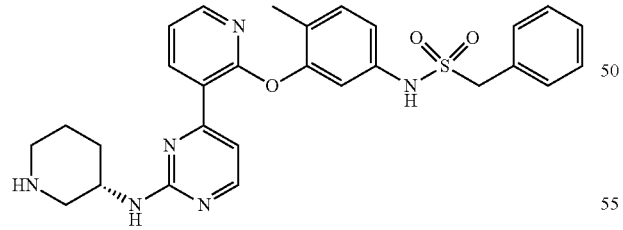

To a solution of (S)-tert-butyl 3-((4-(2-(2-methyl-5-(phenylmethylsulfonamido)phenoxy)pyridin-3-yl)pyrimidin-2-yl)amino)piperidine-1-carboxylate (63 mg, 0.10 mmol) in 1,4-dioxane (0.4 mL) was added 4N HCl in dioxane (1.0 mL, 4.0 mmol), and the mixture was stirred at room temperature. After 90 min, the mixture was diluted with Diethyl ether, and the resulting solids were filtered off, washed with Diethyl ether, dissolved in a mixture of ACN and H$_2$O and lyophilized to provide the title product (41 mg, 72% yield) as a white solid.

Example 18

(S)—N-(2,3-Difluoro-4-(3-(2-(piperidin-3-ylamino)pyrimidin-4-yl)pyridin-2-yloxy)phenyl)-1-(pyridin-2-yl)methanesulfonamide (Compound 238)

Step 1: tert-Butyl (3S)-3-[[4-[2-[2,3-difluoro-4-(2-pyridylmethylsulfonylamino)phenoxy]-3-pyridyl]pyrimidin-2-yl]amino]piperidine-1-carboxylate

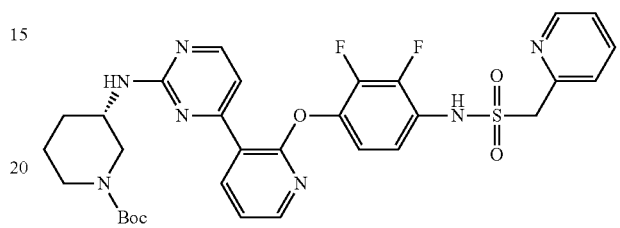

To a vial containing tert-butyl (3S)-3-[[4-[2-(4-amino-2,3-difluoro-phenoxy)-3-pyridyl]pyrimidin-2-yl]amino]piperidine-1-carboxylate (200 mg, 0.40 mmol) was added DCM (4 mL) followed by triethylamine (0.22 mL, 1.61 mmol) and (2-pyridylmethyl)sulfonylchloride triflate (288.6 mg, 0.80 mmol). The reaction mixture was stirred at room temperature for 16 h, quenched with 10 mL of saturated aqueous bicarbonate solution, and DCM was added. The organic extract was dried with magnesium sulfate, filtered and concentrated to afford the title compound as a crude intermediate (quantitative yield). This product was used in the next step without further purification. LCMS (ESI): [M+1]$^+$= 654.

Step 2: (S)—N-(2,3-Difluoro-4-(3-(2-(piperidin-3-ylamino)pyrimidin-4-yl)pyridin-2-yloxy)phenyl)-1-(pyridin-2-yl)methanesulfonamide

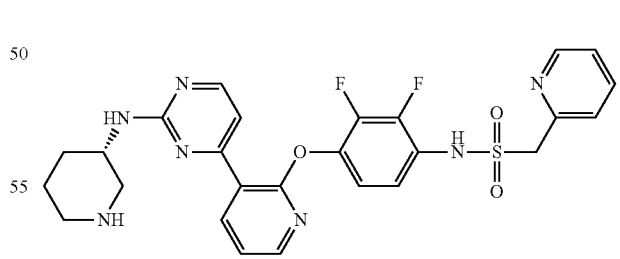

To a vial containing tert-butyl (3S)-3-[[4-[2-[2,3-difluoro-4-(2-pyridylmethylsulfonylamino)phenoxy]-3-pyridyl]pyrimidin-2-yl]amino]piperidine-1-carboxylate in DCM (5 mL) was added 4M HCl in 1,4 dioxane (1.5 mL), and the reaction mixture was stirred at room temperature for 2 h. Concentration to dryness under vacuum and purification by prep-HPLC afforded 112.7 mg (51% yield) of the title compound.

Example 19

(S)-2-Chloro-N-(4-chloro-2-fluoro-3-((3-(2-(piperidin-3-ylamino)pyrimidin-4-yl)pyridin-2-yl)oxy)phenyl)benzenesulfonamide hydrochloride (Compound 137)

Step 1: (3-Amino-6-chloro-2-fluorophenyl)boronic acid

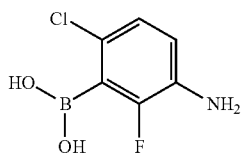

A solution of 4-chloro-2-fluoroaniline (750 mg, 5.15 mmol) in THF (6.9 mL) was cooled to −78° C. and n-BuLi (2.5 M in hexanes, 2.21 mL, 5.51 mmol) was added. After stirring at −78° C. for 30 min, 1,2-bis(chlorodimethylsilylethane) (1.16 g, 5.41 mmol) was added and after 1 h at −78° C. a further portion of n-BuLi (2.5 M in hexanes, 2.27 mL, 5.67 mmol) was added and the cooling bath was removed. After 1 h at room temperature, the mixture was cooled back down to −78° C. and a further portion of n-BuLi (2.5 M in hexanes, 2.37 mL, 5.93 mmol) was added. After 90 min at −78° C., triisopropyl borate (2.90 g, 3.57 mL, 15.5 mmol) was added and the cooling bath was removed followed by stirring at room temperature overnight. After 16 h, the mixture was diluted with 1M HCl and stirred 1 h at room temperature. The organic phase was extracted with EtOAc, and the organic extracts were washed with 1N sodium hydroxide, and the aqueous phase was re-extracted with EtOAc. The combined organic extracts were washed with saturated aqueous NaCl solution, dried over anhydrous MgSO$_4$, filtered and concentrated in vacuo. The residue was triturated with a mixture of DCM, and hexanes and the resulting solids were filtered to provide the title compound (425 mg, 44% yield) as a white solid. $^1$H NMR (400 MHz, d$_6$-DMSO) δ 8.51 (s, 2H), 6.85 (dd, J=8.4, 0.6 Hz, 1H), 6.66 (dd, J=10.0, 8.5 Hz, 1H), 5.13 (s, 2H).

Step 2: (S)-tert-Butyl 3-((4-(2-(3-amino-6-chloro-2-fluorophenoxy)pyridin-3-yl)pyrimidin-2-yl)amino)piperidine-1-carboxylate

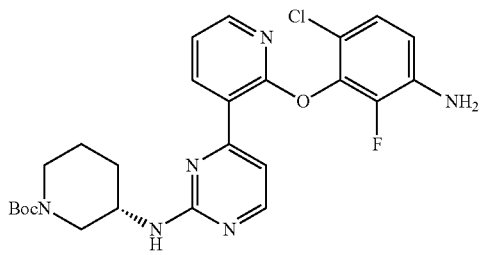 [SMILES: CC(C)(C)OC(=O)N1CCC[C@H](Nc2nccc(-c3cccnc3Oc3c(Cl)ccc(N)c3F)n2)C1]

To a suspension of (3-amino-6-chloro-2-fluorophenyl)boronic acid (150 mg, 0.79 mmol) in 30% w/w aqueous H$_2$O$_2$ (3 mL) was added iodine (10 mg, 0.04 mmol) and the mixture stirred at room temperature overnight. After 16 h, the mixture was diluted with water, sonicated, and the resulting solids were filtered off. The solids were washed with water, then with aqueous Na$_2$S$_2$O$_3$, and dried on a vacuum line to provide crude 3-amino-6-chloro-2-fluorophenol (66 mg, 52% yield) which was used without further purification.

To a solution of crude 3-amino-6-chloro-2-fluorophenol (66 mg, 0.40 mmol) in DMSO (1.3 mL) was added (S)-tert-butyl 3-((4-(2-fluoropyridin-3-yl)pyrimidin-2-yl)amino)piperidine-1-carboxylate (150 mg, 0.40 mmol) followed by potassium carbonate (139 mg, 1.01 mmol), and the mixture was stirred overnight in an oil bath heated to 130° C. After 16 h, the mixture was diluted with H$_2$O and EtOAc, and the phases were separated. The organic extract was washed with 1N NaOH, then with saturated aqueous NaCl solution, dried over anhydrous MgSO$_4$, filtered and concentrated in vacuo to provide the title compound (200 mg, 96% yield), which was used in the next step without further purification. LCMS (ESI) [M+H]$^+$=515.1.

Step 3: (S)-tert-Butyl 3-((4-(2-(6-chloro-3-(2-chlorophenylsulfonamido)-2-fluorophenoxy)pyridin-3-yl)pyrimidin-2-yl)amino)piperidine-1-carboxylate

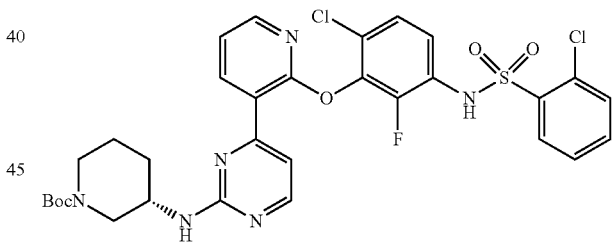

To a solution of crude (S)-tert-butyl 3-((4-(2-(3-amino-6-chloro-2-fluorophenoxy)pyridin-3-yl)pyrimidin-2-yl)amino)piperidine-1-carboxylate (50 mg, 0.10 mmol) in DCM (0.32 mL) was added 2-chlorobenzenesulfonylchloride (41 mg, 0.19 mmol) followed by addition of pyridine (0.12 mL, 1.46 mmol) and the mixture was stirred at room temperature. After 2 h, the volatiles were removed under reduced pressure, and the crude residue was directly purified by C18 reverse phase flash chromatography (60-75% ACN/10 mM aqueous ammonium formate, pH=3.8). The product-containing fractions were combined and concentrated to remove most of the ACN. The residue was then diluted with EtOAc and saturated aqueous NaHCO$_3$, and the phases were separated. The organic extract was washed with saturated aqueous NaCl solution, dried over anhydrous Na$_2$SO$_4$, filtered and concentrated in vacuo to provide the title compound (17 mg, 25% yield). LCMS (ESI) [M+H]$^+$=689.0.

Step 4: (S)-2-Chloro-N-(4-chloro-2-fluoro-3-((3-(2-(piperidin-3-ylamino)pyrimidin-4-yl)pyridin-2-yl)oxy)phenyl)benzenesulfonamide hydrochloride

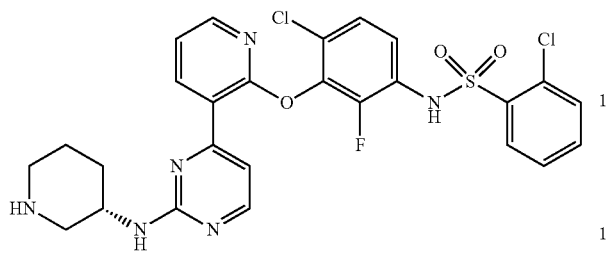

To a solution of (S)-tert-butyl 3-((4-(2-(6-chloro-3-(2-chlorophenylsulfonamido)-2-fluorophenoxy)pyridin-3-yl)pyrimidin-2-yl)amino)piperidine-1-carboxylate (17 mg, 0.02 mmol) in 1,4-dioxane (0.31 mL) was added 4N HCl in dioxane (0.6 mL, 2.4 mmol) and the mixture was stirred at room temperature. After 2 h, the mixture was diluted with diethyl ether and the resulting solids were filtered off, washed with diethyl ether, dissolved in a mixture of ACN and H₂O and lyophilized to provide the title product (15 mg, 97% yield) as a white solid.

Example 20

(S)—N-(4-Chloro-2-fluoro-3-((3-(2-(piperidin-3-ylamino)pyrimidin-4-yl)pyridin-2-yl)oxy)phenyl)-1-phenylmethanesulfonamide (Compound 138)

Step 1: (S)-tert-Butyl 3-((4-(2-(6-chloro-2-fluoro-3-(phenylmethylsulfonamido)phenoxy)pyridin-3-yl)pyrimidin-2-yl)amino)piperidine-1-carboxylate

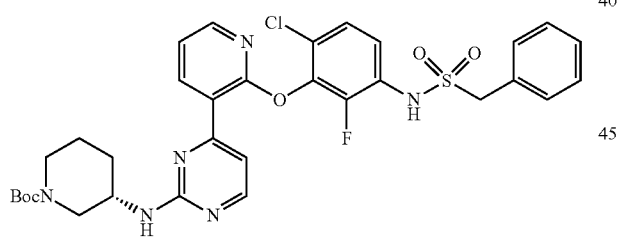

To a solution of crude (S)-tert-butyl 3-((4-(2-(3-amino-6-chloro-2-fluorophenoxy)pyridin-3-yl)pyrimidin-2-yl)amino)piperidine-1-carboxylate (50 mg, 0.10 mmol) in DCM (0.32 mL) was added phenylmethanesulfonyl chloride (37 mg, 0.19 mmol) followed by addition of pyridine (0.12 mL, 1.46 mmol), and the mixture was stirred at room temperature. After 2 h, the volatiles were removed on a rotovap and the crude residue purified by C18 reverse phase flash chromatography (55-75% ACN/10 mM aqueous ammonium formate, pH=3.8). The product-containing fractions were combined and concentrated to remove most of the ACN. The residue was then diluted with EtOAc and saturated aqueous NaHCO₃, and the phases were separated. The organic extracts were washed with saturated aqueous NaCl solution, dried over anhydrous Na₂SO₄, filtered and concentrated in vacuo to provide the title compound (12 mg, 18% yield). LCMS (ESI) [M+H]⁺=669.1.

Step 2: (S)—N-(4-Chloro-2-fluoro-3-((3-(2-(piperidin-3-ylamino)pyrimidin-4-yl)pyridin-2-yl)oxy)phenyl)-1-phenylmethanesulfonamide

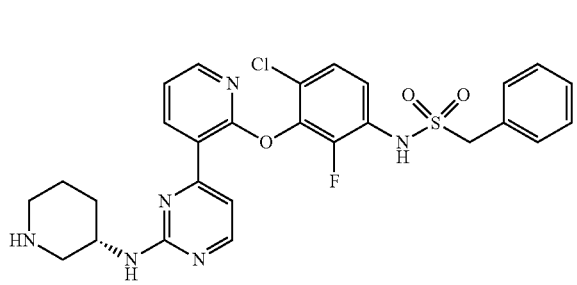 [SMILES: O=S(=O)(Cc1ccccc1)Nc1ccc(Cl)c(Oc2ncccc2-c2ccnc(N[C@H]3CCCNC3)n2)c1F]

To a solution of (S)-tert-butyl 3-((4-(2-(6-chloro-2-fluoro-3-(phenylmethylsulfonamido)phenoxy)pyridin-3-yl)pyrimidin-2-yl)amino)piperidine-1-carboxylate (12 mg, 0.02 mmol) in 1,4-dioxane (0.31 mL) was added 4N HCl in dioxane (0.6 mL, 2.4 mmol) and the mixture stirred at room temperature. After 2 h, the mixture was diluted with Diethyl ether, and the resulting solids were filtered off to provide the crude product which was further purified by C18 reverse phase flash chromatography (20-60% ACN/10 mM aqueous ammonium bicarbonate, pH=10). The product-containing fractions were combined and lyophilized to provide the title product (8 mg, 81% yield) as a white solid.

Example 21

(S)-2-Chloro-N-(2-methyl-3-((3-(2-(piperidin-3-ylamino)pyrimidin-4-yl)pyridin-2-yl)oxy)phenyl)benzenesulfonamide hydrochloride (Compound 139)

Step 1: (S)-tert-Butyl 3-((4-(2-(3-amino-2-methylphenoxy)pyridin-3-yl)pyrimidin-2-yl)amino)piperidine-1-carboxylate

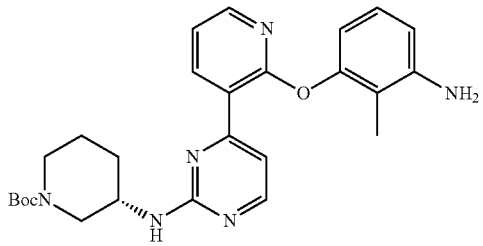 [SMILES: Cc1c(N)cccc1Oc1ncccc1-c1ccnc(N[C@H]2CCCN(C(=O)OC(C)(C)C)C2)n1]

A flask containing a solution of (S)-tert-butyl 3-((4-(2-fluoropyridin-3-yl)pyrimidin-2-yl)amino)piperidine-1-carboxylate (290 mg, 0.58 mmol), 3-amino-2-methylphenol (79 mg, 0.64 mmol), and cesium carbonate (401 mg, 1.22 mmol) in DMSO (2.59 mL) was placed in an oil bath heated to 120° C. and sealed. After 1 h, the mixture was diluted with EtOAc (75 mL), washed with H₂O (10 mL), then with saturated aqueous NaCl (10 mL), dried over MgSO₄, filtered and concentrated in vacuo. The resulting crude material was purified by silica flash column chromatography (0-100% ethyl acetate/DCM) to provide the title compound (291 mg, quant. yield) as a pale yellow solid. LCMS (ESI) [M+H]⁺=477.1.

Step 2: (S)-tert-Butyl 3-((4-(2-(3-(2-chlorophenylsulfonamido)-2-methylphenoxy)pyridin-3-yl)pyrimidin-2-yl)amino)piperidine-1-carboxylate

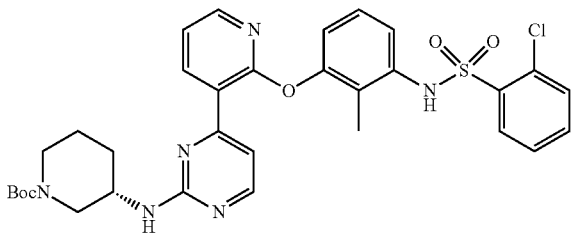 [SMILES: Cc1c(NS(=O)(=O)c2ccccc2Cl)cccc1Oc1ncccc1-c1ccnc(N[C@H]2CCCN(C(=O)OC(C)(C)C)C2)n1]

To a solution of (S)-tert-butyl 3-((4-(2-(3-amino-2-methylphenoxy)pyridin-3-yl)pyrimidin-2-yl)amino)piperidine-1-carboxylate (58 mg, 0.12 mmol) in DCM (0.5 mL) was added 2-chlorobenzenesulfonylchloride (41 mg, 0.19 mmol) and pyridine (0.15 mL) The reaction mixture was stirred at room temperature. After 16 h, the mixture was diluted with EtOAc and saturated aqueous NaHCO₃, and the phases were separated. The organic extracts were washed with saturated aqueous NaCl, dried over anhydrous Na₂SO₄, filtered and concentrated in vacuo. The crude material thus obtained was purified by silica flash column chromatography (0-100% EtOAc/DCM) to provide the title compound (42 mg, 53% yield). LCMS (ESI) [M+H]$^+$=651.1.

Step 3: (S)-2-Chloro-N-(2-methyl-3-((3-(2-(piperidin-3-ylamino)pyrimidin-4-yl)pyridin-2-yl)oxy)phenyl)benzenesulfonamide hydrochloride

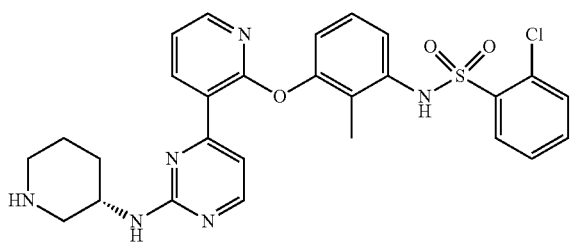 [SMILES: Cc1c(NS(=O)(=O)c2ccccc2Cl)cccc1Oc1ncccc1-c1ccnc(N[C@H]2CCCNC2)n1]

To a solution of (S)-tert-butyl 3-((4-(2-(3-(2-chlorophenylsulfonamido)-2-methylphenoxy)pyridin-3-yl)pyrimidin-2-yl)amino)piperidine-1-carboxylate (42 mg, 0.06 mmol) in 1,4-dioxane (1 mL) was added 4N HCl in dioxane (1.0 mL, 4.0 mmol), and the mixture was stirred at room temperature. After 2 h, the resulting solids were filtered off, washed with 1,4-dioxane, then with diethyl ether, dissolved in a mixture of ACN and H₂O and lyophilized to provide the title product (32 mg, 84% yield) as an off-white solid.

Example 22

(S)—N-(2-Methyl-3-((3-(2-(piperidin-3-ylamino)pyrimidin-4-yl)pyridin-2-yl)oxy)phenyl)-1-phenylmethanesulfonamide hydrochloride (Compound 140)

Step 1: (S)-tert-Butyl 3-((4-(2-(2-methyl-3-(phenylmethylsulfonamido)phenoxy)pyridin-3-yl)pyrimidin-2-yl)amino)piperidine-1-carboxylate

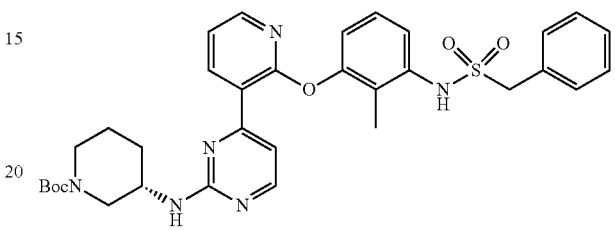

To a solution of (S)-tert-butyl 3-((4-(2-(3-amino-2-methylphenoxy)pyridin-3-yl)pyrimidin-2-yl)amino)piperidine-1-carboxylate (58 mg, 0.12 mmol) in DCM (0.58 mL) was added 2-phenylmethanesulfonylchloride (35 mg, 0.18 mmol) and pyridine (0.15 mL), and the mixture was stirred at room temperature. After 16 h, a further portion of phenylmethanesulfonylchloride (105 mg, 0.54 mmol) was added and stirring continued at room temperature. After a further 18 h, the mixture was diluted with EtOAc and saturated aqueous NaHCO₃, and the phases were separated. The organic extract was washed with saturated aqueous NaCl solution, dried over anhydrous Na₂SO₄, filtered and concentrated in vacuo. The crude material thus obtained was purified by silica flash column chromatography (0-100% EtOAc/DCM) followed by additional purification by C18 reverse phase flash chromatography (40-80% ACN/10 mM aqueous ammonium formate). The product-containing fractions were combined and lyophilized to provide the title compound (12 mg, 16% yield). LCMS (ESI) [M+H]$^+$= 631.1.

Step 2: (S)—N-(2-Methyl-3-((3-(2-(piperidin-3-ylamino)pyrimidin-4-yl)pyridin-2-yl)oxy)phenyl)-1-phenylmethanesulfonamide hydrochloride

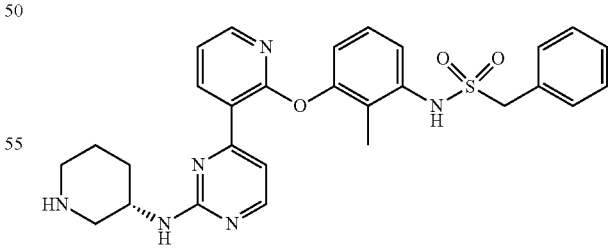

To a solution of (S)-tert-butyl 3-((4-(2-(2-methyl-3-(phenylmethylsulfonamido)phenoxy)pyridin-3-yl)pyrimidin-2-yl)amino)piperidine-1-carboxylate (12 mg, 0.02 mmol) in 1,4-dioxane (1 mL) was added 4N HCl in dioxane (0.29 mL, 1.2 mmol) and the mixture stirred at room temperature. After 2 h, the resulting solids were filtered off, washed with 1,4-dioxane, then with Diethyl ether, dissolved in a mixture of ACN and H₂O and lyophilized to provide the title product (11 mg, 99% yield) as a white solid.

Example 23

(S)-2-Chloro-N-(2-fluoro-3-((3-(2-(piperidin-3-ylamino)pyrimidin-4-yl)pyridin-2-yl)oxy)phenyl)benzenesulfonamide hydrochloride (Compound 141)

Step 1: 3-Amino-2-fluorophenol

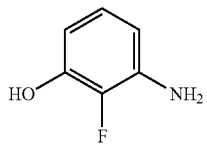

A solution of 3-amino-2-fluorophenol (100 mg, 0.64 mmol) in EtOAc (3 mL) was added to a N₂ flushed flask containing 10% w/w Pd/C (36 mg). The flask was purged with H₂ and stirred under a balloon of H₂ at room temperature overnight. After 4 h, the flask was purged with N₂ and the solution was filtered through celite using EtOAc (40 mL) to wash/elute. Concentration in vacuo provided the title compound (63 mg, 78% yield) as a cream colored solid which was used in the next step without further purification. LCMS (ESI) [M+H]⁺=128.6. ¹H NMR (400 MHz, d6-DMSO) δ 9.29 (s, 1H), 6.59 (td, J=8.0, 1.7 Hz, 1H), 6.17 (td, J=8.0, 1.6 Hz, 1H), 6.09 (td, J=8.0, 1.6 Hz, 1H), 4.94 (s, 2H).

Step 2: (S)-tert-Butyl 3-((4-(2-(3-amino-2-fluorophenoxy)pyridin-3-yl)pyrimidin-2-yl)amino)piperidine-1-carboxylate

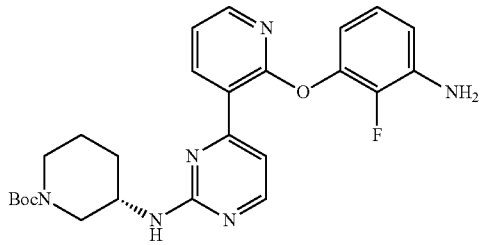

A flask containing a solution of (S)-tert-butyl 3-((4-(2-fluoropyridin-3-yl)pyrimidin-2-yl)amino)piperidine-1-carboxylate (175 mg, 0.47 mmol), 3-amino-2-fluorophenol (65 mg, 0.52 mmol), and cesium carbonate (323 mg, 0.98 mmol) in DMSO (2 mL) was placed in an oil bath heated to 120° C. and sealed. After 90 min, the mixture was diluted with EtOAc (75 mL), washed with H₂O (10 mL), then with 50% saturated aqueous NaCl, dried over anhydrous Na₂SO₄, filtered through celite and concentrated in vacuo to provide the title compound (180 mg, 80% yield) as a brown wax which was used in the next step without further purification. LCMS (ESI) [M+H]⁺=481.0.

Step 3: (S)-tert-Butyl 3-((4-(2-(3-(2-chlorophenylsulfonamido)-2-fluorophenoxy)pyridin-3-yl)pyrimidin-2-yl)amino)piperidine-1-carboxylate

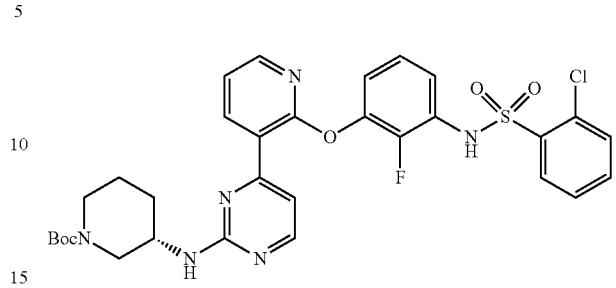

To a solution of crude (S)-tert-butyl 3-((4-(2-(3-amino-2-fluorophenoxy)pyridin-3-yl)pyrimidin-2-yl)amino)piperidine-1-carboxylate (50 mg, 0.10 mmol) in a mixture of DCM (5 mL) and pyridine (1 mL) was added 2-chlorobenzenesulfonylchloride (55 mg, 0.26 mmol) and the mixture stirred at room temperature. After 3 h, a further portion of 2-chlorobenzenesulfonylchloride (55 mg, 0.26 mmol) in DCM (1 mL) was added followed by continued stirring at room temperature. After a further 3 h, the mixture was diluted with DCM (50 mL), washed with saturated NaHCO₃ (10 mL), dried over anydrous Na₂SO₄), filtered and concentrated in vacuo. The crude material was then purified by silica flash chromatography (0-100% EtOAc/hexanes) to provide the title compound (22 mg, 32% yield) as a clear wax. LCMS (ESI) [M+H]⁺=656.2.

Step 4: (S)-2-Chloro-N-(2-fluoro-3-((3-(2-(piperidin-3-ylamino)pyrimidin-4-yl)pyridin-2-yl)oxy)phenyl)benzenesulfonamide hydrochloride

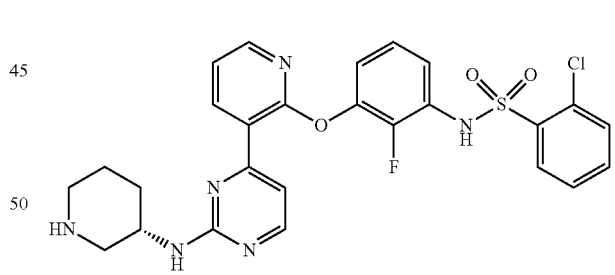

To a solution of (S)-tert-butyl 3-((4-(2-(3-(2-chlorophenylsulfonamido)-2-fluorophenoxy)pyridin-3-yl)pyrimidin-2-yl)amino)piperidine-1-carboxylate (19 mg, 0.03 mmol) in EtOAc (2 mL) was added 4N HCl in dioxane (2.0 mL, 8.0 mmol) and the mixture stirred at room temperature. After 18 h, volatiles were removed under reduced pressure and the crude HCl salt residue was washed with EtOAc (3×3 mL), then ACN (3×3 mL). The crude residue was then sonicated with ACN (3 mL) to produce a suspension and volatiles removed under reduced pressure (process repeated×3) and the resulting solids dissolved in a mixture of H₂O and ACN and lyophilized to provide the title product (11 mg, 64% yield) as a white solid.

Example 24

(S)—N-(2-Fluoro-3-((3-(2-(piperidin-3-ylamino)pyrimidin-4-yl)pyridin-2-yl)oxy)phenyl)-1-phenyl-methanesulfonamide hydrochloride (Compound 142)

Step 1: (S)-tert-Butyl 3-((4-(2-(2-fluoro-3-(phenyl-methylsulfonamido)phenoxy)pyridin-3-yl)pyrimidin-2-yl)amino)piperidine-1-carboxylate

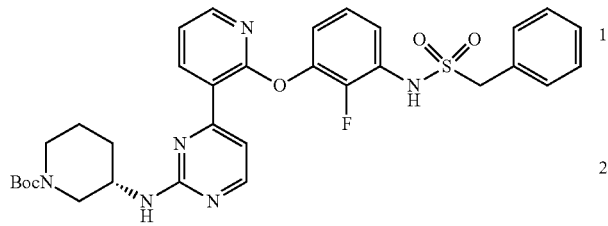

To a solution of crude (S)-tert-butyl 3-((4-(2-(3-amino-2-fluorophenoxy)pyridin-3-yl)pyrimidin-2-yl)amino)piperidine-1-carboxylate (45 mg, 0.09 mmol) in a mixture of DCM (5 mL) and pyridine (1 mL) was added a solution of phenylmethanesulfonyl chloride (45 mg, 0.23 mmol) in DCM (1 mL) and the mixture stirred at room temperature. After 3 h, the mixture was diluted with DCM (50 mL), washed with saturated aqueous NaHCO₃ solution (10 mL), dried over anhydrous Na₂SO₄, filtered and concentrated in vacuo. The crude material was then purified by silica flash chromatography (0-100% EtOAc/hexanes) to provide the title compound (19 mg, 32% yield) as a clear wax. LCMS (ESI) [M+H]⁺=635.3.

Step 2: (S)—N-(2-Fluoro-3-((3-(2-(piperidin-3-ylamino)pyrimidin-4-yl)pyridin-2-yl)oxy)phenyl)-1-phenylmethanesulfonamide hydrochloride

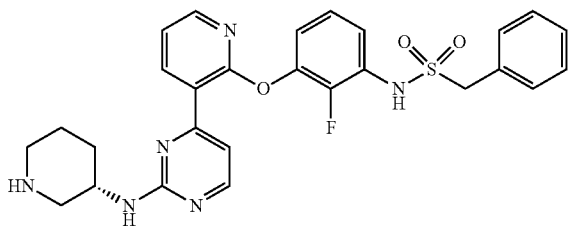 [SMILES: Cc1c(NS(=O)(=O)Cc2ccccc2)cccc1Oc1ncccc1-c1ccnc(N[C@H]2CCCNC2)n1]

To a solution of (S)-tert-butyl 3-((4-(2-(2-fluoro-3-(phenylmethylsulfonamido)phenoxy)pyridin-3-yl)pyrimidin-2-yl)amino)piperidine-1-carboxylate (20 mg, 0.03 mmol) in EtOAc (2 mL) was added 4N HCl in dioxane (2.0 mL, 8.0 mmol) and the mixture stirred at room temperature. After 18 h, the volatiles were removed under reduced pressure and the crude HCl salt residue was washed with EtOAc (3×3 mL) and then acetonitrile (3×3 mL). The crude residue was then sonicated with ACN (3 mL) to produce a suspension, and the volatiles were removed under reduced pressure (process repeated×3). The resulting solids were dissolved in a mixture of H₂O and ACN and lyophilized to provide the title product (11 mg, 61% yield) as a white solid.

Example 25

(S)—N-(4-Chloro-2-fluoro-3-((3-(2-(piperidin-3-ylamino)pyrimidin-4-yl)pyridin-2-yl)oxy)phenyl)propane-1-sulfonamide hydrochloride (Compound 143)

Step 1: (S)-tert-Butyl 3-((4-(2-(6-chloro-2-fluoro-3-(propylsulfonamido)phenoxy)pyridin-3-yl)pyrimidin-2-yl)amino)piperidine-1-carboxylate

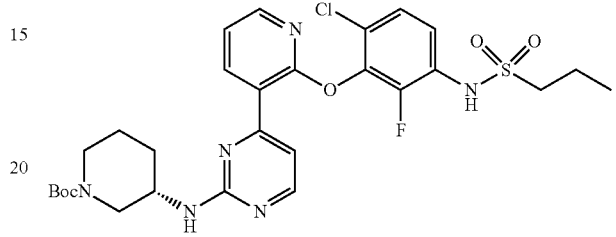

To a solution of crude (S)-tert-butyl 3-((4-(2-(3-amino-6-chloro-2-fluorophenoxy)pyridin-3-yl)pyrimidin-2-yl)amino)piperidine-1-carboxylate (50 mg, 0.10 mmol) in DCM (0.5 mL) was added 1-propanesulfonyl chloride (21 mg, 0.15 mmol) followed by addition of pyridine (0.12 mL, 1.46 mmol) and the mixture stirred at room temperature. After 16 h, a further portion of 1-propanesulfonyl chloride (21 mg, 0.15 mmol) was added and stirring continued at room temperature. After a further 16 h, the mixture was diluted with EtOAc and washed with saturated aqueous NaHCO₃, then saturated aqueous NaCl, then with saturated aqueous NH₄Cl solution. The organic extract was dried over anhydrous MgSO₄, filtered and concentrated in vacuo. The resulting crude residue thus obtained was purified by silica flash column chromatography (0-100% EtOAc/DCM) followed by additional purification by reverse phase prep-HPLC (CSH column, 50-70% ACN/10 mM aqueous ammonium formate, pH=3.8). Appropriate fractions were combined and lyophilized to provide the title compound (14 mg, 23% yield). LCMS (ESI) [M+H]⁺=621.1.

Step 2: (S)—N-(4-Chloro-2-fluoro-3-((3-(2-(piperidin-3-ylamino)pyrimidin-4-yl)pyridin-2-yl)oxy)phenyl)propane-1-sulfonamide hydrochloride

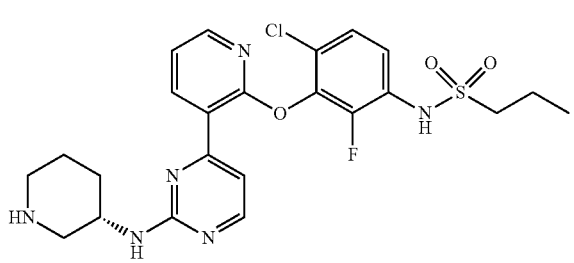

To a solution of (S)-tert-butyl 3-((4-(2-(6-chloro-2-fluoro-3-(propylsulfonamido)phenoxy)pyridin-3-yl)pyrimidin-2-yl)amino)piperidine-1-carboxylate (14 mg, 0.02 mmol) in 1,4-dioxane (1 mL) was added 4N HCl in dioxanes (0.35 mL, 1.4 mmol) and the mixture stirred at room temperature. After 4 h, the resulting solids were filtered off, washed with

Example 26

(S)—N-(2-Fluoro-3-((3-(2-(piperidin-3-ylamino)pyrimidin-4-yl)pyridin-2-yl)oxy)phenyl)propane-1-sulfonamide hydrochloride (Compound 144)

Step 1: (S)-tert-Butyl 3-((4-(2-(2-fluoro-3-(propylsulfonamido)phenoxy)pyridin-3-yl)pyrimidin-2-yl)amino)piperidine-1-carboxylate

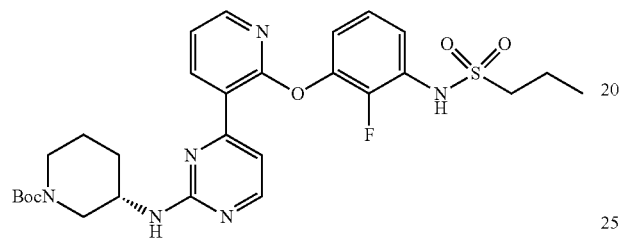

To a solution of crude (S)-tert-butyl 3-((4-(2-(3-amino-2-fluorophenoxy)pyridin-3-yl)pyrimidin-2-yl)amino)piperidine-1-carboxylate (45 mg, 0.09 mmol) in a mixture of DCM (5 mL) and pyridine (1 mL) was added a solution of 1-propanesulfonyl chloride (33 mg, 0.23 mmol) in DCM (1 mL) and the mixture stirred at room temperature. After 16 h, a further portion of 1-propanesulfonyl chloride (33 mg, 0.23 mmol) in DCM (1 mL) was added and stirring continued at room temperature. After a further 18 h, the mixture was diluted with DCM (50 mL), washed with saturated NaHCO$_3$ (10 mL), dried over anhydrous Na$_2$SO$_4$, filtered and concentrated in vacuo. The crude material was then purified by silica flash chromatography (0-100% EtOAc/hexanes) to provide the title compound (14 mg, 25% yield) as a yellow wax. LCMS (ESI) [M+H]$^+$=587.1.

Step 2: (S)—N-(2-Fluoro-3-((3-(2-(piperidin-3-ylamino)pyrimidin-4-yl)pyridin-2-yl)oxy)phenyl)propane-1-sulfonamide hydrochloride

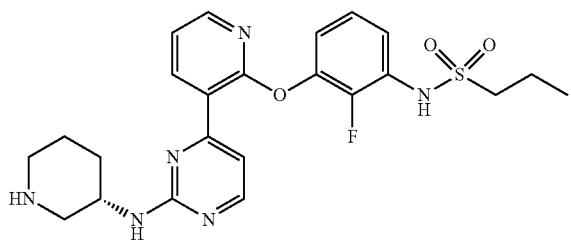 [SMILES: CCCS(=O)(=O)Nc1cccc(Oc2ncccc2-c2ccnc(N[C@H]3CCCNC3)n2)c1F]

To a solution of (S)-tert-butyl 3-((4-(2-(2-fluoro-3-(propylsulfonamido)phenoxy)pyridin-3-yl)pyrimidin-2-yl)amino)piperidine-1-carboxylate (13 mg, 0.02 mmol) in EtOAc (2 mL) was added 4N HCl in dioxane (1.0 mL, 4.0 mmol) and the mixture stirred at room temperature. After 16 h, the volatiles were removed under reduced pressure and the crude HCl salt residue was washed with EtOAc (3×3 mL) and then ACN (3 20×3 mL). The crude residue was then sonicated with ACN (3 mL) to produce a suspension and the volatiles removed under reduced pressure (the process was repeated×3). The resulting solids were dissolved in a mixture of and ACN and lyophilized to provide the title product (9 mg, 78% yield) as a white solid.

Example 27

(S)-1-Cyclohexyl-N-(2,3-difluoro-4-((3-(2-(piperidin-3-ylamino)pyrimidin-4-yl)pyridin-2-yl)oxy)phenyl)methanesulfonamide hydrochloride (Compound 145)

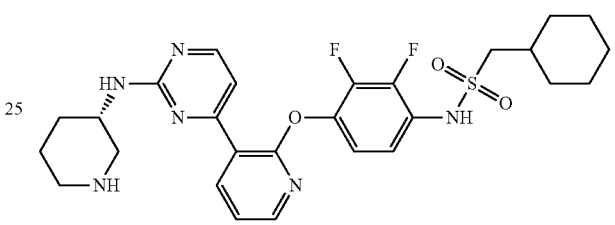

Step 1: tert-Butyl (3S)-3-((4-(2-(4-amino-2,3-difluoro-phenoxy)-3-pyridyl)pyrimidin-2-yl)amino)piperidine-1-carboxylate

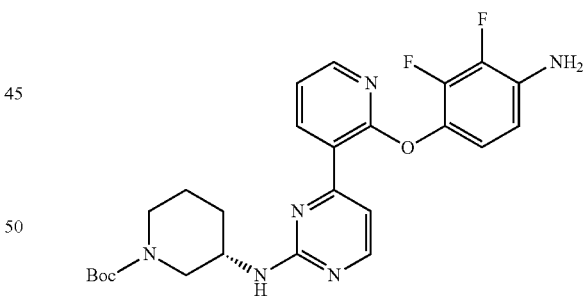

A solution of 4-amino-2,3-difluoro-phenol (1.94 g, 13.4 mmol), tert-butyl (3S)-3-((4-(2-fluoro-3-pyridyl)pyrimidin-2-yl)amino)piperidine-1-carboxylate (5.00 g, 13.4 mmol) and cesium carbonate (7.42 g, 22.8 mmol) in DMSO (45 mL) was stirred at 130° C. for 6 h. LCMS showed complete conversion. The resulting solution was diluted with water and extracted with ethyl acetate. The organic layers were washed twice with brine and dried over anhydrous sodium sulfate. The solvent was concentrated under vacuum. The residue was purified by silica flash chromatography eluting with ethyl acetate/petroleum ether (20%-50%) to afford the title compound (5.60 g, 83.9% yield) as a black solid. LCMS (ESI): [M+H]$^+$=499.2.

Step 2: tert-Butyl (3S)-3-((4-(2-(4-(cyclohexylmeth-ylsulfonylamino)-2,3-difluoro-phenoxy)-3-pyridyl)pyrimidin-2-yl)amino)piperidine-1-carboxylate

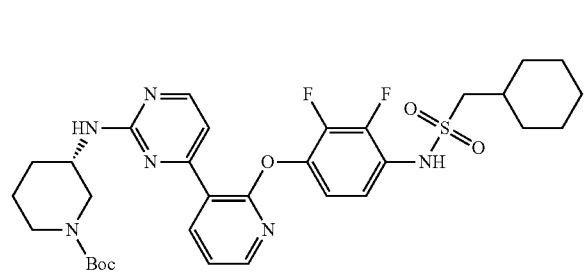 [SMILES: CC(C)(C)OC(=O)N1CCC[C@H](Nc2nccc(-c3cccnc3Oc3ccc(NS(=O)(=O)CC4CCCCC4)c(F)c3F)n2)C1]

Under nitrogen, a solution of tert-butyl (3S)-3-((4-(2-(4-amino-2,3-difluoro-phenoxy)-3-pyridyl)pyrimidin-2-yl)amino)piperidine-1-carboxylate (400 mg, 0.80 mmol) in chloroform (20 mL) was stirred at 20° C. Then 4-methyl-morpholine (487 mg, 4.81 mmol) and cyclohexylmethane-sulfonyl chloride (410 mg, 2.09 mmol) were added followed by stirring at 20° C. for 72 h. The resulting solution was diluted with water and extracted with DCM. The organic layers were combined and the solvent removed under vacuum. The residue was purified by silica flash chromatography eluting with ethyl acetate/petroleum ether (0-35%) to afford the title compound (130 mg, 24.6% yield) as a white solid. LCMS (ESI): [M+H]$^+$=659.2.

Step 3: (S)-1-Cyclohexyl-N-(2,3-difluoro-4-((3-(2-(piperidin-3-ylamino)pyrimidin-4-yl)pyridin-2-yl)oxy)phenyl)methanesulfonamide hydrochloride

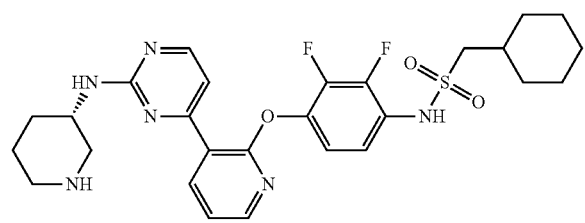

A solution of tert-butyl (3S)-3-((4-(2-(4-(cyclohexylm-ethylsulfonylamino)-2,3-difluoro-phenoxy)-3-pyridyl)pyrimidin-2-yl)amino)piperidine-1-carboxylate (120 mg, 0.18 mmol) in DCM (6 mL) was added 4 M HCl in 1,4-dioxane (2 mL) and stirred at 20° C. for 2 h. The solvent was concentrated under vacuum. The crude product was purified by prep-HPLC. The resulting solution was concentrated under vacuum and diluted with 1 M HCl in water (3 mL). Then the product was concentrated under vacuum to afford the title compound (45.1 mg, 42.6% yield) as a white solid.

Example 28

(S)—N-(2,3-Difluoro-4-(3-(2-(piperidin-3-ylamino)pyrimidin-4-yl)pyridin-2-yloxy)phenyl)cyclopropan-ecarboxamide hydrochloride (Compound 147)

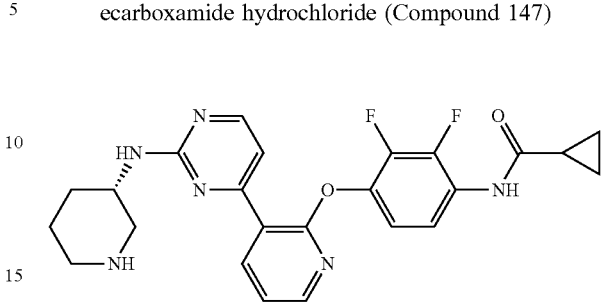

Step 1: (S)-tert-Butyl 3-(4-(2-(4-(cyclopropanecar-boxamido)-2,3-difluorophenoxy)pyridin-3-yl)py-rimidin-2-ylamino)piperidine-1-carboxylate

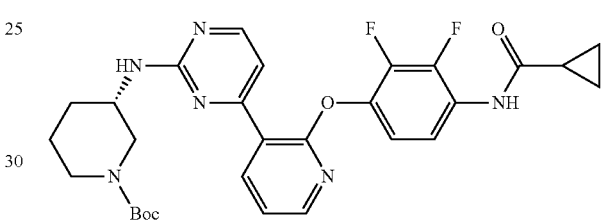

To a solution of tert-butyl (3S)-3-((4-(2-(4-amino-2,3-difluoro-phenoxy)-3-pyridyl)pyrimidin-2-yl)amino)piperi-dine-1-carboxylate (400 mg, 0.80 mmol) in pyridine (4 mL) was added cyclopropanecarbonyl chloride (0.11 mL, 1.22 mmol) and the solution was stirred for 16 h at room temperature. The mixture was evaporated under vacuum. The residue was purified by prep-HPLC to afford the title compound (365 mg, 80.3% yield) as a pink solid. LCMS (ESI): [M+H]$^+$=567.2.

Step 2: (S)—N-(2,3-difluoro-4-(3-(2-(piperidin-3-ylamino)pyrimidin-4-yl)pyridin-2-yloxy)phenyl)cyclopropanecarboxamide hydrochloride

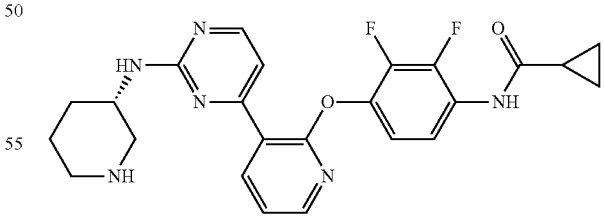

To a solution of tert-butyl (3S)-3-((4-(2-(4-(cyclopropan-ecarbonylamino)-2,3-difluoro-phenoxy)-3-pyridyl)pyrimi-din-2-yl)amino)piperidine-1-carboxylate (365 mg, 0.64 mmol) in DCM (4 mL) was added 4 M hydrogen chloride in 1,4-dioxane (1 mL). The mixture was stirred for 2 h at room temperature. The crude product was purified by prep-HPLC. The resulting solution was concentrated under vacuum and diluted with 1 M HCl in water (3 mL). The product was then concentrated under vacuum to afford the title compound (25.2 mg, 7.8% yield) as a light yellow solid.

Example 29

N-(2,3-Difluoro-4-((3-(2-(((S)-piperidin-3-yl)amino) pyrimidin-4-yl)pyridin-2-yl)oxy)phenyl)spiro[2.2] pentane-1-carboxamide hydrochloride (Compound 150)

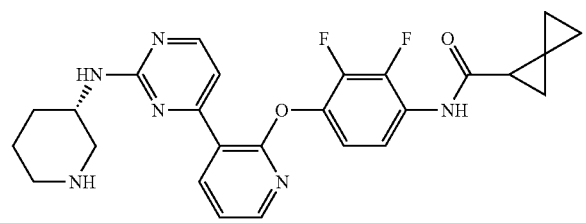 [SMILES: O=C(Nc1ccc(Oc2ncccc2-c2ccnc(N[C@H]3CCCNC3)n2)c(F)c1F)C1CC12CC2]

Step 1: tert-Butyl (3S)-3-((4-(2-(2,3-difluoro-4-(spiro[2.2]pentane-1-carboxamido)phenoxy)pyridin-3-yl)pyrimidin-2-yl)amino)piperidine-1-carboxylate and tert-butyl (3S)-3-((4-(2-(2,3-difluoro-4-(spiro [2.2]pentane-1-carboxamido)phenoxy)pyridin-3-yl) pyrimidin-2-yl)amino)piperidine-1-carboxylate

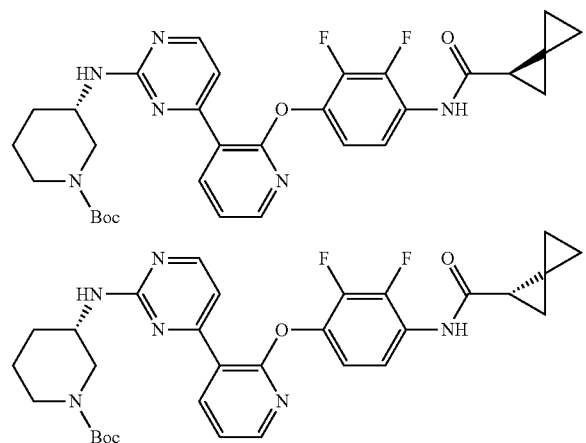

To a solution of spiro[2.2]pentane-2-carboxylic acid (450 mg, 4.01 mmol) in 1,2-DCM (5 mL) was added a drop of DMF. Then ethanedioyl dichloride (509 mg, 4.01 mmol) was added at 0° C. followed by stirring at 0° C. for 30 min. The cold solution was then added to a solution of tert-butyl (3S)-3-[[4-[2-(4-amino-2,3-difluoro-phenoxy)-3-pyridyl] pyrimidin-2-yl]amino]piperidine-1-carboxylate (400 mg, 0.800 mmol) in pyridine (4 mL) followed by stirring at 25° C. for 1 h. The resulting solution was diluted with water and extracted with DCM. The organic layer was washed with brine and concentrated under vacuum. The residue was purified by silica flash chromatography eluting with ethyl acetate/petroleum ether (0-30%). The crude product was further purified by prep-HPLC and chiral HPLC separation to provide two single stereoisomers stereogenic at the 2 position of the amide (conditions: Column: Chiralpak IA, 2×25 cm, 5 μm; Mobile Phase A:MTBE-HPLC, Mobile Phase B: IPA-HPLC; Flow rate: 20 mL/min; Gradient: 2 B to 2 B in 12 min; 254/220 nm).

tert-Butyl (3S)-3-((4-(2-(2,3-difluoro-4-(spiro[2.2]pentane-1-carboxamido)phenoxy)pyridin-3-yl)pyrimidin-2-yl) amino)piperidine-1-carboxylate (isomer 1, 50 mg, 13.7% yield). LCMS (ESI): [M+H]⁺=593.2; (rt=2.044 min, Chiral IA, 0.46×5 cm; 3 um, MTBE (0.1% DEA):IPA=98:2, 1.0 ml/min)

tert-Butyl (3S)-3-((4-(2-(2,3-difluoro-4-(spiro[2.2]pentane-1-carboxamido)phenoxy)pyridin-3-yl)pyrimidin-2-yl) amino)piperidine-1-carboxylate (isomer 2, 50 mg, 13.7% yield). LCMS (ESI): [M+H]⁺=593.2; (rt=2.513 min, chiral IA, 0.46×5 cm; 3 um, MTBE (0.1% DEA):IPA=98:2, 1.0 ml/min)

Step 2: N-(2,3-Difluoro-4-((3-(2-(((S)-piperidin-3-yl)amino)pyrimidin-4-yl)pyridin-2-yl)oxy)phenyl) spiro[2.2]pentane-1-carboxamide hydrochloride

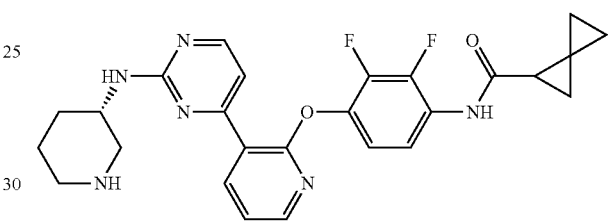

To a solution of tert-butyl (3S)-3-[[4-[2-[2,3-difluoro-4-[[(2S)-spiro[2.2]pentane-2-carbonyl]amino]phenoxy]-3-pyridyl]pyrimidin-2-yl]amino]piperidine-1-carboxylate (50 mg, 0.080 mmol) in DCM (2 mL) was added 4 M HCl in 1,4-dioxane (1 mL) followed by stirring at 20° C. for 1 h. The solvent was concentrated under vacuum. The residue was purified by Prep-HPLC to afford the title product (18.1 mg, 41%) as a white solid. The absolute stereochemistry of the amide wasn't determined.

Example 30

(S)-1-Phenyl-N-(2,3,6-trifluoro-4-((3-(2-(piperidin-3-ylamino)pyrimidin-4-yl)pyridin-2-yl)oxy)phenyl) methanesulfonamide hydrochloride (Compound 153)

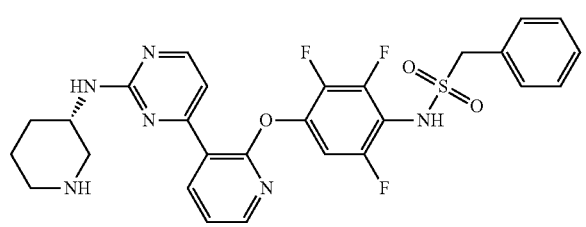

289

Step 1: 1-(Benzyloxy)-2,3,5-trifluoro-4-nitrobenzene

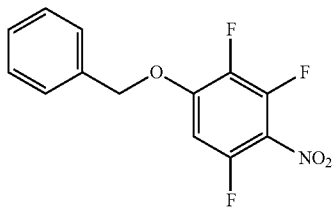 [SMILES: O=[N+]([O-])c1c(F)cc(OCc2ccccc2)c(F)c1F]

A mixture of 2,3,4,6-tetrafluoronitrobenzene (3.00 g, 15.4 mmol), benzyl alcohol (1.27 mL, 12.3 mmol) and tetrabutylammonium hydrogen sulfate (0.522 g, 1.54 mmol) in DCM (75 mL) was added to a solution of sodium hydroxide (0.615 g, 15.4 mmol) in water (75 mL). The mixture was stirred for 18 h at room temperature. The reaction was quenched with water. The resulting solution was extracted with DCM, and the solvent was concentrated under vacuum. The residue was purified by silica flash chromatography eluting with DCM/petroleum ether (1/20) to afford the title compound (1.68 g, 38.6% yield) as a light yellow solid. $^1$H NMR (400 MHz, CDCl$_3$) δ 7.43 (m, 6H), 5.24 (s, 2H).

Step 2: 4-Amino-2,3,5-trifluorophenol

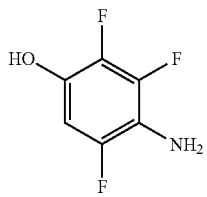 [SMILES: Nc1c(F)cc(O)c(F)c1F]

Under hydrogen, a mixture of 1-benzyloxy-2,3,5-trifluoro-4-nitro-benzene (880 mg, 3.11 mmol) and 10% Pd/C (220 mg) in methyl alcohol (30 mL) was stirred for 3 h at room temperature. Acetic acid (1 mL) was added to the mixture. After filtration, the filtrate was concentrated under reduced pressure. The residue was purified by silica flash chromatography eluting with methanol/DCM (1:20) to afford the title compound (210 mg, 41.4% yield) as a brown solid. LCMS (ESI): [M+H]$^+$=164.2.

Step 3: (S)-tert-Butyl 3-(4-(2-(4-amino-2,3,5-trifluorophenoxy)pyridin-3-yl)pyrimidin-2-ylamino)piperidine-1-carboxylate

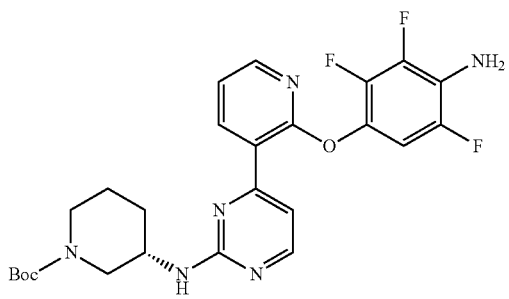 [SMILES: CC(C)(C)OC(=O)N1CCC[C@H](Nc2nccc(-c3cccnc3Oc3cc(F)c(N)c(F)c3F)n2)C1]

290

Under nitrogen, to a solution of 4-amino-2,3,5-trifluorophenol (200 mg, 1.07 mmol) and tert-butyl (3S)-3-((4-(2-fluoro-3-pyridyl)pyrimidin-2-yl)amino)piperidine-1-carboxylate (398 mg, 1.07 mmol) in DMSO (5 mL) was added cesium carbonate (590.9 mg, 1.81 mmol) followed by stirring for 16 h at 130° C. The resulting solution was quenched with water and extracted with ethyl acetate. The organic layers were combined. The organic extract was dried over anhydrous sodium sulfate and concentrated under vacuum. The residue was purified by silica flash chromatography eluting with ethyl acetate/petroleum ether (1:1) to afford the title compound (180 mg, 32.7% yield) as a brown solid. LCMS (ESI): [M+H]$^+$=517.2.

Step 4: (S)-tert-Butyl 3-(4-(2-(2,3,5-trifluoro-4-(phenylmethylsulfonamido)phenoxy)pyridin-3-yl)pyrimidin-2-ylamino)piperidine-1-carboxylate

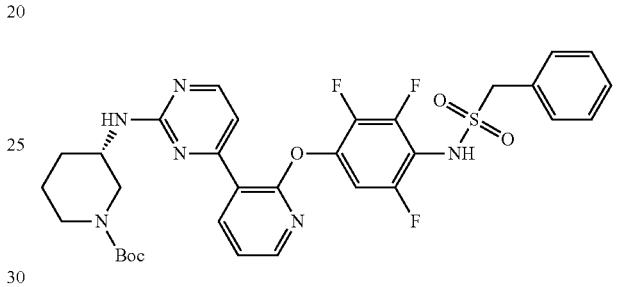

To a solution of alpha-toluenesulfonylchloride (221 mg, 1.16 mmol) and tert-butyl (3S)-3-((4-(2-(4-amino-2,3,5-trifluoro-phenoxy)-3-pyridyl)pyrimidin-2-yl)amino)piperidine-1-carboxylate (150 mg, 0.29 mmol) in pyridine (4 mL) was added 4-dimethylaminopyridine (71 mg, 0.58 mmol). The mixture was stirred for 16 h at room temperature. The solvent was concentrated under vacuum. The residue was purified by silica flash chromatography eluting with ethyl acetate/petroleum ether (1:1) to afford the title compound (96 mg, 49.3% yield) as a brown solid. LCMS (ESI): [M+H]$^+$=671.2.

Step 5: (S)-1-Phenyl-N-(2,3,6-trifluoro-4-((3-(2-(piperidin-3-ylamino)pyrimidin-4-yl)pyridin-2-yl)oxy)phenyl)methanesulfonamide hydrochloride

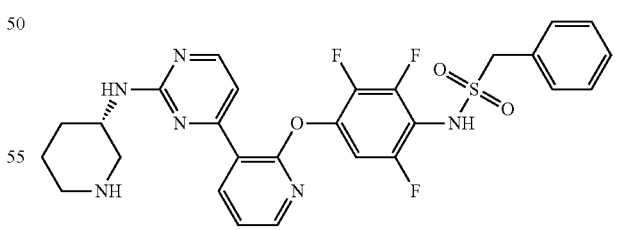

To a solution of tert-butyl (3S)-3-((4-(2-(4-(benzylsulfonylamino)-2,3,5-trifluoro-phenoxy)-3-pyridyl)pyrimidin-2-yl)amino)piperidine-1-carboxylate (86 mg, 0.13 mmol) in DCM (4 mL) was added 4 M HCl in 1,4-dioxane (1 mL) followed by stirring at room temperature for 1 h. The solvent was removed under vacuum. The residue was purified by prep-HPLC to afford the title compound (24 mg, 30.8% yield) as a yellow.

Example 31

(S)—N-(2,6-Difluoro-3-methyl-4-(3-(2-(piperidin-3-ylamino)pyrimidin-4-yl)pyridin-2-yloxy)phenyl)(phenyl)methanesulfonamide hydrochloride

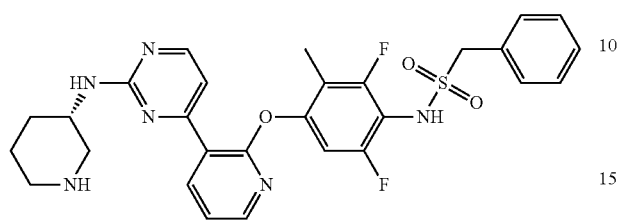

Step 1: 2-Bromo-1,3,5-trifluoro-4-nitro-benzene

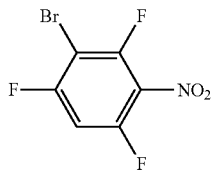 [SMILES: O=[N+]([O-])c1c(F)cc(F)c(Br)c1F]

To 1-bromo-2,4,6-trifluorobenzene (10 g, 47.4 mmol) was successively added a mixture of sulfuric acid (10 mL) and nitric acid (10 mL) at 0° C. The solution was stirred for 1 h at this temperature. TLC (petroleum ether/ethyl acetate=20/1, Rf=0.25) indicated the reaction was completed. The reaction was quenched with water and extracted with DCM. The combined organic extract was washed with water, saturated sodium bicarbonate solution, and brine and dried over anhydrous sodium sulfate. The solvent was removed under vacuum to afford the title compound (8.0 g, 65.9% yield) as yellow oil. $^1$H NMR (400 MHz, CDCl$_3$) δ 7.03 (m, 1H).

Step 2: 1-(Benzyloxy)-2-bromo-3,5-difluoro-4-nitrobenzene

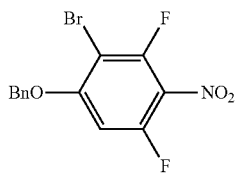 [SMILES: O=[N+]([O-])c1c(F)cc(OCc2ccccc2)c(Br)c1F]

A mixture of 2-bromo-1,3,5-trifluoro-4-nitro-benzene (8.0 g, 31.3 mmol), benzyl alcohol (3.38 g, 31.3 mmol), 2 M sodium hydroxide solution (16 mL, 32 mmol), tetrabutylammonium hydrogen sulfate (1.17 g, 3.44 mmol) in DCM (30 mL) was stirred for 16 h at room temperature. TLC (10% ethyl acetate in petroleum ether, Rf=0.5) indicated the reaction was completed. The reaction was quenched with water and extracted with DCM. The organic extracts were combined, washed with water, brine, and dried over anhydrous sodium sulfate. The solvent was removed under vacuum to give the title compound (9.2 g, 85.5% yield) as a yellow solid. $^1$H NMR (400 MHz, CDCl$_3$) δ 7.30-7.20 (m, 5H), 6.90-6.70 (m, 1H), 5.30-5.20 (m, 2H).

Step 3: 1-Benzyloxy-3,5-difluoro-2-methyl-4-nitro-benzene

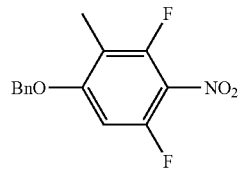 [SMILES: Cc1c(OCc2ccccc2)cc(F)c([N+](=O)[O-])c1F]

Under nitrogen, a mixture of 1-benzyloxy-2-bromo-3,5-difluoro-4-nitro-benzene (3.5 g, 10.2 mmol), trimethylboroxide (3.49 mL, 12.2 mmol), potassium carbonate (4.2 g, 30.5 mmol) and tetrakis(triphenylphosphine) palladium (1.1 g, 1.02 mmol) in toluene (40 mL) and water (10 mL) was stirred at 90° C. for 16 h. The solvent was removed under vacuum. The residue was purified by silica flash chromatography eluting with DCM/petroleum ether (0-100%) to afford the title compound (1.3 g, 38.4% yield) as a yellow solid. $^1$H NMR (400 MHz, CDCl$_3$) δ 7.30-7.20 (m, 5H), 6.65-6.55 (m, 1H), 5.30-5.20 (m, 2H), 2.20 (s, 3H).

Step 4: 4-Amino-3,5-difluoro-2-methyl-phenol

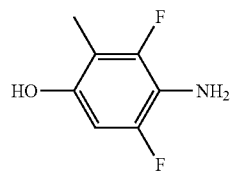

A mixture of 1-benzyloxy-3,5-difluoro-2-methyl-4-nitro-benzene (900 mg, 3.22 mmol) and 20% palladium on activated carbon (300 mg) in methyl alcohol (15 mL) was stirred for 16 h at room temperature under hydrogen. The reaction was quenched with acetic acid (1 mL). The solids were filtered out and the solvent was removed under vacuum. The residue was purified by silica flash chromatography (DCM/petroleum ether 0-100%) to afford the title compound (240 mg, 46.8% yield) as a light yellow solid. LCMS (ESI): [M+H]$^+$=160.1.

Step 5: (S)—N-(2,6-Difluoro-3-methyl-4-(3-(2-(piperidin-3-ylamino)pyrimidin-4-yl)pyridin-2-yloxy)phenyl)(phenyl)methanesulfonamide hydrochloride

The title compound was prepared according to Example 27. This provides the title compound (47.8 mg, 0.079 mmol, 73.4%) as a white solid.

Example 32

(S)—N-(2,3-Difluoro-5-methyl-4-((3-(2-(piperidin-3-ylamino)pyrimidin-4-yl)pyridin-2-yl)oxy)phenyl)-1-phenylmethanesulfonamide

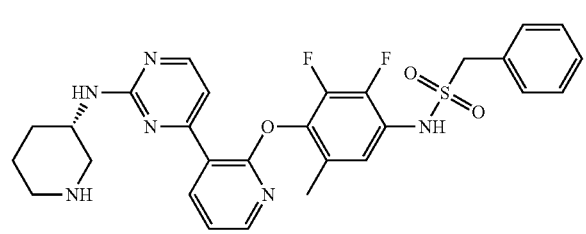

Step 1: 6-Bromo-2,3-difluoro-4-nitro-phenol

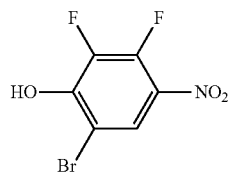 [SMILES: O=[N+]([O-])c1cc(Br)c(O)c(F)c1F]

A solution of 6-bromo-2,3-difluorophenol (2.0 g, 9.57 mmol) in DCM (8 mL) was cooled to −10° C., and then a mixture of nitric acid (0.61 mL, 9.57 mmol) and sulfuric acid (4 mL) was added dropwise. The resulting mixture was stirred at −10° C. for 1 h. The mixture was poured into ice/water, extracted with ethyl acetate, and then washed with water and brine. The organic extract was concentrated in vacuum. The residue was purified by silica flash chromatography (petroleum ether/ethyl acetate 20:1) to provide the title compound (1.8 g, 74.1% yield) as a yellow solid. LCMS (ESI): [M+H]$^+$=252.1.

Step 2:
2-Benzyloxy-1-bromo-3,4-difluoro-5-nitro-benzene

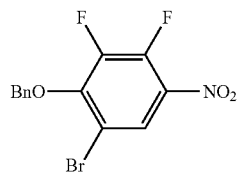 [SMILES: O=[N+]([O-])c1cc(Br)c(OCc2ccccc2)c(F)c1F]

A mixture of 6-bromo-2,3-difluoro-4-nitro-phenol (1.8 g, 7.09 mmol), benzyl bromide (1.74 mL, 14.6 mmol), potassium carbonate (2.96 g, 21.4 mmol) in DMF (20 mL) was stirred for 16 h at room temperature. The reaction was quenched with water and extracted with ethyl acetate. The combined organic extract was washed with brine, concentrated and purified by silica flash chromatography eluting with DCM/petroleum ether (0-100%) to afford the title compound (2.3 g, 94.3% yield) as a yellow solid. $^1$H NMR (300 MHz, CDCl$_3$) δ 8.16 (s, 1H), 7.55-7.30 (m, 5H), 5.36-5.10 (m, 2H).

Step 3:
2-Benzyloxy-3,4-difluoro-1-methyl-5-nitro-benzene

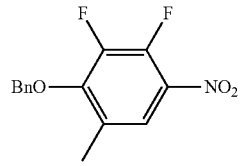 [SMILES: Cc1cc([N+](=O)[O-])c(F)c(F)c1OCc1ccccc1]

Under nitrogen, a mixture of 2-benzyloxy-1-bromo-3,4-difluoro-5-nitro-benzene (2.2 g, 6.39 mmol), trimethylboroxine (2.19 mL, 7.67 mmol), potassium fluoride (1.1 g, 19.31 mmol) and 1,1′-bis(diphenylphosphino)ferrocene-palladium(II)dichloride DCM complex (522 mg, 0.64 mmol) in toluene (40 mL) and water (8 mL) was stirred at 90° C. for 16 h. The solvent was removed under vacuum. The residue was purified by silica flash chromatography (DCM/petroleum ether 0-100%) to afford the title compound (900 mg, 50.4% yield) as a yellow solid. $^1$H NMR (300 MHz, CDCl$_3$) δ 7.70 (m, 1H), 7.46-7.43 (m, 5H), 5.33 (s, 2H), 2.33 (s, 3H).

Step 4: 4-Amino-2,3-difluoro-6-methyl-phenol

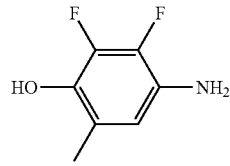

Under hydrogen, a mixture of 2-benzyloxy-3,4-difluoro-1-methyl-5-nitro-benzene (800 mg, 2.86 mmol) and 10% palladium on activated carbon (240 mg) in methyl alcohol (25 mL) was stirred for 2 h at room temperature. The reaction was quenched with acetic acid (1 mL) and the solids were filtered out. The solvent was concentrated under vacuum. The residue was purified by silica flash chromatography (DCM/petroleum ether 0-100%) to afford the title compound (250 mg, 54.8% yield) as a light yellow solid. LCMS (ESI): [M+H]$^+$=160.1.

Step 5: N-(2,3-Difluoro-5-methyl-4-((3-(2-(((3S)-3-piperidyl)amino)pyrimidin-4-yl)-2-pyridyl)oxy)phenyl)-1-phenyl-methanesulfonamide

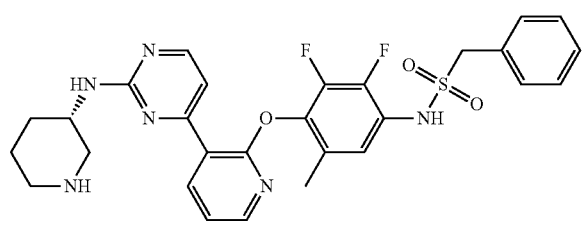 [SMILES: Cc1cc(NS(=O)(=O)Cc2ccccc2)c(F)c(F)c1Oc1ncccc1-c1ccnc(N[C@H]2CCCNC2)n1]

The title compound was prepared according to Example 27 to provide the title compound (50 mg, 36.2% yield) as a white solid.

Example 33

(S)—N-(2,3-Difluoro-6-methyl-4-((3-(2-(piperidin-3-ylamino)pyrimidin-4-yl)pyridin-2-yl)oxy)phenyl)-1-phenylmethanesulfonamide

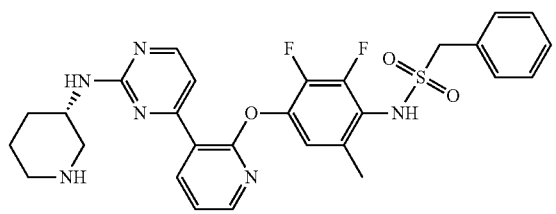 [SMILES: Cc1cc(Oc2ncccc2-c2ccnc(N[C@H]3CCCNC3)n2)c(F)c(F)c1NS(=O)(=O)Cc1ccccc1]

Step 1: (4-Amino-2,3-difluoro-phenyl) acetate

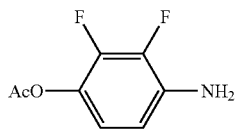

To a solution of 4-amino-2,3-difluoro-phenol (4.0 g, 27.6 mmol) in pyridine (50 mL) was added acetic anhydride (2.59 mL, 27.6 mmol) at 0° C. and the mixture was stirred for 16 h at room temperature. The mixture was concentrated and purified by silica flash chromatography (ethyl acetate/petroleum ether 0-100%) to afford the title compound (3.3 g, 64% yield) as a brown solid.

Step 2: (4-Amino-5-bromo-2,3-difluoro-phenyl) acetate

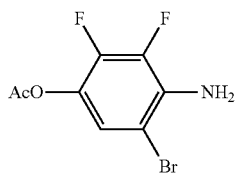

To a solution of (4-amino-2,3-difluoro-phenyl) acetate (1.67 g, 5.62 mmol) in DMF (30 mL) was added 1-bromo-2,5-pyrrolidinedione (1.1 g, 6.19 mmol) at 0° C. and the mixture was stirred for 16 h at room temperature. The mixture was concentrated and purified by silica flash chromatography (ethyl acetate/petroleum ether 0-100%) to afford the title compound (1.0 g, 66.9% yield) as a brown solid. LCMS (ESI): [M+H]$^+$=265.9.

Step 3: tert-Butyl acetyl(6-bromo-2,3-difluoro-4-hydroxyphenyl)carbamate

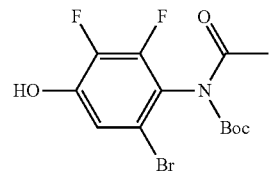 [SMILES: CC(=O)N(C(=O)OC(C)(C)C)c1c(Br)cc(O)c(F)c1F]

A mixture of (4-amino-5-bromo-2,3-difluoro-phenyl) acetate (2.0 g, 7.52 mmol), di-tert-butyldicarbonate (2.0 g, 9.16 mmol), 4-dimethylaminopyridine (100.0 mg, 0.82 mmol) in THF (20 mL) was stirred for 3 h at room temperature. The mixture was concentrated and purified by silica flash chromatography (ethyl acetate/petroleum ether 0-20%) to afford the title compound (900 mg, 32.7% yield) as a yellow solid. LCMS (ESI): (M+42)$^+$=409.1.

Step 4: tert-Butyl acetyl(2,3-difluoro-4-hydroxy-6-methylphenyl)carbamate

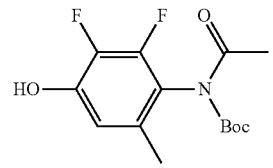 [SMILES: CC(=O)N(C(=O)OC(C)(C)C)c1c(C)cc(O)c(F)c1F]

Under nitrogen, a mixture of tert-butyl acetyl(6-bromo-2,3-difluoro-4-hydroxyphenyl)carbamate (1.0 g, 2.73 mmol), trimethylboroxine (2.5 mL, 8.73 mmol), bis(triphenylphosphine)palladium(II) chloride (193 mg, 0.28 mmol), and sodium bicarbonate (678 mg, 8.07 mmol) in 1,2-dimethoxyethane (30 mL) was stirred at 75° C. for 16 h. The reaction was diluted with ethyl acetate, washed with brine, dried over anhydrous sodium sulfate, concentrated in vacuo and purified by silica flash chromatography eluting with ethyl acetate/petroleum ether (0-40%) to afford the title compound (670 mg, 81.4% yield) as a light yellow oil. LCMS (ESI): [M+H]$^+$=302.1.

Step 5: 4-Amino-2,3-difluoro-5-methyl-phenol

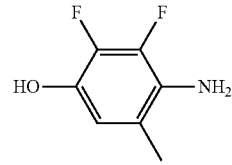

To a suspension of tert-butyl acetyl(2,3-difluoro-4-hydroxy-6-methylphenyl)carbamate (530 mg, 1.76 mmol) in methyl alcohol (10 mL) was added boron trifluoride diethyl etherate (10.0 mL, 81.03 mmol) and the mixture was stirred for 24 h at 75° C. The mixture was diluted with ethyl acetate and washed with water. The organic layer was concentrated in vacuo. The residue was purified by silica flash chromatography (methanol/DCM (0-20%) to afford the title compound (130 mg, 46.4% yield) as a purple solid. LCMS (ESI): [M+H]$^+$=160.1.

Step 6: (S)—N-(2,3-Difluoro-6-methyl-4-((3-(2-(piperidin-3-ylamino)pyrimidin-4-yl)pyridin-2-yl)oxy)phenyl)-1-phenylmethanesulfonamide

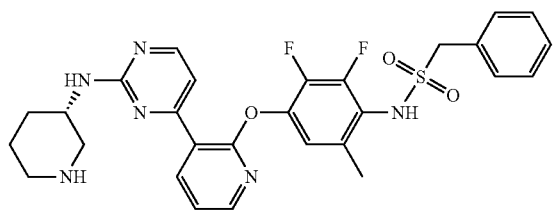

The title compound was prepared according to Example 27 to provide the title compound (23.9 mg, 18.7% yield) as a white solid.

Example 34

(S)—N-(2-Chloro-3-fluoro-4-((3-(2-(piperidin-3-ylamino)pyrimidin-4-yl)pyridin-2-yl)oxy)phenyl)-1-phenylmethanesulfonamide (Compound 161)

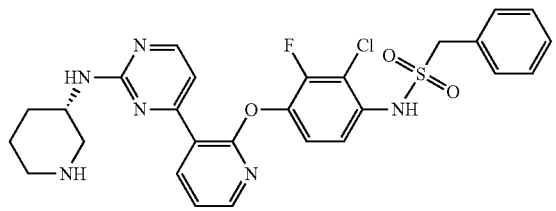 [SMILES: O=S(=O)(Cc1ccccc1)Nc1ccc(Oc2ncccc2-c2ccnc(N[C@H]3CCCNC3)n2)c(F)c1Cl]

Step 1: 4-Bromo-3-chloro-2-fluorophenol

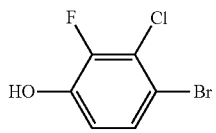

Under nitrogen, a solution of 1-bromo-2-chloro-3-fluoro-4-iodo-benzene (1.50 g, 4.47 mmol), potassium hydroxide (1.00 g, 17.89 mmol), 1,10-phenanthroline (0.32 g, 1.79 mmol), copper iodide (0.17 g, 0.89 mmol) in water (20 mL) and DMSO (20 mL) was stirred overnight at 100° C. 2 M HCl (50 mL) was then added and the solids was filtered out. The resulting solution was extracted with ethyl acetate. The organic layer was washed with brine and removed in vacuo. The residue was purified by silica flash chromatography (petroleum ether/ethyl acetate 10:1) to afford the title compound (300 mg, 29.7% yield). $^1$H NMR (300 MHz, DMSO-$d_6$) δ 10.65 (s, 1H), 7.40 (dd, J=9.0, 2.1 Hz, 1H), 6.93 (t, J=8.8 Hz, 1H).

Step 2: tert-Butyl (3S)-3-((4-(2-(4-bromo-3-chloro-2-fluoro-phenoxy)-3-pyridyl)pyrimidin-2-yl)amino)piperidine-1-carboxylate

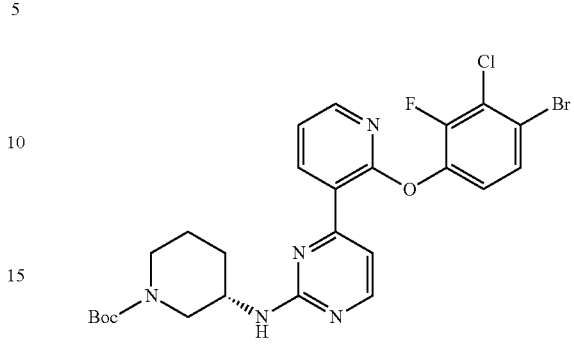

Under nitrogen, a solution of tert-butyl (3S)-3-((4-(2-fluoro-3-pyridyl)pyrimidin-2-yl)amino)piperidine-1-carboxylate (795 mg, 2.13 mmol), 4-bromo-3-chloro-2-fluoro-phenol (600 mg, 2.66 mmol), potassium carbonate (734 mg, 5.32 mmol) in 1-methyl-2-pyrrolidinone (20 mL) was stirred for 16 h at 100° C. The reaction was quenched with water and extracted with ethyl acetate. The combined organic extracts were washed with brine and the solvent was removed. The residue was purified by silica flash chromatography (petroleum ether/ethyl acetate 1:1) to afford the title compound (1.0 g, 46.1% yield). LCMS (ESI): [M+H]$^+$=580.2.

Step 3: tert-Butyl (3S)-3-((4-(2-(4-(benzhydrylideneamino)-3-chloro-2-fluoro-phenoxy)-3-pyridyl)pyrimidin-2-yl)amino)piperidine-1-carboxylate

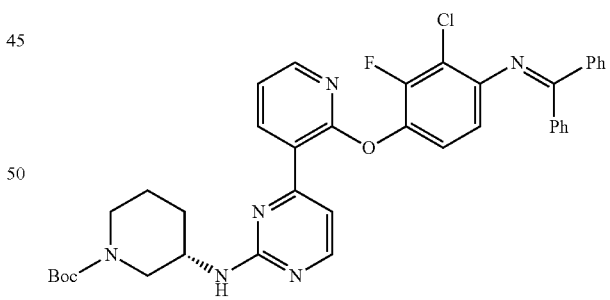

Under nitrogen, a solution of tert-butyl (3S)-3-((4-(2-(4-bromo-3-chloro-2-fluoro-phenoxy)-3-pyridyl)pyrimidin-2-yl)amino)piperidine-1-carboxylate (200 mg, 0.21 mmol), benzophenone imine (34 mg, 0.19 mmol), bis(dibenzylideneacetone)palladium(II) (19 mg, 0.02 mmol), (+/−)-2,2'-bis(diphenylphosphino)-1,1'-binaphthyl (26 mg, 0.04 mmol), sodium tert-butoxide (40 mg, 0.41 mmol) in toluene (5 mL) was stirred for 2 h at 100° C. The solvent was removed and the residue was purified by silica flash chromatography (petroleum ether/ethyl acetate (1:1) to afford the title compound (180 mg, 76.7% yield). LCMS (ESI): [M+H]$^+$=679.1.

Step 4: tert-Butyl (3S)-3-((4-(2-(4-amino-3-chloro-2-fluoro-phenoxy)-3-pyridyl)pyrimidin-2-yl)amino)piperidine-1-carboxylate To a solution of tert-butyl (3S)-3-((4-(2-(4-(benzhydrylideneamino)-3-chloro-2-fluoro-phenoxy)-3-pyridyl)pyrimidin-2-yl)amino)piperidine-1-carboxylate (200 mg, 0.29 mmol) in THF (10 mL) and water (10 mL) was added acetic acid (1 mL). The reaction mixture was stirred for 3 h at 35° C. The solvent was removed in vacuo. The residue was purified by silica flash chromatography (petroleum ether/ ethyl acetate 1:1) to afford the title compound (110 mg, 72.5% yield). LCMS (ESI): [M+H]$^+$=515.2.

Step 5: N-(2-Chloro-3-fluoro-4-((3-(2-(((3S)-3-piperidyl)amino)pyrimidin-4-yl)-2-pyridyl)oxy)phenyl)-1-phenyl-methanesulfonamide To a solution of tert-butyl (3S)-3-((4-(2-(4-amino-3-chloro-2-fluoro-phenoxy)-3-pyridyl)pyrimidin-2-yl)amino)piperidine-1-carboxylate (150 mg, 0.29 mmol) in DCM (15 mL) was added pyridine (0.23 mL) and alpha-toluenesulfonylchloride (83 mg, 0.44 mmol). The solution was stirred for 2 h at 20° C. Then the reaction was quenched with water and extracted with DCM. The solvent was removed and the crude product was dissolved in DCM (4 mL). Then 4 M HCl in 1,4-dioxane (1 mL) was added. The reaction was stirred for 2 h at room temperature. The solvent was removed and the residue was further purified by prep-HPLC to give the title compound (29.2 mg, 17.6% yield) as a light yellow solid.

Example 35

(S)—N-(2-Cyano-3-fluoro-4-((3-(2-(piperidin-3-ylamino)pyrimidin-4-yl)pyridin-2-yl)oxy)phenyl)-1-phenylmethanesulfonamide hydrochloride

Step 1: 1-(Benzyloxy)-3-bromo-2-fluoro-4-nitrobenzene

To a solution of 3-bromo-1,2-difluoro-4-nitro-benzene (5 g, 21.1 mmol), tetrabutyl-ammonium hydrogen sulfate (720 mg, 2.1 mmol) and phenylmethanol (2.5 g, 23.1 mmol) in DCM (100 mL) was added 1 M sodium hydroxide solution (20 ml) dropwise. The mixture was stirred at 25° C. for 1.5 h and subsequently diluted with water. The resulting solution was extracted with ethyl acetate and the organic layers were combined. The organic extract was dried over anhydrous sodium sulfate and concentrated under vacuum. The residue was purified by silica flash chromatography eluting (ethyl acetate/petroleum ether (1:4)) to afford the title compound (6.5 g, 90.1% yield) as a yellow solid. $^1$H NMR (300 MHz, CD$_3$OD) δ 7.86 (dd, J=9.2, 2.1 Hz, 1H), 7.51-0.28 (m, 6H), 5.29 (s, 2H).

Step 2: 3-(Benzyloxy)-2-fluoro-6-nitrobenzonitrile

Under nitrogen, a mixture of 1-benzyloxy-3-bromo-2-fluoro-4-nitro-benzene (2.0 g, 6.13 mmol), copper(I) cyanide (1.1 g, 12.27 mmol) in N,N-dimethylacetamide (40 mL) was stirred at 130° C. for 2 h. The reaction mixture was diluted with water and extracted with ethyl acetate followed by combination of organic layers. The organic extract was dried over anhydrous sodium sulfate and concentrated under vacuum. The residue was purified by silica flash chromatography (ethyl acetate/petroleum ether) to afford the title compound (1.1 g, 64.6% yield) as an off-white solid. $^1$H NMR (400 MHz, DMSO-d$_6$) δ 8.31 (dd, J=9.3, 1.6 Hz, 1H), 7.80 (dd, J=9.4, 8.5 Hz, 1H), 7.54-7.46 (m, 2H), 7.48-7.40 (m, 2H), 7.44-7.35 (m, 1H), 5.43 (s, 2H).

Step 3: 6-Amino-2-fluoro-3-hydroxybenzonitrile

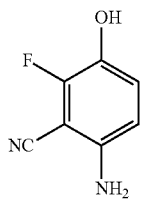

Under hydrogen, a mixture of 3-benzyloxy-2-fluoro-6-nitro-benzonitrile (1.2 g, 4.19 mmol) and 10% Pd/C (500 mg) in ethyl acetate (70 mL) was stirred at 25° C. for 2 h. The mixture was filtered, and the organic layer was concentrated under vacuum. The residue was purified by silica flash chromatography eluting (ethyl acetate/petroleum ether 7:3) to afford the title compound (500 mg, 74.6% yield) as an off-white solid. LCMS (ESI): [M+H]$^+$=153.0.

Step 4: (S)—N-(2-Cyano-3-fluoro-4-((3-(2-(piperidin-3-ylamino)pyrimidin-4-yl)pyridin-2-yl)oxy)phenyl)-1-phenylmethanesulfonamide hydrochloride

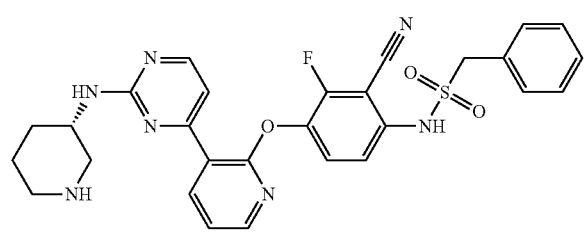 [SMILES: N#Cc1c(NS(=O)(=O)Cc2ccccc2)ccc(Oc2ncccc2-c2ccnc(N[C@H]3CCCNC3)n2)c1F]

The title compound was prepared according to Example 27 to provide the title compound (31 mg, 13.6% yield) as a white solid.

Example 36

N-(2,6-Difluoro-3-methyl-4-((3-(2-(((3S,5R)-5-methyl-3-piperidyl)amino)pyrimidin-4-yl)-2-pyridyl)oxy)phenyl)-1-phenyl-methanesulfonamide Compound 164

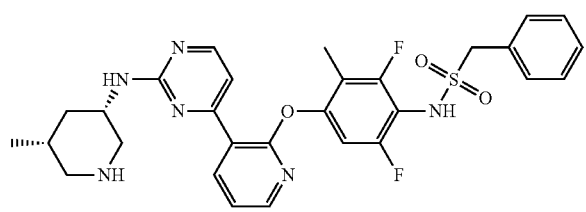 [SMILES: Cc1c(Oc2ncccc2-c2ccnc(N[C@@H]3CNC[C@H](C)C3)n2)cc(F)c(NS(=O)(=O)Cc2ccccc2)c1F]

Step 1: Benzyl (3S,5R)-3-((4-(2-fluoro-3-pyridyl)pyrimidin-2-yl)amino)-5-methyl-piperidine-1-carboxylate

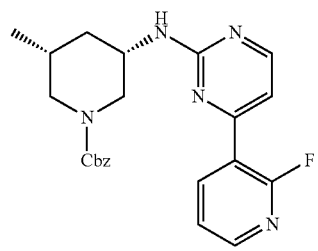 [SMILES: C[C@@H]1C[C@H](Nc2nccc(-c3cccnc3F)n2)CN(C(=O)OCc2ccccc2)C1]

A mixture of 2-chloro-4-(2-fluoro-3-pyridyl)pyrimidine (1.0 g, 4.77 mmol), benzyl (3S,5R)-3-amino-5-methyl-piperidine-1-carboxylate (1.24 g, 5.01 mmol), N,N-diisopropylethylamine (2.36 mL, 14.31 mmol) and cesium fluoride (0.867 mg, 5.72 mmol) in DMSO (25 mL) was stirred at 80° C. for 2 h. The reaction was quenched with water. The mixture was extracted with ethyl acetate, washed with water and dried over anhydrous sodium sulfate followed by concentration under vacuum. The residue was purified by silica flash chromatography (petroleum ether/ethyl acetate 1:1) to afford the title compound (662 mg, 32.9% yield) as a yellow solid. LCMS (ESI): [M+H]$^+$=422.2.

Step 2: Benzyl (3S,5R)-3-((4-(2-(4-amino-3,5-difluoro-2-methyl-phenoxy)-3-pyridyl)pyrimidin-2-yl)amino)-5-methyl-piperidine-1-carboxylate

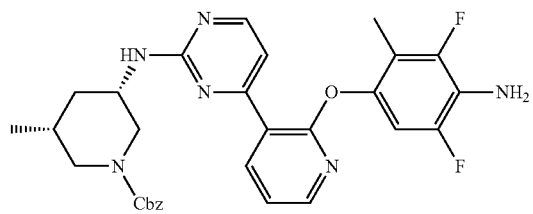 [SMILES: Cc1c(Oc2ncccc2-c2ccnc(N[C@H]3C[C@@H](C)CN(C(=O)OCc4ccccc4)C3)n2)cc(F)c(N)c1F]

A mixture of 4-amino-3,5-difluoro-2-methyl-phenol (120 mg, 0.75 mmol), benzyl (3S,5R)-3-((4-(2-fluoro-3-pyridyl)pyrimidin-2-yl)amino)-5-methyl-piperidine-1-carboxylate (220 mg, 0.52 mmol), cesium carbonate (676 mg, 2.07 mmol) in DMSO (5 mL) was stirred for 16 h at 80° C. The reaction was quenched with water and extracted with ethyl acetate. The resulting solution was washed with water, dried over anhydrous magnesium sulfate and concentrated in vacuo. The mixture was concentrated and purified by silica flash chromatography (ethyl acetate/petroleum ether 0-100%) to afford the title compound (260 mg, 88.9% yield) as a light yellow solid. LCMS (ESI): [M+H]$^+$=561.2.

303

Step 3: Benzyl (3S,5R)-3-((4-(2-(4-(benzylsulfo-nylamino)-3,5-difluoro-2-methyl-phenoxy)-3-pyridyl)pyrimidin-2-yl)amino)-5-methyl-piperidine-1-carboxylate

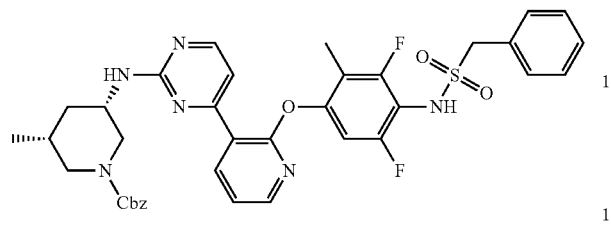

To a solution of benzyl (3S,5R)-3-((4-(2-(4-amino-3,5-difluoro-2-methyl-phenoxy)-3-pyridyl)pyrimidin-2-yl)amino)-5-methyl-piperidine-1-carboxylate (240 mg, 0.43 mmol) in pyridine (4 mL) was added alpha-toluenesulfonylchloride (163 mg, 0.86 mmol). The reaction mixture was stirred for 16 h. The mixture was concentrated and purified by silica flash chromatography (ethyl acetate/petroleum ether (0-100%) to afford the title compound (260 mg, 85% yield) as a yellow solid. LCMS (ESI): [M+H]$^+$=715.2.

Step 4: N-(2,6-Difluoro-3-methyl-4-((3-(2-(((3S,5R)-5-methyl-3-piperidyl)amino)pyrimidin-4-yl)-2-pyridyl)oxy)phenyl)-1-phenyl-methanesulfonamide

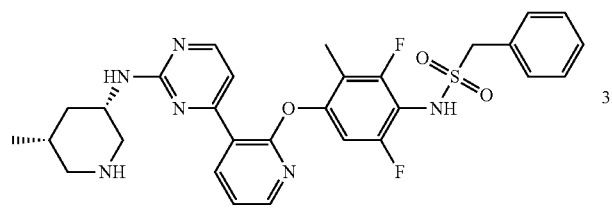

To a solution of benzyl (3S,5R)-3-((4-(2-(4-(benzylsulfonylamino)-3,5-difluoro-2-methyl-phenoxy)-3-pyridyl)pyrimidin-2-yl)amino)-5-methyl-piperidine-1-carboxylate (260 mg, 0.36 mmol) in DCM (4 mL) was added 33% HBr in acetic acid (2 mL). The mixture was stirred for 2 h at room temperature. The mixture was concentrated in vacuo, and the crude product was purified by prep-HPLC to provide the title compound (22.2 mg, 10.5% yield) as a white solid.

Example 37

(S)—N-(2,3-Difluoro-4-((3-(2-(pyrrolidin-3-ylamino)pyrimidin-4-yl)pyridin-2-yl)oxy)phenyl)-1-phenylmethanesulfonamide (Compound 167)

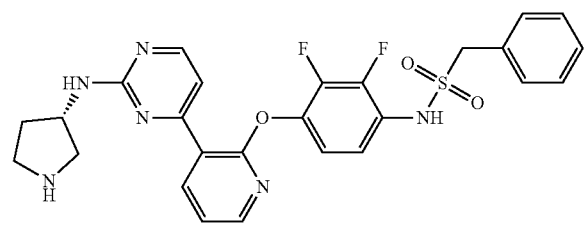 [SMILES: O=S(=O)(Cc1ccccc1)Nc1ccc(Oc2ncccc2-c2ccnc(N[C@H]3CCNC3)n2)c(F)c1F]

304

Step 1: 2,3-Difluoro-4-((3-(2-methylsulfonylpyrimidin-4-yl)-2-pyridyl)oxy)aniline

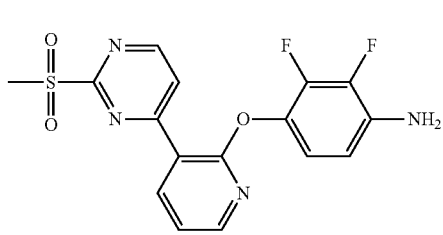 [SMILES: CS(=O)(=O)c1nccc(-c2cccnc2Oc2ccc(N)c(F)c2F)n1]

To a mixture of 2,3-difluoro-4-((3-(2-methylsulfanylpyrimidin-4-yl)-2-pyridyl)oxy)aniline (500 mg, 1.44 mmol) in DCM (20 mL) was added 3-chloroperoxybenzoicacid (548 mg, 3.18 mmol), and the mixture was stirred for 1 h at room temperature. The reaction was quenched with saturated aqueous sodium bisulfite solution and extracted with ethyl acetate. The organic layers were combined and washed with brine, dried over anhydrous sodium sulfate and concentrated in vacuo. The residue was purified by silica flash chromatography (petroleum ether/ethyl acetate 15:85). This resulted in the title compound (370 mg, 67.7% yield) as a yellow solid. LCMS (ESI): [M+H]$^+$=379.1.

Step 2: tert-Butyl (3S)-3-((4-(2-(4-amino-2,3-difluoro-phenoxy)-3-pyridyl)pyrimidin-2-yl)amino)pyrrolidine-1-carboxylate

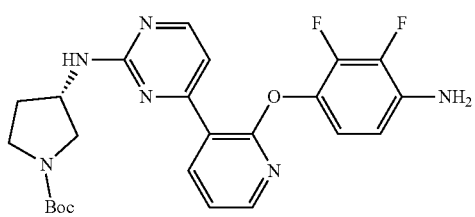 [SMILES: CC(C)(C)OC(=O)N1CC[C@H](Nc2nccc(-c3cccnc3Oc3ccc(N)c(F)c3F)n2)C1]

A mixture of 2,3-difluoro-4-((3-(2-methylsulfonylpyrimidin-4-yl)-2-pyridyl)oxy)aniline (200 mg, 0.55 mmol), tert-butyl (3S)-3-amino-1-pyrrolidinecarboxylate (205 mg, 1.1 mmol), N,N-diisopropylethylamine (0.29 mL, 1.66 mmol) and cesium fluoride (251 mg, 1.65 mmol) in DMSO (5 mL) was stirred at 80° C. for 2 h. The resulting solution was then diluted with water and extracted with ethyl acetate. The combined organic layers were washed with brine, dried over sodium sulfate and concentrated in vacuo. The residue was purified by silica flash chromatography eluting (petroleum ether/ethyl acetate 3:7) to provide the title compound (120 mg, 44.9% yield) as a yellow solid. LCMS (ESI): [M+H]$^+$=485.2.

Step 3: tert-Butyl (3S)-3-((4-(2-(4-(benzylsulfonylamino)-2,3-difluoro-phenoxy)-3-pyridyl)pyrimidin-2-yl)amino)pyrrolidine-1-carboxylate

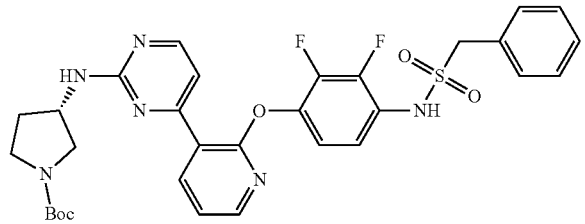 [SMILES: CC(C)(C)OC(=O)N1CC[C@H](Nc2nccc(-c3cccnc3Oc3ccc(NS(=O)(=O)Cc4ccccc4)c(F)c3F)n2)C1]

To a mixture of tert-butyl (3S)-3-((4-(2-(4-amino-2,3-difluoro-phenoxy)-3-pyridyl)pyrimidin-2-yl)amino)pyrrolidine-1-carboxylate (100 mg, 0.21 mmol) in DCM (2 mL) was added pyridine (0.5 mL, 6.21 mmol) and alpha-toluenesulfonylchloride (51 mg, 0.27 mmol), and the mixture was stirred for 2 h at room temperature. The resulting solution was concentrated under vacuum. The residue was purified by silica flash chromatography (DCM/methanol 95:5) to provide the title compound (120 mg, 91% yield) as a yellow solid. LCMS (ESI): [M+H]$^+$=639.2.

Step 4: (S)—N-(2,3-Difluoro-4-((3-(2-(pyrrolidin-3-ylamino)pyrimidin-4-yl)pyridin-2-yl)oxy)phenyl)-1-phenylmethanesulfonamide

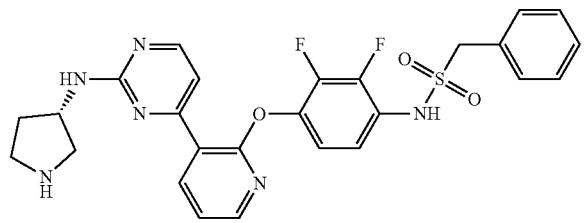 [SMILES: O=S(=O)(Cc1ccccc1)Nc1ccc(Oc2ncccc2-c2ccnc(N[C@H]3CCNC3)n2)c(F)c1F]

To a mixture of tert-butyl (3S)-3-((4-(2-(4-(benzylsulfonylamino)-2,3-difluoro-phenoxy)-3-pyridyl)pyrimidin-2-yl)amino)pyrrolidine-1-carboxylate (120 mg, 0.19 mmol) in DCM (5 mL) was added 4 M HCl in 1,4-dioxane (0.5 mL), and the mixture was stirred for 1 h at room temperature. The solvent was removed under vacuum and the crude product purified by prep-HPLC to afford the title compound (28.9 mg, 27.9% yield) as a white solid.

Example 38

N-(4-((3-(2-(((1r,4r)-4-Aminocyclohexyl)amino)pyrimidin-4-yl)pyridin-2-yl)oxy)-2,3-difluorophenyl)-1-phenylmethanesulfonamide (Compound 169)

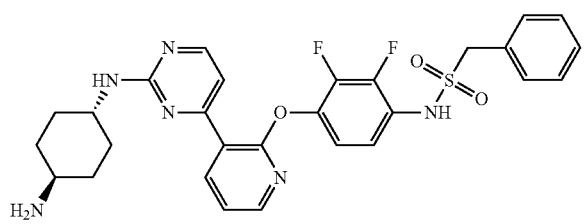 [SMILES: N[C@H]1CC[C@H](Nc2nccc(-c3cccnc3Oc3ccc(NS(=O)(=O)Cc4ccccc4)c(F)c3F)n2)CC1]

Step 1: tert-Butyl ((1r,4r)-4-((4-(2-(2,3-difluoro-4-((phenylmethyl)sulfonamido)phenoxy)pyridin-3-yl)pyrimidin-2-yl)amino)cyclohexyl)carbamate

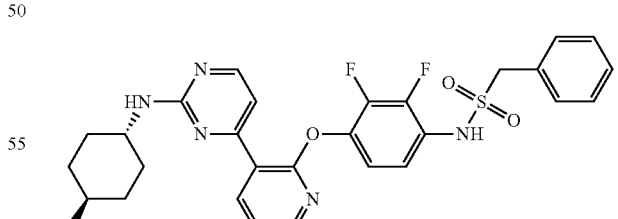

Under nitrogen, a solution of N-(2,3-difluoro-4-((3-(2-methylsulfinylpyrimidin-4-yl)-2-pyridyl)oxy)phenyl)-1-phenyl-methanesulfonamide (200 mg, 0.39 mmol), tert-butyl ((1r,4r)-4-aminocyclohexyl)carbamate (83 mg, 0.39 mmol), cesium fluoride (141 mg, 0.93 mmol), N,N-diisopropylethylamine (150 mg, 1.16 mmol) in DMSO (10 mL) was stirred for 16 h at 80° C. The reaction mixture was diluted with water and extracted with ethyl acetate three times. The combined organic extracts were dried over anhydrous sodium sulfate and concentrated under vacuum. The residue was purified by silica flash chromatography (ethyl acetate/petroleum ether (1:2)) to afford the title compound (190 mg, 73.6% yield) as a brown oil. LCMS (ESI): [M+H]$^+$= 667.3

Step 2: N-(4-((3-(2-(((1r,4r)-4-Aminocyclohexyl)amino)pyrimidin-4-yl)pyridin-2-yl)oxy)-2,3-difluorophenyl)-1-phenylmethanesulfonamide A solution of tert-butyl ((1r,4r)-4-((4-(2-(2,3-difluoro-4-((phenylmethyl)sulfonamido)phenoxy)pyridin-3-yl)pyrimidin-2-yl)amino)cyclohexyl)carbamate (170 mg, 0.25 mmol) in 4 M HCl in 1,4-dioxane (2 mL) was stirred at 15° C. for 0.5 h. The solvent was removed under vacuum and the residue purified by prep-HPLC to give the title compound (62.8 mg, 41.5% yield) as a white solid.

Example 39

(S)—N-(6-Fluoro-2,3-dimethyl-4-((3-(2-(piperidin-3-ylamino)pyrimidin-4-yl)pyridin-2-yl)oxy)phenyl)-1-phenylmethanesulfonamide

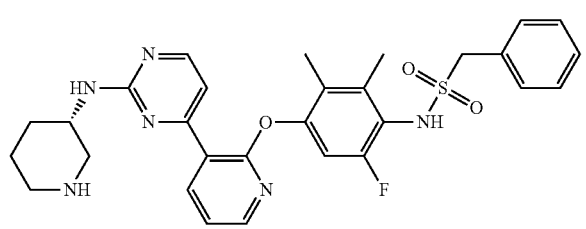

Step 1: 2,4-Dibromo-6-fluoro-3-methyl-aniline

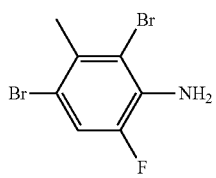

To a mixture of 2-fluoro-5-methylaniline (5.9 g, 47.2 mmol) in acetonitrile (200 mL) was added 1-bromo-2,5-pyrrolidinedione (1.68 g, 94.3 mmol) at 0° C. The mixture was stirred for 0.5 h at room temperature. The solvent was then concentrated under vacuum and purified by silica flash chromatography (petroleum ether/ethyl acetate 9:1) to provide the title compound (1.5 g, 93.7% yield) as a brown solid. LCMS (ESI): [M+H]$^+$=283.9.

Step 2: 2-Bromo-6-fluoro-3-methyl-4-(4,4,5,5-tetramethyl-1,3,2-dioxaborolan-2-yl)aniline

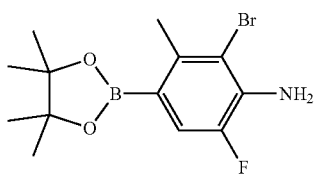 [SMILES: Cc1c(B2OC(C)(C)C(C)(C)O2)cc(F)c(N)c1Br]

A mixture of 2,4-dibromo-6-fluoro-3-methyl-aniline (5 g, 17.7 mmol), bis(pinacolato)diboron (3.59 g, 14.1 mmol), (1,1'-bis(diphenylphosphino)ferrocene)dichloropalladium (II) (1.3 g, 1.77 mmol) and potassium acetate (5.2 g, 53.0 mmol) in 1,4-dioxane (80 mL) was stirred at 90° C. overnight. The resulting solution was diluted with water and extracted with ethyl acetate. The organic extract was dried over anhydrous magnesium sulfate and solvent was removed in vacuo. The residue was purified by silica flash chromatography (petroleum ether/ethyl acetate 93:7) to provide the title compound (2.9 g, 49.7% yield) as a brown oil. LCMS (ESI): [M+H]$^+$=330.1.

Step 2: tert-Butyl N-(2-bromo-6-fluoro-3-methyl-4-(4,4,5,5-tetramethyl-1,3,2-dioxaborolan-2-yl)phenyl)-N-tert-butoxycarbonyl-carbamate

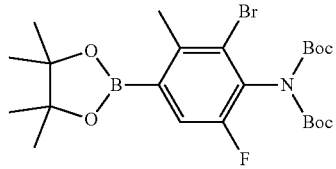 [SMILES: Cc1c(B2OC(C)(C)C(C)(C)O2)cc(F)c(N(C(=O)OC(C)(C)C)C(=O)OC(C)(C)C)c1Br]

A mixture of 2-bromo-6-fluoro-3-methyl-4-(4,4,5,5-tetramethyl-1,3,2-dioxaborolan-2-yl)aniline (1.4 g, 4.24 mmol) and di-tert-butyldicarbonate (2.31 g, 10.61 mmol) in THF (50 mL) was stirred at 70° C. for 2 h. The organic layer was concentrated under vacuum. The residue was purified by silica flash chromatography (petroleum ether/ethyl acetate 92:8) to provide the title compound (1.2 g, 53.3% yield) as a white solid. $^1$H NMR (400 MHz, CDCl$_3$) δ 7.48 (d, 7=9.4 Hz, 1H), 2.64 (s, 3H), 1.49 (s, 6H), 1.41 (s, 18H).

Step 4: tert-Butyl N-(2-bromo-6-fluoro-4-hydroxy-3-methyl-phenyl)-N-tert-butoxycarbonyl-carbamate

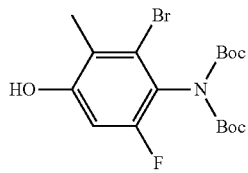

To a mixture of tert-butyl N-(2-bromo-6-fluoro-3-methyl-4-(4,4,5,5-tetramethyl-1,3,2-dioxaborolan-2-yl)phenyl)-N-tert-butoxycarbonyl-carbamate (1.9 g, 3.58 mmol) in THF (30 mL) was added 1 M sodium hydroxide solution (10.75 mL, 10.75 mmol) and 30% hydrogen peroxide (1.2 g, 10.75 mmol). The mixture was stirred for 1 h at room temperature and pH was then adjusted to pH=7 through addition of acetic acid. The resulting solution was extracted with ethyl acetate and the combined organic layers were concentrated in vacuo. The residue was purified by silica flash chromatography (petroleum ether/ethyl acetate 82:18) to provide the title compound (980 mg, 65.1% yield) as a yellow solid. LCMS (ESI): (M–H)$^-$=418.1.

Step 5: tert-Butyl N-(4-benzyloxy-2-bromo-6-fluoro-3-methyl-phenyl)-N-tert-butoxycarbonyl-carbamate

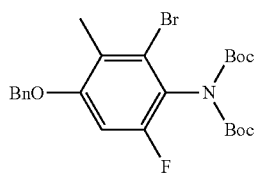

To a mixture of tert-butyl N-(2-bromo-6-fluoro-4-hydroxy-3-methyl-phenyl)-N-tert-butoxycarbonyl-carbamate (980 mg, 2.33 mmol) in DMF (20 mL) were added potassium carbonate (967 mg, 7 mmol) and benzyl bromide (479 mg, 2.8 mmol). The mixture was stirred for 2 h at room temperature, diluted with water and extracted with ethyl acetate. The organic extract was washed with brine and concentrated in vacuo. The residue was purified by silica flash chromatography (petroleum ether/ethyl acetate 92:8) to provide the title compound (1.1 g, 92.4% yield) as a yellow solid. $^1$H NMR (300 MHz, CDCl$_3$) δ 7.53-7.32 (m, 5H), 6.71 (d, J=11.0 Hz, 1H), 5.07 (s, 2H), 2.37 (s, 3H), 1.49 (s, 18H).

Step 6: tert-Butyl-N-(4-benzyloxy-6-fluoro-2,3-dimethyl-phenyl)-N-tert-butoxycarbonyl-carbamate

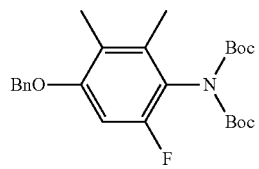 [SMILES: Cc1c(OCc2ccccc2)cc(F)c(N(C(=O)OC(C)(C)C)C(=O)OC(C)(C)C)c1C]

A mixture of tert-butyl-N-(4-benzyloxy-2-bromo-6-fluoro-3-methyl-phenyl)-N-tert-butoxycarbonyl-carbamate (900 mg, 1.76 mmol), methylboronic acid (317 mg, 5.29 mmol), 1,1'-bis(diphenylphosphino)ferrocene-palladium(II) dichloride DCM complex (145 mg, 0.18 mmol) and potassium fluoride (307 mg, 5.29 mmol) in toluene (20 mL) and water (4 mL) was stirred at 90° C. for 2 h under nitrogen. The resulting solution was diluted with water, extracted with ethyl acetate. The organic extract was concentrated in vacuum. The residue was purified by silica flash chromatography eluting with petroleum ether/ethyl acetate (92:8). This resulted in the title compound (700 mg, 89.1% yield) as a white solid. $^1$H NMR (300 MHz, CDCl$_3$) δ 7.52-7.30 (m, 5H), 6.61 (d, J=11.3 Hz, 1H), 5.05 (s, 2H), 2.20 (s, 3H), 2.15 (s, 3H), 1.46 (s, 18H).

Step 7: tert-Butyl N-tert-butoxycarbonyl-N-(6-fluoro-4-hydroxy-2,3-dimethyl-phenyl)carbamate

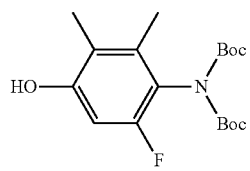

To a mixture of tert-butyl N-(4-benzyloxy-6-fluoro-2,3-dimethyl-phenyl)-N-tert-butoxycarbonyl-carbamate (700 mg, 1.57 mmol) in methyl alcohol (20 mL) was added 10% Pd/C (300 mg), and the mixture was stirred for 2 h at room temperature under hydrogen. The solids were filtered off, and the filtrate was concentrated under reduced pressure. The residue was purified by silica flash chromatography (petroleum ether/ethyl acetate 84:16) to provide the title compound (500 mg, 89.5% yield) as a white solid. LCMS (ESI): [M−H]$^-$=354.1

Step 8: 4-Amino-5-fluoro-2,3-dimethyl-phenol hydrochloride

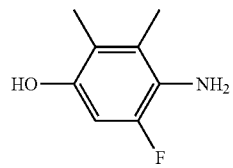

To a mixture of tert-butyl N-tert-butoxycarbonyl-N-(6-fluoro-4-hydroxy-2,3-dimethyl-phenyl)carbamate (580 mg, 1.63 mmol) in DCM (4 mL) was added 4 M HCl in 1,4-dioxane (2 mL). The mixture was stirred for 1 h at room temperature and concentrated in vacuo. The residue was purified by silica flash chromatography (DCM/methanol 4:1) to provide the title compound (200 mg, 64% yield) as a brown solid. LCMS (ESI): [M+H]$^+$=156.1.

Step 9: (S)—N-(6-Fluoro-2,3-dimethyl-4-((3-(2-(piperidin-3-ylamino)pyrimidin-4-yl)pyridin-2-yl)oxy)phenyl)-1-phenylmethanesulfonamide

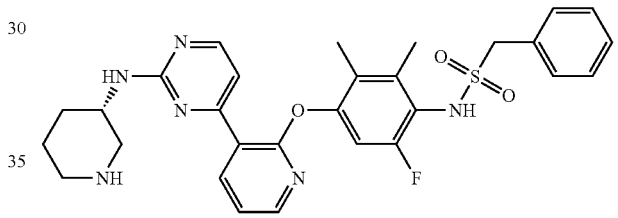

The title compound was prepared according to Example 27 to provide the title compound (27.3 mg, 15.6% yield) as a white solid.

Example 40

1-Phenyl-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 176

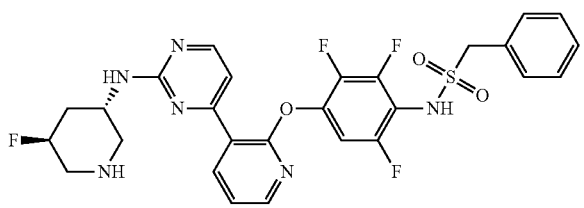

Step 1: Benzyl (3S,5S)-3-fluoro-5-((4-(2-fluoro-3-pyridyl)pyrimidin-2-yl)amino)piperidine-1-carboxylate

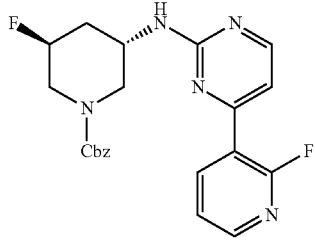 [SMILES: O=C(OCc1ccccc1)N1C[C@@H](F)C[C@H](Nc2nccc(-c3cccnc3F)n2)C1]

Under nitrogen, a solution of 2-chloro-4-(2-fluoro-3-pyridyl)pyrimidine (500 mg, 2.39 mmol), benzyl (3S,5S)-3-amino-5-fluoro-piperidine-1-carboxylate (481 mg, 1.91 mmol), cesium fluoride (1088 mg, 7.16 mmol), N,N-diisopropylethylamine (1.38 mL, 8.35 mmol) in DMSO (10 ml) was stirred at 80° C. for 3 h. The mixture was diluted with brine and extracted with ethyl acetate followed by concentration of the extracts under vacuum. The residue was purified by silica flash chromatography (petroleum ether/ethyl acetate 1:1) to afford the title compound (526 mg, 51.8% yield) as a yellow solid. LCMS (ESI): [M+H]$^+$= 426.1.

Step 2: Benzyl (3S,5S)-3-((4-(2-(4-amino-2,3,5-trifluoro-phenoxy)-3-pyridyl)pyrimidin-2-yl)amino)-5-fluoro-piperidine-1-carboxylate

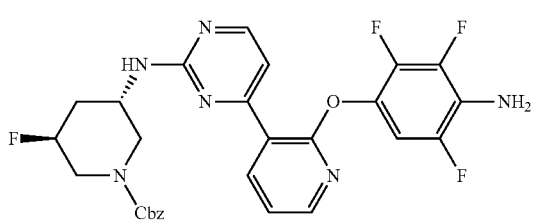

Under nitrogen, a solution of benzyl (3S,5S)-3-fluoro-5-((4-(2-fluoro-3-pyridyl)pyrimidin-2-yl)amino)piperidine-1-carboxylate (150 mg, 0.35 mmol), 4-amino-2,3,5-trifluoro-phenol (86.3 mg, 0.53 mmol), cesium carbonate (574 mg, 1.76 mmol) in DMSO (10 mL) was stirred for 2 h at 100° C. The reaction was quenched with brine and extracted with ethyl acetate. The organic extract was concentrated in vacuo. The residue was purified by silica flash chromatography (petroleum ether/ethyl acetate 1:1) to afford the title compound (190 mg, 62.6% yield). LCMS (ESI): (M+Na)$^+$= 591.2.

Step 3: 1-Phenyl-N-(2,3,6-trifluoro-4-((3-(2-(((3S,5S)-5-fluoro-3-piperidyl)amino)pyrimidin-4-yl)-2-pyridyl)oxy)phenyl)methanesulfonamide

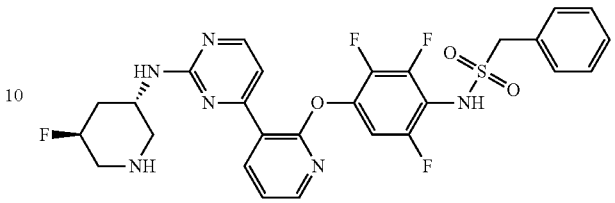

Under nitrogen, a solution of benzyl (3S,5S)-3-((4-(2-(4-amino-2,3,5-trifluoro-phenoxy)-3-pyridyl)pyrimidin-2-yl)amino)-5-fluoro-piperidine-1-carboxylate (289 mg, 0.33 mmol), alpha-toluenesulfonylchloride (89 mg, 0.47 mmol), pyridine (0.54 mL, 6.68 mmol) in DCM (2 mL) was stirred for 2 h at room temperature. The reaction was quenched with water and extracted with ethyl acetate followed by removal of the solvent under vacuum. The residue was purified by silica flash chromatography eluting with petroleum ether/ethyl acetate (1/1) to afford the title compound (180 mg, 74.5% yield) as a yellow solid.

A solution of benzyl (3S,5S)-3-((4-(2-(4-(benzylsulfonylamino)-2,3,5-trifluoro-phenoxy)-3-pyridyl)pyrimidin-2-yl)amino)-5-fluoro-piperidine-1-carboxylate (150 mg, 0.21 mmol) in DCM (4 mL) and 33% HBr in acetic acid (1 mL) was stirred for 2 h at 25° C. The solvent was removed under vacuum. The residue was purified by prep-HPLC to provide the title compound (43.0 mg, 35.2% yield) as a white solid.

Example 41

N-(4-((3-(2-(3-Azabicyclo[3.1.0]hexan-5-ylamino)pyrimidin-4-yl)-2-pyridyl)oxy)-2,3-difluoro-phenyl)-1-phenyl-methanesulfonamide & N-(4-((3-(2-(3-azabicyclo[3.1.0]hexan-5-ylamino)pyrimidin-4-yl)-2-pyridyl)oxy)-2,3-difluoro-phenyl)-1-phenyl-methanesulfonamide (Compound 185 & Compound 186)

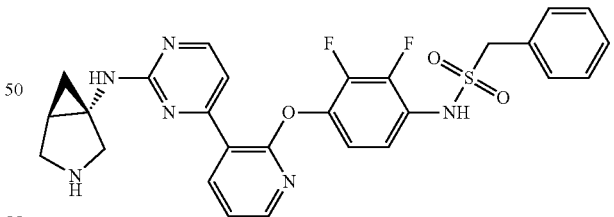

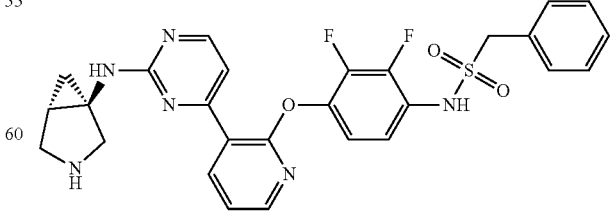

The title compound was prepared according to Example 38. The residue was subjected to chiral HPLC to provide two single stereoisomers.

Isomer 1 (Compound 185): N-(4-((3-(2-(3-Azabicyclo[3.1.0]hexan-5-ylamino)pyrimidin-4-yl)-2-pyridyl)oxy)-2,3-difluoro-phenyl)-1-phenyl-methanesulfonamide (14.4 mg, 9.4% yield), obtained as a white solid, (rt=7.396 min, Chiralpak Cellulose-SB, 0.46×15 cm; 5 μm, Hex (0.1% IPA):EtOH=70:30, 1.0 mL/min).

Isomer 2 (Compound 186): N-(4-((3-(2-(3-Azabicyclo[3.1.0]hexan-5-ylamino)pyrimidin-4-yl)-2-pyridyl)oxy)-2,3-difluoro-phenyl)-1-phenyl-methanesulfonamide (9.1 mg, 6% yield), obtained as a white solid, (rt=8.935 min, Chiralpak Cellulose-SB, 0.46×15 cm; 5 μm, Hex (0.1% IPA):EtOH=70:30, 1.0 mL/min).

Example 42

1-Phenyl-N-(2,3,6-trifluoro-4-((3-(2-(((3S,5S)-5-fluoro-5-methyl-3-piperidyl)amino)pyrimidin-4-yl)-2-pyridyl)oxy)phenyl)methanesulfonamide Compound 190

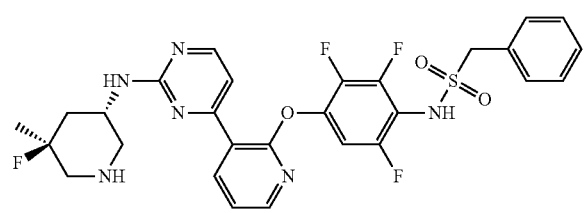 [SMILES: C[C@@]1(F)CNC[C@@H](Nc2nccc(-c3cccnc3Oc3cc(F)c(NS(=O)(=O)Cc4ccccc4)c(F)c3F)n2)C1]

Step 1: 1-(tert-Butyl) 2-methyl (2S,4R)-4-((tert-butyldiphenylsilyl)oxy)pyrrolidine-1,2-dicarboxylate

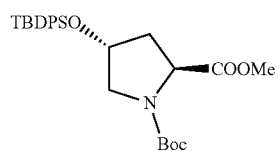

To a solution of 1-(tert-butyl)-2-methyl (2S,4R)-4-hydroxypyrrolidine-1,2-dicarboxylate (20.0 g, 81.54 mmol) and imidazole (16.7 g, 244.6 mmol) in DMF (100 mL) was added tert-butyldiphenylchlorosilane (31.81 mL, 122.3 mmol) dropwise at 0° C. The resulting solution was allowed to react for 16 h at room temperature. The reaction was quenched with water and then extracted with ethyl acetate. The combined organic extracts were washed with brine, dried over anhydrous sodium sulfate and concentrated under vacuum. The residue was purified by silica flash chromatography (petroleum ether/ethyl acetate 10:1) to afford the title compound (39 g, 98.9% yield) as a white solid. LCMS (ESI): [M+H]⁺=484.1.

Step 2: 1-(tert-butyl) 2-methyl (2R,4R)-4-((tert-butyldiphenylsilyl)oxy)-2-methylpyrrolidine-1,2-dicarboxylate and 1-(tert-butyl) 2-methyl (2S,4R)-4-((tert-butyldiphenylsilyl)oxy)-2-methylpyrrolidine-1,2-dicarboxylate

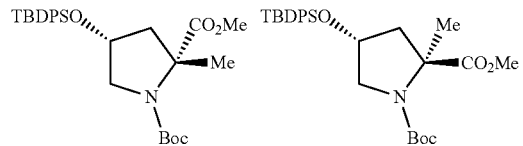

Under nitrogen, to a solution of 1,3-dimethyl-3,4,5,6-tetrahydro-2(1H)-pyrimidinone (35.0 mL, 289.5 mmol) in THF (200 mL) was added lithium diisopropylamide (41.4 mL, 82.7 mmol, 2 M THF solution) dropwise at –20° C., and the solution was stirred for min at the same temperature. A solution of 1-(tert-butyl) 2-methyl (2S,4R)-4-((tert-butyldiphenylsilyl)oxy)pyrrolidine-1,2-dicarboxylate (20.0 g, 41.4 mmol) in THF (100 mL) was added to the above solution dropwise at –20° C. The resulting solution was stirred for 1 h at 0° C. The solution was cooled to –78° C., and iodomethane (19.3 mL, 310.1 mmol) was added dropwise. The reaction mixture was allowed to stir for 4 h at room temperature. The reaction was then quenched with saturated aqueous ammonium chloride solution. The resulting solution was extracted with ethyl acetate, and the organic layer was washed with brine. The organic layer was dried over anhydrous sodium sulfate and concentrated under vacuum. The residue was purified by silica flash chromatography eluting with petroleum ether/ethyl acetate (5/1) and the two diastereoisomers were separated. 1-(tert-butyl) 2-methyl (2R,4R)-4-((tert-butyldiphenylsilyl)oxy)-2-methylpyrrolidine-1,2-dicarboxylate (5.5 g, 27% yield) as a yellow oil. LCMS (ESI): [M+H]⁺=498.2; ¹H NMR (300 MHz, CDCl₃) δ 7.68-7.60 (m, 4H), 7.44-7.39 (m, 6H), 4.35-4.27 (m, 1H), 3.73 (d, J=4.2 Hz, 3H), 3.68-3.59 (m, 1H), 3.51-3.42 (m, 1H), 2.34-2.25 (m, 1H), 1.99-1.83 (m, 1H), 1.43-1.34 (m, 12H), 1.06 (d, J=7.7 Hz, 9H). The other isomer (1-(tert-butyl) 2-methyl (2S,4R)-4-((tert-butyldiphenylsilyl)oxy)-2-methylpyrrolidine-1,2-dicarboxylate) was obtained as a yellow oil (12.5 g, 61% yield). LCMS (ESI): [M+H]⁺=498.2; ¹H NMR (300 MHz, CDCl₃) δ 7.67-7.58 (m, 4H), 7.46-7.32 (m, 6H), 4.41-4.28 (m, 1H), 3.67-3.34 (m, 5H), 2.21-2.08 (m, 1H), 2.04 (s, 2H), 1.99-1.86 (m, 1H), 1.41 (d, J=4.7 Hz, 8H), 1.06 (s, 9H).

Step 3: Methyl (2R,4R)-4-((tert-butyldiphenylsilyl)oxy)-2-methylpyrrolidine-2-carboxylate

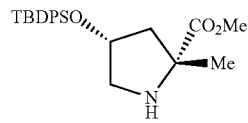

To a solution of 1-(tert-butyl) 2-methyl (2R,4R)-4-((tert-butyldiphenylsilyl)oxy)-2-methylpyrrolidine-1,2-dicarboxylate (15.0 g, 30.1 mmol) in DCM (100 mL) was added TFA (10 mL). The mixture was stirred for 16 h at room temperature, and the solvent was then removed under vacuum. The crude product was used in the next step without further purification. LCMS (ESI): [M+H]+=398.2.

Step 4: Methyl (2R,4R)-1-benzyl-4-((tert-butyldiphenylsilyl)oxy)-2-methylpyrrolidine-2-carboxylate

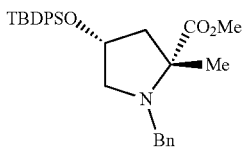

To a solution of methyl (2R,4R)-4-((tert-butyldiphenylsilyl)oxy)-2-methylpyrrolidine-2-carboxylate (11.98 g, 30.14 mmol) in acetonitrile (40 mL) was added potassium carbonate (12.86 g, 93.03 mmol) at room temperature. Benzyl bromide (4.32 mL, 36.33 mmol) was then added dropwise, and the mixture was stirred for 16 h at room temperature. The solids were filtered off and the filtrate was concentrated in vacuo and purified by silica flash chromatography (ethyl acetate/petroleum ether 0-20%) to afford the title compound (13.4 g, 91.2% yield) as a light yellow oil. LCMS (ESI): [M+H]+=488.1.

Step 5: Methyl (2R,4R)-1-benzyl-4-hydroxy-2-methylpyrrolidine-2-carboxylate

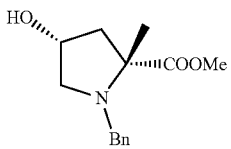 [SMILES: COC(=O)[C@@]1(C)C[C@@H](O)CN1Cc1ccccc1]

To a solution of methyl (2R,4R)-1-benzyl-4-((tert-butyldiphenylsilyl)oxy)-2-methylpyrrolidine-2-carboxylate (13.4 g, 27.5 mmol) in THF (30 mL) was added 1 M tetrabutylammonium fluoride in THF (31.4 mL, 31.4 mmol) at room temperature. The reaction mixture was stirred for 4 h at room temperature. The reaction mixture was quenched with brine and extracted with ethyl acetate. The combined organic layers were washed with brine, dried over anhydrous magnesium sulfate and concentrated in vacuo. The residue was purified by silica flash chromatography (petroleum ether/ethyl acetate 1:1) to afford the title compound (6.6 g, 92.9% yield) as a yellow oil. LCMS (ESI): [M+1]+=250.2.

Step 6: Methyl (2R,4R)-1-benzyl-2-methyl-4-((methylsulfonyl)oxy)pyrrolidine-2-carboxylate

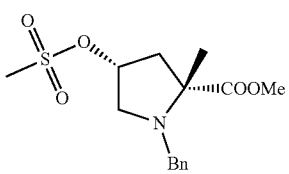 [SMILES: COC(=O)[C@@]1(C)C[C@@H](OS(C)(=O)=O)CN1Cc1ccccc1]

To a solution of methyl (2R,4R)-1-benzyl-4-hydroxy-2-methyl-pyrrolidine-2-carboxylate (12.0 g, 48.1 mmol) in DCM (50 mL) was successively added triethylamine (20.0 mL, 144 mmol) and methanesulfonyl chloride (4.22 mL, 54.5 mmol) at 0° C. The mixture was stirred for 1 h at room temperature and then quenched with water followed by extraction with DCM. The combined organic layers were washed with brine, dried over anhydrous sodium sulfate and concentrated in vacuo. The residue was purified by silica flash chromatography (ethyl acetate/petroleum ether 0-40%) to afford the title compound (14.2 g, 90.1% yield) as a yellow oil. LCMS (ESI): [M+H]+=328.2.

Step 7: Methyl (2R,4S)-4-azido-1-benzyl-2-methylpyrrolidine-2-carboxylate

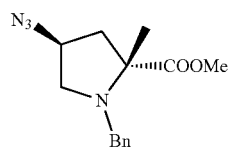 [SMILES: COC(=O)[C@@]1(C)C[C@H](N=[N+]=[N-])CN1Cc1ccccc1]

To a solution of methyl (2R,4R)-1-benzyl-2-methyl-4-((methylsulfonyl)oxy)pyrrolidine-2-carboxylate (14.2 g, 43.4 mmol) in DMF (50 mL) was added sodium azide (3.7 g, 56.9 mmol) at room temperature followed by stirring at 70° C. for 4 h. The reaction was quenched with water and extracted with ethyl acetate. The combined organic layers were washed with brine, dried over anhydrous sodium sulfate and concentrated in vacuo. The residue was purified by silica flash chromatography (ethyl acetate/petroleum ether 0-20%) to afford the title compound (10.3 g, 86.6% yield) as a yellow oil. LCMS (ESI): [M+H]+=275.1.

Step 8: ((2R,4S)-4-Amino-1-benzyl-2-methylpyrrolidin-2-yl)methanol

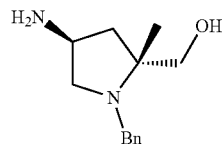 [SMILES: C[C@]1(CO)C[C@H](N)CN1Cc1ccccc1]

To a solution of methyl (2R,4S)-4-azido-1-benzyl-2-methyl-pyrrolidine-2-carboxylate (10.3 g, 37.6 mmol) in THF (100 mL) was added lithium aluminium hydride (3.0 g, 79.0 mmol) at 0° C. The reaction mixture was stirred for 4 h at room temperature and was then quenched with water (3 mL), 15% sodium hydroxide solution (3 mL) and water (9 mL). The solids were filtered. The filtrate was concentrated in vacuo to afford the title compound as a yellow oil that was used in the next step without further purification. LCMS (ESI): [M+H]+=221.0.

Step 9: tert-Butyl ((3S,5R)-1-benzyl-5-(hydroxymethyl)-5-methylpyrrolidin-3-yl)carbamate

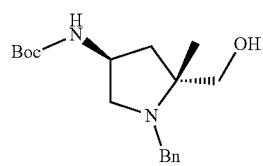

A solution of di-tert-butyldicarbonate (9.83 g, 45.1 mmol) and ((2 ft,4S)-4-amino-1-benzyl-2-methylpyrrolidin-2-yl)methanol (8.27 g, 37.6 mmol) in THF (40 mL) was stirred for 4 h at 25° C. The solvent was removed in vacuo and the residue purified by silica flash chromatography eluting with ethyl acetate/petroleum ether (0-30%) to afford the title compound (11.8 g, 98.1% yield) as a yellow oil. LCMS (ESI): [M+H]⁺=321.0.

Step 10: tert-Butyl ((3S,5S)-1-benzyl-5-fluoro-5-methylpiperidin-3-yl)carbamate

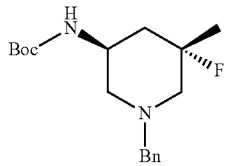

To a solution of tert-butyl ((3S',5R)-1-benzyl-5-(hydroxymethyl)-5-methylpyrrolidin-3-yl)carbamate (6.0 g, 18.7 mmol) in DCM (50 mL) was added diethylaminosulfur trifluoride (3.7 mL, 28.1 mmol) at 0° C. The mixture was stirred for 4 h at room temperature. The reaction was quenched with saturated aqueous sodium carbonate solution and extracted with DCM. The solvent was removed under vacuum, and the residue was purified by silica flash chromatography (ethyl acetate/petroleum ether 0-20%) to afford the title compound (5.8 g, 96.1% yield) as a yellow oil. LCMS (ESI): [M+H]⁺=323.2.

Step 11: tert-Butyl N-((3S,5S)-5-fluoro-5-methyl-3-piperidyl)carbamate

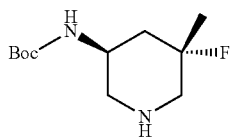 [SMILES: CC(C)(C)OC(=O)N[C@@H]1CNC[C@@](C)(F)C1]

A mixture of tert-butyl N-((3S,5S)-1-benzyl-5-fluoro-5-methyl-3-piperidyl)carbamate (5.7 g, 17.7 mmol) and 10% Pd/C (2.0 g, 1.9 mmol) in methyl alcohol (40 mL) under hydrogen atmosphere was stirred for 2 h at 25° C. The mixture was filtered, and the filtrate was concentrated in vacuo to afford the crude product which was used in the next step without further purification. LCMS (ESI): [M+H]⁺=233.3.

Step 12: Benzyl (3S,5S)-5-(tert-butoxycarbonylamino)-3-fluoro-3-methyl-piperidine-1-carboxylate

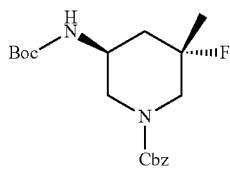 [SMILES: CC(C)(C)OC(=O)N[C@@H]1CN(C(=O)OCc2ccccc2)C[C@@](C)(F)C1]

To a solution of tert-butyl N-((3S,5S)-5-fluoro-5-methyl-3-piperidyl)carbamate (4.4 g, 17.7 mmol) and N,N-diisopropylethylamine (8.76 mL, 53.0 mmol) in DCM (35 mL) was added benzyl chloroformate (2.74 mL, 19.4 mmol) at 0° C. The reaction mixture was stirred for 2 h at 25° C. The reaction mixture was concentrated in vacuo, and the residue was purified by silica flash chromatography (ethyl acetate/petroleum ether 0-20%) to afford the title compound (5.1 g, 78.7% yield) as a light yellow solid. LCMS (ESI): [M+H]⁺= 367.2; ¹H NMR (400 MHz, CDCl₃) δ 7.43-7.30 (m, 5H), 5.29-5.07 (m, 2H), 4.52-4.14 (m, 2H), 3.83 (s, 1H), 2.94-2.12 (m, 3H), 1.67-1.38 (m, 12H).

Step 13: Benzyl (3S,5S)-5-amino-3-fluoro-3-methyl-piperidine-1-carboxylate

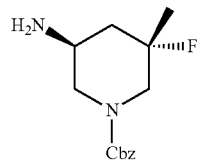

To a solution of benzyl (3S,5S)-5-tert-butoxycarbonylamino)-3-fluoro-3-methyl-piperidine-1-carboxylate (200 mg, 0.55 mmol) in DCM (6 mL) was added a solution of 4 M HCl in 1,4-dioxane (1.5 mL, 6 mmol). The reaction mixture was stirred for 1 h at 25° C. The solvent was removed under vacuum to afford the title compound which was used in the next step without purification. LCMS (ESI): [M+H]⁺=267.0.

Step 14: Benzyl (3S,5S)-3-fluoro-5-((4-(2-fluoro-3-pyridyl)pyrimidin-2-yl)amino)-3-methy 1-piperidine-1-carboxylate

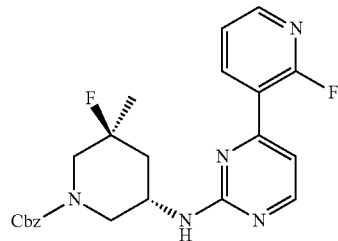 [SMILES: C[C@]1(F)C[C@H](Nc2nccc(-c3cccnc3F)n2)CN(C(=O)OCc2ccccc2)C1]

Under nitrogen, to a solution of ((3S,5S)-1-benzyloxycarbonyl-5-fluoro-5-methyl-3-piperidyl)ammonium chloride (0.58 g, 2.17 mmol), 2-chloro-4-(2-fluoro-3-pyridyl)pyrimidine (0.77 g, 3.68 mmol) and cesium fluoride (0.99 g, 6.5 mmol) in DMSO (7 mL) was added N,N-diisopropylethylamine (0.84 g, 6.5 mmol) at 20° C. The resulting solution was stirred for 7.5 h at 80° C. The reaction mixture was quenched with water and extracted with ethyl acetate. The organic extract was washed with brine, dried over anhydrous sodium sulfate, and concentrated under vacuum. The residue was purified by silica flash chromatography (ethyl acetate/petroleum ether 1:1) to afford the title compound (400 mg, 42% yield) as a yellow solid. LCMS (ESI): [M+H]⁺=440.5.

Step 15: Benzyl (3S,5S)-5-((4-(2-(4-amino-2,3,5-trifluoro-phenoxy)-3-pyridyl)pyrimidin-2-yl)amino)-3-fluoro-3-methyl-piperidine-1-carboxylate

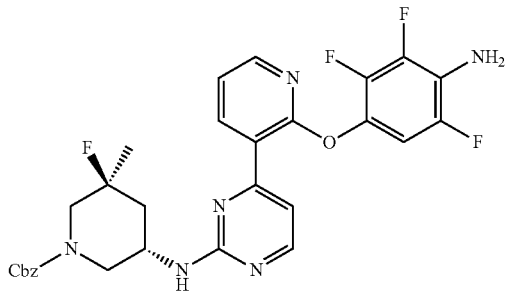 [SMILES: C[C@]1(F)C[C@H](Nc2nccc(-c3cccnc3Oc3cc(F)c(N)c(F)c3F)n2)CN(C(=O)OCc2ccccc2)C1]

Under nitrogen, a mixture of benzyl (3S,5S)-3-fluoro-5-((4-(2-fluoro-3-pyridyl)pyrimidin-2-yl)amino)-3-methyl-piperidine-1-carboxylate (0.38 g, 0.86 mmol), 4-amino-2,3,5-trifluoro-phenol (0.16 g, 0.95 mmol) and cesium carbonate (0.56 g, 1.73 mmol) in DMSO (4 mL) was stirred for 2 h at 100° C. The reaction mixture was diluted with water and extracted with ethyl acetate. The organic extract was washed with brine and dried over anhydrous sodium sulfate, followed by concentration under vacuum. The residue was purified by silica flash chromatography (ethyl acetate/petroleum ether 1:1) to afford the title compound (300 mg, 59.6% yield) as a brown solid. LCMS (ESI): [M+H]$^+$=583.2.

Step 16: Benzyl (3S,5S)-5-((4-(2-(4-(benzylsulfonylamino)-2,3,5-trifluoro-phenoxy)-3-pyridyl)pyrimidin-2-yl)amino)-3-fluoro-3-methyl-piperidine-1-carboxylate

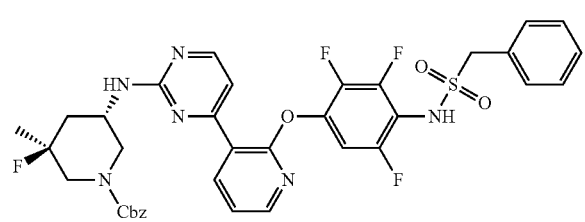 [SMILES: C[C@]1(F)C[C@H](Nc2nccc(-c3cccnc3Oc3cc(F)c(NS(=O)(=O)Cc4ccccc4)c(F)c3F)n2)CN(C(=O)OCc2ccccc2)C1]

To a solution of benzyl (3S,5S)-5-((4-(2-(4-amino-2,3,5-trifluoro-phenoxy)-3-pyridyl)pyrimidin-2-yl)amino)-3-fluoro-3-methyl-piperidine-1-carboxylate (0.15 g, 0.26 mmol) in pyridine (1.5 mL) was added alpha-toluenesulfonylchloride (0.07 g, 0.39 mmol) at 20° C. The resulting solution was stirred for 2 h at 20° C. The reaction mixture was diluted with water and extracted with ethyl acetate. The organic extract was washed with brine and dried over anhydrous sodium sulfate, followed by concentration under vacuum. The residue was purified by silica flash chromatography (ethyl acetate/petroleum ether 4:1) to afford the title compound (150 mg, 79.1% yield) as a brown solid. LCMS (ESI): [M+H]$^+$=737.2.

Step 17: 1-Phenyl-N-(2,3,6-trifluoro-4-((3-(2-(((3S,5S)-5-fluoro-5-methyl-3-piperidyl)amino)pyrimidin-4-yl)-2-pyridyl)oxy)phenyl)methanesulfonamide

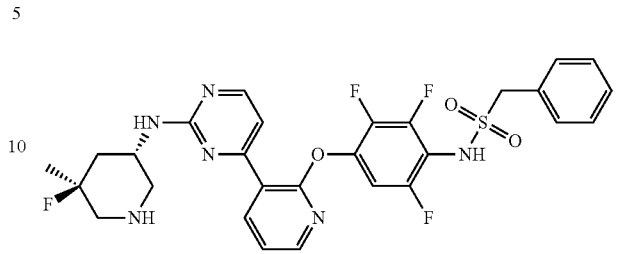

To a solution of benzyl (3S,5S)-5-((4-(2-(4-(benzylsulfonylamino)-2,3,5-trifluoro-phenoxy)-3-pyridyl)pyrimidin-2-yl)amino)-3-fluoro-3-methyl-piperidine-1-carboxylate (150 mg, 0.20 mmol) in DCM (2 mL) was added 33% HBr in acetic acid (2.0 mL). The reaction mixture was stirred at 20° C. for 30 min and the solvent was concentrated under vacuum. The residue was purified by prep-HPLC to afford the title compound (33.3 mg, 17.7% yield) as a white solid.

Example 43

(S)—N-(2-Fluoro-3-((3-(2-(piperidin-3-ylamino)pyrimidin-4-yl)pyridin-2-yl)oxy)benzyl)cyclopropanecarboxamide (Compound 197)

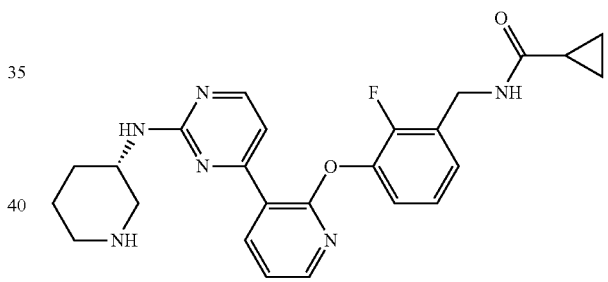

Step 1: Benzyl (3S)-3-((4-(2-fluoro-3-pyridyl)pyrimidin-2-yl)amino)piperidine-1-carboxylate

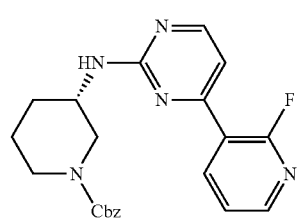 [SMILES: O=C(OCc1ccccc1)N1CCC[C@H](Nc2nccc(-c3cccnc3F)n2)C1]

To a mixture of benzyl (3S)-3-aminopiperidine-1-carboxylate (1.28 g, 5.46 mmol) in DMSO (12 mL) was added 2-chloro-4-(2-fluoro-3-pyridyl)pyrimidine (1.63 g, 7.78 mmol), cesium fluoride (1.58 g, 10.4 mmol) and N,N-diisopropylethylamine (2.9 mL, 16.38 mmol). The reaction mixture was stirred at 80° C. for 2 h and was then diluted with water. The mixture was extracted with ethyl acetate. The combined organic extracts were washed with brine, dried over sodium sulfate and concentrated in vacuo. The residue was purified by silica flash chromatography (ethyl acetate/petroleum ether 10-40%) to afford the title compound (1.8 g, 80.9% yield) as a yellow solid. LCMS (ESI): [M+H]⁺=408.1.

Step 2: Benzyl (3S)-3-((4-(2-(3-bromo-2-fluorophenoxy)-3-pyridyl)pyrimidin-2-yl)amino)piperidine-1-carboxylate

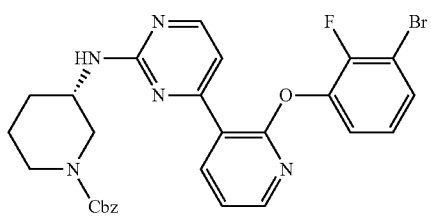 [SMILES: O=C(OCc1ccccc1)N1CCC[C@H](Nc2nccc(-c3cccnc3Oc3cccc(Br)c3F)n2)C1]

To a mixture of benzyl (3S)-3-((4-(2-fluoro-3-pyridyl)pyrimidin-2-yl)amino)piperidine-1-carboxylate (1.1 g, 2.7 mmol) and 3-bromo-2-fluoro-phenol (0.66 g, 3.46 mmol) in DMSO (20 mL) was added cesium carbonate (1.75 g, 5.37 mmol). The mixture was stirred for 1 h at 110° C. The mixture was diluted with water and extracted with ethyl acetate, dried over anhydrous sodium sulfate and concentrated in vacuo. The residue was purified by silica flash chromatography (ethyl acetate/petroleum ether, 10-40%) to afford the title compound (1.2 g, 76.8% yield) as a light yellow solid. LCMS (ESI): [M+H]⁺=578.3.

Step 3: Benzyl (3S)-3-((4-(2-(3-((tert-butoxycarbonylamino)methyl)-2-fluoro-phenoxy)-3-pyridyl)pyrimidin-2-yl)amino)piperidine-1-carboxylate

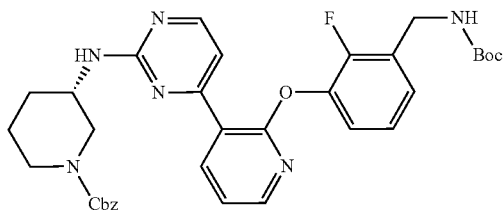 [SMILES: CC(C)(C)OC(=O)NCc1cccc(Oc2ncccc2-c2ccnc(N[C@H]3CCCN(C(=O)OCc4ccccc4)C3)n2)c1F]

To a mixture of benzyl (3S)-3-((4-(2-(3-bromo-2-fluorophenoxy)-3-pyridyl)pyrimidin-2-yl)amino)piperidine-1-carboxylate (0.76 g, 1.31 mmol), potassium (((tert-butoxycarbonyl)amino)methyl)trifluoroborate (1.12 g, 4.7 mmol), cesium carbonate (1.32 g, 4.05 mmol) in 1,4-dioxane (18 mL) and water (3 mL) was added palladium(II)acetate (0.08 g, 0.34 mmol) and 2-dicyclohexylphosphino-2',6'-dimethoxybiphenyl (0.21 g, 0.51 mmol). The mixture was stirred for 16 h at 110° C., diluted with water and extracted with ethyl acetate. The combined organic layers were dried over sodium sulfate and concentrated under vacuum. The residue was purified by silica flash chromatography (ethyl acetate/petroleum ether 20-70%) to afford the title product (550 mg, 66.6% yield) as a light yellow solid. LCMS (ESI): [M+H]⁺=629.3.

Step 4: Benzyl (3S)-3-((4-(2-(3-((cyclopropanecarbonylamino)methyl)-2-fluoro-phenoxy)-3-pyridyl)pyrimidin-2-yl)amino)piperidine-1-carboxylate

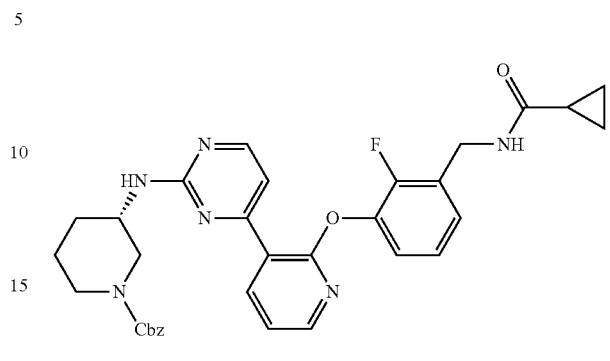

To a solution of benzyl (3S)-3-((4-(2-(3-((tert-butoxycarbonylamino)methyl)-2-fluoro-phenoxy)-3-pyridyl)pyrimidin-2-yl)amino)piperidine-1-carboxylate (0.26 g, 0.41 mmol) in DCM (3 mL) was added 4 M HCl in 1,4-dioxane (9 mL). The reaction mixture was stirred at 20° C. for 1 h. The mixture was concentrated in vacuo and used in the next step without purification. The residue was dissolved in pyridine (1.5 mL), and cyclopropanecarbonyl chloride (68 mg, 0.66 mmol) was added at 20° C. The resulting solution was stirred for 1 h at 20° C. The reaction mixture was diluted with water and extracted with ethyl acetate. The combined organic layers were washed with brine, dried over anhydrous sodium sulfate and concentrated in vacuo. The residue was purified by silica flash chromatography (ethyl acetate/petroleum ether 70:30) to afford the title compound (190 mg, 96.2% yield) as a yellow solid. LCMS (ESI): [M+H]⁺=597.3.

Step 5: (S)—N-(2-Fluoro-3-((3-(2-(piperidin-3-ylamino)pyrimidin-4-yl)pyridin-2-yl)oxy)benzyl)cyclopropanecarboxamide

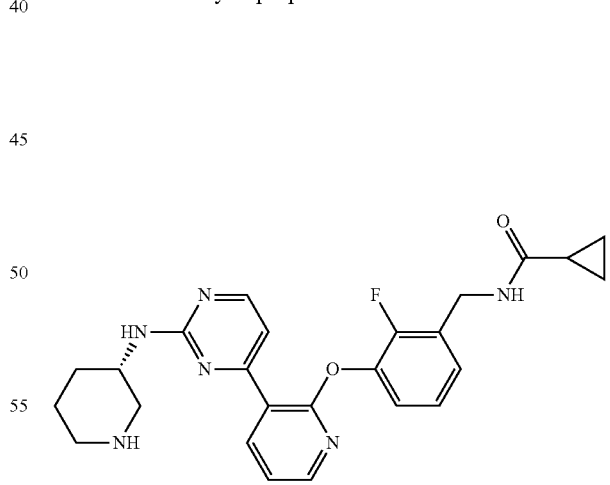

A solution of benzyl (3S)-3-((4-(2-(3-((cyclopropanecarbonylamino)methyl)-2-fluoro-phenoxy)-3-pyridyl)pyrimidin-2-yl)amino)piperidine-1-carboxylate (0.15 g, 0.25 mmol) in DCM (2 mL) was stirred at 20° C. 33% HBr in acetic acid (1 mL) was then added and the reaction mixture was stirred at 20° C. for 1 h. The solvent was removed in vacuo and the residue was purified by prep-HPLC to provide the title compound (24.4 mg, 20.8% yield) as a white solid.

Example 44

1-Phenyl-N-(2,3,6-trifluoro-4-((3-(2-(piperidin-3-ylmethyl)pyrimidin-4-yl)pyridin-2-yl)oxy)phenyl)methanesulfonamide (isomer 1) & 1-phenyl-N-(2,3,6-trifluoro-4-((3-(2-(piperidin-3-ylmethyl)pyrimidin-4-yl)pyridin-2-yl)oxy)phenyl)methanesulfonamide (isomer 2) (Compound 198 & Compound 199)

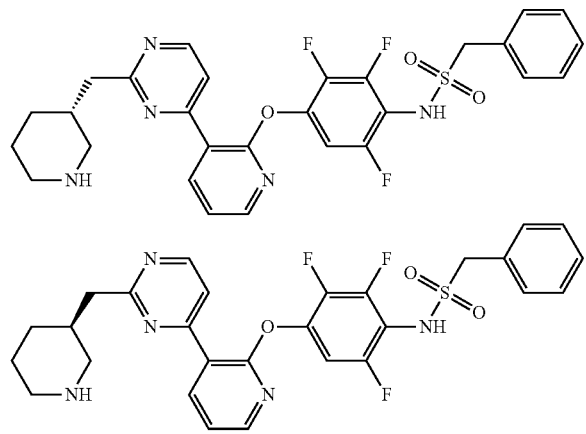

Step 1: tert-Butyl 3-((4-(2-fluoropyridin-3-yl)pyrimidin-2-yl)methyl)piperidine-1-carboxylate

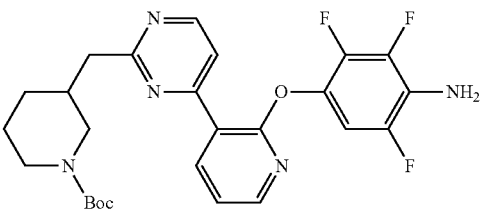 [SMILES: CC(C)(C)OC(=O)N1CCCC(Cc2nccc(-c3cccnc3Oc3cc(F)c(N)c(F)c3F)n2)C1]

To a solution of tert-butyl 3-methylenepiperidine-1-carboxylate (500 mg, 2.53 mmol) in DMF (10 mL) was added 9-borabicyclo(3.3.1)nonane (310 mg, 2.54 mmol) at 0° C. The resulting solution was stirred for 1 h at 75° C. Then 2-chloro-4-(2-fluoro-3-pyridyl)pyrimidine (550 mg, 2.62 mmol), potassium carbonate (1.05 g, 7.6 mmol), (1,1-bis(diphenylphosphino)ferrocene)dichloropalladium(II) (185 mg, 0.25 mmol), and water (2 mL) were added. The mixture was stirred at 75° C. for 1.5 h under nitrogen. The reaction mixture was diluted with water and extracted with ethyl acetate. The organic extract was dried over anhydrous sodium sulfate and concentrated under vacuum. The residue was purified by silica flash chromatography (ethyl acetate/petroleum ether 3:7) to afford the title compound (550 mg, 55.4% yield) as a white solid. LCMS (ESI): [M+H]⁺=373.2.

Step 2: tert-Butyl 3-((4-(2-(4-amino-2,3,5-trifluorophenoxy)pyridin-3-yl)pyrimidin-2-yl)methyl)piperidine-1-carboxylate Under nitrogen, a mixture of tert-butyl 3-((4-(2-fluoro-3-pyridyl)pyrimidin-2-yl)methyl)piperidine-1-carboxylate (258 mg, 0.69 mmol), 4-amino-2,3,5-trifluoro-phenol (100 mg, 0.61 mmol) and cesium carbonate (400 mg, 1.23 mmol) in DMSO (5 mL) was stirred for 2 h at 100° C. The reaction mixture was diluted with water and extracted with ethyl acetate. The organic extract was dried over anhydrous sodium sulfate and concentrated under vacuum. The residue was purified by silica flash chromatography using ethyl acetate/petroleum ether (⅔) to afford the title compound (220 mg, 48.7% yield) as a yellow solid. LCMS (ESI): [M+H]⁺=516.2

Step 3: tert-Butyl 3-((4-(2-(2,3,5-trifluoro-4-((phenylmethyl)sulfonamido)phenoxy)pyridin-3-yl)pyrimidin-2-yl)methyl)piperidine-1-carboxylate

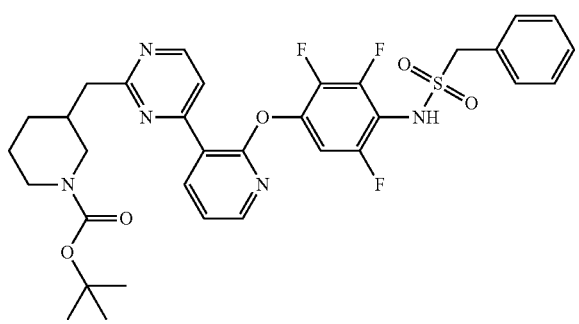 [SMILES: CC(C)(C)OC(=O)N1CCCC(Cc2nccc(-c3cccnc3Oc3cc(F)c(NS(=O)(=O)Cc4ccccc4)c(F)c3F)n2)C1]

To a solution of tert-butyl 3-((4-(2-(4-amino-2,3,5-trifluoro-phenoxy)-3-pyridyl)pyrimidin-2-yl)methyl)piperidine-1-carboxylate (180 mg, 0.35 mmol) and pyridine (200 mg, 2.53 mmol) in DCM (1.5 mL) was added alpha-toluenesulfonylchloride (110 mg, 0.58 mmol) followed by stirring at 25° C. for 2 h. The reaction mixture was diluted with water and the resulting solution was extracted with ethyl acetate. The combined organic layers were dried over anhydrous sodium sulfate and concentrated in vacuo. The residue was purified by silica flash chromatography (ethyl acetate/petroleum ether 45:55) to afford the title compound (190 mg, 40.6% yield) as a yellow solid. LCMS (ESI): [M+H]⁺=670.2.

Step 4: 1-Phenyl-N-(2,3,6-trifluoro-4-((3-(2-(piperidin-3-ylmethyl)pyrimidin-4-yl)pyridin-2-yl)oxy)phenyl)methanesulfonamide (isomer 1) & 1-phenyl-N-(2,3,6-trifluoro-4-((3-(2-(piperidin-3-ylmethyl)pyrimidin-4-yl)pyridin-2-yl)oxy)phenyl)methanesulfonamide (isomer 2)

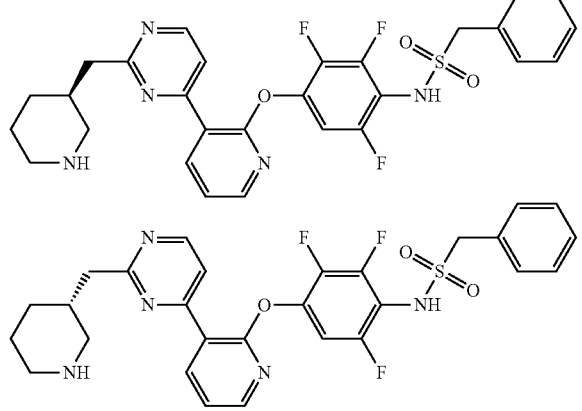

To a solution of tert-butyl 3-((4-(2-(4-(benzylsulfonylamino)-2,3,5-trifluoro-phenoxy)-3-pyridyl)pyrimidin-2-yl)methyl)piperidine-1-carboxylate (190 mg, 0.28 mmol) in DCM (2 mL) was added 4 M HCl in 1,4-dioxane (4 mL, 16 mmol). The reaction mixture was stirred at 25° C. for 1 h and the solvent then removed under vacuum. The crude product was purified by prep-HPLC to separate the two enantiomers.

Isomer 1 (Compound 198): 1-Phenyl-N-(2,3,6-trifluoro-4-((3-(2-(3-piperidylmethyl)pyrimidin-4-yl)-2-pyridyl)oxy)phenyl)methanesulfonamide (7.4 mg, 4.5% yield), obtained as a white solid, (rt=3.649 min, IC, 0.46×10 cm; 5 μm, MTBE (0.2% isopropylamine):EtOH=70:30, 1.0 mL/min).

Isomer 2 (Compound 199): 1-Phenyl-N-(2,3,6-trifluoro-4-((3-(2-(3-piperidylmethyl)pyrimidin-4-yl)-2-pyridyl)oxy)phenyl)methanesulfonamide (11.4 mg, 7% yield), obtained as a white solid, (rt=5.095 min, IC, 0.46×10 cm; 5 μm, MTBE (0.2% isopropylamine):EtOH=70:30, 1.0 mL/min).

Example 45

1,1,1-Trifluoro-3-((2-fluoro-3-((3-(2-(((S)-piperidin-3-yl)amino)pyrimidin-4-yl)pyridin-2-yl)oxy)phenyl)amino)propan-2-ol & 1,1,1-trifluoro-3-((2-fluoro-3-((3-(2-(((S)-piperidin-3-yl)amino)pyrimidin-4-yl)pyridin-2-yl)oxy)phenyl)amino)propan-2-ol (Compound 200 & Compound 201)

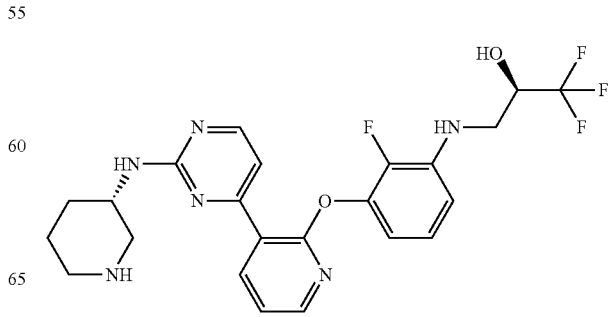

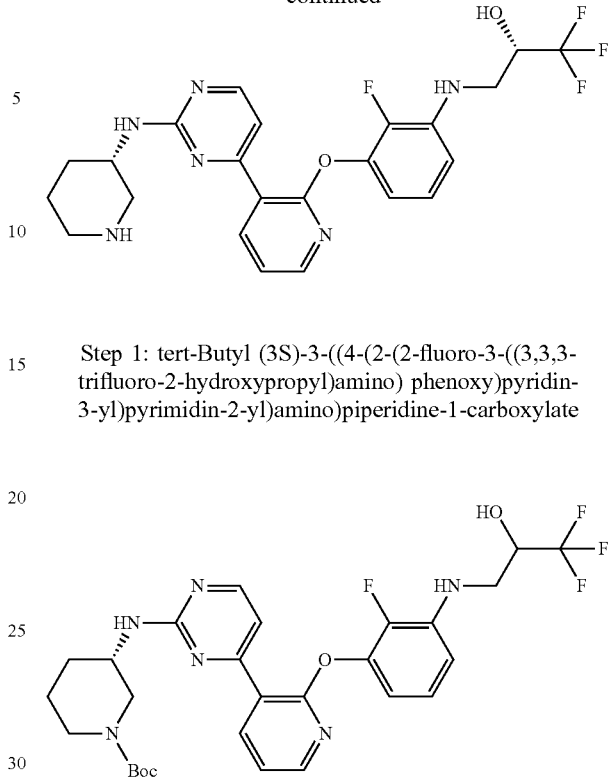

Step 1: tert-Butyl (3S)-3-((4-(2-(2-fluoro-3-((3,3,3-trifluoro-2-hydroxypropyl)amino) phenoxy)pyridin-3-yl)pyrimidin-2-yl)amino)piperidine-1-carboxylate To a solution of tert-butyl (3S)-3-((4-(2-(3-amino-2-fluoro-phenoxy)-3-pyridyl)pyrimidin-2-yl)amino)piperidine-1-carboxylate (100 mg, 0.21 mmol) and calcium trifluoromethanesulfonate (70 mg, 0.21 mmol) in acetonitrile (5 mL) was added 1,1,1-trifluoro-2,3-epoxypropane (0.094 g, 0.8400 mmol) at 25° C. The resulting solution was stirred for 48 h at 60° C. The reaction was quenched with water. The resulting solution was extracted with ethyl acetate and the organic layers were combined. The organic layer was dried over anhydrous sodium sulfate and concentrated under vacuum. The residue was purified by silica flash chromatography (ethyl acetate/petroleum ether 4:6) to provide the title compound (30 mg, 14.6% yield) as a yellow solid. LCMS (ESI): [M+H]⁺=593.4.

Step 2: 1,1,1-Trifluoro-3-((2-fluoro-3-((3-(2-(((S)-piperidin-3-yl)amino)pyrimidin-4-yl)pyridin-2-yl)oxy)phenyl)amino)propan-2-ol (isomer 1) & 1,1,1-trifluoro-3-((2-fluoro-3-((3-(2-(((S)-piperidin-3-yl)amino)pyrimidin-4-yl)pyridin-2-yl)oxy)phenyl)amino)propan-2-ol (isomer 2)

327
-continued

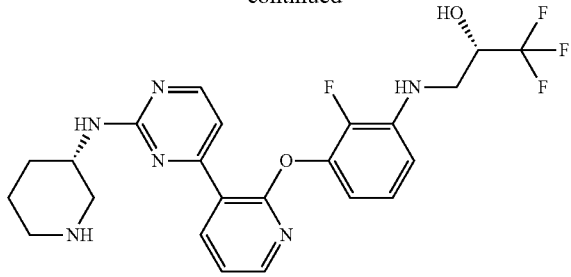

To a solution of tert-butyl (3S)-3-((4-(2-(2-fluoro-3-((3,3,3-trifluoro-2-hydroxy-propyl)amino)phenoxy)-3-pyridyl)pyrimidin-2-yl)amino)piperidine-1-carboxylate (50 mg, 0.080 mmol) in DCM (1 mL) was added 4 M HCl in 1,4-dioxane (1 mL). The resulting solution was stirred for 1 h at 25° C. and the solvent removed under vacuum. The residue was purified by prep-HPLC and the two single diastereomers separated via chiral-HPLC.

Isomer 1 (Compound 200): 1,1,1-Trifluoro-3-(2-fluoro-3-((3-(2-(((3S)-3-piperidyl)amino)pyrimidin-4-yl)-2-pyridyl)oxy)anilino)propan-2-ol (16.4 mg, 39.3% yield), obtained as a light yellow solid, (rt=3.602 min, ADH, 0.46×10 cm; 5 μm, Hex (0.1% DEA), EtOH=70:30, 1.0 mL/min).

Isomer 2 (Compound 201): 1,1,1-Trifluoro-3-(2-fluoro-3-((3-(2-(((3S)-3-piperidyl)amino)pyrimidin-4-yl)-2-pyridyl)oxy)anilino)propan-2-ol (isomer 2) (17.1 mg, 40.9% yield), obtained as a light yellow solid, (rt=4.704 min, ADH, 0.46×10 cm; 5 μm, Hex (0.1% DEA):EtOH=70:30, 1.0 mL/min).

Example 46

N-[2,3-Difluoro-4-[[3-[2-[[(3S)-3-piperidyl]amino]pyrimidin-4-yl]-2-pyridyl]oxy]phenyl]-3,5-difluoro-benzenesulfonamide (Compound 206)

Step 1: tert-Butyl (3S)-3-[[4-[2-[4-[(3,5-difluoro-phenyl)sulfonylamino]-2,3-difluoro-phenoxy]-3-pyridyl]pyrimidin-2-yl]amino]piperidine-1-carboxylate

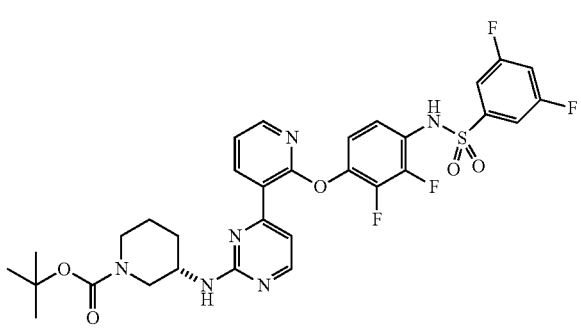 [SMILES: CC(C)(C)OC(=O)N1CCC[C@H](Nc2nccc(-c3cccnc3Oc3ccc(NS(=O)(=O)c4cc(F)cc(F)c4)c(F)c3F)n2)C1]

To a two-dram pressure-cap relief vial was added tert-butyl (S)-3-((4-(2-(4-amino-2,3-difluorophenoxy)pyridin-3-yl)pyrimidin-2-yl)amino)piperidine-1-carboxylate (50 mg, 0.10 mmol) dissolved in DCM (0.5 mL), pyridine (0.12 mL), and 3,5-difluorobenzenesulfonyl chloride (32 mg, 0.15 mmol). The reaction mixture was stirred at room temperature for 16 h. The reaction mixture was then washed with

328

HCl (1N, 2 mL), concentrated, and transitioned to Step 2. LCMS (ESI): [M+H]$^+$=675.4.

Step 2: (S)—N-(2,3-Difluoro-4-((3-(2-(piperidin-3-ylamino)pyrimidin-4-yl)pyridin-2-yl)oxy)phenyl)-3,5-difluorobenzenesulfonamide

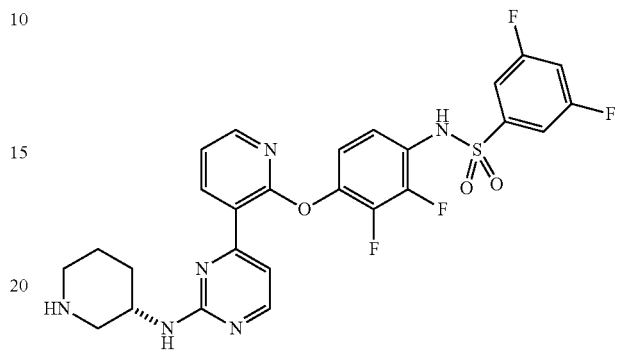

To a solution of tert-butyl (3S)-3-[[4-[2-[4-[(3,5-difluorophenyl)sulfonylamino]-2,3-difluoro-phenoxy]-3-pyridyl]pyrimidin-2-yl]amino]piperidine-1-carboxylate (crude residue) in methanol (1.4 mL) was added hydrochloric acid (4 N in dioxane, 0.25 mL, 1.0 mmol). The reaction mixture was stirred at room temperature for 16 h. The solution was concentrated in vacuo, dissolved in dimethylformamide (1 mL) and purified by prep-HPLC to afford the title compound (3.8 mg, 6.7% yield). LCMS (ESI): [M+H]$^+$=575.1.

Example 47

N-[2-Fluoro-3-methyl-4-[[3-[2-[[(3S)-3-piperidyl]amino]pyrimidin-4-yl]-2-pyridyl]oxy]phenyl]-1 phenylmethanesulfonamide (Compound 237)

Step 1: 4-Amino-3-fluoro-2-methylphenol

To a solution of 3-fluoro-2-methyl-4-nitrophenol (860 mg, 5.02 mmol) in ethanol (20 mL) was added palladium on carbon (10 mass %, 535 mg, 0.50 mmol) and ammonium formate (2.50 g, 40.2 mmol), and the reaction was heated to 60° C. After ~15 minutes (excessive hydrogen gas evolution seen), the reaction mixture was cooled to room temperature, filtered through celite and concentrated to dryness. The crude intermediate was re-suspended in DCM (20 mL) and treated with Biotage MP-TsOH resin (2.9 g, 10.05 mmol) and then placed on an orbital shaker. After shaking overnight (18 h), the resin was collected, rinsed several times with DCM, and the title compound was obtained by rinsing the resin with 7N ammonia in methanol solution (2×10 mL) and subsequent evaporation under vacuum (148 mg, 21% yield). LCMS (ESI): [M+H]$^+$=142.

Step 2: tert-Butyl (3S)-3-[[4-[2-(4-amino-3-fluoro-2-methyl-phenoxy)-3-pyridyl]pyrimidin-2-yl]amino]piperidine-1-carboxylate

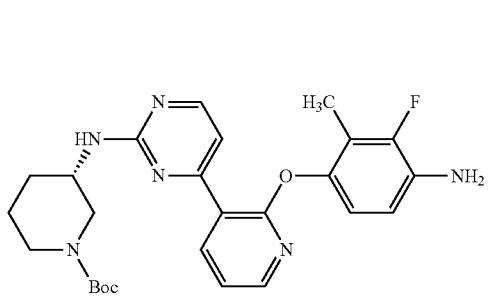 [SMILES: Cc1c(Oc2ncccc2-c2ccnc(N[C@H]3CCCN(C(=O)OC(C)(C)C)C3)n2)ccc(N)c1F]

To a vial kept under nitrogen, tert-butyl (3S)-3-[[4-(2-fluoro-3-pyridyl)pyrimidin-2-yl]amino]piperidine-1-carboxylate (310 mg, 0.83 mmol) and 4-amino-3-fluoro-2-methylphenol (141 mg 0.10 mmol) were added, followed by DMSO (3.3 mL, 47 mmol) and cesium carbonate (811 mg, 2.49 mmol). The vial was capped and heated to 130° C. for 16 h. Upon cooling, the crude intermediate was obtained through trituration from the reaction mixture via addition of water and subsequent filtration. The material was then solubilized in DCM and extracted with brine. The organic layer was dried with magnesium sulfate, filtered and concentrated in vacuo followed by silica column chromatography to afford 260 mg (63.3% yield) of the title compound. LCMS (ESI): [M+1]$^+$=495.

Step 3: tert-Butyl (3S)-3-[[4-[2-[4-(benzylsulfonylamino)-3-fluoro-2-methyl-phenoxy]-3-pyridyl]pyrimidin-2yl]amino]piperidine-1-carboxylate

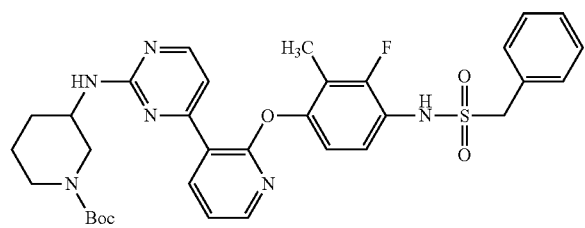 [SMILES: Cc1c(Oc2ncccc2-c2ccnc(NC3CCCN(C(=O)OC(C)(C)C)C3)n2)ccc(NS(=O)(=O)Cc2ccccc2)c1F]

To a solution of tert-butyl (3S)-3-[[4-[2-(4-amino-3-fluoro-2-methyl-phenoxy)-3-pyridyl]pyrimidin-2-yl]amino]piperidine-1-carboxylate in DCM (1 mL) was added pyridine (0.3 mL, 3.7 mmol) followed by alpha-toluenesulfonyl chloride (100 mg, 0.52 mmol). The reaction mixture was stirred at room temperature for 16 h, quenched with 10 mL of saturated aqueous bicarbonate solution, and DCM was added. The organic extract was dried with anhydrous magnesium sulfate, filtered and concentrated under vacuum. The crude reaction mixture was purified by silica column chromatography to afford 160 mg (94% yield) of the title compound. LCMS (ESI): [M+1]$^+$=649.

Step 4: N-[2-Fluoro-3-methyl-4-[[3-[2-[[(3S)-3-piperidyl]amino]pyrimidin-4-yl]-2-pyridyl]oxy]phenyl]-1 phenylmethanesulfonamide

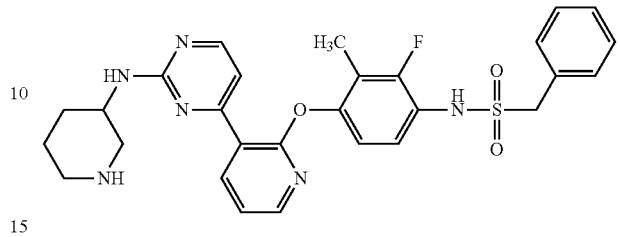

To a solution of tert-butyl (3S)-3-[[4-[2-[4-(benzylsulfonylamino)-3-fluoro-2-methyl-phenoxy]-3-pyridyl]pyrimidin-2yl]amino]piperidine-1-carboxylate in DCM (5 mL) was added 4M HCl in 1,4 dioxane (1.2 mL), and the reaction mixture was stirred at room temperature for 4 h. Concentration to dryness under vacuum and purification by prep-HPLC afforded 42.6 mg (30.5% yield) of the title compound. LCMS (ESI): [M+1]+=549.1.

Example 48

1-(2,3-Difluoro-4-((3-(2-(((S)-piperidin-3-yl)amino)pyrimidin-4-yl)pyridin-2-yl)oxy)phenyl)-3-ethylpyrrolidin-2-one Compound 248 & Compound 249

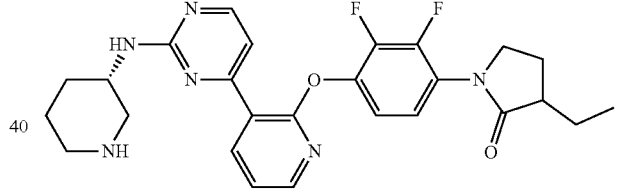

Step 1: 1-(Benzyloxy)-4-bromo-2,3-difluorobenzene

Under nitrogen, a solution of 4-bromo-2,3-difluorophenol (2.0 g, 9.57 mmol) and benzyl bromide (2.46 g, 14.35 mmol) in N,N-dimethylformamide (20 mL) was added potassium carbonate (3.% g, 28.71 mmol), the resulting solution was stirred for 4 h at 25° C. The resulting solution was diluted with water, extracted with ethyl acetate, washed with brine, dried over sodium sulfate and concentrated. The residue was purified by silica flash chromatography eluting with ethyl acetate/petroleum ether (20:80) to afford the title compound (2.74 g, 90.9% yield) as a white solid. LCMS (ESI): [M+H]$^+$= 299.0.

Step 2: 1-(4-(Benzyloxy)-2,3-difluorophenyl)-3-ethylpyrrolidin-2-one

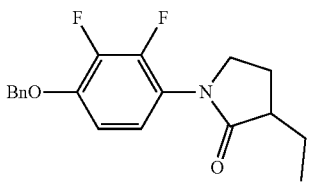 [SMILES: CCC1CCN(c2ccc(OCc3ccccc3)c(F)c2F)C1=O]

Under nitrogen, a solution of 1-benzyloxy-4-bromo-2,3-difluoro-benzene (300 mg, 1.00 mmol) and 3-ethylpyrrolidin-2-one (113 mg, 1.00 mmol) and potassium carbonate (415 mg, 3.01 mmol), $N^1,N^2$-dimethylethane-1,2-diamine (18 mL, 0.20 mmol) and copper(I) iodide (19 mg, 0.10 mmol) in 1,4-dioxane (5 mL) was stirred for 4 h at 110° C. The resulting solution was diluted with water, extracted with ethyl acetate, washed with brine, dried over sodium sulfate and concentrated. The residue was purified by silica flash chromatography eluting with ethyl acetate/petroleum ether (¼) to afford the title compound (170 mg, 48.6% yield) as a brown solid. LCMS (ESI): [M+H]⁺=332.1

Step 3: 1-(2,3-Difluoro-4-hydroxyphenyl)-3-ethylpyrrolidin-2-one

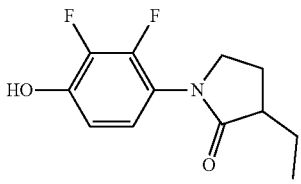 [SMILES: CCC1CCN(c2ccc(O)c(F)c2F)C1=O]

A solution of 1-(4-benzyloxy-2,3-difluoro-phenyl)-3-ethyl-pyrrolidin-2-one (170 mg, 0.51 mmol) and 10% Pd/C (50 mg) in methyl alcohol (3 mL) was stirred for 2 h at rt under hydrogen. The solids were filtered out. After filtration, the filtrate was concentrated under reduced pressure to afford the title compound (120 mg, 82.4% yield) as a brown solid. LCMS (ESI): [M+H]⁺=242.1.

Step 4: tert-Butyl (3S)-3-((4-(2-(4-(3-ethyl-2-oxopyrrolidin-1-yl)-2,3-difluorophenoxy)pyridin-3-yl)pyrimidin-2-yl)amino)piperidine-1-carboxylate

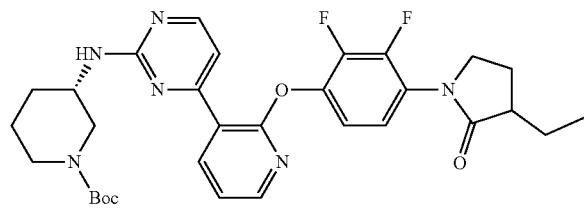 [SMILES: CCC1CCN(c2ccc(Oc3ncccc3-c3ccnc(N[C@H]4CCCN(C(=O)OC(C)(C)C)C4)n3)c(F)c2F)C1=O]

Under nitrogen, a mixture of 1-(2,3-difluoro-4-hydroxyphenyl)-3-ethyl-pyrrolidin-2-one (120 mg, 0.50 mmol), tert-butyl (3S)-3-((4-(2-fluoro-3-pyridyl)pyrimidin-2-yl)amino)piperidine-1-carboxylate (222 mg, 0.60 mmol) and cesium carbonate (490 mg, 1.49 mmol) in dimethyl sulfoxide (3 ml) was stirred for 4 h at 120° C. The resulting solution was diluted with water, extracted with ethyl acetate, washed with brine, dried over sodium sulfate and concentrated. The residue was purified by silica flash chromatography eluting with ethyl acetate/petroleum ether (60:40) to afford the title compound (250 mg, 76.1% yield) as a yellow solid. LCMS (ESI): [M+H]⁺=595.3

Step 5: 1-(2,3-Difluoro-4-((3-(2-(((S)-piperidin-3-yl)amino)pyrimidin-4-yl)pyridin-2-yl)oxy)phenyl)-3-ethylpyrrolidin-2-one & 1-(2,3-difluoro-4-((3-(2-(((S)-piperidin-3-yl)amino)pyrimidin-4-yl)pyridin-2-yl)oxy)phenyl)-3-ethylpyrrolidin-2-one Compound 248 & Compound 249

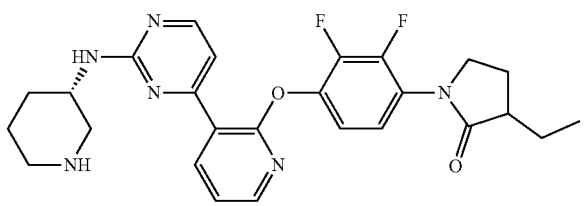 [SMILES: CCC1CCN(c2ccc(Oc3ncccc3-c3ccnc(N[C@H]4CCCNC4)n3)c(F)c2F)C1=O]

To a solution of tert-butyl (3S)-3-((4-(2-(4-(3-ethyl-2-oxo-pyrrolidin-1-yl)-2,3-difluoro-phenoxy)-3-pyridyl)pyrimidin-2-yl)amino)piperidine-1-carboxylate (250 mg, 0.42 mmol) in dichloromethane (2 mL) was added 4 M HCl in dioxane (5 mL), die mixture was stirred for 4 h at rt. The resulting mixture was concentrated under vacuum. The residue was purified by Prep-HPLC and Chiral HPLC to afford the tide compound. After Chiral HPLC, two peaks were isolated out. The fast peak was assigned isomer 1. The slow peak was assigned isomer 2.

1-(2,3-Difluoro-4-((3-(2-(((S)-piperidin-3-yl)amino)pyrimidin-4-yl)pyridin-2-yl)oxy)phenyl)-3-ethylpyrrolidin-2-one (isomer 1) (29.7 mg, 7.1% yield) as a white solid, (rt=4.577 min, CHIRALPAKIC-3, 0.46*5 cm, 3 um, Hex (10 mmolNH₃):EtOH=50:50, 1.0 ml/min).

1-(2,3-Difluoro-4-((3-(2-(((S)-piperidin-3-yl)amino)pyrimidin-4-yl)pyridin-2-yl)oxy)phenyl)-3-ethylpyrrolidin-2-one (isomer 2) (32 mg, 7.6% yield) as a white solid, (rt=5.709 min, CHIRALPAK IC-3, 0.46*5 cm, 3 um, Hex (10 mmolNH₃):EtOH=50:50, 1.0 ml/min).

Example 49

(S)-1-(4-Cyanophenyl)-N-(2,3-difluoro-4-((3-(2-(piperidin-3-ylamino)pyrimidin-4-yl)pyridin-2-yl)oxy)phenyl)methanesulfonamide Compound 250

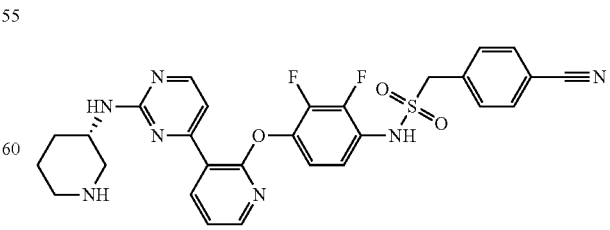

The title compound was prepared according to example 27. This provides the title compound (30.6 mg, 13.6%) as a white solid.

Example 50

1-(3,3-Difluorocyclobutyl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide Compound 251

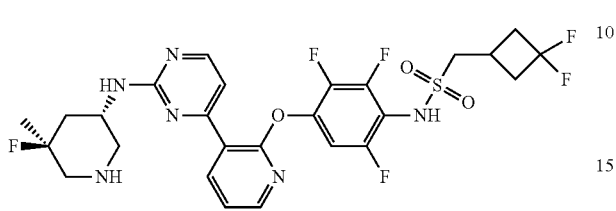

The title compound was prepared according to example 42. This resulted in the title compound (37.1 mg, 45.2% yield) as a white solid.

Example 51

2-Methoxy-N-(2,3,6-trifluoro-4-((3-(2-(((3S,5S)-5-fluoropiperidin-3-yl)amino)pyrimidin-4-yl)pyridin-2-yl)oxy)phenyl)ethane-1-sulfonamide Compound 252

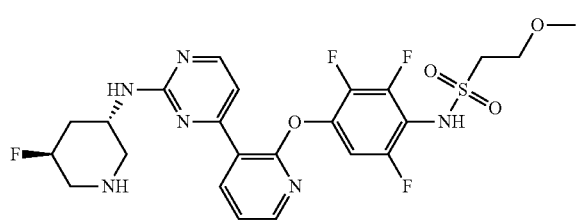 [SMILES: COCCS(=O)(=O)Nc1c(F)cc(Oc2ncccc2-c2ccnc(N[C@@H]3CNC[C@@H](F)C3)n2)c(F)c1F]

The title compound was prepared according to example 40. This resulted in the title compound (3.0 mg, 15.1% yield) as a white solid.

Example 52

3,3-Difluoro-N-(2,3,6-trifluoro-4-((3-(2-(((3S,5S)-5-fluoropiperidin-3-yl)amino)pyrimidin-4-yl)pyridin-2-yl)oxy)phenyl)butane-1-sulfonamide Compound 253

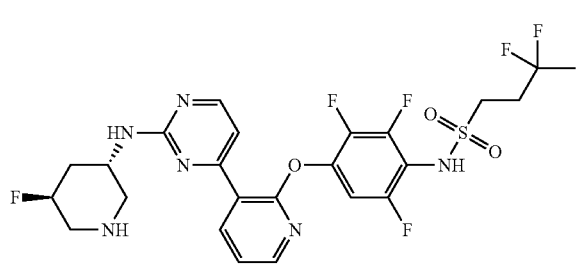 [SMILES: CC(F)(F)CCS(=O)(=O)Nc1c(F)cc(Oc2ncccc2-c2ccnc(N[C@@H]3CNC[C@@H](F)C3)n2)c(F)c1F]

The title compound was prepared according to example 40. This resulted in the title compound (34.6 mg, 40.1% yield) as a white solid.

Example 53

N-(2,3,6-Trifluoro-4-((3-(2-(((3S,5S)-5-fluoropiperidin-3-yl)amino)pyrimidin-4-yl)pyridin-2-yl)oxy)phenyl)-1-(6-(trifluoromethyl)pyridin-3-yl)methanesulfonamide Compound 254

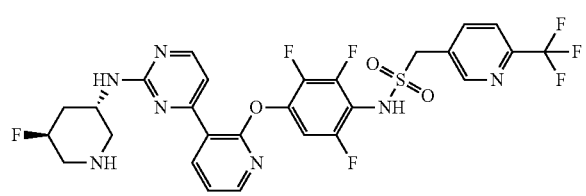 [SMILES: O=S(=O)(Cc1ccc(C(F)(F)F)nc1)Nc1c(F)cc(Oc2ncccc2-c2ccnc(N[C@@H]3CNC[C@@H](F)C3)n2)c(F)c1F]

The title compound was prepared according to example 40. This provides the title compound (12.8 mg, 19.6% yield) as a white solid.

Example 54

1-(4-Cyanophenyl)-N-(2,3,6-trifluoro-4-((3-(2-(((3S,5S)-5-fluoropiperidin-3-yl)amino)pyrimidin-4-yl)pyridin-2-yl)oxy)-5-methylphenyl)methanesulfonamide Compound 255

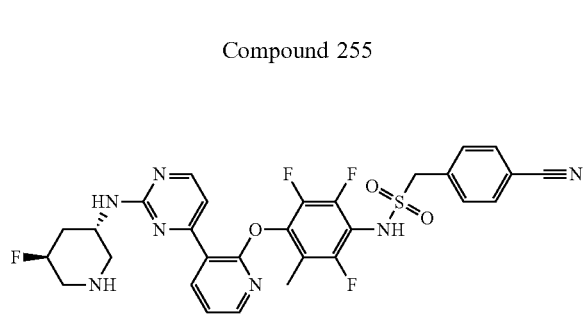

Step 1: 1,3,4-Trifluoro-5-methoxy-2-nitrobenzene

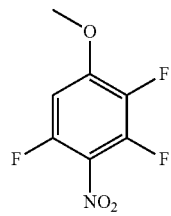

To a solution of 2,3,4,6-tetrafluoronitrobenzene (1.53 g, 7.84 mmol) in methyl alcohol (15 mL) was added sodium methanolate (450 mg, 8.33 mmol) slowly and stirred at rt for 16 h. The solvent was concentrated under vacuum. The residue was purified by silica flash chromatography eluting with ethyl acetate/petroleum ether (8%) to afford the title compound (820 mg, 45.4% yield) as a white solid. ¹H NMR (400 MHz, CD₃OD) δ 6.70 (ddd, J=11.5, 6.4, 2.2 Hz, 1H), 4.00 (s, 3H).

Step 2: 2,3,6-Trifluoro-4-methoxyaniline

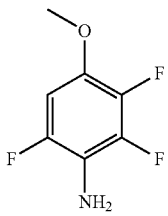

A solution of 1,3,4-trifluoro-5-methoxy-2-nitro-benzene (1.5 g, 6.88 mmol), ammonium chloride (2.6 g, 48.61 mmol) and iron (2.0 g, 35.81 mmol) in ethanol (30 mL) and water (18 mL) was stirred at 95° C. for 16 h. The solids were filtered out. After filtration, the filtrate was concentrated under vacuum. The residue was purified by silica flash chromatography eluting with ethyl acetate/petroleum ether (7%) to afford the tide compound (880 mg, 72.2% yield) as an off-white solid. LCMS (ESI): [M+H]⁺=178.0

Step 3: tert-Butyl N-tert-butoxycarbonyl-N-(2,3,6-trifluoro-4-methoxy-phenyl)carbamate

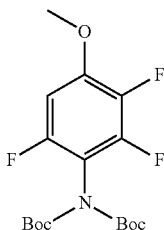

A mixture of 2,3,6-trifluoro-4-methoxyaniline (880 mg, 4.47 mmol), 4-dimethylaminopyridine (120 mg, 0.98 mmol), di-tert-butyldicarbonate (4.0 g, 18.33 mmol) in tetrahydrofuran (18 mL) were stirred at 75° C. for 12 h. The resulting solution was diluted with water, extracted with ethyl acetate, washed with brine, dried over sodium sulfate and concentrated. The residue was purified by silica flash chromatography eluting with ethyl acetate/petroleum ether (¼) to afford the title compound (1.7 g, 90.7% yield) as a white solid. ¹H NMR (300 MHz, CD₃OD) δ 6.58 (ddd, J=10.9, 7.0, 2.3 Hz, 1H), 3.92 (s, 3H), 1.46 (s, 18H).

Step 4: tert-Butyl N-tert-butoxycarbonyl-N-(2,3,6-trifluoro-4-methoxy-5-methyl-phenyl)carbamate

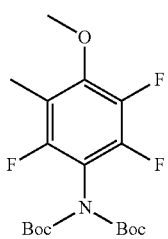

Under nitrogen, to a solution of tert-butyl N-tert-butoxycarbonyl-N-(2,3,6-trifluoro-4-methoxy-phenyl)carbamate (816 mg, 2.16 mmol) in tetrahydrofuran (16 mL) was added 2 M lithium diisopropylamide in tetrahydrofuran (2.4 mL, 4.8 mmol) at −60° C. The resulting solution was stirred for 2 h at −20° C. Then iodomethane (760 mg, 5.35 mmol) was added at −60° C. and stirred at −20° C. for 1 h. The reaction was quenched with sat. ammonium chloride. The resulting solution was extracted with ethyl acetate, washed with brine, dried over sodium sulfate and concentrated. The residue was purified by silica flash chromatography eluting with ethyl acetate/petroleum ether (18%) to afford the title compound (500 mg, 59.1% yield) as a white solid. ¹H NMR (300 MHz, DMSO-d₆) δ 3.98 (d, J=1.9 Hz, 3H), 3.17-3.03 (m, 3H), 1.46 (s, 18H).

Step 5: 4-Amino-2,3,5-trifluoro-6-methylphenol

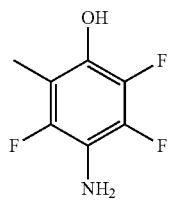

A mixture of tert-butyl N-tert-butoxycarbonyl-N-(2,3,6-trifluoro-4-methoxy-5-methyl-phenyl)carbamate (550 mg, 1.41 mmol) and 40% hydrobromic acid (7 mL) in water (3 mL) was stirred at 100° C. for 24 h. The organic layer was concentrated under vacuum. The crude product would be directly used in the next step without purification. LCMS (ESI): [M+H]⁺=178.0

Step 6: 2,3,6-Trifluoro-5-methyl-4-((3-(2-(methylthio)pyrimidin-4-yl)pyridin-2-yl)oxy)aniline

To a mixture of 4-amino-2,3,5-trifluoro-6-methyl-phenol (170 mg, 0.48 mmol), 4-amino-2,3,5-trifluoro-6-methy1-phenol (170 mg, 0.48 mmol) and cesium carbonate (500 mg, 1.53 mmol) in dimethyl sulfoxide (3 mL) was stirred for 4 h at 100° C. The resulting solution was diluted with water, extracted with ethyl acetate, washed with brine, dried over sodium sulfate and concentrated. The residue was purified by silica flash chromatography eluting with ethyl acetate/petroleum ether (20%) to afford the title compound (130 mg, 62.2% yield) as an off-white solid. LCMS (ESI): [M+H]⁺=379.1

Step 7: 1-(4-Cyanophenyl)-N-(2,3,6-trifluoro-5-methyl-4-((3-(2-(methylthio)pyrimidin-4-yl)pyridin-2-yl)oxy)phenyl)methanesulfonamide

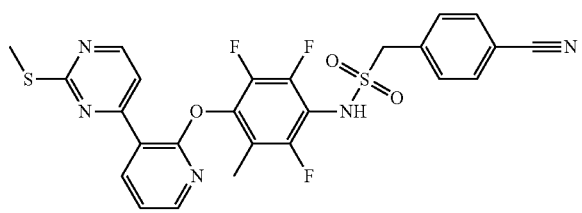 [SMILES: CSc1nccc(-c2cccnc2Oc2c(C)c(F)c(NS(=O)(=O)Cc3ccc(C#N)cc3)c(F)c2F)n1]

To a solution of 2,3,6-trifluoro-5-methyl-4-((3-(2-methylsulfanylpyrimidin-4-yl)-2-pyridyl)oxy)aniline (110 mg, 0.26 mmol) in pyridine (0.50 mL) was added (4-cyanophenyl)methanesulfonyl chloride (88 mg, 0.41 mmol), the mixture was stirred at rt for 1 h. The resulting solution was diluted with water, extracted with ethyl acetate, washed with brine, dried over sodium sulfate and concentrated. The residue was purified by silica flash chromatography eluting with ethyl acetate/petroleum ether (1:1) to afford the title compound (130 mg, 86.6% yield) as a white solid. LCMS (ESI): [M+H]$^+$=558.1

Step 8: 1-(4-Cyanophenyl)-N-(2,3,6-trifluoro-5-methyl-4-((3-(2-(methylsulfonyl)pyrimidin-4-yl)pyridin-2-yl)oxy)phenyl)methanesulfonamide

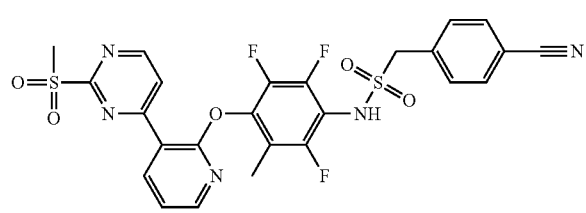 [SMILES: Cc1c(F)c(NS(=O)(=O)Cc2ccc(C#N)cc2)c(F)c(F)c1Oc1ncccc1-c1ccnc(S(C)(=O)=O)n1]

To a solution of 1-(4-cyanophenyl)-N-(2,3,6-trifluoro-5-methyl-4-((3-(2-methylsulfanylpyrimidin-4-yl)-2-pyridyl)oxy)phenyl)methanesulfonamide (115 mg, 0.21 mmol) in dichloromethane (3 mL) was added 3-chloroperoxybenzoic acid (80 mg, 0.44 mmol), the mixture was stirred for 2 h at rt. The reaction was quenched with sat. sodium sulfite. The resulting solution was diluted with water, extracted with ethyl acetate, washed with brine, dried over sodium sulfate and concentrated. The residue was purified by silica flash chromatography eluting with ethyl acetate/petroleum ether (80%) to afford the title compound (120 mg, 94.7% yield) as an off-white solid. LCMS (ESI): [M+H]$^+$=590.1

Step 9: Benzyl (3S,5S)-3-((4-(2-(4-(((4-cyanophenyl)methyl)sulfonamido)-2,3,5-trifluoro-6-methylphenoxy)pyridin-3-yl)pyrimidin-2-yl)amino)-5-fluoropiperidine-1-carboxylate

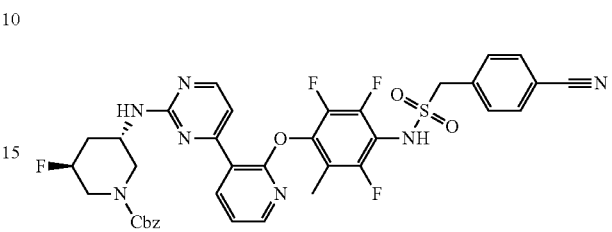

Under nitrogen, a mixture of benzyl (3S,5S)-3-amino-5-fluoro-piperidine-1-carboxylate (50 mg, 0.20 mmol), N,N-Diisopropylethylamine (70 mg, 0.54 mmol), 1-(4-cyanophenyl)-N-(2,3,6-trifluoro-5-methyl-4-((3-(2-methylsulfonylpyrimidin-4-yl)-2-pyridyl)oxy)phenyl)methanesulfonamide (180 mg, 0.18 mmol), caesium fluoride (85 mg, 0.56 mmol) in dimethyl sulfoxide (3 mL) was stirred at 90° C. for 2 h. The resulting solution was diluted with water, extracted with ethyl acetate, washed with brine, dried over sodium sulfate and concentrated. The residue was purified by silica flash chromatography eluting with ethyl acetate/petroleum ether (15%) to afford the title compound (100 mg, 68.8% yield) as an off-white solid. LCMS (ESI): [M+H]$^+$=762.2

Step 10: 1-(4-Cyanophenyl)-N-(2,3,6-trifluoro-4-((3-(2-(((3S,5S)-5-fluoropiperidin-3-yl)amino)pyrimidin-4-yl)pyridin-2-yl)oxy)-5-methylphenyl)methanesulfonamide Compound 255

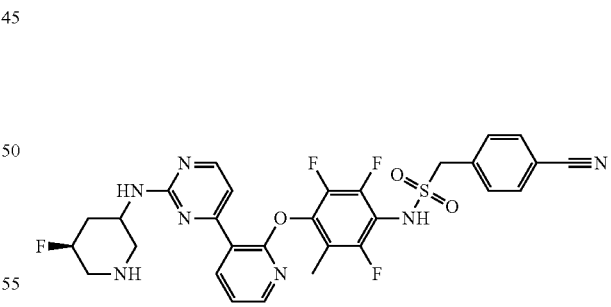

To a solution of benzyl (3S,5S)-3-((4-(2-(4-(((4-cyanophenyl)methyl)sulfonamido)-2,3,5-trifluoro-6-methylphenoxy)pyridin-3-yl)pyrimidin-2-yl)amino)-5-fluoropiperidine-1-carboxylate (95 mg, 0.12 mmol) in dichloromethane (1 mL) was added 33% hydrobromic acid in acetic acid (0.5 mL) and stirred at rt for 1 h. The solvent was removed under vacuum. The crude product was purified by Prep-HPLC to afford the title compound (22 mg, 27.2% yield) as a white solid.

Example 55

1-(Pyridin-3-yl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 256

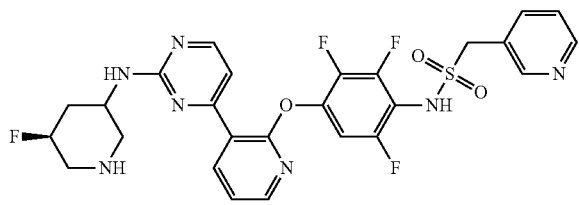 [SMILES: O=S(=O)(Cc1cccnc1)Nc1c(F)cc(Oc2ncccc2-c2ccnc(NC3CNC[C@@H](F)C3)n2)c(F)c1F]

The title compound was prepared according to example 40. This provides the title compound (26.1 mg, 53.4% yield) as a white solid.

Example 56

1-Phenyl-N-(2,3,6-trifluoro-4-((3-(2-(((3S,6S)-6-methylpiperidin-3-yl)amino)pyrimidin-4-yl)pyridin-2-yl)oxy)phenyl)methanesulfonamide Compound 257

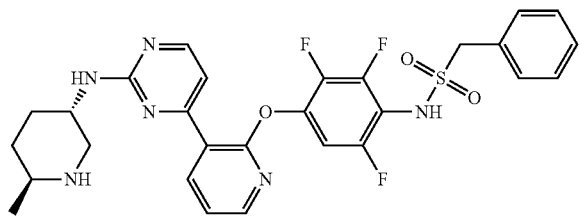 [SMILES: C[C@H]1CC[C@H](Nc2nccc(-c3cccnc3Oc3cc(F)c(NS(=O)(=O)Cc4ccccc4)c(F)c3F)n2)CN1]

Step 1: Benzyl (2S,5S)-2-methyl-5-((4-(2-(2,3,5-trifluoro-4-((phenylmethyl)sulfonamido)phenoxy)pyridin-3-yl)pyrimidin-2-yl)amino)piperidine-1-carboxylate

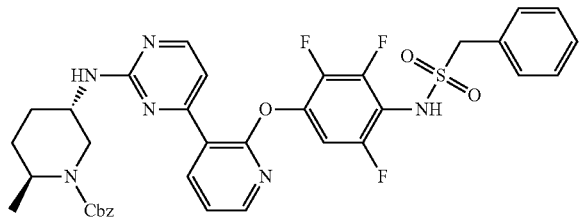 [SMILES: C[C@H]1CC[C@H](Nc2nccc(-c3cccnc3Oc3cc(F)c(NS(=O)(=O)Cc4ccccc4)c(F)c3F)n2)CN1C(=O)OCc1ccccc1]

Into the solution of 1-phenyl-N-(2,3,6-trifluoro-4-((3-(2-methylsulfonylpyrimidin-4-yl)-2-pyridyl)oxy)phenyl)methanesulfonamide (96 mg, 0.17 mmol) in dimethyl sulfoxide (1.5 mL) was added benzyl (2S,5S)-5-amino-2-methyl-piperidine-1-carboxylate hydrochloride (74 mg, 0.26 mmol), cesium fluoride (79 mg, 0.52 mmol) and N,N-Diisopropylethylamine (0.15 mL, 0.91 mmol). The mixture was stirred for 2.5 h at 90° C. under nitrogen. The mixture was diluted with ethyl acetate and washed with water. The solution was dried over sodium sulfate and concentrated under vacuum. The residue was purified by silica flash chromatography eluting with ethyl acetate/petroleum ether (20-70%) to afford the title compound (80 mg, 63.8% yield) as a light brown solid. LCMS (ESI): [M+H]$^+$=719.2

Step 2: 1-Phenyl-N-(2,3,6-trifluoro-4-((3-(2-(((3S,6S)-6-methylpiperidin-3-yl)amino)pyrimidin-4-yl)pyridin-2-yl)oxy)phenyl)methanesulfonamide Compound 257

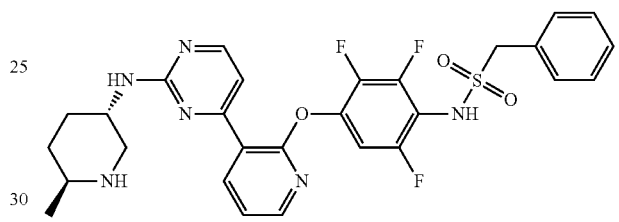

Into the solution of benzyl (2S,5S)-2-methyl-5-((4-(2-(2,3,5-trifluoro-4-((phenylmethyl)sulfonamido)phenoxy)pyridin-3-yl)pyrimidin-2-yl)amino)piperidine-1-carboxylate (80 mg, 0.11 mmol) in dichloromethane (3 mL) was added 33% HBr in acetic acid (3 mL). The mixture was stirred at rt for 0.5 h. The mixture was concentrated under vacuum. The residue was purified with Prep-HPLC to afford the title compound (27 mg, 41.5% yield) as a white solid.

Example 57

N-(2,3,6-Trifluoro-4-((3-(2-(((3S,5S)-5-fluoropiperidin-3-yl)amino)pyrimidin-4-yl)pyridin-2-yl)oxy)phenyl)pyrrolidine-1-sulfonamide Compound 258

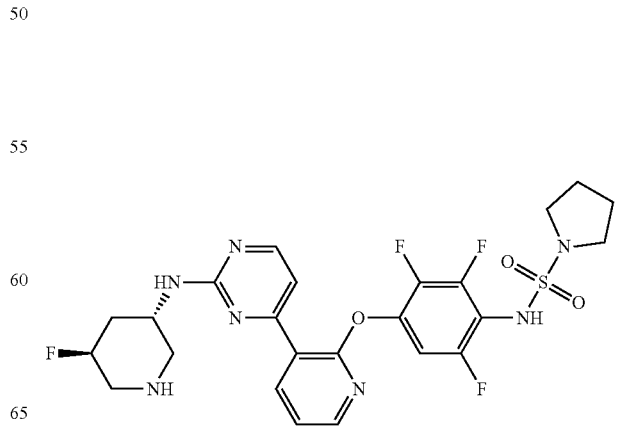

Step 1: N-(2,3,6-Trifluoro-4-((3-(2-(methylthio)pyrimidin-4-yl)pyridin-2-yl)oxy)phenyl)pyrrolidine-1-sulfonamide

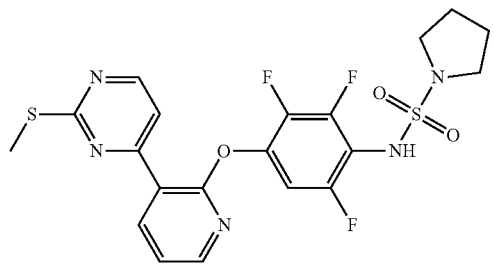 [SMILES: CSc1nccc(-c2cccnc2Oc2cc(F)c(NS(=O)(=O)N3CCCC3)c(F)c2F)n1]

To a solution of 2,3,6-trifluoro-4-((3-(2-methylsulfanylpyrimidin-4-yl)-2-pyridyl)oxy)aniline (0.16 g, 0.45 mmol) in pyridine (1.2 mL) was added pyrrolidine-1-sulfonyl chloride (0.76 g, 4.47 mmol), the mixture was stirred at 45° C. for 1 h. The resulting solution was diluted with water, extracted with ethyl acetate, washed with brine, dried over sodium sulfate and concentrated. The residue was purified by silica flash chromatography eluting with ethyl acetate/petroleum ether (1:1) to afford the title compound (120 mg, 47.4% yield) as a light brown solid. LCMS (ESI): [M+H]⁺= 498.1.

Step 2: N-(2,3,6-Trifluoro-4-((3-(2-(((3S,5S)-5-fluoropiperidin-3-yl)amino)pyrimidin-4-yl)pyridin-2-yl)oxy)phenyl)pyrrolidine-1-sulfonamide Compound 258

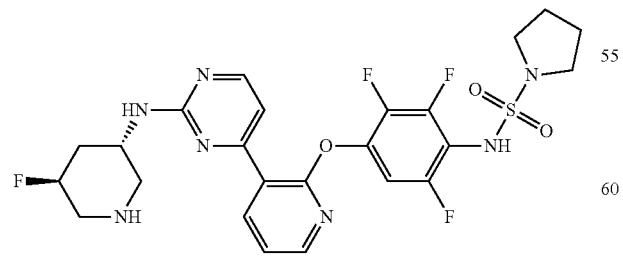

The title compound was prepared according to example 54. This provides the title compound (25.0 mg, 64.7% yield) as a white solid.

Example 58

1-Phenyl-N-(2,3,6-trifluoro-4-((3-(2-(((3S,5R)-5-fluoropiperidin-3-yl)amino)pyrimidin-4-yl)pyridin-2-yl)oxy)phenyl)methanesulfonamide Compound 259

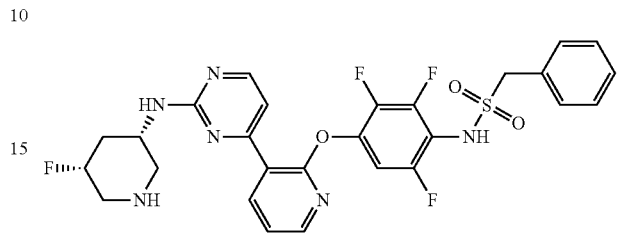

The title compound was prepared according to Example 40. This resulted in the title compound (14.9 mg, 19.2% yield) as a yellow solid.

Example 59

2,2,2-Trifluoro-N-(2,3,6-trifluoro-4-((3-(2-(((3S,5S)-5-fluoropiperidin-3-yl)amino)pyrimidin-4-yl)pyridin-2-yl)oxy)phenyl)ethane-1-sulfonamide hydrochloride Compound 260

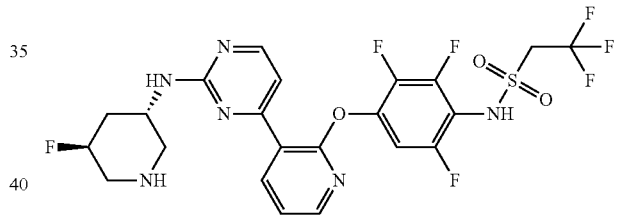

The title compound was prepared according to example 40. This resulted in the title compound (12.4 mg, 18% yield) as a white solid and as HCl salt.

Example 60

1-(1-Fluorocyclopropyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 261

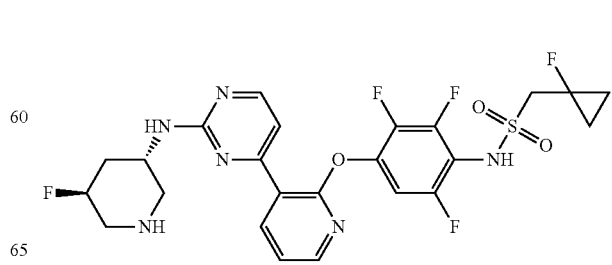

Example 61

1-Phenyl-N-(2,3,6-trifluoro-4-((3-(2-(((3S,5R)-5-(fluoromethyl)piperidin-3-yl)amino)pyrimidin-4-yl)pyridin-2-yl)oxy)phenyl)methanesulfonamide Compound 266

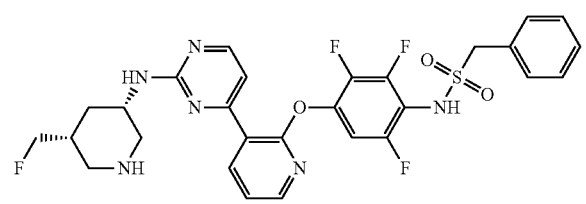

Step 1: tert-Butyl (3R,5S)-3-(fluoromethyl)-5-((4-(2-(2,3,5-trifluoro-4-((phenylmethyl)sulfonamido)phenoxy)pyridin-3-yl)pyrimidin-2-yl)amino)piperidine-1-carboxylate

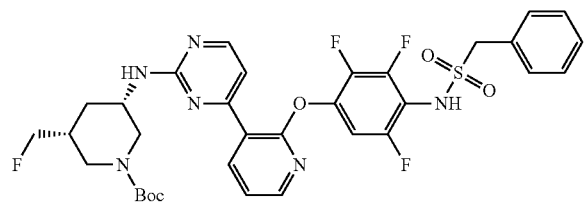

Under nitrogen, a mixture of 1-phenyl-N-(2,3,6-trifluoro-4-((3-(2-methylsulfonylpyrimidin-4-yl)-2-pyridyl)oxy)phenyl)methanesulfonamide (110 mg, 0.20 mmol), N,N-Diisopropylethylamine (50 mg, 0.39 mmol), tert-butyl (3S,5R)-3-amino-5-(fluoromethyl)piperidine-1-carboxylate (40 mg, 0.17 mmol) and caesium fluoride (70 mg, 0.46 mmol) in dimethyl sulfoxide (2 mL) was stirred at 90° C. for 2 h under nitrogen. The resulting solution was diluted with water, extracted with ethyl acetate, washed with brine, dried over Sodium sulfate and concentrated. The residue was purified by silica flash chromatography eluting with ethyl acetate/petroleum ether (80%) to afford the title compound (95 mg, 40.8% yield) as an off-white solid. LCMS (ESI): [M+H]$^+$= 703.2

Step 2: 1-Phenyl-N-(2,3,6-trifluoro-4-((3-(2-(((3S,5R)-5-(fluoromethyl)piperidin-3-yl)amino)pyrimidin-4-yl)pyridin-2-yl)oxy)phenyl)methanesulfonamide Compound 266

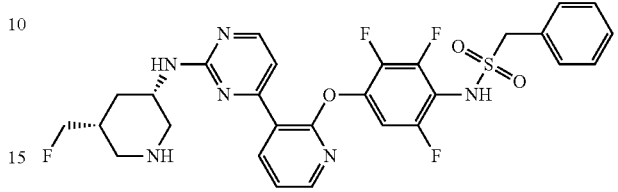

To a solution of tert-Butyl (3S,5S)-3-(fluoromethyl)-5-((4-(2-(2,3,5-trifluoro-4-((phenylmethyl)sulfonamido)phenoxy)pyridin-3-yl)pyrimidin-2-yl)amino)piperidine-1-carboxylate (90 mg, 0.07 mmol) in dichloromethane (0.5 mL) was added 4 M HCl in dioxane (1 mL) and stirred at rt for 1 h. The solvent was concentrated under vacuum. The crude product was purified by Prep-HPLC to afford the title compound (21 mg, 51.3% yield) as a white solid.

Example 62

N-(2,3,6-Trifluoro-4-((3-(2-(((3S,5S)-5-fluoropiperidin-3-yl)amino)pyrimidin-4-yl)pyridin-2-yl)oxy)phenyl)piperidine-1-sulfonamide Compound 263

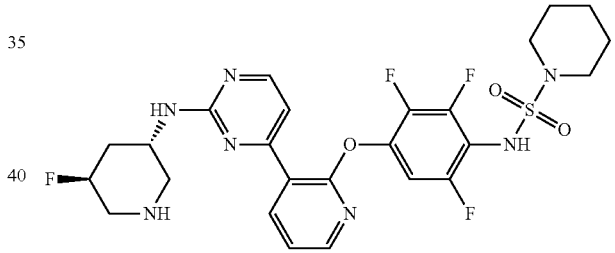

The title compound was prepared according to example 57. This resulted in the title compound (17.8 mg, 30.7% yield) as a white solid.

Example 63

1-(2,2-Difluorocyclobutyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 264 & Compound 265

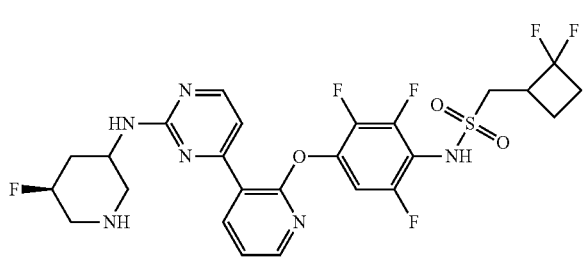 [SMILES: O=S(=O)(CC1CCC1(F)F)Nc1c(F)cc(Oc2ncccc2-c2ccnc(NC3CNC[C@@H](F)C3)n2)c(F)c1F]

The title compound was prepared according to Example 40. This resulted in the title compound (37.7 mg, 23.3% yield) as a white solid.

The title compound was prepared according to example 40. The residue was purified by Prep-HPLC and Chiral HPLC to afford the title compound. After Chiral HPLC, two peaks were isolated out. The fast peak was assigned isomer 1. The slow peak was assigned isomer 2.

1-(2,2-Difluorocyclobutyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide (isomer 1, Compound 264) (15.2 mg, 17% yield) as a white solid, (rt=2.039 min (CHIRALPAKIG-3, 0.46*5 cm; 3.5 um, MtBE (0.2% IPAmine): MeOH=90:10, 1.0 ml/min).

1-(2,2-Difluorocyclobutyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide (isomer 2, Compound 265) (13.5 mg, 12% yield) as a white solid, (rt=3.503 min (CHIRALPAK IG-3, 0.46*5 cm; 3.5 um, MtBE (0.2% IPAmine): MeOH=90:10, 1.0 ml/min)

Example 64

4-(2-(4-(Dimethylsulfamoylamino)-2,3,5-trifluoro-phenoxy)-3-pyridyl)-2-(((3S,5S)-5-fluoro-3-piperidyl)amino)pyrimidine Compound 266

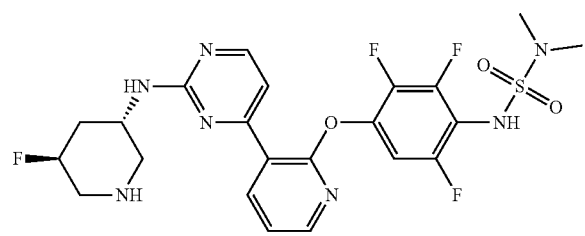 [SMILES: CN(C)S(=O)(=O)Nc1c(F)cc(Oc2ncccc2-c2ccnc(N[C@@H]3CNC[C@@H](F)C3)n2)c(F)c1F]

Step 1: Benzyl (3S,5S)-3-((4-(2-(4-((N,N-dimethylsulfamoyl)amino)-2,3,5-trifluorophenoxy)pyridin-3-yl)pyrimidin-2-yl)amino)-5-fluoropiperidine-1-carboxylate

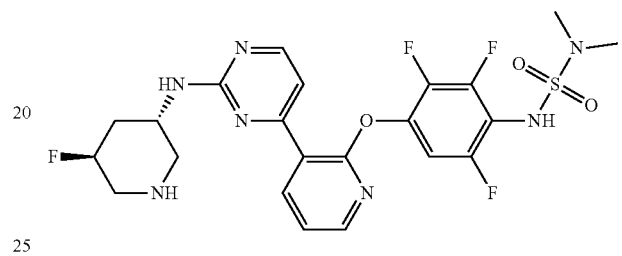

Under nitrogen, a solution of benzyl (3S,5S)-3-((4-(2-(4-amino-2,3,5-trifluoro-phenoxy)-3-pyridyl)pyrimidin-2-yl)amino)-5-fluoro-piperidine-1-carboxylate (0.12 g, 0.20 mmol) in pyridine (0.25 mL) was added 4-dimethylaminopyridine (0.05 g, 0.2 mmol) and dimethylsulfamoyl chloride (0.1 g, 0.50 mmol) at 20° C. The resulting solution was stirred for 48 h at 80° C. The reaction was quenched with water and extracted with ethyl acetate and the organic layers were combined. The organic layer was dried over anhydrous sodium sulfate and concentrated under vacuum. The residue was purified by silica flash chromatography eluting with ethyl acetate/petroleum ether (2/1) to afford the title compound (50 mg, 36% yield) as a yellow solid. LCMS (ESI): [M+H]$^+$=676.5.

Step 4: 4-(2-(4-(Dimethylsulfamoylamino)-2,3,5-trifluoro-phenoxy)-3-pyridyl)-2-(((3S,5S)-5-fluoro-3-piperidyl)amino)pyrimidine Compound 266

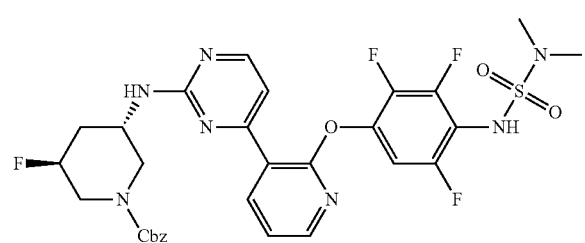 [SMILES: CN(C)S(=O)(=O)Nc1c(F)cc(Oc2ncccc2-c2ccnc(N[C@H]3C[C@H](F)CN(C(=O)OCc4ccccc4)C3)n2)c(F)c1F]

A solution of benzyl (3S,5S)-3-((4-(2-(4-((N,N-dimethylsulfamoyl)amino)-2,3,5-trifluorophenoxy)pyridin-3-yl)pyrimidin-2-yl)amino)-5-fluoropiperidine-1-carboxylate (0.05 g, 0.07 mmol) in acetonitrile (1 mL) and dichloromethane (1 mL) was added dimethyl sulfide (1 mL) and boron trifluoride etherate (1 mL) at 0° C. The resulting solution was stirred for 1 h at 0° C. The reaction was quenched with sat. sodium carbonate and extracted with dichloromethane. The organic layers were combined. The organic layer was dried over anhydrous sodium sulfate and concentrated under vacuum. The crude product was purified by Prep-HPLC to afford the title compound (15.2 mg, 42.1% yield) as a white solid.

Example 65

2-Cyclopropyl-N-(2,3,6-trifluoro-4-((3-(2-(((3S,5S)-5-fluoropiperidin-3-yl)amino)pyrimidin-4-yl)pyridin-2-yl)oxy)phenyl)ethane-1-sulfonamide Compound 267

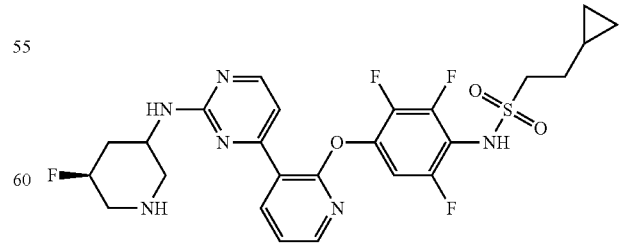

The title compound was prepared according to example 40. This provides the title compound (34.8 mg, 39.1% yield) as a white solid.

Example 66

2,2-Difluoro-N-(2,3,6-trifluoro-4-((5-fluoro-3-(2-(((3S,5S)-5-fluoropiperidin-3-yl)amino)pyrimidin-4-yl)pyridin-2-yl)oxy)phenyl)butane-1-sulfonamide Compound 268

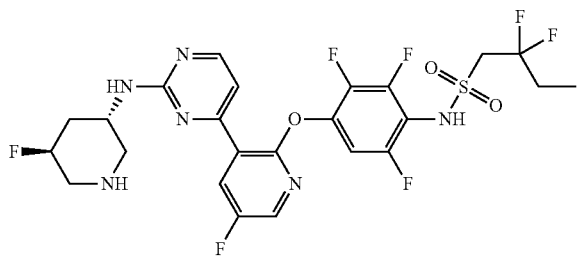 [SMILES: CCC(F)(F)CS(=O)(=O)Nc1c(F)cc(Oc2ncc(F)cc2-c2ccnc(N[C@@H]3CNC[C@@H](F)C3)n2)c(F)c1F]

The title compound was prepared according to example 40. This provides the title compound (20.0 mg, 38.4% yield) as a white solid.

Example 67

4-(2-(4-((Ethyl(methyl)sulfamoyl)amino)-2,3,5-trifluoro-phenoxy)-3-pyridyl)-2-(((3S,5S)-5-fluoro-3-piperidyl)amino)pyrimidine Compound 269

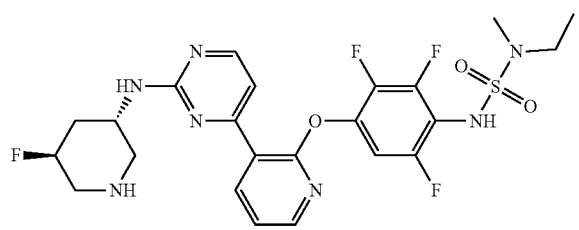 [SMILES: CCN(C)S(=O)(=O)Nc1c(F)cc(Oc2ncccc2-c2ccnc(N[C@@H]3CNC[C@@H](F)C3)n2)c(F)c1F]

The title compound was prepared according to example 64. This provides the title compound (17.0 mg, 42.2% yield) as a white solid.

Example 68

2,2-Difluoro-N-(2,3,6-trifluoro-4-((3-(2-(((3S,5S)-5-fluoropiperidin-3-yl)amino)pyrimidin-4-yl)-6-methylpyridin-2-yl)oxy)phenyl)butane-1-sulfonamide Compound 270

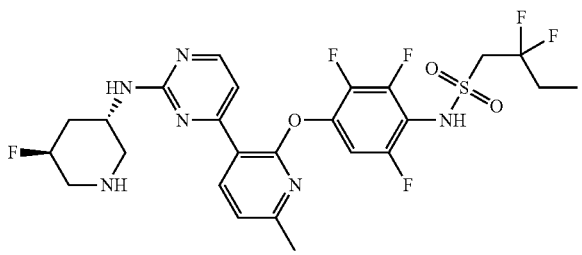 [SMILES: CCC(F)(F)CS(=O)(=O)Nc1c(F)cc(Oc2nc(C)ccc2-c2ccnc(N[C@@H]3CNC[C@@H](F)C3)n2)c(F)c1F]

The title compound was prepared according to example 40. This resulted in the title compound (3.5 mg, 5% yield) as an off-white solid.

Example 69

1-(2,2-Difluorocyclopropyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 271

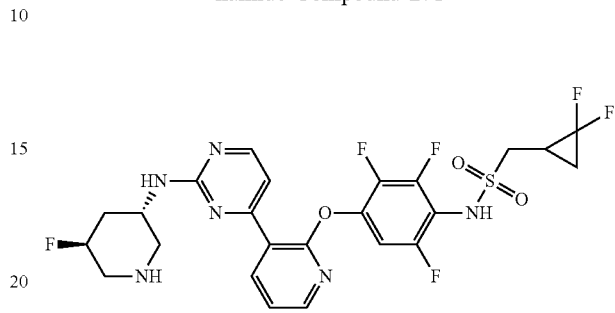

The title compound was prepared according to example 40. This resulted in the title compound (90 mg, 92.1% yield) as a brown solid.

Example 70

N-(4-((3-(2-(((1r,4r)-4-(Dimethylamino)cyclohexyl)amino)pyrimidin-4-yl)pyridin-2-yl)oxy)-2,3,6-trifluorophenyl)-1-phenylmethanesulfonamide hydrochloride Compound 272

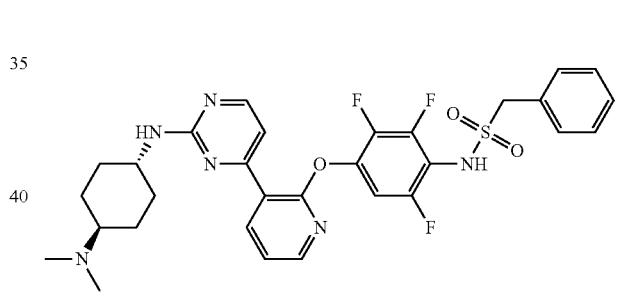

The title compound was prepared according to example 38. This provides the title compound (29 mg, 35.1% yield) as a light yellow solid and as HCl salt.

Example 71

N-(2,3-Difluoro-4-((3-(2-(((S)-piperidin-3-yl)amino)pyrimidin-4-yl)pyridin-2-yl)oxy)phenyl)-N'-methyl-1-phenylmethanesulfonimidamide Compound 273 & Compound 274

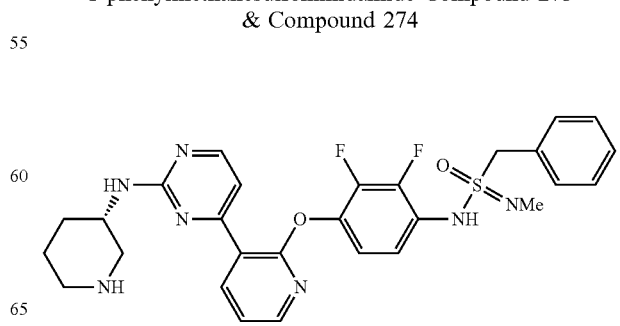

Step 1: N-(4-Bromo-2,3-difluorophenyl)-1-phenyl-methanesulfonamide

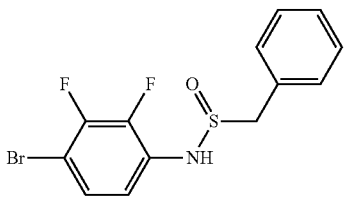 [SMILES: O=S(Cc1ccccc1)Nc1ccc(Br)c(F)c1F]

Under nitrogen, to a solution of 4-bromo-2,3-difluoroaniline (2.0 g, 9.62 mmol) in toluene (20 mL) was added thionylchloride (1.5 mL, 20.68 mmol) and stirred for 2 h at 90° C. The solvent was removed under vacuum. The residue was dissolved in dry tetrahydrofuran (20 mL) and 1 M benzylmagnesiumbromide in tetrahydrofuran (15 mL) was added at 0° C. The resulting solution was stirred for 16 h at rt. The reaction was quenched with methanol. The resulting solution was diluted with water, extracted with ethyl acetate, washed with brine, dried over sodium sulfate and concentrated. The residue was purified by silica flash chromatography eluting with ethyl acetate/petroleum ether (1:1) to afford the title compound (2.5 g, 67.6% yield) as an off-white solid. LCMS (ESI): $[M+H]^+=347.0$

Step 2: N-(Bromo-2,3-difluorophenyl)-N'-methyl-1-phenylmethanesulfonimidamide

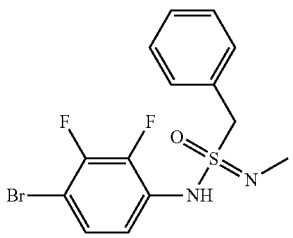 [SMILES: CN=S(=O)(Cc1ccccc1)Nc1ccc(Br)c(F)c1F]

Under nitrogen, a solution of N-(4-bromo-2,3-difluorophenyl)-1-phenyl-methanesulfinamide (600 mg, 1.73 mmol) in Carbon tetrachloride (12 mL) was added tert-butyl hypochlorite (0.4 mL, 3.56 mmol) at 0° C. and stirred for 2 h at the same temperature. Then 2 M methylamine in tetrahydrofuran (5 mL) was added into the mixture and stirred for 2 h at 0° C. The reaction was quenched with brine and extracted with ethyl acetate. The solvent was removed under vacuum. The residue was purified by silica flash chromatography eluting with ethyl acetate/petroleum ether (1/1) to afford the title compound (330 mg, 45.7% yield) as a yellow solid. LCMS (ESI): $[M+H]^+=375.0$.

Step 3: N-(2,3-Difluoro-4-(4,4,5,5-tetramethyl-1,3,2-dioxaborolan-2-yl)phenyl)-N'-methyl-1-phenyl-methanesulfonimidamide

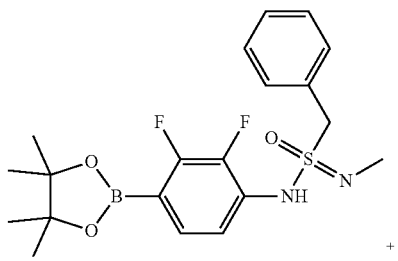

Under nitrogen, a solution of N-(4-bromo-2,3-difluorophenyl)-N'-methyl-1-phenylmethanesulfonimidamide (280 mg, 0.75 mmol), bis(pinacolato)diboron (380 mg, 1.50 mmol), Potassium Acetate (190 mg, 1.94 mmol) and (1,1'-bis(diphenylphosphino)ferrocene)dichloropalladium(II) (100 mg, 0.13 mmol) in 1,4-dioxane (6 mL) was stirred for 2 h at 90° C. The solvent was removed under vacuum to afford the title compound (800 mg, 76.2% yield) as a brown solid. The crude product would be directly used in the next step without purification. LCMS (ESI): $[M+H]^+=423.2$

Step 4: N-(2,3-Difluoro-4-hydroxyphenyl)-N'-methyl-1-phenylmethanesulfonimidamide

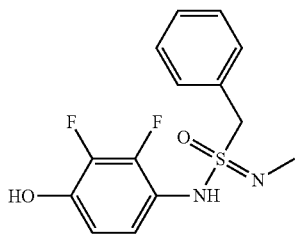

To a solution of N-(2,3-difluoro-4-(4,4,5,5-tetramethyl-1,3,2-dioxaborolan-2-yl)phenyl)-N'-methyl-1-phenylmethanesulfonimidamide (800 mg, 0.57 mmol) in tetrahydrofuran (6 mL) was added sodium hydroxide in water (2 mL, 2M) and hydrogen peroxide (230 mg, 2.03 mmol), then stirred at rt for 0.5 h. The reaction was quenched with sat. sodium sulfite. The resulting solution was diluted with water, extracted with ethyl acetate, washed with brine, dried over sodium sulfate and concentrated. The residue was purified by silica flash chromatography eluting with dichloromethane/methanol (97:3) to afford the title compound (130 mg, 65.9% yield) as a brown solid. LCMS (ESI): $[M+H]^+=313.1$.

Step 5: tert-Butyl (3S)-3-((4-(2-(2,3-difluoro-4-((N'-methyl-1-phenylmethyl)sulfonoamidimidamido)phenoxy)pyridin-3-yl)pyrimidin-2-yl)amino)piperidine-1-carboxylate

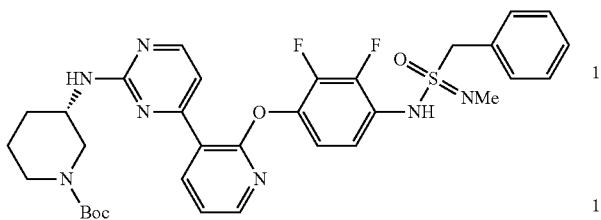

A mixture of N-(2,3-difluoro-4-hydroxyphenyl)-N-methyl-1-phenylmethanesulfonimidamide (170 mg, 0.49 mmol), tert-butyl (3S)-3-((4-(2-fluoro-3-pyridyl)pyrimidin-2-yl)amino)piperidine-1-carboxylate (250 mg, 0.67 mmol) and cesium carbonate (306 mg, 0.94 mmol) in dimethyl sulfoxide (4 mL) was stirred at 80° C. for 1 h. The resulting solution was diluted with water, extracted with ethyl acetate, washed with brine, dried over sodium sulfate and concentrated. The residue was purified by silica flash chromatography eluting with ethyl acetate/petroleum ether (1/1) to afford the title compound (230 mg, 66.3% yield) as a brown solid. LCMS (ESI): [M+H]$^+$=666.3

Step 6: N-(2,3-Difluoro-4-((3-(2-(((S)-piperidin-3-yl)amino)pyrimidin-4-yl)pyridin-2-yl)oxy)phenyl)-N'-methyl-1-phenylmethanesulfonimidamide & N-(2,3-difluoro-4-((3-(2-(((S)-piperidin-3-yl)amino)pyrimidin-4-yl)pyridin-2-yl)oxy)phenyl)-N'-methyl-1-phenylmethanesulfonimidamide Compound 273 & Compound 274

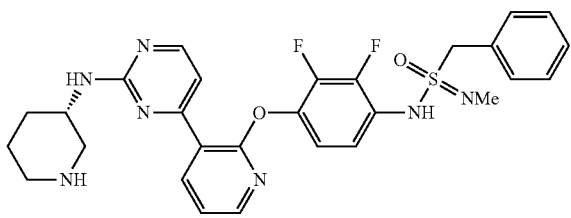

A solution of tert-butyl (3S)-3-((4-(2-(4-((S-benzyl-N-methyl-sulfonimidoyl)amino)-2,3-difluoro-phenoxy)-3-pyridyl)pyrimidin-2-yl)amino)piperidine-1-carboxylate (300 mg, 0.45 mmol) in dichloromethane (2 mL) was added 4 M HCl in dioxane (1 mL) dropwise and stirred at rt for 1 h. The solvent was concentrated under vacuum. The residue was purified by Prep-HPLC and Chiral HPLC to afford the title compound. After Chiral HPLC, two peaks were isolated out. The fast peak was assigned isomer 1. The slow peak was assigned isomer 2.

N-(2,3-difluoro-4-((3-(2-(((S)-piperidin-3-yl)amino)pyrimidin-4-yl)pyridin-2-yl)oxy)phenyl)-N'-methyl-1-phenylmethanesulfonimidamide (isomer 1, Compound 273) (45.3 mg, 17.6% yield) as a white solid, (rt=5.122 min, CHIRAL-PAKIG-3, 0.46*5 cm, 3 um, MtBE (0.1% DEA):EtOH=70:30, 1.0 ml/min).

N-(2,3-difluoro-4-((3-(2-(((S)-piperidin-3-yl)amino)pyrimidin-4-yl)pyridin-2-yl)oxy)phenyl)-N'-methyl-1-phenylmethanesulfonimidamide (isomer 2, Compound 274) (31.0 mg, 12% yield) as a white solid, (rt=8.972 min, CHIRAL-PAK IG-3, 0.46*5 cm, 3 um, MtBE (0.1% DEA):EtOH=70:30, 1.0 ml/min).

Example 72

1-(2-Fluorophenyl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide Compound 275

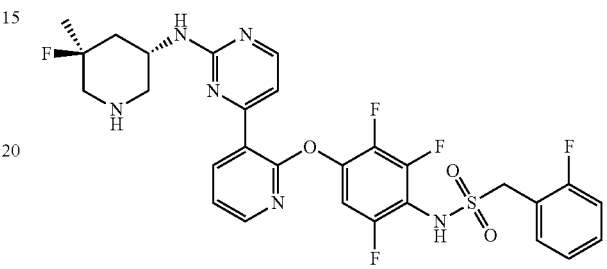

The title compound was prepared according to example 42. This resulted in the title compound (19.5 mg, 50.5% yield) as a white solid.

Example 73

1-(4-((3-(2-(((3S,5S)-5-Fluoropiperidin-3-yl)amino)pyrimidin-4-yl)pyridin-2-yl)oxy)phenyl)-3-(3-(trifluoromethyl)phenyl)urea Compound 276

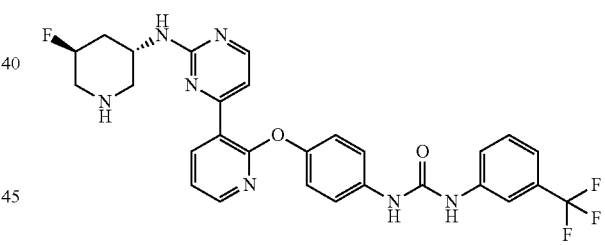

Step 1: Benzyl (3S,5S)-3-fluoro-5-((4-(2-(4-(3-(3-(trifluoromethyl)phenyl)ureido)phenoxy)pyridin-3-yl)pyrimidin-2-yl)amino)piperidine-1-carboxylate

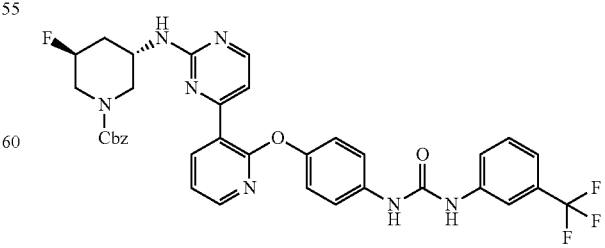

Under nitrogen, a solution of benzyl (3S,5S)-3-((4-(2-(4-aminophenoxy)-3-pyridyl)pyrimidin-2-yl)amino)-5-fluoropiperidine-1-carboxylate (70 mg, 0.14 mmol) in dichloromethane (2 mL) was added 3-(trifluoromethyl)phenyl isocyanate (50 mg, 0.27 mmol) and stirred for 1 h at rt. The reaction mixture was diluted with water and extracted with ethyl acetate. The organic layers were combined. The organic layer was dried over anhydrous sodium sulfate and concentrated under vacuum. The residue was purified by silica flash chromatography eluting with ethyl acetate/petroleum ether (½) to afford the title compound (47 mg, 49.2% yield) as a brown solid. LCMS (ESI): [M+H]⁺=702.3.

Step 2: 1-(4-((3-(2-(((3S,5S)-5-Fluoropiperidin-3-yl)amino)pyrimidin-4-yl)pyridin-2-yl)oxy)phenyl)-3-(3-(trifluoromethyl)phenyl)urea Compound 276

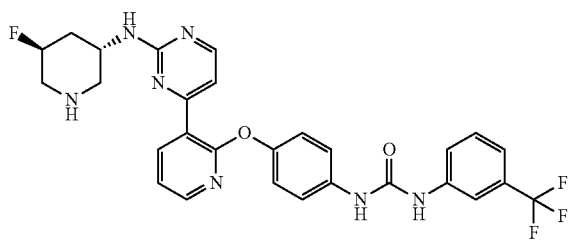 [SMILES: O=C(Nc1ccc(Oc2ncccc2-c2ccnc(N[C@@H]3CNC[C@@H](F)C3)n2)cc1)Nc1cccc(C(F)(F)F)c1]

A solution of benzyl (3S,5S)-3-fluoro-5-((4-(2-(4-(3-(3-(trifluoromethyl)phenyl)ureido)phenoxy)pyridin-3-yl)pyrimidin-2-yl)amino)piperidine-1-carboxylate (30 mg, 0.04 mmol) in dichloromethane (1 mL) was added 33% HBr in acetic acid (0.5 mL) and stirred for 0.5 h at rt. The solvent was removed under vacuum. The residue was purified by Prep-HPLC to afford the title compound (12.9 mg, 53.2% yield) as a white solid.

Example 74

1-Phenyl-N-(2,3,6-trifluoro-4-((3-(2-((5-(fluoromethyl)piperidin-3-yl)amino)pyrimidin-4-yl)pyridin-2-yl)oxy)phenyl)methanesulfonamide Compound 277 & Compound 278

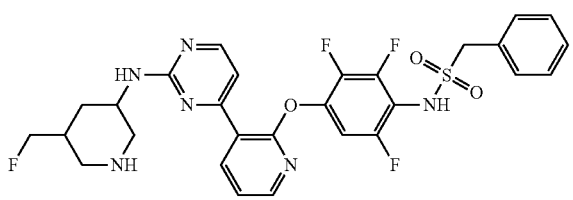

Step 1: 1-(tert-Butyl) 3-methyl 5-((methylsulfonyl)oxy)piperidine-1,3-dicarboxylate

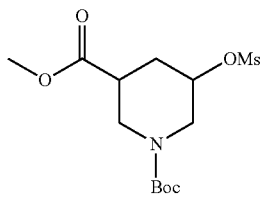 [SMILES: COC(=O)C1CC(OS(C)(=O)=O)CN(C(=O)OC(C)(C)C)C1]

A solution of 1-tert-butyl 3-methyl 5-hydroxypiperidine-1,3-dicarboxylate (1.0 g, 3.86 mmol), triethylamine (1.6 mL, 11.53 mmol) in dichloromethane (20 mL) was added methane sulfonyl chloride (0.4 mL, 5.17 mmol) at 0° C. and stirred for 1 h at rt. The reaction mixture was quenched with water and extracted with ethyl acetate and the organic layers were combined. The organic layer was washed by brine and dried over anhydrous sodium sulfate and concentrated under vacuum to afford the title compound (1.2 g, 83% yield) as colorless oil. LCMS (ESI): [M+H−56]⁺=282.1.

Step 2: 1-(tert-Butyl) 3-methyl 5-azidopiperidine-1,3-dicarboxylate

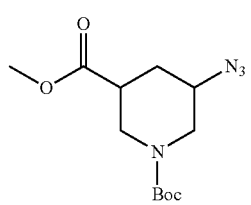 [SMILES: COC(=O)C1CC(N=[N+]=[N-])CN(C(=O)OC(C)(C)C)C1]

A solution of 1-(tert-Butyl) 3-methyl 5-((methylsulfonyl)oxy)piperidine-1,3-dicarboxylate (1.38 g, 3.68 mmol) and sodium azide (360 mg, 5.54 mmol) in N,N-dimethylformamide (16 mL) was stirred for 4 h at 80° C. The reaction was quenched with water and extracted with ethyl acetate. The combined organic was washed with brine and the organic layer was concentrated under vacuum to afford the title compound (1.0 g, 86% yield) as a yellow oil. LCMS (ESI): [M+H]⁺=285.2.

Step 3: 1-(tert-Butyl) 3-methyl 5-aminopiperidine-1,3-dicarboxylate

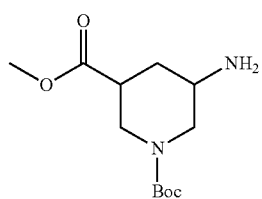 [SMILES: COC(=O)C1CC(N)CN(C(=O)OC(C)(C)C)C1]

Under hydrogen, a mixture of 1-(tert-butyl) 3-methyl 5-azidopiperidine-1,3-dicarboxylate (1.40 g, 3.45 mmol), 10% Pd/C (0.30 g, 0.28 mmol) in methanol (30 mL) was stirred at for 2 h at rt. After filtration, the filtration was concentrated under vacuum to afford the title compound (1.2 g, 94.3% yield) as colorless oil. LCMS (ESI): [M+H]⁺=259.1.

Step 4: 1-(tert-Butyl) 3-methyl 5-(((benzyloxy)carbonyl)amino)piperidine-1,3-dicarboxylate

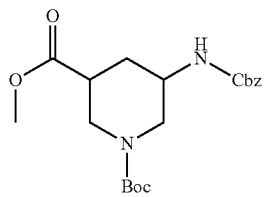 [SMILES: COC(=O)C1CC(NC(=O)OCc2ccccc2)CN(C(=O)OC(C)(C)C)C1]

To a solution of sodium bicarbonate (1.05 g, 12.5 mmol) and 1-(tert-Butyl) 3-methyl 5-aminopiperidine-1,3-dicarboxylate (1.0 g, 2.71 mmol) in tetrahydrofuran (12.5 mL) was added benzyl chloroformate (0.7 g, 4.1 mmol) dropwise and stirred at rt for 4 h. The reaction was quenched with ice water and extracted with ethyl acetate. The organic layer was dried over anhydrous sodium sulfate and concentrated under vacuum. The residue was purified by silica flash chromatography eluting with methanol/dichloromethane (3%) to afford the title compound (0.86 g, 76.8% yield) as a colorless oil. LCMS (ESI): [M+H−56]$^+$=337.2

Step 5: tert-Butyl 3-(((benzyloxy)carbonyl)amino)-5-(hydroxymethyl)piperidine-1-carboxylate

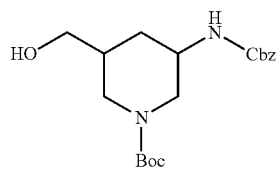 [SMILES: CC(C)(C)OC(=O)N1CC(CO)CC(NC(=O)OCc2ccccc2)C1]

To a solution of 1-(tert-butyl) 3-methyl 5-(((benzyloxy)carbonyl)amino)piperidine-1,3-dicarboxylate (860 mg, 2.19 mmol) in tetrahydrofuran (15 mL) was added sodium borohydride (210 mg, 5.55 mmol) slowly at 0° C. The resulting solution was stirred at rt for 24 h. The reaction was quenched with water and extracted with ethyl acetate, the organic layers were combined. The organic layer was dried over anhydrous sodium sulfate and concentrated under vacuum. The residue was purified by silica flash chromatography eluting with methanol/dichloromethane (6%) to afford the title compound (650 mg, 77.3% yield) as colorless oil. LCMS (ESI): [M+H]$^+$=365.2

Step 6: tert-Butyl 3-(((benzyloxy)carbonyl)amino)-5-(fluoromethyl)piperidine-1-carboxylate

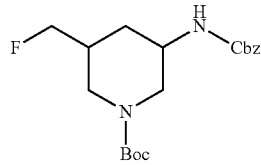 [SMILES: CC(C)(C)OC(=O)N1CC(CF)CC(NC(=O)OCc2ccccc2)C1]

A solution of tert-butyl 3-(benzyloxycarbonylamino)-5-(hydroxymethyl)piperidine-1-carboxylate (1.20 g, 3.29 mmol) in toluene (20 mL) was added 1,8-diazabicyclo[5.4.0]undec-7-ene (1.72 mL, 11.51 mmol) at 0° C. Then pyridine-2-sulfonyl fluoride (1.10 g, 6.83 mmol) was added. Then the reach CHI was stirred at 50° C. for 16 h. The reaction mixture was diluted with water and extracted with ethyl acetate, the organic layers were combined. The organic layer was dried over anhydrous sodium sulfate and concentrated under vacuum. The residue was purified by silica flash chromatography eluting with methanol/dichloromethane (6%) to afford the title compound (850 mg, 42.3% yield) as a colorless oil. LCMS (ESI): [M+H]$^+$=367.2.

Step 7: tert-Butyl 3-amino-5-(fluoromethyl)piperidine-1-carboxylate

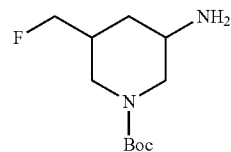 [SMILES: CC(C)(C)OC(=O)N1CC(N)CC(CF)C1]

Under hydrogen, a mixture of tert-butyl 3-(fluoromethyl)-5-(phenoxycarbonylamino)piperidine-1-carboxylate (700 mg, 1.99 mmol), 10% Pd/C (155 mg, 0.15 mmol) in methanol (10 mL) was stirred at rt for 24 h. After filtration, the filtration was concentrated under vacuum to afford the title compound (450 mg, 97.5% yield) as a white solid. LCMS (ESI): [M+H]$^+$=233.2.

Step 8: tert-Butyl 3-(fluoromethyl)-5-((4-(2-(2,3,5-trifluoro-4-((phenylmethyl)sulfonamido)phenoxy)pyridin-3-yl)pyrimidin-2-yl)amino)piperidine-1-carboxylate

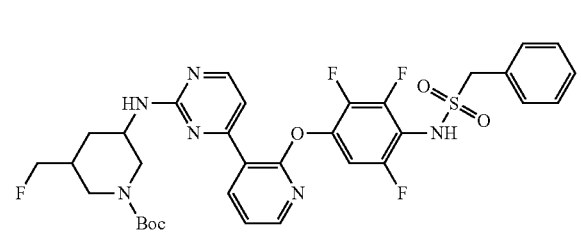 [SMILES: CC(C)(C)OC(=O)N1CC(CF)CC(Nc2nccc(-c3cccnc3Oc3cc(F)c(NS(=O)(=O)Cc4ccccc4)c(F)c3F)n2)C1]

Under nitrogen, a solution of 1-phenyl-N-(2,3,6-trifluoro-4-((3-(2-methylsulfonylpyrimidin-4-yl)-2-pyridyl)oxy)phenyl)methanesulfonamide (450 mg, 0.82 mmol), tert-butyl 3-amino-5-(fluoromethyl)piperidine-1-carboxylate (230 mg, 0.99 mmol), cesium fluoride (900 mg, 5.92 mmol) and N,N-diisopropylethylamine (90 mg, 0.70 mmol) in dimethyl sulfoxide (11 mL) was stirred at 60° C. for 16 h. The reaction mixture was diluted with water and extracted with ethyl acetate. The organic layer was concentrated under vacuum. The residue was purified by silica flash chromatography eluting with methanol/dichloromethane (5%) to afford the title compound (450 mg, 47% yield) as a brown solid. LCMS (ESI): [M+H]$^+$=703.2

Step 9: 1-Phenyl-N-(2,3,6-trifluoro-4-((3-(2-((5-(fluoromethyl)piperidin-3-yl)amino)pyrimidin-4-yl)pyridin-2-yl)oxy)phenyl)methanesulfonamide & 1-phenyl-N-(2,3,6-trifluoro-4-((3-(2-((5-(fluoromethyl)piperidin-3-yl)amino)pyrimidin-4-yl)pyridin-2-yl)oxy)phenyl)methanesulfonamide Compound 277 & Compound 278

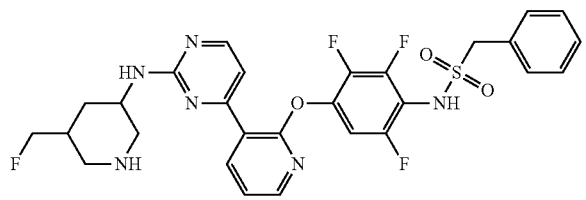

A solution of tert-Butyl 3-(fluoromethyl)-5-((4-(2-(2,3,5-trifluoro-4-((phenylmethyl)sulfonamido)phenoxy)pyridin-3-yl)pyrimidin-2-yl)amino)piperidine-1-carboxylate (400 mg, 0.34 mmol) in dichloromethane (8 mL) was added 4 M HCl in dioxane (12 mL, 48 mmol) dropwise and stirred at rt for 1 h. The solvent was concentrated under vacuum. The residue was purified by Prep-HPLC and Chiral HPLC. After Chiral HPLC, two peaks were isolated out. The fast peak was assigned isomer 1. The slow peak was assigned isomer 2.

1-Phenyl-N-(2,3,6-trifluoro-4-((3-(2-((5-(fluoromethyl)piperidin-3-yl)amino)pyrimidin-4-yl)pyridin-2-yl)oxy)phenyl)methanesulfonamide (isomer 1, Compound 277) (7.8 mg, 3.7%) as a white solid, (rt=17.64 min, CHIRALPAK IG, 0.46*5 cm; 3 um; Hex (0.1% DEA):EtOH=50:50; 1.0 ml/min). Compound 277 & Compound 278 are enantiomers.

1-Phenyl-N-(2,3,6-trifluoro-4-((3-(2-((5-(fluoromethyl)piperidin-3-yl)amino)pyrimidin-4-yl)pyridin-2-yl)oxy)phenyl)methanesulfonamide (isomer 2, Compound 278) (7.5 mg, 3.6%) as a white solid, (rt=4.293 min, CHIRALPAK IG, 0.46*5 cm; 3 um; Hex (0.1% DEA):EtOH=50:50; 1.0 ml/min). Compound 277 & Compound 278 are enantiomers.

Example 75

N-(2,3-Difluoro-4-((3-(2-(((3S,5S)-5-fluoro-5-methylpiperidin-3-yl)amino)pyrimidin-4-yl)pyridin-2-yl)oxy)-6-methylphenyl)-1-phenylmethanesulfonamide Compound 279

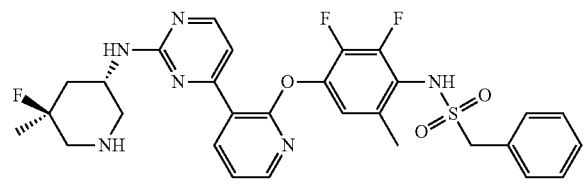 [SMILES: Cc1cc(Oc2ncccc2-c2ccnc(N[C@@H]3CNC[C@@](C)(F)C3)n2)c(F)c(F)c1NS(=O)(=O)Cc1ccccc1]

The title compound was prepared according to example 42. This resulted in the title compound (20.3 mg, 40.4% yield) as a white solid.

Example 76

N-(2,3-Difluoro-4-((3-(2-(((3S,5S)-5-fluoropiperidin-3-yl)amino)pyrimidin-4-yl)pyridin-2-yl)oxy)-6-methylphenyl)-1-phenylmethanesulfonamide Compound 280

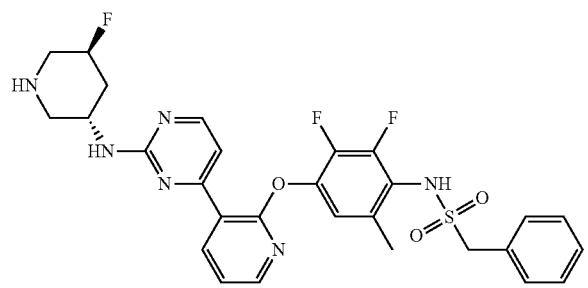 [SMILES: Cc1cc(Oc2ncccc2-c2ccnc(N[C@@H]3CNC[C@@H](F)C3)n2)c(F)c(F)c1NS(=O)(=O)Cc1ccccc1]

The title compound was prepared according to example 40. This resulted in the title compound (22.3 mg, 44.9% yield) as a white solid.

Example 77

1-(2,4-Difluorophenyl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide Compound 281

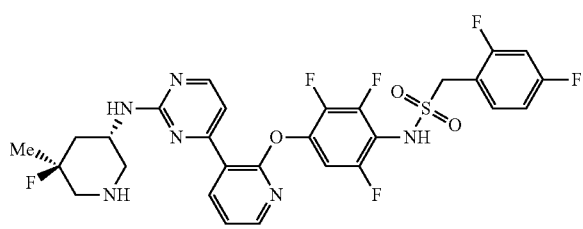 [SMILES: C[C@@]1(F)CNC[C@@H](Nc2nccc(-c3cccnc3Oc3cc(F)c(NS(=O)(=O)Cc4ccc(F)cc4F)c(F)c3F)n2)C1]

The title compound was prepared according to example 42. This resulted in the title compound (8.5 mg, 34.3% yield) as a white solid.

Example 78

1-(2,6-Difluorophenyl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide Compound 282

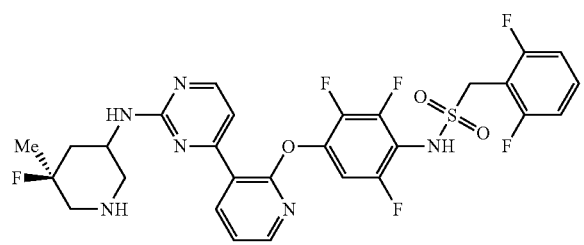 [SMILES: C[C@@]1(F)CNCC(Nc2nccc(-c3cccnc3Oc3cc(F)c(NS(=O)(=O)Cc4c(F)cccc4F)c(F)c3F)n2)C1]

The title compound was prepared according to example 42. This resulted in the title compound (12.1 mg, 48.8% yield) as a white solid.

Example 79

N-(2,3-Difluoro-4-((3-(2-(((3S,5S)-5-fluoropiperidin-3-yl)amino)pyrimidin-4-yl)pyridin-2-yl)oxy)-5-methylphenyl)-1-(2,6-difluorophenyl)methanesulfonamide Compound 283

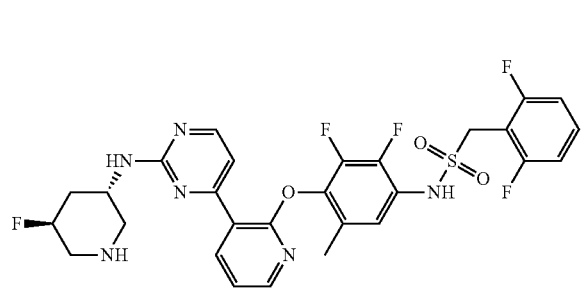 [SMILES: Cc1cc(NS(=O)(=O)Cc2c(F)cccc2F)c(F)c(F)c1Oc1ncccc1-c1ccnc(N[C@@H]2CNC[C@@H](F)C2)n1]

The title compound was prepared according to example 40. This resulted in the title compound (10.3 mg, 20.6% yield) as a white solid.

Example 80

1-p-Tolyl-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide Compound 284

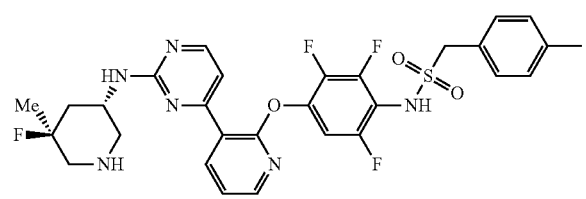 [SMILES: Cc1ccc(CS(=O)(=O)Nc2c(F)cc(Oc3ncccc3-c3ccnc(N[C@@H]4CNC[C@@](C)(F)C4)n3)c(F)c2F)cc1]

The title compound was prepared according to example 42. This resulted in the title compound (5.3 mg, 32.3% yield) as a white solid.

Example 81

1-(4-((3-(2-(((3S,5S)-5-Fluoropiperidin-3-yl)amino)pyrimidin-4-yl)pyridin-2-yl)oxy)phenyl)-3-(4-((4-methylpiperazin-1-yl)methyl)-3-(trifluoromethyl)phenyl)urea hydrochloride Compound 285

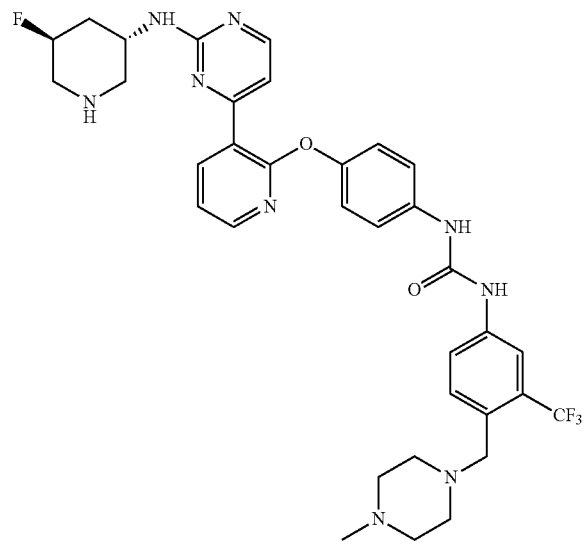 [SMILES: CN1CCN(Cc2ccc(NC(=O)Nc3ccc(Oc4ncccc4-c4ccnc(N[C@@H]5CNC[C@@H](F)C5)n4)cc3)cc2C(F)(F)F)CC1]

Step 1: Benzyl (3S,5S)-3-((4-(2-(4-aminophenoxy)-3-pyridyl)pyrimidin-2-yl)amino)-5-fluoro-piperidine-1-carboxylate

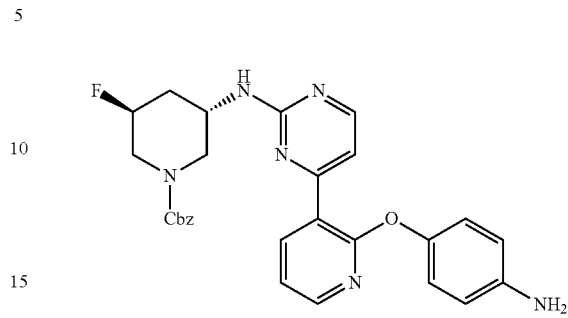

Under nitrogen, a mixture of benzyl (3S,5S)-3-fluoro-5-((4-(2-fluoro-3-pyridyl)pyrimidin-2-yl)amino)piperidine-1-carboxylate (0.3 g, 0.71 mmol), 4-aminophenol (0.08 g, 0.71 mmol) and cesium carbonate (0.35 g, 1.07 mmol) in dimethyl sulfoxide (10 mL) was stirred at 100° C. for 1 h. The resulting solution was diluted with water, extracted with ethyl acetate, washed with brine, dried over Sodium sulfate and concentrated. The residue was purified by silica flash chromatography eluting with ethyl acetate/petroleum ether (70%) to afford the title compound (337 mg, 92.9% yield) as a brown solid. LCMS (ESI): [M+H]$^+$=515.2.

Step 2: Benzyl (3S,5S)-3-fluoro-5-((4-(2-(4-(3-(4-((4-methylpiperazin-1-yl)methyl)-3-(trifluoromethyl)phenyl)ureido)phenoxy)pyridin-3-yl)pyrimidin-2-yl)amino)piperidine-1-carboxylate

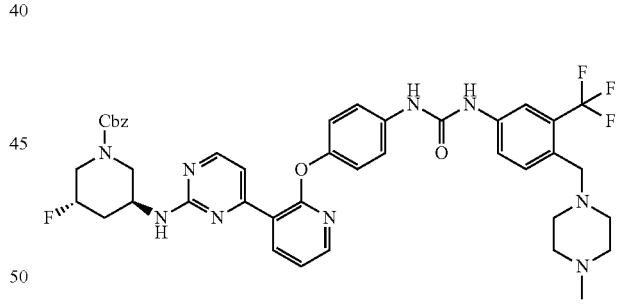

A solution of benzyl (3S,5S)-3-((4-(2-(4-aminophenoxy)-3-pyridyl)pyrimidin-2-yl)amino)-5-fluoro-piperidine-1-carboxylate (60 mg, 0.12 mmol), phenyl chloroformate (20 mg, 0.13 mmol) and pyridine (28 mg, 0.35 mmol) in dichloromethane (3 mL) was stirred at rt for 1 h. The solvent was concentrated under vacuum. 4-((4-methylpiperazin-1-yl)methyl)-3-(trifluoromethyl)aniline (35 mg, 0.13 mmol) and N,N-diisopropylethylamine (46 mg, 0.36 mmol) was added to the above residue in 1,4-dioxane (3 mL) and stirred at 100° C. for 5 h under nitrogen. The solvent was concentrated under vacuum. The residue was purified by silica flash chromatography eluting with dichloromethane/methanol (90:10) to afford the title compound (69 mg, 72.7% yield) as a yellow solid. LCMS (ESI): [M+H]$^+$=814.3

Step 3: 1-(4-((3-(2-(((3S,5S)-5-Fluoropiperidin-3-yl) amino)pyrimidin-4-yl)pyridin-2-yl)oxy)phenyl)-3- (4-((4-methylpiperazin-1-yl)methyl)-3-(trifluoromethyl)phenyl)urea hydrochloride Compound 285

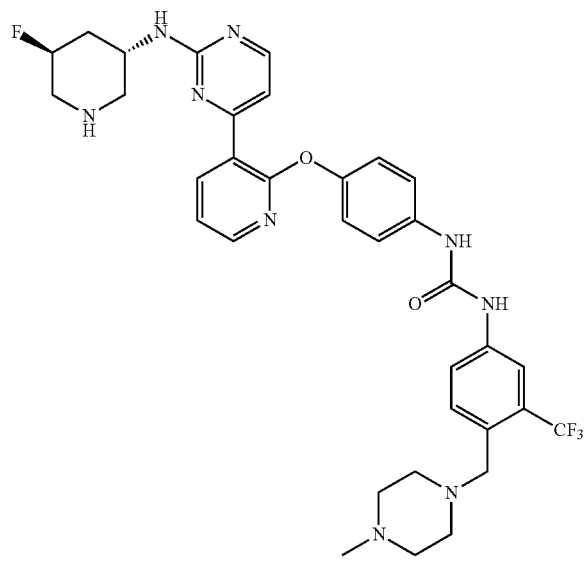 [SMILES: CN1CCN(Cc2ccc(NC(=O)Nc3ccc(Oc4ncccc4-c4ccnc(N[C@@H]5CNC[C@@H](F)C5)n4)cc3)cc2C(F)(F)F)CC1]

A solution of benzyl (3S,5S)-3-fluoro-5-((4-(2-(4-(3-(4-((4-methylpiperazin-1-yl)methyl)-3-(trifluoromethyl)phenyl)ureido)phenoxy)pyridin-3-yl)pyrimidin-2-yl)amino)piperidine-1-carboxylate (65 mg, 0.08 mmol) in dichloromethane (2 mL) was added 33% HBr in Acetic Acid (1 mL) and stirred at rt for 1 h. The solvent was concentrated under vacuum. The residue was purified by Prep-HPLC to afford the title compound (13.1 mg, 22.9% yield) as a yellow solid and as HCl salt.

Example 82

1-(3-((3-(2-(((3S,5S)-5-Fluoropiperidin-3-yl)amino) pyrimidin-4-yl)pyridin-2-yl)oxy)phenyl)-3-(4-((4-methylpiperazin-1-yl)methyl)-3-(trifluoromethyl) phenyl)urea hydrochloride Compound 286

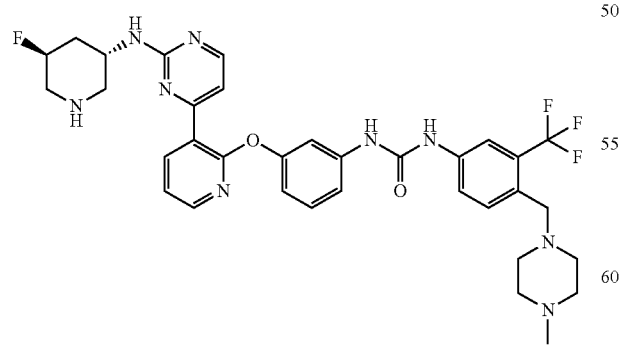

The title compound was prepared according to example 81. This resulted in the title compound (39.6 mg, 37.5% yield) as a yellow solid and as HCl salt.

Example 83

N-(4-((3-(2-((1-Azabicyclo[3.3.1]nonan-3-yl)amino) pyrimidin-4-yl)pyridin-2-yl)oxy)-2,3,6-trifluorophenyl)-1-phenylmethanesulfonamide hydrochloride Compound 287 & Compound 288

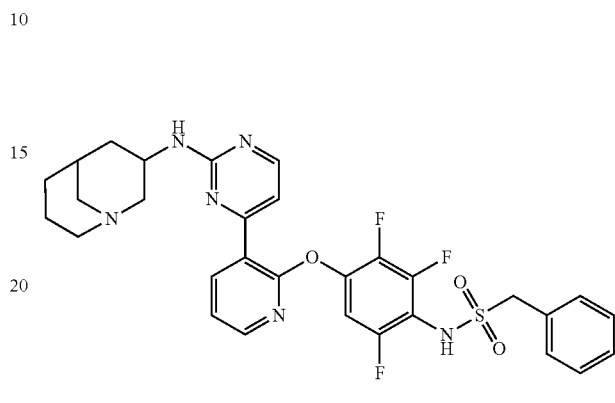

The title compound was prepared according to example 38. After Prep-HPLC, two peaks were isolated out. The fast peak was assigned isomer 1. The slow peak was assigned isomer 2.

N-(4-((3-(2-((1-azabicyclo[3.3.1]nonan-3-yl)amino)pyrimidin-4-yl)pyridin-2-yl)oxy)-2,3,6-trifluorophenyl)-1-phenylmethanesulfonamide hydrochloride (isomer 1) (22.9 mg, 8% yield) as a white solid and as HCl salt.

N-(4-((3-(2-((1-azabicyclo[3.3.1]nonan-3-yl)amino)pyrimidin-4-yl)pyridin-2-yl)oxy)-2,3,6-trifluorophenyl)-1-phenylmethanesulfonamide (isomer 2) (6.7 mg, 2.4% yield) as a white solid.

Example 84

1-o-Tolyl-N-(2,3,6-trifluoro-4-((3-(2-(((3S,5S)-5-fluoro-5-methylpiperidin-3-yl)amino)pyrimidin-4-yl) pyridin-2-yl)oxy)phenyl)methanesulfonamide Compound 290

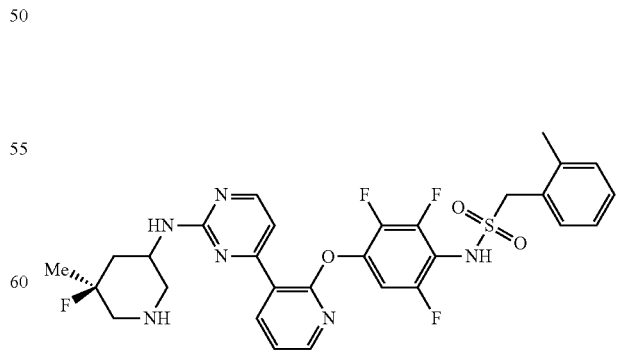

The title compound was prepared according to example 42. This resulted in the title compound (11.1 mg, 33.8% yield) as a yellow solid.

Example 85

1-(3-Methoxyphenyl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide Compound 291

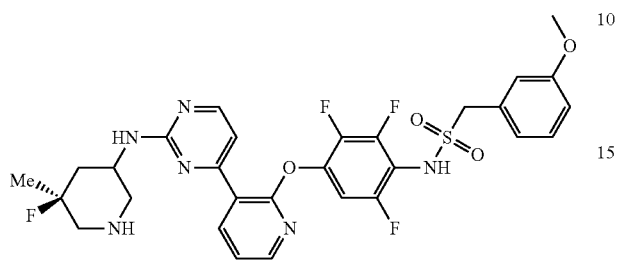

The title compound was prepared according to example 42. This resulted in the title compound (10.8 mg, 43.6% yield) as a yellow solid.

Example 86

N-(2,6-Difluoro-4-((3-(2-(((3S,5S)-5-fluoro-5-methylpiperidin-3-yl)amino)pyrimidin-4-yl)pyridin-2-yl)oxy)-3-methylphenyl)-1-phenylmethanesulfonamide Compound 292

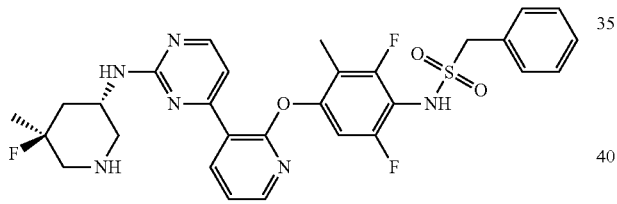

The title compound was prepared according to example 42. This resulted in the title compound (5.5 mg, 33.7% yield) as a white solid.

Example 87

N-(2,6-Difluoro-4-((3-(2-(((3S,5S)-5-fluoropiperidin-3-yl)amino)pyrimidin-4-yl)pyridin-2-yl)oxy)-3-methylphenyl)-1-(2,6-difluorophenyl)methanesulfonamide Compound 293

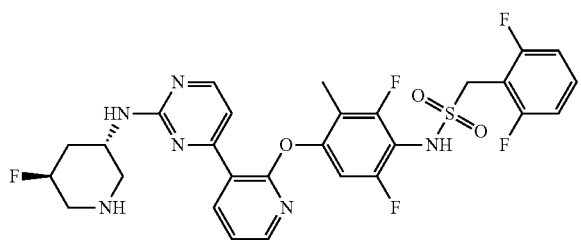 [SMILES: Cc1c(Oc2ncccc2-c2ccnc(N[C@@H]3CNC[C@@H](F)C3)n2)cc(F)c(NS(=O)(=O)Cc2c(F)cccc2F)c1F]

The title compound was prepared according to example 40. This resulted in the title compound (12.1 mg, 29.4% yield) as a white solid.

Example 88

1-Phenyl-N-(2,3,6-trifluoro-4-((3-(2-((5-(fluoromethyl)-5-methylpiperidin-3-yl)amino)pyrimidin-4-yl)pyridin-2-yl)oxy)phenyl)methanesulfonamide Compound 294 & Compound 295

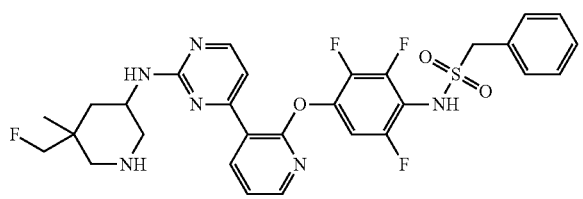 [SMILES: CC1(CF)CNCC(Nc2nccc(-c3cccnc3Oc3cc(F)c(NS(=O)(=O)Cc4ccccc4)c(F)c3F)n2)C1]

Step 1: 1-(tert-Butyl) 3-methyl 5-((diphenylmethylene)amino)piperidine-1,3-dicarboxylate

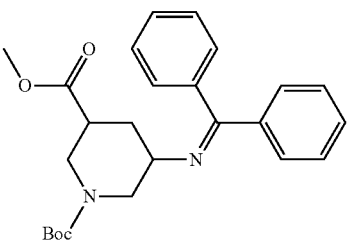 [SMILES: COC(=O)C1CC(N=C(c2ccccc2)c2ccccc2)CN(C(=O)OC(C)(C)C)C1]

Under hydrogen, a mixture of 1-(tert-butyl) 3-methyl 5-(((benzyloxy)carbonyl)amino)piperidine-1,3-dicarboxylate (5.0 g, 12.74 mmol) and 10% Pd/C (1.0 g, 0.94 mmol) in ethyl acetate (50 mL) was stirred at 50° C. for 4 h. The solid was filtered out. After filtration, the filtrate was dried over anhydrous sodium sulfate and concentrated under vacuum to afford 1-(tert-butyl) 3-methyl 5-((diphenylmethylene)amino)piperidine-1,3-dicarboxylate as a brown solid.

Under nitrogen, a mixture of 1-(tert-butyl) 3-methyl 5-((diphenylmethylene)amino)piperidine-1,3-dicarboxylate (3.0 g, 11.62 mmol), benzophenone imine (4.0 g, 22.07 mmol) and triethylamine (8.0 g, 79.21 mmol) in 1,2-dichlorobenzene (20 mL) was stirred at 80° C. for 16 h. The resulting mixture was concentrated under vacuum. The residue was purified by silica flash chromatography eluting with ethyl acetate/petroleum ether (⅓) to afford the title compound (4 g, 66.9% yield) as brown oil. LCMS (ESI): [M+H]$^+$=423.2

Step 4: 1-(tert-butyl) 3-Methyl 5-((diphenylmethylene)amino)-3-methylpiperidine-1,3-dicarboxylate

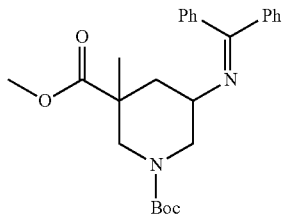 [SMILES: COC(=O)C1(C)CC(N=C(c2ccccc2)c2ccccc2)CN(C(=O)OC(C)(C)C)C1]

Under nitrogen, to a solution of 1-(tert-butyl) 3-methyl 5-((diphenylmethylene)amino)piperidine-1,3-dicarboxylate (2.8 g, 5.96 mmol) in tetrahydrofuran (30 mL) was added 2.0 M lithium diisopropylamide (9.0 mL, 18 mmol) dropwise at −60° C. and stirred at −60° C. for 1 h. Then iodomethane (1.7 mL, 27.31 mmol) was added dropwise at −60° C. and stirred at rt for 4 h. The reaction was quenched with sat. ammonium chloride. The resulting solution was diluted with water, extracted with ethyl acetate, washed with brine, dried over sodium sulfate and concentrated to afford the title compound (2.8 g, 75.3% yield). LCMS (ESI): [M+H]$^+$=437.2

Step 5: 1-(tert-Butyl) 3-methyl 5-(((benzyloxy)carbonyl)amino)-3-methylpiperidine-1,3-dicarboxylate

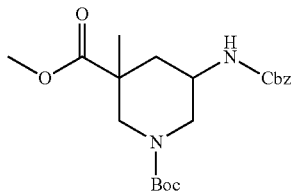 [SMILES: COC(=O)C1(C)CC(NC(=O)OCc2ccccc2)CN(C(=O)OC(C)(C)C)C1]

A mixture of 1-(tert-butyl) 3-methyl 5-((diphenylmethylene)amino)-3-methyl piperidine-1,3-dicarboxylate (2.8 g, 5.46 mmol) and acetic acid (15 mL) in tetrahydrofuran (30 mL) and water (30 mL) was stirred at rt for 2 h. The reaction mixture was adjusted to pH=9 with sat. sodium bicarbonate. The resulting solution was extracted with ethyl acetate and the organic layers were combined. The organic layer was dried over anhydrous sodium sulfate and concentrated under vacuum to afford 1-(tert-butyl) 3-methyl 5-amino-3-methylpiperidine-1,3-dicarboxylate (2.8 g, 94.4% yield) as a brown oil.

To a solution of 1-(tert-butyl) 3-methyl 5-amino-3-methylpiperidine-1,3-dicarboxylate (2.8 g, 5.16 mmol), sodium bicarbonate (1.6 g, 19.05 mmol) in tetrahydrofuran (25 mL) was added benzyl chloroformate (1.5 g, 8.79 mmol) and stirred at rt for 5 h. The resulting solution was diluted with water, extracted with ethyl acetate, washed with brine, dried over sodium sulfate and concentrated. The residue was purified by silica flash chromatography eluting with dichloromethane/methanol (96:4) to afford the title compound (1.8 g, 81.8% yield) as colorless oil. LCMS (ESI): [M+H]$^+$=407.2

Step 6: tert-Butyl 5-(((benzyloxy)carbonyl)amino)-3-(hydroxymethyl)-3-methylpiperidine-1-carboxylate

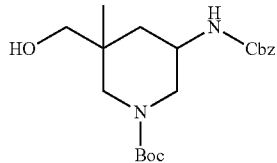

To a solution of 1-(tert-butyl) 3-methyl 5-(((benzyloxy)carbonyl)amino)-3-methylpiperidine-1,3-dicarboxylate (1.8 g, 4.43 mmol) in tetrahydrofuran (25 mL) was added sodium borohydride (500 mg, 13.22 mmol) at 0° C. The resulting solution was stirred at rt for 24 h. The reaction was quenched with water. The resulting solution was extracted with ethyl acetate, dried over anhydrous sodium sulfate and concentrated under vacuum. The residue was purified by silica flash chromatography eluting with dichloromethane/methanol (96:4) to afford the title compound (1.7 g, 96.4% yield) as brown oil. LCMS (ESI): [M+H]$^+$=379.2

Step 7: tert-Butyl 5-((diphenylmethylene)amino)-3-(hydroxymethyl)-3-methylpiperidine-1-carboxylate

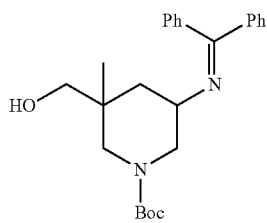

Under hydrogen, a mixture of tert-butyl 5-(benzyloxycarbonylamino)-3-(hydroxymethyl)-3-methyl-piperidine-1-carboxylate (1.7 g, 4.08 mmol) and 10% Pd/C (0.6 g) in ethyl acetate (50 mL) was stirred at 50° C. for 16 h. The solids were filtered out. After filtration, the filtrate was concentrated under vacuum to afford tert-butyl 5-amino-3-(hydroxymethyl)-3-methyl-piperidine-1-carboxylate (1.1 g, 96.8% yield) as a colorless oil.

Under nitrogen, a mixture of tert-butyl 5-amino-3-(hydroxymethyl)-3-methy 1-piperidine-1-carboxylate (0.7 g, 2.58 mmol), triethylamine (2 g, 13.41 mmol) and benzophenone imine (1.0 g, 5.52 mmol) in 1,2-dichlorobenzene (12 mL) was stirred at 80° C. for 16 h. The organic layer was concentrated under vacuum. The residue was purified by silica flash chromatography eluting with dichloromethane/methanol (96:4) to afford the title compound (970 mg, 78.3% yield) as yellow oil. LCMS (ESI): [M+H]$^+$=409.2

Step 8: tert-Butyl 5-((diphenylmethylene)amino)-3-methyl-3-(((methylsulfonyl)oxy)methyl)piperidine-1-carboxylate

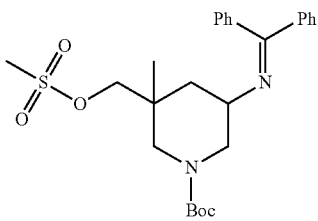 [SMILES: CC1(COS(C)(=O)=O)CC(N=C(c2ccccc2)c2ccccc2)CN(C(=O)OC(C)(C)C)C1]

To a solution of tert-butyl 5-(benzhydrylideneamino)-3-(hydroxymethyl)-3-methyl-piperidine-1-carboxylate (980 mg, 2.04 mmol), triethylamine (0.87 mL, 6.23 mmol) in dichloromethane (10 mL) was added methane sufonyl chloride (0.24 mL, 3.06 mmol) at 0° C. and stirred at rt for 1 h. The resulting solution was diluted with water, extracted with ethyl acetate, washed with brine, dried over Sodium sulfate and concentrated. The residue was purified by silica flash chromatography eluting with dichloromethane/methanol (96:4) to afford the title compound (850 mg, 84.2% yield) as a colorless solid. LCMS (ESI): [M+H]$^+$=487.2

Step 9: tert-Butyl 5-((diphenylmethylene)amino)-3-(fluoromethyl)-3-methylpiperidine-1-carboxylate

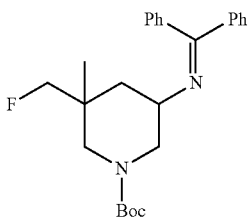 [SMILES: CC1(CF)CC(N=C(c2ccccc2)c2ccccc2)CN(C(=O)OC(C)(C)C)C1]

To a mixture of tert-butyl 5-(benzhydrylideneamino)-3-methyl-3-(methylsulfonyloxymethyl)piperidine-1-carboxylate (800 mg, 1.32 mmol) and triethylamine trihydrofluoride in tetrahydrofuran (10 mL, 10 mmol) was stirred at 80° C. for 16 h. The resulting solution was diluted with water, extracted with ethyl acetate, washed with brine, dried over sodium sulfate and concentrated. The residue was purified by silica flash chromatography eluting with dichloromethane/methanol (98:2) to afford the title compound (300 mg, 52.8% yield) as yellow oil. LCMS (ESI): [M+H]$^+$=411.2

Step 10: tert-Butyl 5-amino-3-(fluoromethyl)-3-methylpiperidine-1-carboxylate

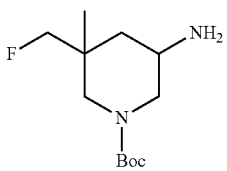

To a mixture of tert-butyl 5-(benzhydrylideneamino)-3-(fluoromethyl)-3-methyl-piperidine-1-carboxylate (490 mg, 1.19 mmol) and acetic acid (3 mL) in water (6 mL) and tetrahydrofuran (6 mL) was stirred at rt for 1 h. The solvent was removed under vacuum. The residue was purified by silica flash chromatography eluting with dichloromethane/methanol (88/12) to afford the title compound (325 mg, 88% yield) as a white solid. LCMS (ESI): [M+H]$^+$=247.2

Step 11: tert-Butyl 3-(fluoromethyl)-3-methyl-5-((4-(2-(2,3,5-trifluoro-4-((phenylmethyl)sulfonamido)phenoxy)pyridin-3-yl)pyrimidin-2-yl)amino)piperidine-1-carboxylate

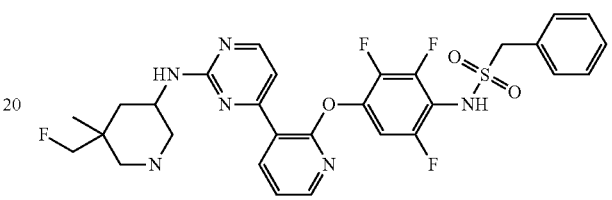

Under nitrogen, a mixture of tert-butyl 5-amino-3-(fluoromethyl)-3-methylpiperidine-1-carboxylate (200 mg, 0.65 mmol), 1-phenyl-N-(2,3,6-trifluoro-4-((3-(2-methylsulfonylpyrimidin-4-yl)-2-pyridyl)oxy)phenyl)methanesulfonamide (350 mg, 0.64 mmol), cesium fluoride (500 mg, 3.29 mmol) and N,N-diisopropylethylamine (250 mg, 1.93 mmol) in dimethyl sulfoxide (7 mL) was stirred at 80° C. for 1 h. The resulting solution was diluted with water, extracted with ethyl acetate, washed with brine, dried over sodium sulfate and concentrated. The residue was purified by silica flash chromatography eluting with dichloromethane/methanol (96:4) to afford the title compound (300 mg, 66.9% yield) as a white solid. LCMS (ESI): [M+H]$^+$=717.2

Step 12: 1-Phenyl-N-(2,3,6-trifluoro-4-((3-(2-((5-(fluoromethyl)-5-methylpiperidin-3-yl)amino)pyrimidin-4-yl)pyridin-2-yl)oxy)phenyl)methanesulfonamide & 1-phenyl-N-(2,3,6-trifluoro-4-((3-(2-((5-(fluoromethyl)-5-methylpiperidin-3-yl)amino)pyrimidin-4-yl)pyridin-2-yl)oxy)phenyl)methanesulfonamide Compound 294 & Compound 295

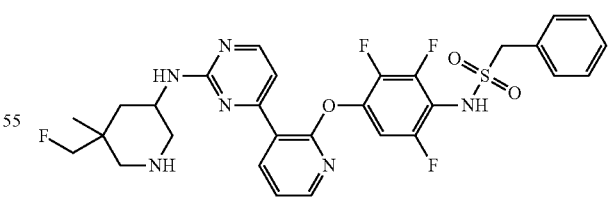

To a solution of tert-butyl 3-(fluoromethyl)-3-methyl-5-((4-(2-(2,3,5-trifluoro-4-((phenylmethyl)sulfonamido)phenoxy)pyridin-3-yl)pyrimidin-2-yl)amino)piperidine-1-carboxylate (300 mg, 0.42 mmol) in dichloromethane (4 mL) was added 4 M HCl in dioxane (1 mL) dropwise and stirred at rt for 1 h. The solvent was removed under vacuum. The residue was purified by Prep-HPLC and Chiral HPLC to afford the title compound. After Chiral HPLC, two peaks were isolated out. The fast peak was assigned isomer 1. The slow peak was assigned isomer 2.

1-Phenyl-N-(2,3,6-trifluoro-4-((3-(2-((5-(fluoromethyl)-5-methylpiperidin-3-yl)amino)pyrimidin-4-yl)pyridin-2-yl)oxy)phenyl)methanesulfonamide (isomer 1) (34.1 mg, 13.2% yield) as a white solid, (rt=3.394 min, SFC CHIRALPAK AD-3 3*100 mm, 3 um, IPA (0.1% DEA); 3 mL/min).

1-Phenyl-N-(2,3,6-trifluoro-4-((3-(2-((5-(fluoromethyl)-5-methylpiperidin-3-yl)amino)pyrimidin-4-yl)pyridin-2-yl)oxy)phenyl)methanesulfonamide (isomer 2) (34.7 mg, 13.4% yield) as a white solid, (rt=3.879 min, SFC CHIRALPAK AD-3 3*100 mm, 3 um, IPA (0.1% DEA); 2 mL/min).

Example 89

N-(2-Fluoro-4-((3-(2-(((3S,5S)-5-fluoropiperidin-3-yl)amino)pyrimidin-4-yl)pyridin-2-yl)oxy)-6-methoxyphenyl)-1-phenylmethanesulfonamide Compound 296

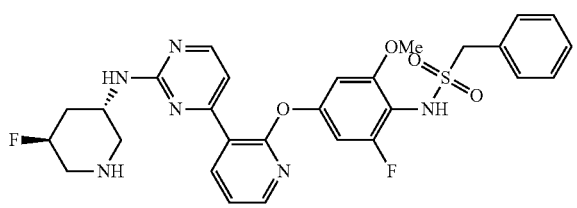 [SMILES: COc1cc(Oc2ncccc2-c2ccnc(N[C@@H]3CNC[C@@H](F)C3)n2)cc(F)c1NS(=O)(=O)Cc1ccccc1]

The title compound was prepared according to Example 40. This resulted in the title compound (9.9 mg, 9.4% yield) as a white solid.

Example 90

N-(2,3-Difluoro-4-((3-(2-(((3S,5S)-5-fluoro-5-methylpiperidin-3-yl)amino)pyrimidin-4-yl)pyridin-2-yl)oxy)-5-methylphenyl)-1-(p-tolyl)methanesulfonamide Compound 297

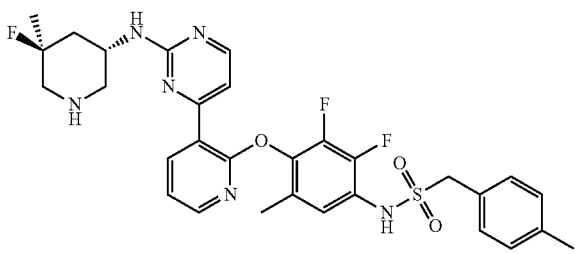 [SMILES: Cc1ccc(CS(=O)(=O)Nc2cc(C)c(Oc3ncccc3-c3ccnc(N[C@@H]4CNC[C@@](C)(F)C4)n3)c(F)c2F)cc1]

The title compound was prepared according to example 42. This resulted in the title compound (26.6 mg, 43.7% yield) as a white solid.

Example 91

N-(4-((3-(2-((1,1-Difluoro-5-azaspiro[2.5]octan-7-yl)amino)pyrimidin-4-yl)pyridin-2-yl)oxy)-2,3,6-trifluorophenyl)-1-phenylmethanesulfonamide Compound 298 & Compound 299 & Compound 300 & Compound 301

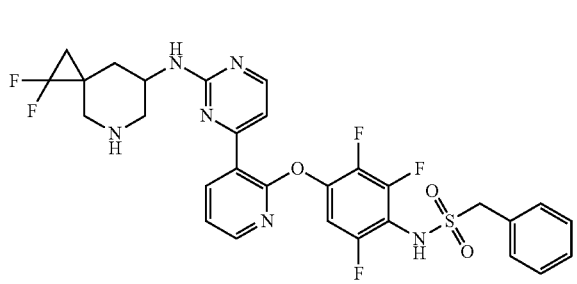 [SMILES: O=S(=O)(Cc1ccccc1)Nc1c(F)cc(Oc2ncccc2-c2ccnc(NC3CNCC4(C3)CC4(F)F)n2)c(F)c1F]

Step 1: 1-(tert-butyl) 3-Methyl 5-oxopiperidine-1,3-dicarboxylate

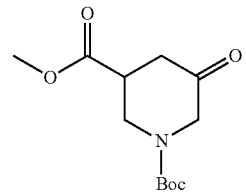 [SMILES: COC(=O)C1CC(=O)CN(C(=O)OC(C)(C)C)C1]

Under nitrogen, a solution of ethanedioyl dichloride (4 mL, 47 mmol) in dichloromethane (200 mL) was added dimethyl sulfoxide (6.6 mL, 93 mmol) in dichloromethane (5 mL) at −78° C. The solution was stirred at −78° C. for 1 h. A solution of 1-tert-butyl 3-methyl 5-hydroxypiperidine-1,3-dicarboxylate (3.0 g, 11.6 mmol) in dichloromethane (10 mL) was added to the above solution at −78° C. The solution was stirred at −78° C. for 1.5 h. A solution of triethylamine (16 mL, 115 mmol) in dichloromethane (10 mL) was added at −78° C. The solution was stirred at rt for 16 h. The mixture was diluted with water and extracted with dichloromethane. The organic layers were collected. The solution was concentrate under vacuum. The residue was purified by silica flash chromatography eluting with ethyl acetate/petroleum ether (1/3) to afford the title compound (2.1 g, 70.5% yield) as light brown oil. $^1$H NMR (300 MHz, CDCl$_3$) δ 4.05 (s, 2H), 3.95-3.84 (m, 2H), 3.73 (s, 3H), 3.16-3.03 (m, 1H), 2.82-2.57 (m, 2H), 1.48 (s, 9H).

Step 2: Methyl 1-(tert-butoxymethyl)-5-methylenepiperidine-3-carboxylate

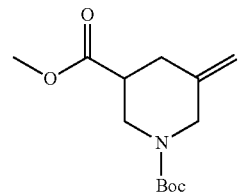

Under nitrogen, a solution of methyltriphenylphosphonium bromide (12.0 g, 34 mmol) in tetrahydrofuran (200 mL) was added potassium tert-butoxide (3.8 g, 31 mmol). The mixture was stirred for 3 h at rt. Then a solution of 1-(tert-butyl) 3-methyl 5-oxopiperidine-1,3-dicarboxylate (2.0 g, 7.8 mmol) in tetrahydronfuran (10 ml) was added. The mixture was stirred for 16 h at rt. The reaction was diluted with sat. ammonium chloride and extracted with ethyl acetate. The organic layer was combined. The organic layer was dried over sodium sulfate and concentrated under vacuum. The residue was purified by silica flash chromatography eluting with ethyl acetate/petroleum ether (20%) to afford the title compound (1.5 g, 80% yield) as colorless oil. $^1$H NMR (300 MHz, CDCl$_3$) δ 4.90 (d, J=2.1 Hz, 2H), 4.37-4.14 (m, 2H), 3.72 (s, 3H), 3.51-3.44 (m, 1H), 3.20-3.02 (m, 1H), 2.69-2.54 (m, 2H), 2.46-2.34 (m, 1H), 1.48 (s, 9H).

Step 3: 5-(tert-Butyl) 7-methyl 1,1-difluoro-5-azaspiro[2.5]octane-5,7-dicarboxylate

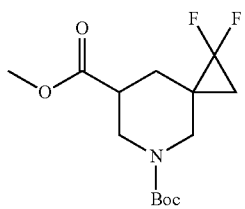 [SMILES: COC(=O)C1CN(C(=O)OC(C)(C)C)CC2(C1)CC2(F)F]

Under nitrogen, a solution of methyl 1-(tert-butoxymethyl)-5-methylene-piperidine-3-carboxylate (2.13 g, 8.34 mmol) in ethanol (28 mL) was added sodium iodide (0.45 g, 3.1 mmol) and (trifluoromethyl)trimethylsilane (4.32 g, 30 mmol). The mixture was stirred for 16 h at 65° C. The mixture was diluted with water and extracted with ethyl acetate. The combined organic layer was dried over sodium sulfate and concentrated under vacuum. The residue was purified by silica flash chromatography eluting with ethyl acetate/petroleum ether (20%) to afford the title compound (1.5 g, 58.9% yield) as light yellow oil. $^1$H NMR (300 MHz, CDCl$_3$) δ 4.52-4.38 (brs, 1H), 3.84-3.80 (m, 1H), 3.72 (s, 3H), 3.15-3.08 (m, 1H), 2.65-2.58 (m, 1H), 1.99-1.95 (m, 1H), 1.62-1.59 (m, 1H), 1.48 (s, 9H), 1.31-1.15 (m, 2H).

Step 4: 5-tert-Butoxycarbonyl-2,2-difluoro-5-azaspiro[2.5]octane-7-carboxylic acid

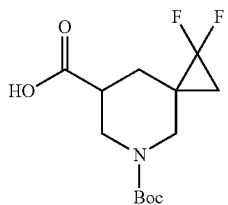

Into the solution of 5-(tert-butyl) 7-methyl 1,1-difluoro-5-azaspiro[2.5]octane-5,7-dicarboxylate (1.5 g, 4.91 mmol) in tetrahydrofuran (30 mL) and water (6 mL) was added lithium hydroxide monohydrate (780 mg, 19 mmol). The solution was stirred at rt for 3 h. The reaction was adjusted pH to 5 by hydrochloric acid (0.5 M). The mixture was extracted with ethyl acetate and the organic layers were combined. The solution was dried over sodium sulfate and concentrated under vacuum to afford the title compound (1.4 g, 97.8% yield) as colorless oil. LCMS (ESI): [M+H−56]$^+$=236.1.

Step 5: tert-Butyl 7-(benzyloxycarbonylamino)-2,2-difluoro-5-azaspiro[2.5]octane-5-carboxylate

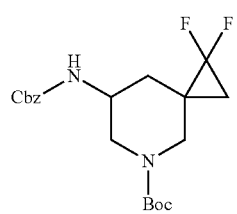 [SMILES: CC(C)(C)OC(=O)N1CC(NC(=O)OCc2ccccc2)CC2(C1)CC2(F)F]

Into the solution of 5-tert-butoxycarbonyl-2,2-difluoro-5-azaspiro[2.5]octane-7-carboxylic acid (900 mg, 3.1 mmol) in toluene (120 mL) was added N,N-diisopropylethylamine (1.8 mL, 10 mmol) and diphenylphosphoryl azide (0.9 mL, 4.2 mmol). The solution was stirred at 110° C. for 2 h. Then benzyl alcohol (2.7 mL, 26 mmol) was added. The solution was stirred at 110° C. for 2 h. The solution was diluted with water and extracted with ethyl acetate. The combined solution was concentrated under vacuum. The residue was purified by silica flash chromatography eluting with ethyl acetate/petroleum ether (35%) to afford the title compound (640 mg, 52.3% yield) as colorless oil. LCMS (ESI): [M+H]$^+$=397.2

Step 6: tert-Butyl 7-amino-2,2-difluoro-5-azaspiro[2.5]octane-5-carboxylate

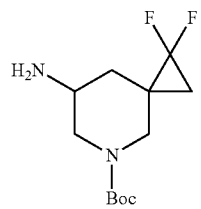

Into the solution of tert-butyl 7-(benzyloxycarbonylamino)-2,2-difluoro-5-azaspiro[2.5]octane-5-carboxylate (234 mg, 0.59 mmol) in methyl alcohol (40 mL) was added 10% Pd/C (20 mg). The mixture was stirred at rt for 1 h under hydrogen. The solid was filtered out and the solution was concentrated under vacuum to afford the title compound (140 mg, 90.4% yield) as colorless oil. LCMS (ESI): [M+H]$^+$=263.1.

Step 7: tert-Butyl 1,1-difluoro-7-((4-(2-(2,3,5-trifluoro-4-((phenylmethyl)sulfonamido)phenoxy)pyridin-3-yl)pyrimidin-2-yl)amino)-5-azaspiro[2.5]octane-5-carboxylate

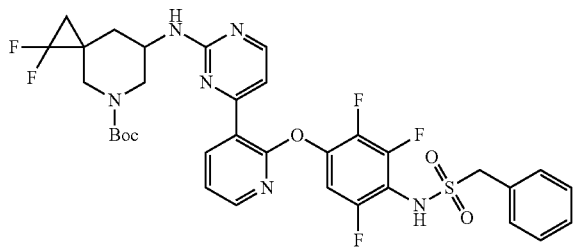 [SMILES: CC(C)(C)OC(=O)N1CC(Nc2nccc(-c3cccnc3Oc3cc(F)c(NS(=O)(=O)Cc4ccccc4)c(F)c3F)n2)CC2(C1)CC2(F)F]

Under nitrogen, into the solution of 1-phenyl-N-(2,3,6-trifluoro-4-((3-(2-methylsulfonylpyrimidin-4-yl)-2-pyridyl)oxy)phenyl)methanesulfonamide (260 mg, 0.47 mmol) in dimethyl sulfoxide (2.5 mL) was added tert-butyl 7-amino-2,2-difluoro-5-azaspiro[2.5]octane-5-carboxylate (150 mg, 0.57 mmol), cesium fluoride (130 mg, 0.86 mmol) and N,N-diisopropylethylamine (0.3 mL, 1.8 mmol). The mixture was stirred at 80° C. for 2 h. The mixture was diluted with water and extracted with ethyl acetate and the organic layer was combined. The solution was washed with water, dried over sodium sulfate, and concentrated under vacuum. The residue was purified by silica flash chromatography eluting with ethyl acetate/petroleum ether (30%-90%) to afford the title compound. Two isomers were isolated out. The fast peak was assigned as isomer 1 and the slow peak was assigned as isomer 2.

tert-Butyl 1,1-difluoro-7-((4-(2-(2,3,5-trifluoro-4-((phenylmethyl)sulfonamido) phenoxy)pyridin-3-yl)pyrimidin-2-yl)amino)-5-azaspiro[2.5]octane-5-carboxylate (isomer 1) (190 mg, 54.9% yield) as a light yellow solid. LCMS (ESI): [M+H]$^+$=733.1.

tert-Butyl 1,1-difluoro-7-((4-(2-(2,3,5-trifluoro-4-((phenylmethyl)sulfonamido) phenoxy)pyridin-3-yl)pyrimidin-2-yl)amino)-5-azaspiro[2.5]octane-5-carboxylate (isomer 2) (200 mg, 57.8% yield) as a light yellow solid. LCMS (ESI): [M+H]$^+$=733.2.

Step 8: N-(4-((3-(2-((1,1-Difluoro-5-azaspiro[2.5]octan-7-yl)amino)pyrimidin-4-yl)pyridin-2-yl)oxy)-2,3,6-trifluorophenyl)-1-phenylmethanesulfonamide Compound 298 & Compound 299

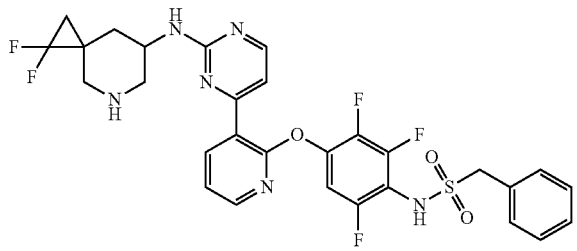 [SMILES: O=S(=O)(Cc1ccccc1)Nc1c(F)cc(Oc2ncccc2-c2ccnc(NC3CNCC4(C3)CC4(F)F)n2)c(F)c1F]

Into the solution of 5% trifluoroacetic acid in hexafluoroisopropanol (10 mL, 0.26 mmol) was added tert-butyl 1,1-difluoro-7-((4-(2-(2,3,5-trifluoro-4-((phenylmethyl)sulfonamido)phenoxy)pyridin-3-yl)pyrimidin-2-yl)amino)-5-azaspiro[2.5]octane-5-carboxylate (isomer 1 of Step 7) (190 mg, 0.26 mmol). The solution was stirred at rt for 2 h. The solution was concentrated under vacuum. The residue was purified with Prep-HPLC and Chiral HPLC to afford the title compound. The fast peak was assigned as isomer 1 and the slow peak was assigned as isomer 2.

N-(4-((3-(2-((1,1-Difluoro-5-azaspiro[2.5]octan-7-yl)amino)pyrimidin-4-yl)pyridin-2-yl)oxy)-2,3,6-trifluorophenyl)-1-phenylmethanesulfonamide (isomer 1, Compound 298) (28.4 mg, 17.3% yield) as a white solid, (rt=2.047 min, CHIRALPAKIG-3, 0.46×5 cm; 3 um, MtBE (0.1% DEA): EtOH=95:5, 1.0 mL/min).

N-(4-((3-(2-((1,1-Difluoro-5-azaspiro[2.5]octan-7-yl)amino)pyrimidin-4-yl)pyridin-2-yl)oxy)-2,3,6-trifluorophenyl)-1-phenylmethanesulfonamide (isomer 2, Compound 299) (38.7 mg, 23.5% yield) as a white solid, (rt=3.114 min, CHIRALPAK IG-3, 0.46×5 cm; 3 um, MtBE (0.1% DEA): EtOH=95:5, 1.0 mL/min).

Step 8: N-(4-((3-(2-((1,1-Difluoro-5-azaspiro[2.5]octan-7-yl)amino)pyrimidin-4-yl)pyridin-2-yl)oxy)-2,3,6-trifluorophenyl)-1-phenylmethanesulfonamide Compound 300 & Compound 301

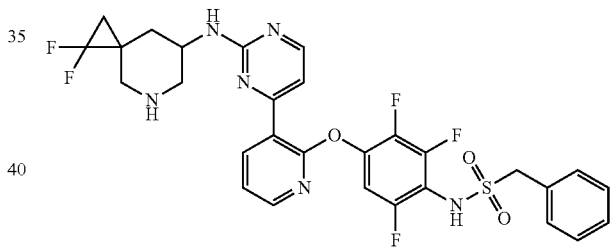

Into the solution of 5% trifluoroacetic acid in hexafluoroisopropanol (10 mL, 0.26 mmol) was added tert-butyl 1,1-difluoro-7-((4-(2-(2,3,5-trifluoro-4-((phenylmethyl)sulfonamido)phenoxy)pyridin-3-yl)pyrimidin-2-yl)amino)-5-azaspiro[2.5]octane-5-carboxylate (isomer 2 of Step 7) (220 mg, 0.30 mmol). The solution was stirred at rt for 2 h. The solution was concentrated under vacuum. The residue was purified with Prep-HPLC and Chiral HPLC to afford the title compound. The fast peak was assigned as isomer 3 and the slow peak was assigned as isomer 4.

N-(4-((3-(2-((1,1-Difluoro-5-azaspiro[2.5]octan-7-yl)amino)pyrimidin-4-yl)pyridin-2-yl)oxy)-2,3,6-trifluorophenyl)-1-phenylmethanesulfonamide (isomer 3, Compound 300) (39.8 mg, 20.9% yield) as a white solid, (rt=3.013 min, CHIRALPAK IE-3, 0.46×5 cm; 3 um, hex (0.1% DEA): EtOH=50:50, 1.0 mL/min).

N-(4-((3-(2-((1,1-Difluoro-5-azaspiro[2.5]octan-7-yl)amino)pyrimidin-4-yl)pyridin-2-yl)oxy)-2,3,6-trifluorophenyl)-1-phenylmethanesulfonamide (isomer 4, Compound 301) (46.1 mg, 24.2% yield) as a white solid, (rt=3.906 min, CHIRALPAK IE-3, 0.46×5 cm; 3 um, hex (0.1% DEA): EtOH=50:50, 1.0 mL/min).

Example 92

N-(4-((3-(2-((5-(Difluoromethyl)piperidin-3-yl)amino)pyrimidin-4-yl)pyridin-2-yl)oxy)-2,3,6-trifluorophenyl)-1-phenylmethanesulfonamide Compound 302 & Compound 303

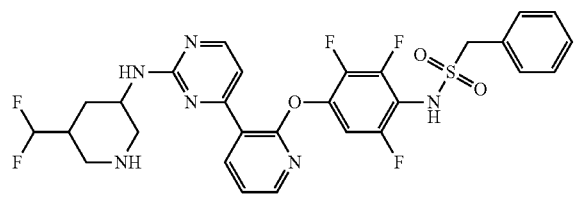 [SMILES: O=S(=O)(Cc1ccccc1)Nc1c(F)cc(Oc2ncccc2-c2ccnc(NC3CNCC(C(F)F)C3)n2)c(F)c1F]

Step 1: tert-Butyl 3-(benzyloxy)-5-formylpiperidine-1-carboxylate

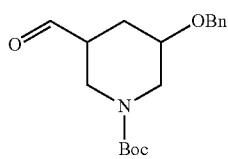 [SMILES: CC(C)(C)OC(=O)N1CC(C=O)CC(OCc2ccccc2)C1]

To a solution of tert-butyl 3-benzyloxy-5-(hydroxymethyl)piperidine-1-carboxylate (2.3 g, 7.16 mmol) and triethylamine (3.8 g, 37.62 mmol) in dimethyl sulfoxide (20 mL) was added sulfurtrioxide-pyridine complex (4.6 g, 28.9 mmol) at 0° C. and stirred at rt for 2 h. The resulting solution was diluted with water, extracted with ethyl acetate, washed with brine, dried over sodium sulfate and concentrated. The residue was purified by flash chromatography on silica gel eluting with dichloromethane/methanol (96:4) to afford the title compound (1.1 g, 45.7% yield) as colorless oil. LCMS (ESI): [M+H]$^+$=320.2

Step 4: 1-(tert-Butyl) 3-methyl 5-(((diphenylmethylene)amino)-3-methylpiperidine-1,3-dicarboxylate

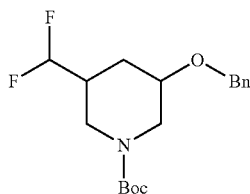 [SMILES: CC(C)(C)OC(=O)N1CC(OCc2ccccc2)CC(C(F)F)C1]

Under nitrogen, to a solution of tert-butyl 3-benzyloxy-5-formyl-piperidine-1-carboxylate (1000 mg, 3.13 mmol) in dichloromethane (20 mL) was added diethylaminosulfur trifluoride (1700 mg, 10.55 mmol) in dichloromethane (3 mL) dropwise at 0° C. and stirred for 1 h at the same temperature. The reaction mixture was diluted with ethyl acetate and quenched with sat. sodium bicarbonate. The resulting solution was extracted with ethyl acetate, washed with brine, dried over sodium sulfate and concentrated. The residue was purified by silica flash chromatography eluting with dichloromethane/methanol (99:1) to afford the title compound (450 mg, 40% yield) as colorless oil. LCMS (ESI): [M+H]$^+$=342.2

Step 5: tert-Butyl 3-(difluoromethyl)-5-hydroxypiperidine-1-carboxylate

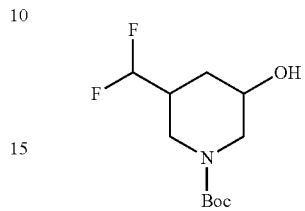

Under hydrogen, a mixture of tert-butyl 3-benzyloxy-5-(difluoromethyl)piperidine-1-carboxylate (450 mg, 1.32 mmol) and 10% Pd/C (150 mg, 0.14 mmol) in methyl alcohol (10 mL) was stirred at rt for 4 h. The solid was filtered out After filtration, the filtrate was dried over anhydrous sodium sulfate and concentrated under vacuum to afford the title compound (330 mg, 89.7% yield) as brown oil. LCMS (ESI): [M+H]$^+$=252.1

Step 6: tert-Butyl 3-amino-5-(difluoromethyl)piperidine-1-carboxylate

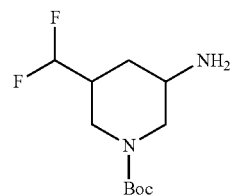 [SMILES: CC(C)(C)OC(=O)N1CC(N)CC(C(F)F)C1]

A solution of tert-butyl 3-(difluoromethyl)-5-hydroxypiperidine-1-carboxylate (330 mg, 1.18 mmol), Triethylamine (0.03 mL, 0.25 mmol) in dichloromethane (8 mL) was added methanesulfonyl chloride (0.02 mL, 0.22 mmol) at 0° C. and stirred at rt for 1 h. The resulting solution was diluted with water, extracted with ethyl acetate, washed with brine, dried over sodium sulfate and concentrated to afford tert-butyl 3-(difluoromethyl)-5-methylsulfonyloxy-piperidine-1-carboxylate (0.34 g, 78.6% yield) as a white solid.

A solution of tert-butyl 3-(difluoromethyl)-5-methylsulfonyloxy-piperidine-1-carboxylate (280 mg, 0.85 mmol) and sodium azide (170 mg, 2.61 mmol) in N,N-dimethylformamide (4 mL) was stirred for 4 h at 80° C. The reaction was quenched with water, extracted with ethyl acetate, washed with brine, dried over sodium sulfate and concentrated to afford tert-butyl 3-azido-5-(difluoromethyl)piperidine-1-carboxylate (0.22 g, 89% yield) as a brown oil.

Under hydrogen, a mixture of tert-butyl 3-azido-5-(difluoromethyl)piperidine-1-carboxylate (310 mg, 1.07 mmol) and 10% Pd/C (200 mg, 0.19 mmol) in methanol (10 mL) was stirred at rt for 16 h. The solid was filtered out. After filtration, the filtration was concentrated under vacuum to afford the title compound (270 mg, 91.1% yield) as brown oil. LCMS (ESI): [M+H]$^+$=251.2

Step 7: tert-Butyl 3-(difluoromethyl)-5-((4-(2-(2,3,5-trifluoro-4-((phenylmethyl)sulfonamido)phenoxy)pyridin-3-yl)pyrimidin-2-yl)amino)piperidine-1-carboxylate

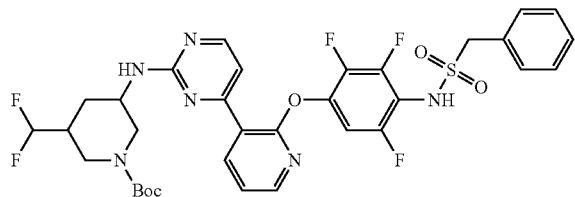 [SMILES: CC(C)(C)OC(=O)N1CC(Nc2nccc(-c3cccnc3Oc3cc(F)c(NS(=O)(=O)Cc4ccccc4)c(F)c3F)n2)CC(C(F)F)C1]

Under nitrogen, a mixture of tert-butyl 3-amino-5-(difluoromethyl)piperidine-1-carboxylate (260 mg, 0.93 mmol), 1-phenyl-N-(2,3,6-trifluoro-4-((3-(2-methylsulfonylpyrimidin-4-yl)-2-pyridyl)oxy)phenyl)methanesulfonamide (375 mg, 0.68 mmol), cesium fluoride (510 mg, 3.36 mmol) and N,N-diisopropylethylamine (280 mg, 2.17 mmol) in dimethyl sulfoxide (6 mL) was stirred at 80° C. for 1 h. The resulting solution was diluted with water, extracted with ethyl acetate, washed with brine, dried over sodium sulfate and concentrated. The residue was purified by silica flash chromatography eluting with dichloromethane/methanol (96:4) to afford the title compound (380 mg, 69.7% yield) as a yellow solid. LCMS (ESI): $[M+H]^+=721.2$

Step 8: N-(4-((3-(2-((5-(Difluoromethyl)piperidin-3-yl)amino)pyrimidin-4-yl)pyridin-2-yl)oxy)-2,3,6-trifluorophenyl)-1-phenylmethanesulfonamide Compound 302 & Compound 303

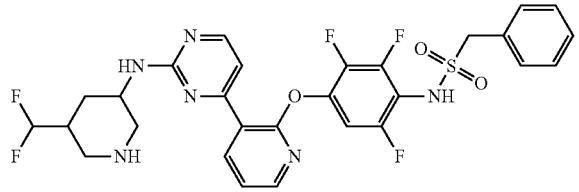

To a solution of tert-butyl 3-(difluoromethyl)-5-((4-(2-(2,3,5-trifluoro-4-((phenylmethyl)sulfonamido)phenoxy)pyridin-3-yl)pyrimidin-2-yl)amino)piperidine-1-carboxylate (260 mg, 0.36 mmol) in dichloromethane (3 mL) was added 4 M HCl in dioxane (5 mL) and stirred at rt for 1 h. The solvent was concentrated under vacuum. The residue was purified by Prep-HPLC and Chiral HPLC to afford the title compound. After Chiral HPLC, two peaks were isolated out. The fast peak was assigned isomer 1. The slow peak was assigned isomer 2.

N-(4-((3-(2-((5-(Difluoromethyl)piperidin-3-yl)amino)pyrimidin-4-yl)pyridin-2-yl)oxy)-2,3,6-trifluorophenyl)-1-phenylmethanesulfonamide (isomer 1) (105.2 mg, 45.7% yield) as a white solid, (rt=3.361 min, CHIRALPAK AD-3, 3*100 mm, 3 um, IPA (0.1% DEA); 3 mL/min).

N-(4-((3-(2-((5-(Difluoromethyl)piperidin-3-yl)amino)pyrimidin-4-yl)pyridin-2-yl)oxy)-2,3,6-trifluorophenyl)-1-phenylmethanesulfonamide (isomer 2) (84.8 mg, 37.6% yield) as a white solid, (rt=3.764 min, CHIRALPAK AD-3, 3*100 mm, 3 um, IPA (0.1% DEA); 3 mL/min).

Example 93

1-(4-Methoxyphenyl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide Compound 304

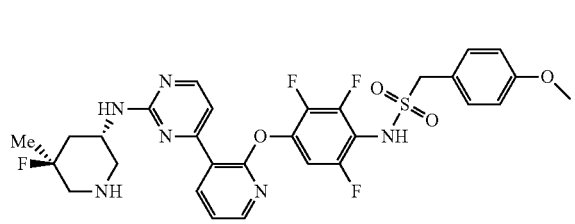 [SMILES: COc1ccc(CS(=O)(=O)Nc2c(F)cc(Oc3ncccc3-c3ccnc(N[C@@H]4CNC[C@@](C)(F)C4)n3)c(F)c2F)cc1]

Step 1: 1-(4-Bromophenyl)-N-(2,3,6-trifluoro-4-((3-(2-(methylthio)pyrimidin-4-yl)pyridin-2-yl)oxy)phenyl)methanesulfonamide

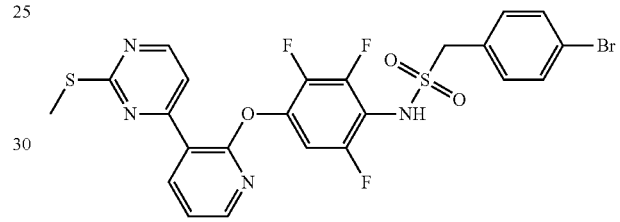

To a mixture of 2,3,6-trifluoro-4-((3-(2-methylsulfanylpyrimidin-4-yl)-2-pyridyl)oxy)aniline (0.25 g, 0.69 mmol) and triethylamine (0.21 g, 2.06 mmol) in dichloromethane (2 mL) was added 4-bromobenzylsulfonyl chloride (0.55 g, 2.06 mmol), the mixture was stirred for 2 h at rt. The resulting solution was diluted with water and extracted with ethyl acetate, the organic layers was washed with brine and dried over sodium sulfate and concentrated. The residue was purified by flash chromatography on silica gel eluting with petroleum ether/ethyl acetate (1/2) to afford the title compound (280 mg, 68.3% yield) as a brown solid. LCMS (ESI): $[M+H]^+=597.1$.

Step 2: 1-(4-Methoxyphenyl)-N-(2,3,6-trifluoro-4-((3-(2-(methylthio)pyrimidin-4-yl)pyridin-2-yl)oxy)phenyl)methanesulfonamide

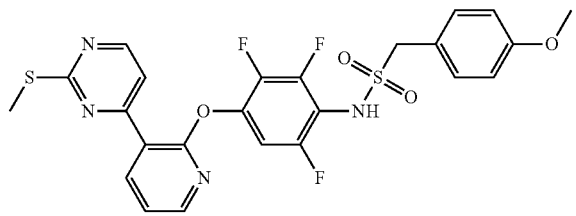

A mixture of 1-(4-bromophenyl)-N-(2,3,6-trifluoro-4-((3-(2-(methylthio)pyrimidin-4-yl)pyridin-2-yl)oxy)phenyl)methanesulfonamide (0.28 g, 0.47 mmol), cesium carbonate (0.46 g, 1.41 mmol), allylpalladium chloride dimer (0.02 g, 0.05 mmol) and Rockphos (0.04 g, 0.09 mmol) in methyl alcohol (0.50 mL) and toluene (2.5 mL) was stirred at 85° C. for 2 h under nitrogen. The resulting solution was diluted with water and extracted with ethyl acetate, the solvent was removed under vacuum. The residue was purified by flash chromatography on silica gel eluting with petroleum ether/ethyl acetate (1:1) to afford the title compound (190 mg, 73.9% yield) as a dark yellow solid. LCMS (ESI): [M+H]+= 549.2.

Step 3: 1-(4-Methoxyphenyl)-N-(2,3,6-trifluoro-4-((3-(2-(((3S,5S)-5-fluoro-5-methylpiperidin-3-yl)amino)pyrimidin-4-yl)pyridin-2-yl)oxy)phenyl)methanesulfonamide Compound 304

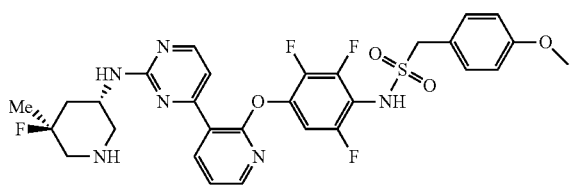 [SMILES: COc1ccc(CS(=O)(=O)Nc2c(F)cc(Oc3ncccc3-c3ccnc(N[C@@H]4CNC[C@@](C)(F)C4)n3)c(F)c2F)cc1]

The title compound was prepared according to example 42. This resulted in the title compound (25.8 mg, 34.7% yield) as a white solid.

Example 94

N-(2,3-Difluoro-4-((3-(2-(((3S,5S)-5-fluoro-5-methylpiperidin-3-yl)amino)pyrimidin-4-yl)pyridin-2-yl)oxy)-6-methylphenyl)-1-(p-tolyl)methanesulfonamide Compound 305

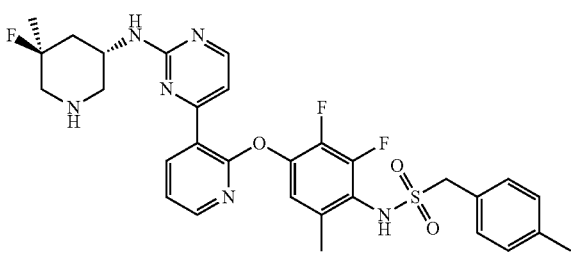 [SMILES: Cc1ccc(CS(=O)(=O)Nc2c(C)cc(Oc3ncccc3-c3ccnc(N[C@@H]4CNC[C@@](C)(F)C4)n3)c(F)c2F)cc1]

The title compound was prepared according to example 42. This resulted in the title compound (23.6 mg, 32.0% yield) as a white solid.

Example 95

N-(4-((3-(2-((4-(Dimethylamino)-3-fluorocyclohexyl)amino)pyrimidin-4-yl)pyridin-2-yl)oxy)-2,3,6-trifluorophenyl)-1-phenylmethanesulfonamide Compound 306 & Compound 307 & Compound 308

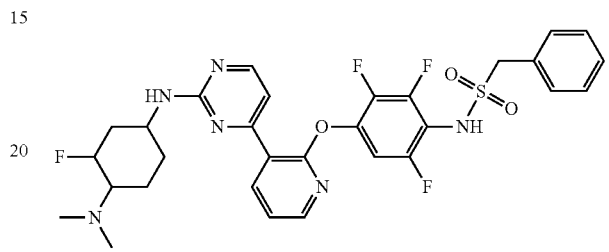

Step 1: Ethyl 3-fluoro-4-oxocyclohexane-1-carboxylate

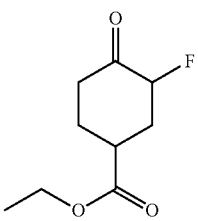

Under nitrogen, a solution of ethyl 4-oxocyclohexanecarboxylate (10 mL, 62.8 mmol) in methyl alcohol (200 mL) was added 1-chloromethyl-4-fluoro-1,4-diazoniabicyclo[2.2.2]octane bis(tetrafluoroborate) (30 g, 94 mmol) and con. sulfuric acid (0.1 mL, 1.84 mmol). The resulting solution was stirred for 16 h at 60° C. The reaction was quenched with brine and extracted with ethyl acetate. The solvent was removed under vacuum. The crude product was dissolved in dichloromethane (50 mL). And 2,2,2-trifluoroacetic acid (20 mL) was added. The resulting solution was stirred for 2 h at rt. The solvent was removed. The residue was dissolved in ethyl acetate and washed with sat. sodium bicarbonate. The solvent was removed. The residue was purified by silica flash chromatography eluting with ethyl acetate/petroleum ether (1/10) to afford the title compound (11.2 g, 94.8% yield) as a yellow solid. $^1$H NMR (400 MHz, DMSO-$d_6$) δ 5.38-5.08 (m, 1H), 4.19-4.08 (m, 2H), 3.11-2.95 (m, 1H), 2.63-2.52 (m, 1H), 2.52-2.13 (m, 2H), 2.12-1.89 (m, 1H), 1.92-1.59 (m, 1H), 1.22 (dt, J=13.5, 7.1 Hz, 3H).

Step 2: Ethyl 4-(dimethylamino)-3-fluorocyclohexane-1-carboxylate

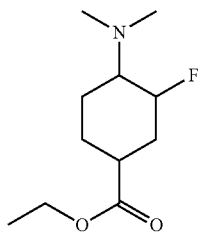

A solution of ethyl 3-fluoro-4-oxo-cyclohexanecarboxylate (10.0 g, 53.1 mmol) in 1,2-dichloroethane (150 mL) was added N,N-dimethylamine (35 mL, 70 mmol) and sodium triacetoxyborohydride (17 g, 80.2 mmol). Then acetic acid (3 mL) was added. The resulting solution was stirred for 12 h at rt. The reaction was quenched with sat sodium carbonate and extracted with ethyl acetate. The solvent was removed under vacuum. The residue was purified by silica flash chromatography eluting with dichloromethane/methanol (5/1) to afford the title compound (9.5 g, 82.3% yield) as yellow oil. LCMS (ESI, m/z): $[M+H]^+=218.2$.

Step 3: 4-(Dimethylamino)-3-fluorocyclohexane-1-carboxylic acid hydrochloride

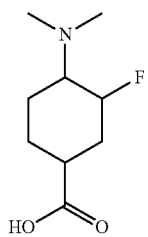

A solution of ethyl 4-(dimethylamino)-3-fluorocyclohexane-1-carboxylate (9.5 g, 46.7 mmol) in 1,4-dioxane (50 mL) was added 4 M HCl in dioxane (50 mL) and stirred for 24 h at 100° C. The solvent was removed under vacuum to afford the title compound (10 g, 94.8% yield) as a yellow solid and as HCl salt. LCMS (ESI, m/z): $[M+H]^+=190.1$.

Step 4: Benzyl (4-(dimethylamino)-3-fluorocyclohexyl)carbamate

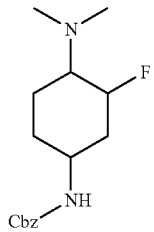 [SMILES: CN(C)C1CCC(NC(=O)OCc2ccccc2)CC1F]

Under nitrogen, a solution of 4-(dimethylamino)-3-fluoro-cyclohexanecarboxylic acid hydrochloride (10.0 g, 44.3 mmol) in toluene (200 mL) was added diphenylphosphoryl azide (11 mL, 51.1 mmol) and N,N-diisopropylethylamine (40 mL, 241.9 mmol) at rt and then stirred for 4 h at 100° C. Then the solution was cooled to 50° C. Benzyl alcohol (20 mL, 193 mmol) was added and stirred for 2 h at 100° C. The reaction was quenched with brine and extracted with ethyl acetate. The residue was purified by silica flash chromatography eluting with dichloromethane/menthol (5/1) and reverse phase (ACN/10 mM NH$_4$HCO$_3$) to afford title compound (4.6 g, 35.3% yield) as a yellow oil. LCMS (ESI, m/z): $[M+H]^+=295.1$.

Step 5: 2-Fluoro-N,N-dimethylcyclohexane-1,4-diamine hydrochloride

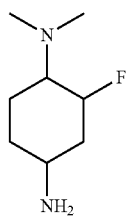

Under hydrogen, a mixture of benzyl (4-(dimethylamino)-3-fluorocyclohexyl)carbamate (2.0 g, 6.79 mmol) and 10% Pd/C (0.2 g) in methyl alcohol (30 mL) was added con. HCl (0.1 mL) and stirred for 2 h at rt. The solids were filtered out. The filtrate was concentrated under vacuum to afford the title compound (1.2 g, 89.8% yield) as a white solid. LCMS (ESI, m/z): $[M+H]^+=161.1$.

Step 6: N-(4-((3-(2-((4-(Dimethylamino)-3-fluorocyclohexyl)amino)pyrimidin-4-yl)pyridin-2-yl)oxy)-2,3,6-trifluorophenyl)-1-phenylmethanesulfonamide & N-(4-((3-(2-((4-(Dimethylamino)-3-fluorocyclohexyl)amino)pyrimidin-4-yl)pyridin-2-yl)oxy)-2,3,6-trifluorophenyl)-1-phenylmethanesulfonamide hydrochloride Compound 306 & Compound 307 & Compound 308

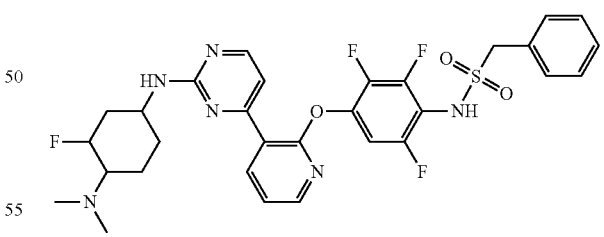

Under nitrogen, a solution of 1-phenyl-N-(2,3,6-trifluoro-4-((3-(2-methylsulfonylpyrimidin-4-yl)-2-pyridyl)oxy)phenyl)methanesulfonamide (2.0 g, 3.63 mmol), 2-fluoro-N,N-dimethylcyclohexane-1,4-diamine hydrochloride (857 mg, 4.36 mmol), caesium fluoride (1.1 g, 7.27 mmol), N,N-diisopropylethylamine (1.8 mL, 10.9 mmol) in dimethyl sulfoxide (20 mL) was stirred for 2 h at 90° C. The reaction was quenched with brine and extracted with ethyl acetate. The solvent was removed under vacuum. The residue was purified by silica flash chromatography eluting with dichloromethane/methanol (10/1). The crude product was further purified by Prep-HPLC and Chiral HPLC.

After Prep-HPLC, two components were isolated out. The first component was assigned as isomer 1 (mixture of enantiomers). The second component was separated by Chiral HPLC. After Chiral HPLC, the fast peak was assigned as isomer 2 and the slow peak was assigned as isomer 3.

N-(4-((3-(2-((4-(Dimethylamino)-3-fluorocyclohexyl) amino)pyrimidin-4-yl)pyridin-2-yl)oxy)-2,3,6-trifluorophenyl)-1-phenylmethanesulfonamide hydrochloride as mixture (isomer 1, Compound 307) (666.9 mg, 27.5% yield).

N-(4-((3-(2-((4-(Dimethylamino)-3-fluorocyclohexyl) amino)pyrimidin-4-yl)pyridin-2-yl)oxy)-2,3,6-trifluorophenyl)-1-phenylmethanesulfonamide (isomer 2, Compound 306) (31.5 mg, 1.4% yield) as white solid, (rt=1.332 min, CHIRALPAK IA-3, 0.46×5 cm; 3 um, (Hex:DCM=3:1) (0.1% DEA&0.1% FA):IPA=80:20, 1.0 ml/min). Compound 306 and Compound 308 are enantiomers.

N-(4-((3-(2-((4-(Dimethylamino)-3-fluorocyclohexyl) amino)pyrimidin-4-yl)pyridin-2-yl)oxy)-2,3,6-trifluorophenyl)-1-phenylmethanesulfonamide (isomer 3, Compound 308) (36.1 mg, 1.6% yield) as white solid, (rt=2.518 min, CHIRALPAK IA-3, 0.46×5 cm; 3 um, (Hex:DCM=3:1) (0.1% DEA&0.1% FA):IPA=80:20, 1.0 ml/min). Compound 306 and Compound 308 are enantiomers.

Example 96

N-(4-((3-(2-(((1r,4r)-4-(Dimethylamino)cyclohexyl) amino)pyrimidin-4-yl)pyridin-2-yl)oxy)-2,3,6-trifluorophenyl)propane-1-sulfonamide Compound 309

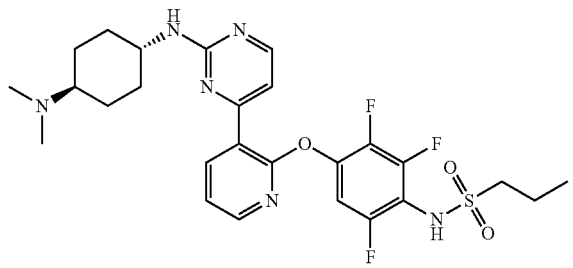 [SMILES: CCCS(=O)(=O)Nc1c(F)cc(Oc2ncccc2-c2ccnc(N[C@H]3CC[C@H](N(C)C)CC3)n2)c(F)c1F]

The title compound was prepared according to example 38. This resulted in the title compound (43.2 mg, 16.6% yield) as a white solid.

Example 96a

N-(4-((3-(2-(((1r,4r)-4-(Dimethylamino)cyclohexyl) amino)pyrimidin-4-yl)pyridin-2-yl)oxy)-2,3,6-trifluorophenyl)-3,3-difluorobutane-1-sulfonamide Compound 310

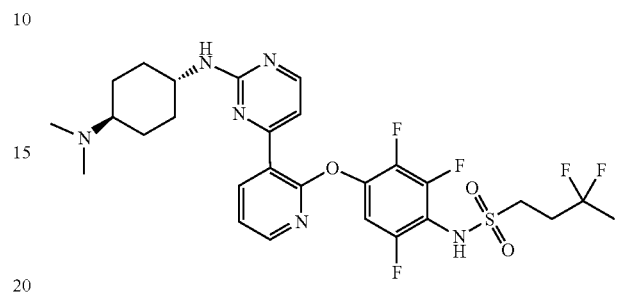

The title compound was prepared according to Example 38. This resulted in the title compound (56.5 mg, 24.2% yield) as a white solid.

Example 97

N-(2,5-Difluoro-4-((3-(2-(((3S,5S)-5-fluoro-5-methylpiperidin-3-yl)amino)pyrimidin-4-yl)pyridin-2-yl) oxy)-3-methylphenyl)-1-(p-tolyl)methanesulfonamide Compound 311

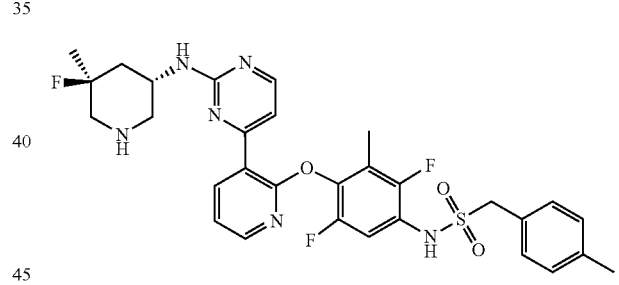

Step 1: 2-Bromo-3,6-difluorophenol

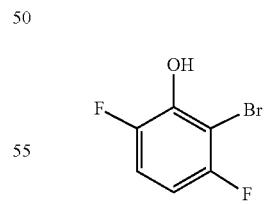

A solution of 2,5-difluorophenol (5.8 g, 45 mmol) and isopropylamine (3.3 mL) in tetrahydrofuran (120 mL) was stirred at −40° C. Then 1-bromo-2,5-pyrrolidinedione (8.3 g, 47 mmol) was added and stirred at −40° C. for 2 h. The reaction mixture was diluted with 1 M hydrochloric acid (20 mL). The resulting solution was extracted with ethyl acetate and the organic layers were combined. The organic layer was dried over anhydrous sodium sulfate and concentrated under vacuum. The residue was purified by flash chromatography on silica gel eluting with ethyl acetate/petroleum ether (0-5%) to afford the title compound (8.0 g, 85.3% yield) as a yellow oil. LCMS (ESI): [M−H]⁻=207.2.

Step 2: 2-Bromo-3,6-difluoro-4-nitrophenol

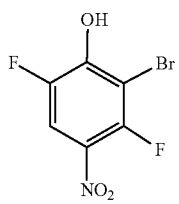

Under nitrogen, a solution of 2-bromo-3,6-difluoro-phenol (3.2 g, 15 mmol) in dichloromethane (30 mL) was added nitric acid (1.5 mL, 14 mmol) in sulfuric acid (3 mL) at 0° C. and stirred for 2 h. The reaction was quenched with ice water and extracted with dichloromethane and the organic layers were combined. The organic layer was dried over anhydrous sodium sulfate and concentrated under vacuum. The residue was purified by silica flash chromatography eluting with ethyl acetate/petroleum ether (0-5%) to afford the title compound (2 g, 51.4% yield) as brown oil. LCMS (ESI): [M−H]⁻=252.2.

Step 3: 2-(Benzyloxy)-3-bromo-1,4-difluoro-5-nitrobenzene

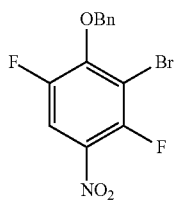

A solution of 2-bromo-3,6-difluoro-4-nitro-phenol (1.9 g, 7.48 mmol) and potassium carbonate (2.6 g, 19 mmol) in N,N-dimethylacetamide (40 mL) was stirred at rt for 0.5 h. Then benzyl bromide (1.6 g, 9.4 mmol) was added and stirred at rt for 1.5 h. The solvent was concentrated under vacuum. The residue was purified by silica flash chromatography eluting with ethyl acetate/petroleum ether (1%) to afford the title compound (2.1 g, 81.6% yield) as a light yellow solid.

Step 4: 2-(Benzyloxy)-1,4-difluoro-3-methyl-5-nitrobenzene

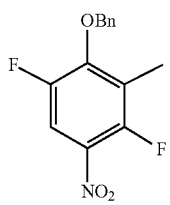

Into a solution of 2-benzyloxy-3-bromo-1,4-difluoro-5-nitro-benzene (1 g, 2.91 mmol) in toluene (10 mL), water (1 mL) was added methylboronicacid (523 mg, 8.74 mmol), (1,1'-bis(diphenylphosphino)ferrocene)dichloropalladium (II) (213 mg, 0.29 mmol) and potassium fluoride (506 mg, 8.72 mmol), the mixture was stirred at 90° C. for 2 h under nitrogen. The reaction mixture was diluted with water and extracted with ethyl acetate and the organic layers were combined. The organic layer was dried over anhydrous sodium sulfate and concentrated under vacuum. The residue was purified by silica flash chromatography eluting with ethyl acetate/petroleum ether (0-5%) to afford the title compound (700 mg, 86.3% yield) as yellow oil.

Step 5: 4-Amino-3,6-difluoro-2-methylphenol

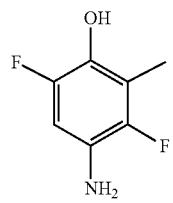

Into a solution of 2-benzyloxy-1,4-difluoro-3-methyl-5-nitro-benzene (800 mg, 2.86 mmol) in methanol (7 mL) was added 10% Pd/C (80 mg), the mixture was stirred at rt for 1.5 hours under hydrogen. The solids were filtered out. The solvent was removed under vacuum. The residue was purified by silica flash chromatography eluting with ethyl acetate/petroleum ether (20%) to afford the title compound (254 mg, 55% yield) as a purple solid. LCMS (ESI): [M+H]⁺=160.2.

Step 6: N-(2,5-Difluoro-4-((3-(2-(((3S,5S)-5-fluoro-5-methylpiperidin-3-yl)amino)pyrimidin-4-yl)pyridin-2-yl)oxy)-3-methylphenyl)-1-(p-tolyl)methanesulfonamide Compound 311

The title compound was prepared according to example 42. This resulted in the title compound (26.0 mg, 22.6% yield) as a white solid.

Example 98

1-(4-(Methylsulfonyl)phenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 312

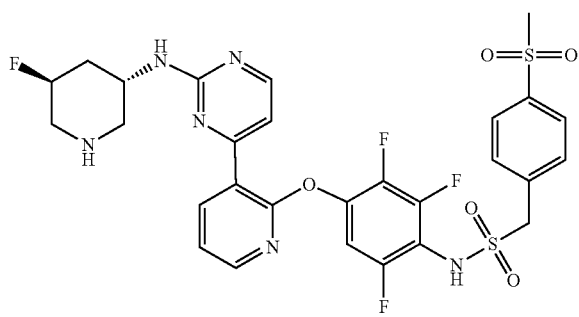 [SMILES: CS(=O)(=O)c1ccc(CS(=O)(=O)Nc2c(F)cc(Oc3ncccc3-c3ccnc(N[C@@H]4CNC[C@@H](F)C4)n3)c(F)c2F)cc1]

Step 1: 1-(4-Bromophenyl)-N-(2,3,6-trifluoro-4-((3-(2-(methylthio)pyrimidin-4-yl)pyridin-2-yl)oxy)phenyl)methanesulfonamide

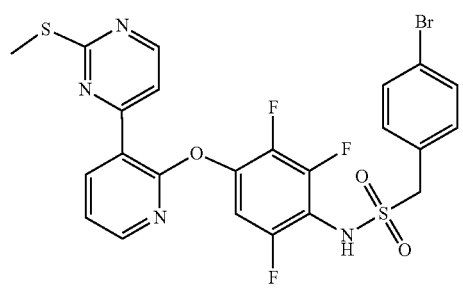 [SMILES: CSc1nccc(-c2cccnc2Oc2cc(F)c(NS(=O)(=O)Cc3ccc(Br)cc3)c(F)c2F)n1]

To a mixture of 2,3,6-trifluoro-4-((3-(2-methylsulfanylpyrimidin-4-yl)-2-pyridyl)oxy)aniline (500 mg, 1.37 mmol) in pyridine (3 mL) was added 4-bromobenzylsulfonyl chloride (820 mg, 3.04 mmol), the mixture was stirred for 1 h at rt. The resulting solution was diluted with water, extracted with ethyl acetate, washed with brine, dried over sodium sulfate and concentrated. The residue was purified by silica flash chromatography eluting with ethyl acetate/petroleum ether (1:1) to afford the title compound (450 mg, 54.9% yield) as a brown solid. LCMS (ESI): [M+H]⁺=597.0.

Step 2: 1-(4-(Methylthio)phenyl)-N-(2,3,6-trifluoro-4-((3-(2-(methylthio)pyrimidin-4-yl)pyridin-2-yl)oxy)phenyl)methanesulfonamide

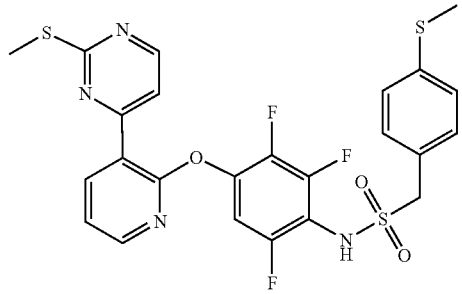

A mixture of 1-(4-bromophenyl)-N-(2,3,6-trifluoro-4-((3-(2-(methylthio)pyrimidin-4-yl)pyridin-2-yl)oxy)phenyl)methanesulfonamide (200 mg, 0.33 mmol), sodium thiomethoxide (40 mg, 0.57 mmol), 4,5-bis(diphenylphosphino)-9,9-dimethylxanthene (30 mg, 0.05 mmol), tris(dibenzylideneacetone)dipalladium(0) (40 mg, 0.04 mmol) and N,N-diisopropylethylamine (130 mg, 0.14 mmol) in toluene (2 mL) was stirred at 110° C. for 2 h under nitrogen. The resulting solution was diluted with water, extracted with ethyl acetate and the organic layers were combined. The residue was purified by silica flash chromatography eluting with ethyl acetate/petroleum ether (¼) to afford the title compound (180 mg, 95.2% yield) as a white solid. LCMS (ESI): [M+H]⁺=565.1.

Step 3: 1-(4-(Methylsulfonyl)phenyl)-N-(2,3,6-trifluoro-4-((3-(2-(methylsulfonyl)pyrimidin-4-yl)pyridin-2-yl)oxy)phenyl)methanesulfonamide

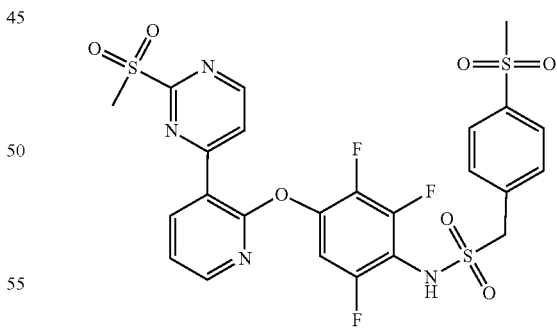

To a mixture of 1-(4-(methylthio)phenyl)-N-(2,3,6-trifluoro-4-((3-(2-(methylthio)pyrimidin-4-yl)pyridin-2-yl)oxy)phenyl)methanesulfonamide (150 mg, 0.27 mmol) in dichloromethane (2 mL) was added 3-chloroperoxybenzoic acid (150 mg, 0.87 mmol), the mixture was stirred for 1 h at rt. The resulting solution was diluted with water, extracted with ethyl acetate and the organic layer was concentrated under vacuum. The crude would be directly used in the next step without purification. LCMS (ESI): [M+H]⁺=629.0

Step 4: Benzyl (3S,5S)-3-fluoro-5-((4-(2-(2,3,5-trifluoro-4-(((4-(methylsulfonyl)phenyl)methyl)sulfonamido)phenoxy)pyridin-3-yl)pyrimidin-2-yl)amino)piperidine-1-carboxylate

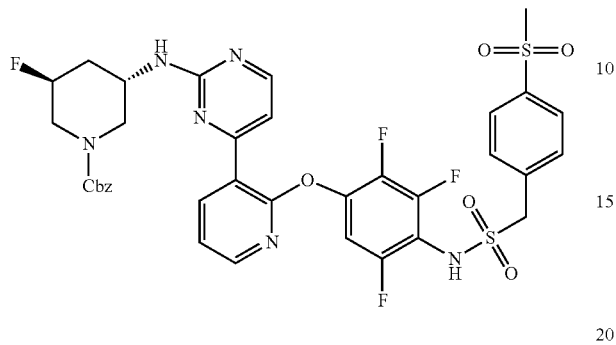

A mixture of 1-(4-(methylsulfonyl)phenyl)-N-(2,3,6-trifluoro-4-((3-(2-(methylsulfonyl)pyrimidin-4-yl)pyridin-2-yl)oxy)phenyl)methanesulfonamide (150 mg, 0.24 mmol), benzyl (3S,5S)-3-amino-5-fluoro-piperidine-1-carboxylate (66 mg, 0.26 mmol), caesium fluoride (108 mg, 0.71 mmol) and N,N-diisopropylethylamine (108 mg, 0.84 mmol) in dimethyl sulfoxide (2 mL) was stirred at 80° C. for 2 h under nitrogen. The resulting solution was diluted with water, extracted with ethyl acetate, washed with brine, dried over sodium sulfate and concentrated. The residue was purified by silica flash chromatography eluting with ethyl acetate/petroleum ether (3/1) to afford the title compound (150 mg, 78.5% yield) as a white solid. LCMS (ESI): [M+H]$^+$=801.2

Step 5: 1-(4-(Methylsulfonyl)phenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 312

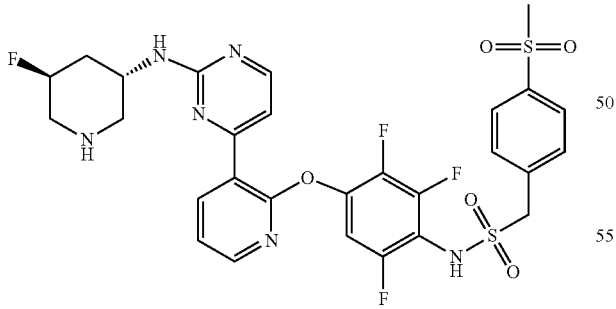

A mixture of benzyl (3S,5S)-3-fluoro-5-((4-(2-(2,3,5-trifluoro-4-(((4-(methylsulfonyl)phenyl)methyl)sulfonamido)phenoxy)pyridin-3-yl)pyrimidin-2-yl)amino)piperidine-1-carboxylate (160 mg, 0.2 mmol) in dichloromethane (1 mL) was added 33% HBr in acetic acid (0.5 mL) and stirred at rt for 1 h. The solvent was removed under vacuum. The crude product was purified by Prep-HPLC to afford the title compound (43.1 mg, 32.4% yield) as a white solid.

Example 99

N-(2,3-Difluoro-4-((3-(2-(((3S,5S)-5-fluoropiperidin-3-yl)amino)pyrimidin-4-yl)pyridin-2-yl)oxy)-5-methylphenyl)-1-phenylethane-1-sulfonamide hydrochloride Compound 313 & Compound 314

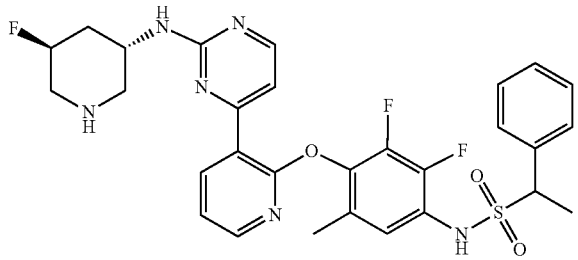 [SMILES: Cc1cc(NS(=O)(=O)C(C)c2ccccc2)c(F)c(F)c1Oc1ncccc1-c1ccnc(N[C@@H]2CNC[C@@H](F)C2)n1]

Step 1: N-(2,3-Difluoro-5-methyl-4-((3-(2-(methylthio)pyrimidin-4-yl)pyridin-2-yl)oxy)phenyl)-N-(methoxymethyl)-1-phenylmethanesulfonamide

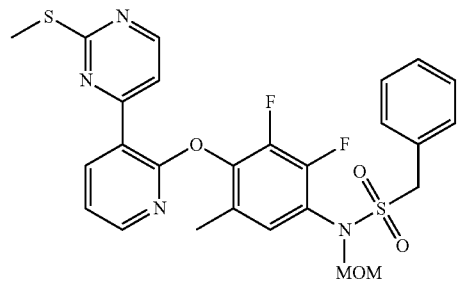

Into the solution of N-(2,3-difluoro-5-methyl-4-((3-(2-methylsulfanylpyrimidin-4-yl)-2-pyridyl)oxy)phenyl)-1-phenyl-methanesulfonamide (610 mg, 1.2 mmol) in dichloromethane (20 mL) was added N,N-diisopropylethylamine (0.6 mL, 3.6 mmol) and chloromethyl methyl ether (0.14 mL, 1.9 mmol). The solution was stirred at rt for 1.5 h. The solution was diluted with water and extracted with dichloromethane. The organic solution was concentrated under vacuum. The residue was purified by silica flash chromatography eluting with ethyl acetate/petroleum ether (0%-30%) to afford the title compound (660 mg, 90% yield) as a light yellow solid. LCMS (ESI): [M+H]$^+$=559.1.

Step 2: N-(2,3-Difluoro-5-methyl-4-((3-(2-(methylthio)pyrimidin-4-yl)pyridin-2-yl)oxy)phenyl)-N-(methoxymethyl)-1-phenylethane-1-sulfonamide

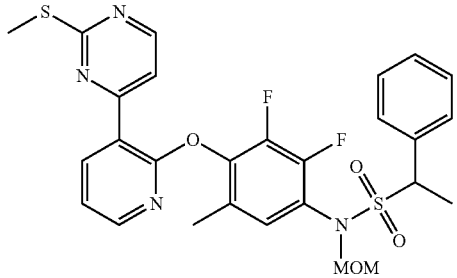

Into the solution of N-(2,3-difluoro-5-methyl-4-((3-(2-(methylthio)pyrimidin-4-yl)pyridin-2-yl)oxy)phenyl)-N-(methoxymethyl)-1-phenylmethanesulfonamide (660 mg, 1.2 mmol) in tetrahydrofuran (20 mL) was added 1 M lithiumbis(trimethylsilyl)amide in tetrahydrofuran (1.68 mL, 1.7 mmol) at −70° C. The solution was stirred for 1 h at −70° C. Iodomethane (171 mg, 1.2 mmol) in tetrahydrofuran (5 mL) was added at −70° C. The reaction was allowed to warm to rt slowly, The solution was stirred for 3 h at rt. The reaction was quenched with sat ammonium chloride and extracted with ethyl acetate. The solution was dried over sodium sulfate and concentrated under vacuum. The residue was purified by silica flash chromatography eluting with ethyl acetate/petroleum ether (10%-40%) to afford the title compound (540 mg, 79.8% yield) as a light yellow solid. LCMS (ESI): [M+H]$^+$=573.1.

Step 3: N-(2,3-Difluoro-5-methyl-4-((3-(2-(methylthio)pyrimidin-4-yl)pyridin-2-yl)oxy)phenyl)-1-phenylethane-1-sulfonamide

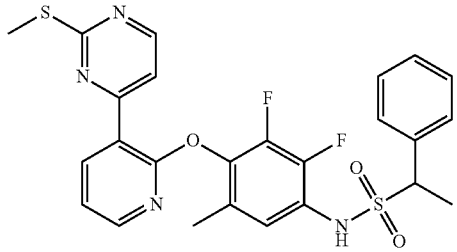 [SMILES: CSc1nccc(-c2cccnc2Oc2c(C)cc(NS(=O)(=O)C(C)c3ccccc3)c(F)c2F)n1]

A solution of N-(2,3-difluoro-5-methyl-4-((3-(2-(methylthio)pyrimidin-4-yl)pyridin-2-yl)oxy)phenyl)-N-(methoxymethyl)-1-phenylethane-1-sulfonamide (540 mg, 0.94 mmol) in 2,2,2-trifluoroacetic acid (10 mL) and water (1 mL) was stirred at rt for 3 h. The solution was diluted with water and adjusted to pH=9 with sodium carbonate. The mixture was extracted with dichloromethane and the organic layer was combined. The solution was dried over sodium sulfate and concentrated under vacuum. The residue was purified by silica flash chromatography eluting with ethyl acetate/petroleum ether (0%-40%) to afford the title compound (410 mg, 82.3% yield) as a light yellow solid. LCMS (ESI): [M+H]$^+$=529.1.

Step 4: N-(2,3-Difluoro-5-methyl-4-((3-(2-(methylsulfonyl)pyrimidin-4-yl)pyridin-2-yl)oxy)phenyl)-1-phenylethane-1-sulfonamide

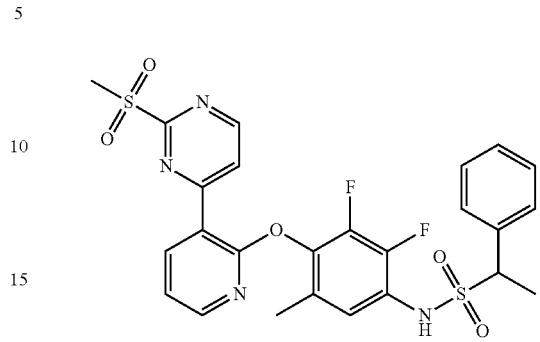

Into the solution of N-(2,3-difluoro-5-methyl-4-((3-(2-(methylthio)pyrimidin-4-yl)pyridin-2-yl)oxy)phenyl)-1-phenylethane-1-sulfonamide (410 mg, 0.78 mmol) in dichloromethane (20 mL) was added 3-chloroperoxybenzoic acid (475 mg, 2.3 mmol). The solution was stirred at rt for 2.5 h. The reaction was quenched with sat sodium sulfite and extracted with dichloromethane. The organic layer was washed with sat. sodium bicarbonate, dried over sodium sulfate and concentrated under vacuum to afford the title compound (435 mg, 99% yield) as a light yellow solid. LCMS (ESI): [M+1]$^+$=561.1.

Step 5: Benzyl (3S,5S)-3-((4-(2-(2,3-difluoro-6-methyl-4-((1-phenylethyl)sulfonamido)phenoxy)pyridin-3-yl)pyrimidin-2-yl)amino)-5-fluoropiperidine-1-carboxylate

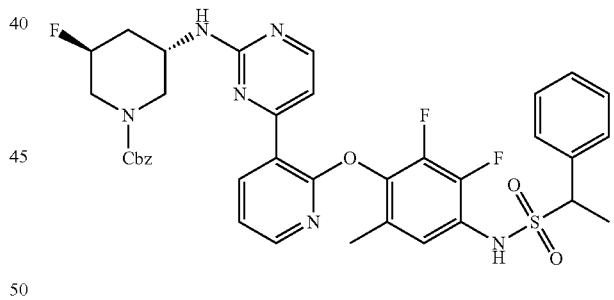

Under nitrogen, into the solution of N-(2,3-difluoro-5-methyl-4-((3-(2-(methylsulfonyl)pyrimidin-4-yl)pyridin-2-yl)oxy)phenyl)-1-phenylethane-1-sulfonamide (435 mg, 0.78 mmol) in dimethyl sulfoxide (4 mL) was added benzyl (3S,5S)-3-amino-5-fluoro-piperidine-1-carboxylate hydrochloride (280 mg, 0.97 mmol), cesium fluoride (236 mg, 1.55 mmol) and N,N-diisopropylethylamine (0.5 mL, 3.0 mmol). The mixture was stirred at 80° C. for 16 h. The mixture was diluted with ethyl acetate and water. The mixture was extracted with ethyl acetate and the organic layers were combined. The organic layer was washed with water, dried over sodium sulfate, filtered and concentrated under vacuum. The residue was purified by silica flash chromatography eluting with ethyl acetate/petroleum ether (40%-60%) to afford the title compound (430 mg, 75.6% yield) as a light yellow solid. LCMS (ESI): [M+H]$^+$=733.2.

Step 6: N-(2,3-Difluoro-4-((3-(2-(((3S,5S)-5-fluoropiperidin-3-yl)amino)pyrimidin-4-yl)pyridin-2-yl)oxy)-5-methylphenyl)-1-phenylethane-1-sulfonamide hydrochloride & N-(2,3-difluoro-4-((3-(2-(((3S,5S)-5-fluoropiperidin-3-yl)amino)pyrimidin-4-yl)pyridin-2-yl)oxy)-5-methylphenyl)-1-phenylethane-1-sulfonamide Compound 313 & Compound 314

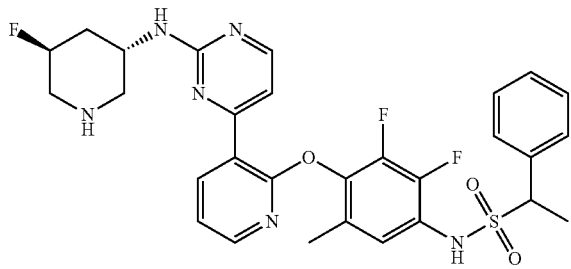 [SMILES: Cc1cc(NS(=O)(=O)C(C)c2ccccc2)c(F)c(F)c1Oc1ncccc1-c1ccnc(N[C@@H]2CNC[C@@H](F)C2)n1]

Into the solution of benzyl (3S,5S)-3-((4-(2-(2,3-difluoro-6-methyl-4-((1-phenylethyl)sulfonamido)phenoxy)pyridin-3-yl)pyrimidin-2-yl)amino)-5-fluoropiperidine-1-carboxylate (430 mg, 0.59 mmol) in dichloromethane (10 mL) was added 33% hydrobromicacid in acetic acid (2 mL). The solution was stirred at rt for 2 h. The mixture was concentrated under vacuum. The residue was purified with Prep-HPLC and Chiral-HPLC to afford the title compound. The fast peak was assigned as isomer 1. The slow peak was assigned as isomer 2.

N-(2,3-Difluoro-4-((3-(2-(((3S,5S)-5-fluoropiperidin-3-yl)amino)pyrimidin-4-yl)pyridin-2-yl)oxy)-5-methylphenyl)-1-phenylethane-1-sulfonamide hydrochloride (isomer 1, Compound 313) (50.1 mg, 13.4% yield) as a white solid and as HCl salt, (rt=1.712 min, CHIRALPAK IC-3, 0.46×5 cm; 3 um, (Hex:DCM=3:1)(0.1% DEA):EtOH=80:20, 1.0 mL/min).

N-(2,3-Difluoro-4-((3-(2-(((3S,5S)-5-fluoropiperidin-3-yl)amino)pyrimidin-4-yl)pyridin-2-yl)oxy)-5-methylphenyl)-1-phenylethane-1-sulfonamide (isomer 2, Compound 314) (58.7 mg, 16.7% yield) as a white solid, (rt=2.099 min, CHIRALPAK IC-3, 0.46×5 cm; 3 um, (Hex:DCM=3:1)(0.1% DEA):EtOH=80:20, 1.0 mL/min).

Example 100

1-(4-Cyclopropylphenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 315

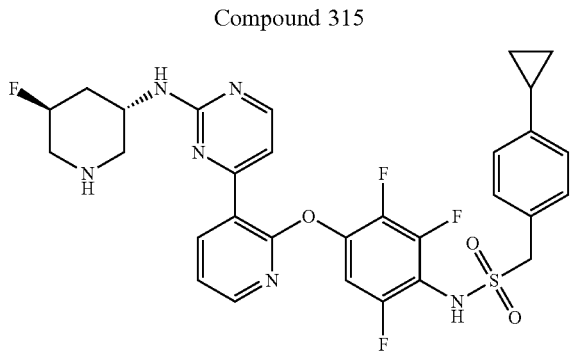

Step 1: 1-(4-Cyclopropylphenyl)-N-(2,3,6-trifluoro-4-((3-(2-(methylthio)pyrimidin-4-yl)pyridin-2-yl)oxy)phenyl)methanesulfonamide

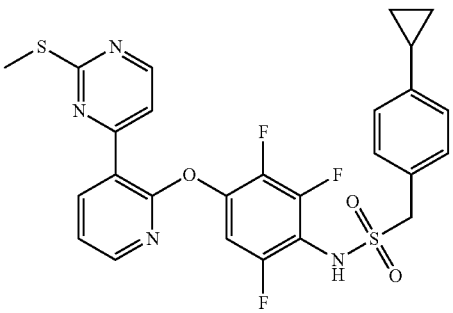 [SMILES: CSc1nccc(-c2cccnc2Oc2cc(F)c(NS(=O)(=O)Cc3ccc(C4CC4)cc3)c(F)c2F)n1]

To a mixture of 1-(4-bromophenyl)-N-(2,3,6-trifluoro-4-((3-(2-methylsulfanylpyrimidin-4-yl)-2-pyridyl)oxy)phenyl)methanesulfonamide (300 mg, 0.50 mmol) and di-iodobis(tri-t-butylphosphino)dipalladium(I) (44 mg, 0.06 mmol) in toluene (3 mL) was added bromo (cyclopropyl)zinc (4 mL, 2 mmol) for 10 min at rt under nitrogen, the mixture was stirred for 2 h at rt. The reaction was quenched with water, extracted with ethyl acetate, washed with brine, dried over anhydrous sodium sulfate and concentrated under vacuum. The residue was purified by silica flash chromatography eluting with ethyl acetate/petroleum ether (5%-20%) to afford the title compound (261 mg, 93% yield) as a white solid. LCMS (ESI): [M+H]$^+$=559.10.

Step 3: 1-(4-Cyclopropylphenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 315

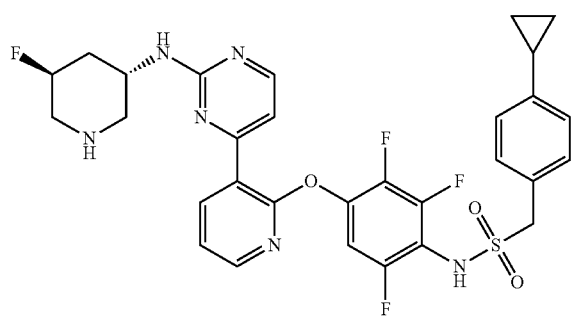 [SMILES: O=S(=O)(Cc1ccc(C2CC2)cc1)Nc1c(F)cc(Oc2ncccc2-c2ccnc(N[C@@H]3CNC[C@@H](F)C3)n2)c(F)c1F]

The title compound was prepared according to example 98. This provides the title compound (39 mg, 40.8% yield) as a white solid.

Example 101

1-(4-Fluorophenyl)-N-(2,3,6-trifluoro-4-((3-(2-(((3S,5S)-5-(fluoromethyl)piperidin-3-yl)amino)pyrimidin-4-yl)pyridin-2-yl)oxy)phenyl)methanesulfonamide Compound 316

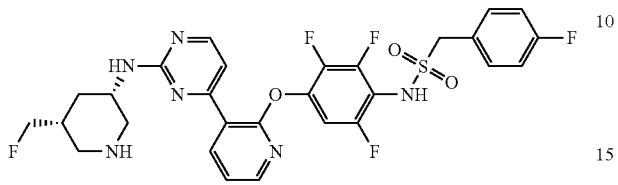

The title compound was prepared according to example 64. This provides the title compound (28 mg, 27.1% yield) as a white solid.

Example 102

1-Phenyl-N-(2,3,6-trifluoro-4-((3-(2-((5-methoxypiperidin-3-yl)amino)pyrimidin-4-yl)pyridin-2-yl)oxy)phenyl)methanesulfonamide &1-phenyl-N-(2,3,6-trifluoro-4-((3-(2-((5-methoxypiperidin-3-yl)amino)pyrimidin-4-yl)pyridin-2-yl)oxy)phenyl)methanesulfonamide Compound 317 & Compound 318 & Compound 319

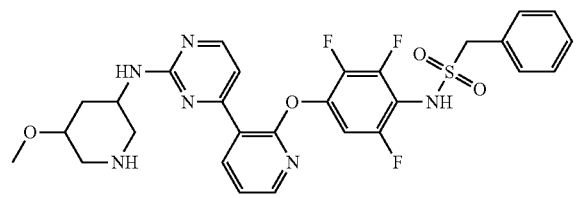 [SMILES: COC1CNCC(Nc2nccc(-c3cccnc3Oc3cc(F)c(NS(=O)(=O)Cc4ccccc4)c(F)c3F)n2)C1]

Step 1: 1-(tert-Butyl) 3-methyl 5-methoxypiperidine-1,3-dicarboxylate

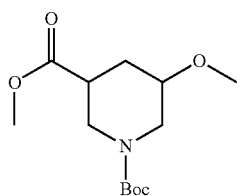 [SMILES: COC(=O)C1CC(OC)CN(C(=O)OC(C)(C)C)C1]

To a solution of 1-tert-butyl 3-methyl 5-hydroxypiperidine-1,3-dicarboxylate (1.0 g, 3.86 mmol) in N,N-dimethylformamide (10 mL) was added sodium hydride (0.3 g, 7.50 mmol) at 0° C. and stirred for 0.5 h at the same temperature. Then iodomethane (0.6 mL, 9.64 mmol) was added and stirred at rt for 1 h. The reaction was quenched with sat. ammonium chloride and extracted with ethyl acetate. The organic layers were washed with brine and concentrated under vacuum to afford the title compound (1 g, 85.4% yield) as a white solid. LCMS (ESI): [M+H]⁺= 274.2

Step 2: 1-(tert-butoxycarbonyl)-5-methoxypiperidine-3-carboxylic acid

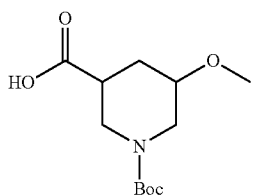 [SMILES: COC1CC(C(=O)O)CN(C(=O)OC(C)(C)C)C1]

To a solution of 1-(tert-butyl) 3-methyl 5-methoxypiperidine-1,3-dicarboxylate (1.0 g, 3.66 mmol) in methyl alcohol (10 mL) and water (2 mL) was added potassium carbonate (1.0 g, 7.24 mmol) at rt. The mixture was stirred under 80° C. for 16 h. The resulting solution was adjust pH to 5 with 1M HCl. The resulting solution was extracted with ethyl acetate, washed with brine, dried over sodium sulfate and concentrated to afford the title compound (1.1 g, 92.8% yield) as yellow oil. LCMS (ESI): [M+H]⁺=260.1

Step 3: tert-Butyl 3-(((benzyloxy)carbonyl)amino)-5-methoxypiperidine-1-carboxylate

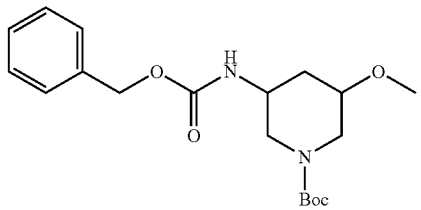 [SMILES: COC1CC(NC(=O)OCc2ccccc2)CN(C(=O)OC(C)(C)C)C1]

Under nitrogen, a mixture of 1-(tert-butoxycarbonyl)-5-methoxypiperidine-3-carboxylic acid (1.0 g, 3.86 mmol), diphenylphosphoryl azide (1.5 g, 5.45 mmol) and triethylamine (1.1 mL, 5.36 mmol) in toluene (10 mL) was stirred for 2 h at 100° C. Then benzyl alcohol (4 mL, 38.67 mmol) was added at 50° C. and stirred at 100° C. for 2 h. The resulting solution was diluted with water, extracted with ethyl acetate, washed with brine, dried over sodium sulfate and concentrated. The residue was purified by silica flash chromatography eluting with dichloromethane/methanol (99:1) to afford the title compound (0.70 g, 39.8% yield) as brown oil. LCMS (ESI): [M+H]⁺=365.2.

Step 4: tert-Butyl 3-amino-5-methoxypiperidine-1-carboxylate

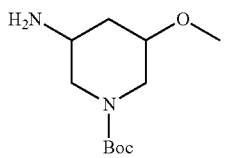 [SMILES: COC1CC(N)CN(C(=O)OC(C)(C)C)C1]

Under hydrogen, a mixture of tert-butyl 3-(((benzyloxy)carbonyl)amino)-5-methoxypiperidine-1-carboxylate (700 mg, 1.34 mmol) and 10% Pd/C (360 mg, 0.34 mmol) in ethyl acetate (15 mL) was stirred at 50° C. for 3 h. The solids were filtered out After filtration, the solvent was concentrated under vacuum to afford the title compound (430 mg, 97.2% yield) as black oil. LCMS (ESI): [M+H]$^+$=231.2

Step 5: 1-Phenyl-N-(2,3,6-trifluoro-4-((3-(2-((5-methoxypiperidin-3-yl)amino)pyrimidin-4-yl)pyridin-2-yl)oxy)phenyl)methanesulfonamide Compound 317 & Compound 318 & Compound 319

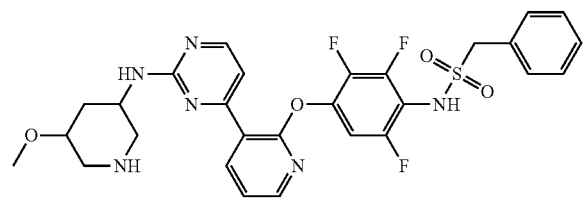 [SMILES: COC1CNCC(Nc2nccc(-c3cccnc3Oc3cc(F)c(NS(=O)(=O)Cc4ccccc4)c(F)c3F)n2)C1]

The title compound was prepared according to example Compound 328 & Compound 329 & Compound 331.

1-Phenyl-N-(2,3,6-trifluoro-4-((3-(2-((5-methoxypiperidin-3-yl)amino)pyrimidin-4-yl)pyridin-2-yl)oxy)phenyl)methanesulfonamide (36.9 mg, 51.6% yield) as a white solid.

1-Phenyl-N-(2,3,6-trifluoro-4-((3-(2-((5-methoxypiperidin-3-yl)amino)pyrimidin-4-yl)pyridin-2-yl)oxy)phenyl)methanesulfonamide (Compound 317) (30.5 mg, 42.7% yield) as a white solid.

1-Phenyl-N-(2,3,6-trifluoro-4-((3-(2-((5-methoxypiperidin-3-yl)amino)pyrimidin-4-yl)pyridin-2-yl)oxy)phenyl)methanesulfonamide (Compound 318) (30.3 mg, 42.5% yield) as a white solid.

1-Phenyl-N-(2,3,6-trifluoro-4-((3-(2-((5-methoxypiperidin-3-yl)amino)pyrimidin-4-yl)pyridin-2-yl)oxy)phenyl)methanesulfonamide (Compound 319) (47.1 mg, 57% yield) as a white solid.

Example 103

1-(2,4-Difluorophenyl)-N-(2,3,6-trifluoro-4-((3-(2-(((3S,5R)-5-(fluoromethyl)piperidin-3-yl)amino)pyrimidin-4-yl)pyridin-2-yl)oxy)phenyl)methanesulfonamide Compound 320

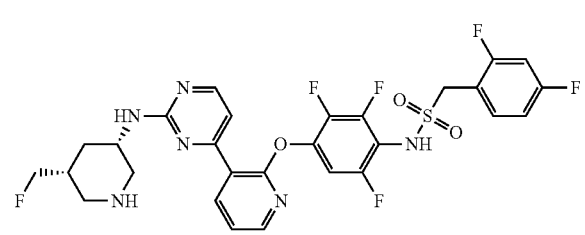 [SMILES: O=S(=O)(Cc1ccc(F)cc1F)Nc1c(F)cc(Oc2ncccc2-c2ccnc(N[C@@H]3CNC[C@H](CF)C3)n2)c(F)c1F]

The title compound was prepared according to example 64. This provides the title compound (43 mg, 35.5% yield) as a white solid.

Example 104

1-(4-Cyanophenyl)-N-(2,3,6-trifluoro-4-((3-(2-(((3S,5R)-5-(fluoromethyl)piperidin-3-yl)amino)pyrimidin-4-yl)pyridin-2-yl)oxy)phenyl)methanesulfonamide Compound 321

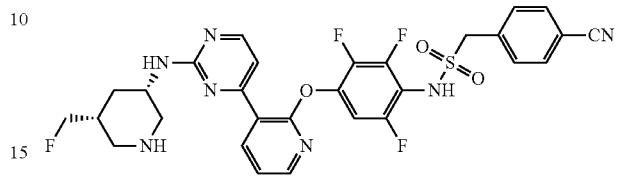

The title compound was prepared according to example 64. This provides the title compound (20.1 mg, 23.3% yield) as a white solid.

Example 105

1-(4-Fluoro-2-methylphenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 322

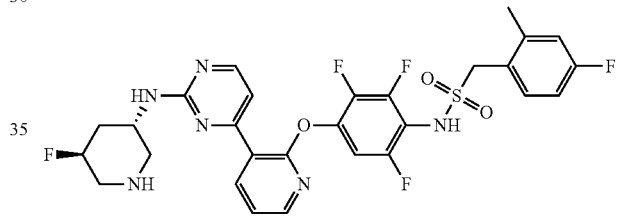

The title compound was prepared according to example 40. This resulted in the title compound (56.9 mg, 46.4% yield) as a white solid.

Example 106

N-(6-Chloro-2,3-difluoro-4-((3-(2-(((3S,5S)-5-fluoropiperidin-3-yl)amino)pyrimidin-4-yl)pyridin-2-yl)oxy)phenyl)-1-(2-fluorophenyl)methanesulfonamide Compound 323

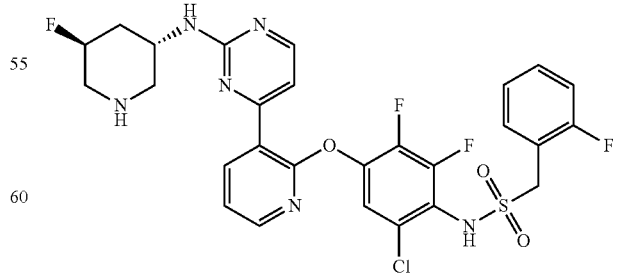

The title compound was prepared according to example 40. This resulted in the title compound (22 mg, 39.3% yield) as a white solid.

Example 107

N-(4-((3-(2-((5-Cyclopropylpiperidin-3-yl)amino)pyrimidin-4-yl)pyridin-2-yl)oxy)-2,3,6-trifluorophenyl)-1-(2-fluorophenyl)methanesulfonamide &

Compound 324 & Compound 325 & Compound 326 & Compound 327

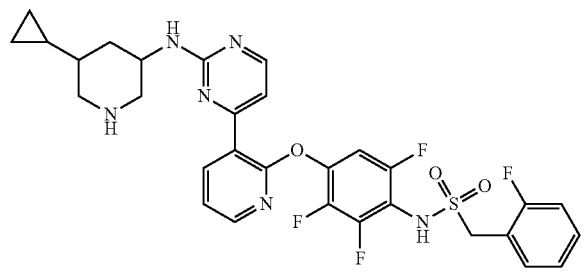 [SMILES: O=S(=O)(Cc1ccccc1F)Nc1c(F)cc(Oc2ncccc2-c2ccnc(NC3CNCC(C4CC4)C3)n2)c(F)c1F]

Step 1: 5-Cyclopropylpyridin-3-amine

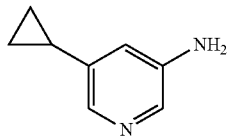

Under nitrogen, a mixture of 5-bromo-3-pyridinamine (5.0 g, 28.9 mmol), cyclopropylboronicacid (5.0 g, 58.21 mmol), tetrakis(triphenylphosphine)palladium (1.8 g, 1.56 mmol), cesium carbonate (2.9 g, 89.01 mmol) in water (5 mL) and 1,4-dioxane (45 mL) was stirred at 100° C. for 16 h. The reaction mixture was diluted with water. The resulting solution was diluted with water, extracted with ethyl acetate, washed with brine, dried over sodium sulfate and concentrated. The residue was purified by silica flash chromatography eluting with ethyl acetate/petroleum ether (1:1) to afford the title compound (4.2 g, 97.5% yield) as a brown solid. LCMS (ESI): $[M+H]^+=135.1$.

Step 2: tert-Butyl (5-cyclopropylpyridin-3-yl)carbamate

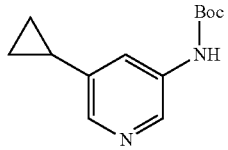

To a solution of 5-cyclopropylpyridin-3-amine (3.40 g, 22.81 mmol) and sodium bis(trimethylsilyl)amide (25 mL, 50 mmol) in tetrahydrofuran (50 mL) was added di-tert-butyldicarbonate (1.4 g, 64.15 mmol) and stirred at 25° C. for 16 h. The reaction was quenched with saturated ammonium chloride solution. The resulting solution was extracted with ethyl acetate and the organic layers were combined. The organic layer was dried over anhydrous sodium sulfate and concentrated under vacuum. The crude product was dissolved in methanol (20 mL) and tetrahydrofuran (40 mL) was added sodium hydroxide solution (20 mL, 1 M) dropwise and stirred at rt for 5 h. The resulting solution was extracted with ethyl acetate and the organic layers were combined. The organic layer was dried over anhydrous sodium sulfate and concentrated under vacuum. The residue was purified by silica flash chromatography eluting with ethyl acetate/petroleum ether (70:30) to afford the title compound (4.9 g, 73.4% yield) as a brown solid. LCMS (ESI): $[M+H]^+=235.1$

Step 3: tert-Butyl (5-cyclopropylpiperidin-3-yl)carbamate

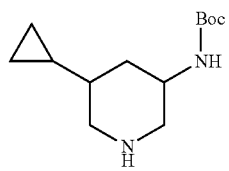 [SMILES: CC(C)(C)OC(=O)NC1CNCC(C2CC2)C1]

A mixture of tert-butyl N-(5-cyclopropyl-3-pyridyl)carbamate (5.0 g, 10.67 mmol), Rh/C (550 mg, 0.26 mmol), platinum (Iv) oxide (1.0 g, 4.4 mmol) and acetic acid (500 mL) was stirred at 70° C. under hydrogen (15 atm) for 24 h. After cooling to rt, the solids were filtered. And the filtrate was concentrated under reduced pressure to afford the title compound (2.5 g, 63.4% yield) as a brown oil. LCMS (ESI) $[M+H]^+=241.2$

Step 4: Benzyl 3-((tert-butoxycarbonyl)amino)-5-cyclopropylpiperidine-1-carboxylate

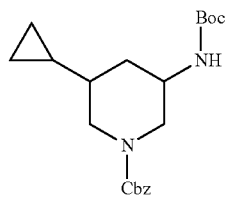 [SMILES: CC(C)(C)OC(=O)NC1CC(C2CC2)CN(C(=O)OCc2ccccc2)C1]

To a solution of tert-butyl N-(5-cyclopropyl-3-piperidyl)carbamate (3.5 g, 7.28 mmol) and triethylamine (4.0 g, 39.53 mmol) in tetrahydrofuran (40 mL) was added benzyl chloroformate (3.5 g, 20.52 mmol) and stirred at rt for 2 h. The resulting solution was diluted with water, extracted with ethyl acetate, washed with brine, dried over anhydrous sodium sulfate and concentrated. The residue was purified by silica flash chromatography eluting with dichloromethane/methanol (99:1) to afford the title compound (2.6 g, 66.7% yield) as brown oil. LCMS (ESI) $[M+H]^+=375.2$.

Step 5: Benzyl 3-amino-5-cyclopropylpiperidine-1-carboxylate

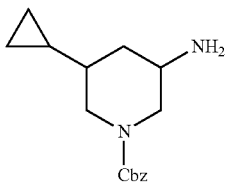 [SMILES: NC1CC(C2CC2)CN(C(=O)OCc2ccccc2)C1]

To a solution of benzyl 3-(tert-butoxycarbonylamino)-5-cyclopropyl-piperidine-1-carboxylate (2.7 g, 5.05 mmol) in dichloromethane (10 mL) was added 4 M HCl in dioxane (15 mL) and stirred at rt for 2 h. The solvent was concentrated under vacuum. The crude product was purified by Prep-HPLC to afford the title compound (700 mg, 48% yield) as brown oil. LCMS (ESI): [M+H]$^+$=275.2

Step 6: Benzyl 3-cyclopropyl-5-((4-(2-(2,3,5-trifluoro-4-(((2-fluorophenyl)methyl)sulfonamido)phenoxy)pyridin-3-yl)pyrimidin-2-yl)amino)piperidine-1-carboxylate

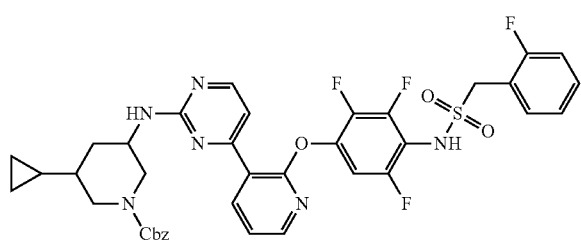 [SMILES: O=C(OCc1ccccc1)N1CC(Nc2nccc(-c3cccnc3Oc3cc(F)c(NS(=O)(=O)Cc4ccccc4F)c(F)c3F)n2)CC(C2CC2)C1]

Under nitrogen, a mixture of benzyl 3-amino-5-cyclopropyl-piperidine-1-carboxylate hydrochloride (426 mg, 1.37 mmol), 1-(2-fluorophenyl)-N-(2,3,6-trifluoro-4-((3-(2-methylsulfonylpyrimidin-4-yl)-2-pyridyl)oxy)phenyl)methanesulfonamide (1.5 g, 1.32 mmol), cesium fluoride (1200 mg, 7.9 mmol) and N,N-diisopropylethylamine (600 mg, 4.64 mmol) in dimethyl sulfoxide (12 mL) was stirred at 85° C. for 1 h. The resulting solution was diluted with water, extracted with ethyl acetate, washed with brine, dried over sodium sulfate and concentrated. The residue was purified by silica flash chromatography eluting with ethyl acetate/petroleum ether (80:20). The crude product was further purified by Prep-HPLC and Chiral HPLC to afford four isomers. Isomer 1, isomer 2, isomer 3, isomer 4 were assigned arbitrarily.

Benzyl 3-cyclopropyl-5-((4-(2-(2,3,5-trifluoro-4-(((2-fluorophenyl)methyl)sulfonamido)phenoxy)pyridin-3-yl)pyrimidin-2-yl)amino)piperidine-1-carboxylate (isomer 1) (48 mg, 4.7% yield) as a white solid. LCMS (ESI): [M+H]$^+$=763.2.

Benzyl 3-cyclopropyl-5-((4-(2-(2,3,5-trifluoro-4-(((2-fluorophenyl)methyl)sulfonamido)phenoxy)pyridin-3-yl)pyrimidin-2-yl)amino)piperidine-1-carboxylate (isomer 2) (46 mg, 4.5% yield) as a white solid. LCMS (ESI): [M+H]$^+$=763.2.

Benzyl 3-cyclopropyl-5-((4-(2-(2,3,5-trifluoro-4-(((2-fluorophenyl)methyl)sulfonamido)phenoxy)pyridin-3-yl)pyrimidin-2-yl)amino)piperidine-1-carboxylate (isomer 3) (200 mg, 19.7% yield) as a white solid. LCMS (ESI): [M+H]$^+$=763.2.

Benzyl 3-cyclopropyl-5-((4-(2-(2,3,5-trifluoro-4-(((2-fluorophenyl)methyl)sulfonamido)phenoxy)pyridin-3-yl)pyrimidin-2-yl)amino)piperidine-1-carboxylate (isomer 4) (210 mg, 20.7% yield) as a white solid. LCMS (ESI): [M+H]$^+$25=763.2.

Step 7: N-(4-((3-(2-((5-Cyclopropylpiperidin-3-yl)amino)pyrimidin-4-yl)pyridin-2-yl)oxy)-2,3,6-trifluorophenyl)-1-(2-fluorophenyl)methanesulfonamide Compound 324

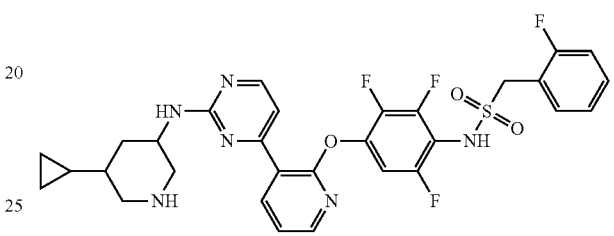

To a solution of benzyl 3-cyclopropyl-5-((4-(2-(2,3,5-trifluoro-4-((2-fluorophenyl)methylsulfonylamino)phenoxy)-3-pyridyl)pyrimidin-2-yl)amino)piperidine-1-carboxylate (isomer 1 of step 6) (48 mg, 0.06 mmol) in dichloromethane (0.3 mL) and acetonitrile (0.30 mL) was added dimethyl sulfide (0.5 mL) and boron trifluoride etherate (0.5 mL) and stirred at rt for 2 h. The reaction was quenched with sat. sodium bicarbonate. The resulting solution was extracted with ethyl acetate, washed with brine, and concentrated. The product was purified by Prep-HPLC to afford the title compound (24.9 mg, 61.6% yield) as a white solid.

Step 8: N-(4-((3-(2-((5-Cyclopropylpiperidin-3-yl)amino)pyrimidin-4-yl)pyridin-2-yl)oxy)-2,3,6-trifluorophenyl)-1-(2-fluorophenyl)methanesulfonamide Compound 325

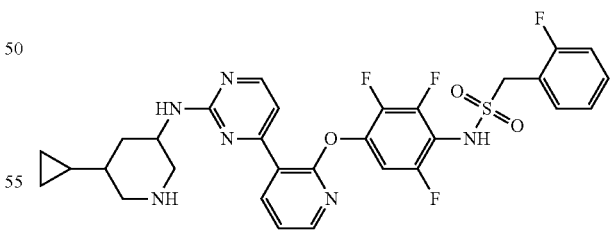

To a solution of benzyl 3-cyclopropyl-5-((4-(2-(2,3,5-trifluoro-4-((2-fluorophenyl)methylsulfonylamino)phenoxy)-3-pyridyl)pyrimidin-2-yl)amino)piperidine-1-carboxylate (isomer 2 of step 6) (46 mg, 0.06 mmol) in dichloromethane (0.3 mL) and acetonitrile (0.30 mL) was added dimethyl sulfide (0.5 mL) and boron trifluoride etherate (0.5 mL) and stirred at rt for 2 h. The reaction was quenched with sat. sodium bicarbonate. The resulting solution was extracted with ethyl acetate, washed with brine, and concentrated. The product was purified by Prep-HPLC to afford the title compound (23.4 mg, 61% yield) as a white solid.

Step 9: N-(4-((3-(2-((5-Cyclopropylpiperidin-3-yl)amino)pyrimidin-4-yl)pyridin-2-yl)oxy)-2,3,6-trifluorophenyl)-1-(2-fluorophenyl)methanesulfonamide Compound 326

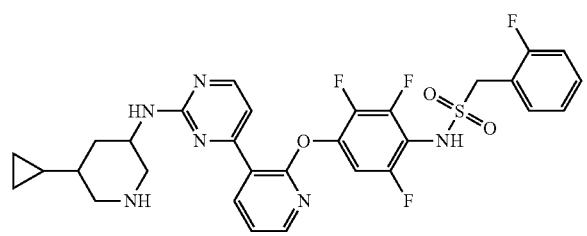 [SMILES: O=S(=O)(Cc1ccccc1F)Nc1c(F)cc(Oc2ncccc2-c2ccnc(NC3CNCC(C4CC4)C3)n2)c(F)c1F]

To a solution of benzyl 3-cyclopropyl-5-((4-(2-(2,3,5-trifluoro-4-((2-fluorophenyl)methylsulfonylamino)phenoxy)-3-pyridyl)pyrimidin-2-yl)amino)piperidine-1-carboxylate (isomer 3 of step 6) (200 mg, 0.26 mmol) in dichloromethane (1.25 mL) and acetonitrile (1.25 mL) was added dimethyl sulfide (1.5 mL) and boron trifluoride etherate (1.5 mL) was added and stirred at rt for 2 h. The reaction was quenched with sat. sodium bicarbonate. The resulting solution was diluted with water, extracted with ethyl acetate, washed with brine, and concentrated. The product was purified by Prep-HPLC to afford the title compound (104.8 mg, 63% yield) as a white solid.

Step 10: N-(4-((3-(2-((5-Cyclopropylpiperidin-3-yl)amino)pyrimidin-4-yl)pyridin-2-yl)oxy)-2,3,6-trifluorophenyl)-1-(2-fluorophenyl)methanesulfonamide Compound 327

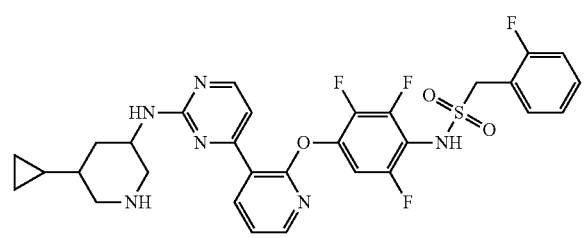 [SMILES: O=S(=O)(Cc1ccccc1F)Nc1c(F)cc(Oc2ncccc2-c2ccnc(NC3CNCC(C4CC4)C3)n2)c(F)c1F]

To a solution of benzyl 3-cyclopropyl-5-((4-(2-(2,3,5-trifluoro-4-((2-fluorophenyl)methylsulfonylamino)phenoxy)-3-pyridyl)pyrimidin-2-yl)amino)piperidine-1-carboxylate (isomer 4 of step 6) (210 mg, 0.27 mmol) in dichloromethane (1.25 mL) and acetonitrile (1.25 mL) was added dimethyl sulfide (1.5 mL) and boron trifluoride etherate (1.5 mL) was added and stirred at rt for 2 h. The reaction was quenched with sat. sodium bicarbonate. The resulting solution was diluted with water, extracted with ethyl acetate, washed with brine, and concentrated. The product was purified by Prep-HPLC to afford the title compound (107.5 mg, 64.6% yield) as a white solid.

Example 108

1-Phenyl-N-(2,3,6-trifluoro-4-((3-(2-((5-(methoxymethyl)piperidin-3-yl)amino)pyrimidin-4-yl)pyridin-2-yl)oxy)phenyl)methanesulfonamide Compound 328 & Compound 329 & Compound 331

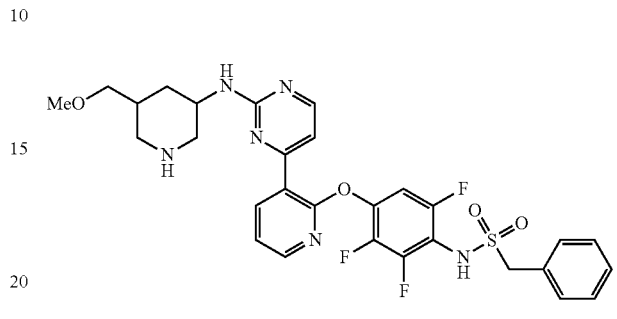

Step 1: 1-(tert-Butyl) 3-methyl 5-(benzyloxy)piperidine-1,3-dicarboxylate

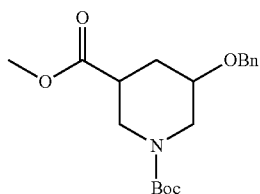 [SMILES: COC(=O)C1CC(OCc2ccccc2)CN(C(=O)OC(C)(C)C)C1]

To a solution of 1-tert-butyl 3-methyl 5-hydroxypiperidine-1,3-dicarboxylate (8.0 g, 31 mmol) in N,N-dimethylformamide (80 mL) was added sodium hydride (1.85 g, 46 mmol) at 0° C. and reacted for 0.5 h at rt. Then benzyl bromide (0.99 mL, 8.34 mmol) was added and stirred at rt for 2 h. The reaction was quenched with sat ammonium chloride and extracted with ethyl acetate. The organic layer was washed with brine (10 mL), dried over anhydrous sodium sulfate and concentrated under vacuum. The organic layer was dried over anhydrous sodium sulfate and concentrated under vacuum. The residue was purified by flash chromatography on silica gel eluting with dichloromethane/petroleum ether (0-100%) to afford the title compound (8.2 g, 75.8% yield) as a colorless oil. LCMS (ESI): [M+H]+ = 350.1.

Step 2: tert-Butyl 3-(benzyloxy)-5-(hydroxymethyl)piperidine-1-carboxylate

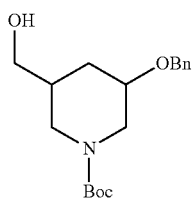 [SMILES: CC(C)(C)OC(=O)N1CC(CO)CC(OCc2ccccc2)C1]

A solution of 1-tert-butyl 3-methyl 5-benzyloxypiperidine-1,3-dicarboxylate (2.7 g, 7.7 mmol) and calcium chloride (1.59 g, 14 mmol) in tetrahydrofuran (60 mL) was stirred at 0° C. for 0.5 h. Then sodium borohydride (1.36 g, 36 mmol) was added and stirred at rt for 24 h. The reaction was quenched with ice water (50 mL). The resulting solution was extracted with ethyl acetate and the organic layers were combined. The organic layer was dried over anhydrous sodium sulfate and concentrated under vacuum. The residue was purified by silica flash chromatography eluting with methanol/dichloromethane (0-5%) to afford the title compound (2.4 g, 96.6% yield) as a colorless oil. LCMS (ESI): [M+H]$^+$=322.2.

Step 3: tert-Butyl 3-(benzyloxy)-5-(methoxymethyl)piperidine-1-carboxylate

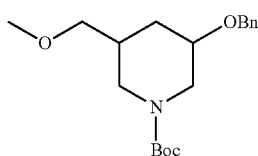 [SMILES: COCC1CC(OCc2ccccc2)CN(C(=O)OC(C)(C)C)C1]

Into a solution of tert-butyl 3-benzyloxy-5-(hydroxymethyl)piperidine-1-carboxylate (2.5 g, 7.9 mmol) in tetrahydrofuran (25 mL) was added sodium hydride (450 mg, 11 mmol), the mixture was stirred at 0° C. for 0.5 h, then iodomethane (3.3 g, 23 mmol) was added at the same temperature and stirred for 24 h at rt. The reaction was quenched with sat. ammonium chloride (40 mL). The resulting solution was extracted with ethyl acetate and the organic layers were combined. The organic layer was dried over anhydrous sodium sulfate and concentrated under vacuum. The residue was purified by silica flash chromatography eluting with ethyl acetate/petroleum ether (0-40%) to afford the title compound (2.6 g, 99.7% yield) as colorless oil. LCMS (ESI): [M+H]$^+$=336.1.

Step 4: tert-Butyl 3-hydroxy-5-(methoxymethyl)piperidine-1-carboxylate

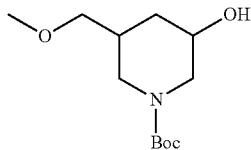 [SMILES: COCC1CC(O)CN(C(=O)OC(C)(C)C)C1]

Into a solution of tert-butyl 3-benzyloxy-5-(methoxymethyl)piperidine-1-carboxylate (2.6 g, 7.8 mmol) in methyl alcohol (100 mL) was added 10% Pd/C (700 mg), the mixture was stirred at rt for 2 h under hydrogen. The reaction was filtered out. The solvent was removed under vacuum to afford the title compound (1.9 g, 99.9% yield) as brown oil. LCMS (ESI): [M+H]$^+$=246.

Step 5: tert-Butyl 3-(methoxymethyl)-5-((methylsulfonyl)oxy)piperidine-1-carboxylate

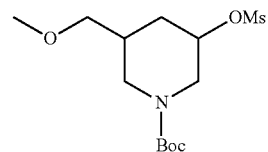 [SMILES: COCC1CC(OS(C)(=O)=O)CN(C(=O)OC(C)(C)C)C1]

Into a solution of tert-butyl 3-hydroxy-5-(methoxymethyl)piperidine-1-carboxylate (2.3 g, 9.4 mmol) in dichloromethane (40 mL) was added triethylamine (3.8 g, 37 mmol) and methanesulfonyl chloride (1.83 g, 16 mmol), the mixture was stirred at 0° C. for 2 h. The reaction mixture was diluted with water (20 mL). The resulting solution was extracted with dichloromethane and the organic layers were combined. The organic layer was dried over anhydrous sodium sulfate and concentrated under vacuum to afford the title compound (3.0 g, 98.9% yield) as dark red oil. LCMS (ESI): [M+H]$^+$=324.1.

Step 6: tert-Butyl 3-azido-5-(methoxymethyl)piperidine-1-carboxylate

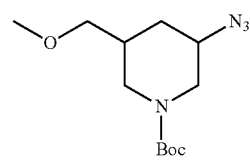 [SMILES: COCC1CC(N=[N+]=[N-])CN(C(=O)OC(C)(C)C)C1]

Into a solution of tert-butyl 3-(methoxymethyl)-5-methylsulfonyloxy-piperidine-1-carboxylate (3.0 g, 9.3 mmol) in N,N-dimethylacetamide (70 mL) was added sodium azide (1.3 g, 20 mmol), the mixture was stirred at 80° C. for 6 h under nitrogen. The reaction mixture was diluted with water and extracted with ethyl acetate. The solvent was removed under vacuum to afford the title compound (2.5 g, 99.7% yield) as brown oil. LCMS (ESI): [M+H]$^+$=271.2.

Step 7: tert-Butyl 3-amino-5-(methoxymethyl)piperidine-1-carboxylate

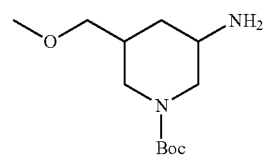 [SMILES: COCC1CC(N)CN(C(=O)OC(C)(C)C)C1]

Into a solution of tert-butyl 3-azido-5-(methoxymethyl)piperidine-1-carboxylate (2.5 g, 9.25 mmol) in methyl alcohol (50 mL) was added 10% Pd/C (800 mg), the mixture was stirred at rt for 1.5 h under hydrogen. The solids were filtered out. The solvent was removed under vacuum to afford the title compound (2.1 g, 92.9% yield) as a brown oil. LCMS (ESI): [M+H]$^+$=245.1.

Step 8: tert-Butyl 3-(methoxymethyl)-5-((4-(2-(2,3,5-trifluoro-4-((phenylmethyl)sulfonamido)phenoxy)pyridin-3-yl)pyrimidin-2-yl)amino)piperidine-1-carboxylate

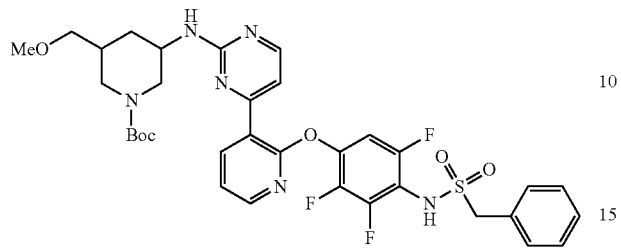

Under nitrogen, a solution of tert-butyl 3-amino-5-(methoxymethyl)piperidine-1-carboxylate (330 mg, 1.35 mmol) and 1-phenyl-N-(2,3,6-trifluoro-4-((3-(2-methylsulfonylpyrimidin-4-yl)-2-pyridyl)oxy)phenyl)methanesulfonamide (500 mg, 0.9 mmol), caesium fluoride (415 mg, 2.73 mmol), N,N-diisopropylethylamine (350.0 mg, 2.71 mmol) in dimethyl sulfoxide (4 mL) was stirred for 1 h at 80° C. The reaction mixture was diluted with water and extracted with ethyl acetate. The solvent was removed under vacuum. The residue was purified by silica flash chromatography eluting with ethyl acetate/petroleum ether (0-100%). The crude product was further purified by Prep-HPLC and Chiral HPLC to afford four isomers. Isomer 1, isomer 2, isomer 3, isomer 4 were assigned arbitrarily.

tert-Butyl 3-(methoxymethyl)-5-((4-(2-(2,3,5-trifluoro-4-((phenylmethyl)sulfonamido)phenoxy)pyridin-3-yl)pyrimidin-2-yl)amino)piperidine-1-carboxylate (isomer 1) (60 mg, 9.2% yield). LCMS (ESI): [M+H]$^+$=715.2.

tert-Butyl 3-(methoxymethyl)-5-((4-(2-(2,3,5-trifluoro-4-((phenylmethyl)sulfonamido)phenoxy)pyridin-3-yl)pyrimidin-2-yl)amino)piperidine-1-carboxylate (isomer 2) (60 mg, 9.2% yield). LCMS (ESI): [M+H]$^+$=715.2.

tert-Butyl 3-(methoxymethyl)-5-((4-(2-(2,3,5-trifluoro-4-((phenylmethyl)sulfonamido)phenoxy)pyridin-3-yl)pyrimidin-2-yl)amino)piperidine-1-carboxylate (isomer 3) (68 mg, 10.5% yield). LCMS (ESI): [M+H]$^+$=715.2.

tert-Butyl 3-(methoxymethyl)-5-((4-(2-(2,3,5-trifluoro-4-((phenylmethyl)sulfonamido)phenoxy)pyridin-3-yl)pyrimidin-2-yl)amino)piperidine-1-carboxylate (isomer 4) (80 mg, 12.3% yield). LCMS (ESI): [M+H]$^+$=715.2.

Step 9: 1-Phenyl-N-(2,3,6-trifluoro-4-((3-(2-((5-(methoxymethyl)piperidin-3-yl)amino)pyrimidin-4-yl)pyridin-2-yl)oxy)phenyl)methanesulfonamide Compound 328

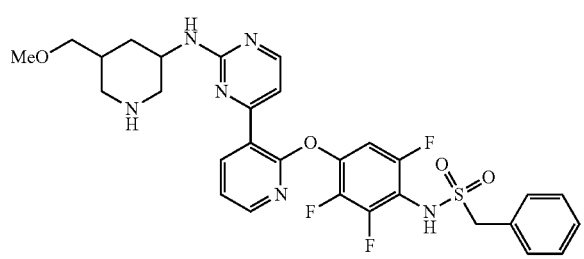 [SMILES: COCC1CNCC(Nc2nccc(-c3cccnc3Oc3cc(F)c(NS(=O)(=O)Cc4ccccc4)c(F)c3F)n2)C1]

Into a solution of tert-butyl 3-(methoxymethyl)-5-((4-(2-(2,3,5-trifluoro-4-((phenylmethyl)sulfonamido)phenoxy)pyridin-3-yl)pyrimidin-2-yl)amino)piperidine-1-carboxylate (isomer 1) (60 mg, 0.08 mmol) in dichloromethane (2 mL) was added 4 M HCl in dioxane (1 mL), the mixture was stirred at rt for 2 h. The reaction mixture was concentrated under vacuum. The residue was purified by Prep-HPLC to afford the title compound (21.7 mg, 42.1% yield) as a white solid.

Step 10: 1-Phenyl-N-(2,3,6-trifluoro-4-((3-(2-((5-(methoxymethyl)piperidin-3-yl)amino)pyrimidin-4-yl)pyridin-2-yl)oxy)phenyl)methanesulfonamide Compound 329

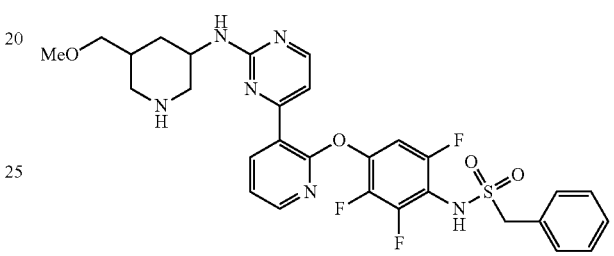

A solution of tert-butyl 3-(methoxymethyl)-5-((4-(2-(2,3,5-trifluoro-4-((phenylmethyl)sulfonamido)phenoxy)pyridin-3-yl)pyrimidin-2-yl)amino)piperidine-1-carboxylate (isomer 2) (60 mg, 0.08 mmol) in dichloromethane (2 mL) was added 4 M HCl in 1,4-dioxane (1 mL), the mixture was stirred at rt for 2 h. The reaction mixture was concentrated under vacuum. The residue was purified by Prep-HPLC to afford the title compound (25.1 mg, 48.6% yield) as a white solid.

Step 11: 1-Phenyl-N-(2,3,6-trifluoro-4-((3-(2-((5-(methoxymethyl)piperidin-3-yl)amino)pyrimidin-4-yl)pyridin-2-yl)oxy)phenyl)methanesulfonamide Compound 330

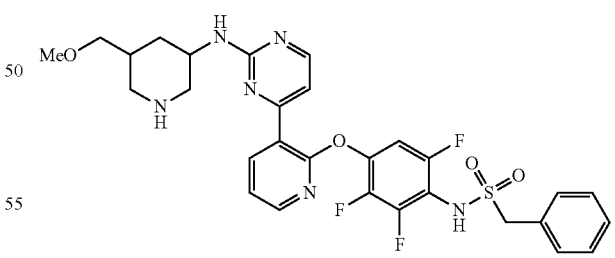

A solution of tert-butyl 3-(methoxymethyl)-5-((4-(2-(2,3,5-trifluoro-4-((phenylmethyl)sulfonamido)phenoxy)pyridin-3-yl)pyrimidin-2-yl)amino)piperidine-1-carboxylate (isomer 3) (68 mg, 0.1 mmol) in dichloromethane (2 mL) was added 4 M HCl in 1,4-dioxane (1 mL), the mixture was stirred at rt for 2 h. The reaction mixture was concentrated under vacuum. The residue was purified by Prep-HPLC to afford the title compound (29.4 mg, 50.3% yield) as a white solid.

Step 12: 1-Phenyl-N-(2,3,6-trifluoro-4-((3-(2-((5-(methoxymethyl)piperidin-3-yl)amino)pyrimidin-4-yl)pyridin-2-yl)oxy)phenyl)methanesulfonamide Compound 331

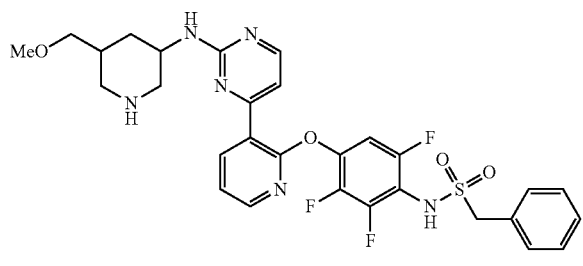 [SMILES: COCC1CNCC(Nc2nccc(-c3cccnc3Oc3cc(F)c(NS(=O)(=O)Cc4ccccc4)c(F)c3F)n2)C1]

A solution of tert-butyl 3-(methoxymethyl)-5-((4-(2-(2,3,5-trifluoro-4-((phenylmethyl)sulfonamido)phenoxy)pyridin-3-yl)pyrimidin-2-yl)amino)piperidine-1-carboxylate (isomer 4) (80 mg, 0.11 mmol) in dichloromethane (2 mL) was added 4 M HCl in 1,4-dioxane (1 mL), the mixture was stirred at rt for 2 h. The reaction mixture was concentrated under vacuum. The residue was purified by Prep-HPLC to afford the title compound (36.3 mg, 52.8% yield) as a white solid.

Example 109

N-(3-Chloro-2,6-difluoro-4-((3-(2-(((3S,5S)-5-fluoropiperidin-3-yl)amino)pyrimidin-4-yl)pyridin-2-yl)oxy)phenyl)-1-(2-fluorophenyl)methanesulfonamide Compound 332

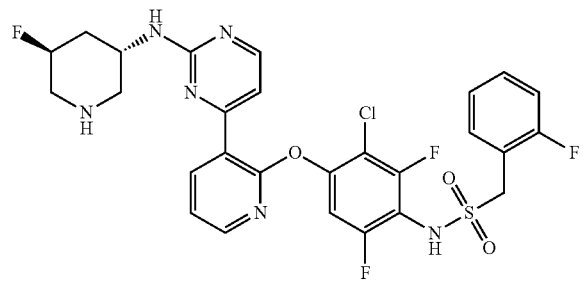

The title compound was prepared according to example 112. This resulted in the title compound (45.7 mg, 61.9% yield) as a yellow solid.

Example 110

1-Phenyl-N-(2,3,6-trifluoro-4-((3-(2-((5-(2-fluoropropan-2-yl)piperidin-3-yl)amino)pyrimidin-4-yl)pyridin-2-yl)oxy)phenyl)methanesulfonamide hydrochloride Compound 333 & Compound 334 & Compound 335 & Compound 336

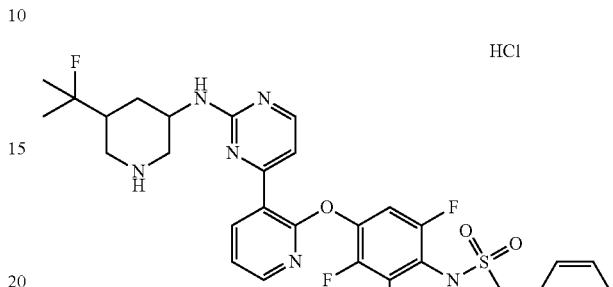

Step 1: tert-Butyl 3-benzyloxy-5-(1-hydroxy-1-methyl-ethyl)piperidine-1-carboxylate

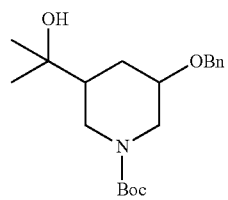 [SMILES: CC(C)(C)OC(=O)N1CC(OCc2ccccc2)CC(C(C)(C)O)C1]

To a mixture of 1-(tert-butyl) 3-methyl 5-(benzyloxy)piperidine-1,3-dicarboxylate (3.0 g, 8.6 mmol) in tetrahydrofuran (60 mL) was added 3 M methylmagnesium bromide in tetrahydrofuran (9 mL, 27 mmol) at −78° C. and stirred for 2 h at the same temperature. The reaction was quenched with sat ammonium chloride (40 mL). The resulting solution was extracted with ethyl acetate and the organic layers were combined. The organic layer was dried over anhydrous sodium sulfate and concentrated under vacuum. The residue was purified by flash chromatography on silica gel eluting with ethyl acetate/petroleum ether (0-40%) to afford the title compound (1.6 g, 53.3% yield) as a colorless oil. LCMS (ESI): $[M+H]^+=350.3$

Step 2: tert-Butyl 3-(benzyloxy)-5-(2-fluoropropan-2-yl)piperidine-1-carboxylate

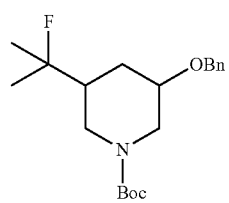 [SMILES: CC(C)(C)OC(=O)N1CC(OCc2ccccc2)CC(C(C)(C)F)C1]

A mixture of tert-butyl 3-benzyloxy-5-(l-hydroxy-1-methyl-ethyl)piperidine-1-carboxylate (2.7 g, 7.7 mmol) in diethylaminosulfur trifluoride (12 mL, 7.7 mmol) was stirred at rt for 1 h under nitrogen. The resulting solution was poured into sat. sodium carbonate at 0° C. The resulting solution was extracted with ethyl acetate and washed with brine, dried over sodium sulfate and concentrated. The residue was purified by silica flash chromatography eluting with ethyl acetate/petroleum ether (¼) to afford the title compound (1.3 g 47.9% yield) as colorless oil. LCMS (ESI): [M+H]⁺=352.3

Step 3: 1-Phenyl-N-(2,3,6-trifluoro-4-((3-(2-((5-(2-fluoropropan-2-yl)piperidin-3-yl)amino)pyrimidin-4-yl)pyridin-2-yl)oxy)phenyl)methanesulfonamide hydrochloride Compound 333 & Compound 334 & Compound 335 & Compound 336

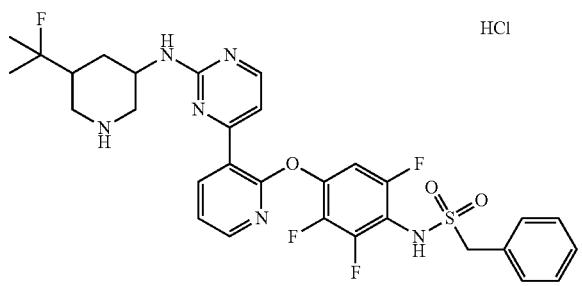 [SMILES: CC(C)(F)C1CNCC(Nc2nccc(-c3cccnc3Oc3cc(F)c(NS(=O)(=O)Cc4ccccc4)c(F)c3F)n2)C1 ; Cl]

The title compound was prepared according to example 108.

1-Phenyl-N-(2,3,6-trifluoro-4-((3-(2-((5-(2-fluoropropan-2-yl)piperidin-3-yl)amino)pyrimidin-4-yl)pyridin-2-yl)oxy)phenyl)methanesulfonamide hydrochloride Compound 333 (21.1 mg, 51.4% yield) as a white solid.

1-Phenyl-N-(2,3,6-trifluoro-4-((3-(2-((5-(2-fluoropropan-2-yl)piperidin-3-yl)amino)pyrimidin-4-yl)pyridin-2-yl)oxy)phenyl)methanesulfonamide hydrochloride (Compound 334) (20.8 mg, 49.5% yield) as a white solid.

1-Phenyl-N-(2,3,6-trifluoro-4-((3-(2-((5-(2-fluoropropan-2-yl)piperidin-3-yl)amino)pyrimidin-4-yl)pyridin-2-yl)oxy)phenyl)methanesulfonamide hydrochloride (Compound 335) (20.9 mg, 61.9% yield) as a white solid.

1-Phenyl-N-(2,3,6-trifluoro-4-((3-(2-((5-(2-fluoropropan-2-yl)piperidin-3-yl)amino)pyrimidin-4-yl)pyridin-2-yl)oxy)phenyl)methanesulfonamide hydrochloride (Compound 336) (18.9 mg, 50.5% yield) as a white solid.

Example 111

N-(4-((3-(2-((5-(1,1-Difluoroethyl)piperidin-3-yl)amino)pyrimidin-4-yl)pyridin-2-yl)oxy)-2,3,6-trifluorophenyl)-1-phenylmethanesulfonamide hydrochloride (mixture of enantiomers) Compound 337 & Compound 338 & Compound 339

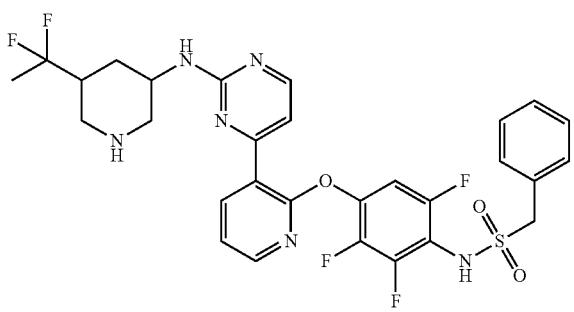 [SMILES: CC(F)(F)C1CNCC(Nc2nccc(-c3cccnc3Oc3cc(F)c(NS(=O)(=O)Cc4ccccc4)c(F)c3F)n2)C1]

Step 1: 5-Benzyloxy-1-tert-butoxycarbonyl-piperidine-3-carboxylic acid

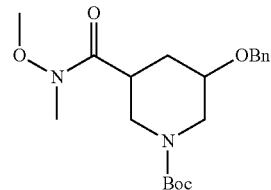 [SMILES: CON(C)C(=O)C1CC(OCc2ccccc2)CN(C(=O)OC(C)(C)C)C1]

Into the solution of 1-(tert-butyl) 3-methyl 5-(benzyloxy)piperidine-1,3-dicarboxylate (6.1 g, 17 mmol) in tetrahydrofuran (30 mL), ethanol (30 mL) and water (10 mL) was added lithium hydroxide monohydrate (5.4 g, 129 mmol). The mixture was stirred at rt for 4 h. The mixture was diluted with water and adjusted to pH=4 with hydrochloric acid (0.5 M). The mixture was extracted with ethyl acetate. The organic layer was dried over sodium sulfate and concentrated under vacuum to afford the title compound (5.8 g, 99.1% yield) as a white solid. LCMS (ESI): [M+H−56]⁺= 280.1.

Step 2: tert-Butyl 3-benzyloxy-5-(methoxy(methyl)carbamoyl)piperidine-1-carboxylate Into the solution of 5-benzyloxy-1-tert-butoxycarbonyl-piperidine-3-carboxylic acid (6.5 g, 19 mmol) in dichloromethane (150 mL) was added N,O-dimethylhydroxylamine hydrochloride (2.9 g, 29 mmol), N-(3- dimethylaminopropyl)-N'-ethylcarbodiimide hydrochloride (5.7 g, 29 mmol), 4-hydroxybenzotriazole (4.0 g, 29 mmol) and N,N-diisopropylethylamine (13 mL, 81 mmol). The solution was stirred at rt for 16 h. The solution was diluted with water and extracted with dichloromethane. The solution was dried over sodium sulfate and concentrated under vacuum. The residue was purified by silica flash chromatography eluting with ethyl acetate/petroleum ether (10%-50%) to afford the title compound (5.5 g, 75% yield) as colorless oil. LCMS (ESI): [M+H]$^+$=379.1.

Step 3: tert-Butyl 3-acetyl-5-benzyloxy-piperidine-1-carboxylate

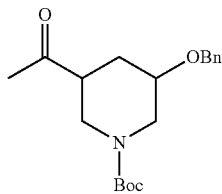 [SMILES: CC(=O)C1CC(OCc2ccccc2)CN(C(=O)OC(C)(C)C)C1]

Under nitrogen, into the solution of tert-butyl 3-benzyloxy-5-(methoxy(methyl)carbamoyl)piperidine-1-carboxylate (17.5 g, 46 mmol) in tetrahydrofuran (120 mL) was added 3 M methylmagnesiumbromide in tetrahydrofuran (50 mL, 150 mmol) at −60° C. The solution was stirred at rt for 3 h. The reaction was quenched with sat. ammonium chloride and extracted with ethyl acetate. The solution was dried over sodium sulfate and concentrated under vacuum. The residue was purified by silica flash chromatography eluting with dichloromethane/petroleum ether (10%-80%) to afford the title compound (14.2 g, 92.1% yield) as colorless oil. LCMS (ESI): [M+H+22]$^+$=356.1

Step 4: tert-Butyl 3-benzyloxy-5-(1,1-difluoroethyl) piperidine-1-carboxylate

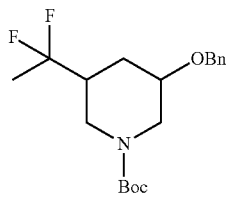 [SMILES: CC(C)(C)OC(=O)N1CC(OCc2ccccc2)CC(C(C)(F)F)C1]

A solution of tert-butyl 3-acetyl-5-benzyloxy-piperidine-1-carboxylate (2.5 g, 7.5 mmol) in bis(2-methoxyethyl)aminosulfur trifluoride (15 mL, 82 mmol) was stirred at 50° C. for 3 h. The solution was diluted with dichloromethane and quenched with sat. sodium bicarbonate. The mixture was extracted with dichloromethane. The solution was dried over sodium sulfate and concentrated under vacuum. The residue was purified by silica flash chromatography eluting with ethyl acetate/petroleum ether (0%-40%) to afford the title compound (1.2 g, 45% yield) as colorless oil. LCMS (ESI): [M+H−56]$^+$=300.1.

Step 5: N-(4-((3-(2-((5-(1,1-Difluoroethyl)piperidin-3-yl)amino)pyrimidin-4-yl)pyridin-2-yl)oxy)-2,3,6-trifluorophenyl)-1-phenylmethanesulfonamide hydrochloride (mixture of enantiomers) Compound 337 & Compound 338 & Compound 339

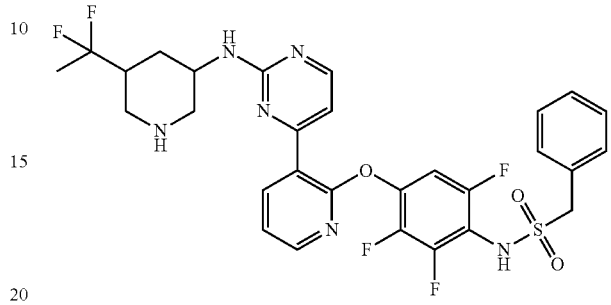

The title compound was prepared according to example 108.

N-(4-((3-(2-((5-(1,1-Difluoroethyl)piperidin-3-yl)amino) pyrimidin-4-yl)pyridin-2-yl)oxy)-2,3,6-trifluorophenyl)-1-phenylmethanesulfonamide hydrochloride (Compound 337, mixture of enantiomers) (17.9 mg, 98% yield) as a white solid and as HCl salt.

N-(4-((3-(2-((5-(1, 1-Difluoroethyl)piperidin-3-yl)amino) pyrimidin-4-yl)pyridin-2-yl)oxy)-2,3,6-trifluorophenyl)-1-phenylmethanesulfonamide (Compound 338) (92.2 mg, 23.7% yield) as a light brown solid, (rt=3.05 min, SFC CHIRALPAK AD-3 3*100 mm, 3 um, EtOH (0.1% DEA), 10% to 50% in 4.0 min, hold 2.0 min at 50%, 2.0 mL/min). Compound 338 & Compound 339 are enantiomers.

N-(4-((3-(2-((5-(1, 1-Difluoroethyl)piperidin-3-yl)amino) pyrimidin-4-yl)pyridin-2-yl)oxy)-2,3,6-trifluorophenyl)-1-phenylmethanesulfonamide (Compound 339) (97.5 mg, 25.1% yield) as a light brown solid, (rt=3.274 min, SFC CHIRALPAK AD-3 3*100 mm, 3 um, EtOH (0.1% DEA), 10% to 50% in 4.0 min, hold 2.0 min at 50%, 2.0 mL/min). Compound 338 & Compound 339 are enantiomers.

Example 112

N-(5-Chloro-2,3-difluoro-4-((3-(2-(((3S,5S)-5-fluoropiperidin-3-yl)amino)pyrimidin-4-yl)pyridin-2-yl)oxy)phenyl)-1-(2-fluorophenyl)methanesulfonamide Compound 340

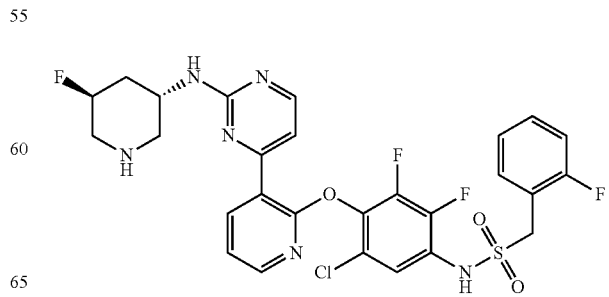

Step 1:
2-(Benzyloxy)-5-bromo-1-chloro-3,4-difluorobenzene

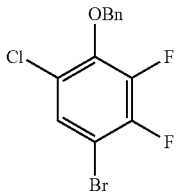 [SMILES: Fc1c(Br)cc(Cl)c(OCc2ccccc2)c1F]

A solution of 4-bromo-6-chloro-2,3-difluoro-phenol (840 mg, 3.5 mmol) and sodium hydride (278 mg, 7.0 mmol) in N,N-dimethylacetamide (5 mL) was stirred at 0° C. for 0.5 h. Then benzyl bromide (1781 mg, 10 mmol) was added and stirred at rt for 16 h. The reaction was quenched with sat ammonium chloride and extracted with ethyl acetate and washed with brine, dried over anhydrous sodium sulfate and concentrated under vacuum. The residue was purified by silica flash chromatography eluting with ethyl acetate/petroleum ether (1%) to afford the title compound (810 mg, 70.4% yield) as colorless oil. $^1$H NMR (300 MHz, CDCl$_3$) δ 7.65-7.51 (m, 1H), 7.50-7.37 (m, 5H), 5.28-5.17 (m, 2H).

Step 2: N-(4-(benzyloxy)-5-chloro-2,3-difluorophenyl)-1,1-diphenylmethanimine

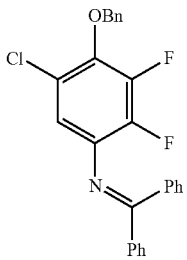 [SMILES: Fc1c(N=C(c2ccccc2)c2ccccc2)cc(Cl)c(OCc2ccccc2)c1F]

Under nitrogen, a solution of 4-benzyloxy-1-bromo-5-chloro-2,3-difluoro-benzene (600 mg, 1.8 mmol), benzophenone imine (488 mg, 2.7 mmol), tris(dibenzylideneacetone)dipalladium(0) (163 mg, 0.18 mmol), 4,5-bis(diphenylphosphino)-9,9-dimethylxanthene (208 mg, 0.36 mmol), cesium carbonate (1164 mg, 3.6 mmol) in 1,4-dioxane (4 mL) was stirred for 2 h at 80° C. The reaction was quenched with water and extracted with ethyl acetate and washed with brine, dried over anhydrous sodium sulfate and concentrated under vacuum. The residue was purified by silica flash chromatography eluting with ethyl acetate/petroleum ether (20%) to afford the title compound (700 mg, 89.7% yield) as yellow oil. LCMS (ESI): [M+H]$^+$=434.2.

Step 3: 4-(Benzyloxy)-5-chloro-2,3-difluoroaniline

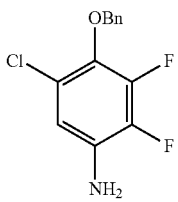

Into a solution of N-(4-benzyloxy-5-chloro-2,3-difluorophenyl)-1,1-diphenyl-methanimine (700 mg, 1.6 mmol) in water (3 mL) was added tetrahydrofuran (10 mL) and acetic acid (10 mL), the mixture was stirred at rt for 16 h. The reaction was extracted with ethyl acetate and washed with brine, dried over anhydrous sodium sulfate and concentrated under vacuum. The residue was purified by silica flash chromatography eluting with ethyl acetate/petroleum ether (1/1) to afford the title compound (200 mg, 46% yield) as a light yellow solid. LCMS (ESI): [M+H]$^+$=270.2.

Step 4: N-(4-(Benzyloxy)-5-chloro-2,3-difluorophenyl)-1-(2-fluorophenyl)methanesulfonamide

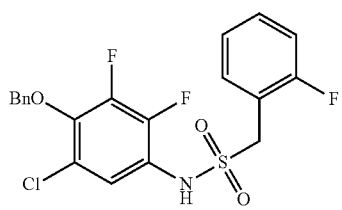 [SMILES: O=S(=O)(Cc1ccccc1F)Nc1cc(Cl)c(OCc2ccccc2)c(F)c1F]

A solution of (2-fluorophenyl)methanesulfonyl chloride (233 mg, 1.12 mmol) and 4-benzyloxy-5-chloro-2,3-difluoro-aniline (200 mg, 0.74 mmol) in pyridine (1 mL) was stirred at rt for 1 h. The reaction was quenched with water and extracted with ethyl acetate and washed with brine, dried over anhydrous sodium sulfate and concentrated under vacuum. The residue was purified by silica flash chromatography eluting with ethyl acetate/petroleum ether (0-50%) to afford the title compound (254 mg, 77.5% yield) as a yellow solid. LCMS (ESI): [M+H]$^+$=442.2.

Step 5: N-(5-Chloro-2,3-difluoro-4-hydroxyphenyl)-1-(2-fluorophenyl)methanesulfonamide

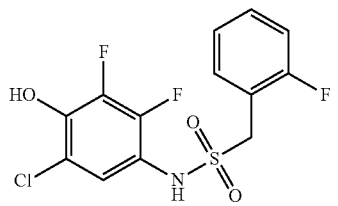 [SMILES: O=S(=O)(Cc1ccccc1F)Nc1cc(Cl)c(O)c(F)c1F]

Into a solution of N-(4-benzyloxy-5-chloro-2,3-difluorophenyl)-1-(2-fluorophenyl)methanesulfonamide (154 mg, 0.35 mmol) in methyl alcohol (20 mL) was added 10% Pd/C (50 mg), the mixture was stirred at rt for 1.5 h under hydrogen. The solids were filtered out. The solvent was removed. The residue was purified by silica flash chromatography eluting with ethyl acetate/petroleum ether (0-60%) to afford the title compound (120 mg, 99% yield) as a white solid. LCMS (ESI): [M−H]$^-$=350.1.

417

Step 6: tert-Butyl (3S,5S)-3-((4-(2-(6-chloro-2,3-difluoro-4-(((2-fluorophenyl)methyl)sulfonamido)phenoxy)pyridin-3-yl)pyrimidin-2-yl)amino)-5-fluoropiperidine-1-carboxylate

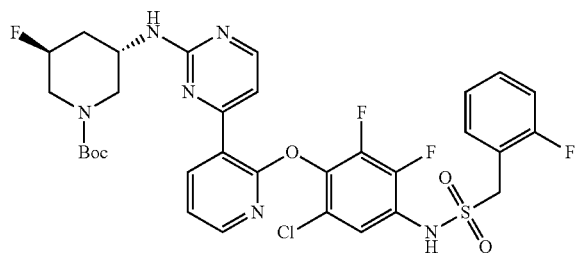 [SMILES: CC(C)(C)OC(=O)N1C[C@@H](F)C[C@H](Nc2nccc(-c3cccnc3Oc3c(Cl)cc(NS(=O)(=O)Cc4ccccc4F)c(F)c3F)n2)C1]

Under nitrogen, a solution of tert-butyl (3S,5S)-3-fluoro-5-((4-(2-fluoro-3-pyridyl)pyrimidin-2-yl)amino)piperidine-1-carboxylate (120 mg, 0.31 mmol), N-(5-chloro-2,3-difluoro-4-hydroxy-phenyl)-1-(2-fluorophenyl)methanesulfonamide (132 mg, 0.38 mmol) and cesium carbonate (498 mg, 1.53 mmol) in dimethyl sulfoxide (2 mL) was stirred at 100° C. for 1.5 h. The reaction was quenched with water and extracted with ethyl acetate and washed with brine, dried over anhydrous sodium sulfate and concentrated under vacuum. The residue was purified by silica flash chromatography eluting with ethyl acetate/petroleum ether (0-80%) to afford the title compound (145 mg, 65.4% yield) as a yellow solid. LCMS (ESI): [M+H]⁺=723.1.

Step 7: N-(5-Chloro-2,3-difluoro-4-((3-(2-(((3S,5S)-5-fluoropiperidin-3-yl)amino)pyrimidin-4-yl)pyridin-2-yl)oxy)phenyl)-1-(2-fluorophenyl)methanesulfonamide Compound 340

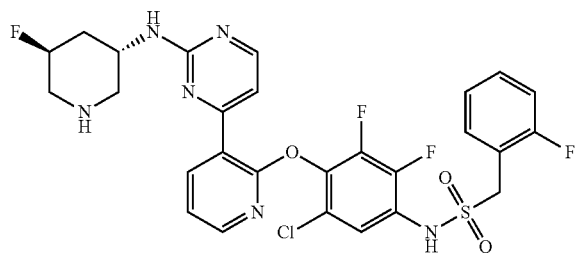 [SMILES: O=S(=O)(Cc1ccccc1F)Nc1cc(Cl)c(Oc2ncccc2-c2ccnc(N[C@@H]3CNC[C@@H](F)C3)n2)c(F)c1F]

Into a solution of tert-butyl (3S,5S)-3-((4-(2-(6-chloro-2,3-difluoro-4-(((2-fluorophenyl)methyl)sulfonamido)phenoxy)pyridin-3-yl)pyrimidin-2-yl)amino)-5-fluoropiperidine-1-carboxylate (130 mg, 0.18 mmol) in dichloromethane (2 mL) was added 4 M HCl in 1,4-dioxane (1 mL, 4 mmol), the mixture was stirred at rt for 1.5 h. The reaction was concentrated under vacuum. The residue was purified by Prep-HPLC to afford the title compound (45.4 mg, 40.5% yield) as a white solid.

418

Example 113

1-(4-Fluorophenyl)-N-(2,3,6-trifluoro-4-((3-(2-(((1r,4r)-4-((2-methoxyethyl)(methyl)amino)cyclohexyl)amino)pyrimidin-4-yl)pyridin-2-yl)oxy)phenyl)methanesulfonamide hydrochloride Compound 341

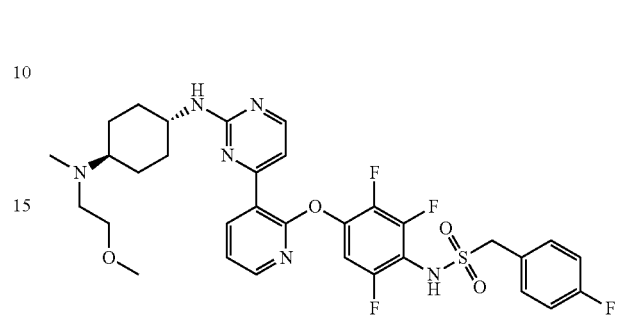

The title compound was prepared according to example 38. This provides the title compound (39.9 mg, 17.7% yield) as a white solid and as HCl salt.

Example 114

1-Phenyl-N-(2,3,6-trifluoro-4-((3-(2-((5-(1-fluoroethyl)piperidin-3-yl)amino)pyrimidin-4-yl)pyridin-2-yl)oxy)phenyl)methanesulfonamide hydrochloride Compound 342 Compound 343 Compound 344 Compound 345 & 1-Phenyl-N-(2,3,6-trifluoro-4-((3-(2-((5-(1-fluoroethyl)piperidin-3-yl)amino)pyrimidin-4-yl)pyridin-2-yl)oxy)phenyl)methanesulfonamide Compound 346 Compound 347 Compound 348 Compound 349

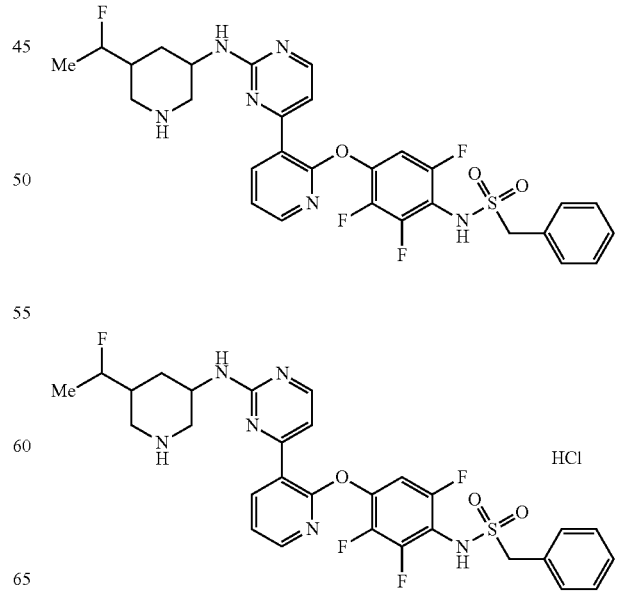

Step 1: tert-Butyl 3-benzyloxy-5-(1-hydroxyethyl) piperidine-1-carboxylate

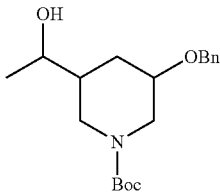 [SMILES: CC(O)C1CC(OCc2ccccc2)CN(C(=O)OC(C)(C)C)C1]

To a solution of tert-butyl 3-acetyl-5-benzyloxy-piperidine-1-carboxylate (3.2 g, 9.6 mmol) in methyl alcohol (80 mL) was added sodium borohydride (768 mg, 20 mmol). The solution was stirred for 20 min at rt. The reaction was quenched with water and extracted with dichloromethane. The combined organic layer was dried over anhydrous sodium sulfate and concentrated under vacuum to afford the title compound (3.2 g, 99.4% yield) as a light yellow oil. LCMS (ESI): [M+1-56]$^+$=280.1

Step 2: tert-Butyl 3-benzyloxy-5-(1-fluoroethyl) piperidine-1-carboxylate

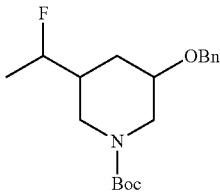 [SMILES: CC(F)C1CC(OCc2ccccc2)CN(C(=O)OC(C)(C)C)C1]

A solution of tert-butyl 3-benzyloxy-5-(1-hydroxyethyl) piperidine-1-carboxylate (3.2 g, 9.5 mmol) in diethylaminosulfur trifluoride (21 mL) was stirred at rt for 2 h. the solution was diluted with dichloromethane. The above solution was slowly added into ice/water and extracted with dichloromethane. The solution was dried over anhydrous sodium sulfate and concentrated under vacuum. The residue was purified by silica flash chromatography eluting with dichloromethane/petroleum ether (30%-90%) to afford the title compound (1.3 g, 40.4% yield) as an orange oil.

Step 3: 1-Phenyl-N-(2,3,6-trifluoro-4-((3-(2-((5-(1-fluoroethyl)piperidin-3-yl)amino)pyrimidin-4-yl)pyridin-2-yl)oxy)phenyl)methanesulfonamide hydrochloride Compound 342 Compound 343 Compound 344 Compound 345 & 1-Phenyl-N-(2,3,6-trifluoro-4-((3-(2-((5-(1-fluoroethyl)piperidin-3-yl)amino)pyrimidin-4-yl)pyridin-2-yl)oxy)phenyl) methanesulfonamide Compound 346 Compound 347 Compound 348 Compound 349

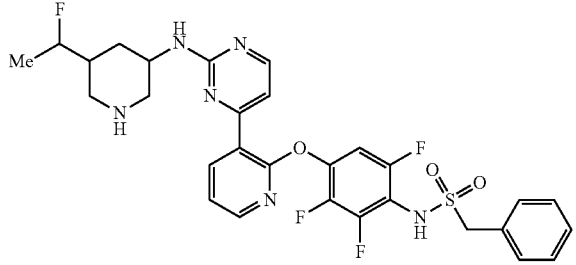

-continued

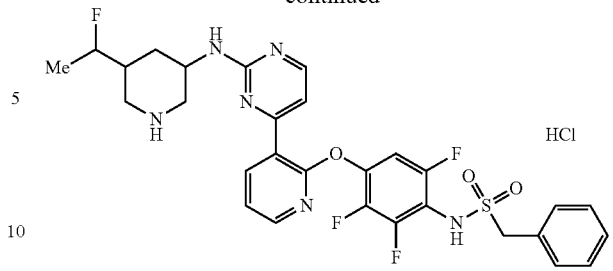

The title compound was prepared according to example 108.

1-Phenyl-N-(2,3,6-trifluoro-4-((3-(2-((5-(1-fluoroethyl) piperidin-3-yl)amino)pyrimidin-4-yl)pyridin-2-yl)oxy)phenyl)methanesulfonamide hydrochloride Compound 342 (47.5 mg, 73.4% yield) as a white solid and as HCl salt.

1-Phenyl-N-(2,3,6-trifluoro-4-((3-(2-((5-(1-fluoroethyl) piperidin-3-yl)amino)pyrimidin-4-yl)pyridin-2-yl)oxy)phenyl)methanesulfonamide Compound 346 (3.6 mg, 34.9% yield) as a white solid.

1-Phenyl-N-(2,3,6-trifluoro-4-((3-(2-((5-(1-fluoroethyl) piperidin-3-yl)amino)pyrimidin-4-yl)pyridin-2-yl)oxy)phenyl)methanesulfonamide hydrochloride Compound 343 (19.8 mg, 62.1% yield) as a white solid as HCl salt.

1-Phenyl-N-(2,3,6-trifluoro-4-((3-(2-((5-(1-fluoroethyl) piperidin-3-yl)amino)pyrimidin-4-yl)pyridin-2-yl)oxy)phenyl)methanesulfonamide Compound 347 (13.9 mg, 27.9% yield) as a white solid.

1-Phenyl-N-(2,3,6-trifluoro-4-((3-(2-((5-(1-fluoroethyl) piperidin-3-yl)amino)pyrimidin-4-yl)pyridin-2-yl)oxy)phenyl)methanesulfonamide hydrochloride Compound 344 (20.2 mg, 88.7% yield) as a white solid as HCl salt.

1-Phenyl-N-(2,3,6-trifluoro-4-((3-(2-((5-(1-fluoroethyl) piperidin-3-yl)amino)pyrimidin-4-yl)pyridin-2-yl)oxy)phenyl)methanesulfonamide hydrochloride Compound 345 (22.9 mg, 43.3% yield) as a white solid as HCl salt.

1-Phenyl-N-(2,3,6-trifluoro-4-((3-(2-((5-(1-fluoroethyl) piperidin-3-yl)amino)pyrimidin-4-yl)pyridin-2-yl)oxy)phenyl)methanesulfonamide Compound 348 (48.9 mg, 59.8% yield) as a white solid.

1-Phenyl-N-(2,3,6-trifluoro-4-((3-(2-((5-(1-fluoroethyl) piperidin-3-yl)amino)pyrimidin-4-yl)pyridin-2-yl)oxy)phenyl)methanesulfonamide hydrochloride Compound 349 (1.2 mg, 9.4% yield) as a white solid as HCl salt.

Example 115

N-(2,3,6-Trifluoro-4-((3-(2-(((1r,4r)-4-((2-methoxyethyl)(methyl)amino)cyclohexyl)amino)pyrimidin-4-yl)pyridin-2-yl)oxy)phenyl)cyclohexanesulfonamide Compound 350

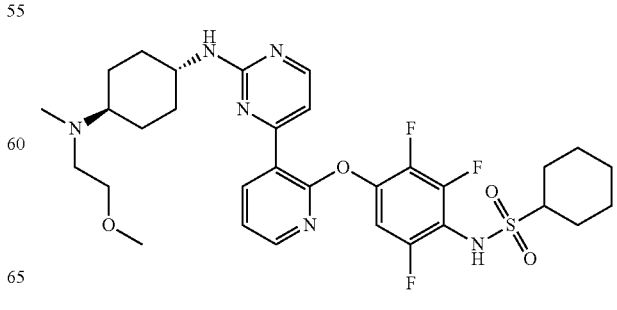

Step 1: N-(2,3,6-Trifluoro-4-((3-(2-(methylthio)pyrimidin-4-yl)pyridin-2-yl)oxy)phenyl)cyclohexanesulfonamide

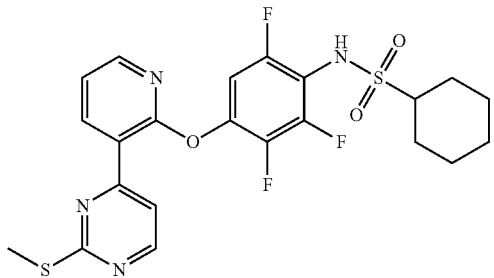 [SMILES: CSc1nccc(-c2cccnc2Oc2cc(F)c(NS(=O)(=O)C3CCCCC3)c(F)c2F)n1]

To a mixture of 2,3,6-trifluoro-4-((3-(2-methylsulfanylpyrimidin-4-yl)-2-pyridyl)oxy)aniline (0.25 g, 0.69 mmol) in 1,8-diazabicyclo[5.4.0]undec-7-ene (2 mL) was added cyclohexanesulfonylchloride (0.38 g, 2.1 mmol), the mixture was stirred for 48 h at rt. The resulting solution was diluted with water and extracted with ethyl acetate, the organic layers was washed with brine and dried over sodium sulfate and concentrated. The residue was purified by silica flash chromatography eluting with ethyl acetate/petroleum ether (2:1) to afford the title compound (130 mg, 37.1% yield) as a brown solid. LCMS (ESI): [M+H]$^+$=511.3.

Step 2: N-(2,3,6-trifluoro-4-((3-(2-(methylsulfonyl)pyrimidin-4-yl)pyridin-2-yl)oxy)phenyl)cyclohexanesulfonamide

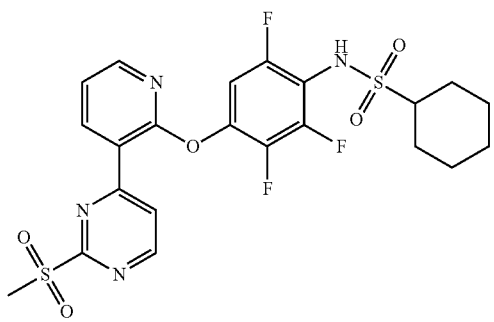 [SMILES: CS(=O)(=O)c1nccc(-c2cccnc2Oc2cc(F)c(NS(=O)(=O)C3CCCCC3)c(F)c2F)n1]

To a mixture of N-(2,3,6-trifluoro-4-((3-(2-(methylthio)pyrimidin-4-yl)pyridin-2-yl)oxy)phenyl)cyclohexanesulfonamide (0.11 g, 0.22 mmol) in dichloromethane (3 mL) was added 3-chloroperoxybenzoic acid (0.11 g, 0.65 mmol), the mixture was stirred for 1 h at rt. The reaction was quenched with sat. sodium bisulfite. The resulting solution was extracted with dichloromethane and dried over sodium sulfate and concentrated. The crude would be directly used in the next step without purification. LCMS (ESI): [M+H]$^+$= 543.3

Step 3: N-(2,3,6-Trifluoro-4-((3-(2-(((1r,4r)-4-((2-methoxyethyl)(methyl)amino)cyclohexyl)amino)pyrimidin-4-yl)pyridin-2-yl)oxy)phenyl)cyclohexanesulfonamide Compound 350

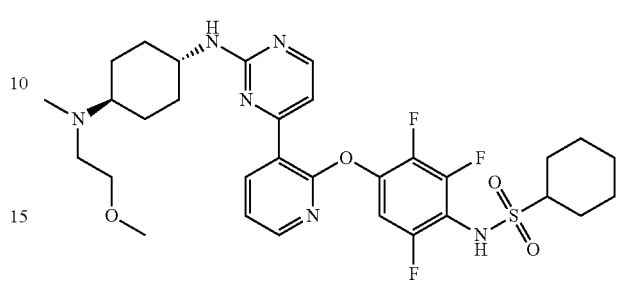

A mixture of N-(2,3,6-trifluoro-4-((3-(2-(methylsulfonyl)pyrimidin-4-yl)pyridin-2-yl)oxy)phenyl)cyclohexanesulfonamide (0.1 g, 0.18 mmol), N$^4$-(2-methoxyethyl)-N$^4$-methyl-cyclohexane-1,4-diamine (0.03 g, 0.18 mmol), caesium fluoride (0.08 g, 0.55 mmol) and N,N-diisopropylethylamine (71 mg, 0.55 mmol) in dimethyl sulfoxide (3 mL) was stirred at 85° C. for 2 h under nitrogen. The crude product was directly purified by reverse phase and Prep-HPLC to afford the title compound (38.9 mg, 32.5% yield) as a white solid.

Example 116

1-(2,4-Difluorophenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide Compound 351

The title compound was prepared according to example 40. This resulted in the title compound (25 mg, 38% yield) as a white solid.

423

Example 117

1-(2-Chlorophenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide Compound 352

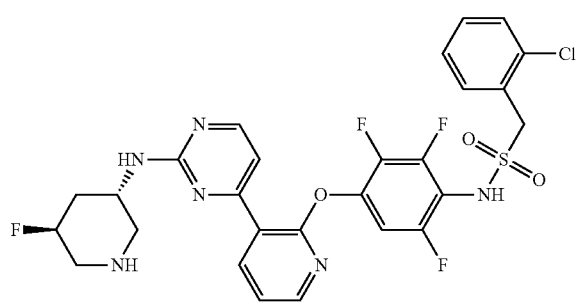 [SMILES: O=S(=O)(Cc1ccccc1Cl)Nc1c(F)cc(Oc2ncccc2-c2ccnc(N[C@@H]3CNC[C@@H](F)C3)n2)c(F)c1F]

The title compound was prepared according to example 40. This resulted in the title compound (52 mg, 79% yield) as a white solid.

Example 118

1-(3-Chlorophenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide Compound 353

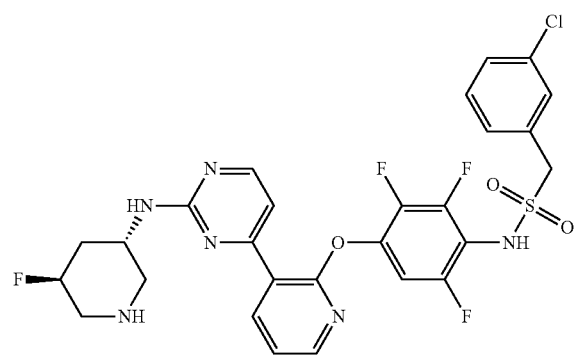

The title compound was prepared according to example 40. This resulted in the title compound (12 mg, 18% yield) as a white solid.

424

Example 119

1-(4-Chlorophenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide Compound 354

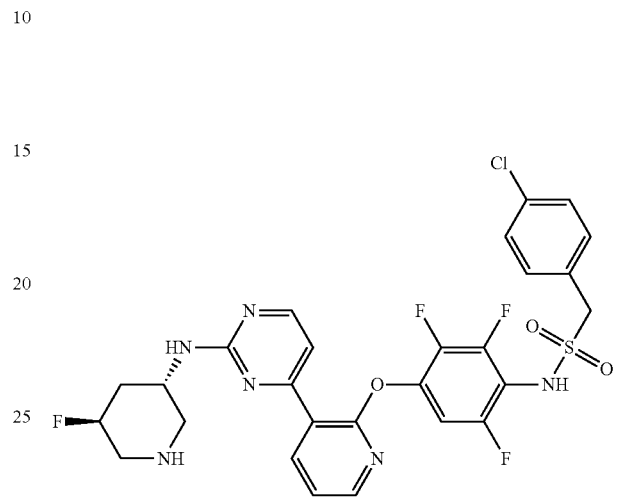

The title compound was prepared according to example 40. This resulted in the title compound (37 mg, 56% yield) as a white solid.

Example 120

1-(2-Fluorophenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide Compound 355

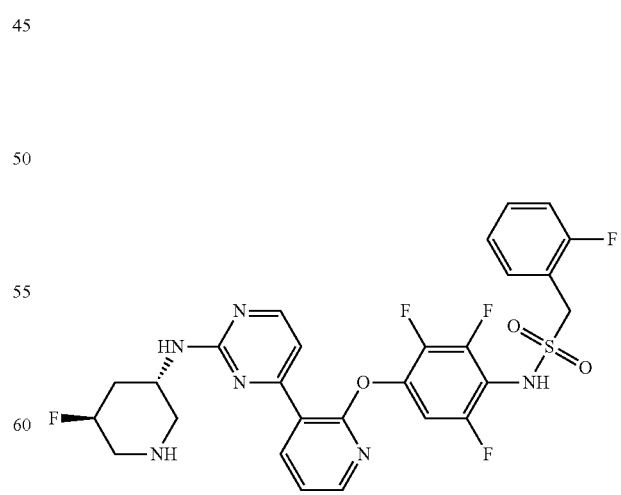

The title compound was prepared according to example 40. This resulted in the title compound (20 mg, 31% yield) as a white solid.

Example 121

1-(2-Pyridyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide Compound 356

Step 1: Benzyl (3S,5S)-3-fluoro-5-[[4-[2-[2,3,5-trifluoro-4-(2-pyridylmethylsulfonylamino)phenoxy]-3-pyridyl]pyrimidin-2-yl]amino]piperidine-1-carboxylate

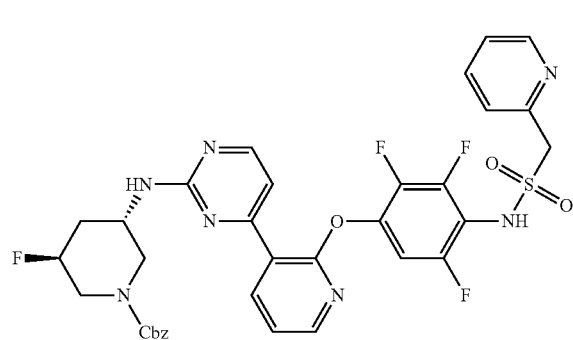 [SMILES: O=C(OCc1ccccc1)N1C[C@@H](F)C[C@H](Nc2nccc(-c3cccnc3Oc3cc(F)c(NS(=O)(=O)Cc4ccccn4)c(F)c3F)n2)C1]

To benzyl (3S,5S)-3-[[4-[2-(4-amino-2,3,5-trifluoro-phenoxy)-3-pyridyl]pyrimidin-2-yl]amino]-5-fluoro-piperidine-1-carboxylate (40 mg, 0.07 mmol) in DCM (0.1 M) was added trimethylamine (0.28 mmol, 40 μL). The reaction was quenched after 1 min with a saturated sodium bicarbonate solution. FastworX-S resin (~300 mg) was added and the remaining DCM was removed in vacuo. The reaction mixture was filtered to collect the resin directly into a solid loading cartridge. Normal phase chromatography (ISCO) was run using 0-20% MeOH/DCM gradient and 54 mg of the title compound (~quantitative yield) was isolated as a mixture of monomer and dimer. LCMS (ESI): [M+H]$^+$=724/879.

Step 2: 1-(2-Pyridyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide Compound 356

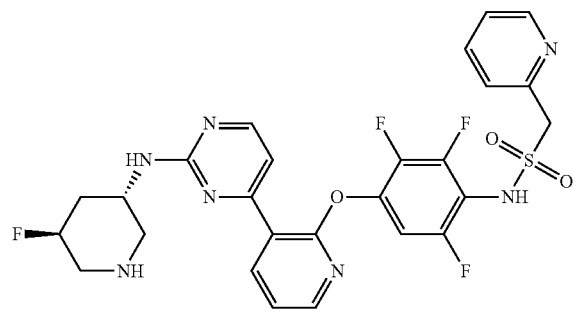

The title compound was prepared according to example 40 step 2. This resulted in the title compound (2.4 mg, 5.4% yield) as a white solid.

Example 122

1-(2-Cyano-4-fluoro-phenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide Compound 357

The title compound was prepared according to example 40. This resulted in the title compound (13 mg, 20% yield) as a white solid.

Example 123

1-(2-Cyano-4-fluoro-phenyl)-N-[2,3,6-trifluoro-4-((3-[2-[[(3S,5S)-5-fluoro-piperidyl]amino]pyrimidin-4-yl]-2-pyridyl]oxy]phenyl]methanesulfonamide Compound 358

Example 124

1-(2-Cyano-4-fluoro-phenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide Compound 359

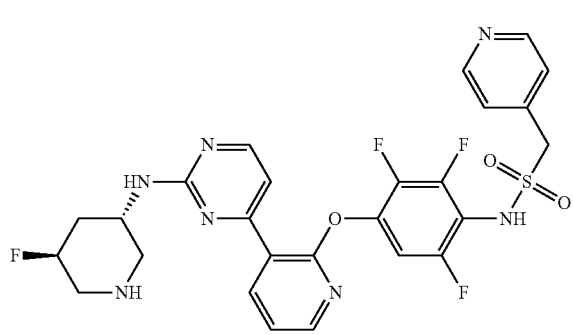

The title compound was prepared according to example 40. This resulted in the title compound (2 mg, 4% yield) as a white solid.

Example 125

3-Fluoro-4-[[2,3,6-trifluoro-4-[[3-[2-[[(3S,5S)-5-fluoro-3-piperidyl]amino]pyrimidin-4-yl]-2-pyridyl]oxy]phenyl]sulfamoylmethyl]benzamide Compound 360

Step 1: tert-Butyl (3S,5S)-3-[[4-[2-(4-amino-2,3,5-trifluoro-phenoxy)-3-pyridyl]pyrimidin-2-yl]amino]-5-fluoro-piperidine-1-carboxylate

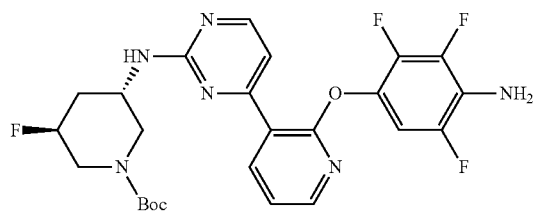

2,3,6-Trifluoro-4-[[3-(2-methylsulfonylpyrimidin-4-yl)-2-pyridyl]oxy]aniline (750 mg, 1.89 mmol) in dimethyl sulfoxide (9.5 mL) was added tert-butyl (3S,5S)-3-amino-5-fluoropiperidine-1-carboxylate (2.2 mmol), N,N-diisopropylethylamine (1.1.mL, 6.4 mmol) and cesium fluoride (5.7 mmol). The mixture was stirred at 90° C. for 16 h. The mixture was diluted with water (50 mL) and ethyl acetate (50 mL). The mixture was extracted with ethyl acetate (3×50 mL) and the organic layer was combined. The solution was washed with water (3×10 mL), brine (20 mL), dried over sodium sulfate and concentrated under vacuum. The residue was applied onto a silica gel column with isoproyl acetate in heptanes (0-100%) to the title compound (550 mg, 54% yield) as a white solid. LCMS (ESI): [M+H]$^+$=536.1.

Step 2: tert-Butyl (3S,5S)-3-[[4-[2-[4-[(4-cyano-2-fluoro-phenyl)methylsulfonylamino]-2,3,5-trifluoro-phenoxy]-3-pyridyl]pyrimidin-2-yl]amino]-5-fluoro-piperidine-1-carboxylate

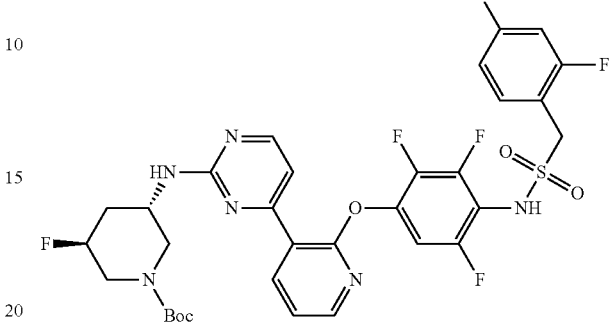

To tert-butyl (3S,5S)-3-[[4-[2-(4-amino-2,3,5-trifluoro-phenoxy)-3-pyridyl]pyrimidin-2-yl]amino]-5-fluoro-piperidine-1-carboxylate (50 mg, 0.09 mmol) in DCM (0.25 M) was added pyridine (38 μL, 0.47 mmol) followed by (4-cyano-2-fluorophenyl)methanesulfonyl chloride (27 mg, 0.11 mmol). The reaction was stirred at room temperature for 2 hours then quenched with saturated sodium bicarbonate solution (10 mL) and extracted with DCM (10 mL). The crude organic layers was dried with magnesium sulfate, filtered, dried and taken into the next step without further purification to afford the title compound in quantitative yield. LCMS (ESI): [M+H]$^+$=732.1

Step 3: 3-Fluoro-4-[[2,3,6-trifluoro-4-[[3-[2-[[(3S,5S)-5-fluoro-3-piperidyl]amino]pyrimidin-4-yl]-2-pyridyl]oxy]phenyl]sulfamoylmethyl]benzamide Compound 360

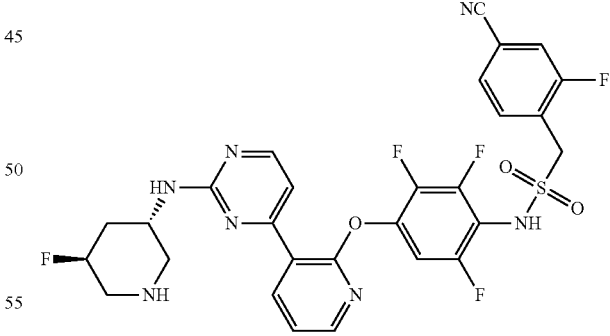

To tert-butyl (3S,5S)-3-[[4-[2-[4-[(4-cyano-2-fluoro-phenyl)methylsulfonylamino]-2,3,5-trifluoro-phenoxy]-3-pyridyl]pyrimidin-2-yl]amino]-5-fluoro-piperidine-1-carboxylate (68 mg, 0.09 mmol) in MeOH (2 mL) was added hydrochloric acid (4.0 mol/L) in dioxane (0.9 mmol, 0.24 mL). The reaction was stirred for 6 hours at room temperature and then concentrated to dryness and submitted for reverse phase HPLC purification to afford the title compound (31 mg, 47% yield).

Example 126

3-Fluoro-4-[[2,3,6-trifluoro-4-[[3-[2-[[(3S,5S)-5-fluoro-3-piperidyl]amino]pyrimidin-4-yl]-2-pyridyl]oxy]phenyl]sulfamoylmethyl]benzamide Compound 361

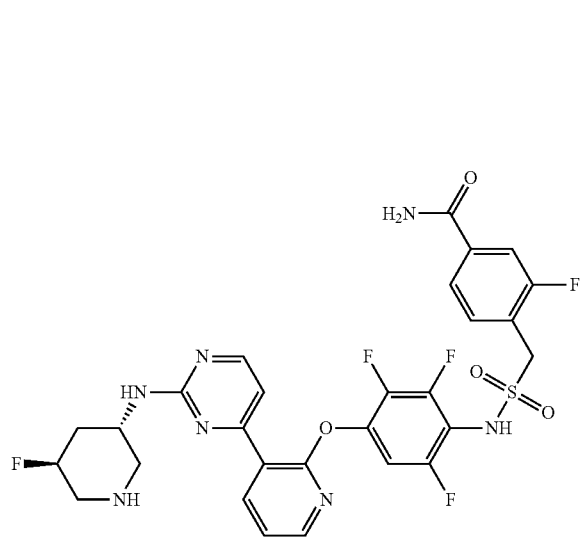 [SMILES: NC(=O)c1ccc(CS(=O)(=O)Nc2c(F)cc(Oc3ncccc3-c3ccnc(N[C@@H]4CNC[C@@H](F)C4)n3)c(F)c2F)c(F)c1]

The title compound was prepared according to example 40. This resulted in the title compound (23 mg, 34% yield) as a white solid.

Example 127

3-Fluoro-4-[[2,3,6-trifluoro-4-[[3-[2-[[(3S,5S)-5-fluoro-3-piperidyl]amino]pyrimidin-4-yl]-2-pyridyl]oxy]phenyl]sulfamoylmethyl]benzamide Compound 362

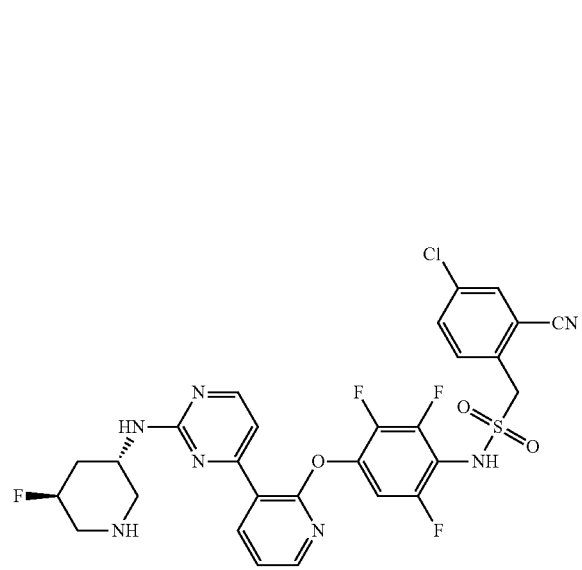

The title compound was prepared according to example 40. This resulted in the title compound (11 mg, 16% yield) as a white solid.

Example 128

1-(2,6-Difluorophenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide Compound 363

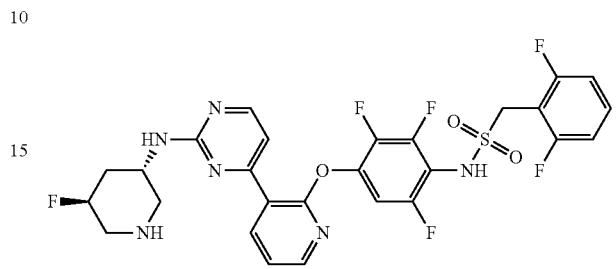

The title compound was prepared according to example 40. This resulted in the title compound (12 mg, 19% yield) as a white solid.

Example 129

1-(4-Chloro-2-fluoro-phenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide Compound 364

Step 1: Benzyl (3S,5S)-3-[[4-[2-[4-[(4-chloro-2-fluoro-phenyl)methylsulfonylamino]-2,3,5-trifluoro-phenoxy]-3-pyridyl]pyrimidin-2-yl]amino]-5-fluoro-piperidine-1-carboxylate

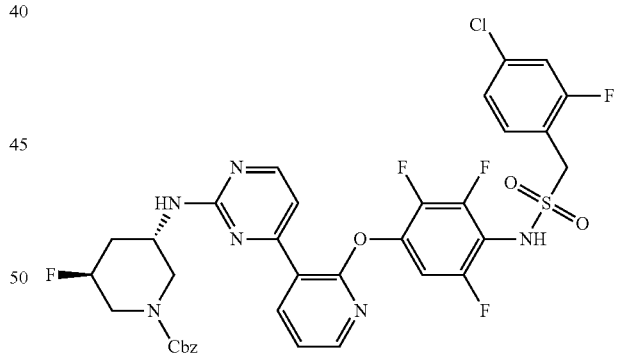

To benzyl (3S,5S)-3-[[4-[2-(4-amino-2,3,5-trifluoro-phenoxy)-3-pyridyl]pyrimidin-2-yl]amino]-5-fluoro-piperidine-1-carboxylate (100 mg, 0.18 mmol) in DCM (0.1 M) was added 1,8-diazabicyclo[5.4.0]undec-7-ene (0.54 mmol, 80 µL). The reaction was stirred at 40° C. and quenched with saturated sodium bicarbonate solution (~20 mL). FastworX-S resin (~400 mg) was added and the remaining DCM was removed in vacuo. The resin was filtered/collected and the crude intermediate was eluted with DCM (~5 mL). Alternatively, this workup can be done without FastworX-S resin using DCM to extract the aqueous layer (~20 mL) to afford the title compound as a crude intermediate (~quantitative yield). If the sulfonylation reaction produces mostly dimer, the dimer can be hydrolyzed to monomer using NaHCO3 (3-5 eq) and heating crude intermediate in a mixture of 2:1 acetone/water at 50° C. for 1-18 hours. LCMS (ESI): [M+H]$^+$=775.0.

Step 2: 1-(4-Chloro-2-fluoro-phenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide Compound 364

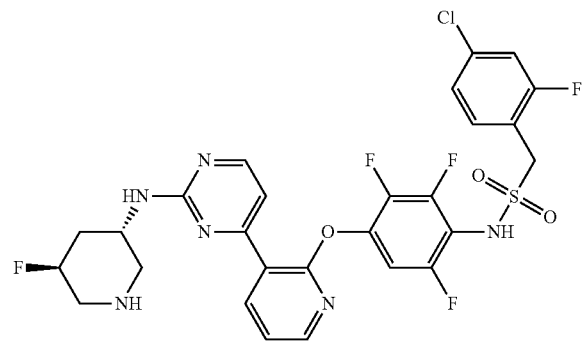 [SMILES: O=S(=O)(Cc1ccc(Cl)cc1F)Nc1c(F)cc(Oc2ncccc2-c2ccnc(N[C@@H]3CNC[C@@H](F)C3)n2)c(F)c1F]

To benzyl (3S,5S)-3-[[4-[2-[4-[(4-chloro-2-fluoro-phenyl)methylsulfonylamino]-2,3,5-trifluoro-phenoxy]-3-pyridyl]pyrimidin-2-yl]amino]-5-fluoro-piperidine-1-carboxylate in DCM (0.2 M) was added hydrobromic acid (33 wt % in acetic acid, 3 equiv., 0.54 mmol). The reaction was stirred for 2 h at room temperature and quenched with water or methanol (1 mL), concentrated to dryness and submitted for reverse phase purification to afford the title compound (31 mg, 28% yield).

Example 130

1-(2-Chloro-4-fluoro-phenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide Compound 365

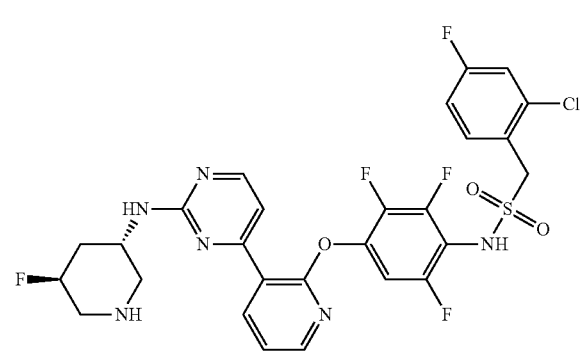 [SMILES: O=S(=O)(Cc1ccc(F)cc1Cl)Nc1c(F)cc(Oc2ncccc2-c2ccnc(N[C@@H]3CNC[C@@H](F)C3)n2)c(F)c1F]

The title compound was prepared according to example 129. This resulted in the title compound (18 mg, 27% yield) as a white solid.

Example 131

1-(3-Chloro-4-fluoro-phenyl)-N-[2,3,6-trifluoro-4-[[3-[2-[[(3S,5S)-5-fluoro-3-piperidyl]amino]pyrimidin-4-yl]-2-pyridyl]oxy]phenyl]methanesulfonamide Compound 366

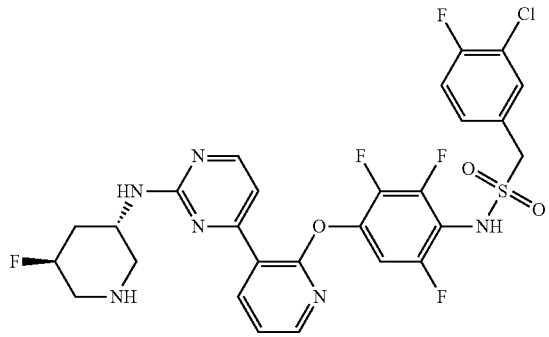 [SMILES: O=S(=O)(Cc1ccc(F)c(Cl)c1)Nc1c(F)cc(Oc2ncccc2-c2ccnc(N[C@@H]3CNC[C@@H](F)C3)n2)c(F)c1F]

The title compound was prepared according to example 129. This resulted in the title compound (8 mg, 10% yield) as a white solid.

Example 132

1-(2-Chloro-6-fluorophenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 367

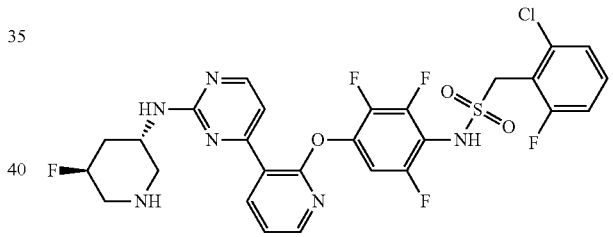

The title compound was prepared according to example 129. This resulted in the title compound (30 mg, 36% yield) as a white solid.

Example 133

N-(2,3,6-Trifluoro-4-((3-(2-(((3S,5S)-5-fluoropiperidin-3-yl)amino)pyrimidin-4-yl)pyridin-2-yl)oxy)phenyl)cyclohexanesulfonamide Compound 368™

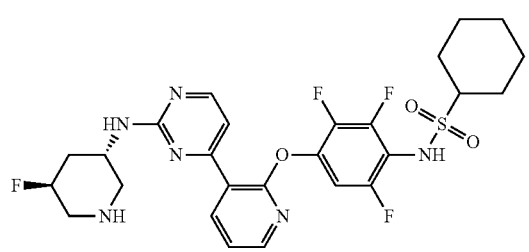 [SMILES: O=S(=O)(Nc1c(F)cc(Oc2ncccc2-c2ccnc(N[C@@H]3CNC[C@@H](F)C3)n2)c(F)c1F)C1CCCCC1]

Example 134

N-(2,3,6-Trifluoro-4-((3-(2-(((3S,5S)-5-fluoropiperidin-3-yl)amino)pyrimidin-4-yl)pyridin-2-yl)oxy)phenyl)cyclopentanesulfonamide Compound 369

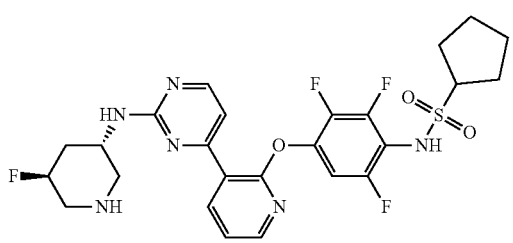 [SMILES: O=S(=O)(Nc1c(F)cc(Oc2ncccc2-c2ccnc(N[C@@H]3CNC[C@@H](F)C3)n2)c(F)c1F)C1CCCC1]

The title compound was prepared according to example 129. This resulted in the title compound (12 mg, 34% yield) as a white solid.

Example 135

N-(2,3,6-Trifluoro-4-((3-(2-(((3S,5S)-5-fluoropiperidin-3-yl)amino)pyrimidin-4-yl)pyridin-2-yl)oxy)phenyl)-1-(4-(trifluoromethyl)phenyl)methanesulfonamide Compound 370

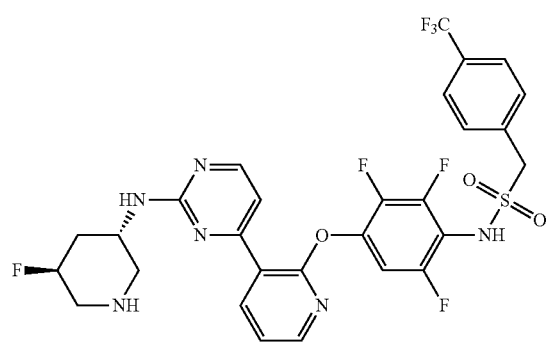

The title compound was prepared according to example 129. This resulted in the title compound (15 mg, 25% yield) as a white solid.

Example 136

1-(4-(Difluoromethyl)phenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 371

The title compound was prepared according to example 129. This resulted in the title compound (11 mg, 19% yield) as a white solid.

Example 137

1-(4-Fluorophenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 372

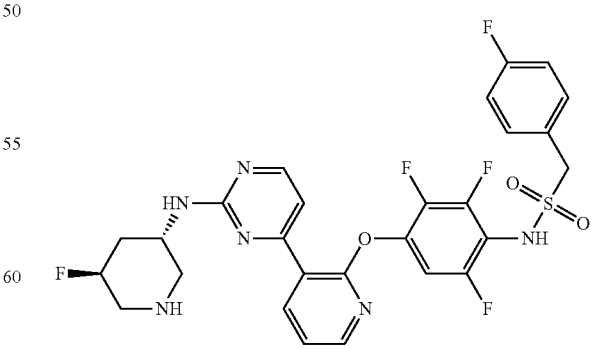

The title compound was prepared according to example 129. This resulted in the title compound (4 mg, 7% yield) as a white solid.

Example 138

N-(2,3,6-Trifluoro-4-((3-(2-(((3S,5S)-5-fluoropiperidin-3-yl)amino)pyrimidin-4-yl)pyridin-2-yl)oxy)phenyl)-1-(2-(trifluoromethyl)phenyl)methanesulfonamide Compound 373

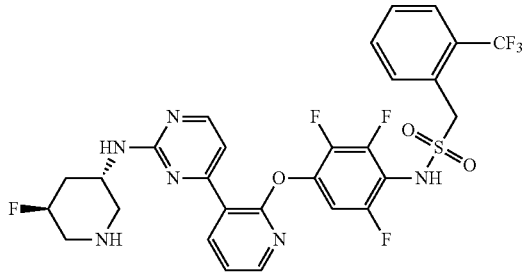 [SMILES: O=S(=O)(Cc1ccccc1C(F)(F)F)Nc1c(F)cc(Oc2ncccc2-c2ccnc(N[C@@H]3CNC[C@@H](F)C3)n2)c(F)c1F]

The title compound was prepared according to example 129. This resulted in the title compound (17 mg, 27% yield) as a white solid.

Example 139

N-(2,3,6-Trifluoro-4-((3-(2-(((3S,5S)-5-fluoropiperidin-3-yl)amino)pyrimidin-4-yl)pyridin-2-yl)oxy)phenyl)-1-(3-(trifluoromethyl)phenyl)methanesulfonamide Compound 374

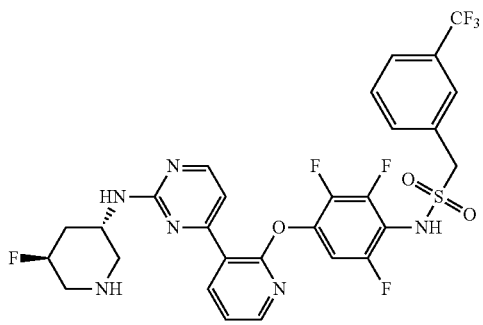 [SMILES: O=S(=O)(Cc1cccc(C(F)(F)F)c1)Nc1c(F)cc(Oc2ncccc2-c2ccnc(N[C@@H]3CNC[C@@H](F)C3)n2)c(F)c1F]

The title compound was prepared according to example 129. This resulted in the title compound (24 mg, 28% yield) as a white solid.

Example 140

1-p-Tolyl-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 375

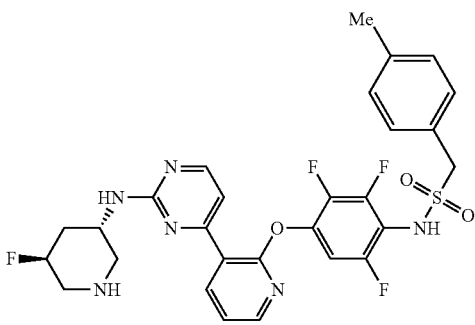 [SMILES: Cc1ccc(CS(=O)(=O)Nc2c(F)cc(Oc3ncccc3-c3ccnc(N[C@@H]4CNC[C@@H](F)C4)n3)c(F)c2F)cc1]

The title compound was prepared according to example 129. This resulted in the title compound (10 mg, 29% yield) as a white solid.

Example 141

1-(Bicyclo[2.2.1]heptan-1-yl)N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 376

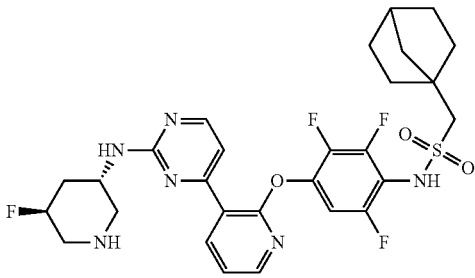 [SMILES: O=S(=O)(CC12CCC(CC1)C2)Nc1c(F)cc(Oc2ncccc2-c2ccnc(N[C@@H]3CNC[C@@H](F)C3)n2)c(F)c1F]

The title compound was prepared according to example 129. This resulted in the title compound (27 mg, 32% yield) as a white solid.

Example 142

1-(Bicyclo[2.2.2]octan-1-yl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 377

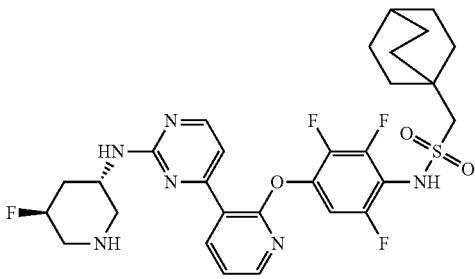 [SMILES: O=S(=O)(CC12CCC(CC1)CC2)Nc1c(F)cc(Oc2ncccc2-c2ccnc(N[C@@H]3CNC[C@@H](F)C3)n2)c(F)c1F]

The title compound was prepared according to example 129. This resulted in the title compound (18 mg, 22% yield) as a white solid.

Example 143

1-(2,5-Difluorophenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 378

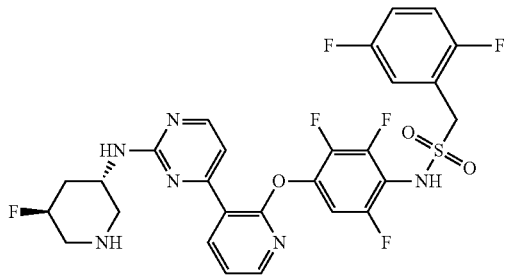 [SMILES: O=S(=O)(Cc1cc(F)ccc1F)Nc1c(F)cc(Oc2ncccc2-c2ccnc(N[C@@H]3CNC[C@@H](F)C3)n2)c(F)c1F]

The title compound was prepared according to example 129. This resulted in the title compound (7 mg, 13% yield) as a white solid.

Example 144

1-(4-Cyanophenyl)-N-(2,3-difluoro-4-((3-(2-(((S)-piperidin-3-yl)amino)pyrimidin-4-yl)pyridin-2-yl)oxy)phenyl)ethane-1-sulfonamide Compound 379

Step 1: tert-Butyl (3S)-3-[[4-[2-(4-bromo-2,3-difluoro-phenoxy)-3-pyridyl]pyrimidin-2-yl]amino]piperidine-1-carboxylate

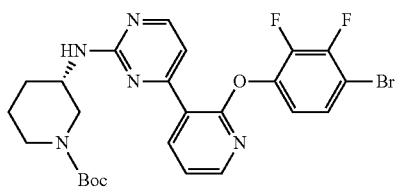 [SMILES: CC(C)(C)OC(=O)N1CCC[C@H](Nc2nccc(-c3cccnc3Oc3ccc(Br)c(F)c3F)n2)C1]

To a solution of tert-butyl (3S)-3-[[4-(2-fluoro-3-pyridyl)pyrimidin-2-yl]amino]piperidine-1-carboxylate (3 g, 8 mmol) in DMSO (32 mL) was added 4-bromo-2,3-difluorophenol (2.2 g, 10 mmol), Cs$_2$CO$_3$ (5.2 g, 16.1 mmol) and the reaction was stirred for 2 h at 90° C. The reaction was quenched with water (100 mL) and extracted with DCM (100 mL). The organic layer was dried over anhydrous magnesium sulfate, concentrated and purified by ISCO (0-70% Heptanes/IprOAc) to afford the title compound (2.5 g, 55% yield). LCMS (ESI): [M+2H]$^+$=565.0.

Step 2: tert-Butyl (3S)-3-[[4-[2-[4-[1-(4-cyanophenyl)ethylsulfonylamino]-2,3-difluoro-phenoxy]-3-pyridyl]pyrimidin-2-yl]amino]piperidine-1-carboxylate

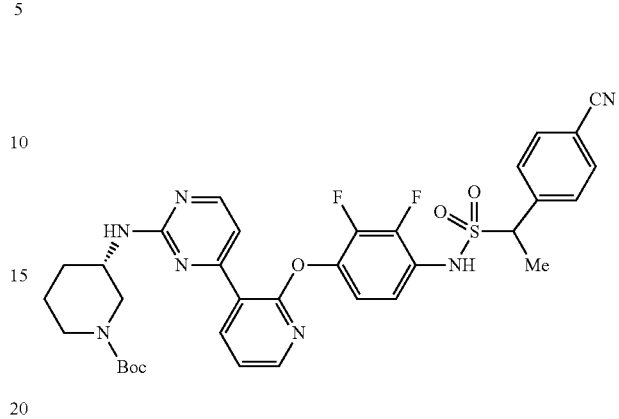

A vial containing tert-butyl (3S)-3-[[4-[2-(4-bromo-2,3-difluoro-phenoxy)-3-pyridyl]pyrimidin-2-yl]amino]piperidine-1-carboxylate (50 mg, 0.09 mmol) and 1-(4-cyanophenyl)ethane-1-sulfonamide (29.5 mg, 0.13 mmol) was purged with nitrogen whereupon tBuBrettPhos G3 (7.9 mg, 0.009 mmol) and potassium carbonate (25 mg, 0.18 mmol) were added and the vial was re-purged with nitrogen. Degassed 1,4-dioxane (0.1M, 0.9 mL) was added via syringe and the reaction was heated to 80° C. for 18 hours. The reaction mixture was cooled and then FastworX-S resin (~200 mg) was added and the remaining DCM was removed in vacuo. The resin was filtered/collected and the crude intermediate was eluted with DCM (~5 mL) to afford the title compound as a crude intermediate (~quantitative yield). LCMS (ESI): [M+H]$^+$=692.1.

Step 3: 1-(4-Cyanophenyl)-N-(2,3-difluoro-4-((3-(2-(((S)-piperidin-3-yl)amino)pyrimidin-4-yl)pyridin-2-yl)oxy)phenyl)ethane-1-sulfonamide Compound 379

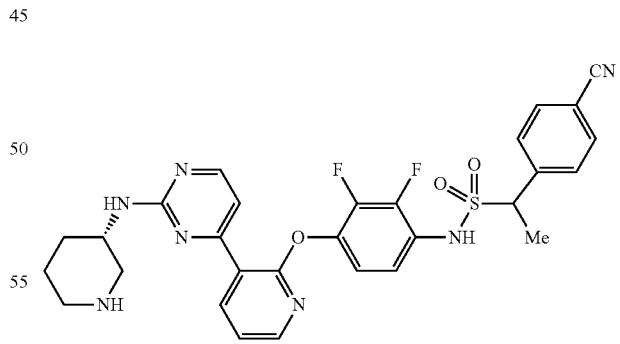

To tert-butyl (3S)-3-[[4-[2-[4-[1-(4-cyanophenyl)ethylsulfonylamino]-2,3-difluoro-phenoxy]-3-pyridyl]pyrimidin-2-yl]amino]piperidine-1-carboxylate (61 mg, 0.09 mmol) in MeOH (2 mL) was added hydrochloric acid (4.0 mol/L) in dioxane (0.9 mmol, 0.24 mL). The reaction was stirred for 18 hours at room temperature and then concentrated to dryness and submitted for reverse phase HPLC purification to afford the title compound (19 mg, 36% yield).

Example 145

(S)—N-(2,3-Difluoro-4-((3-(2-(piperidin-3-ylamino)pyrimidin-4-yl)pyridin-2-yl)oxy)phenyl)-1-(2-methoxyphenyl)methanesulfonamide Compound 380

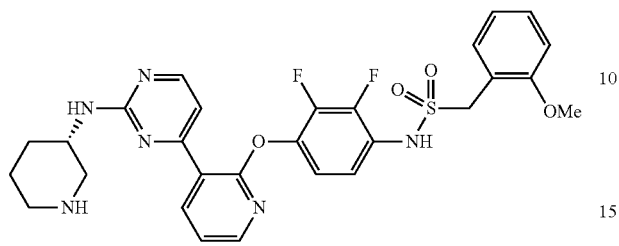

The title compound was prepared according to example 144. This resulted in the title compound (26 mg, 33% yield) as a white solid.

Example 146

(S)—N-(2,3-Difluoro-4-((3-(2-(piperidin-3-ylamino)pyrimidin-4-yl)pyridin-2-yl)oxy)phenyl)-9H-fluorene-9-sulfonamide Compound 381

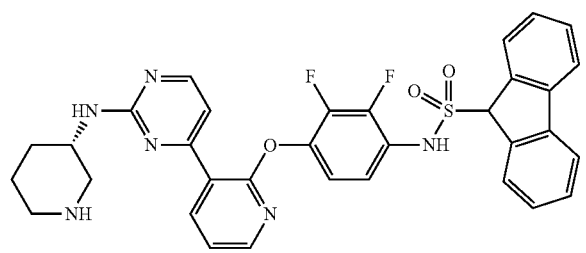 [SMILES: O=S(=O)(Nc1ccc(Oc2ncccc2-c2ccnc(N[C@H]3CCCNC3)n2)c(F)c1F)C1c2ccccc2-c2ccccc21]

The title compound was prepared according to example 144. This resulted in the title compound (8 mg, 31% yield) as a white solid.

Example 147

N-(4-((3-(2-(((1r,4r)-4-(Dimethylamino)cyclohexyl)amino)pyrimidin-4-yl)pyridin-2-yl)oxy)-2,3,6-trifluorophenyl)-3,3,3-trifluoropropane-1-sulfonamide Compound 382

Step 1: N$^1$-[4-[2-(4-Amino-2,3,5-trifluoro-phenoxy)-3-pyridyl]pyrimidin-2-yl]-N$^4$,N$^4$-dimethyl-cyclohexane-1,4-diamine

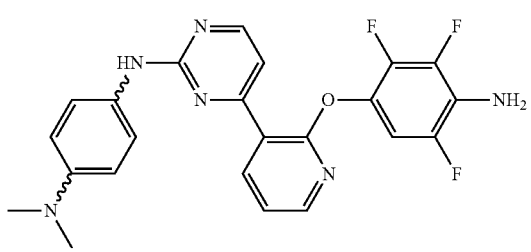 [SMILES: CN(C)c1ccc(Nc2nccc(-c3cccnc3Oc3cc(F)c(N)c(F)c3F)n2)cc1]

2,3,6-Trifluoro-4-[[3-(2-methylsulfonylpyrimidin-4-yl)-2-pyridyl]oxy]aniline was reacted with N$^1$,N$^1$-dimethylcyclohexane-1,4-diamine dihydrochloride similar as in example 125 step 1 to afford the title compound (180 mg, 62%) as a mixture of cis/trans isomers.

Step 2: N-(4-((3-(2-(((1r,4r)-4-(Dimethylamino)cyclohexyl)amino)pyrimidin-4-yl)pyridin-2-yl)oxy)-2,3,6-trifluorophenyl)-3,3,3-trifluoropropane-1-sulfonamide Compound 382

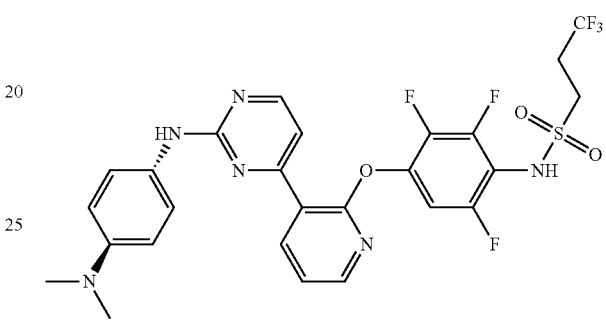

N$^1$-[4-[2-(4-Amino-2,3,5-trifluoro-phenoxy)-3-pyridyl]pyrimidin-2-yl]-N$^4$,N$^4$-dimethyl-cyclohexane-1,4-diamine was reacted with 3,3,3-trifluoropropane-1-sulfonyl chloride similar as in example 129 step 1 to afford the title compound (4 mg, 3% based on theoretical yield of desired trans product).

Example 148

1-m-Tolyl-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 383

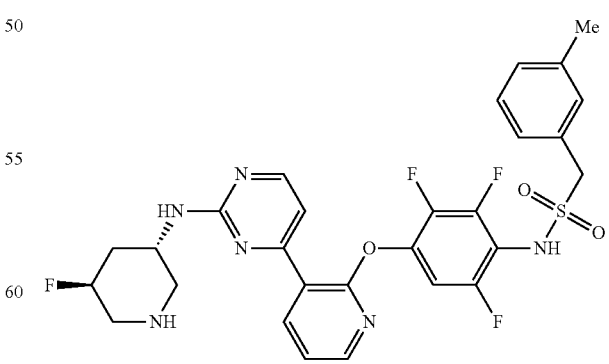

The title compound was prepared according to example 129. This resulted in the title compound (7 mg, 9% yield) as a white solid.

Example 149

1-(2-Fluoro-4-methylphenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 384

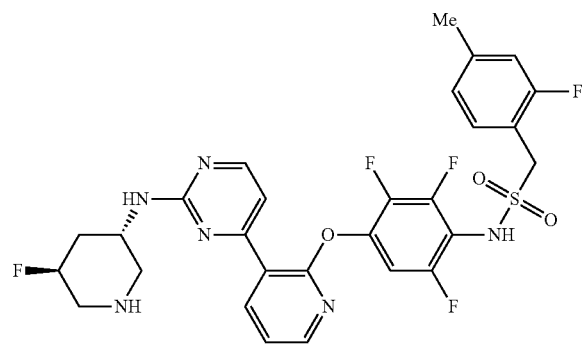 [SMILES: Cc1ccc(CS(=O)(=O)Nc2c(F)cc(Oc3ncccc3-c3ccnc(N[C@@H]4CNC[C@@H](F)C4)n3)c(F)c2F)c(F)c1]

The title compound was prepared according to example 129. This resulted in the title compound (22 mg, 24% yield) as a white solid.

Example 150

1-(3-Methoxyphenyl)-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 385

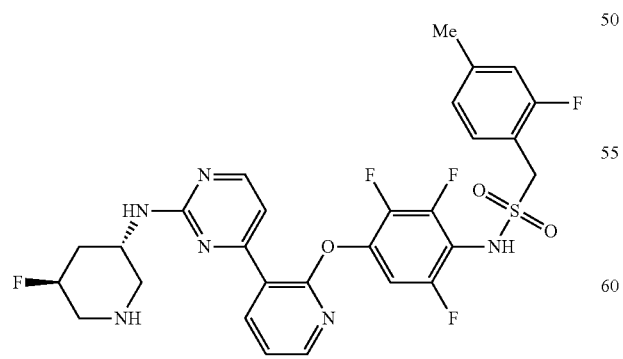

The title compound was prepared according to example 129. This resulted in the title compound (18 mg, 20% yield) as a white solid.

Example 151

1-o-Tolyl-N-(2,3,6-trifluoro-4-((3-(2-(((3S,5S)-5-fluoropiperidin-3-yl)amino)pyrimidin-4-yl)pyridin-2-yl)oxy)phenyl)methanesulfonamide Compound 386

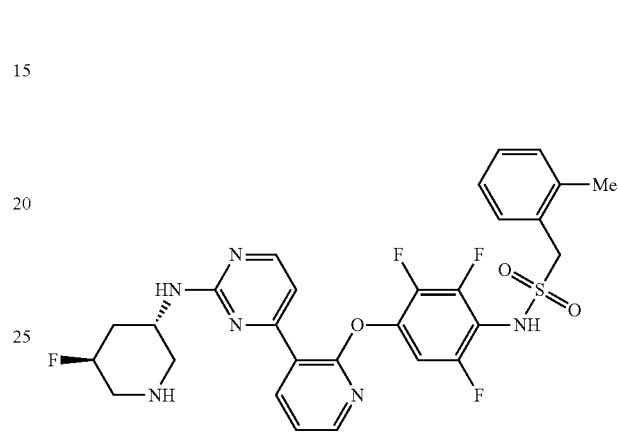

The title compound was prepared according to example 129. This resulted in the title compound (14 mg, 18% yield) as a white solid.

Example 153

N-(2,3,6-Trifluoro-4-((3-(2-(((3S,5S)-5-fluoropiperidin-3-yl)amino)pyrimidin-4-yl)pyridin-2-yl)oxy)phenyl)-1-(2-(trifluoromethyl)pyridin-3-yl)methanesulfonamide Compound 389

The title compound was prepared according to example 129. This resulted in the title compound (41 mg, 55% yield) as a white solid.

Example 154

(*S)-1-Phenyl-N-(2,3,6-trifluoro-4-((3-(2-(((3S,5S)-5-fluoropiperidin-3-yl)amino)pyrimidin-4-yl)pyridin-2-yl)oxy)phenyl)ethane-1-sulfonamide Compound 387 & (*R)-1-phenyl-N-(2,3,6-trifluoro-4-((3-(2-(((3S,5S)-5-fluoropiperidin-3-yl)amino)pyrimidin-4-yl)pyridin-2-yl)oxy)phenyl)ethane-1-sulfonamide Compound 388. *=arbitrarily assigned)

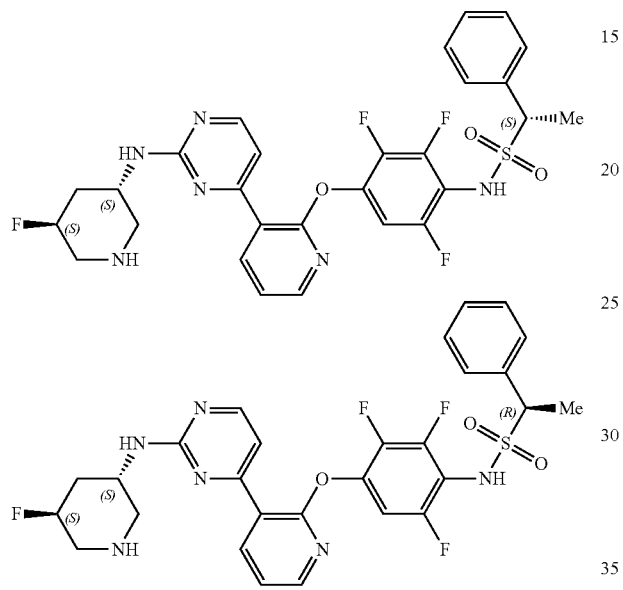

The title compounds were prepared according to example 99. This resulted in the title compounds (Compound 387; 21 mg, 54% yield and Compound 388; 28 mg, 71% yield) as white solids.

Biological Examples

Exemplary compounds of Formula (I) were tested to assess compound inhibition of IRE1 in binding assays and functional assays.

Example B1: IRE1α TR-FRET Competition Binding Assay

To determine the affinity of compound binding to the kinase domain of IRE1 alpha, a Time Resolved Fluorescence Resonance Energy Transfer (TR-FRET) competition assay was used. A His-tagged IRE1 alpha kinase dead construct containing the kinase and RNase domains (KR, AA G547-L977, D688N) was expressed in Sf9 insect cells. The purified protein (final concentration 0.006 µM micromolar) was pre-incubated with anti-His Europium labeled antibody (Life Technologies PV5596, final concentration 0.002 µM micromolar) for one hour at 4° C. in 1X TR-FRET Assay Buffer (50 mM HEPES, pH 7.5.10 mM $MgCl_2$, 0.083 mM Brij 35, 1 mM DTT, and 0.1% bovine gamma globulin) prior to addition to test compounds. A fluorescent labeled probe based on an ATP competitive inhibitor (Kinase Tracer 236, Life Technologies PV5592) is added to a final concentration of 0.1 µM (micromolar). Reactions were carried out for one hour at room temperature in a final volume of 20 µL (microliter) in 384 well white ProxiPlates (Perkin Elmer 6008289). Binding of the tracer to the IRE1 protein alpha was detected in an Envision instrument (PerkinElmer) equipped with a TRF laser option and a LANCE/Delfia Dual/Bias D400/D630 mirror (Ex 347 nm, $1^{st}$ Em 665 nm, $2^{nd}$ Em 615 nm).

Exemplary compounds in Table A1 were tested in the IRE1α binding assays. The $IC_{50}$ values determined are listed in Table B1.

TABLE B1

| Compound No. | IRE1α TR-FRET $IC_{50}$ (µM) |
|---|---|
| 101 | 0.013 |
| 102 | 0.010 |
| 103 | 0.030 |
| 104 | 0.0059 |
| 105 | 0.027 |
| 106 | 0.0057 |
| 107 | 0.0052 |
| 108 | 0.0034 |
| 109 | 0.026 |
| 110 | 0.0097 |
| 111 | 0.0044 |
| 112 | 0.0046 |
| 113 | 0.011 |
| 114 | 0.0073 |
| 115 | 0.03 |
| 116 | 0.023 |
| 117 | 0.021 |
| 118 | 0.047 |
| 119 | 0.013 |
| 120 | 0.11 |
| 121 | 0.026 |
| 122 | 0.02 |
| 123 | 0.05 |
| 124 | 0.21 |
| 125 | 0.027 |
| 126 | 0.28 |
| 127 | 0.37 |
| 128 | 0.011 |
| 129 | 0.23 |
| 130 | 0.17 |
| 131 | 0.059 |
| 132 | 0.032 |
| 133 | 0.12 |
| 134 | 0.021 |
| 135 | 0.041 |
| 136 | 0.20 |
| 137 | 0.0074 |
| 138 | 0.015 |
| 139 | 0.046 |
| 140 | 0.026 |
| 141 | 0.017 |
| 142 | 0.016 |
| 143 | 0.034 |
| 144 | 0.37 |
| 145 | 0.0078 |
| 146 | 0.0040 |
| 147 | 0.21 |
| 148 | 0.0065 |
| 149 | 0.0087 |
| 150 | 0.30 |
| 151 | 0.084 |
| 152 | 0.0039 |
| 153 | 0.0038 |
| 154 | 0.0038 |
| 155 | 0.0045 |
| 156 | 0.0046 |
| 157 | 0.029 |
| 158 | 0.0051 |
| 159 | 0.011 |
| 160 | 0.0054 |
| 161 | 0.0042 |
| 162 | 0.0069 |
| 163 | 0.0066 |
| 164 | 0.0040 |

TABLE B1-continued

| Compound No. | IRE1α TR-FRET IC$_{50}$ (μM) |
|---|---|
| 165 | 0.0027 |
| 166 | 0.0035 |
| 167 | 0.017 |
| 168 | 0.067 |
| 169 | 0.0041 |
| 170 | 0.011 |
| 171 | 0.18 |
| 172 | 0.042 |
| 173 | 0.0083 |
| 174 | 0.0031 |
| 175 | 0.0052 |
| 176 | 0.0025 |
| 177 | 0.0049 |
| 178 | 0.0035 |
| 179 | 0.0043 |
| 180 | 0.038 |
| 181 | 0.036 |
| 182 | 0.0095 |
| 183 | 0.0085 |
| 184 | 0.057 |
| 185 | 0.0094 |
| 186 | 0.020 |
| 187 | 0.0029 |
| 188 | 0.011 |
| 189 | 0.0050 |
| 190 | 0.0047 |
| 191 | 0.0043 |
| 192 | 0.0097 |
| 193 | 0.033 |
| 194 | 0.0040 |
| 195 | 0.0046 |
| 196 | 0.0025 |
| 197 | 0.49 |
| 198 | 1.30 |
| 199 | 0.11 |
| 200 | 0.53 |
| 201 | 0.21 |
| 202 | 0.0044 |
| 203 | 0.0033 |
| 204 | 0.0041 |
| 205 | 0.0044 |
| 206 | 0.0082 |
| 207 | 0.0074 |
| 208 | 0.011 |
| 209 | 0.0075 |
| 210 | 0.023 |
| 211 | 0.033 |
| 212 | 0.025 |
| 213 | 0.0059 |
| 214 | 0.044 |
| 215 | 0.011 |
| 216 | 0.013 |
| 217 | 0.016 |
| 218 | 0.016 |
| 219 | 0.053 |
| 220 | 0.019 |
| 221 | 0.38 |
| 222 | 0.24 |
| 223 | 0.026 |
| 224 | 0.04 |
| 225 | 0.0061 |
| 226 | 0.018 |
| 227 | 0.0048 |
| 228 | 0.0092 |
| 229 | 0.0064 |
| 230 | 0.014 |
| 231 | 0.0072 |
| 232 | 0.015 |
| 233 | 0.009 |
| 234 | 0.007 |
| 235 | 0.004 |
| 236 | 0.009 |
| 237 | 0.0084 |
| 238 | 0.014 |
| 248 | 0.045 |
| 249 | 0.16 |
| 250 | 0.00490 |
| 251 | 0.0028 |
| 252 | 0.014 |
| 253 | 0.0019 |
| 254 | 0.00062 |
| 255 | 0.23 |
| 256 | 0.001 |
| 257 | 0.024 |
| 258 | 0.0052 |
| 259 | 0.002 |
| 260 | 0.0026 |
| 261 | 0.0035 |
| 262 | 0.00025 |
| 263 | 0.0015 |
| 264 | 0.0016 |
| 265 | 0.0014 |
| 266 | 0.0086 |
| 267 | 0.0022 |
| 268 | 0.0011 |
| 269 | 0.0011 |
| 270 | 0.00054 |
| 271 | 0.0036 |
| 272 | 0.00015 |
| 273 | 0.41 |
| 274 | 0.4 |
| 275 | 0.00023 |
| 276 | 0.18 |
| 277 | 0.027 |
| 278 | 0.00078 |
| 279 | 0.00023 |
| 280 | 0.00031 |
| 281 | 0.00034 |
| 282 | 0.00027 |
| 283 | 0.00041 |
| 284 | 0.00015 |
| 285 | 0.0089 |
| 286 | 0.26 |
| 287 | 0.0015 |
| 288 | 0.0011 |
| 290 | 0.0004 |
| 291 | 0.00028 |
| 292 | 0.00033 |
| 293 | 0.00041 |
| 294 | 0.00059 |
| 295 | 0.041 |
| 296 | 0.014 |
| 297 | 0.00028 |
| 298 | 0.0018 |
| 299 | 0.00038 |
| 300 | 0.0087 |
| 301 | 0.00036 |
| 302 | 0.00044 |
| 303 | 0.035 |
| 304 | 0.00023 |
| 305 | 0.00021 |
| 306 | 0.043 |
| 307 | 0.00031 |
| 308 | 0.083 |
| 309 | 0.0011 |
| 310 | 0.00032 |
| 311 | 0.00029 |
| 312 | 0.00014 |
| 313 | 0.0012 |
| 314 | 0.00024 |
| 315 | 0.00023 |
| 316 | 0.00035 |
| 317 | 0.14 |
| 318 | 0.0003 |
| 319 | 0.00048 |
| 320 | 0.035 |
| 321 | 0.00065 |
| 322 | 0.00042 |
| 323 | 0.00033 |
| 324 | 0.0004 |
| 325 | 0.022 |
| 326 | 0.00061 |
| 327 | 0.00026 |
| 328 | 0.011 |
| 329 | 0.012 |
| 330 | 0.087 |

TABLE B1-continued

| Compound No. | IRE1α TR-FRET IC$_{50}$ (μM) |
|---|---|
| 331 | 0.00082 |
| 332 | 0.056 |
| 333 | 0.00019 |
| 334 | 0.0098 |
| 335 | 0.33 |
| 336 | 0.00042 |
| 337 | 0.0089 |
| 338 | 0.0026 |
| 339 | 0.00024 |
| 340 | 0.0075 |
| 341 | 0.0005 |
| 342 | 0.00016 |
| 343 | 0.00078 |
| 344 | 0.019 |
| 345 | 0.00017 |
| 346 | 0.072 |
| 347 | 0.049 |
| 348 | 0.0002 |
| 349 | 0.21 |
| 350 | 0.00042 |
| 351 | 0.00091 |
| 352 | 0.0002 |
| 353 | 0.0003 |
| 354 | 0.0002 |
| 355 | 0.0002 |
| 356 | 0.0002 |
| 357 | 0.001 |
| 358 | 0.0003 |
| 359 | 0.0003 |
| 360 | 0.0008 |
| 361 | 0.0003 |
| 362 | 0.0002 |
| 363 | 0.0002 |
| 364 | 0.0003 |
| 365 | 0.0007 |
| 366 | 0.0002 |
| 367 | 0.0002 |
| 368 | 0.0002 |
| 369 | 0.0012 |
| 370 | 0.002 |
| 371 | 0.0003 |
| 372 | 0.0002 |
| 373 | 0.0003 |
| 374 | 0.0002 |
| 375 | 0.0004 |
| 376 | 0.0002 |
| 377 | 0.0008 |
| 378 | 0.0011 |
| 379 | 0.0003 |
| 380 | 0.0009 |
| 381 | 0.001 |
| 382 | 0.002 |
| 383 | 0.0007 |
| 384 | 0.0003 |
| 385 | 0.0002 |
| 386 | 0.0003 |
| 387 | 0.0002 |
| 388 | 0.0008 |
| 389 | 0.0003 |

Example B2: IRE1 alpha RNase Activity Assay

Inhibitors of the RNase activity of IRE1α were assessed by Fluorescence (Forster) resonance energy transfer (FRET) using a mini-XBP-1 stem-loop RNA as a substrate for the IRE1α RNase activity. A 5'-Carboxy fluorescein (FAM)- and 3'-Black Hole Quencher (BHQ)-labeled XBP1 single stem-loop mini-substrate oligonucleotide, TAQMAN® (Roche Molecular Systems) probe (Kutyavin et al (2000) Nucleic Acids Research, 28(2):655-661) is cleaved by IRE1α. When the oligonucleotide is intact, the fluorescence signal is quenched by BHQ. Upon cleavage, the fluorescence is no longer quenched and can be quantified.

An IRE1 alpha construct corresponding to the linker, kinase and RNase domains (LKR, AA Q470-L977) was expressed in Sf9 insect cells. All reagent preparation and procedures are done under RNase free conditions. Test compounds and purified enzyme were combined in RNase Assay Buffer (20 mM HEPES, pH 7.5, 50 mM KAc, 1 mM MgAc, 1 mM DTT, and 0.05% Triton X-100) in a 384 well white ProxiPlate (Perkin Elmer 6008289). Upon addition of the RNA substrate (final assay volume 20 μL, microliter), the plates were placed into a Flexstation 3 instrument (Molecular Devices) for kinetic fluorescence reading at 2 minute intervals (Ex 485, Em 535). The velocity of the reaction, using the first 50 minutes, was used to calculate the RNase activity and inhibition of test compounds.

Exemplary compounds Table A1 had activity in the IRE1α RNase activity assay with an IC$_{50}$ of less than 10 μmol (micromolar).

Example B2: IRE1 Alpha Ribonuclease Luciferase Reporter Assay

HEK293 cells expressing a pBABE.puro HA-2xXBP1 delta DBD firefly luciferase reporter (Mendez et al., (2015) "Endoplasmic reticulum stress-independent activation of unfolded protein response kinases by a small molecule ATP-mimic", eLife; 4:e05434) were cultured in DMEM high glucose media containing L-glutamine, 10% fetal bovine serum, 100 units/mL of penicillin and 100 μg/mL (microgram per milliliter) of streptomycin, plus 2 μg/ml puromycin to maintain selective pressure. Upon stimulation of IRE1 and activation of the endogenous RNase activity, a 26 nt intron is removed from XBP1 resulting in a frame shift allowing the transcription of the luciferase.

Cells were seeded without puromycin at 10,000/well in 384 well clear bottom white tissue culture plates (Corning 3707), 25 μL volume. The following morning, test compounds were added and incubated for one hour at 37° C. prior to stimulation of the cells with thapsigargin at 50 μM (micromolar) final concentration for an additional 5 hours. After equilibration to room temperature, 25 μL (microliters) of One-Glo® luciferase detection reagent (Promega cat #E6120) was added, plates sealed and shaken for 5 minutes to lyse cells, then luciferase quantified by luminescence detection using an Envision instrument (PerkinElmer).

Exemplary compound in Table A1 had activity in the XBP1s-LUC reporter assay with IC$_{50}$ of less than 10 μmol (micromolar).

It is to be noted that the term "a" or "an" entity refers to one or more of that entity; for example, "a polypeptide" is understood to represent one or more polypeptides. As such, the terms "a" (or "an"), "one or more," and "at least one" can be used interchangeably herein.

All technical and scientific terms used herein have the same meaning. Efforts have been made to ensure accuracy with respect to numbers used (e.g. amounts, temperature, etc.) but some experimental errors and deviations should be accounted for.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed herein. The upper and lower limits of these small ranges which can independently be included in the smaller rangers is also encompassed herein, subject to any specifically excluded limit in the stated range. Where the stated range includes one or both of the limits, ranges excluding either or both of those included limits are also included herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:
1. A compound of Formula (I):

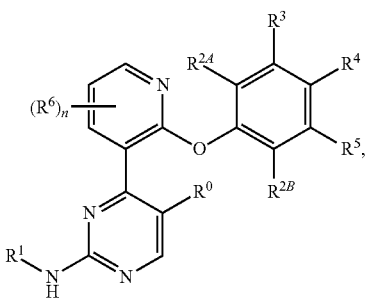

(I)

or a pharmaceutically acceptable salt thereof, wherein:
$R^0$ is hydrogen or fluoro;
$R^1$ is $C_{3-12}$ cycloalkyl, 3- to 14-membered heterocyclyl, 5- to 14-membered heteroaryl, —($C_{1-6}$ alkylene)-($C_3$-$C_{12}$ cycloalkyl), or —($C_{1-6}$ alkylene)-(3- to 14-membered heterocyclyl), —($C_{1-6}$ alkylene)-$OR^{1c}$, or —($C_{1-6}$ alkylene)-$NR^{1a}R^{1b}$; wherein the $C_{3-12}$ cycloalkyl, 3- to 14-membered heterocyclyl, 5- to 14-membered heteroaryl, and $C_{1-6}$ alkylene of $R^1$ are independently optionally substituted with 1, 2, 3, 4 or 5 substituents independently selected from $R^{10}$;
each $R^{1a}$, $R^{1b}$ and $R^{1c}$ is independently hydrogen, $C_{1-6}$ alkyl, $C_{3-8}$ cycloalkyl, $C_{6-10}$ aryl, 5-to 14-membered heteroaryl or 3- to 12-membered heterocyclyl; wherein the $C_{1-6}$ alkyl, $C_{3-8}$ cycloalkyl, $C_{6-10}$ aryl, 5- to 14-membered heteroaryl and 3- to 12-membered heterocyclyl of $R^{1a}$ and $R^{1b}$ are optionally substituted with 1, 2, 3, 4 or 5 substituents independently selected from $R^{10}$;
$R^{2A}$ and $R^{2B}$ are independently hydrogen, halogen, cyano, $C_{1-6}$ alkyl, $C_{1-6}$ haloalkyl, $C_{3-6}$ cycloalkyl, —O($C_{1-6}$ alkyl), or —O($C_{1-6}$ haloalkyl);

$R^3$ is hydrogen, halogen, cyano, $C_{1-6}$ alkyl, $C_{1-6}$ haloalkyl, $C_{3-6}$ cycloalkyl, —O($C_{1-6}$ alkyl), or —O($C_{1-6}$ haloalkyl);
$R^4$ and $R^5$ are independently hydrogen, halogen, cyano, nitro, $C_{1-6}$ alkyl, $C_{2-6}$ alkenyl, $C_{2-6}$ alkynyl, $C_{3-12}$ cycloalkyl, $C_{6-20}$ aryl, 3- to 14-membered heterocyclyl, 5- to 14-membered heteroaryl, —$OR^{7A}$, —$NR^{8A}R^{8B}$, —$NR^8C(O)R^7$, —$NR^8C(O)OR^{7A}$, —$NR^8C(O)NR^{8A}R^{8B}$, —$NR^8SO_2R^9$, —$NR^8SO_2NR^{8A}R^{8B}$, —$NR^8S(O)(=NR^{8C})R^9$, —$C(O)N(R^8)SO_2R^9$, —$C(O)R^7$, —$C(O)OR^{7A}$, —$SO_2R^9$, —$NR^8S(O)(=NR^{8C})R^9$, or —$SO_2NR^{8A}R^{8B}$; wherein the $C_{1-6}$ alkyl, $C_{3-12}$ cycloalkyl, $C_{6-20}$ aryl, 3- to 14-membered heterocyclyl, and 5- to 14-membered heteroaryl of $R^4$ and $R^5$ are optionally substituted with 1, 2, 3, 4 or 5 substituents independently selected from $R^{10}$;
n is 0, 1, 2, or 3;
each $R^6$ is independently halogen, cyano, nitro, $C_{1-6}$ alkyl, $C_{1-6}$ haloalkyl, $C_{3-6}$ cycloalkyl, —O($C_{1-6}$ alkyl), —O($C_{1-6}$ haloalkyl), —$SO_2$($C_{1-6}$ alkyl) or —$SO_2$($C_{1-6}$ haloalkyl);
each $R^7$ is independently hydrogen, $C_{1-6}$ alkyl, $C_{2-6}$ alkenyl, $C_{3-8}$ cycloalkyl, 5- to 14-membered heteroaryl, or 3- to 12-membered heterocyclyl; wherein the $C_{1-6}$ alkyl, $C_{2-6}$ alkenyl, $C_{3-8}$ cycloalkyl, 5- to 14-membered heteroaryl and 3- to 12-membered heterocyclyl of $R^7$ and $R^{7A}$ are optionally substituted with 1, 2, 3, 4 or 5 substituents independently selected from $R^{10}$;
each $R^{7A}$ is independently hydrogen, $C_{1-6}$ alkyl, $C_{2-6}$ alkenyl, $C_{3-8}$ cycloalkyl, $C_{6-10}$ aryl, 5-to 14-membered heteroaryl, or 3- to 12-membered heterocyclyl; wherein the $C_{1-6}$ alkyl, $C_{2-6}$ alkenyl, $C_{3-8}$ cycloalkyl, $C_{6-10}$ aryl, 5- to 14-membered heteroaryl and 3- to 12-membered heterocyclyl of $R^7$ and $R^{7A}$ are optionally substituted with 1, 2, 3, 4 or 5 substituents independently selected from $R^{10}$;
each $R^8$ is independently hydrogen or $C_1$-$C_6$ alkyl;
each $R^{8A}$ is independently hydrogen or $C_1$-$C_6$ alkyl;
each $R^{8B}$ is independently hydrogen, $C_{1-6}$ alkyl, $C_{2-6}$ alkenyl, $C_{3-8}$ cycloalkyl, $C_{6-10}$ aryl, or 3- to 12-membered heterocyclyl; wherein the $C_{1-6}$ alkyl, $C_{2-6}$ alkenyl, $C_{3-8}$ cycloalkyl, $C_{6-10}$ aryl, and 3- to 12-membered heterocyclyl of $R^{8B}$ are optionally substituted with 1, 2, 3, 4 or 5 substituents independently selected from $R^{10}$;
each $R^{8C}$ is independently hydrogen or $C_1$-$C_6$ alkyl;
each $R^9$ is independently $C_{1-6}$ alkyl, $C_{2-6}$ alkenyl, $C_{3-8}$ cycloalkyl, $C_{6-10}$ aryl, 5- to 14-membered heteroaryl and 3- to 12-membered heterocyclyl; wherein the $C_{1-6}$ alkyl, $C_{2-6}$ alkenyl, $C_{3-8}$ cycloalkyl, $C_{6-10}$ aryl, 5- to 14-membered heteroaryl and 3- to 12-membered heterocyclyl are optionally substituted with 1, 2, 3, 4 or 5 substituents independently selected from $R^{10}$;
each $R^{10}$ is independently oxo, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl, 3- to 12-membered heterocyclyl, halogen, cyano, —$C(O)R^a$, —$C(O)OR^b$, —$C(O)NR^cR^d$, —$OR^b$, —$OC(O)R^a$, —$OC(O)NR^cR^d$, —$SR^b$, —$S(O)R^e$, —$S(O)_2R^e$, —$S(O)(=NH)R^e$, —$S(O)_2NR^cR^d$, —$NR^cR^d$, —$N(R^f)C(O)R^a$, —$N(R^f)C(O)OR^b$, —$N(R^f)C(O)NR^cR^d$, —$N(R^f)S(O)_2R^e$, —$N(R^f)S(O)_2NR^cR^d$, —$P(O)R^gR^h$, or —$SiR^iR^jR^k$; wherein the $C_{1-6}$ alkyl, $C_{2-6}$ alkenyl, $C_{2-6}$ alkynyl, $C_{3-8}$ cycloalkyl, $C_{6-14}$ aryl, 5- to 14-membered heteroaryl and 3- to 14-membered heterocyclyl of $R^{10}$ are each optionally substituted with 1, 2, 3 or 4 substituents independently selected from $R^{11}$;

each $R^a$ is independently hydrogen, $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{2-6}$ alkenyl, $C_{2-6}$ alkynyl, $C_{3-8}$ cycloalkyl, $C_{6-10}$ aryl, 5- to 10-membered heteroaryl and 3-to 12-membered heterocyclyl of $R^a$ are each optionally substituted with 1, 2, 3 or 4 substituents independently selected from $R^{11}$;

each $R^b$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^b$ are each optionally substituted with 1, 2, 3 or 4 substituents independently selected from $R^{11}$;

each $R^c$ and $R^d$ is independently hydrogen, $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^c$ and $R^d$ are each optionally substituted with 1, 2, 3 or 4 substituents independently selected from $R^{11}$;

or $R^c$ and $R^d$ are taken together with the nitrogen atom to which they are attached to form a 4- to 12-membered heterocyclyl optionally substituted with 1, 2, 3 or 4 substituents independently selected from $R^{11}$;

each $R^e$ is independently $C_{1-6}$ alkyl, $C_{3-8}$ cycloalkyl, $C_{6-10}$ aryl, 5- to 10-membered heteroaryl or 3- to 12-membered heterocyclyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^e$ are each optionally substituted with 1, 2, 3 or 4 substituents independently selected from $R^{11}$;

each $R^f$ is independently hydrogen or $C_{1-6}$ alkyl;

each $R^g$ and $R^h$ is independently $C_{1-6}$ alkyl, $C_{3-8}$ cycloalkyl, $C_{6-10}$ aryl, 5- to 10-membered heteroaryl, 3- to 12-membered heterocyclyl, or —O—$C_{1-6}$ alkyl; wherein the $C_{1-6}$ alkyl, $C_{3-8}$ cycloalkyl, $C_{6-10}$ aryl, 5- to 10-membered heteroaryl and 3- to 12-membered heterocyclyl of $R^g$ and $R^h$ are each optionally substituted with 1, 2, 3 or 4 substituents independently selected from $R^{11}$;

or $R^g$ and $R^h$ are taken together with the phosphorus atom to which they are attached to form a 4- to 12-membered heterocyclyl optionally substituted with 1, 2, 3 or 4 substituents independently selected from $R^{11}$;

each $R^i$, $R^j$ and $R^k$ is independently $C_{1-6}$ alkyl;

each $R^{11}$ is independently oxo, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl, 3- to 8-membered heterocyclyl, halogen, cyano, —C(O)$R^{a1}$, —C(O)O$R^{b1}$, —C(O)NR$^{c1}$R$^{d1}$, —O$R^{b1}$, —OC(O)$R^{a1}$, —OC(O)NR$^{c1}$R$^{d1}$, —S$R^{b1}$, —S(O)$R^{e1}$, —S(O)$_2$$R^{e1}$, —S(O)$_2$NR$^{c1}$R$^{d1}$, —NR$^{c1}$R$^{d1}$, —N($R^{f1}$)C(O)$R^{a1}$, —N($R^{f1}$)C(O)O$R^{a1}$, —N($R^{f1}$)C(O)NR$^{c1}$R$^{d1}$, —N($R^{f1}$)S(O)$_2$$R^{e1}$, —N($R^{f1}$)S(O)$_2$NR$^{c1}$R$^{d1}$, —P(O)$R^{g1}$$R^{h1}$, or —Si$R^{i1}$$R^{j1}$$R^{k1}$; wherein the $C_{1-6}$ alkyl, $C_{2-6}$ alkenyl, $C_{2-6}$ alkynyl, $C_{3-6}$ cycloalkyl, $C_{6-14}$ aryl, 5- to 14-membered heteroaryl and 3- to 14-membered heterocyclyl of $R^{11}$ are each optionally substituted with 1, 2, 3 or 4 substituents independently selected from $R^{12}$;

each $R^{a1}$ is independently hydrogen, $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{2-6}$ alkenyl, $C_{2-6}$ alkynyl, $C_{3-6}$ cycloalkyl, $C_{6-10}$ aryl, 5- to 10-membered heteroaryl and 3-to 8-membered heterocyclyl of $R^{a1}$ are each optionally substituted with 1, 2, 3 or 4 substituents independently selected from $R^{12}$;

each $R^{b1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{b1}$ are each optionally substituted with 1, 2, 3 or 4 substituents independently selected from $R^{12}$;

each $R^{c1}$ and $R^{d1}$ is independently hydrogen, $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{c1}$ and $R^{d1}$ are each optionally substituted with 1, 2, 3 or 4 substituents independently selected from $R^{12}$;

or $R^{c1}$ and $R^{d1}$ are taken together with the nitrogen atom to which they are attached to form a 4- to 8-membered heterocyclyl optionally substituted with 1, 2, 3 or 4 substituents independently selected from $R^{12}$;

each $R^{e1}$ is independently $C_{1-6}$ alkyl, $C_{3-6}$ cycloalkyl, $C_{6-10}$ aryl, 5- to 10-membered heteroaryl or 3- to 8-membered heterocyclyl; wherein the $C_{1-6}$ alkyl, $C_{3-6}$ cycloalkyl, $C_{6-10}$ aryl, 5-to 10-membered heteroaryl and 3- to 8-membered heterocyclyl of $R^{e1}$ are each optionally substituted with 1, 2, 3 or 4 substituents independently selected from $R^{12}$;

each $R^{f1}$ is independently hydrogen or $C_{1-6}$ alkyl;

each $R^{g1}$ and $R^{h1}$ is independently $C_{1-6}$ alkyl, $C_{3-6}$ cycloalkyl, $C_{6-10}$ aryl, 5- to 10-membered heteroaryl, 3- to 8-membered heterocyclyl, or —O—$C_{1-6}$ alkyl; wherein the $C_{1-6}$ alkyl, $C_{3-6}$ cycloalkyl, $C_{6-10}$ aryl, 5- to 10-membered heteroaryl and 3- to 8-membered heterocyclyl of $R^{g1}$ and $R^{h1}$ are each optionally substituted with 1, 2, 3 or 4 substituents independently selected from $R^{12}$;

or $R^{g1}$ and $R^{h1}$ are taken together with the phosphorus atom to which they are attached to form a 4- to 8-membered heterocyclyl optionally substituted with 1, 2, 3 or 4 substituents independently selected from $R^{12}$;

each $R^{i1}$, $R^{j1}$ and $R^{k1}$ is independently $C_{1-6}$ alkyl;

each $R^{12}$ is independently oxo, $C_{1-6}$ alkyl, $C_{3-6}$ cycloalkyl, $C_6$ aryl, 5- to 6-membered heteroaryl, 3- to 6-membered heterocyclyl, halogen, cyano, —C(O)$R^{a2}$, —C(O)O$R^{b2}$, —C(O)NR$^{e2}$R$^{d2}$, —O$R^{b2}$, —OC(O)$R^{a2}$, —OC(O)NR$^{e2}$R$^{d2}$, —S(O)$_2$$R^{e2}$, —S(O)$_2$NR$^{c2}$R$^{d2}$, —NR$^{c2}$R$^{d2}$, —N($R^{f2}$)C(O)$R^{a2}$, —N($R^{f2}$)C(O)O$R^{b2}$, —N($R^{f2}$)C(O)NR$^{e2}$R$^{d2}$, —N($R^{f2}$)S(O)$_2$$R^{e2}$, —N($R^{f2}$)S(O)$_2$NR$^{c2}$R$^{d2}$, or —P(O)$R^{g2}$$R^{h2}$; wherein the $C_{1-6}$ alkyl, $C_{3-6}$ cycloalkyl, $C_6$ aryl, 5- to 6-membered heteroaryl and 3- to 6-membered heterocyclyl of $R^{12}$ are each optionally substituted with 1, 2, 3 or 4 substituents independently selected from $R^{13}$;

each $R^{a2}$ is independently hydrogen, $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^{a2}$ are each optionally substituted with 1, 2, 3 or 4 substituents independently selected from $R^{13}$;

each $R^{b2}$ is independently hydrogen, $C_{1-6}$ alkyl, $C_{3-6}$ cycloalkyl or 3- to 6-membered heterocyclyl; wherein the $C_{1-6}$ alkyl, $C_{3-6}$ cycloalkyl and 3- to 6-membered heterocyclyl of $R^{b2}$ are each optionally substituted with 1, 2, 3 or 4 substituents independently selected from $R^{13}$;

each $R^{c2}$ and $R^{d2}$ is independently hydrogen, $C_{1-6}$ alkyl, $C_{3-6}$ cycloalkyl or 3- to 8-membered heterocyclyl; wherein the $C_{1-6}$ alkyl, $C_{3-6}$ cycloalkyl and 3- to 8-membered heterocyclyl of $R^{c2}$ and $R^{d2}$ are each optionally substituted with 1, 2, 3 or 4 substituents independently selected from $R^{13}$;

or $R^{c2}$ and $R^{d2}$ are taken together with the nitrogen atom to which they are attached to form a 4- to 6-membered heterocyclyl optionally substituted with 1, 2, 3 or 4 substituents independently selected from $R^{13}$;

each $R^{e2}$ is independently $C_{1-6}$ alkyl, $C_{3-6}$ cycloalkyl, $C_6$ aryl, 5- to 6-membered heteroaryl or 3- to 6-membered heterocyclyl; wherein the $C_{1-6}$ alkyl, $C_{3-6}$ cycloalkyl, $C_6$ aryl, 5- to 6-membered heteroaryl and 3- to 6-membered heterocyclyl of $R^2$ are each optionally substituted with 1, 2, 3 or 4 substituents independently selected from $R^{13}$;

each $R^{f2}$ is independently hydrogen or $C_{1-6}$ alkyl;

each $R^{g2}$ and $R^{h2}$ is independently $C_{1-6}$ alkyl, $C_{3-6}$ cycloalkyl, 3- to 8-membered heterocyclyl, or —O—$C_{1-6}$ alkyl; wherein the $C_{1-6}$ alkyl, $C_{3-6}$ cycloalkyl, and 3- to 8-membered heterocyclyl of $R^{g2}$ and $R^2$ are each optionally substituted with 1, 2, 3 or 4 substituents independently selected from $R^{13}$;

or $R^{g2}$ and R are taken together with the phosphorus atom to which they are attached to form a 4- to 6-membered heterocyclyl optionally substituted with 1, 2, 3 or 4 substituents independently selected from $R^{13}$; and each $R^{13}$ is independently oxo, halogen, hydroxyl, —O($C_{1-6}$ alkyl), cyano, $C_{1-6}$ alkyl or $C_{1-6}$ haloalkyl; provided that the compound is other than

| No. | Name |
|---|---|
| 2x | 2-Pyrrolidinone, 1-[3-[[4-[2-(4-amino-2-methylphenoxy)-3-pyridinyl]-2-pyrimidinyl]amino]propyl]-, |
| 3x | 4-Morpholinepropanamine, N-[4-[2-(4-amino-2-methylphenoxy)-3-pyridinyl]-2-pyrimidinyl]-, |
| 4x | Urea, N-(3-fluoro-4-methylphenyl)-N'-[4-[[3-[2-[[3-(4-morpholinyl)propyl]amino]-4-pyrimidinyl]-2-pyridinyl]oxy]phenyl]-, |
| 5x | Urea, N-(2,3-dihydro-1H-inden-5-yl)-N'-[4-[[3-[2-[[3-(4-morpholinyl)propyl]amino]-4-pyrimidinyl]-2-pyridinyl]oxy]phenyl]-, |
| 6x | Urea, N-(4-chlorophenyl)-N'-[4-[[3-[2-[[3-(4-morpholinyl)propyl]amino]-4-pyrimidinyl]-2-pyridinyl]oxy]phenyl]-, |
| 7x | Urea, N-[3-methyl-4-[[3-[2-[[3-(2-oxo-1-pyrrolidinyl)propyl]amino]-4-pyrimidinyl]-2-pyridinyl]oxy]phenyl]-N'-[3-(trifluoromethyl)phenyl]-, |
| 8x | Urea, N-(5-chloro-2-methoxyphenyl)-N'-[3-methyl-4-[[3-[2-[[3-(2-oxo-1-pyrrolidinyl)propyl]amino]-4-pyrimidinyl]-2-pyridinyl]oxy]phenyl]-, or |
| 9x | Urea, N-(5-chloro-2-methoxyphenyl)-N'-[3-methyl-4-[[3-[2-[[3-(4-morpholinyl)propyl]amino]-4-pyrimidinyl]-2-pyridinyl]oxy]phenyl]-, | and salts thereof.

2. The compound of claim 1, wherein $R^{2A}$ and $R^{2B}$ are independently H, F, Cl or $C_1$-$C_6$ alkyl.

3. The compound of claim 2, wherein $R^{2A}$ is H, F or methyl, and $R^{2B}$ is H, F, Cl or —$CH_3$.

4. The compound of claim 1, wherein $R^3$ is H, F, Cl, —CN, $C_{1-6}$ alkyl, or $C_{1-6}$ haloalkyl.

5. The compound of claim 1, wherein $R^5$ is H, F, Cl, —CN, $C_{1-6}$ alkyl optionally substituted with 1, 2, 3, 4 or 5 substituents independently selected from $R^{10}$, —$NR^8SO_2R^9$, —$NR^{8A}R^{8B}$, or —C(O)N($R^8$)$SO_2R^9$.

6. The compound of claim 5, wherein $R^5$ is $C_{1-6}$ alkyl substituted with 1, 2, 3, 4 or 5 substituents independently selected from $R^{10}$, —$NR^8SO_2R^9$, —$NR^{8A}R^{8B}$, or —C(O)N($R^8$)$SO_2R^9$.

7. The compound of claim 6, wherein $R^5$ is —$CH_2NHC(O)$-(cyclopropyl), —$NHCH_2CH(OH)CF_3$, or —C(O)$NHSO_2$-(2-chlorophenyl).

8. The compound of claim 6, wherein $R^5$ is —$NHSO_2R^9$, and $R^9$ is $C_{1-6}$ alkyl optionally substituted with 1, 2, 3, 4 or 5 substituents independently selected from $R^{10}$, or $C_{6-10}$ aryl optionally substituted with 1, 2, 3, 4 or 5 substituents independently selected from $R^{10}$.

9. The compound of claim 1, wherein $R^4$ is —$NR^8C(O)R^7$ or —$NR^8SO_2R^9$.

10. The compound of claim 9, wherein $R^4$ is —NH—$SO_2R^9$, and $R^9$ is $C_{1-6}$ alkyl, $C_{3-8}$ cycloalkyl, $C_{6-10}$ aryl, or 5- to 14-membered heteroaryl, wherein the $C_{1-6}$ alkyl, $C_{3-8}$ cycloalkyl, $C_{6-10}$ aryl and 5- to 14-membered heteroaryl of $R^9$ are independently optionally substituted with 1, 2, 3, 4 or 5 substituents independently selected from $R^{10}$.

11. The compound of claim 10, wherein $R^9$ is $C_{1-6}$ alkyl, $C_{3-8}$ cycloalkyl, $C_{6-10}$ aryl, or 5- to 14-membered heteroaryl, each optionally substituted with 1, 2, 3, 4 or 5 substituents independently selected from $R^{10}$.

12. The compound of claim 10, wherein $R^9$ is selected from the group consisting of cyclopentyl, cyclohexyl, phenyl, 2-chlorophenyl, 3-cyanophenyl, 4-cyanophenyl, 2-methoxyphenyl, 3-methoxyphenyl, 4-methoxyphenyl, 3-(difluoromethoxy)phenyl, 3-(trifluoromethoxy)phenyl, 4-(trifluoromethoxy)phenyl, 3,5-difluorophenyl, 3-pyridyl, 1-methyl-1H-imidazol-4-yl, 1-methyl-1H-pyrazol-4-yl, benzyl, 2-fluorobenzyl, 3-fluorobenzyl, 4-fluorobenzyl, 2-cyanobenzyl, 4-cyanobenzyl, 3-chlorobenzyl, 4-chlorobenzyl, (1-methyl-1H-pyrazol-3-yl)methyl, (5-methylisoxazol-3-yl)methyl, (pyridin-2-yl)methyl, (pyridin-3-yl)methyl, (pyridin-4-yl)methyl, (6-(trifluoromethyl)pyridin-3-yl)methyl, (1-fluorocyclopropyl)methyl, cyclobutylmethyl, (2,2-difluorocyclobutyl)methyl, (3,3-difluorocyclobutyl)methyl, cyclopentylmethyl, cyclohexylmethyl, (spiro[3.3]heptan-2-yl)methyl, 2-(cyclohexyl)ethyl, 2-(2,2-difluorocyclopropyl)ethyl, n-propyl, 3-cyano-2,2-dimethylpropyl, 3,3,3-trifluoropropyl, n-butyl, 2,2-difluorobutyl, 3,3-difluorobutyl, 3,3-dimethylbutyl, 3-cyano-3-methylbutyl and 4,4-dimethylpentyl.

13. The compound of claim 9, wherein $R^7$ is selected from the group consisting of cyclopropyl, spiro[2.2]pentyl, cyclohexylmethyl and 4-chlorobenzyl.

14. The compound of claim 1, wherein $R^1$ is $C_{3-12}$ cycloalkyl; 3- to 14-membered heterocyclyl; —($C_{1-6}$ alkylene)-(3- to 14-membered heterocyclyl), or —($C_{1-6}$ alkylene)-$NR^{1a}R^{1b}$; wherein the $C_{3-12}$ cycloalkyl, 3- to 14-membered heterocyclyl, and $C_{1-6}$ alkylene of $R^1$ are independently optionally substituted with 1, 2, 3, 4 or 5 substituents independently selected from $R^{10}$.

15. The compound of claim 14, wherein $R^1$ is selected from the group consisting of piperidin-3-yl, 5-fluoropiperidin-3-yl, 5-methylpiperidin-3-yl and 5-fluoro-5-methylpiperidin-3-yl.

16. The compound of claim 1, wherein the compound is of the Formula (Ia) or Formula (Ic):

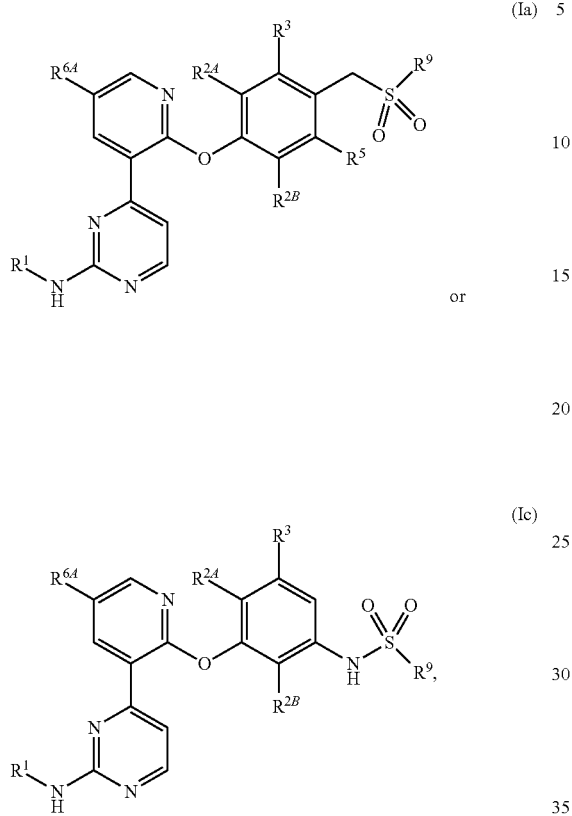

wherein $R^{6A}$ is hydrogen or $R^6$; and $R^1$, $R^{2A}$, $R^{2B}$, $R^3$, $R^5$, $R^6$ and $R^9$ are as defined in claim 1.

17. The compound of claim 1, wherein the compound is of the Formula (Ie):

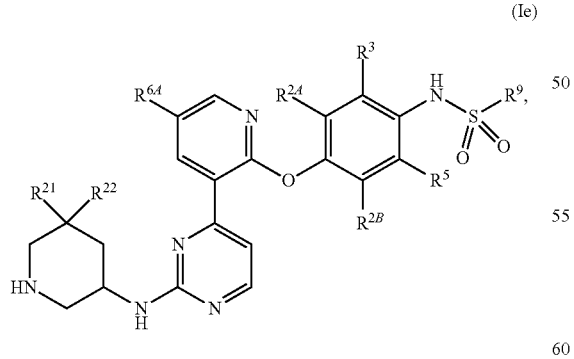

wherein $R^{6A}$ is hydrogen or $R^6$; $R^{21}$ and $R^{22}$ are independently H, F, —CH$_3$ or —NH$_2$, and $R^{2A}$, $R^{2B}$, $R^3$, $R^5$, $R^6$ and $R^9$ are as defined in claim 1.

18. The compound of claim 17, wherein the compound is of the Formula (Ie-1), (Ie-2), (Ie-3), (Ie-4), (Ie-5), (Ie-6) or (Ie-7):

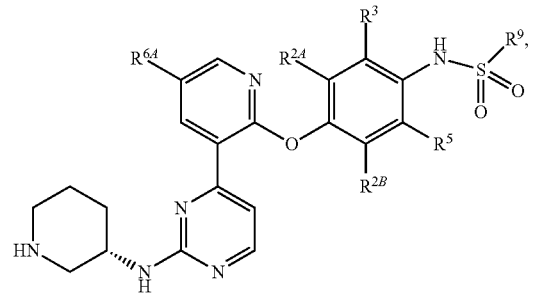

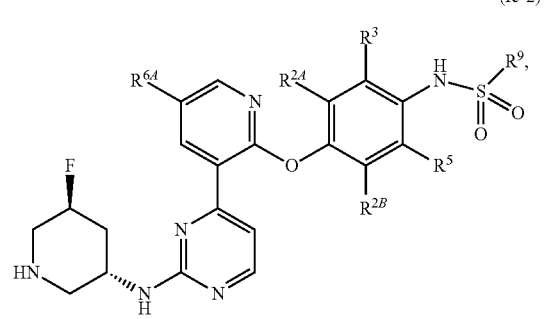

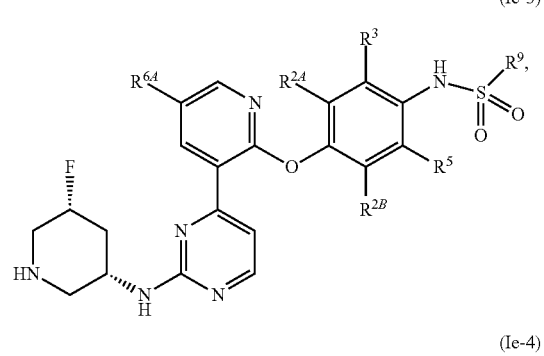

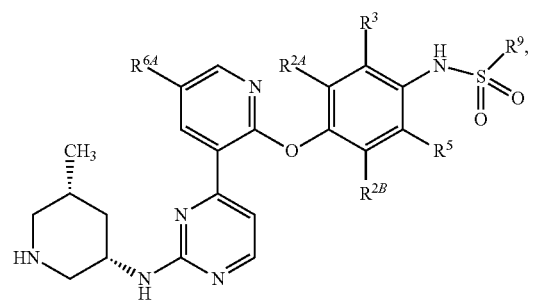

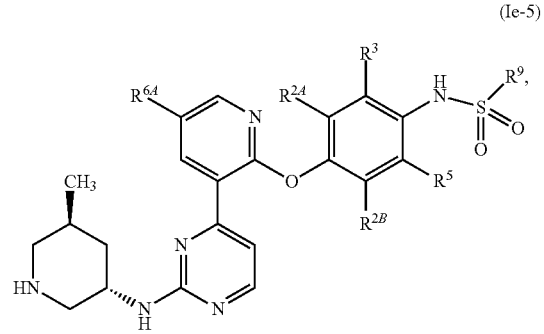

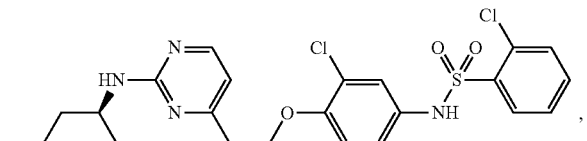
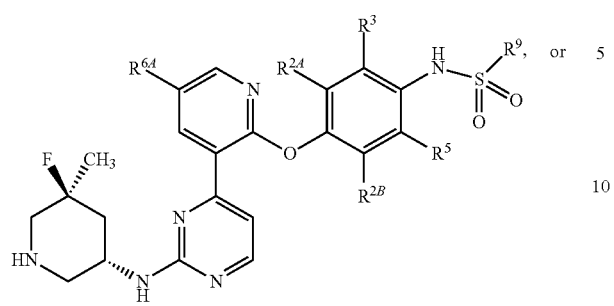
19. The compound of claim 1, wherein the compound is selected from the group consisting of
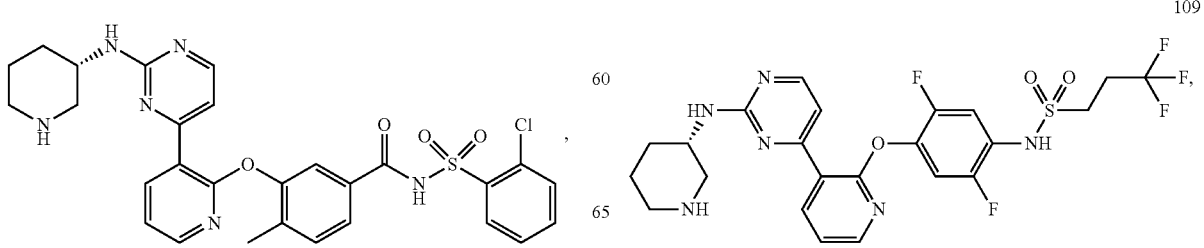

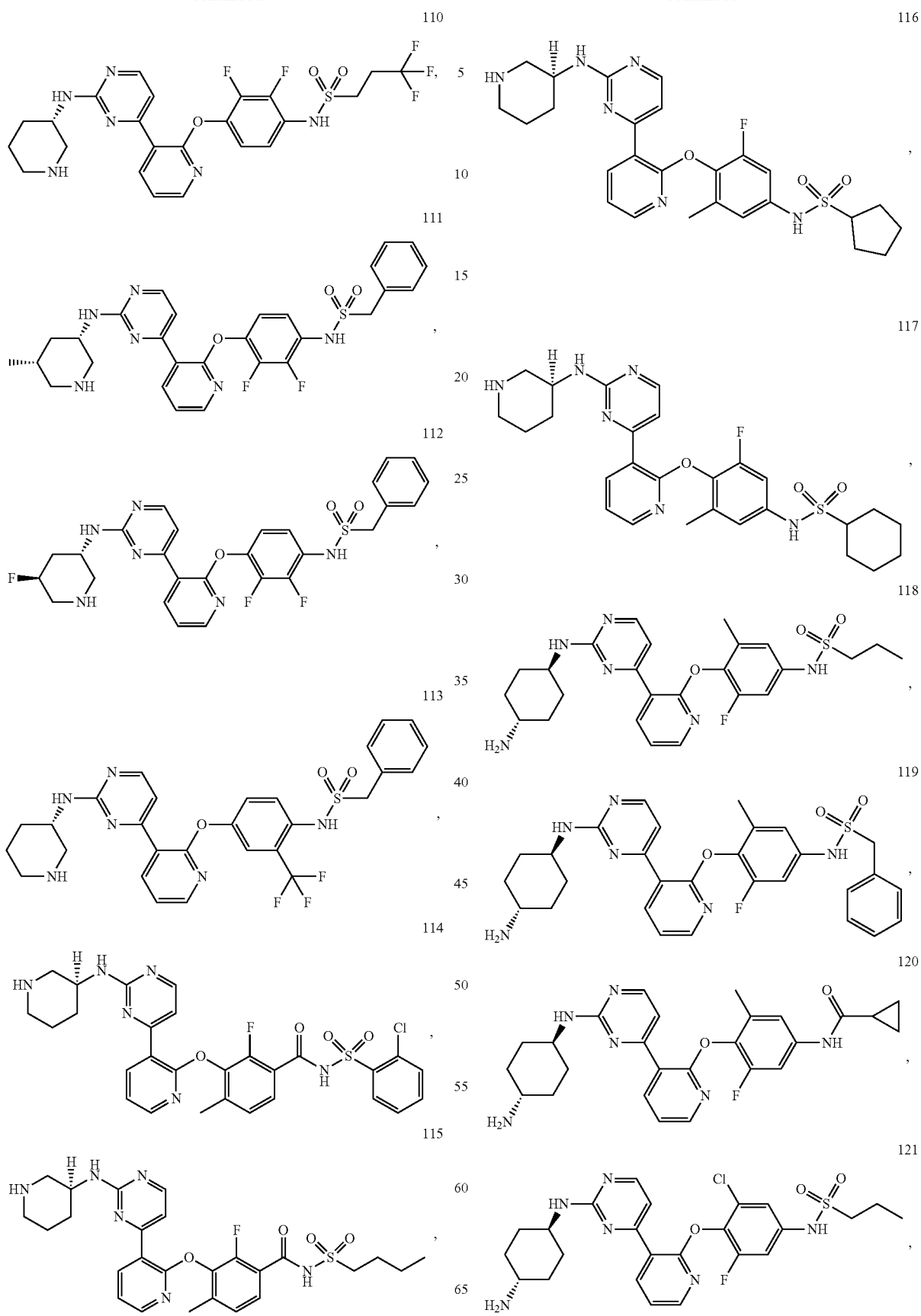

122
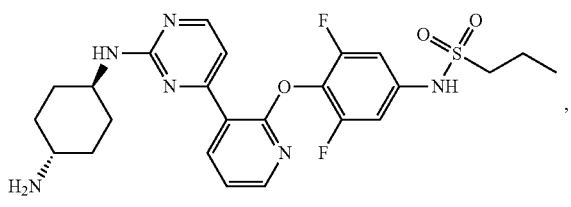
127
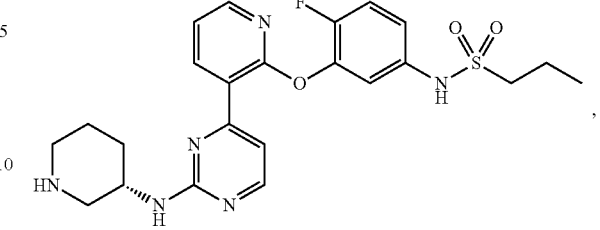
123
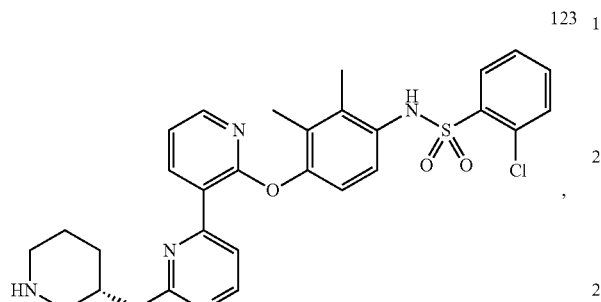
128
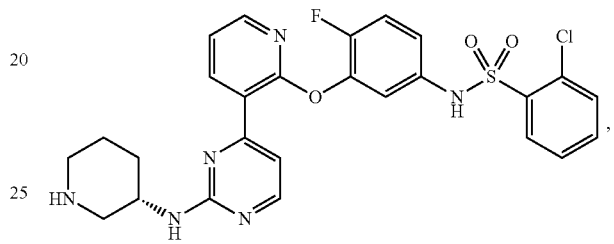
124
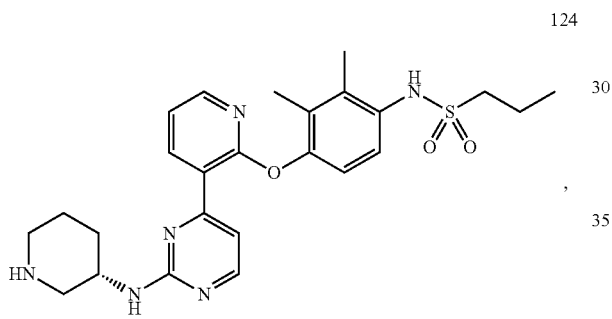
129
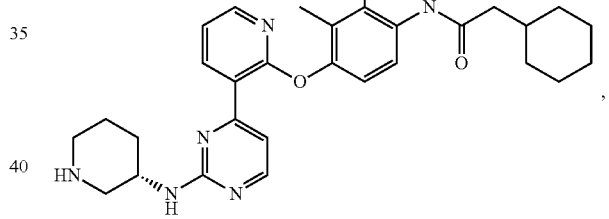
125
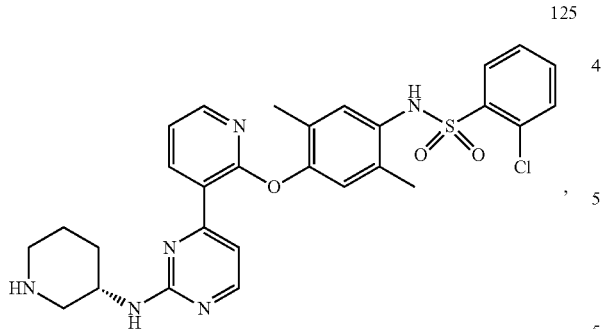
130
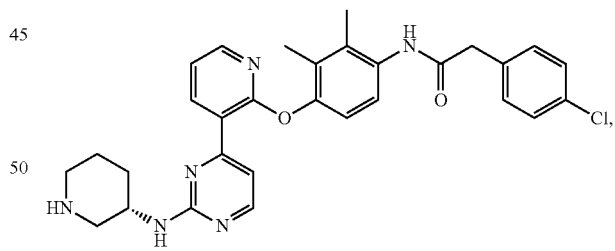
126
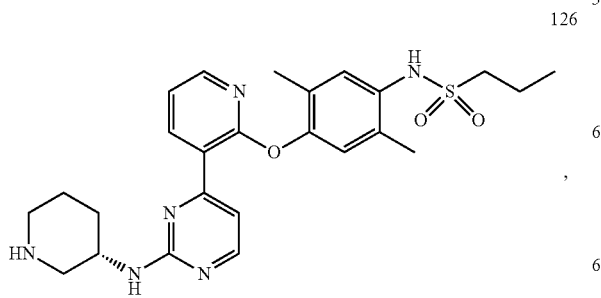
131
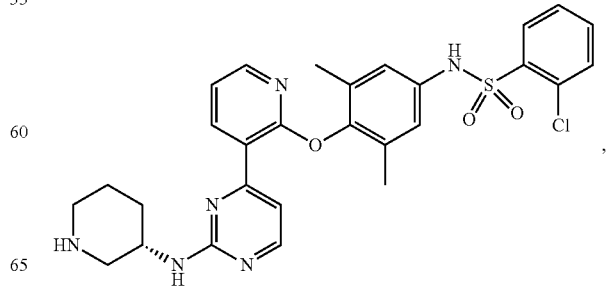

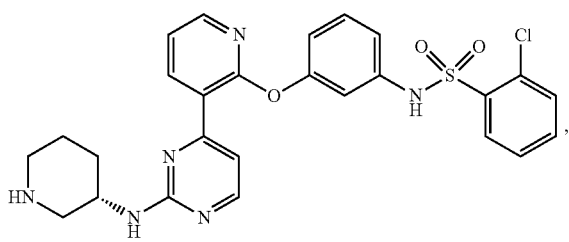
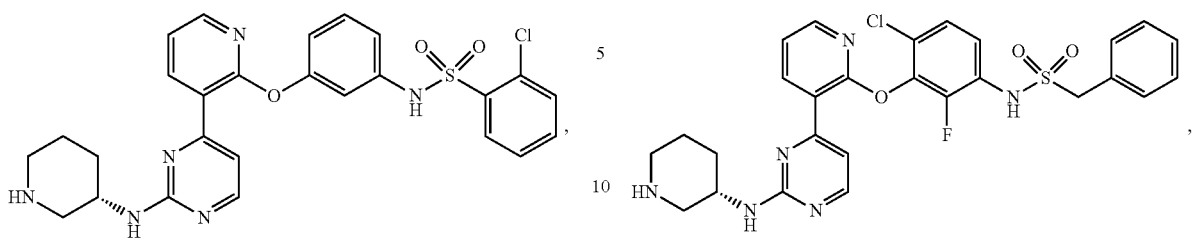
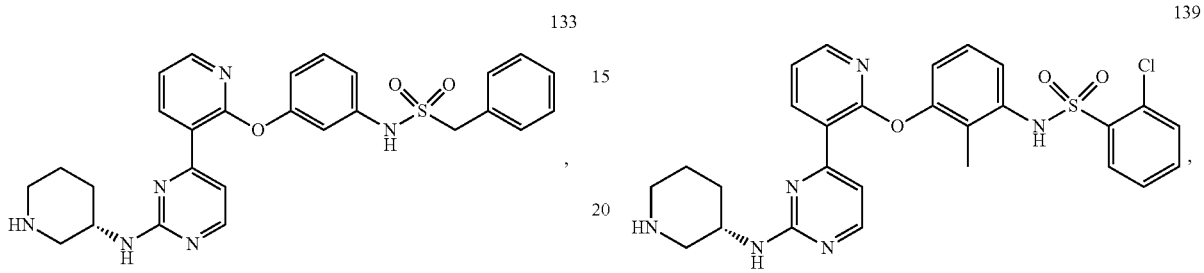
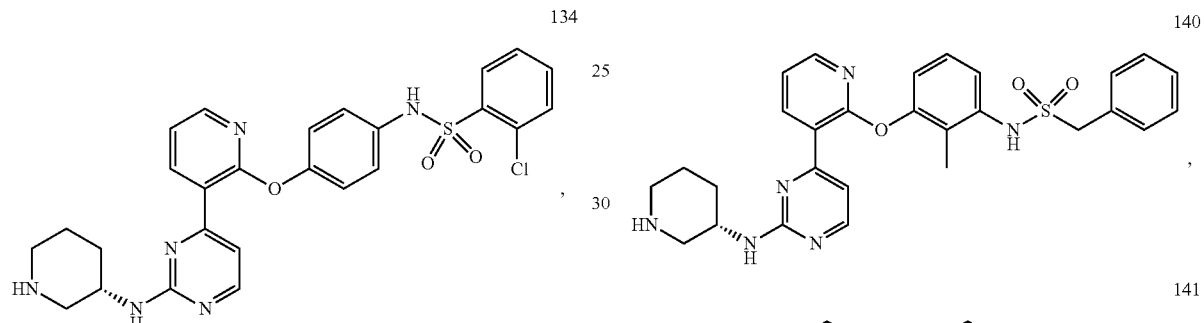
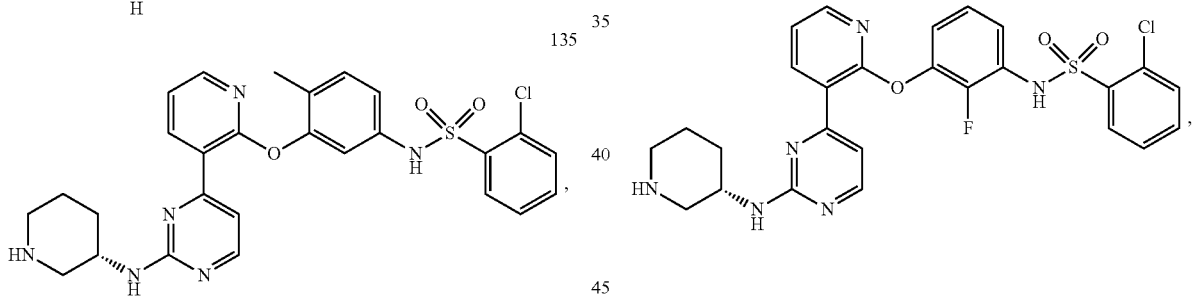
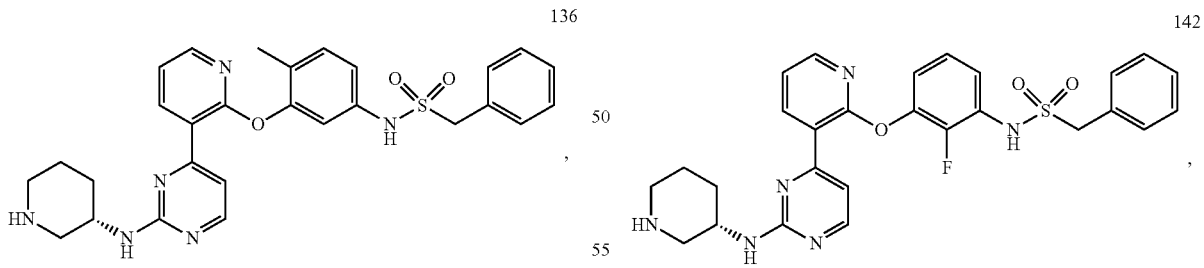
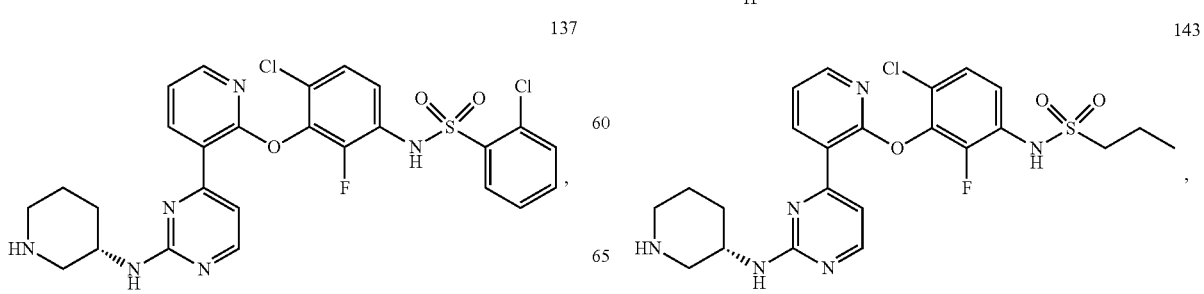

144
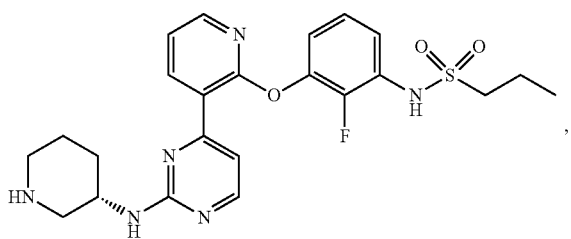
145
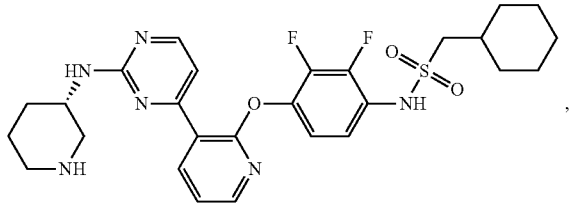
146
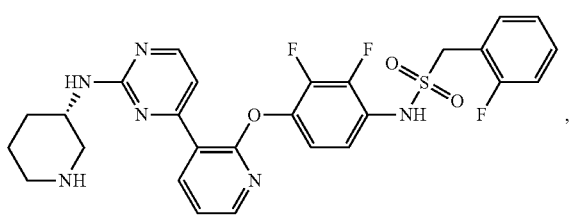
147
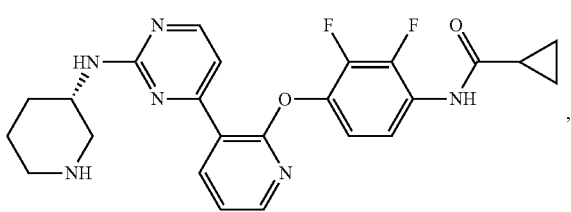
148
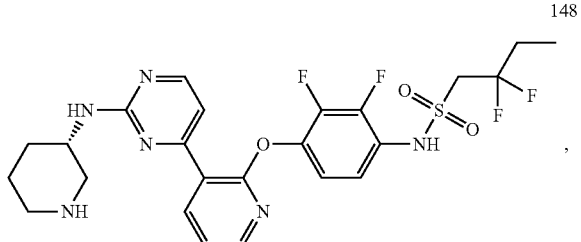
149
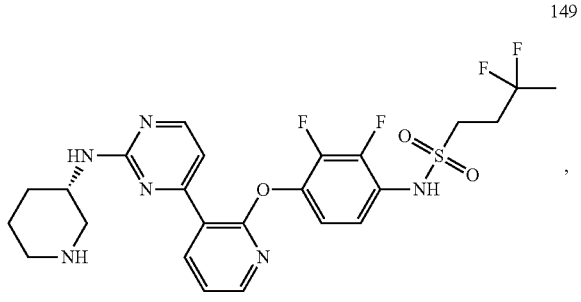
150
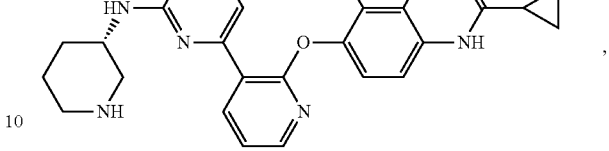
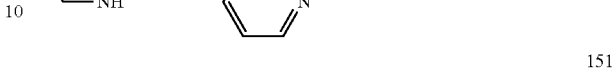
151
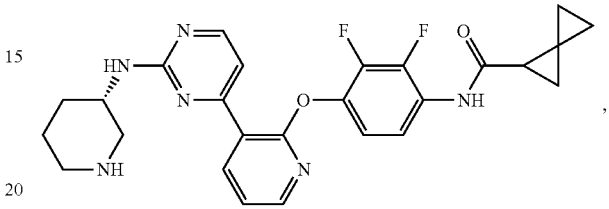
152
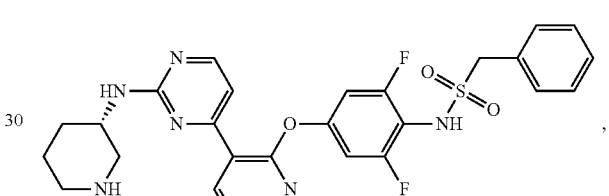
153
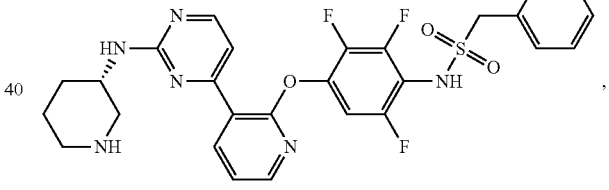
154
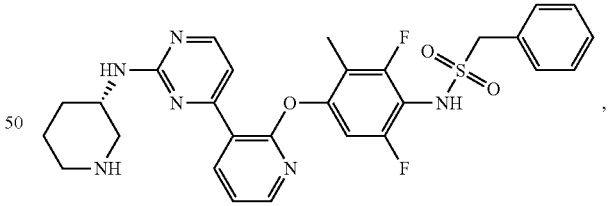
155
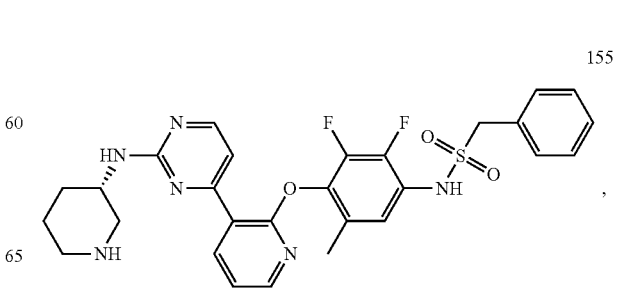

-continued
156
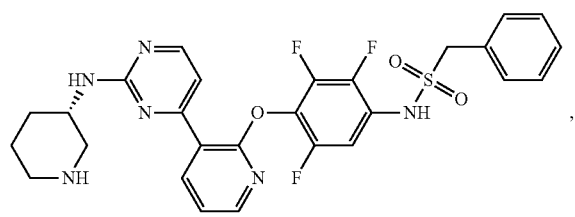,
157
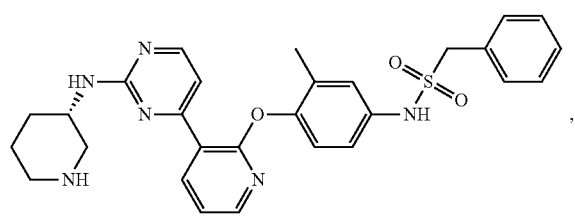,
158
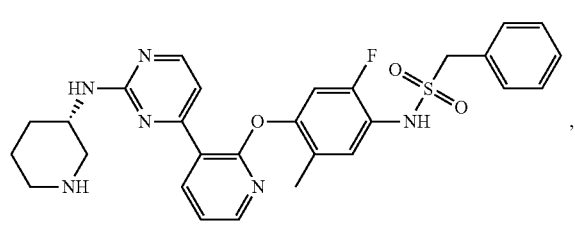,
159
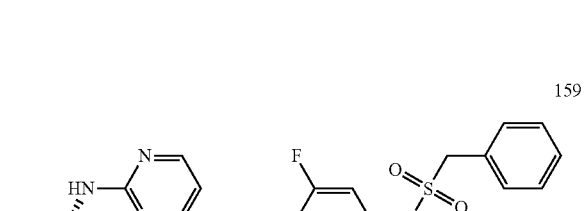,
160
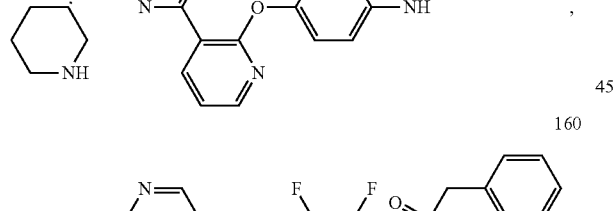,
161
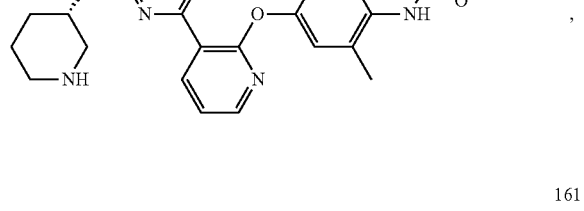,
-continued
162
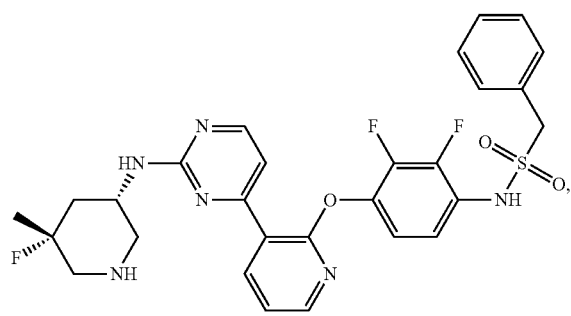,
163
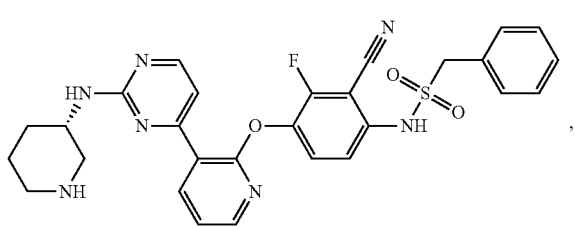,
164
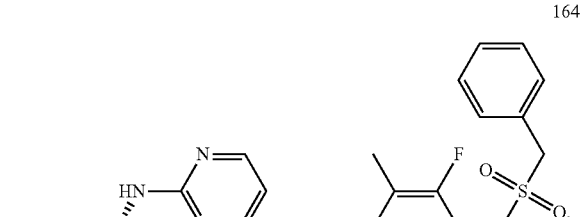,
165
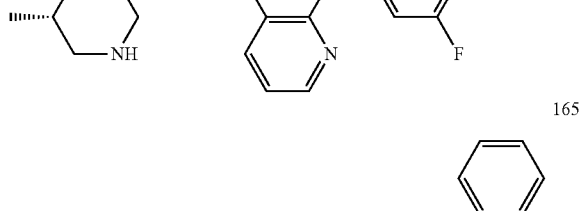,
166
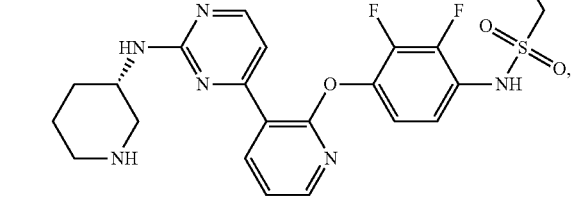

167
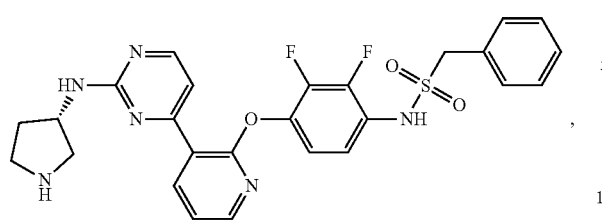
168
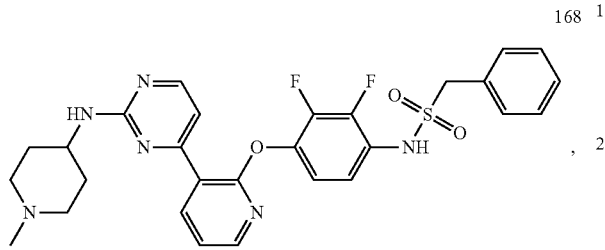
169
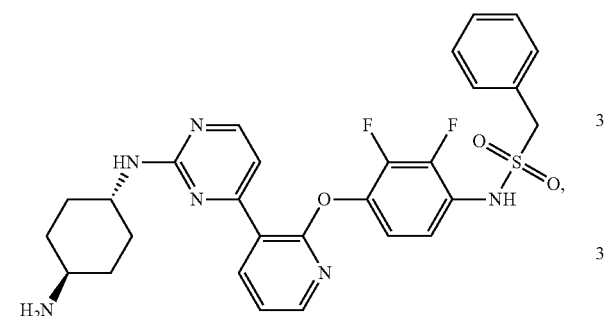
170
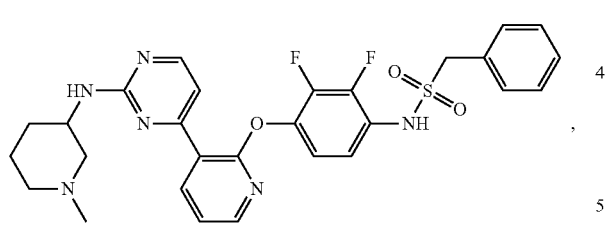
171
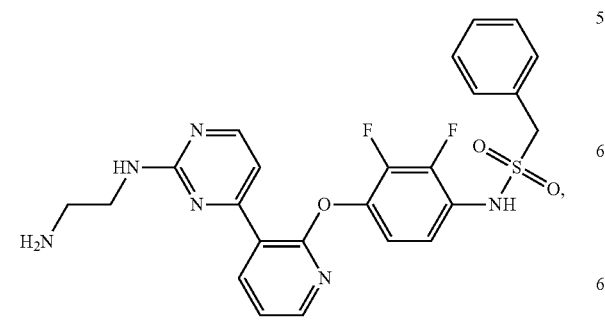
172
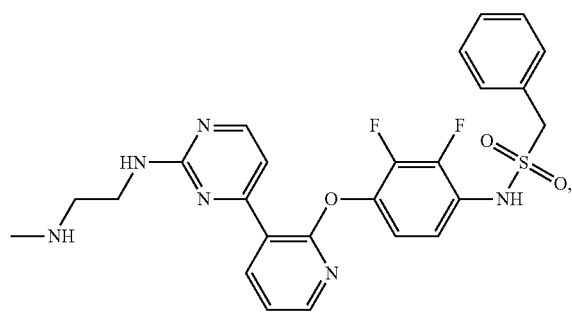
173
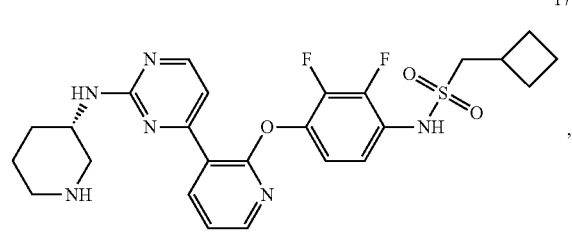
174
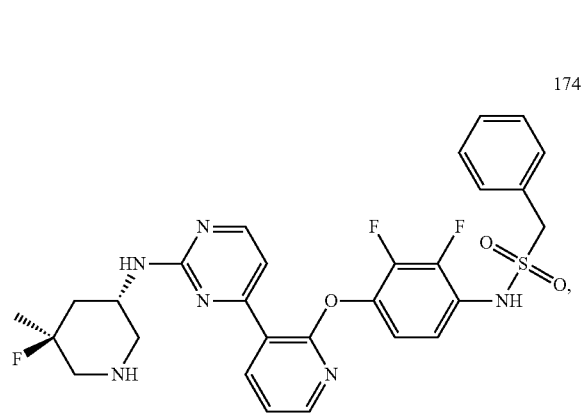
175
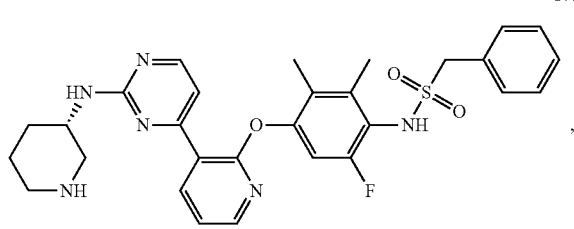
176
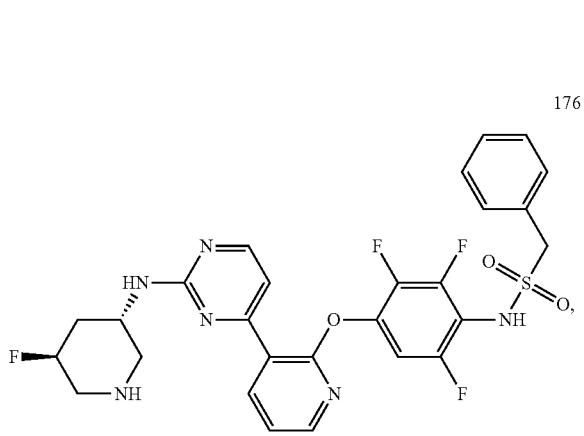

-continued
177
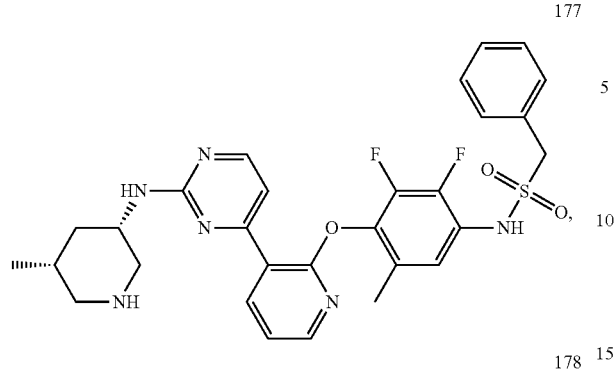
178
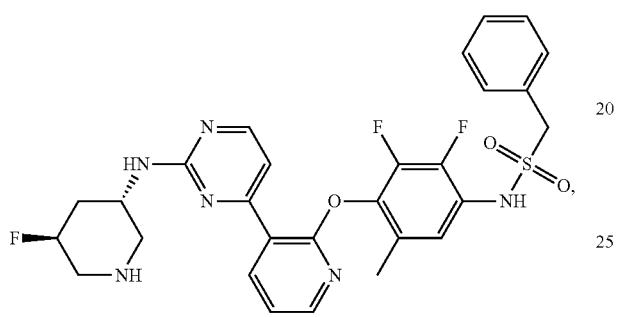
179
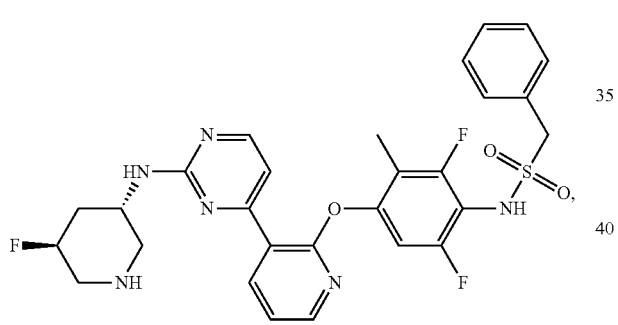
180
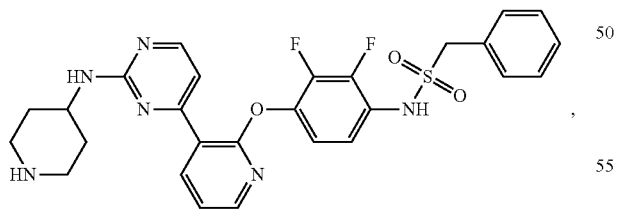
181
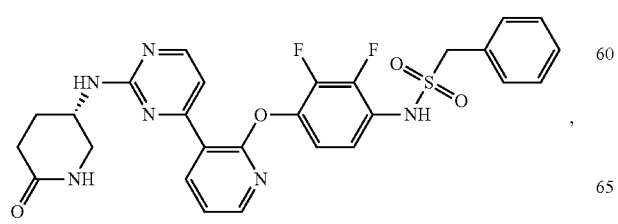
-continued
182
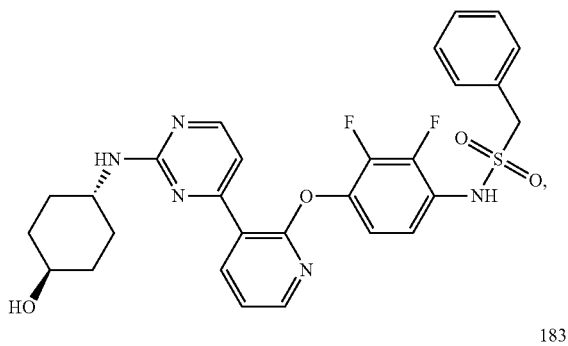
183
184
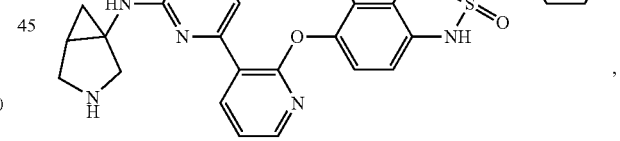
185
186
187
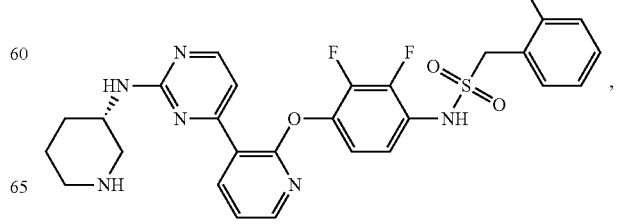

473
-continued
188
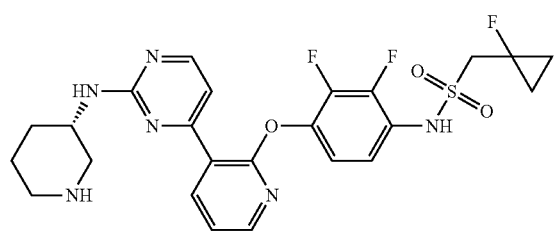
189
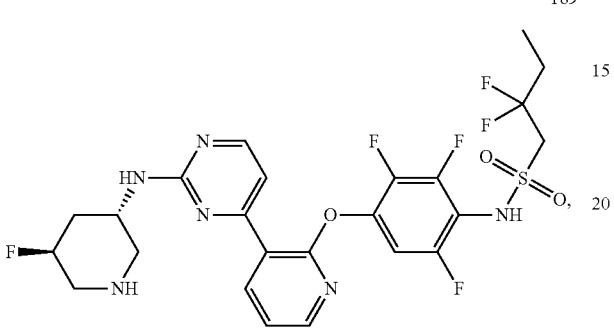
190
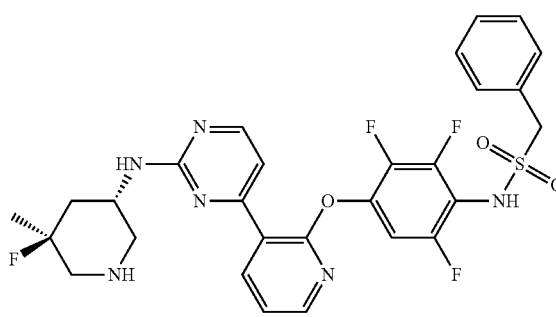
191
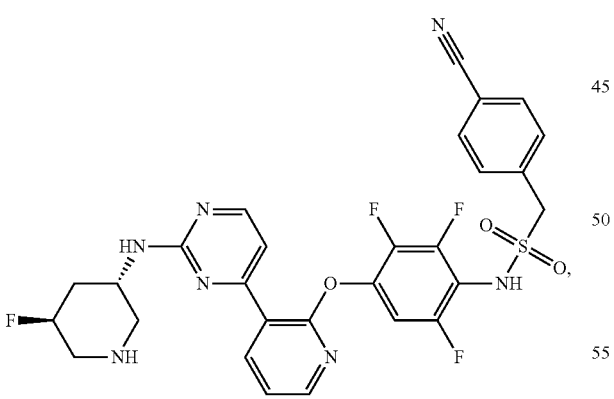
192
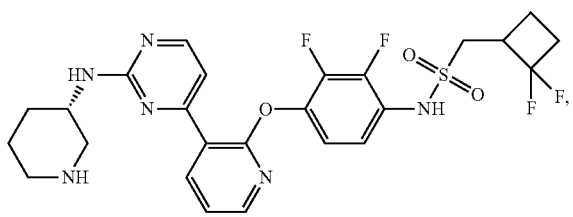
474
-continued
193
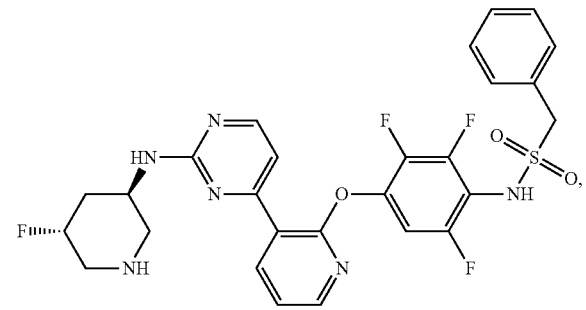
194
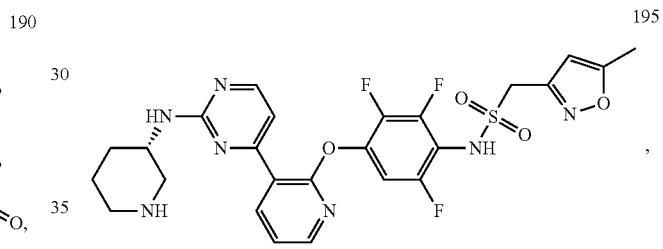
195
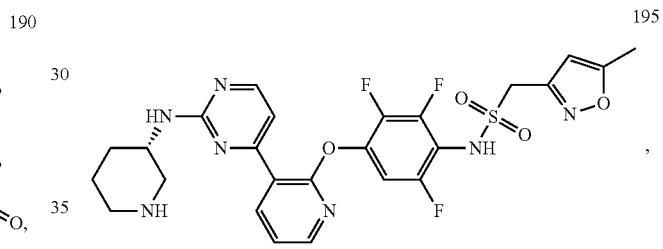
196
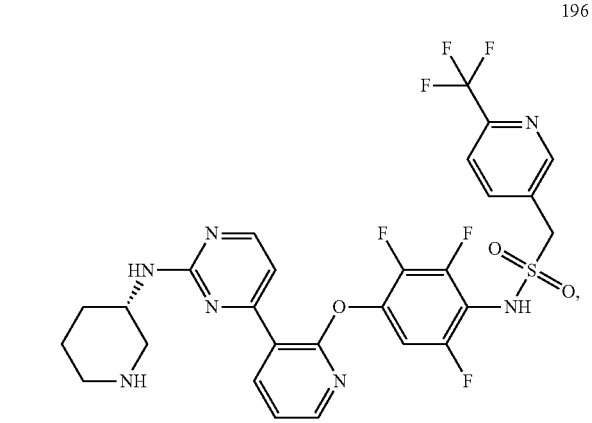
197
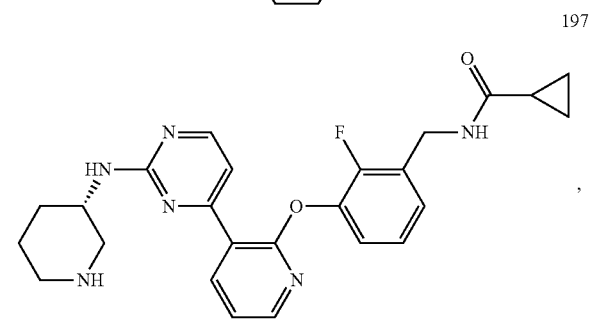

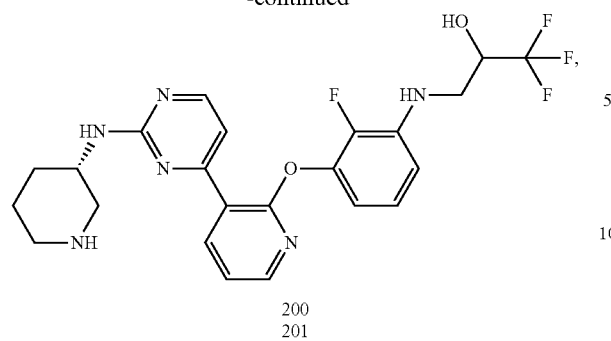
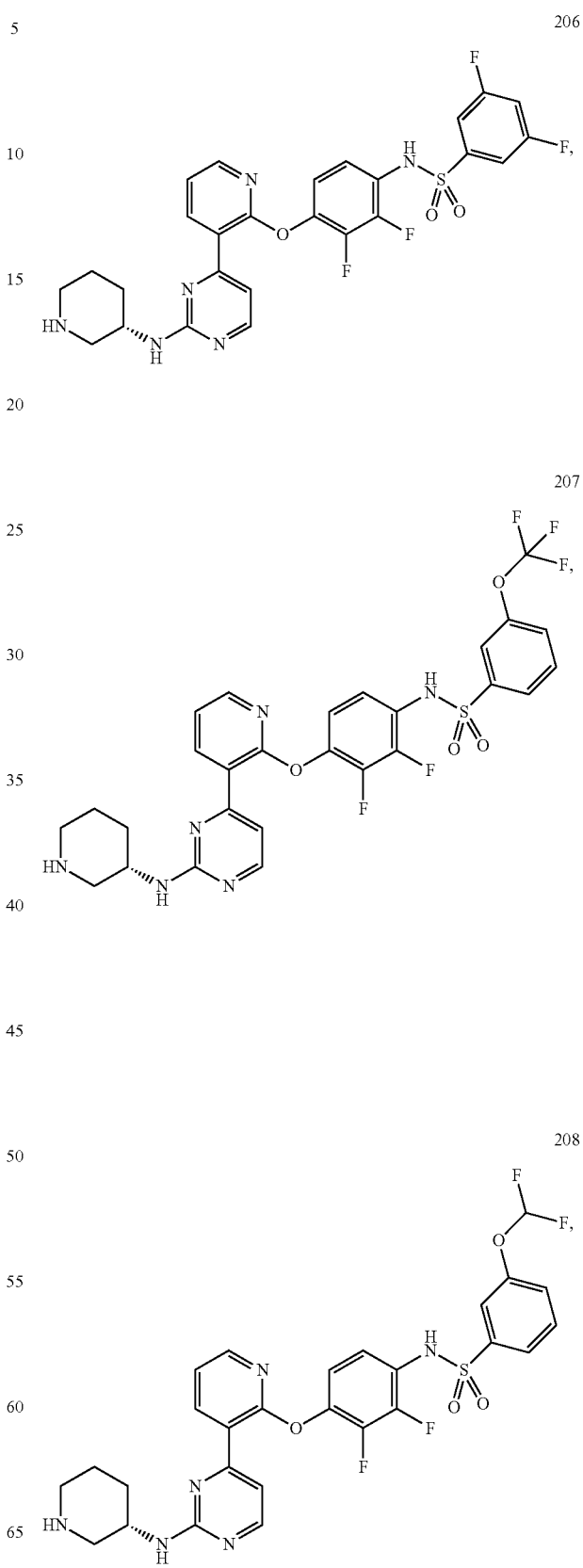

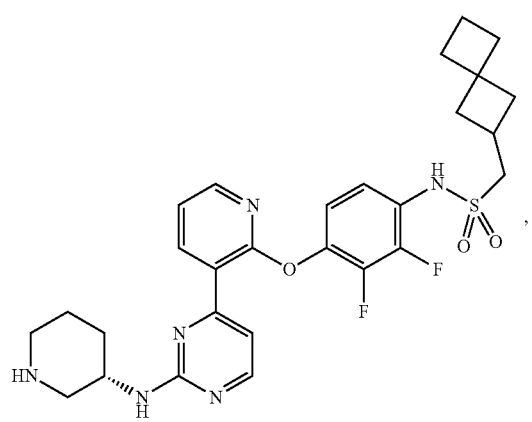
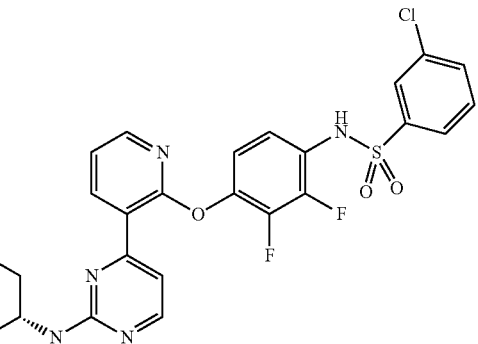
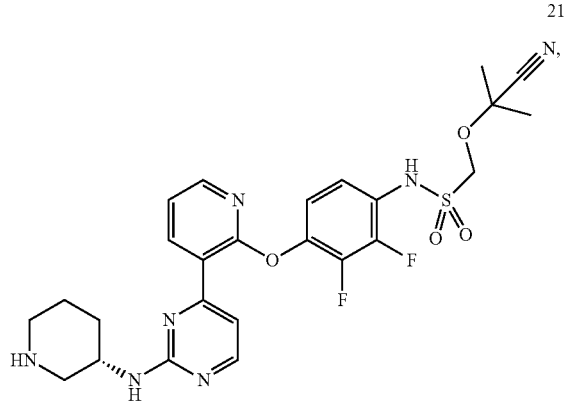
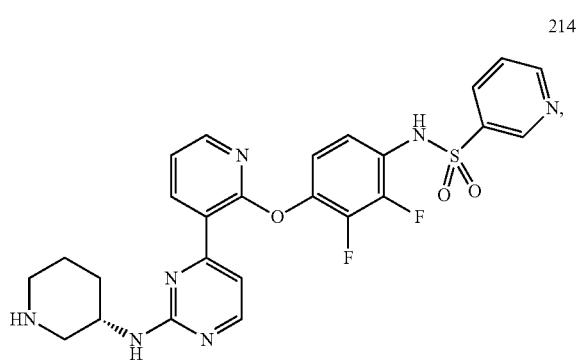
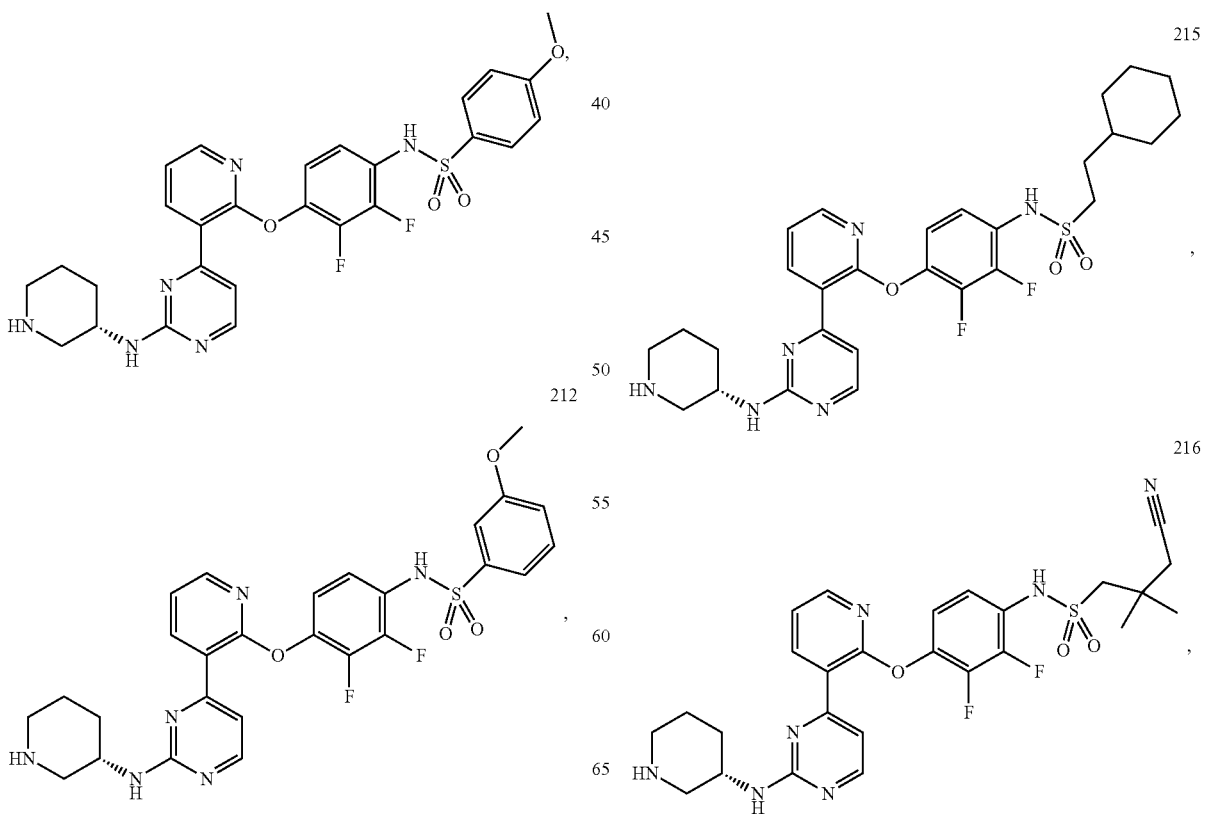

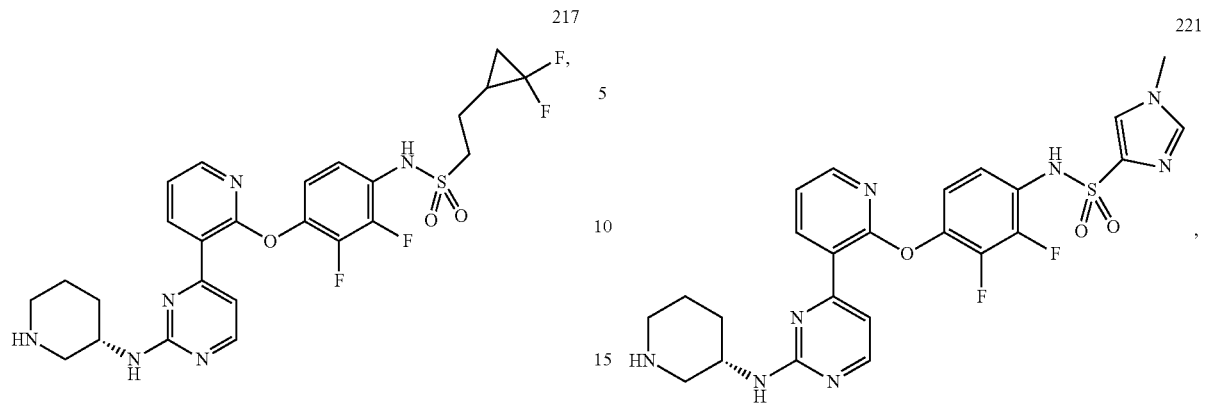
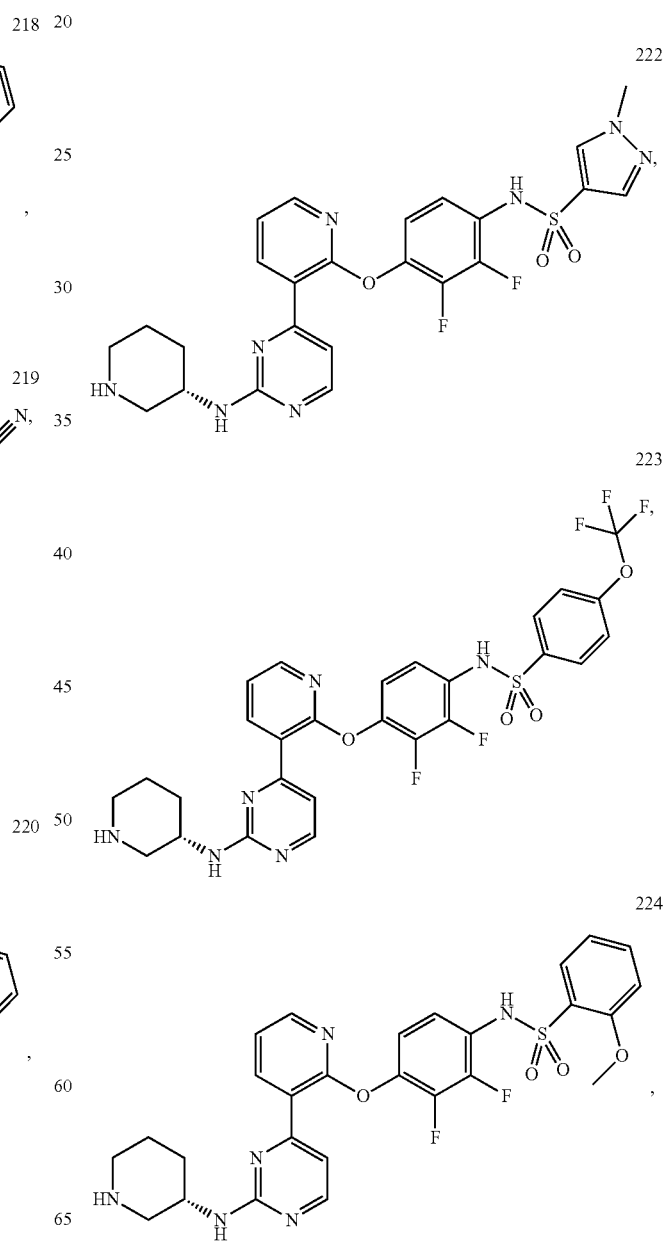

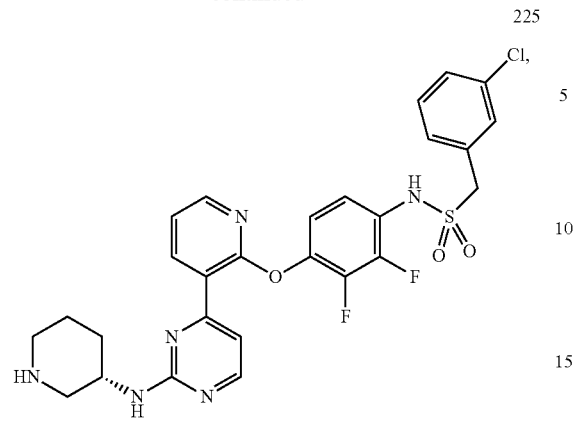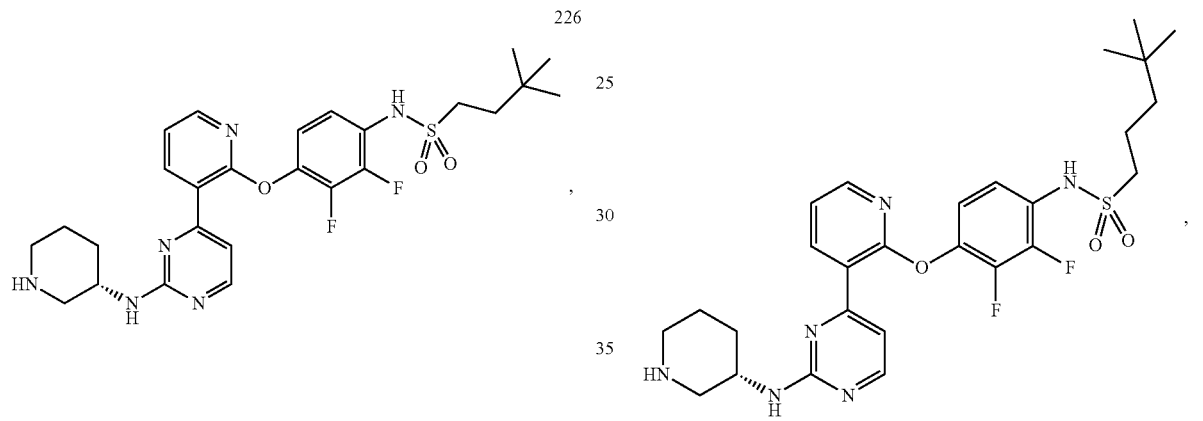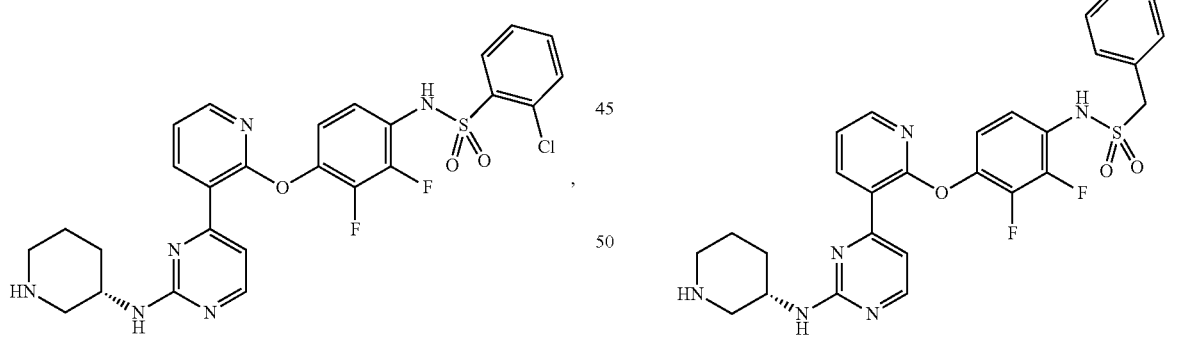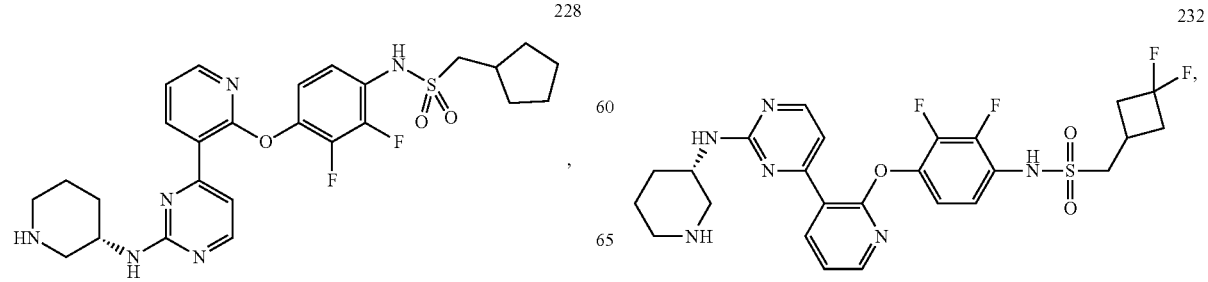

233
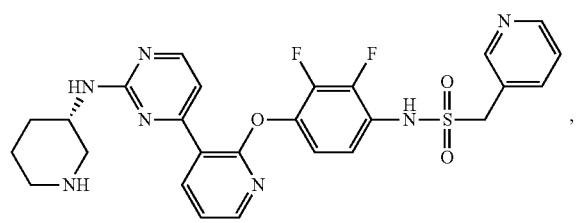
234
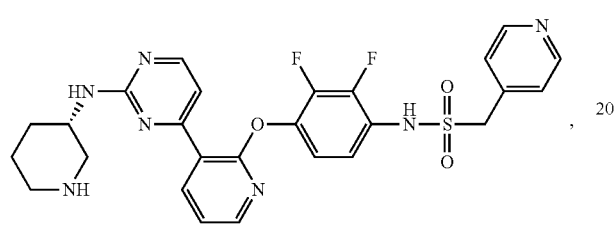
235
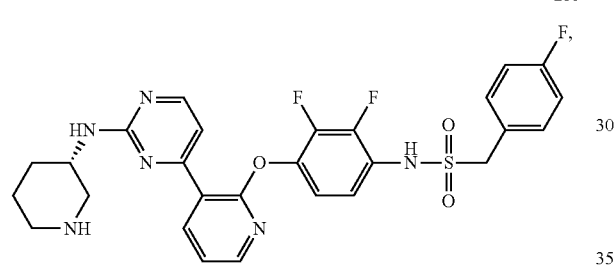
236
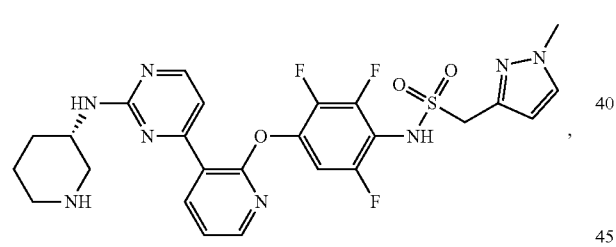
237
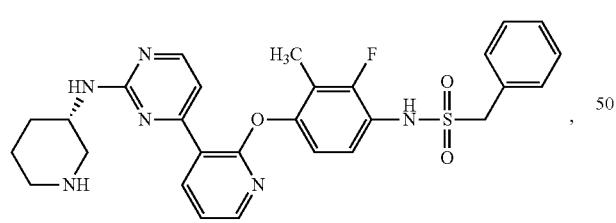
238
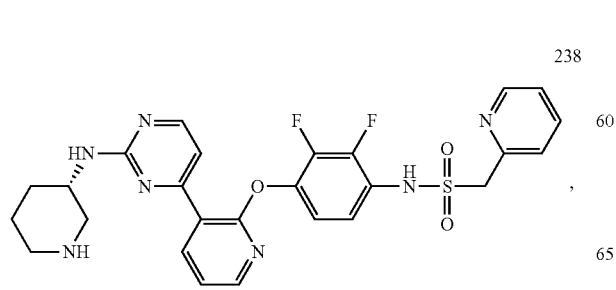
239
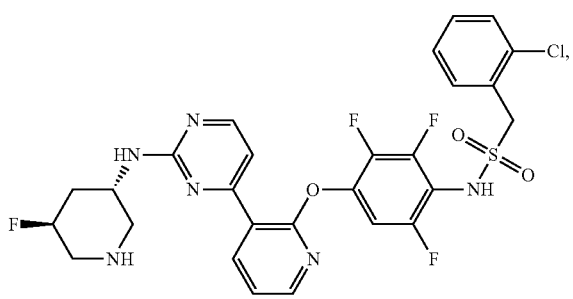 [SMILES: Cc1ccccc1CS(=O)(=O)Nc1c(F)cc(Oc2ncccc2-c2ccnc(N[C@@H]3CNC[C@@H](F)C3)n2)c(F)c1F]
240
241
242
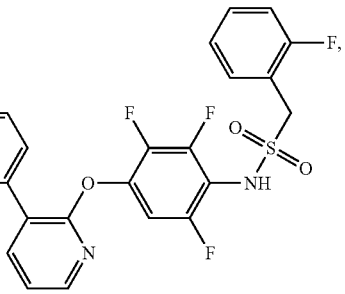

243
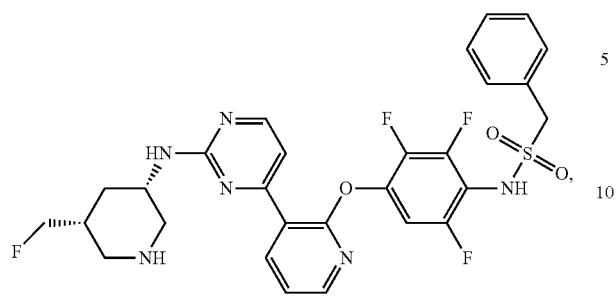
244
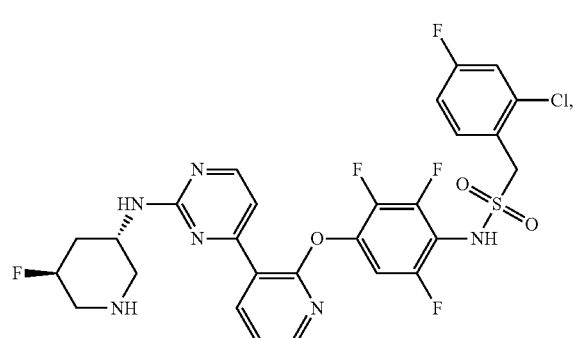
245
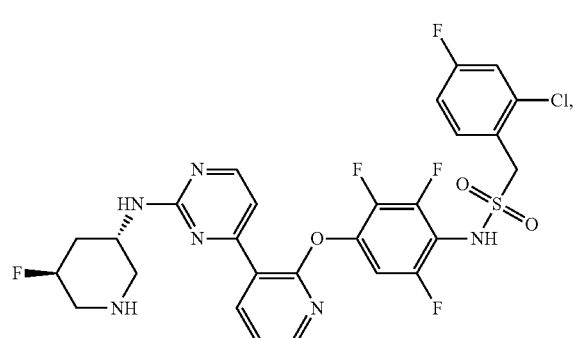
246
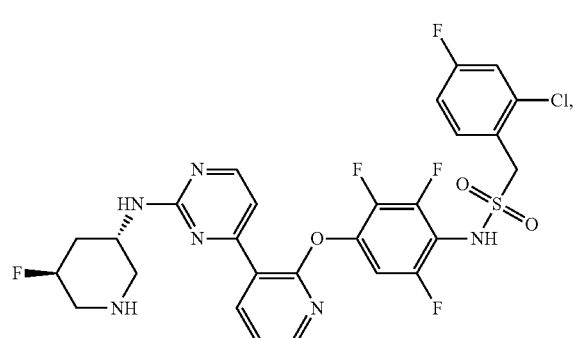
247
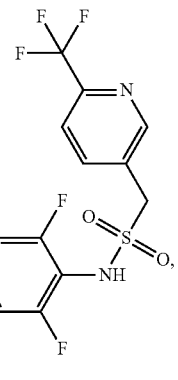
or a pharmaceutically acceptable salt thereof, or,
101
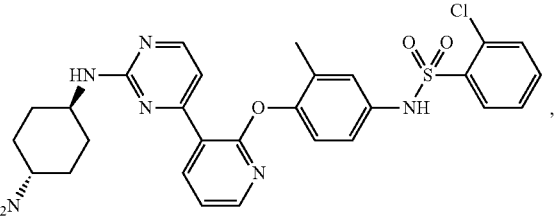
102
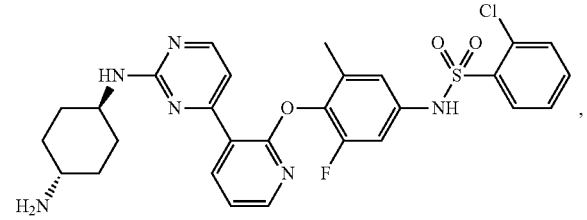
103
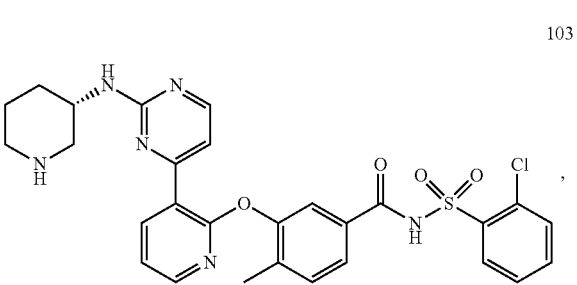
104
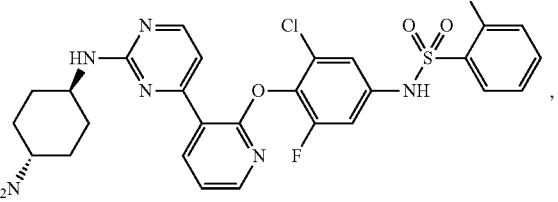

487
-continued
488
-continued
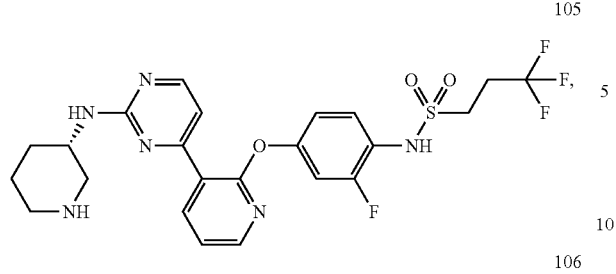
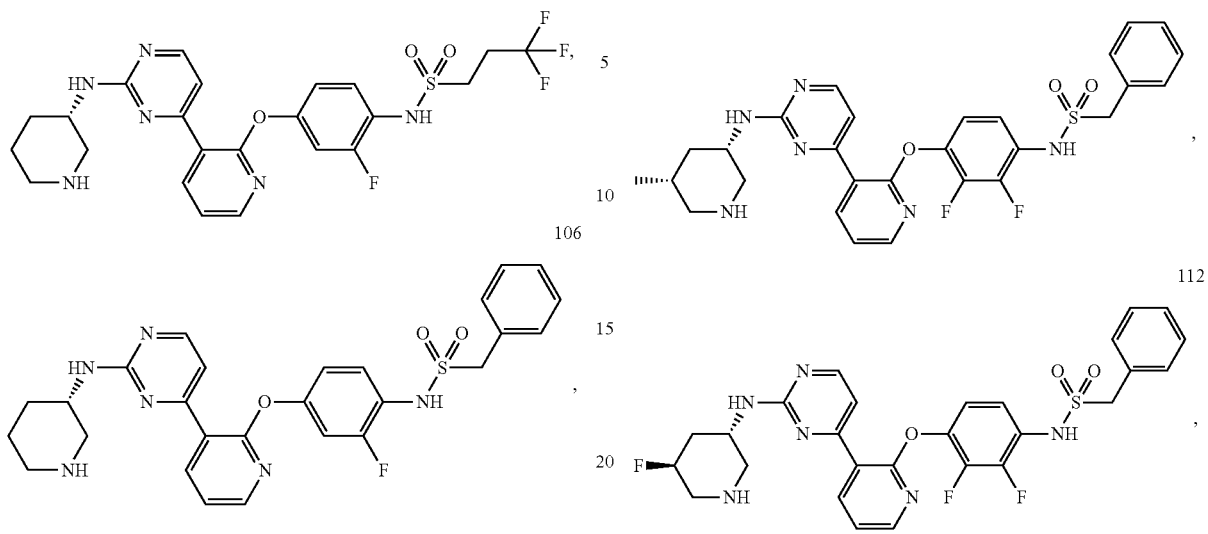
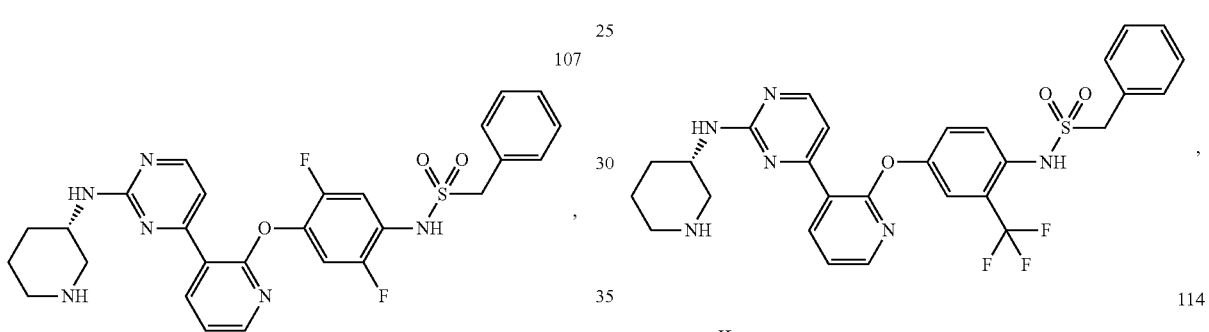
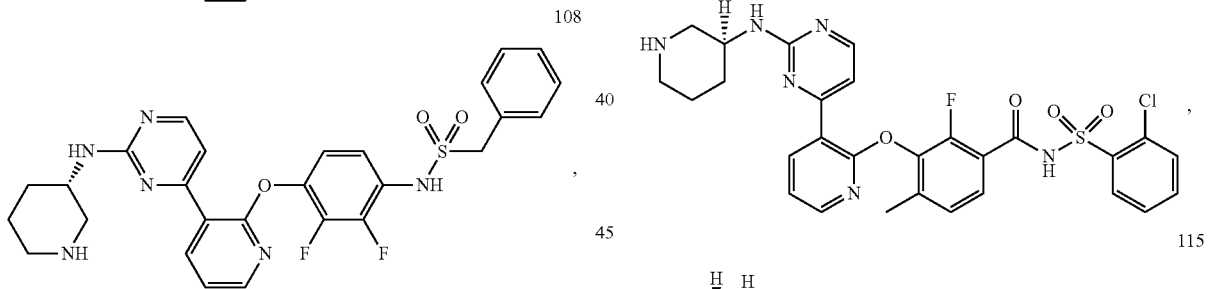
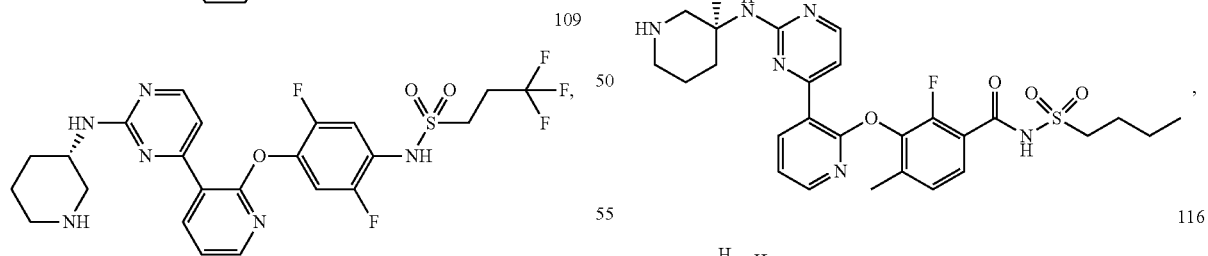
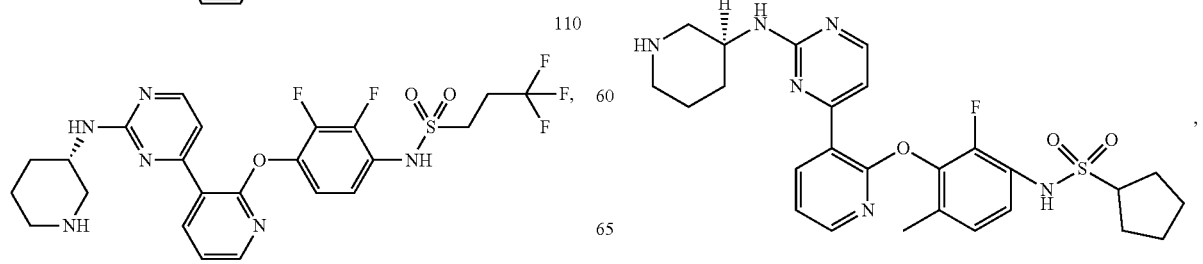

489
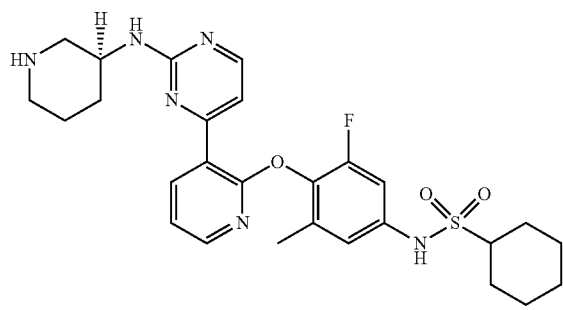
117
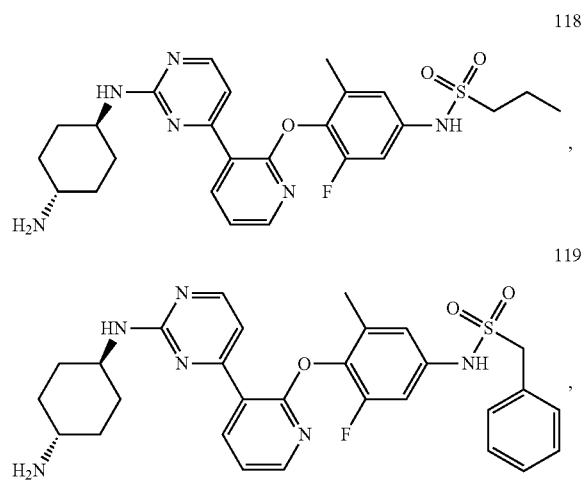
118
119
120
121
122
490
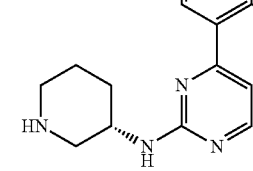
123
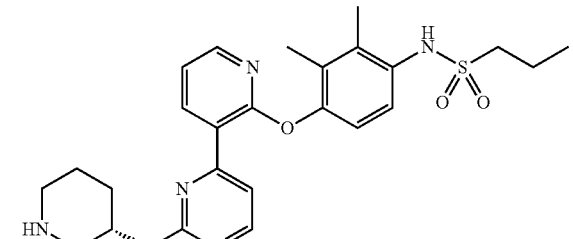
124
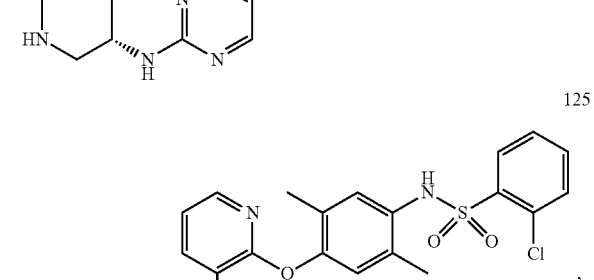
125
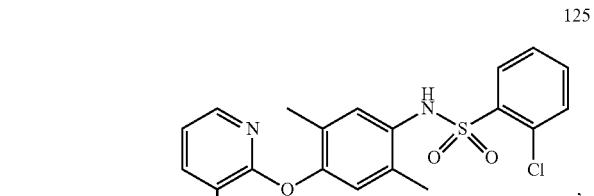
126
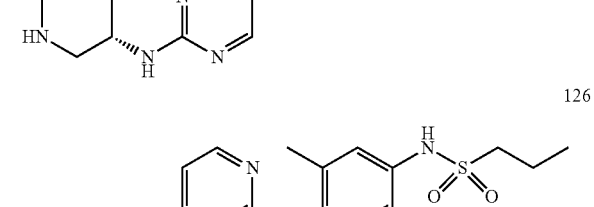
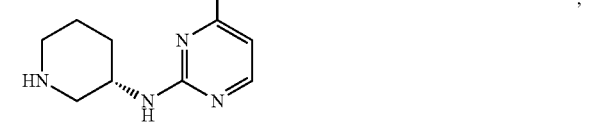
127
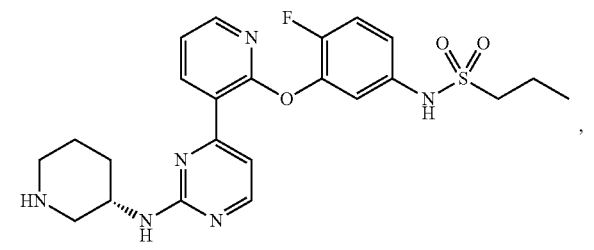

128
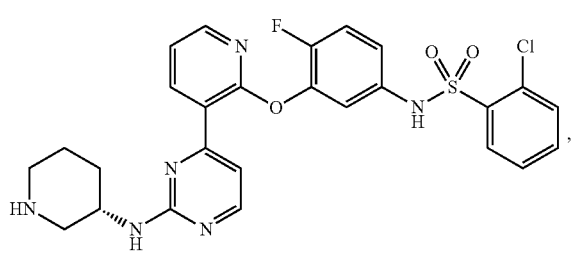
129
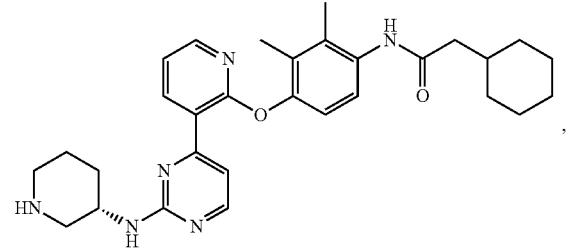
130
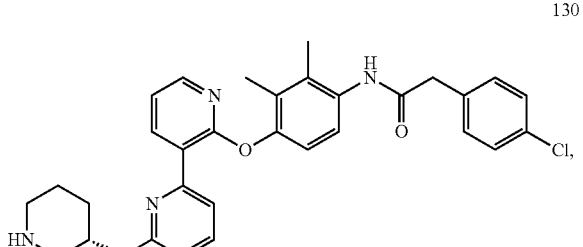
131
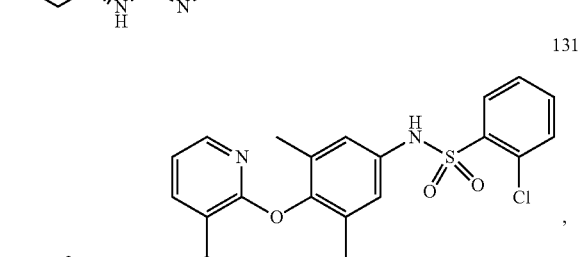
132
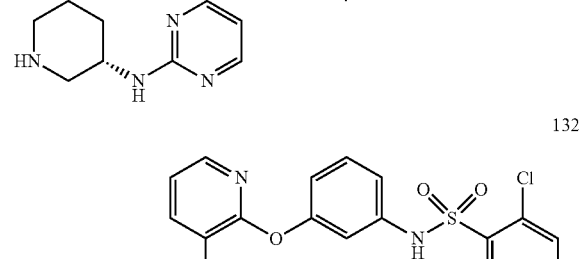
133
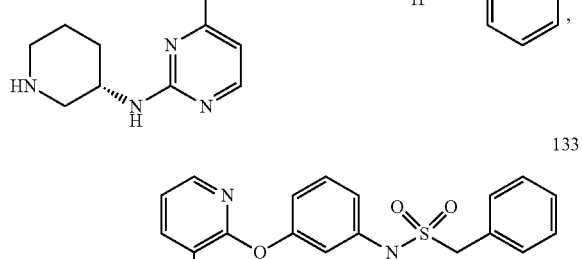
134
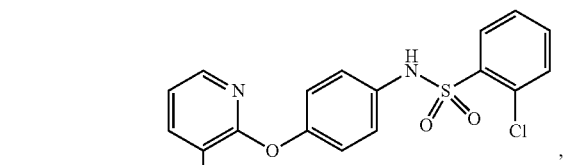
135
136
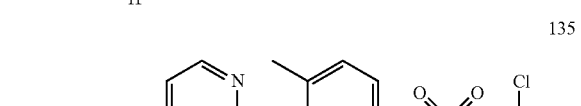
137
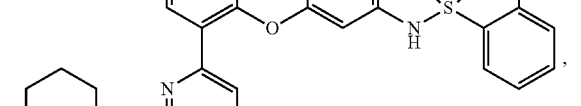
138
139
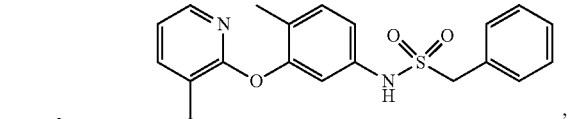

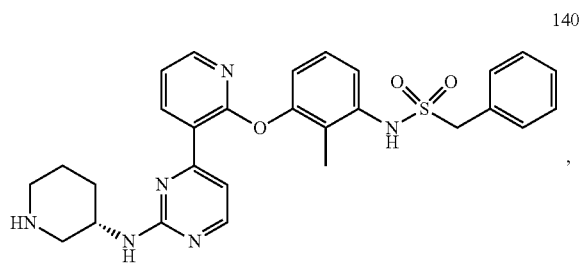
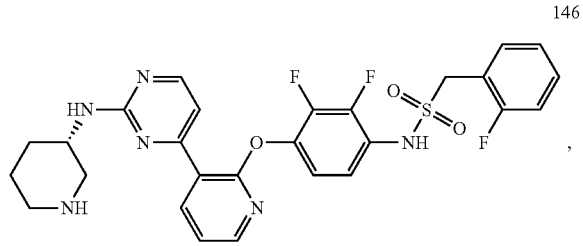

152 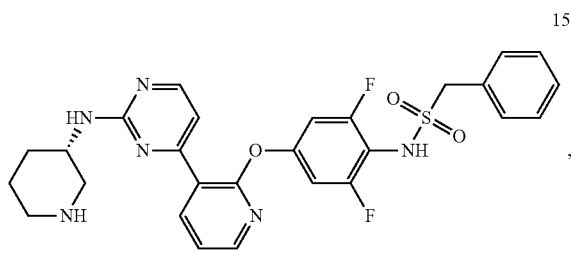,
153 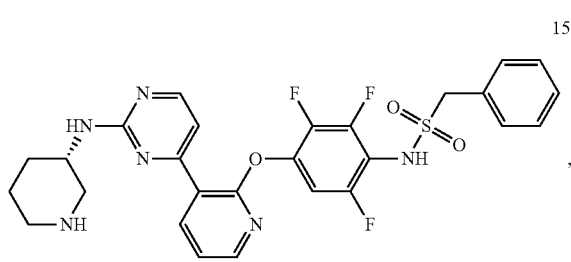,
154 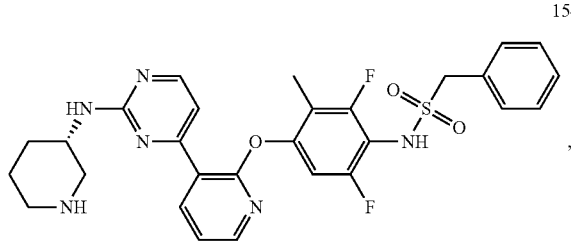,
155 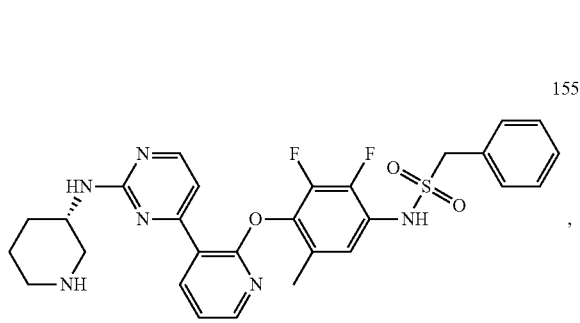,
156 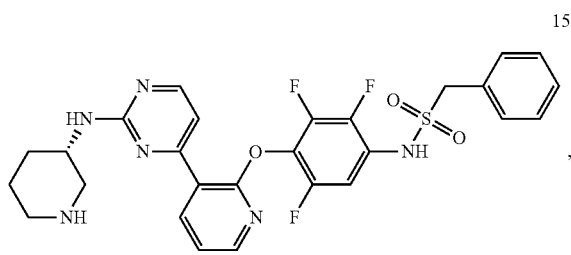,
157 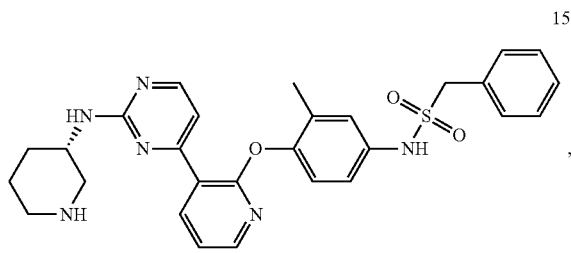,
158 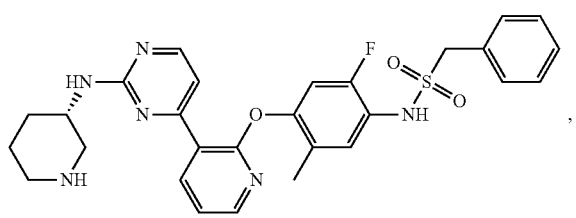,
159 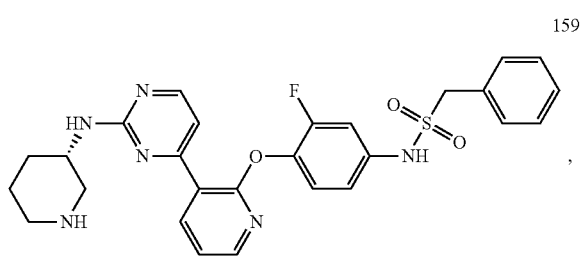,
160 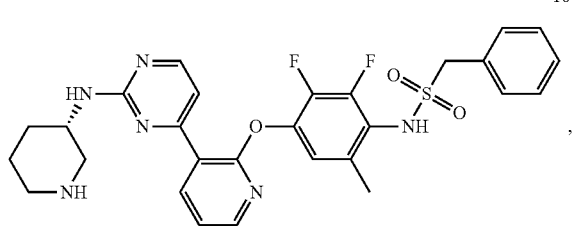,
161 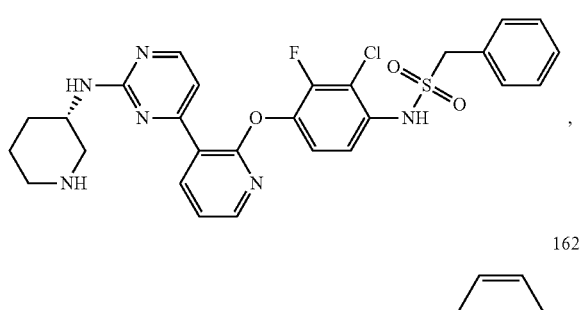,
162 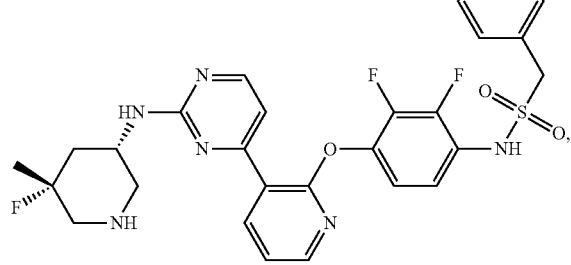,
163 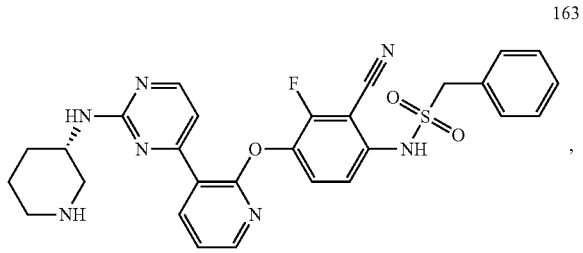,

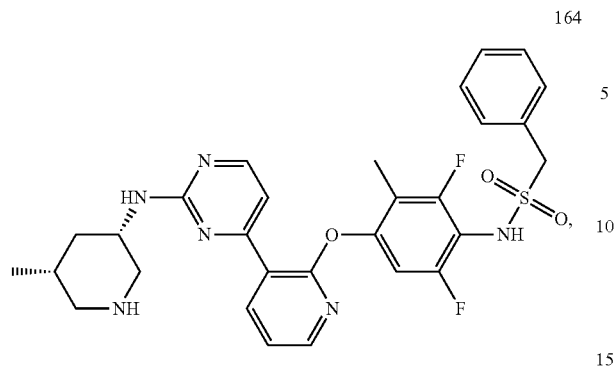
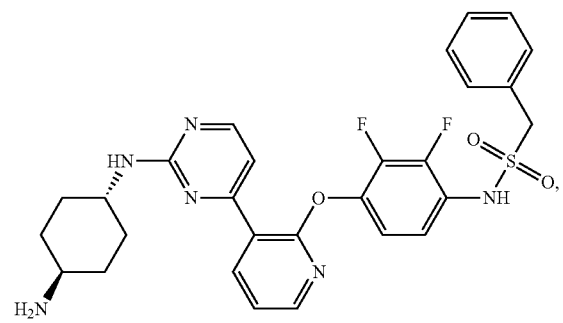
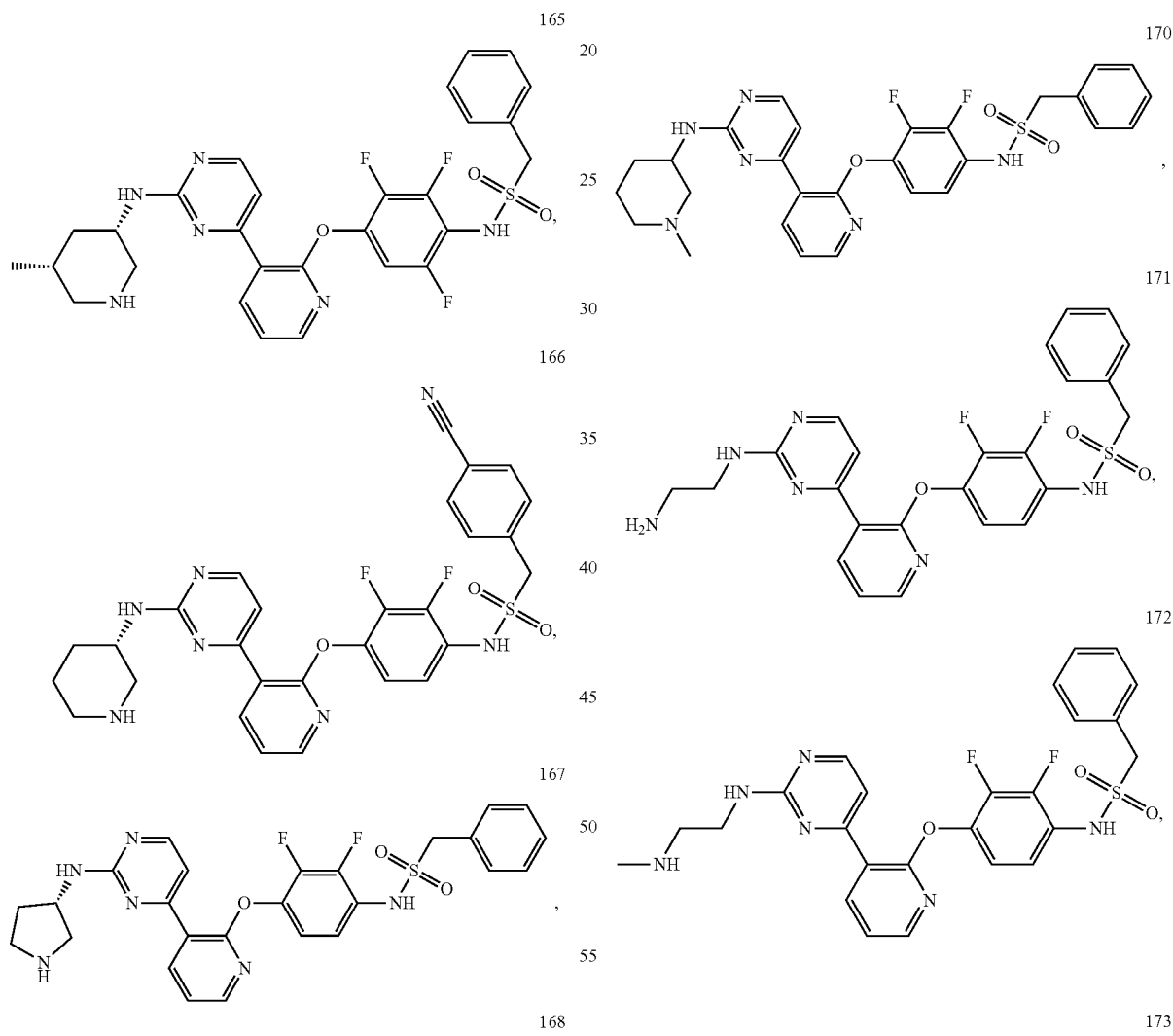
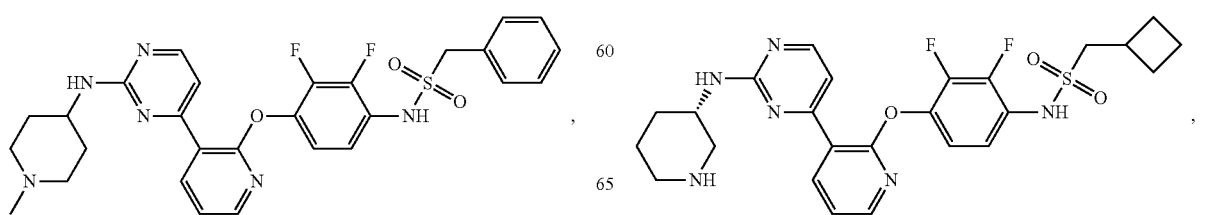

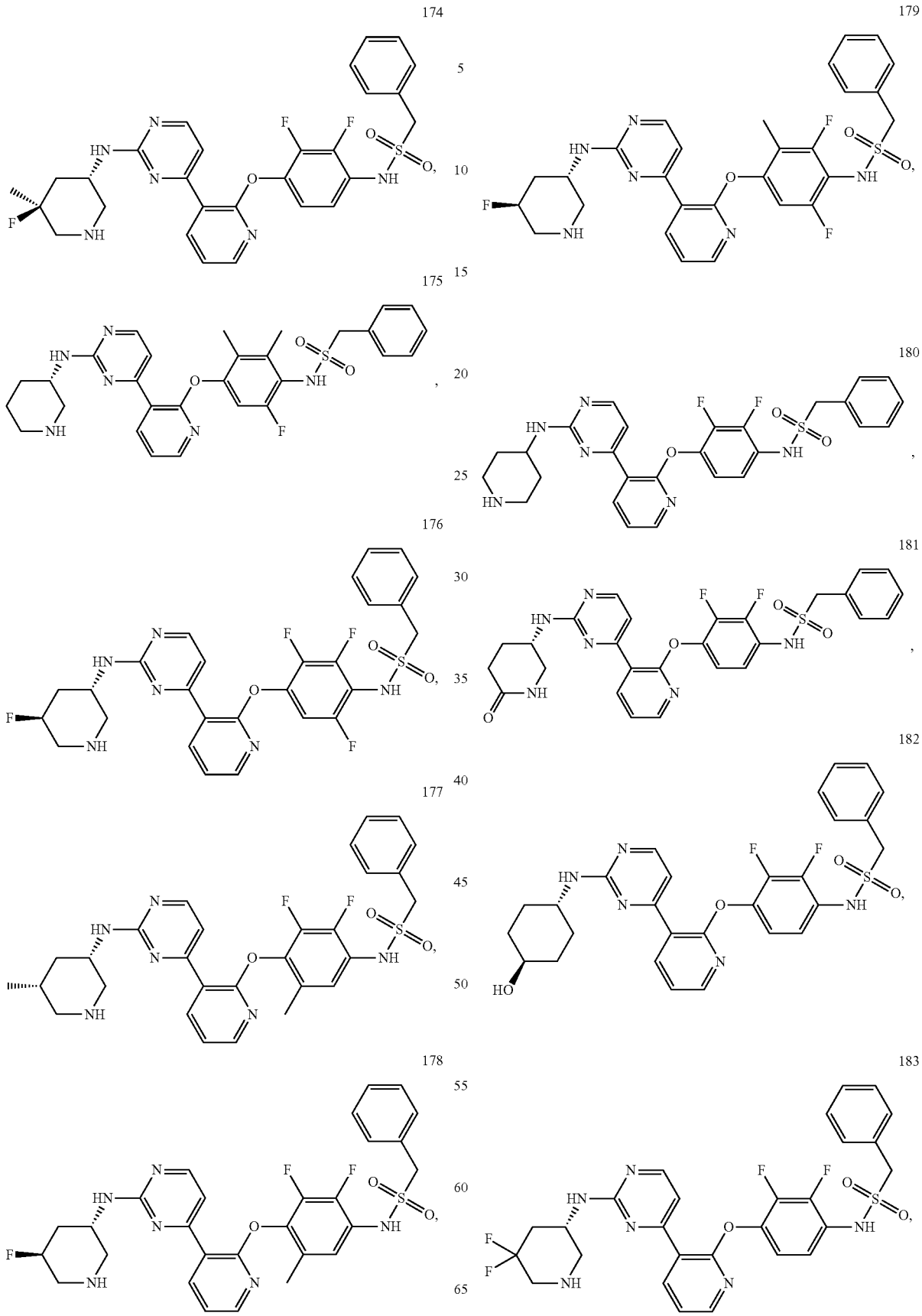

501
-continued
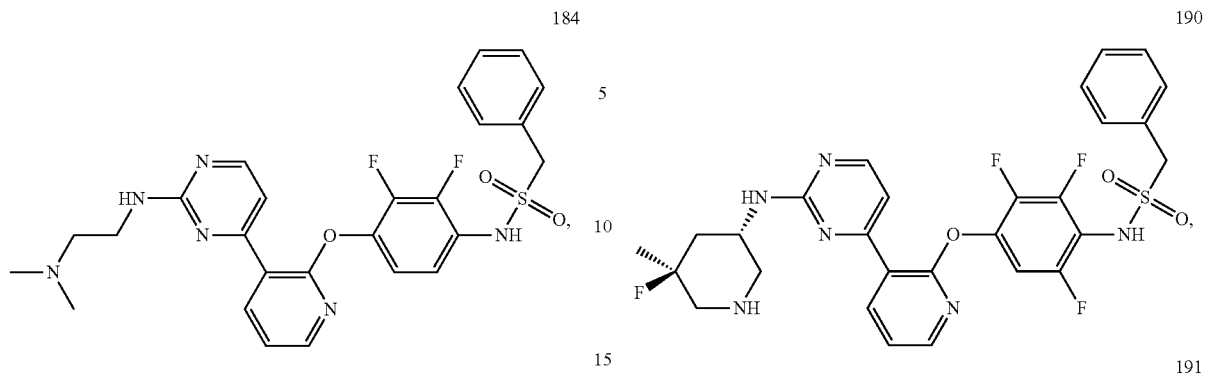
184
185
186
187
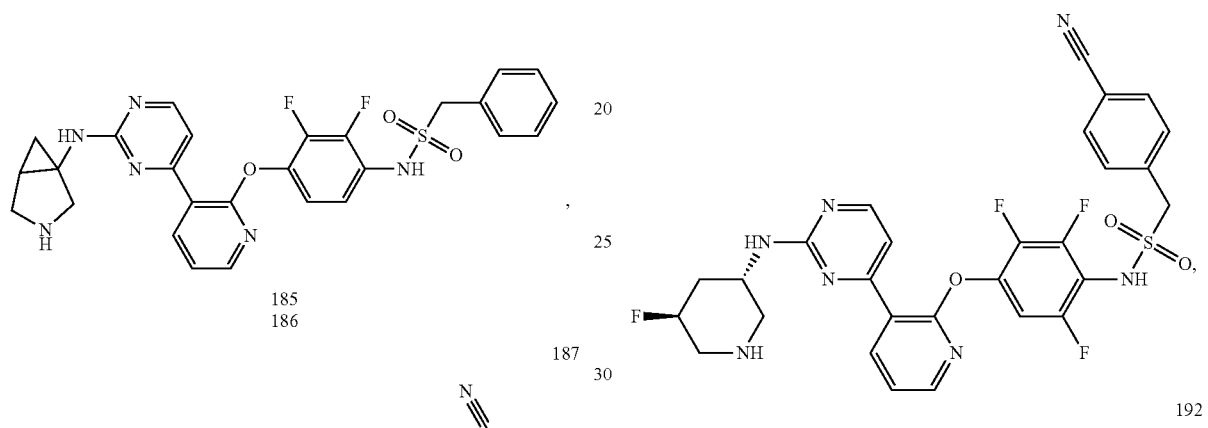
188
189
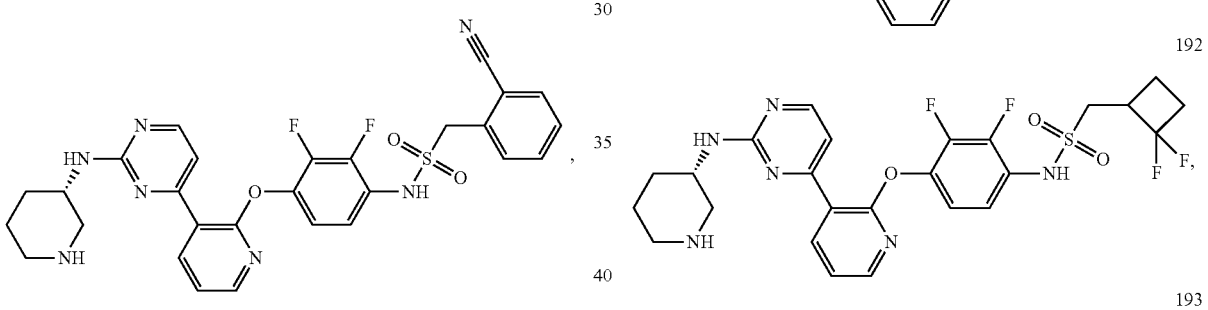
502
-continued
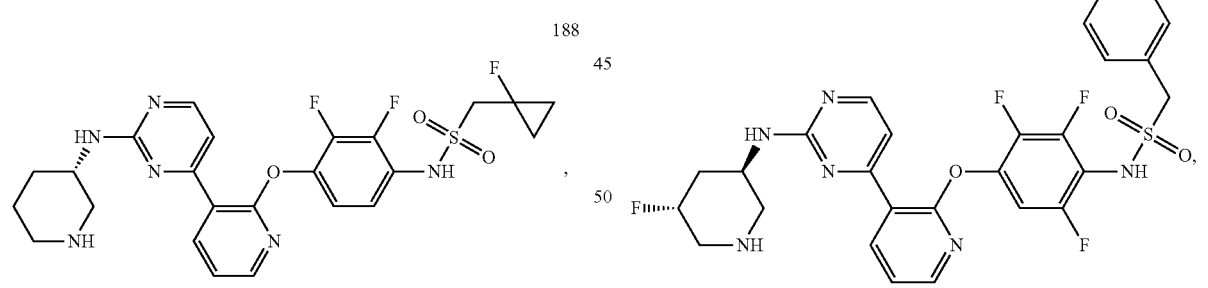
190
191
192
193
194
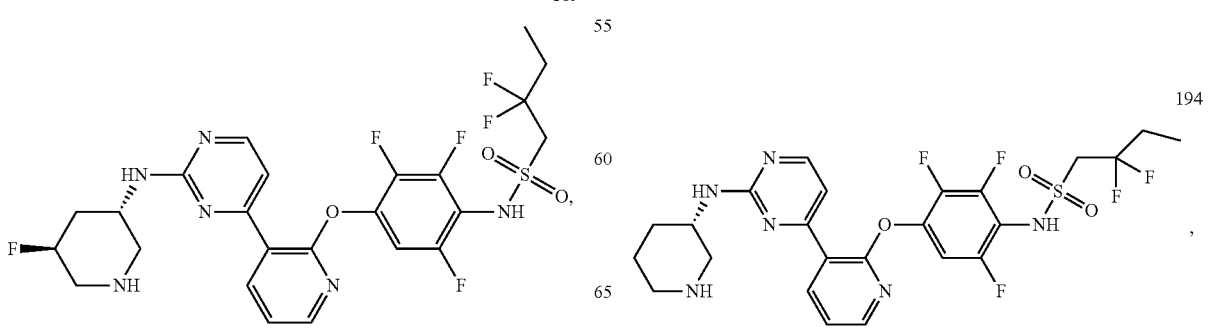

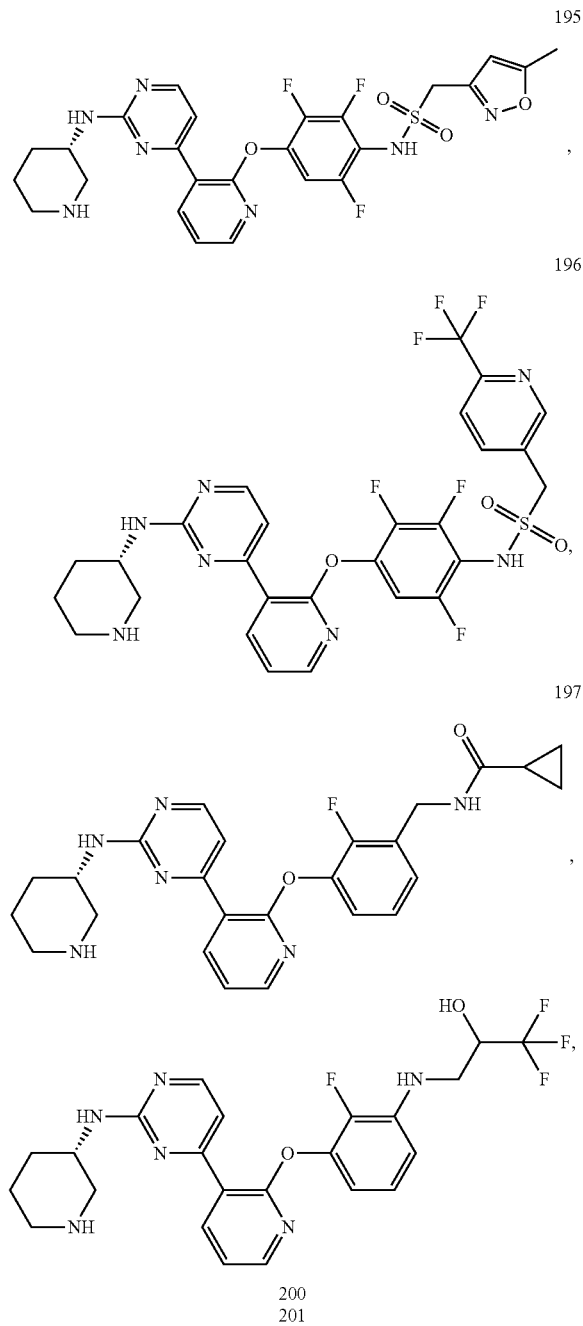
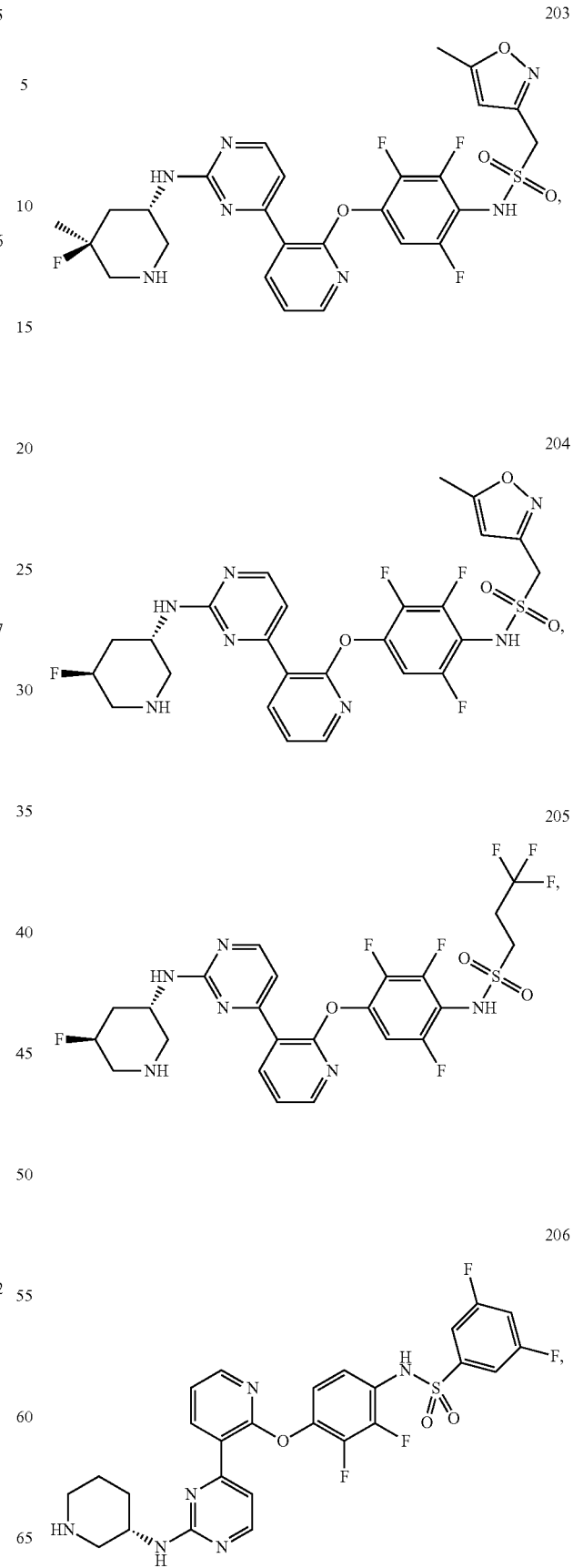

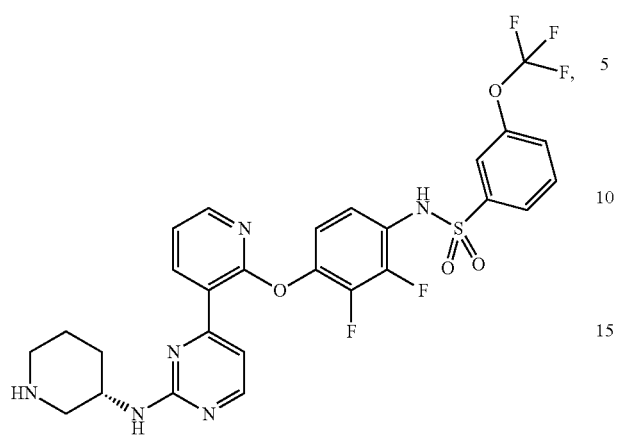
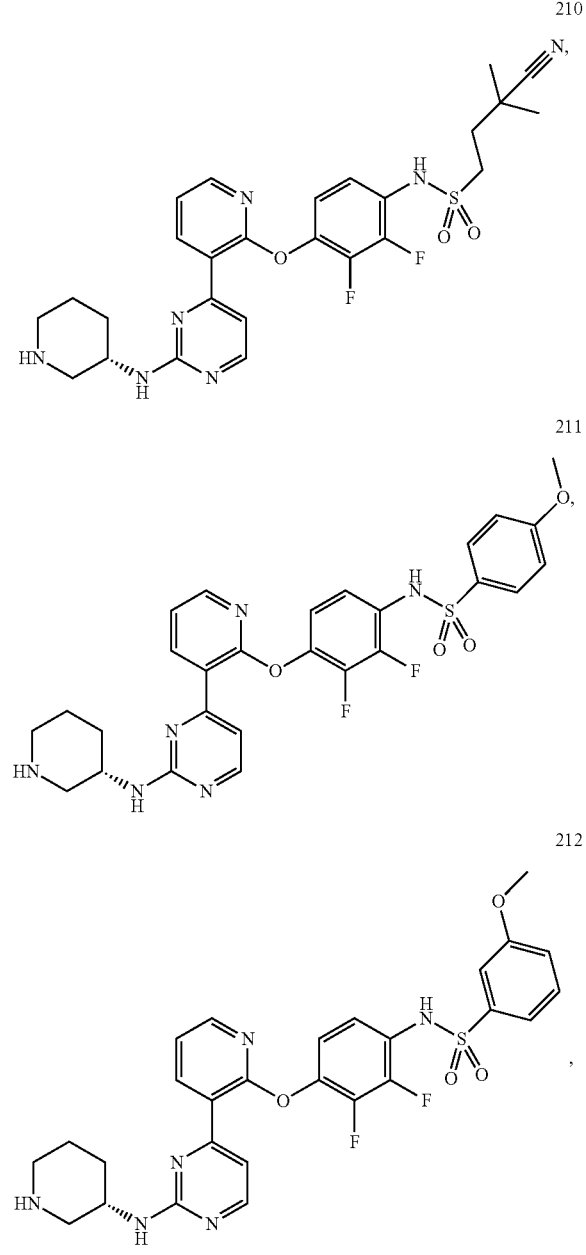
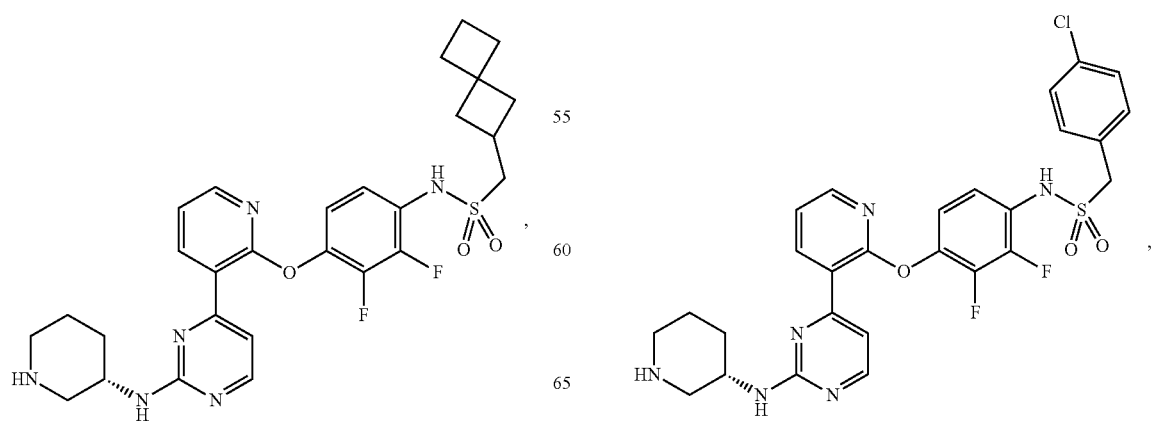

214
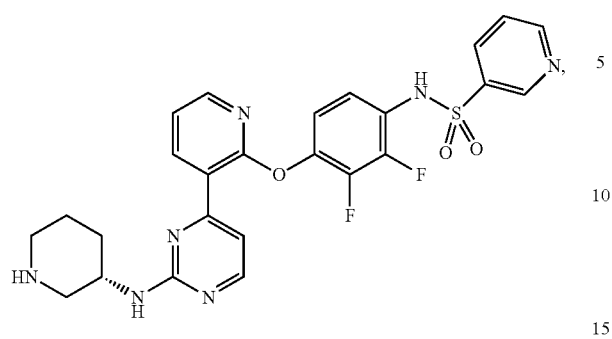
215
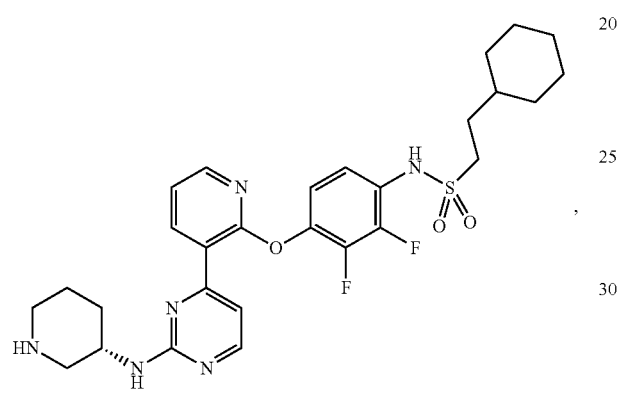
216
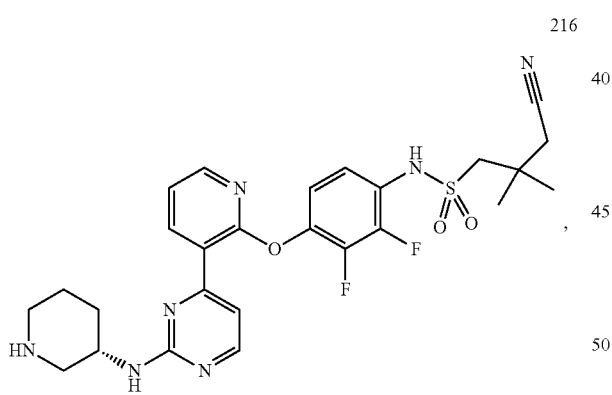
217
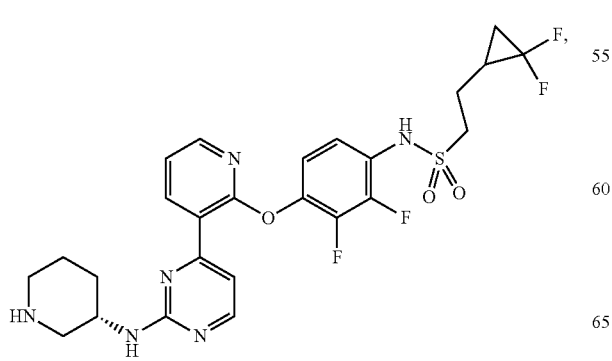
218
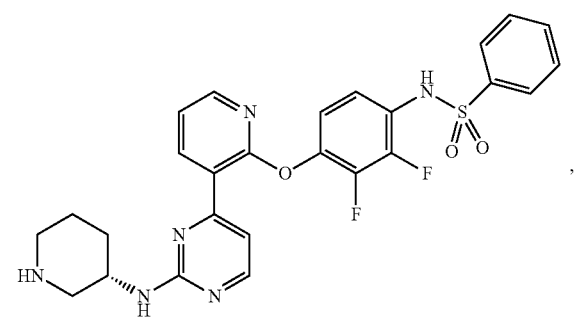
219
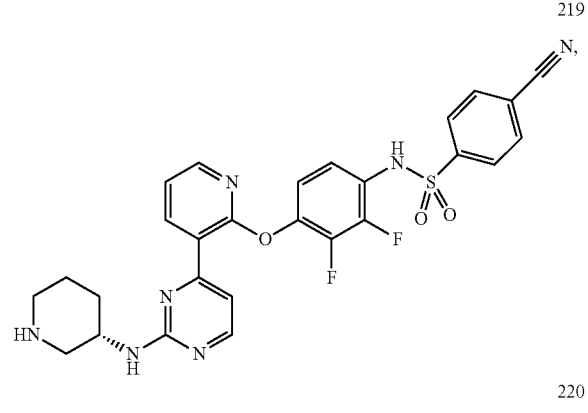
220
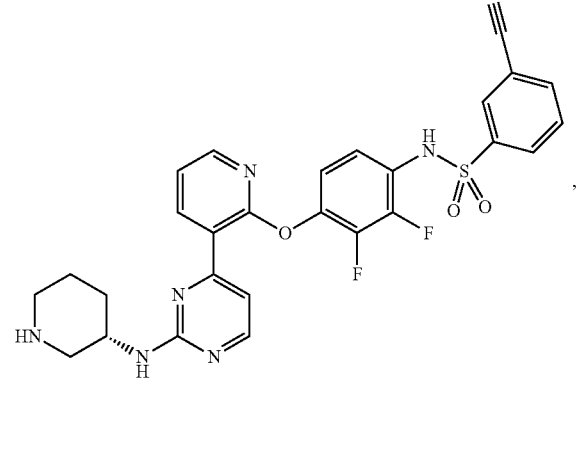
221
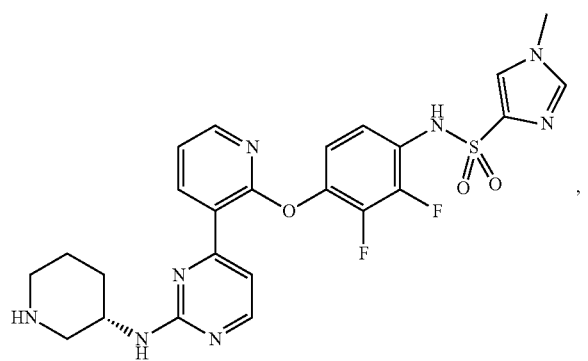

509
-continued
222
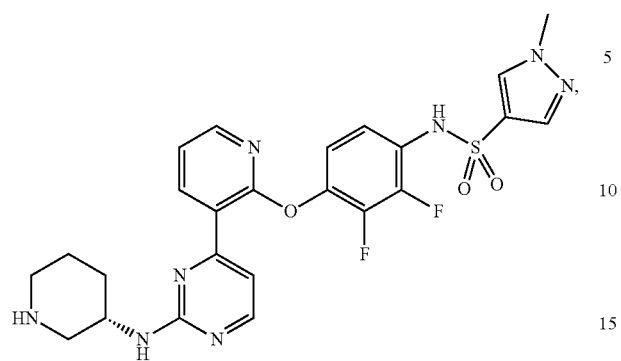
223
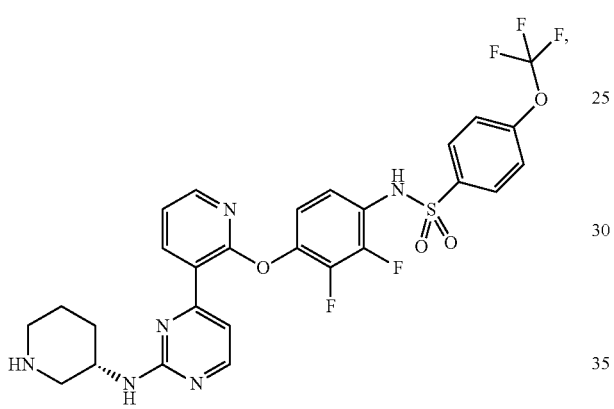
224
225
510
-continued
226
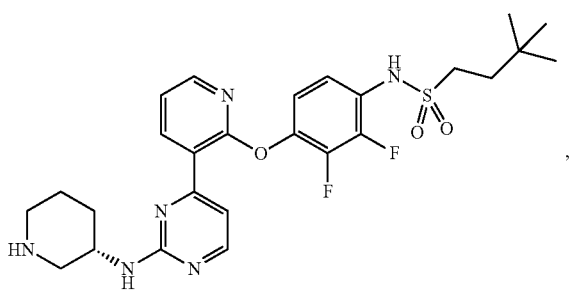
227
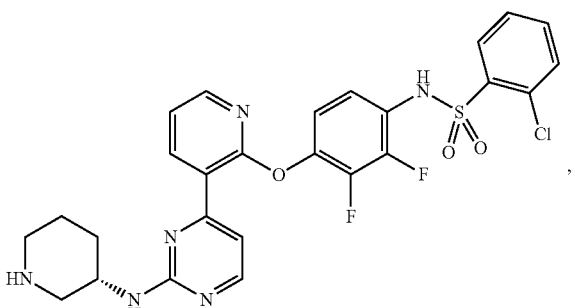
228
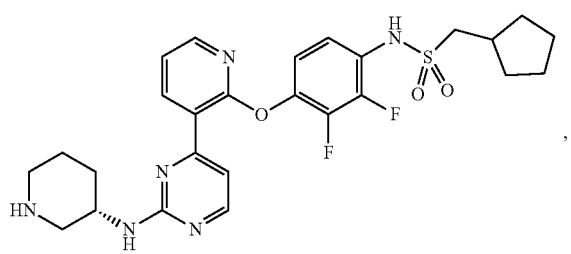
229
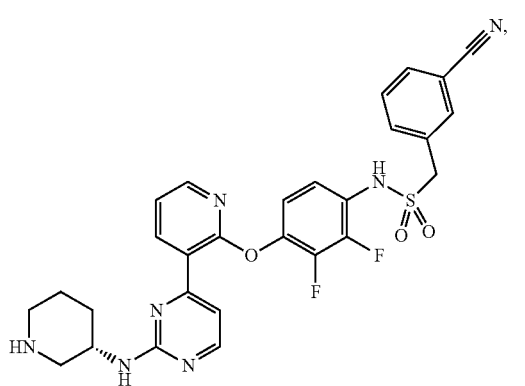

230
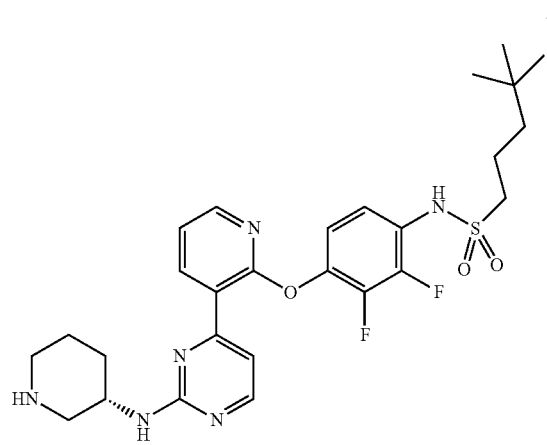
231
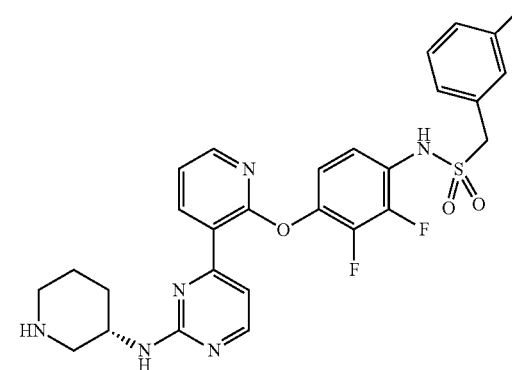
232
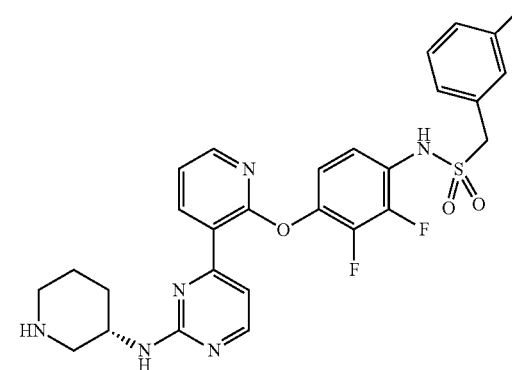
233
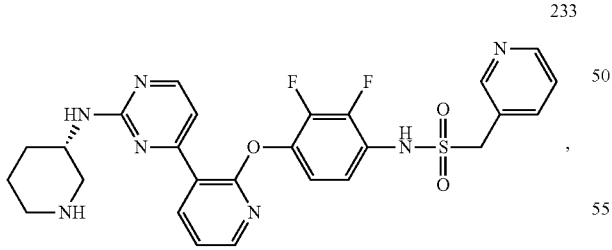
234
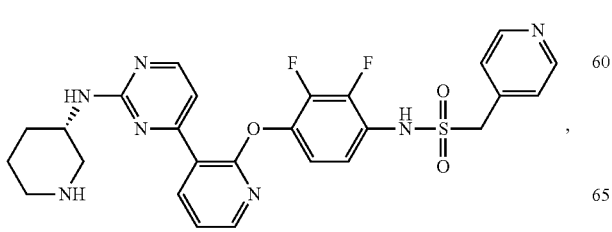
235
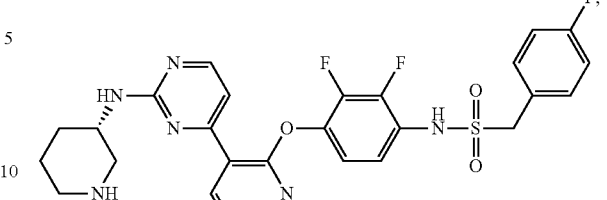
236
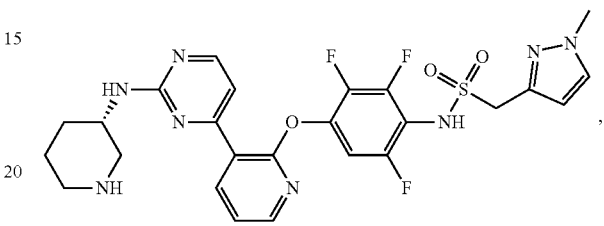
237
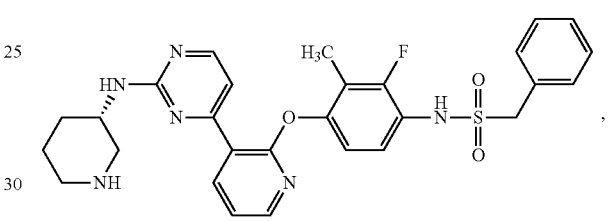
238
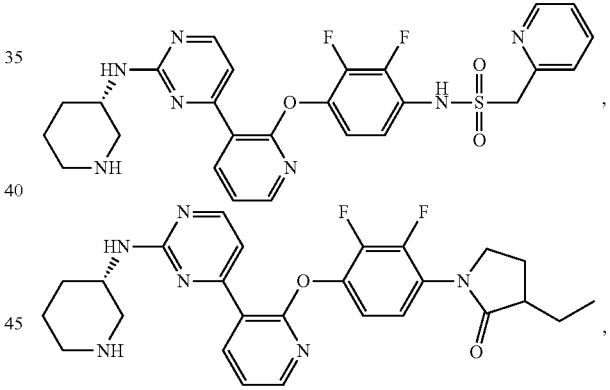
248
249
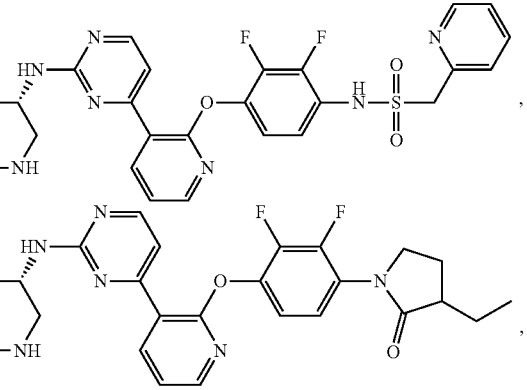
250
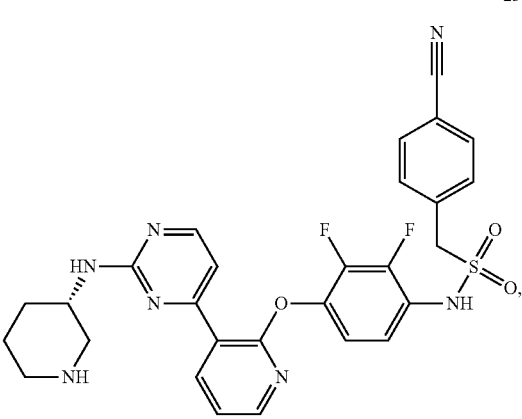

251
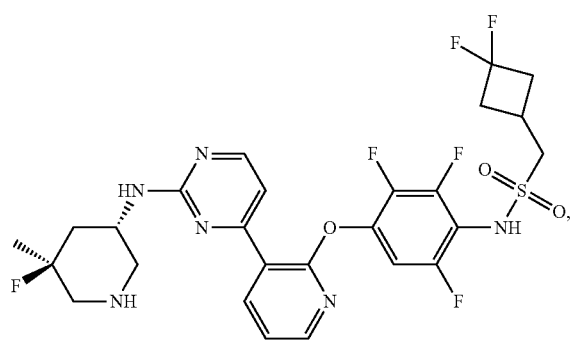
252
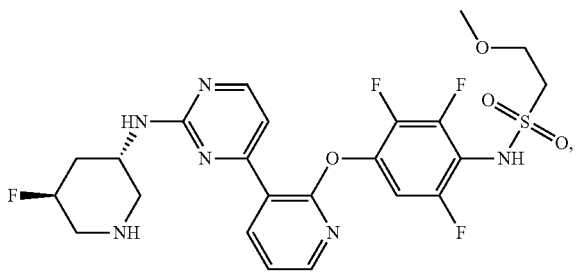
253
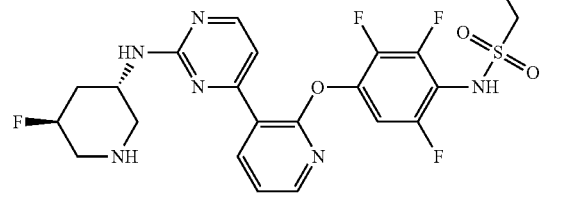
254
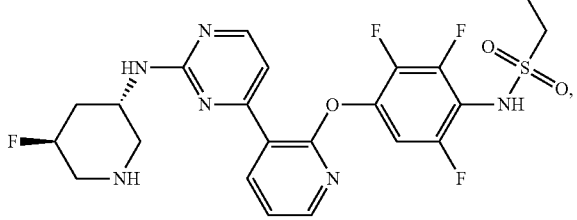
255
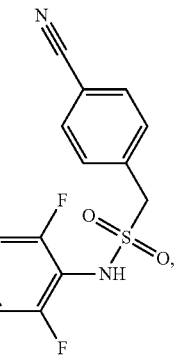
256
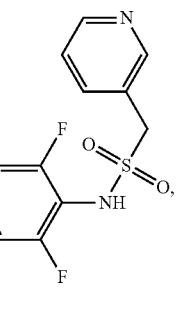
257
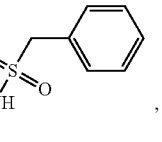
258
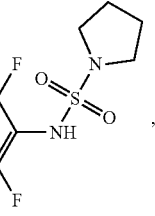
259
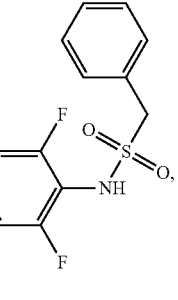

515
-continued
260
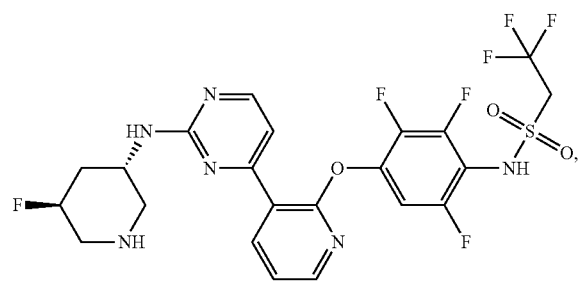
261
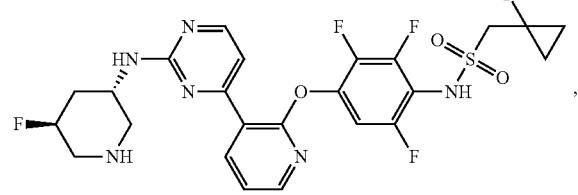
262
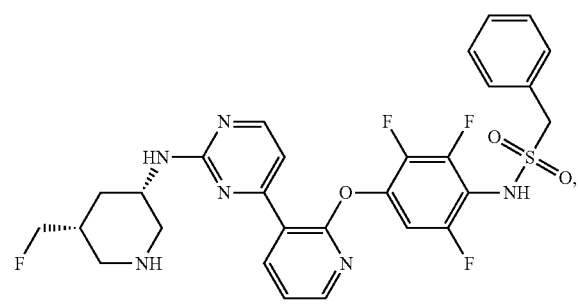
263
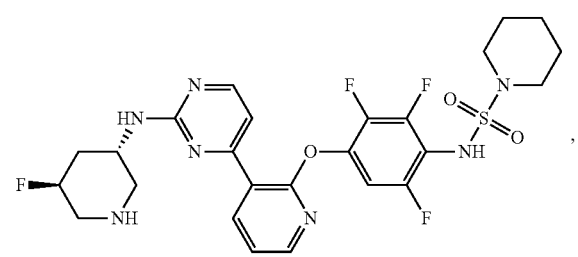
264
265
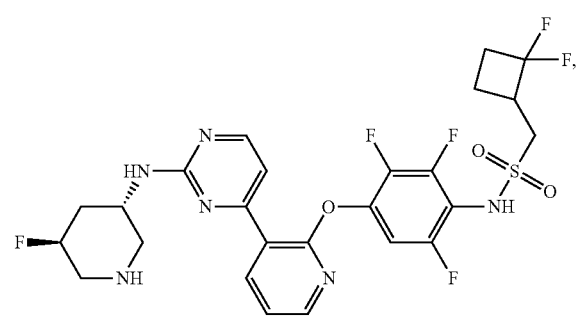
516
-continued
266
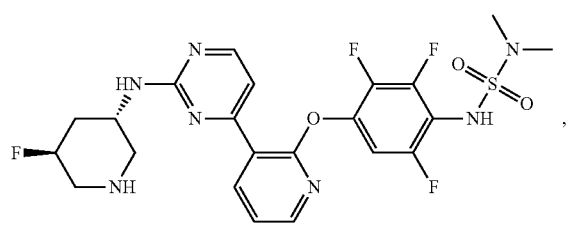
267
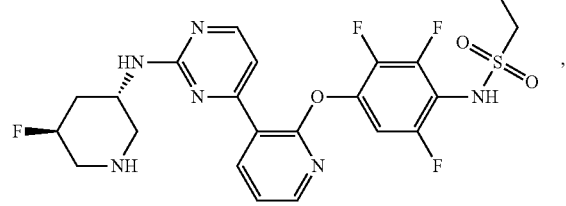
268
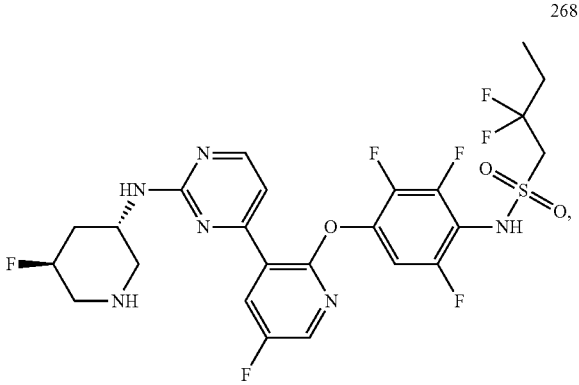
269
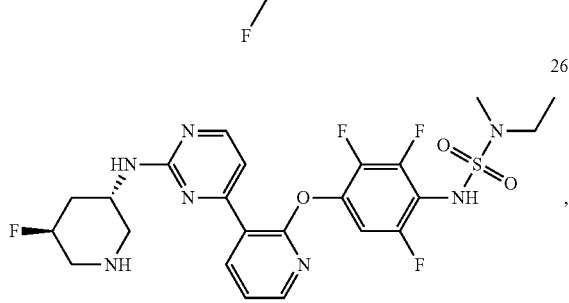
270
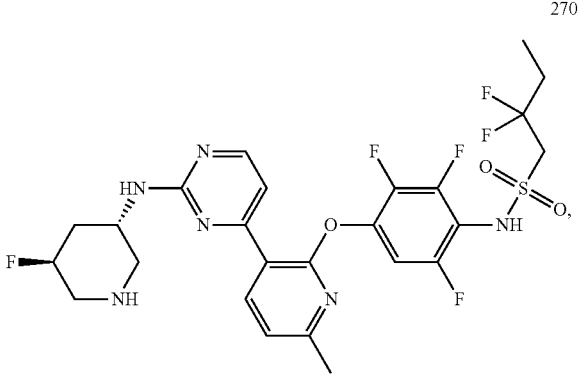

517
-continued
518
-continued
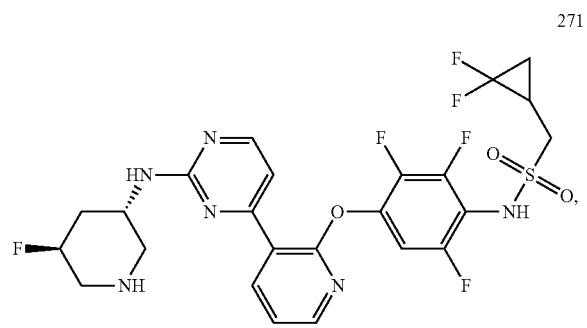
271
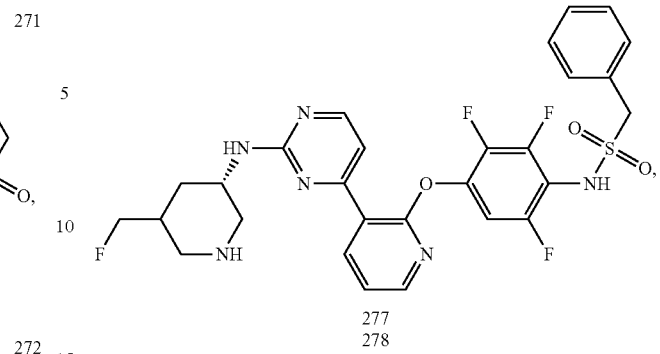
277
278
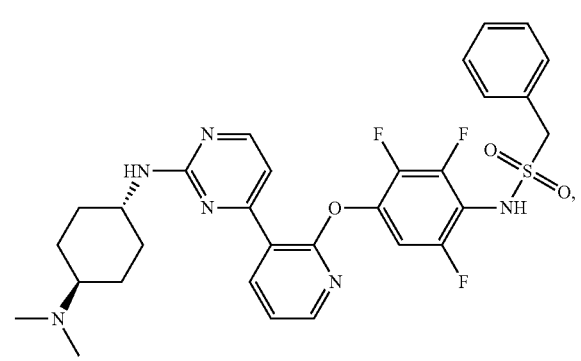
272
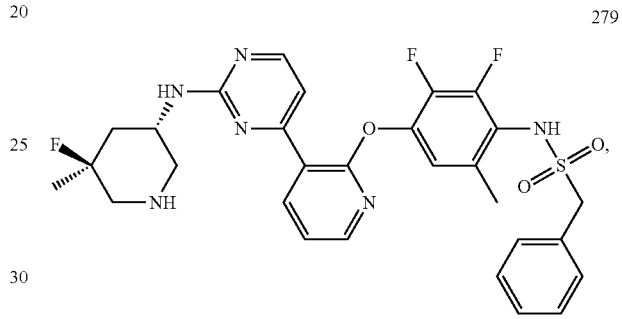
279
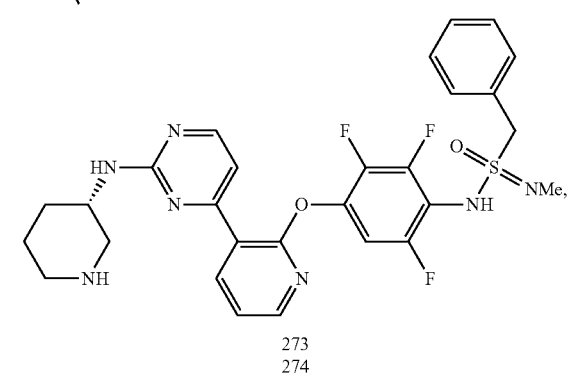
273
274
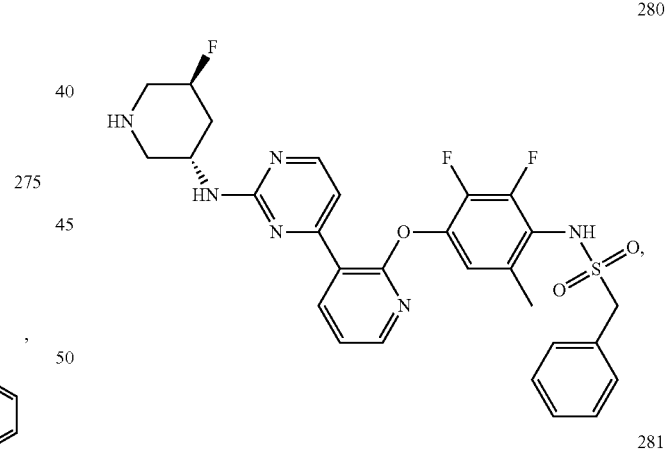
280
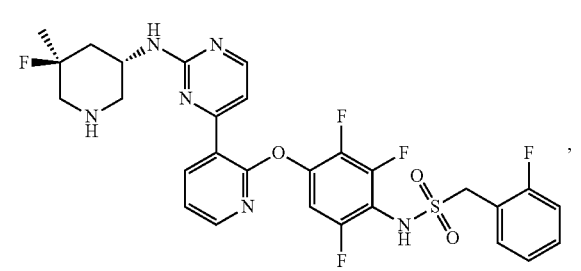
275
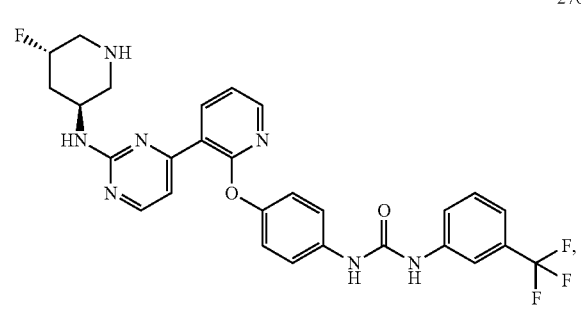
276
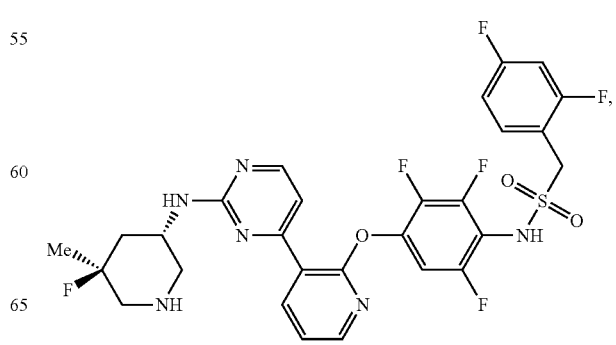
281

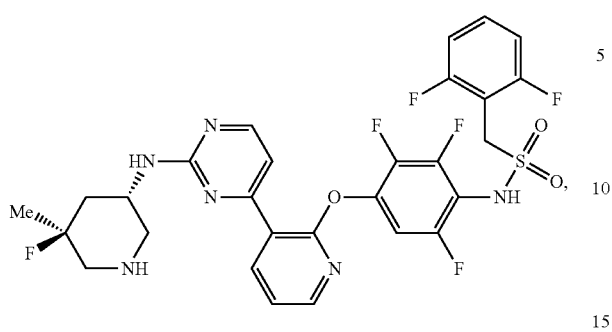
282
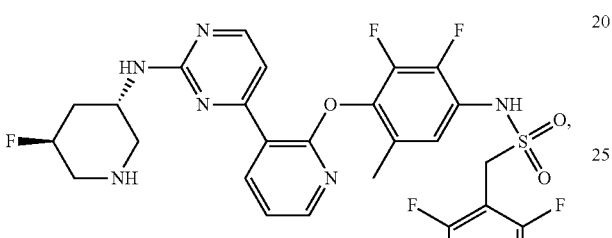
283
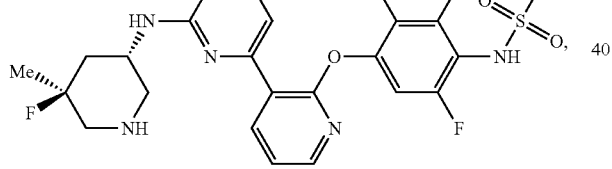
284
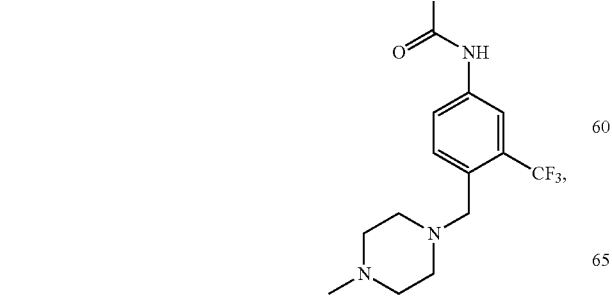
285
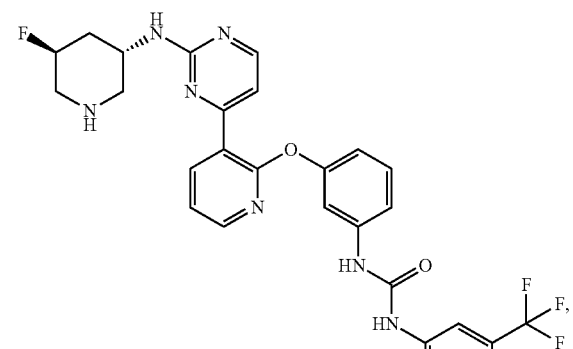
286
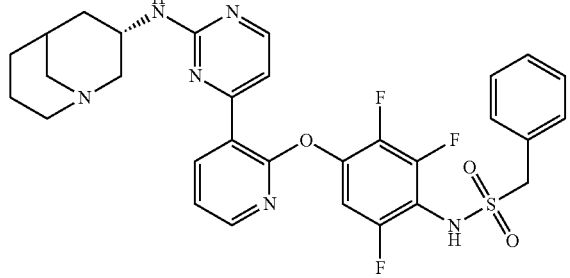
287
288
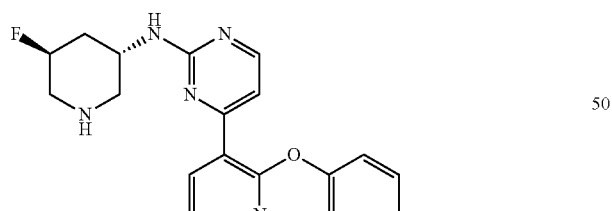
290
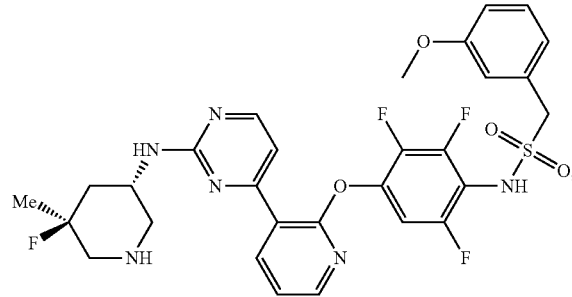
291

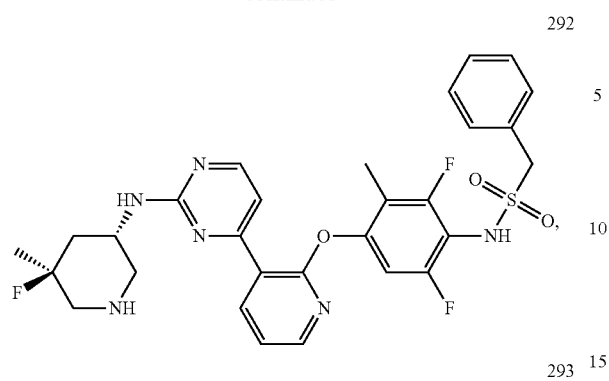
292
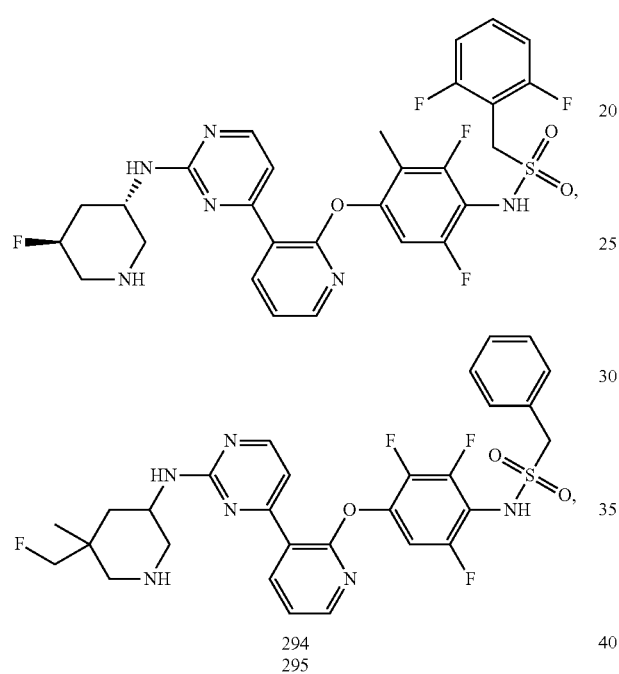
293
294
295
296
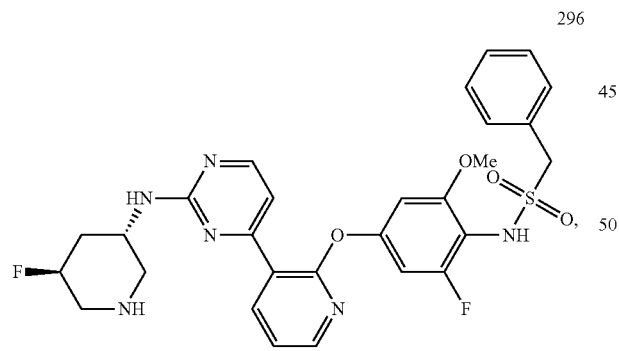
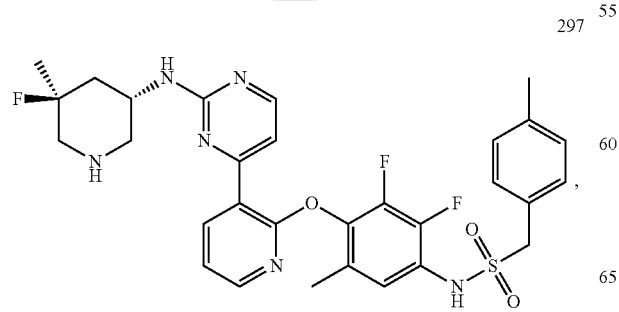
297
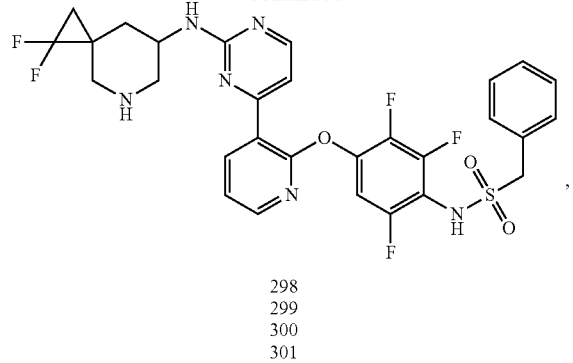
298
299
300
301
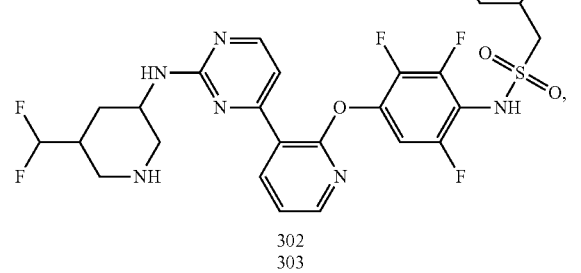
302
303
304
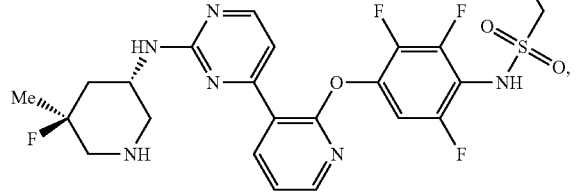
305
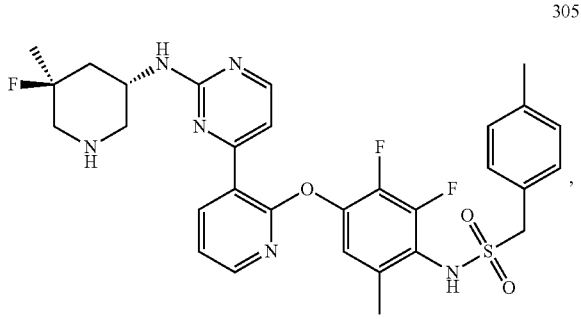

523
-continued
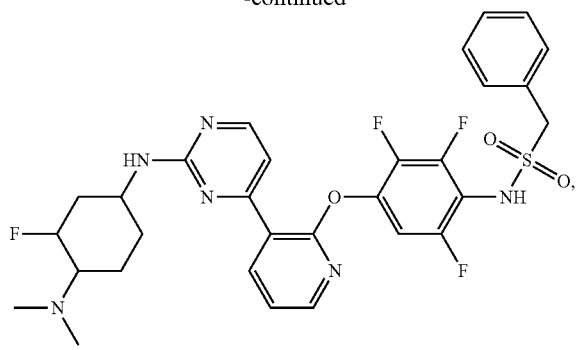
306
307
308
309
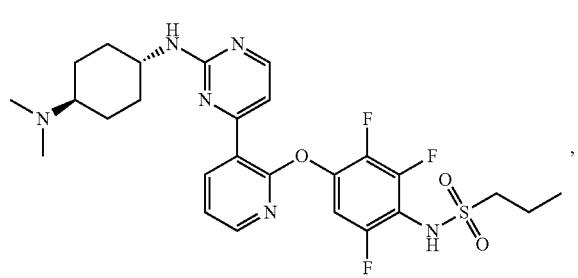
310
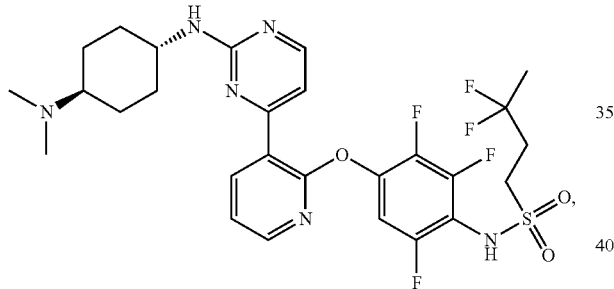
311
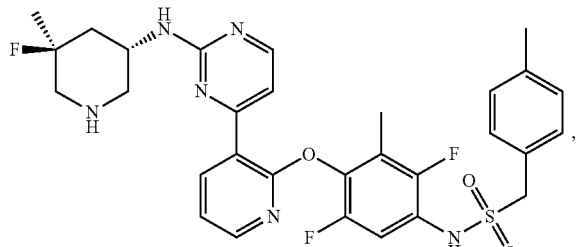
312
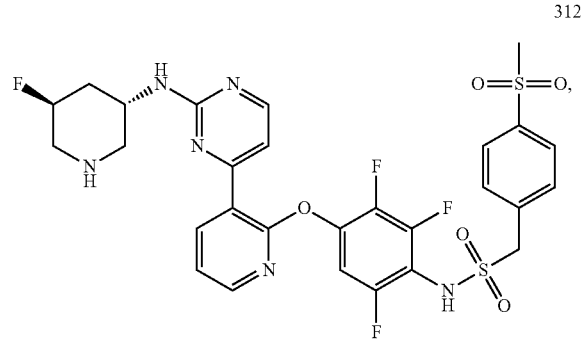
524
-continued
313
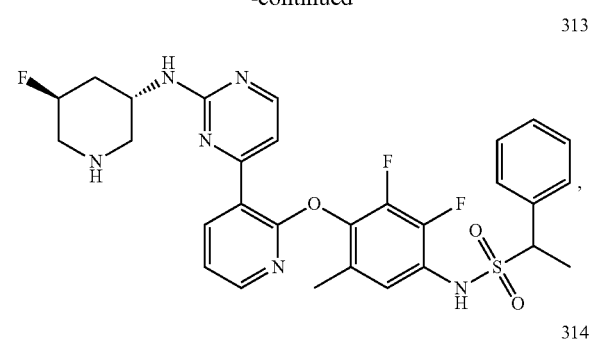
314
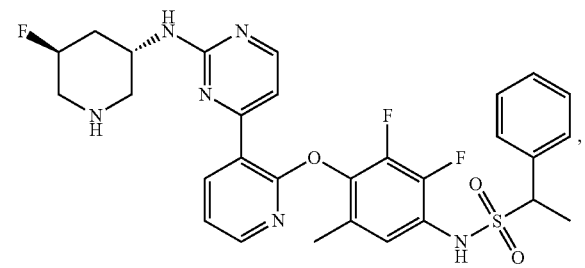
315
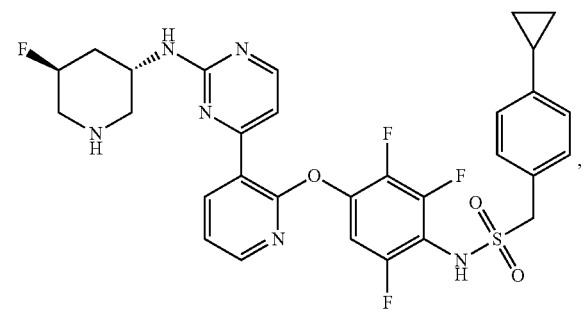
316
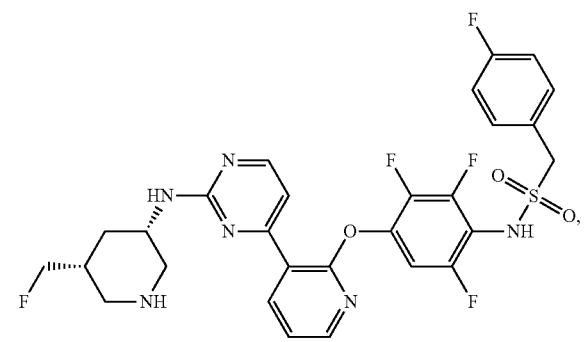
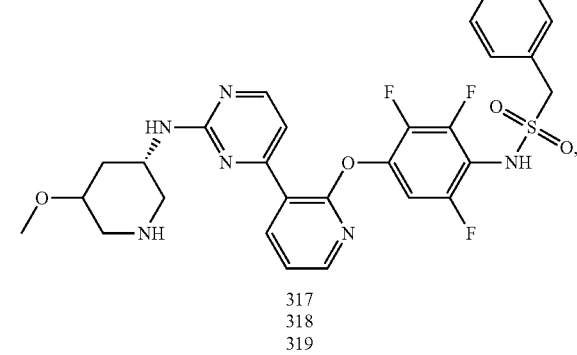
317
318
319

-continued
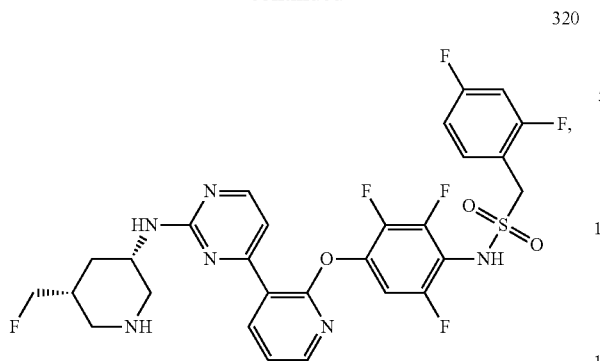
320
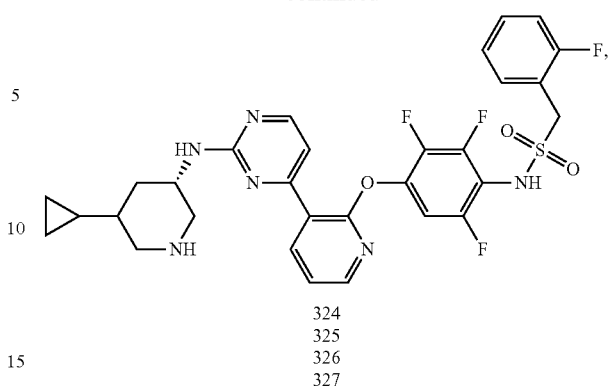
324
325
326
327
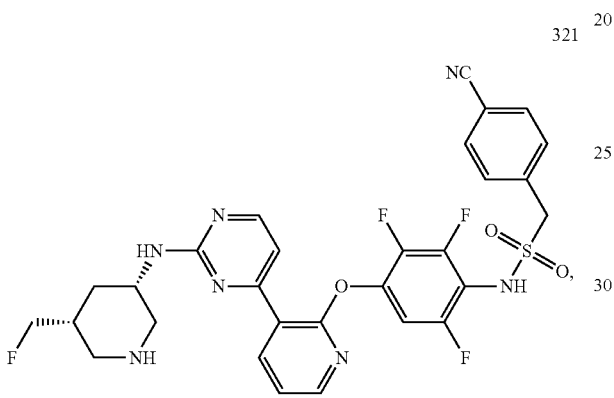
321
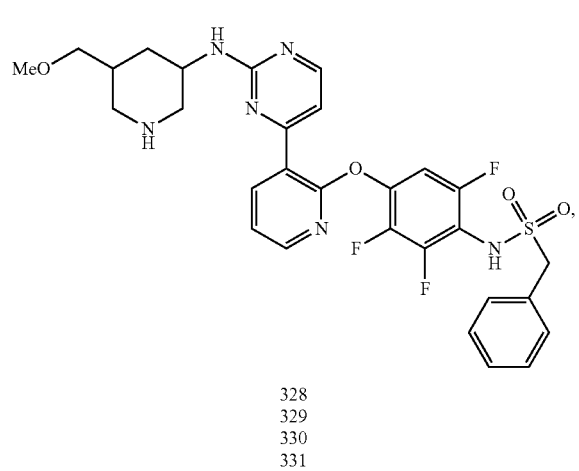
328
329
330
331
332
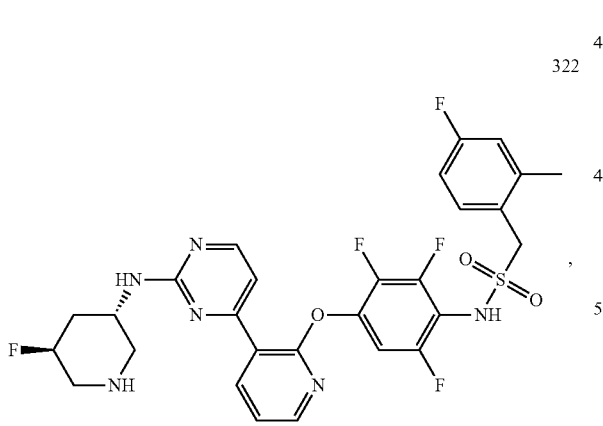
322
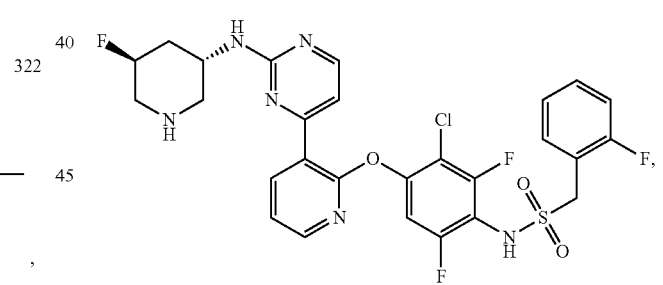
333
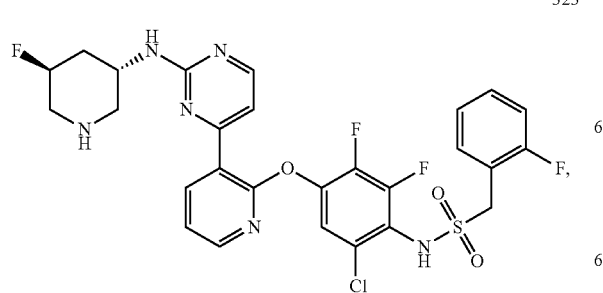
323
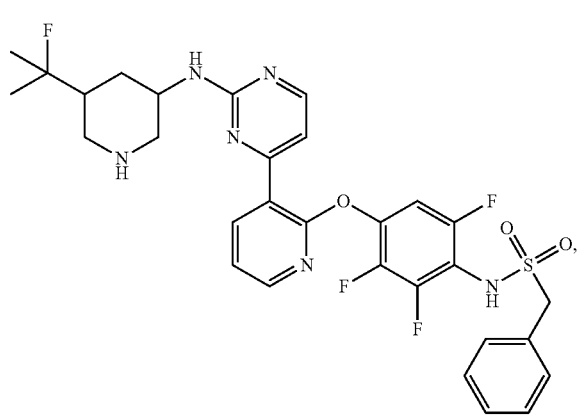

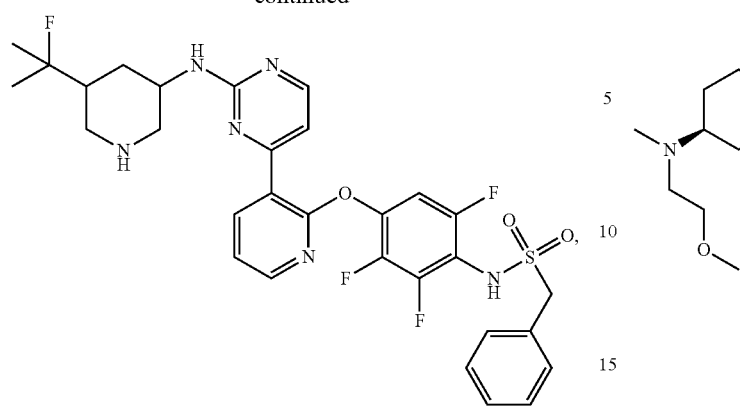
334
335
336
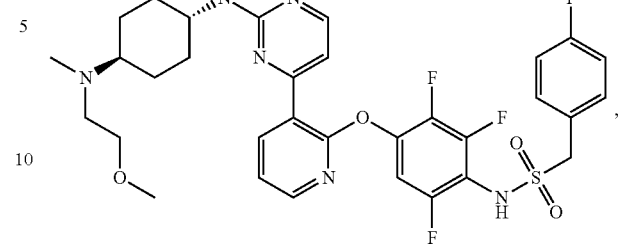
337
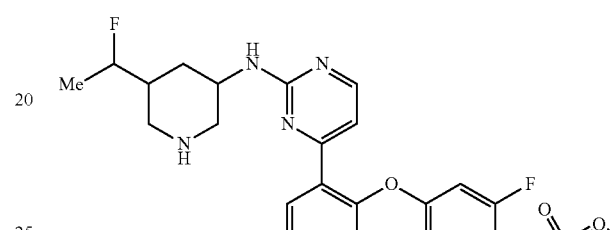
338
339
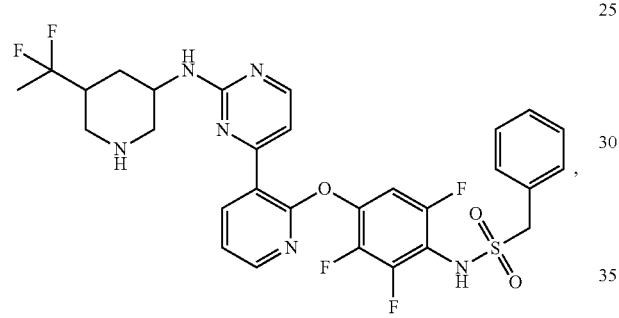
340
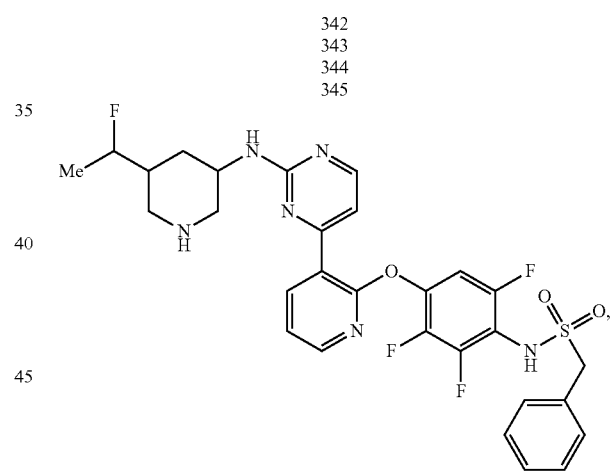
341
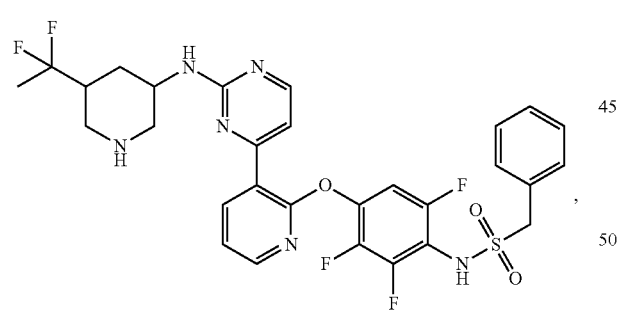
342
343
344
345
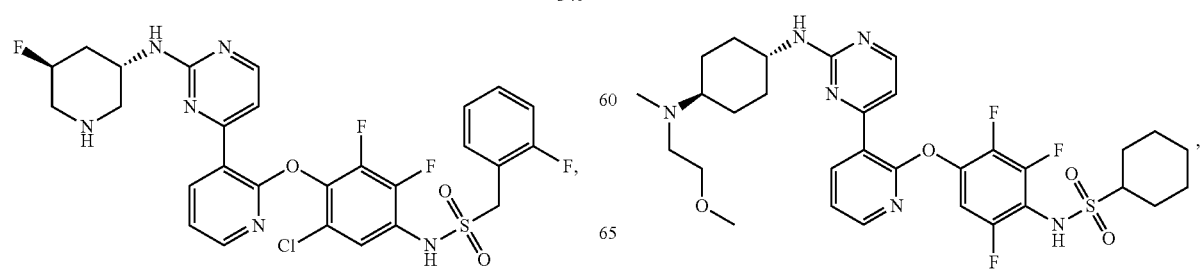
346
347
348
349
350

529
-continued
351
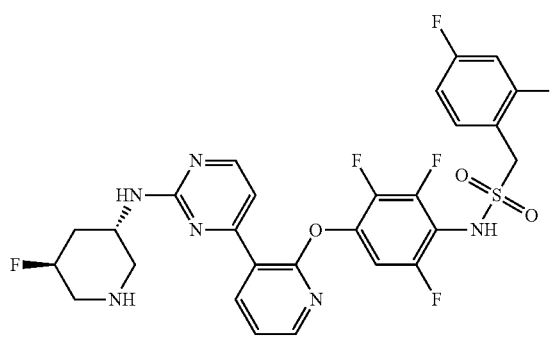
352
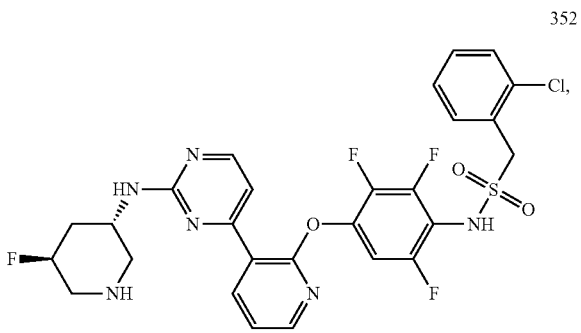
353
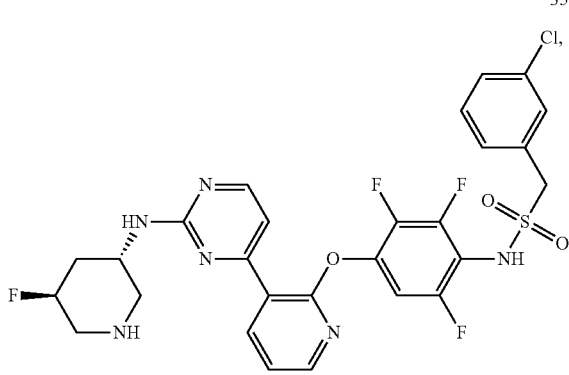
354
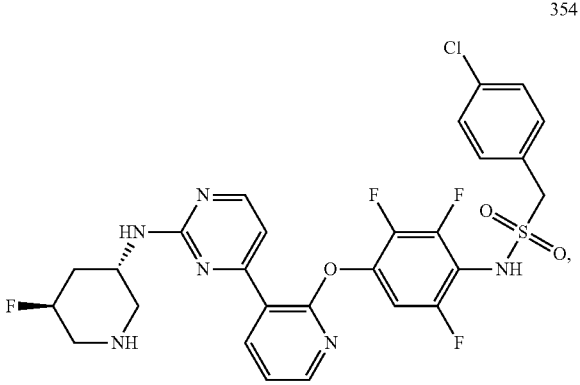
530
-continued
355
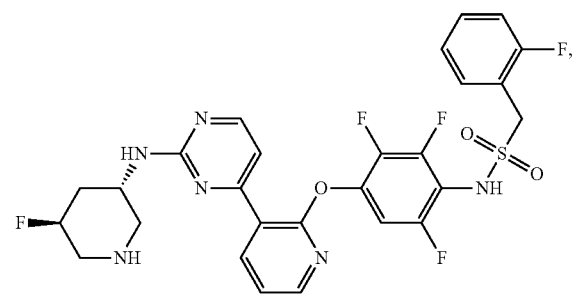
356
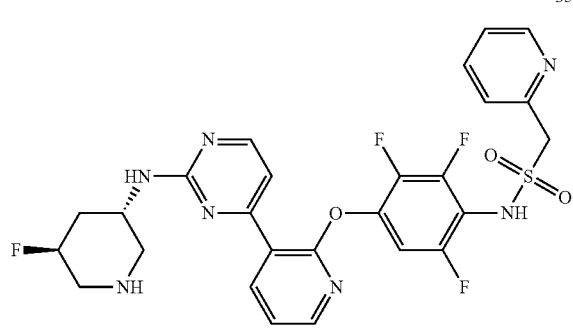
357
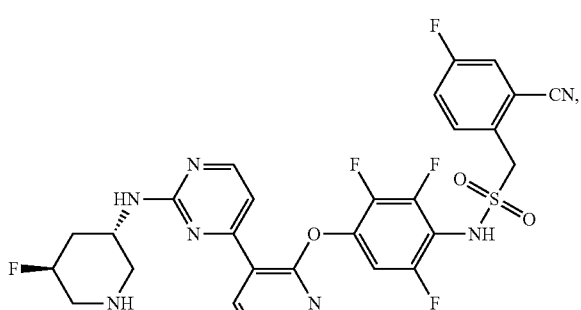
358
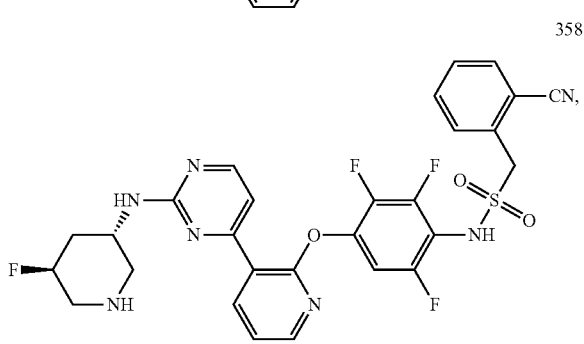
359
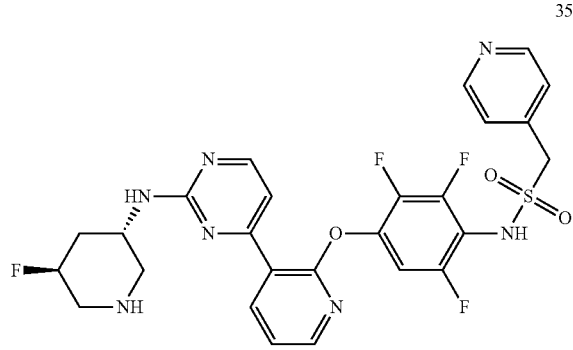

531
-continued
360
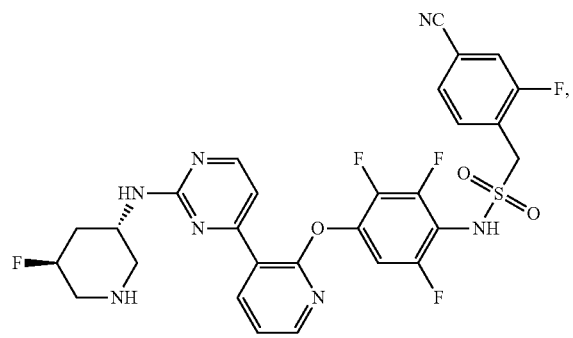
361
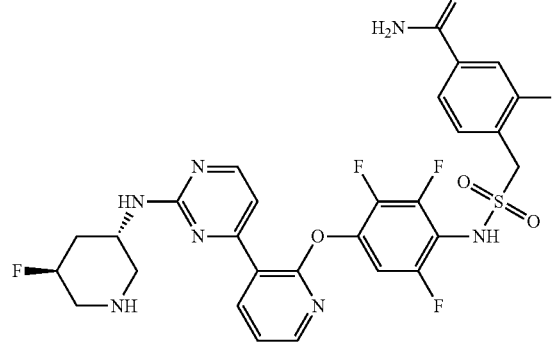
362
363
532
-continued
364
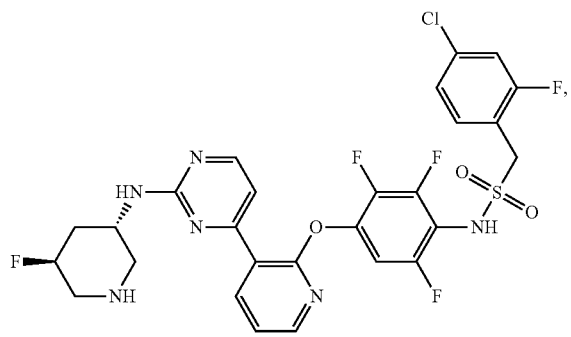
365
366
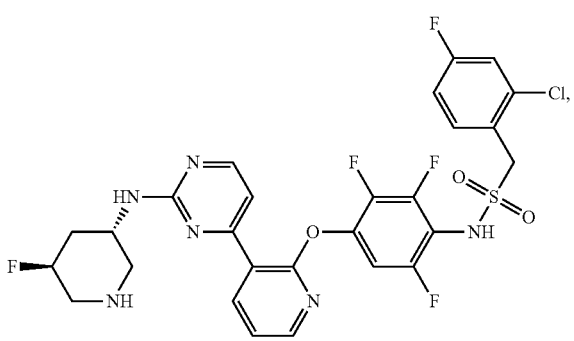
367
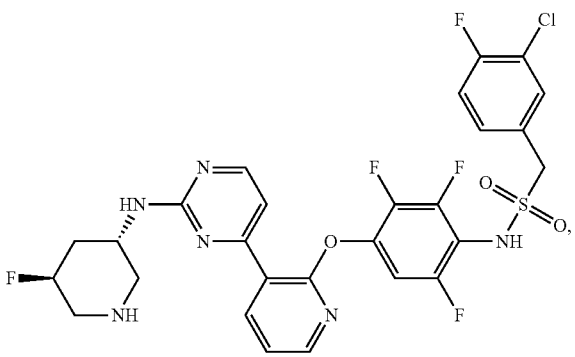
368
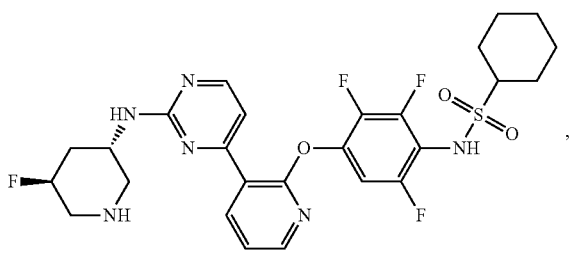

369
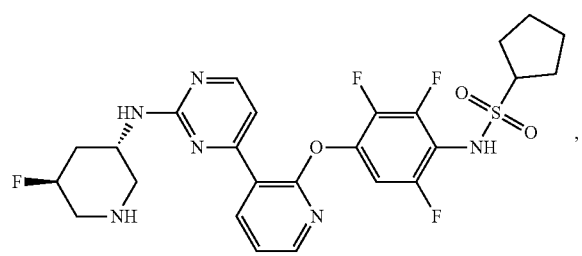
370
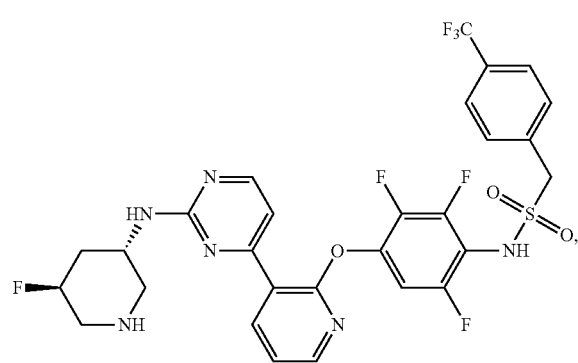
371
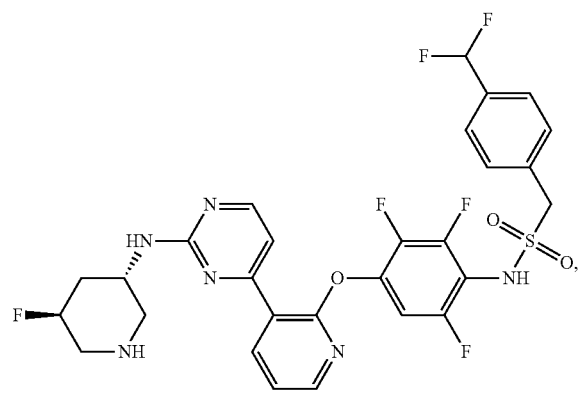
372
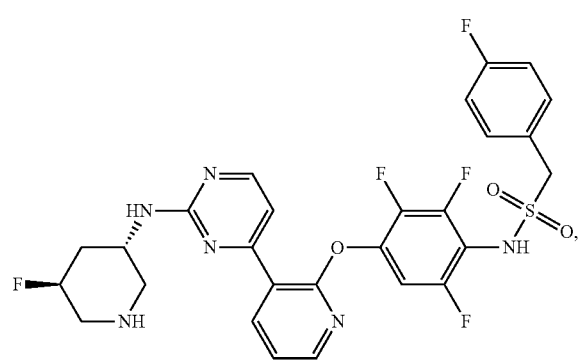
373
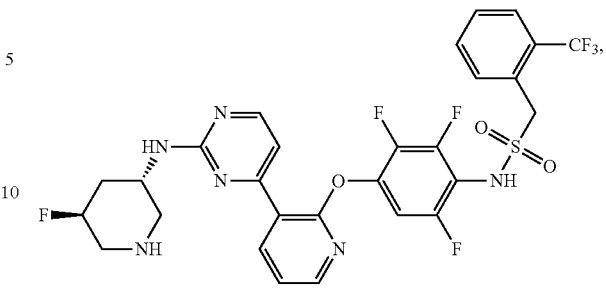
374
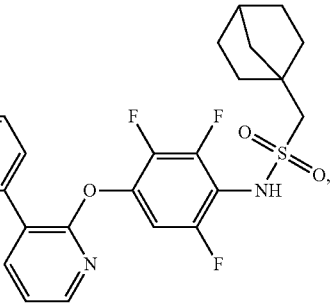
375
376

377
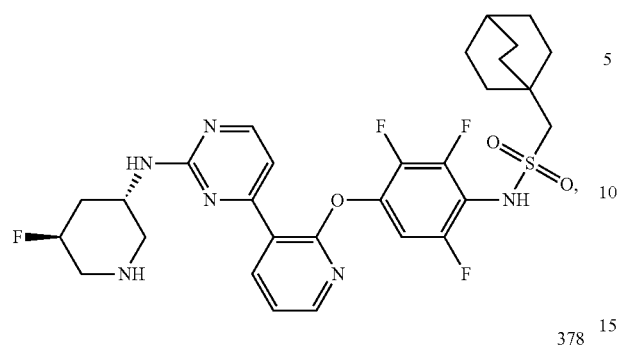
378
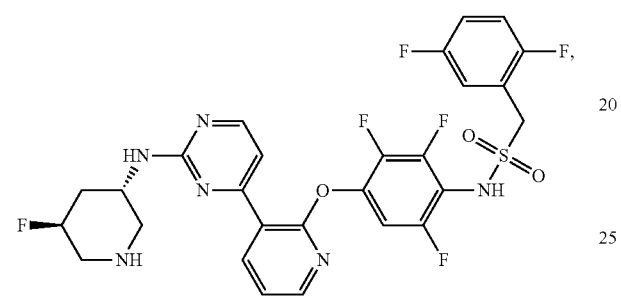
379
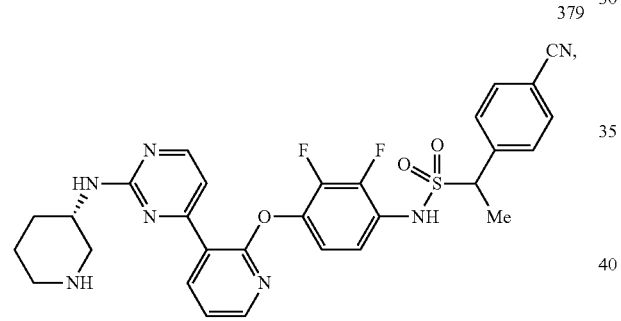
380
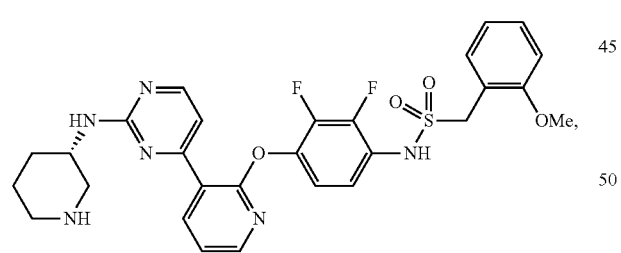
382
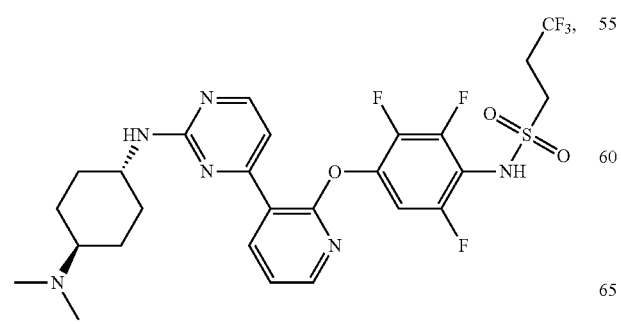
383
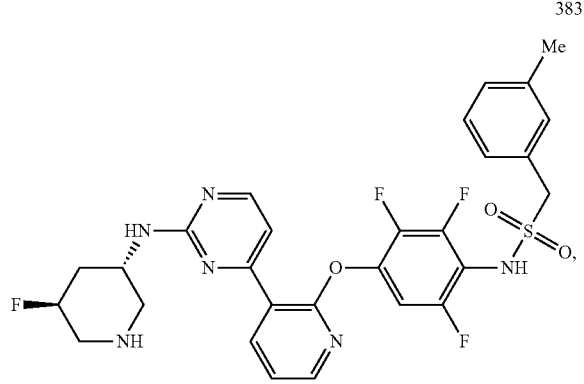
384
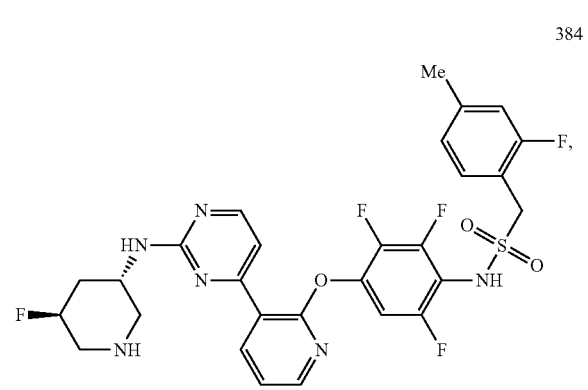
385
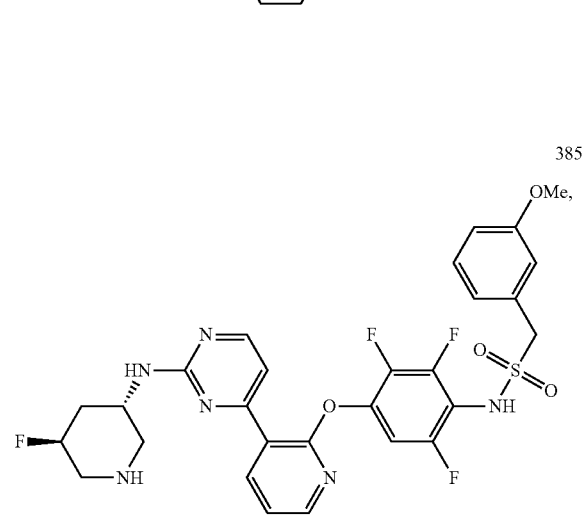
386

387
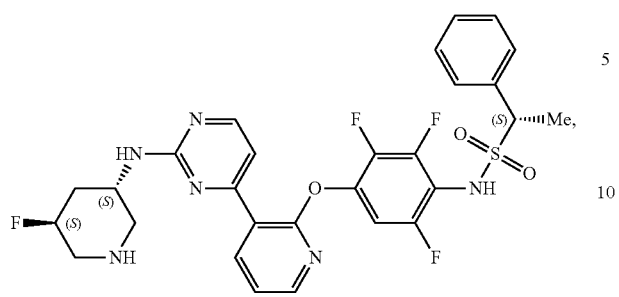
388
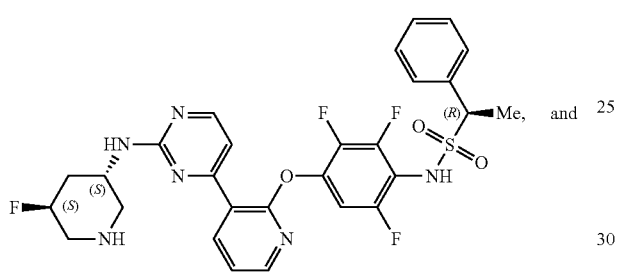
389
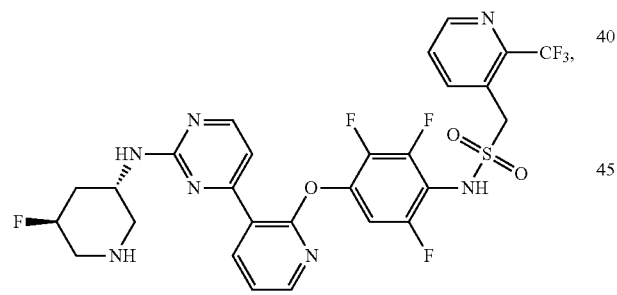
or a pharmaceutically acceptable salt thereof, or
248
249
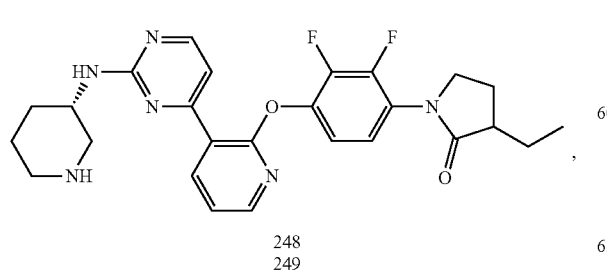
250
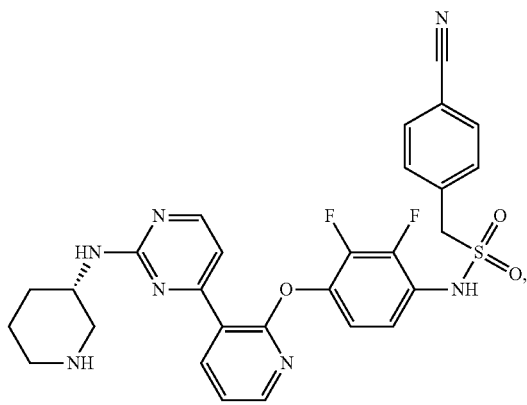
251
252
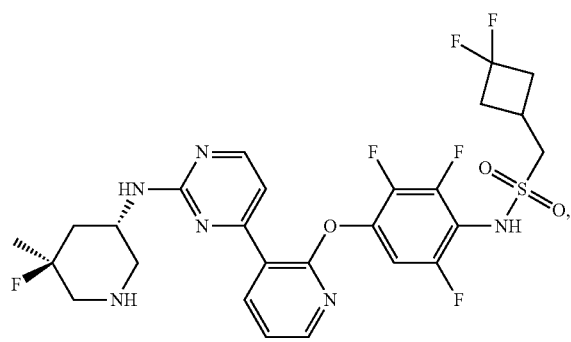
253
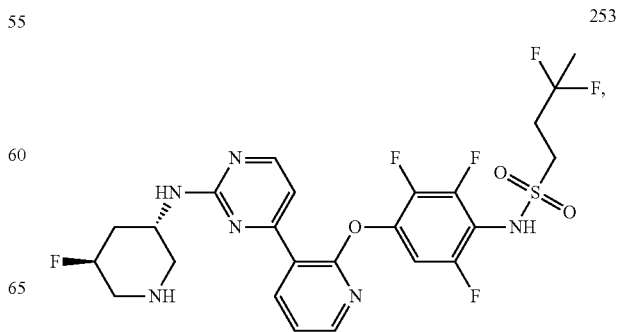

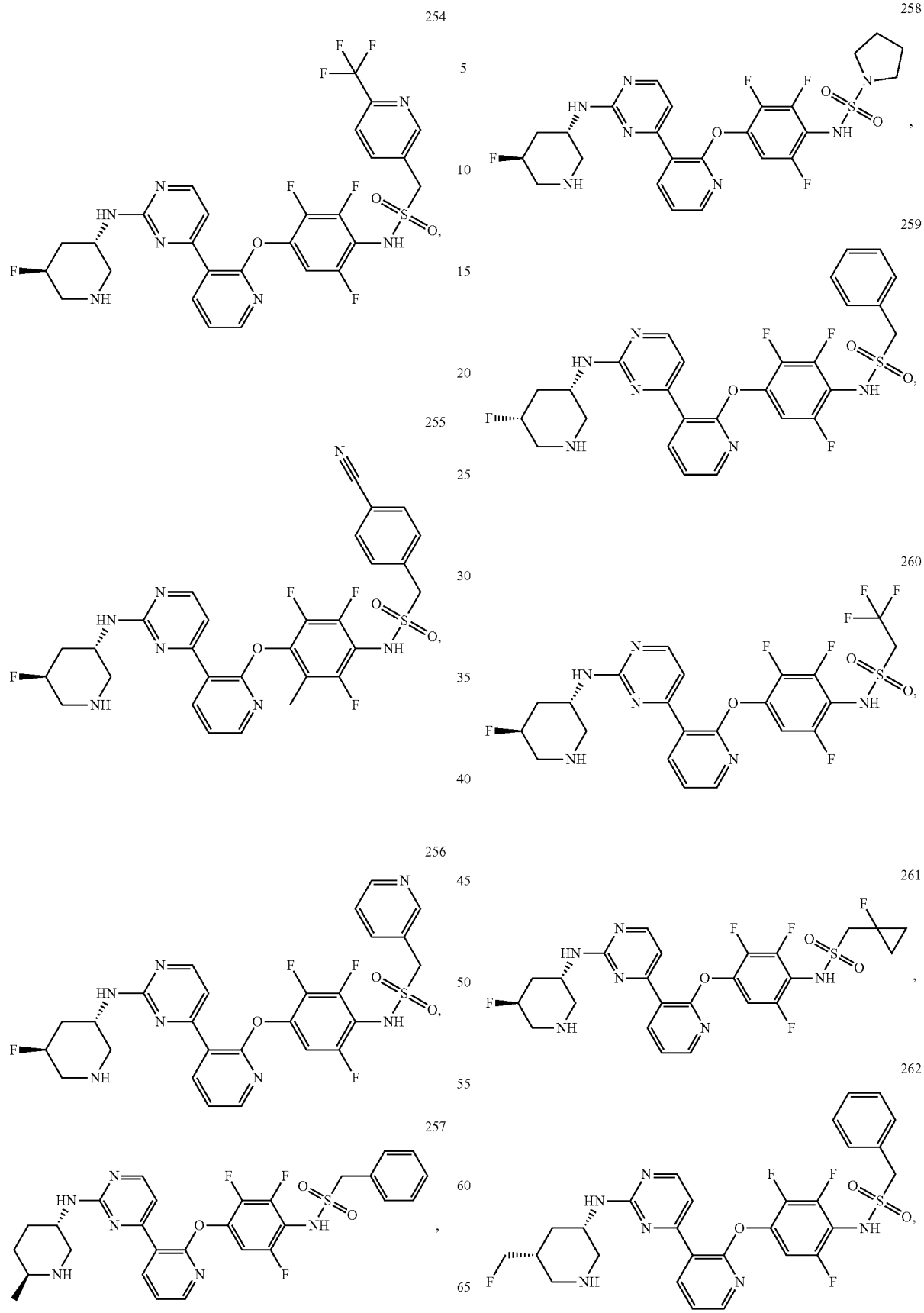

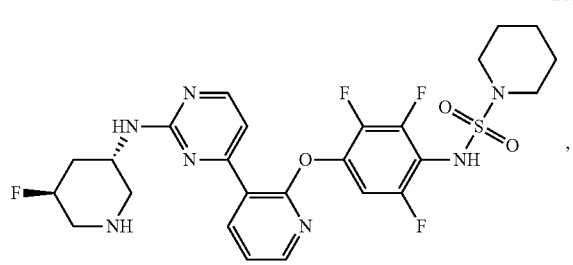
263
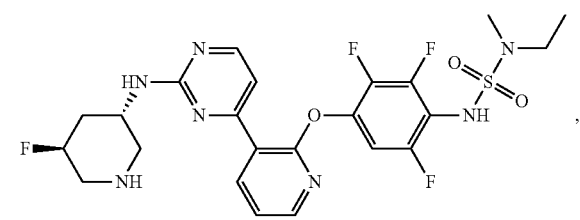
269
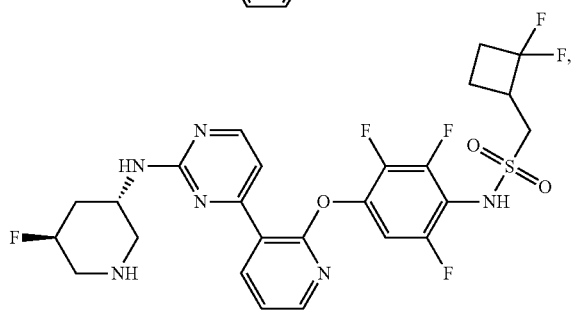
264
265
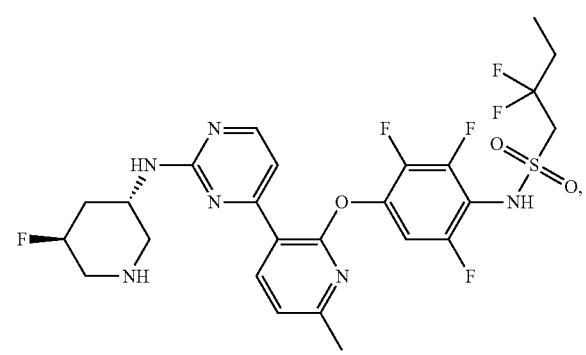
270
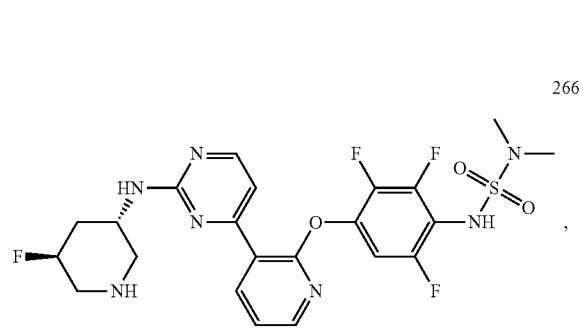
266
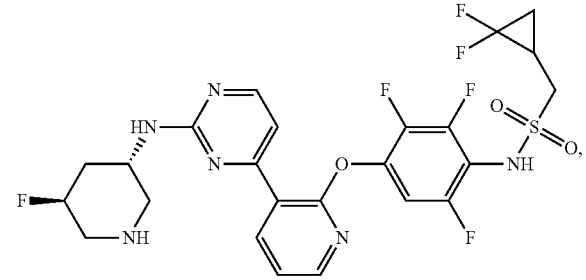
271
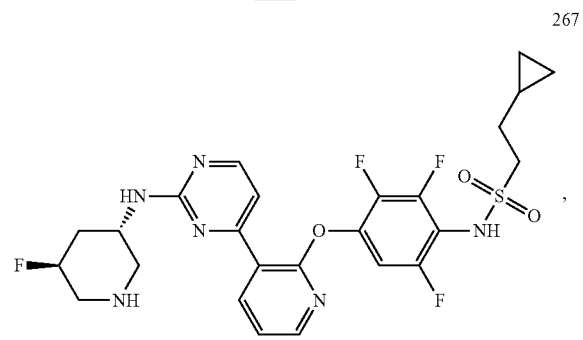
267
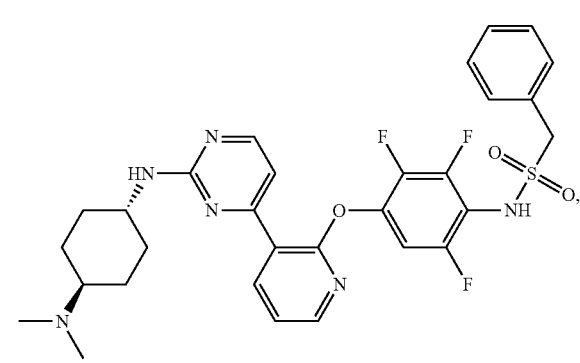
272
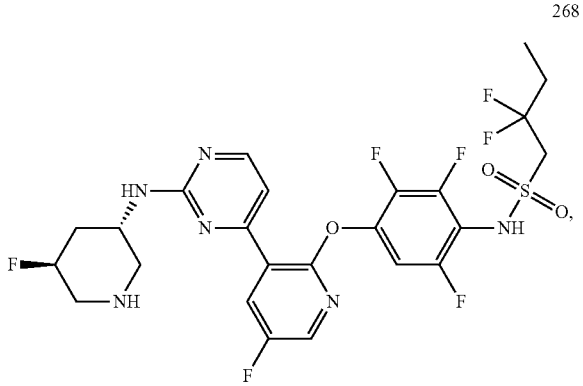
268
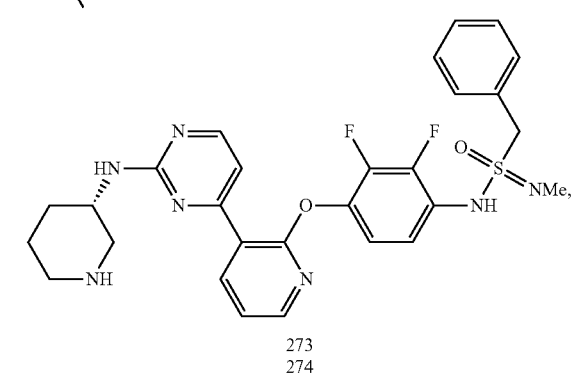
273
274

275
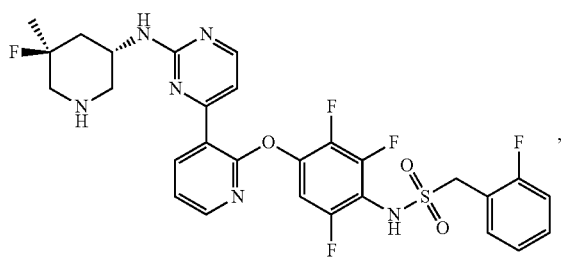
276
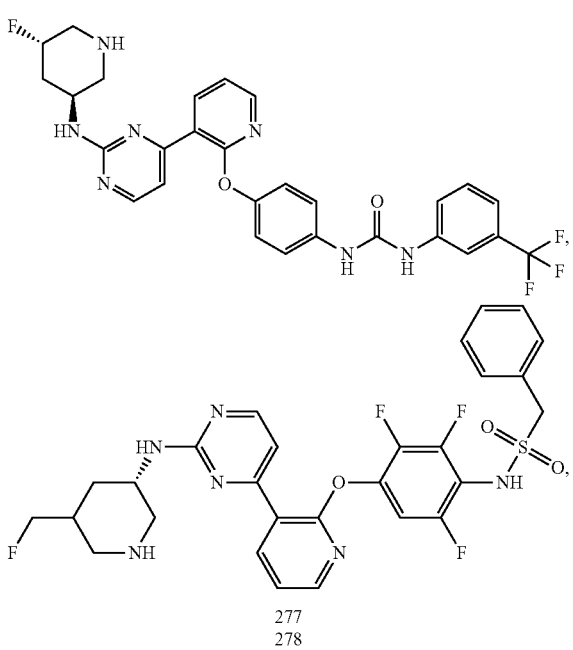
277
278
279
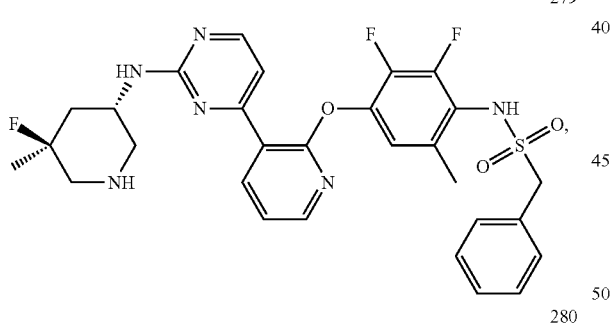
280
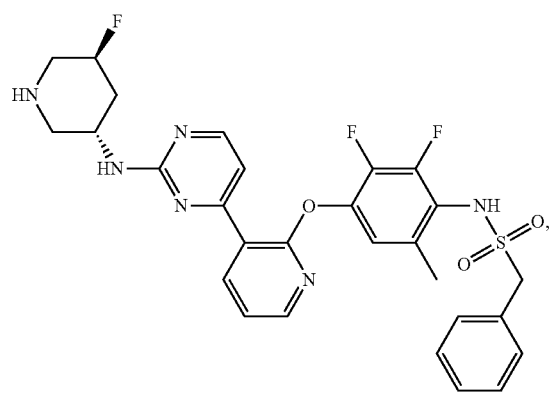
281
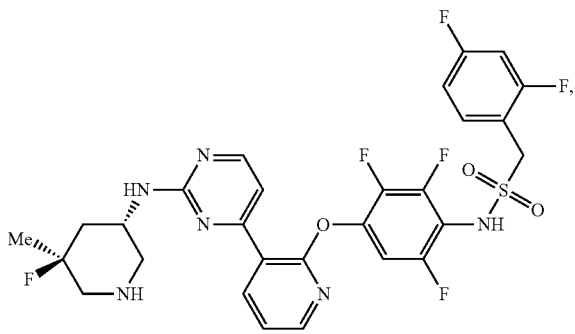
282
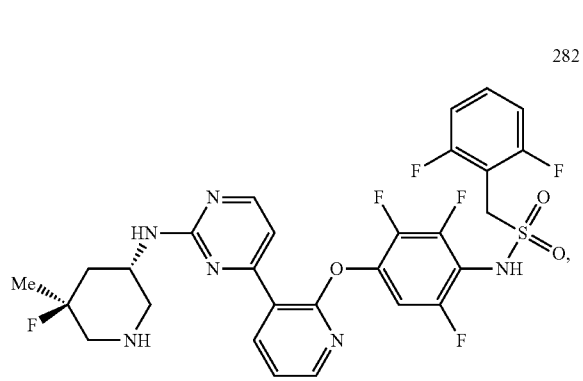
283
284

285
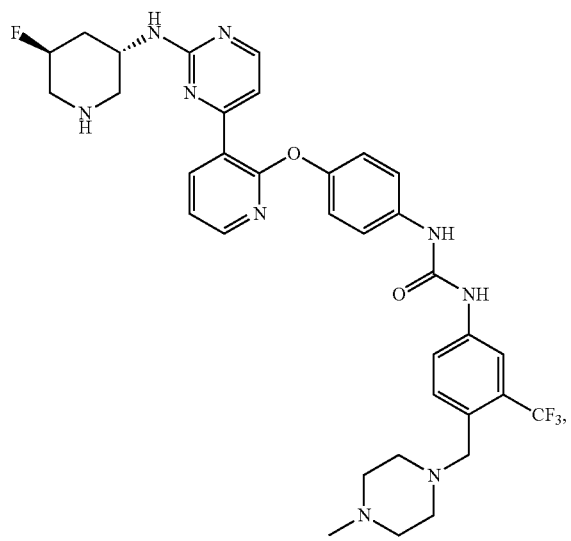
286
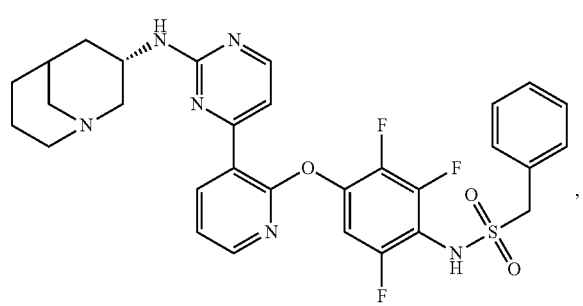
287
288
290
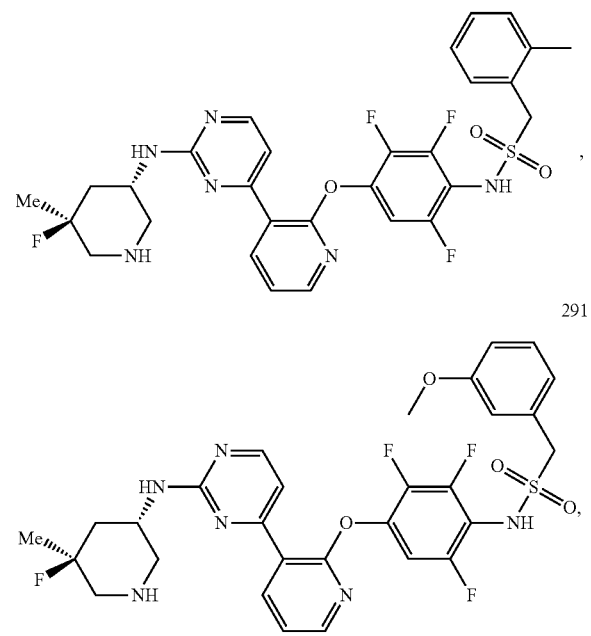
291
292
293
294
295

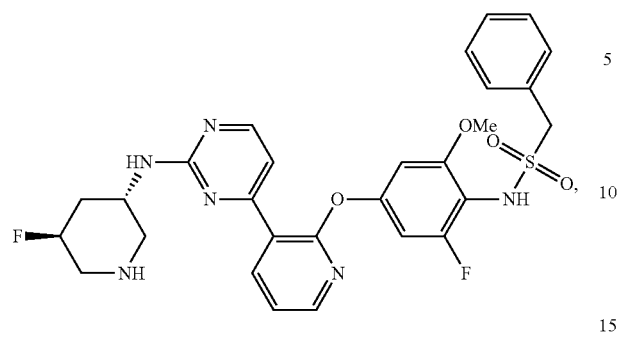
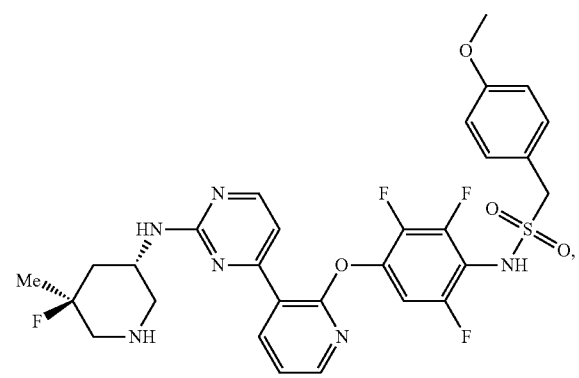
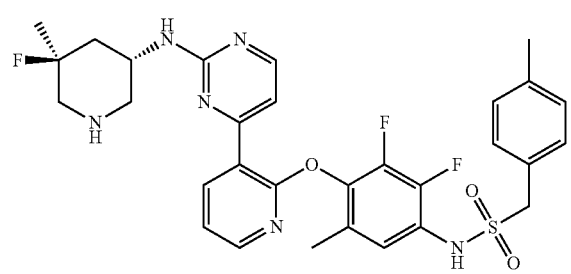
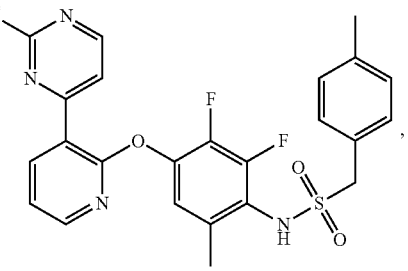
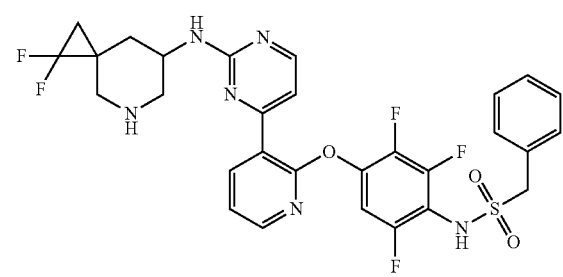

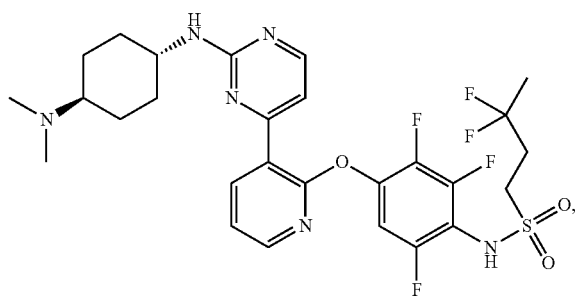
310
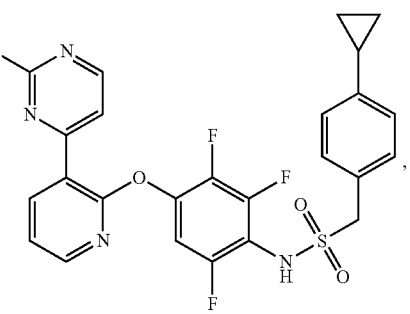
315
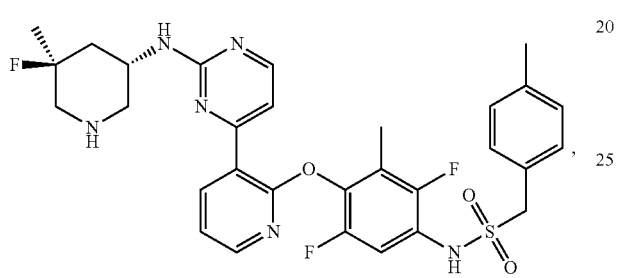
311
316
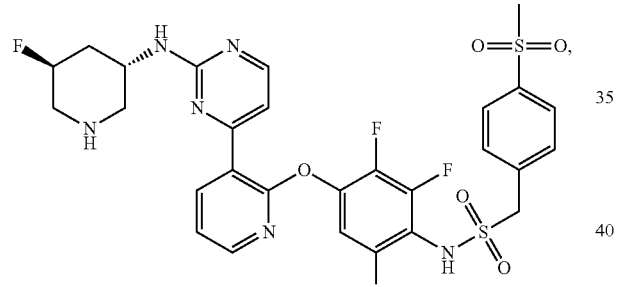
312
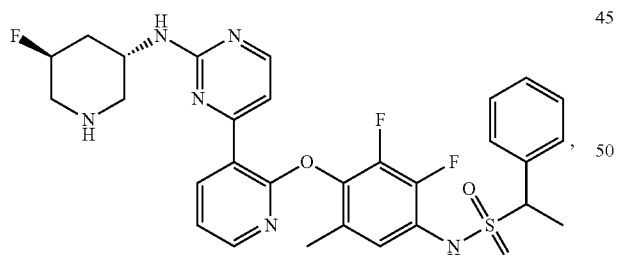
313
317
318
319
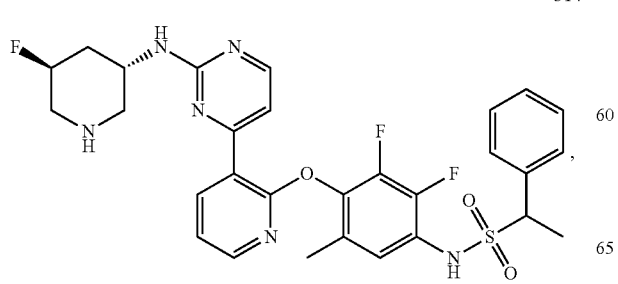
314
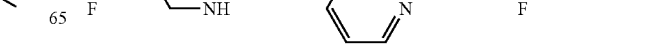
320

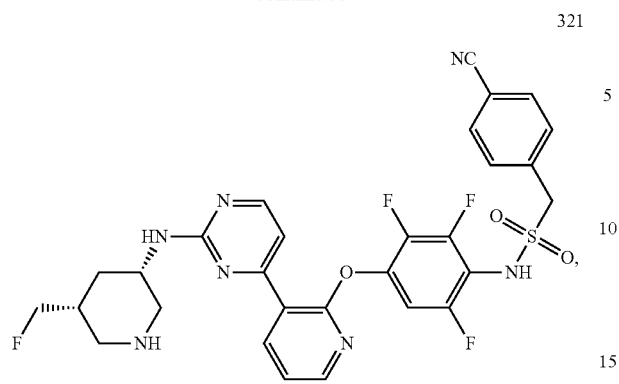
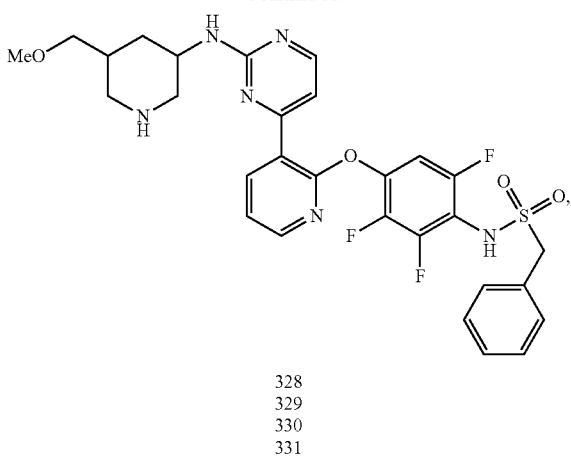
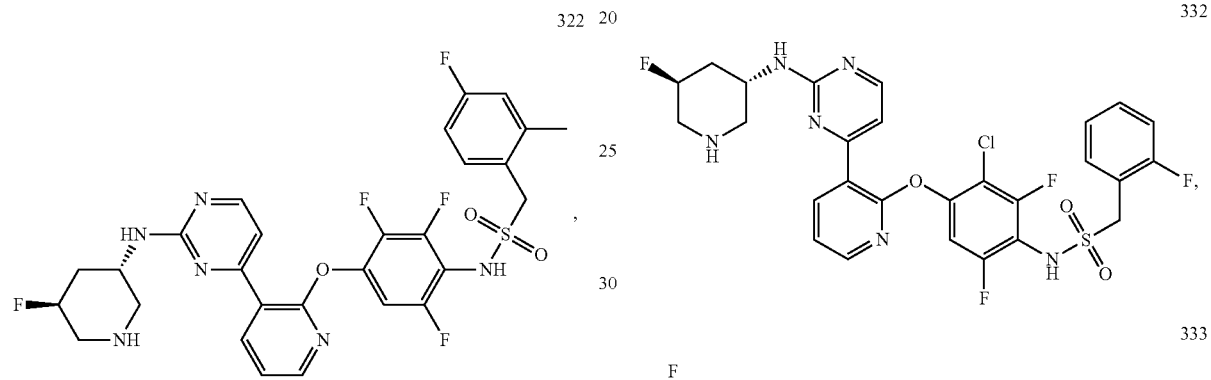
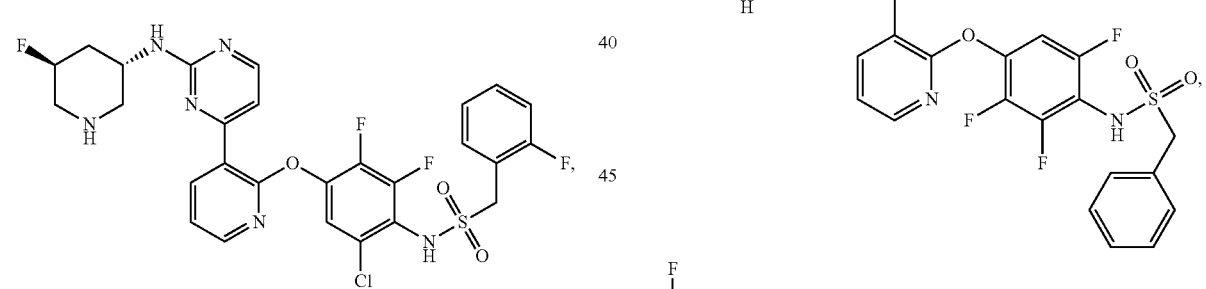
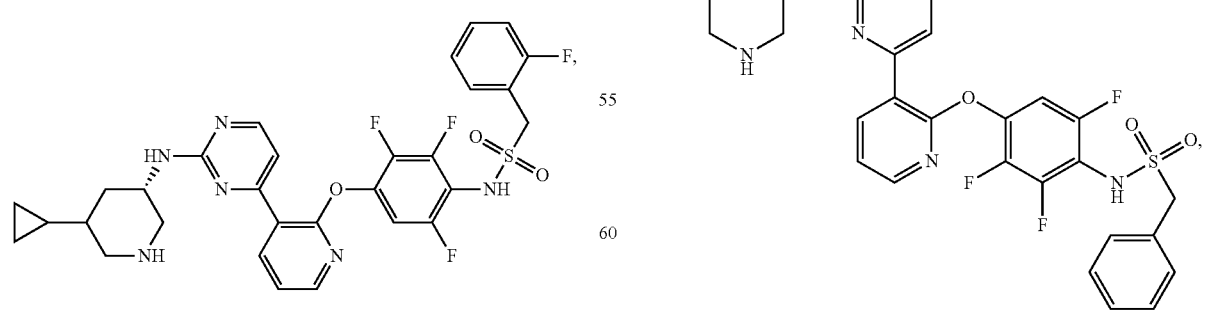

553
-continued
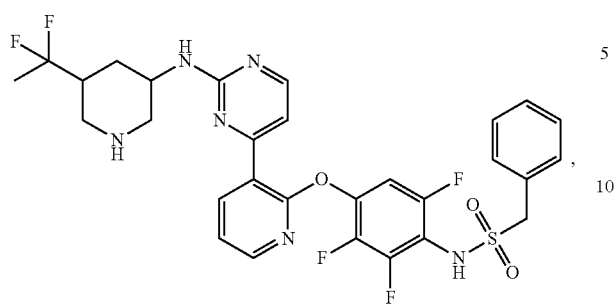
337
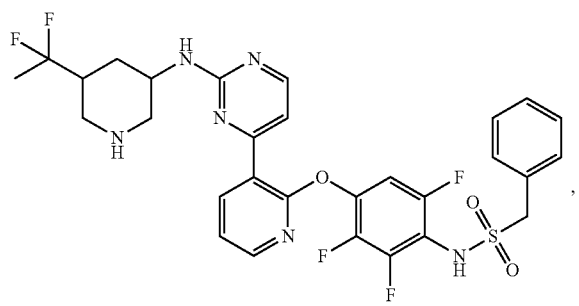
338
339
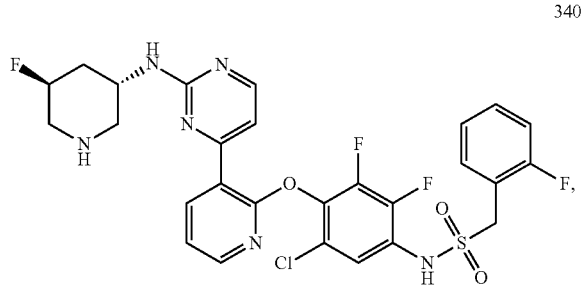
340
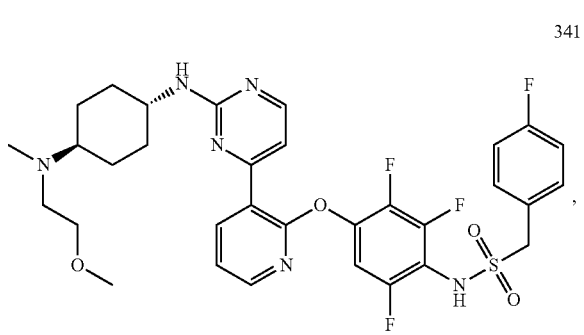
341
554
-continued
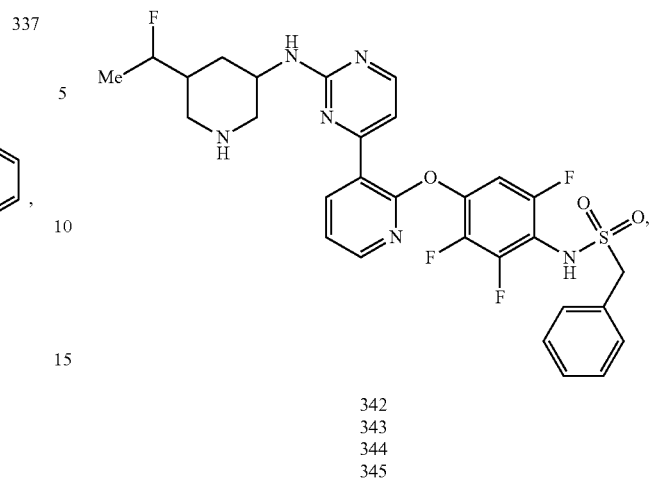
342
343
344
345
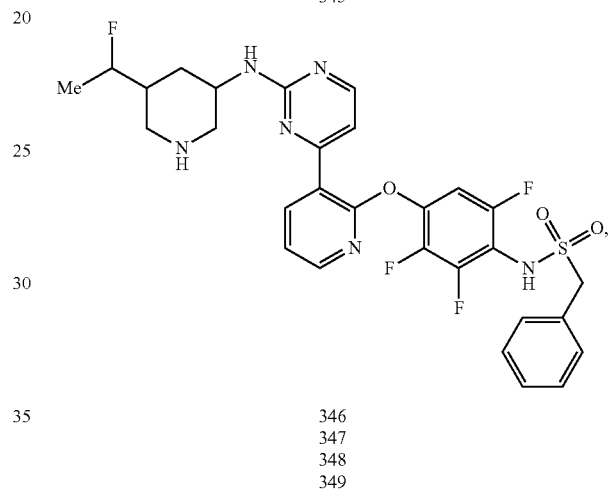
346
347
348
349
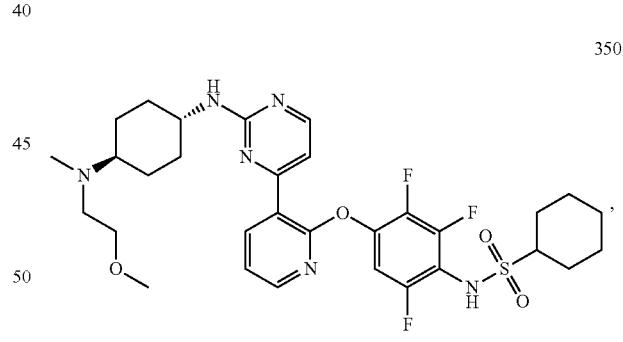
350
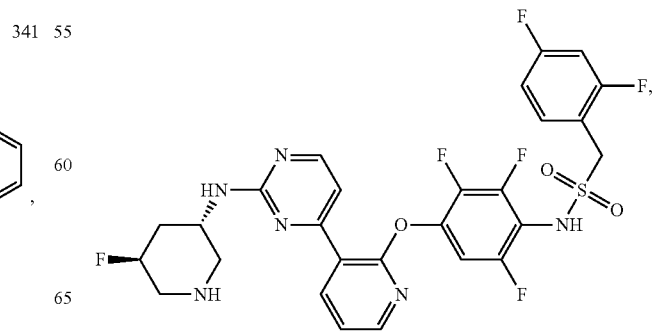
351

| 352 | 356 |
|---|---|
| 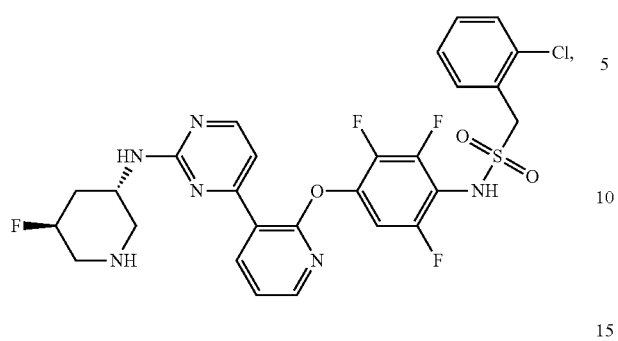 | 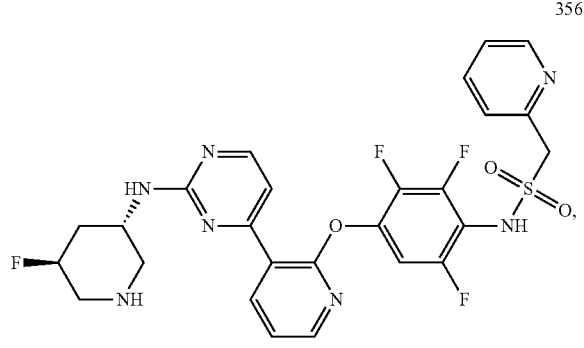 |
| 353 | 357 |
|---|---|
| 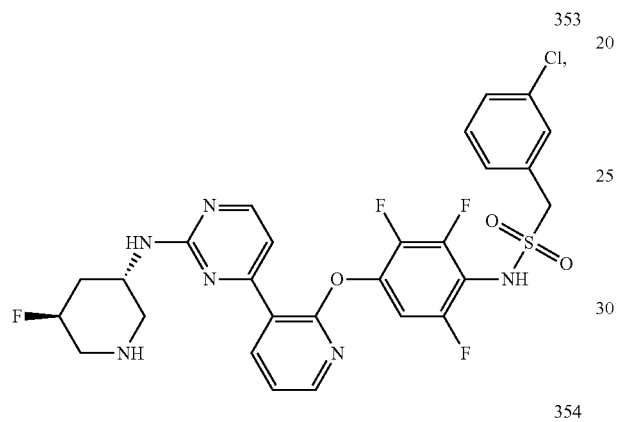 | 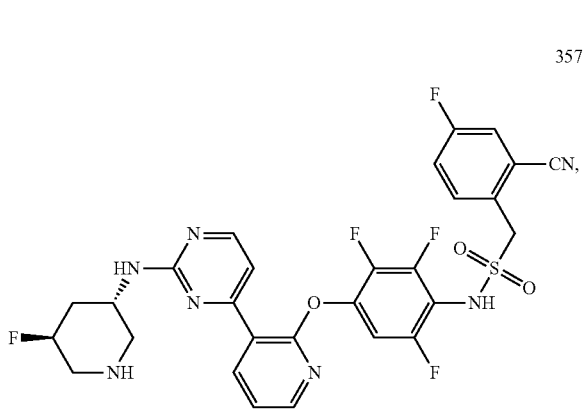 |
| 354 | 358 |
|---|---|
| 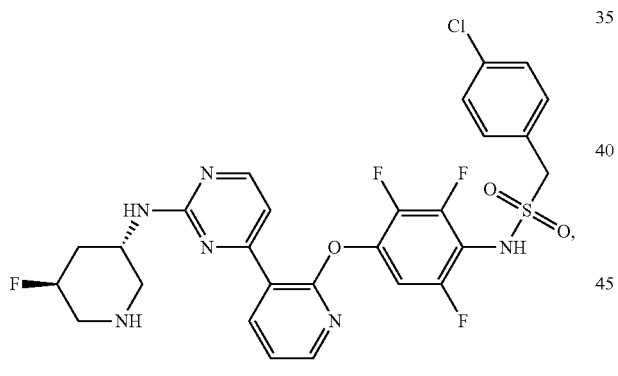 | 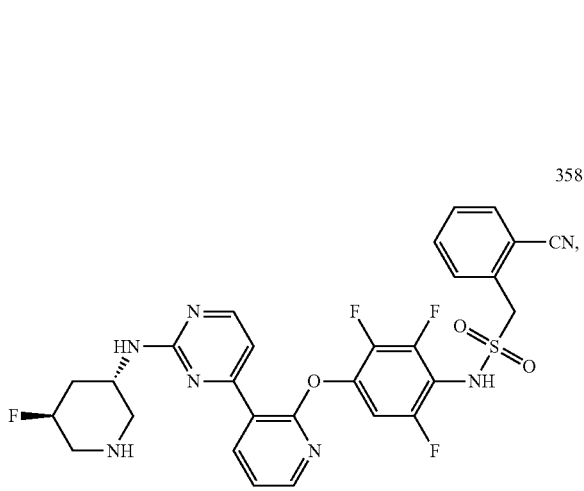 |
| 355 | 359 |
|---|---|
| 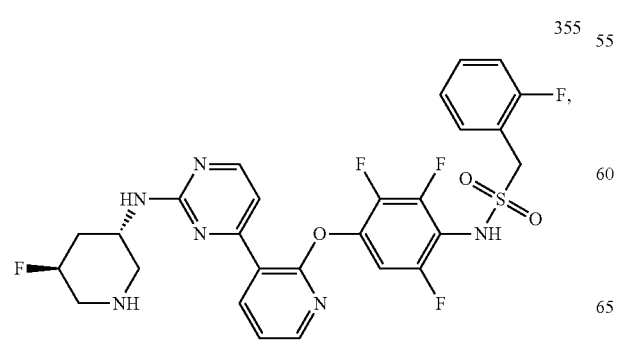 | 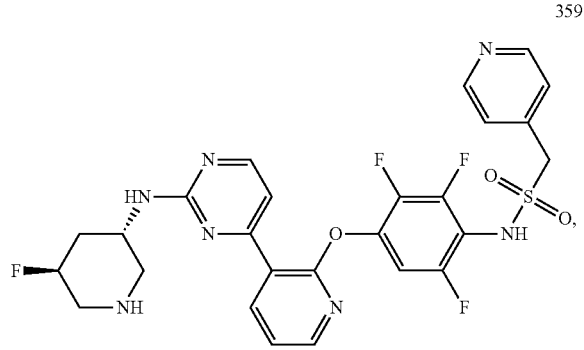 |

360 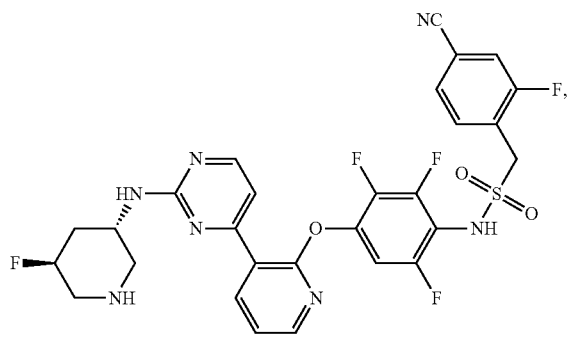
361 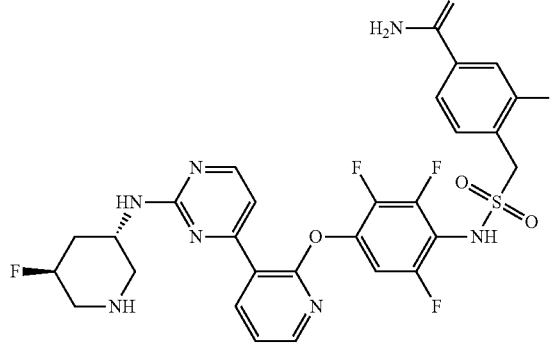
362 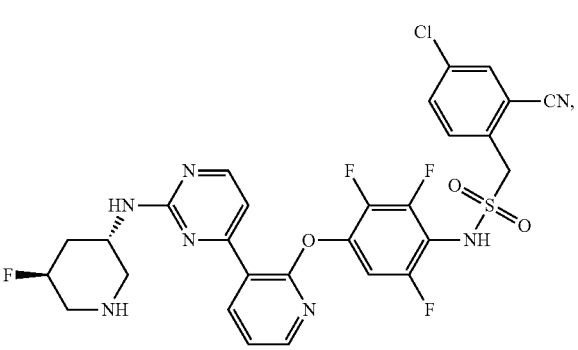
363 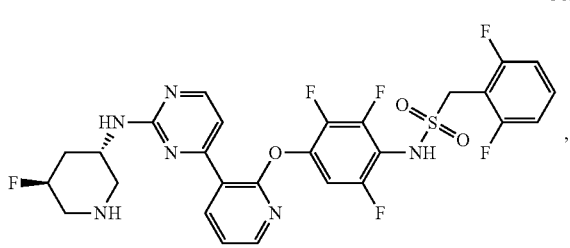
364 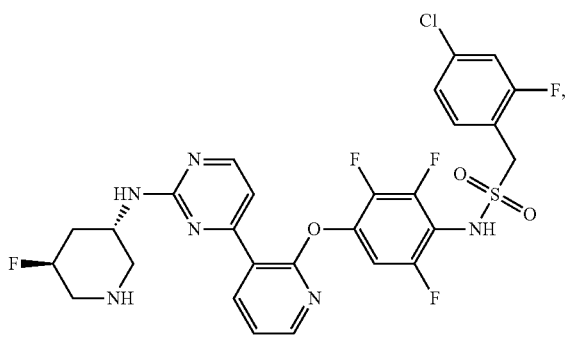
365 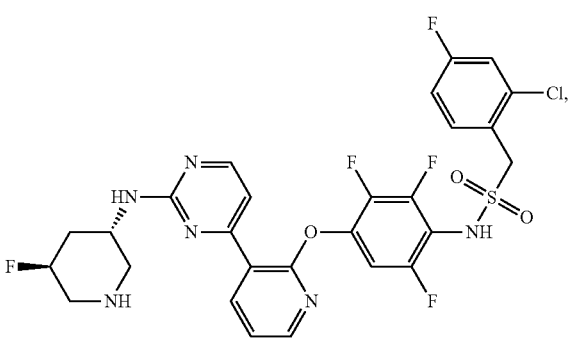
366 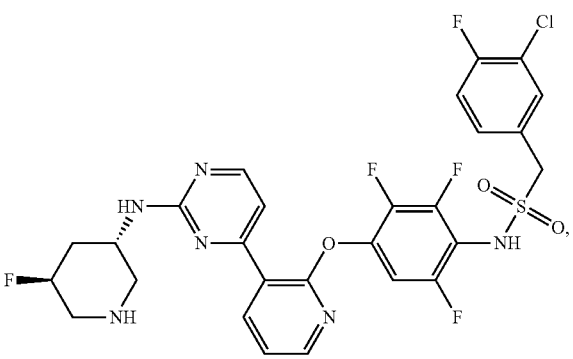
367 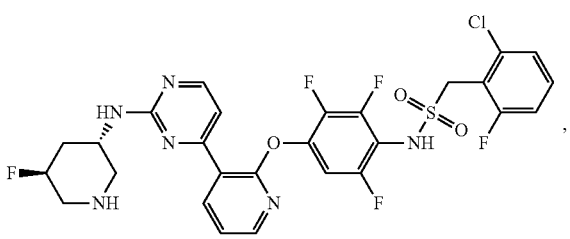
368 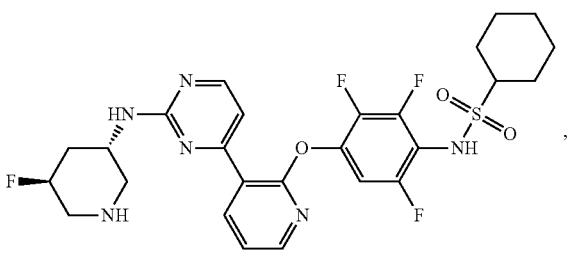

559
-continued
369
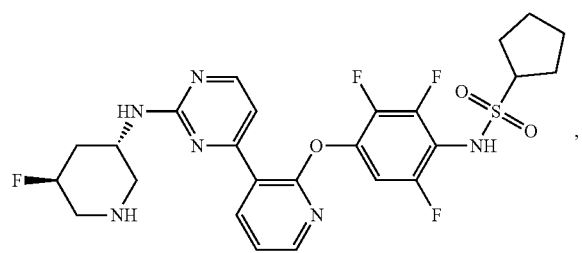
370
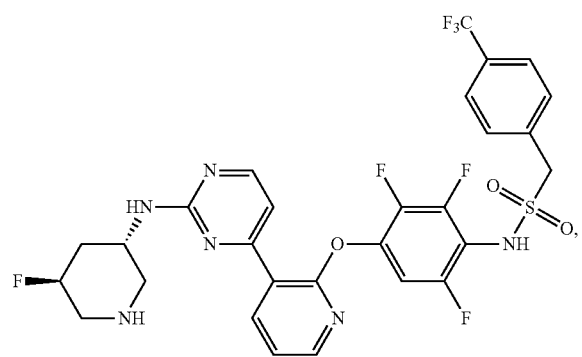
371
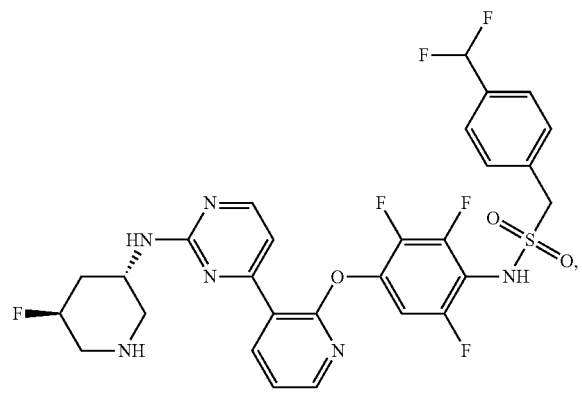
372
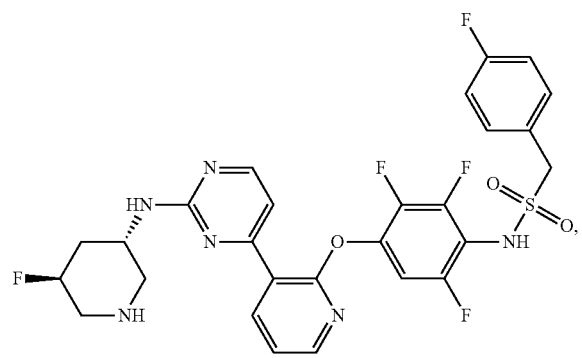
560
-continued
373
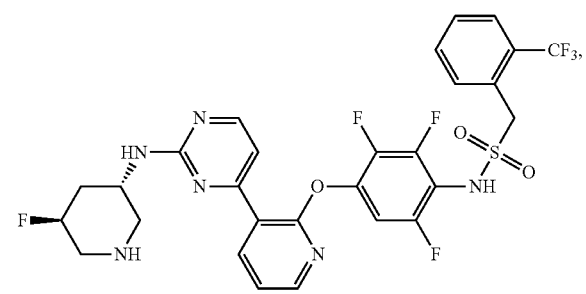
374
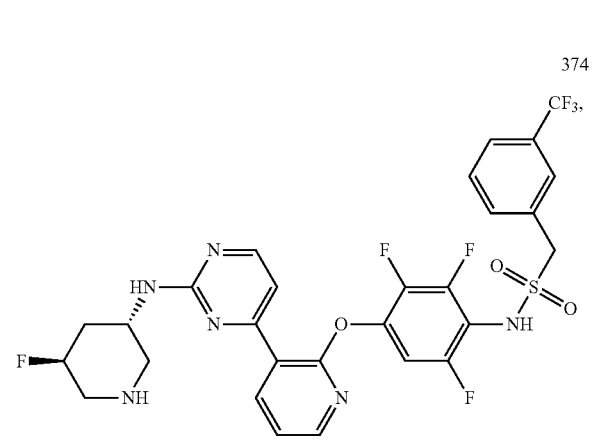
375
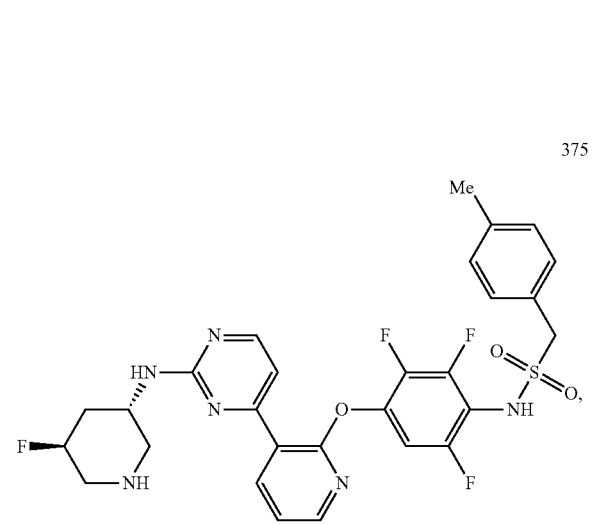
376
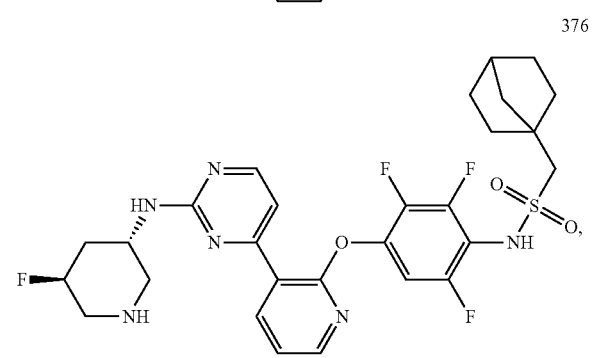

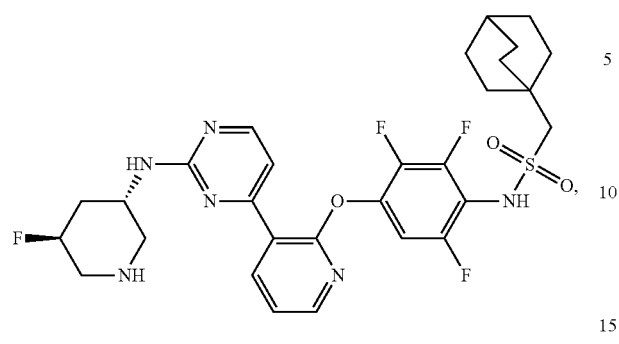
377
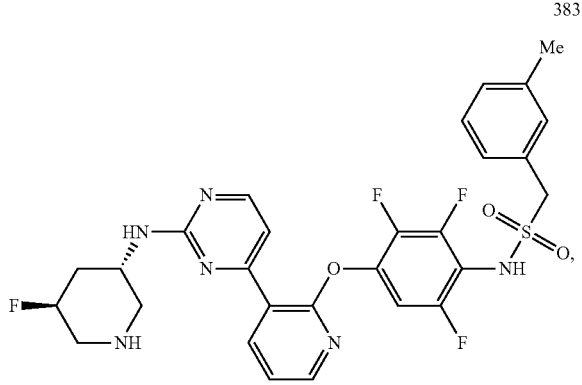
383
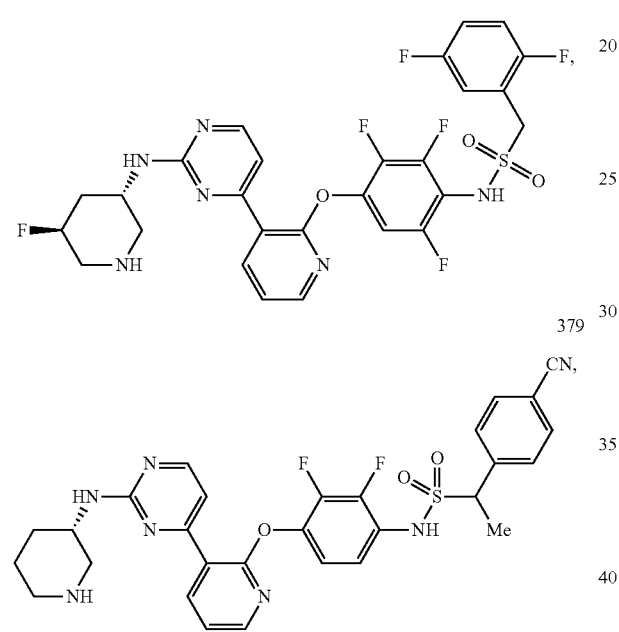
378
379
380
382
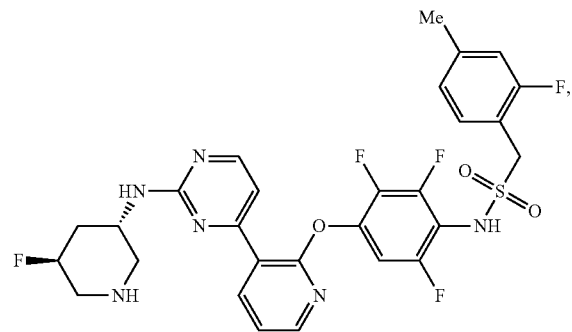
384
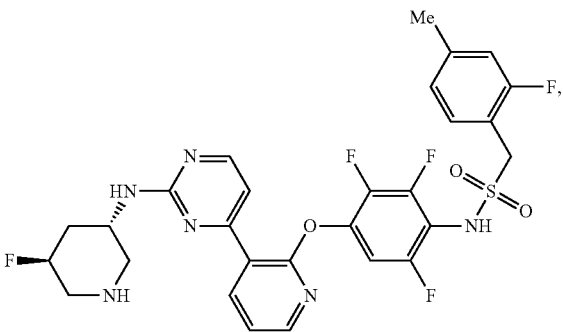
385
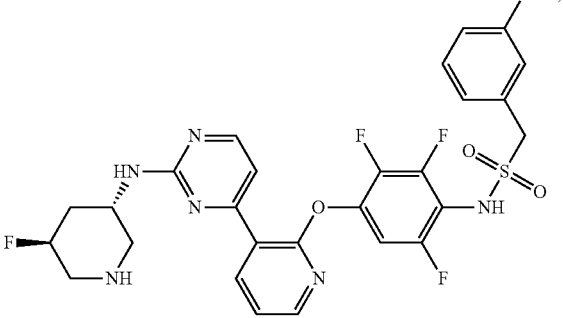
386

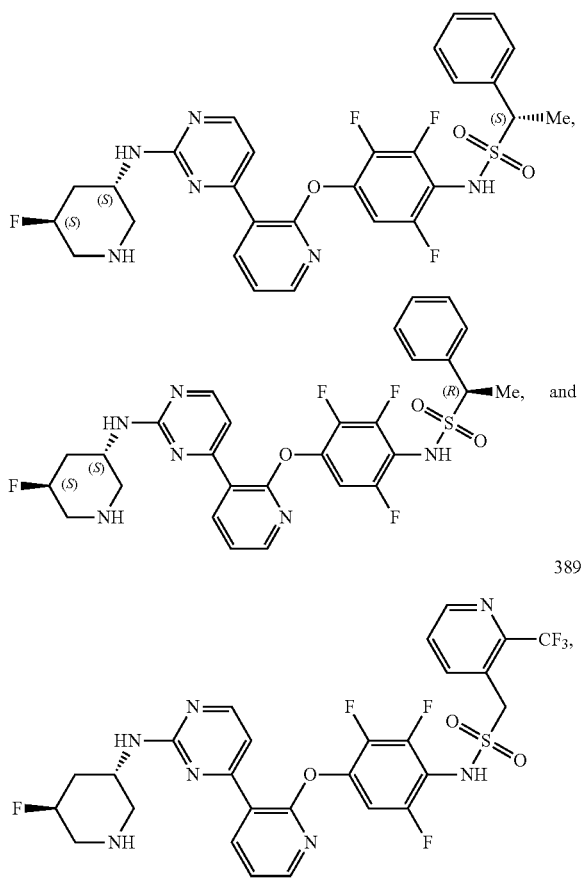

or a pharmaceutically acceptable salt thereof.

20. A pharmaceutical composition comprising a compound of claim 1, or a pharmaceutically acceptable salt thereof, and one or more pharmaceutically acceptable excipients.

21. A method of treating an IRE1-related disease or disorder, the method comprising administering to a subject having an IRE1-related disease or disorder an effective amount of the compound of claim 1, wherein the IRE1-related disease or disorder is cancer.

22. The method of claim 21, wherein the cancer is squamous cell carcinoma, small-cell lung cancer, non-small cell lung cancer (NSCLC), lung adenocarcinoma, squamous cell lung cancer, peritoneum cancer, hepatocellular cancer, stomach cancer, gastrointestinal cancer, esophageal cancer, pancreatic cancer, glioblastoma, cervical cancer, ovarian cancer, liver cancer, bladder cancer, breast cancer, colon cancer, rectal cancer, colorectal cancer, endometrial cancer, uterine cancer, salivary gland carcinoma, renal cancer, prostate cancer, vulval cancer, thyroid cancer, hepatocellular carcinoma (HCC), anal carcinoma, penile carcinoma, or head and neck cancer.

23. The method of claim 21, wherein the cancer is lymphoma, lymphocytic leukemia, multiple myeloma (MM), acute myelogenous leukemia (AML), chronic myelogenous leukemia (CML), myelodysplastic syndrome (MDS), or myeloproliferative disease (MPD).

24. The method of claim 21, wherein the cancer is multiple myeloma or triple-negative breast cancer (TNBC).

25. The method of claim 21, further comprising administering one or more additional therapeutic agents selected from the group consisting of a corticosteroid, a proteasome inhibitor, an immunomodulatory agent, an anti-CD38 antibody, an anti-VEGF-A antibody, an anti-PD-1 antibody, an anti-PD-L1 antibody, and an anti-interleukin-6 antibody, or a combination thereof.

26. The method of claim 25, wherein the corticosteroid comprises dexamethasone: wherein the proteasome inhibitor comprises carfilzomib, ixazomib or bortezomib; wherein the immunomodulatory agent comprises lenalidomide or pomalidomide; wherein the anti-PD-L1 antibody comprises avelumab, durvalumab, or atezolizumab; and wherein the anti-PD-1 antibody comprises pembrolizumab or nivolumab.

* * * * *

UNITED STATES PATENT AND TRADEMARK OFFICE
CERTIFICATE OF CORRECTION

PATENT NO. : 12,071,425 B2
APPLICATION NO. : 17/275606
DATED : August 27, 2024
INVENTOR(S) : Braun et al.

Page 1 of 11

It is certified that error appears in the above-identified patent and that said Letters Patent is hereby corrected as shown below:

On the Title Page

Above item (54), delete "86".

In the Claims

In Column 451, Line 40, Claim 1, delete "$R^g$and" and insert -- $R^g$ and --, therefor.

In Column 451, Line 43, Claim 1, delete "$R^9$" and insert -- $R^g$ --, therefor.

In Column 451, Line 55, Claim 1, delete "$OR^{a1}$," and insert -- $OR^{b1}$, --, therefor.

In Column 452, Line 49, Claim 1, delete "-$C(O)NR^{e2}R^{d2}$," and insert -- -$C(O)NR^{c2}R^{d2}$, --, therefor.

In Column 452, Line 50, Claim 1, delete "-$OC(O)NR^{e2}R^{d2}$," and insert -- -$OC(O)NR^{c2}R^{d2}$, --, therefor.

In Column 452, Line 52, Claim 1, delete "-$N(R^{f2})C(O)NR^{e2}R^{d2}$," and insert -- -$N(R^{f2})C(O)NR^{c2}R^{d2}$, --, therefor.

In Column 453, Line 20, Claim 1, delete "$R^2$" and insert -- $R^{e2}$ --, therefor.

In Column 453, Line 27, Claim 1, delete "$R^2$" and insert -- $R^{h2}$ --, therefor.

In Column 453, Line 30, Claim 1, delete "R" and insert -- $R^{h2}$ --, therefor.

Signed and Sealed this
Eighteenth Day of March, 2025

Coke Morgan Stewart
*Acting Director of the United States Patent and Trademark Office*

In Column 455, Lines 5-15, Claim 16, delete " 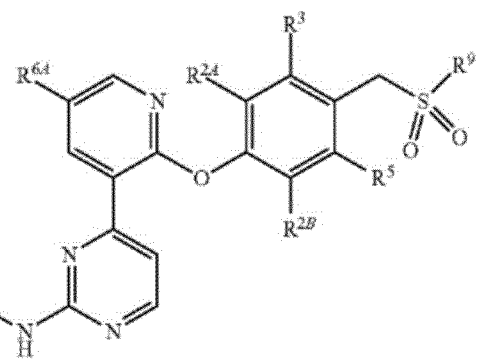 or " and insert -- 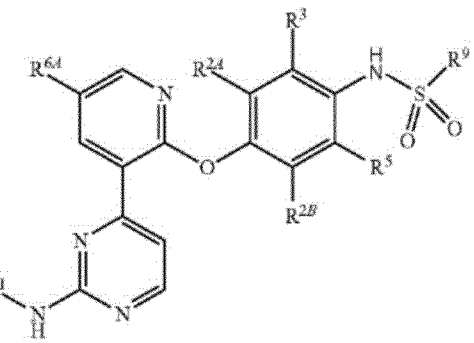 or --, therefor.
In Column 459, Lines 49-56, Claim 19, delete " 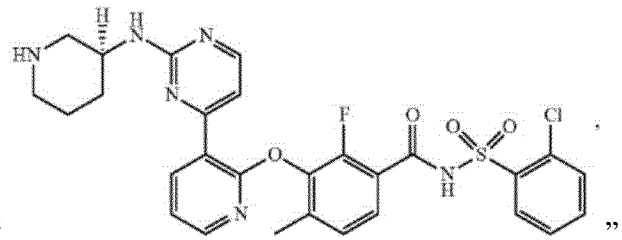 " and insert -- 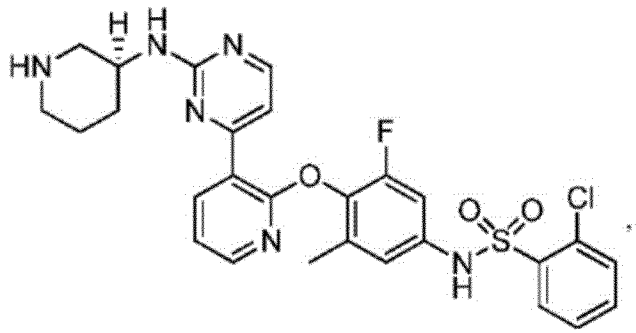 --, therefor.

CERTIFICATE OF CORRECTION (continued)

In Column 459, Lines 59-65, Claim 19, delete " 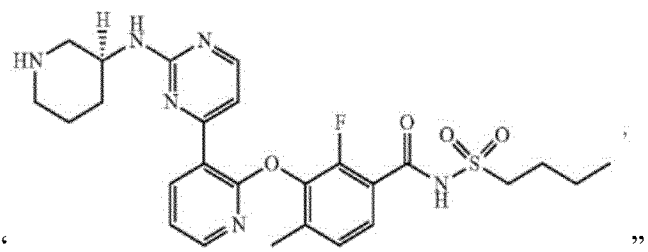 "

and insert -- 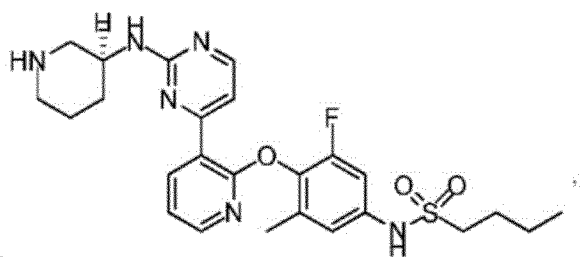 --, therefor.

In Column 477, Lines 21-34, Claim 19, delete

" 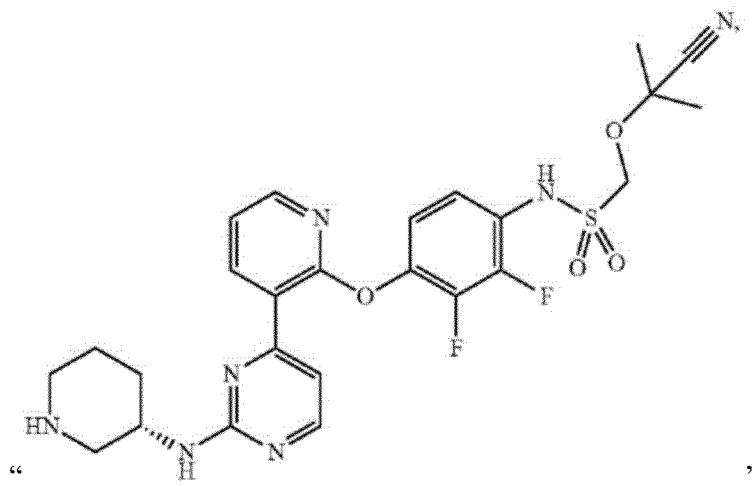 " and insert

-- 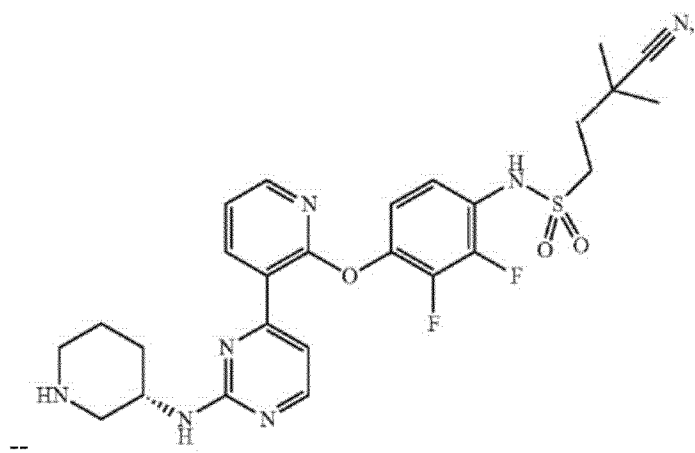 --, therefor.

CERTIFICATE OF CORRECTION (continued)
U.S. Pat. No. 12,071,425 B2

In Column 478, Lines 2-16, Claim 19, delete

" 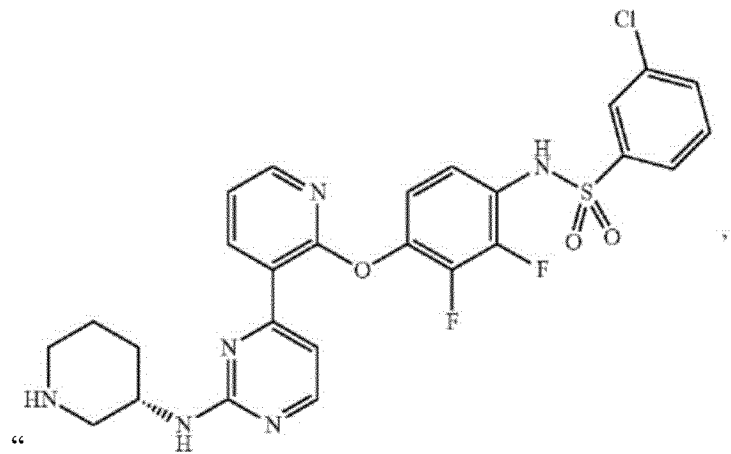 " and insert

-- 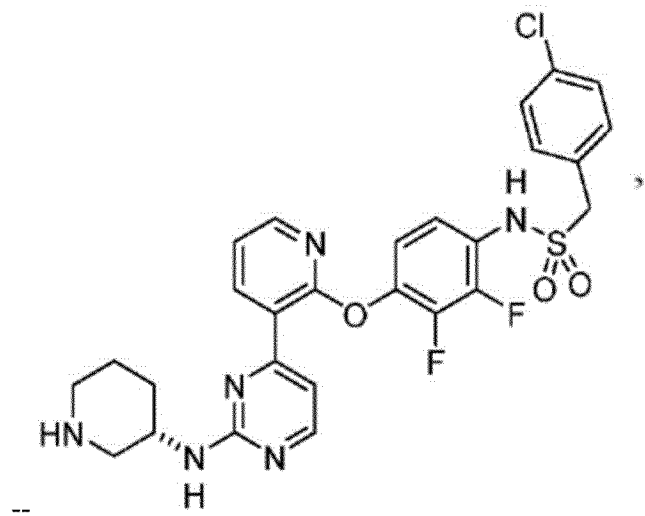 --, therefor.

In Column 486, Line 20, Claim 19, delete "thereof," and insert -- thereof; --, therefor.

In Column 488, Lines 35-44, Claim 19, delete

" 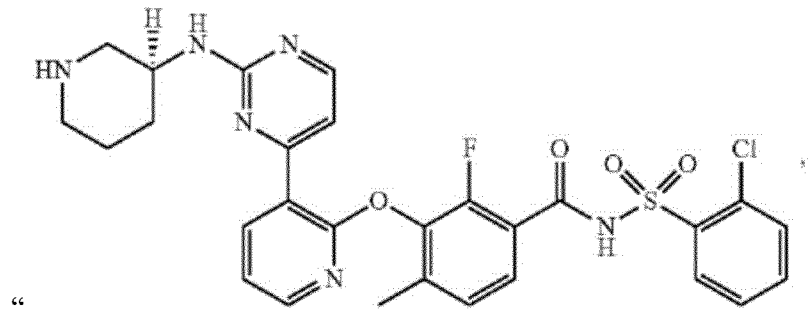 " and insert

CERTIFICATE OF CORRECTION (continued)
U.S. Pat. No. 12,071,425 B2

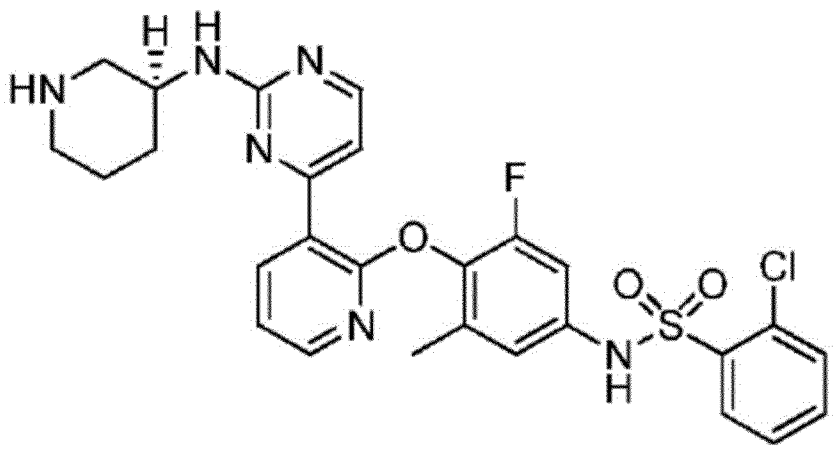 --, therefor.

In Column 488, Lines 45-54, Claim 19, delete

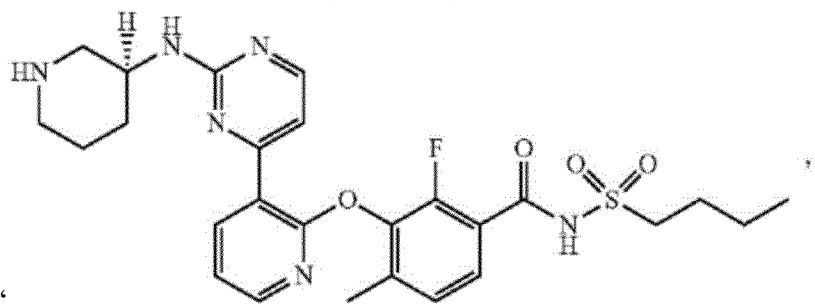 " and insert

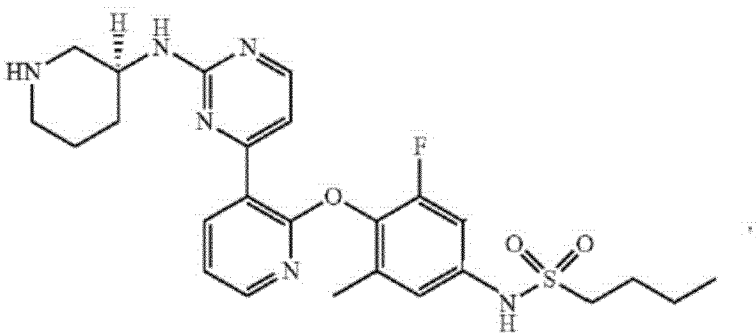 --, therefor.

In Column 498, Lines 20-28, Claim 19, delete

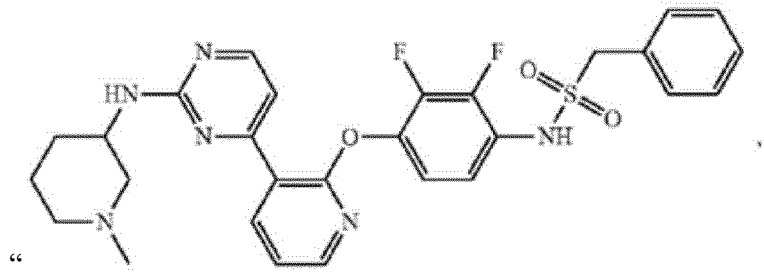 " and insert

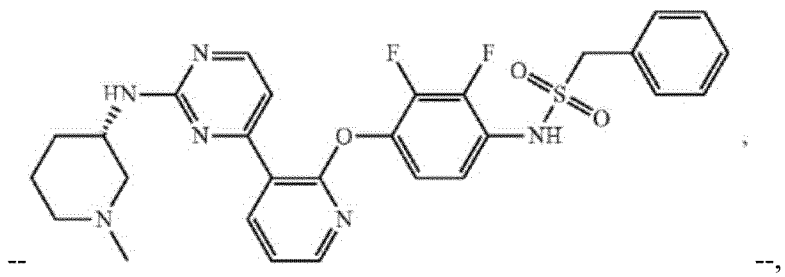 --, therefor.
In Column 517, Lines 29-40, Claim 19, delete
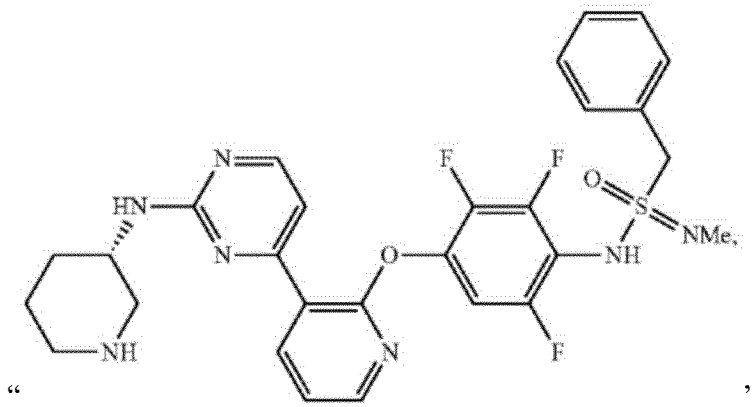 " and insert
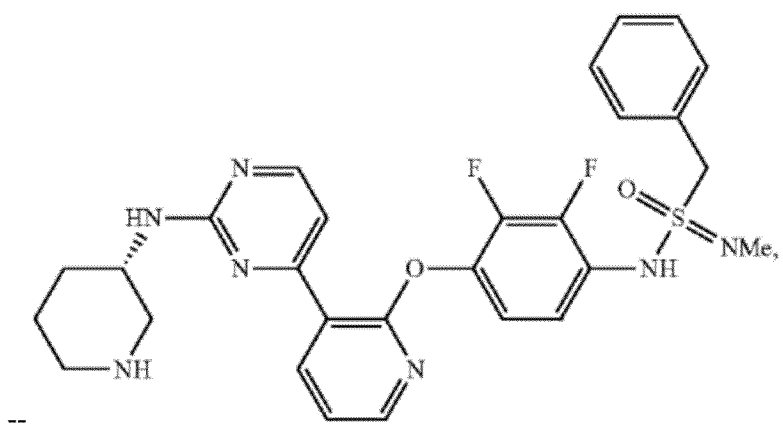 --, therefor.
In Column 520, Lines 27-39, Claim 19, delete
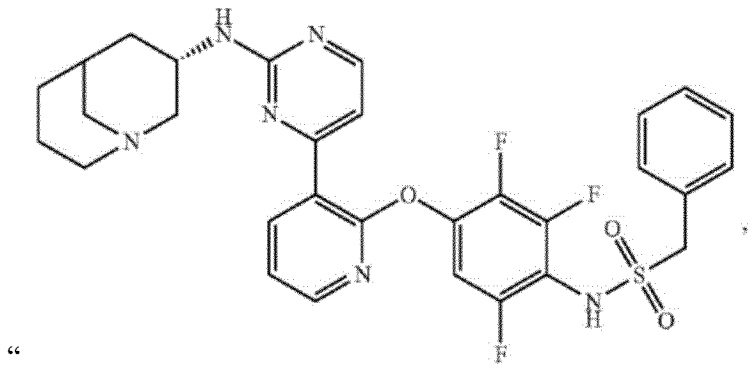 " and insert

CERTIFICATE OF CORRECTION (continued)
U.S. Pat. No. 12,071,425 B2

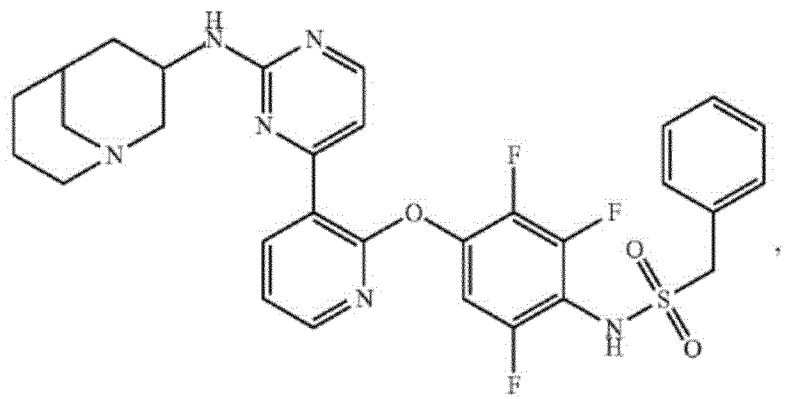

--, therefor.

In Column 524, Lines 54-64, Claim 19, delete "

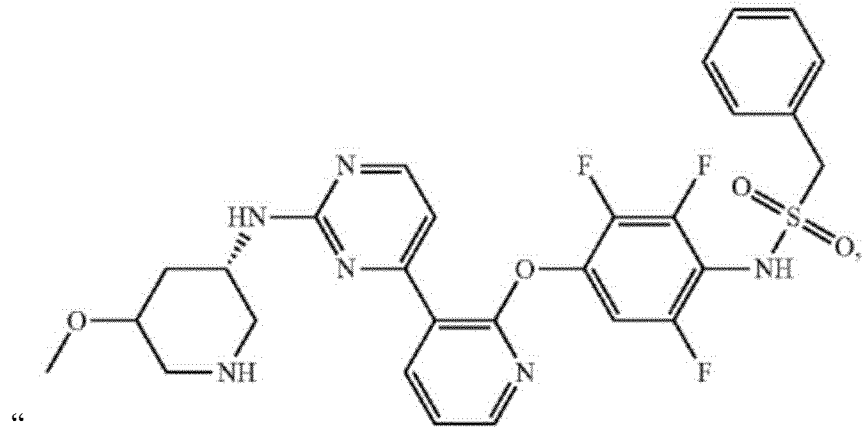

" and insert

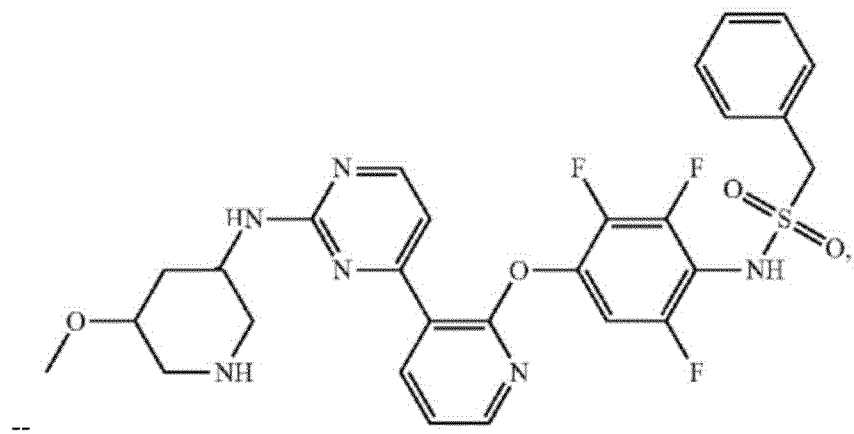

--, therefor.

CERTIFICATE OF CORRECTION (continued)
U.S. Pat. No. 12,071,425 B2

In Column 526, Lines 1-13, Claim 19, delete

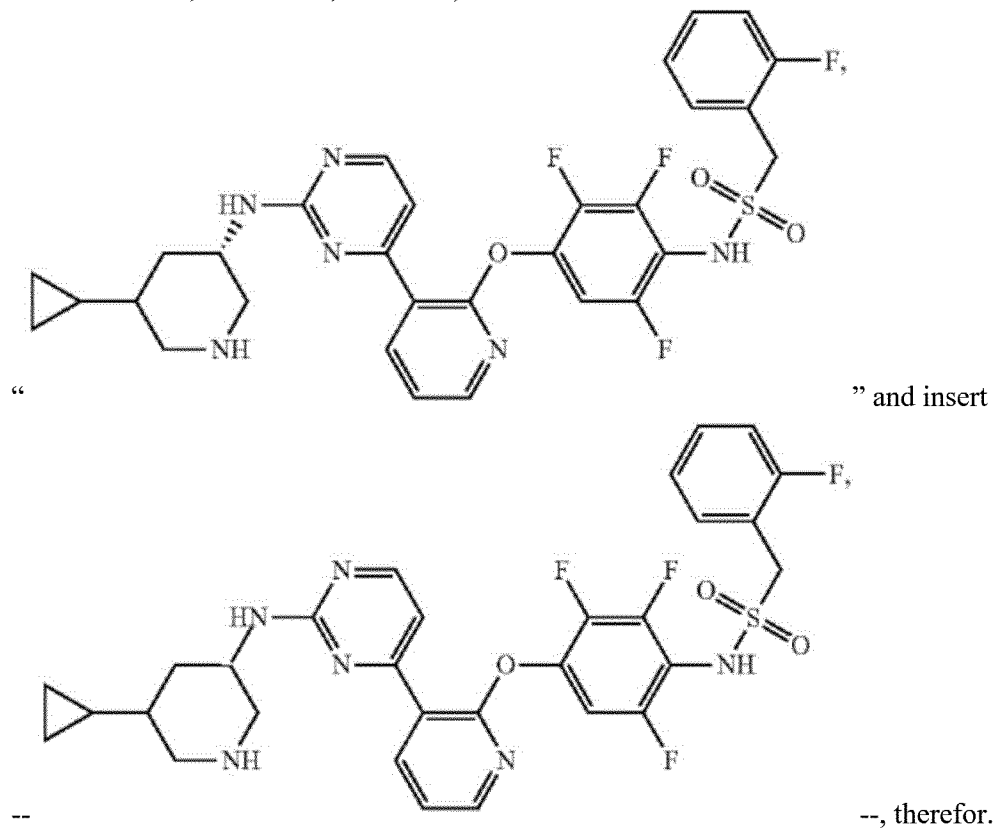

" and insert -- --, therefor.

In Column 537, Line 52, Claim 19, delete "thereof," and insert -- thereof; --, therefor.

In Column 543, Lines 25-38, Claim 19, delete

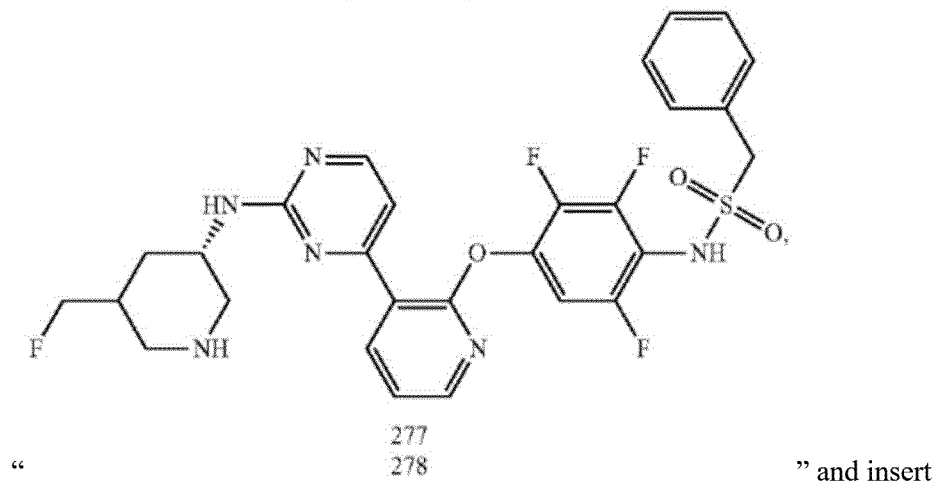

" and insert

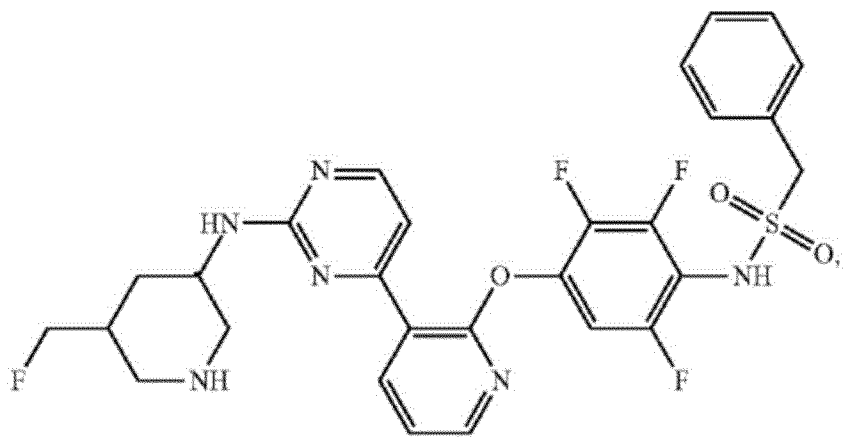
-- --, therefor.
In Column 546, Lines 54-65, Claim 19, delete
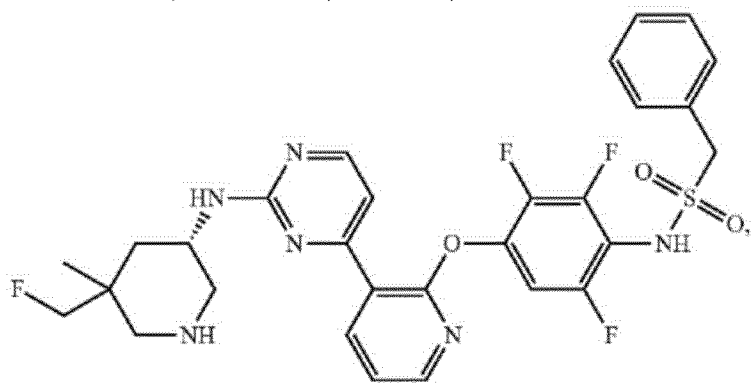
" " and insert
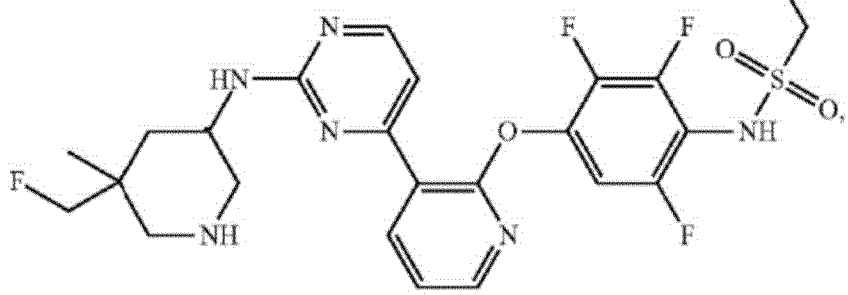
-- --, therefor.

CERTIFICATE OF CORRECTION (continued)
U.S. Pat. No. 12,071,425 B2

In Column 547, Lines 54-65, Claim 19, delete "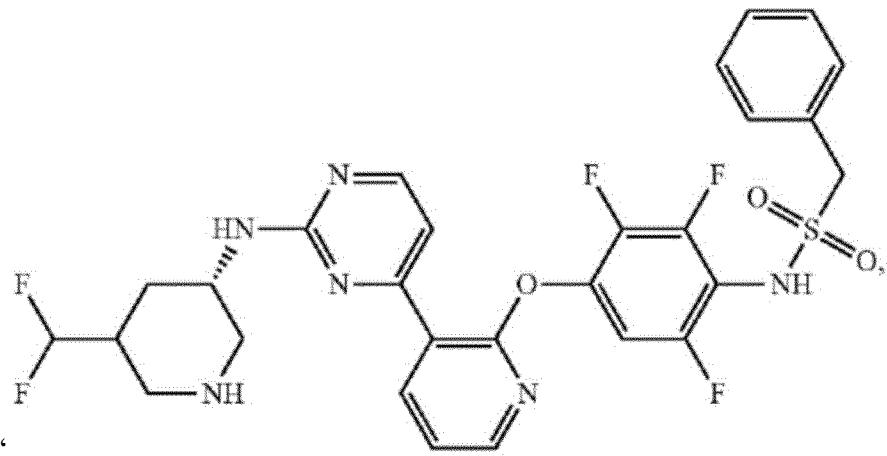" and insert --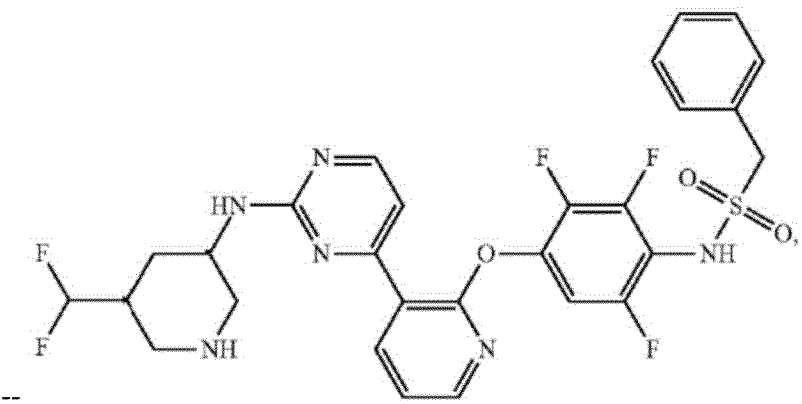--, therefor.

In Column 550, Lines 37-49, Claim 19, delete "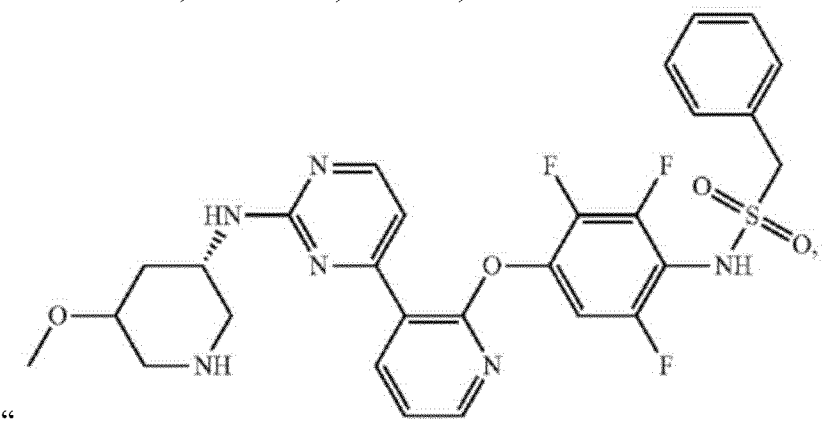" and insert

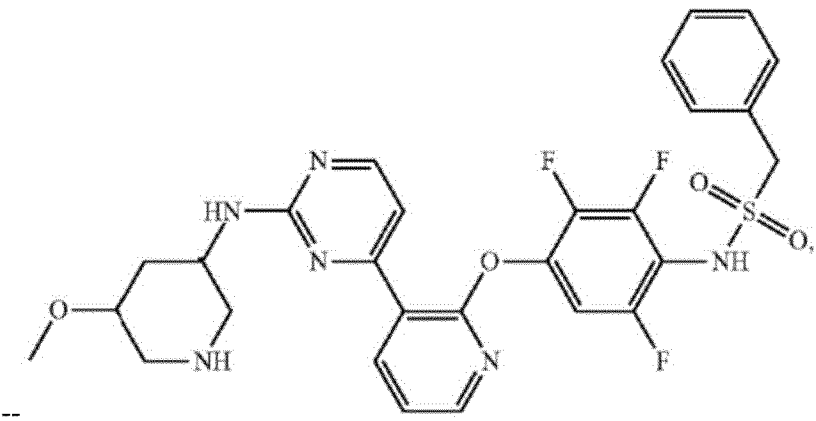
-- --, therefor.
In Column 551, Lines 53-63, Claim 19, delete
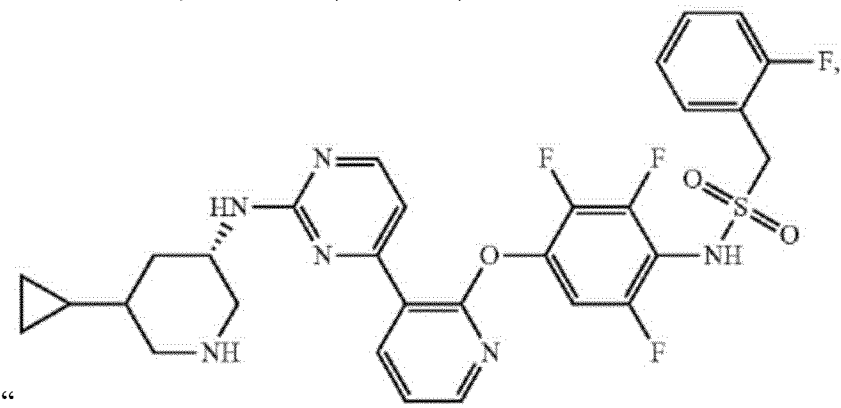
" " and insert
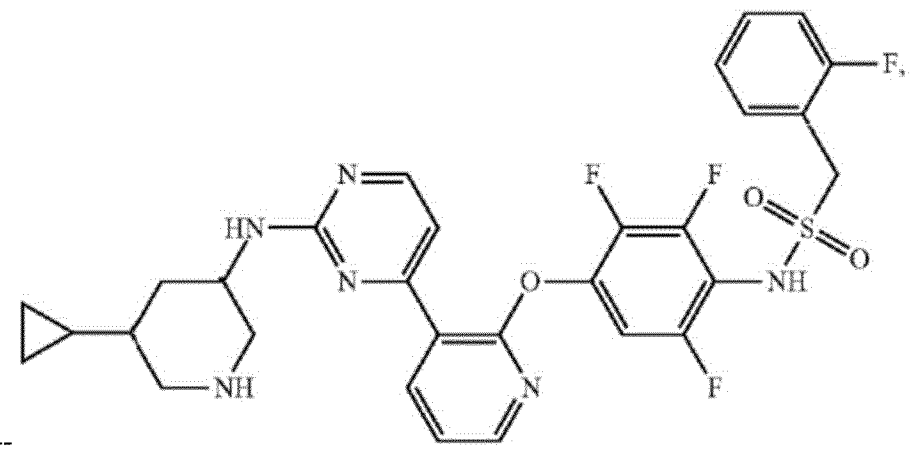
-- --, therefor.
In Column 564, Line 34, Claim 26, delete "dexamethasone:" and insert -- dexamethasone; --, therefor.